US011993776B2

(12) United States Patent
Johnson et al.

(10) Patent No.: US 11,993,776 B2
(45) Date of Patent: May 28, 2024

(54) TRANS-SPLICING MOLECULES

(71) Applicants: Ascidian Therapeutics, Inc., Boston, MA (US); The Trustees of the University of Pennsylvania, Philadelphia, PA (US)

(72) Inventors: Philip R. Johnson, Bryn Mawr, PA (US); Bruce C. Schnepp, Havertown, PA (US); Jean Bennett, Bryn Mawr, PA (US); Scott J. Dooley, Philadelphia, PA (US); Krishna Jawaharlal Fisher, Durham, NC (US); Junwei Sun, Philadelphia, PA (US)

(73) Assignees: Ascidian Therapeutics, Inc., Boston, MA (US); The Trustees of the University of Pennsylvania, Philadelphia, PA (US)

( * ) Notice: Subject to any disclaimer, the term of this patent is extended or adjusted under 35 U.S.C. 154(b) by 452 days.

(21) Appl. No.: 17/047,496

(22) PCT Filed: Apr. 17, 2019

(86) PCT No.: PCT/US2019/027981

§ 371 (c)(1),
(2) Date: Oct. 14, 2020

(87) PCT Pub. No.: WO2019/204514

PCT Pub. Date: Oct. 24, 2019

(65) Prior Publication Data

US 2021/0155938 A1 May 27, 2021

Related U.S. Application Data

(60) Provisional application No. 62/658,667, filed on Apr. 17, 2018, provisional application No. 62/658,658, filed on Apr. 17, 2018.

(51) Int. Cl.
*C12N 15/113* (2010.01)
*C07K 14/705* (2006.01)
*C12Q 1/68* (2018.01)

(52) U.S. Cl.
CPC ........ *C12N 15/1138* (2013.01); *C07K 14/705* (2013.01); *C07K 2319/71* (2013.01); *C07K 2319/85* (2013.01); *C12N 2320/33* (2013.01); *C12N 2320/34* (2013.01)

(58) Field of Classification Search
None
See application file for complete search history.

(56) References Cited

U.S. PATENT DOCUMENTS

| | | | |
|---|---|---|---|
| 6,013,487 A | 1/2000 | Mitchell |
| 6,280,978 B1 | 8/2001 | Mitchell et al. |
| 7,943,374 B2 | 5/2011 | Hildinger |
| 8,053,232 B2 | 11/2011 | Puttaraju et al. |
| 8,076,461 B2 | 12/2011 | Pearce et al. |
| 8,173,377 B2 | 5/2012 | Agris et al. |
| 8,236,557 B2 | 8/2012 | Dongsheng et al. |
| 8,323,910 B2 | 12/2012 | Agris et al. |
| 8,697,355 B2 | 4/2014 | Agris et al. |
| 8,735,366 B2 | 5/2014 | Bauer et al. |
| 9,249,425 B2 | 2/2016 | Bennett et al. |
| 9,567,376 B2 | 2/2017 | Cronin et al. |
| 9,896,665 B2 | 2/2018 | Bennett et al. |
| 10,155,794 B2 | 12/2018 | Drivas et al. |
| 10,266,845 B2 | 4/2019 | Cronin et al. |
| 10,301,366 B2 | 5/2019 | Drivas et al. |
| 10,987,433 B2 | 4/2021 | Bennett et al. |
| 2013/0059901 A1 | 3/2013 | Bauer et al. |
| 2013/0071951 A1 | 3/2013 | Agris et al. |
| 2014/0087444 A1 | 3/2014 | Bennett et al. |
| 2014/0243388 A1 | 8/2014 | Hastings |
| 2015/0202269 A1 | 7/2015 | Beltran et al. |
| 2015/0252358 A1 | 9/2015 | Maeder et al. |
| 2017/0342414 A1 | 11/2017 | Collin et al. |

(Continued)

FOREIGN PATENT DOCUMENTS

| | | |
|---|---|---|
| EP | 2151248 A1 | 2/2010 |
| JP | 2016-516424 A | 6/2016 |
| WO | WO-97/22250 A1 | 6/1997 |

(Continued)

OTHER PUBLICATIONS

Helou et al., “Mutation analysis of NPHP6/CEP290 in patients with Joubert syndrome and Senior-Løken syndrome,” J Med Genet 44(10):657-63 (2007).
International Search Report and Written Opinion for International Patent Application No. PCT/US2019/027981, dated Aug. 6, 2019 (33 pages).
Extended European Search Report for European Patent Application No. 19789043.7, dated Sep. 20, 2022 (10 pages).
Liemberger et al., “RNA Trans-Splicing Modulation via Antisense Molecule Interference,” Int J Mol Sci. 19(3):762 (Mar. 7, 2018) (18 pages).

(Continued)

*Primary Examiner* — Sean McGarry
(74) *Attorney, Agent, or Firm* — Clark & Elbing LLP

(57) ABSTRACT

The present invention features nucleic acid trans-splicing molecules (e.g., pre-mRNA trans-splicing molecules (RTMs)) capable of correcting one or more mutations in the ABCA4 gene or the CEP290 gene. Such molecules are useful in the treatment of disorders associated with mutations in ABCA4, such as Stargardt Disease (e.g., Stargardt Disease 1) and disorders associated with a mutation in CEP290, such as Leber congenital amourosis 10 (LCA 10). Also provided by the invention described herein are methods of using the nucleic acid trans-splicing molecules for correcting mutations in ABCA4 and CEP290 and for treating disorders associated with mutations in ABCA4 and CEP290, such as Stargardt Disease and LCA 10.

21 Claims, 29 Drawing Sheets

Specification includes a Sequence Listing.

(56) References Cited

U.S. PATENT DOCUMENTS

2018/0369412 A1* 12/2018 Bennett .................. C12N 15/00

FOREIGN PATENT DOCUMENTS

| | | | |
|---|---|---|---|
| WO | WO-98/14275 | A1 | 4/1998 |
| WO | WO-2001/049745 | A1 | 7/2001 |
| WO | WO-2003/003014 | A1 | 1/2003 |
| WO | WO-2003/069311 | A2 | 8/2003 |
| WO | WO-2003/072739 | A2 | 9/2003 |
| WO | WO-2003/104412 | A2 | 12/2003 |
| WO | WO-2003/104416 | A2 | 12/2003 |
| WO | WO-2004/006678 | A1 | 1/2004 |
| WO | WO-2004/038380 | A2 | 5/2004 |
| WO | WO-2005/023990 | A2 | 3/2005 |
| WO | WO-2005/070023 | A2 | 8/2005 |
| WO | WO-2005/070948 | A1 | 8/2005 |
| WO | WO-2006/026611 | A2 | 3/2006 |
| WO | WO-2009/103562 | A1 | 8/2009 |
| WO | WO-2010/012472 | A1 | 2/2010 |
| WO | WO-2012/158757 | A1 | 11/2012 |
| WO | WO-2014/124282 | A1 | 8/2014 |
| WO | WO-2014/170480 | A1 | 10/2014 |
| WO | WO-2015/009575 | A1 | 1/2015 |
| WO | WO-2016/139321 | A1 | 9/2016 |
| WO | WO-2017/087900 | A1 | 5/2017 |
| WO | WO-2017/106370 | A1 | 6/2017 |
| WO | WO-2019/025984 | A1 | 2/2019 |
| WO | WO-2020/214973 | A1 | 10/2020 |
| WO | WO-2020/214990 | A1 | 10/2020 |

OTHER PUBLICATIONS

Applicants' Response and Amendment filed Jan. 8, 2020 in European Patent Application No. EP16867296.2 (9 pages).

Communication pursuant to Article 94(3) EPC issued in European Patent Application No. EP16867296.2, dated Sep. 2, 2020 (4 pages).

Communication pursuant to Rule 164(1) EPC issued in European Patent Application No. EP16867296.2, dated Mar. 1, 2019 (10 pages).

Supplementary European Search Report issued in related European Patent Application No. EP16867296.2, dated Feb. 15, 2019 (4 pages).

Written Opinion for International Patent Application No. PCT/US2016/062941, dated Feb. 16, 2017 (6 pages).

International Search Report for International Patent Application No. PCT/US2016/062941, dated Feb. 16, 2017 (3 pages).

Gérard et al., "Intravitreal Injection of Splice-switching Oligonucleotides to Manipulate Splicing in Retinal Cells," Mol Ther Nucleic Acids. 4(9):e250 (2015) (8 pages).

Collin et al., "Antisense Oligonucleotide (AON)-based Therapy for Leber Congenital Amaurosis Caused by a Frequent Mutation in CEP290," Mol Ther Nucleic Acids. 1(3):e14 (2012) (7 pages).

Garanto et al., "Species-Dependent Splice Recognition of a Cryptic Exon Resulting from a Recurrent Intronic CEP290 Mutation that Causes Congenital Blindness," Int J Mol Sci. 16(3):5285-5298 (2015).

Garanto et al., "In Vitro and In Vivo Rescue of Aberrant Splicing in CEP290-associated LCA by Antisense Oligonucleotide Delivery," Hum Mol Genet. 25(12):2552-2563 (2016).

Koller et al., "A novel screening system improves genetic correction by internal exon replacement," Nucleic Acids Res. 39(16):e108 (2011) (11 pages).

Zhang et al., "Protein misfolding and the pathogenesis of ABCA4-associated retinal degenerations," Hum Mol Genet. 24(11):3220-3237 (2015).

Maia-Lopes et al., "ABCA4 mutations in Portuguese Stargardt patients: identification of new mutations and their phenotypic analysis," Mol Vis. 15:584-591 (2009).

Havens et al., "Targeting RNA Splicing for Disease Therapy," Wiley Interdiscip Rev RNA. 4(3):247-266 (2013).

Bacchi et al., "Splicing-Correcting Therapeutic Approaches for Retinal Dystrophies: Where Endogenous Gene Regulation and Specificity Matter," Invest Ophthalmol Vis Sci. 55(5):3285-3294 (2014).

Colella et al., "Efficient gene delivery to the cone-enriched pig retina by dual AAV vectors," Investigative Ophthalmology and Visual Science. 55(13):3332 (Apr. 2014) (abstract) (2 pages).

* cited by examiner

FIG. 12A

Guide 1: hABCA4-g1 GGAGCCAGAGGCGCTCTTAA

Guide 2: hABCA4-g2 GTTAAGAGCGCCTCTGGCTC (Guides expressed off plasmid with U6 promoter and Cas9)

5'ARM:

5arm 2F CCTGGGCAAGATAAGCTATTCCTCCC

Puro GT R GAGCTGCAAGAACTCTTCCTCA

3' ARM:

CAG F gcctctgctaaccatgttcatgccttcttc

3arm 1R gcagctcccagggtcctaatc

Cell lines 17+06 AND 17+21 were chosen as representative ABCA4 knock-outs.

FIG. 18

Alleles in 17+06

| | Exon 3 | Exon 4 | Effect of sum mutations |
|---|---|---|---|
| Allele 1 | Mutation A | Mutation a | Early stop – likely NMD |
| Allele 2 | Mutation B | Mutation a | Early stop – likely NMD |
| Allele 3 | Mutation B | Wild type | Early stop – likely NMD |
| Allele 4 – not expressed | Mutation C | Mutation c | No Promoter insertion on this allele, no RNA, no Protein |

Alleles in 17+21

| | Exon 3 | Exon 4 | Effect of sum mutations |
|---|---|---|---|
| Allele 1 | Mutation A | Mutation a | Early stop – likely NMD |
| Allele 2 | Mutation B | Mutation a | Early stop – likely NMD |
| Allele 3 | Mutation B | Wild type | Early stop – likely NMD |
| Allele 4 – not expressed | Mutation C | Mutation c | No Promoter insertion on this allele, no RNA, no Protein |

SEQUENCE LISTING

<160> NUMBER OF SEQ ID NOS: 113

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
gtaagagagc tcgttgcgat attat 25

<210> SEQ ID NO 2
<211> LENGTH: 33
<212> TYPE: DNA
<213> ORGANISM: Artificial Sequence
<220> FEATURE:
<223> OTHER INFORMATION: Synthetic Construct

<400> SEQUENCE: 2
tactaactgg tacctcttct tttttttctg cag 33

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
tggtacctct tctttttttt ctg 23

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
agatctcgtt gcgatattat 20

<210> SEQ ID NO 5
<211> LENGTH: 27
<212> TYPE: DNA
<213> ORGANISM: Artificial Sequence
<220> FEATURE:
<223> OTHER INFORMATION: Synthetic Construct

<400> SEQUENCE: 5
gagaacatta ttatagcgtt gctcgag 27

<210> SEQ ID NO 6
<211> LENGTH: 135313
<212> TYPE: RNA
<213> ORGANISM: Homo sapiens

<400> SEQUENCE: 6
aguccccagu cuuugcuuag gccccuacgu acacaaacug aaccuaguga cccagcaugg 60
ccucuaauuu cucaacacuu cuguacuucu guaaugauua acccaugcuu cucacagauc 120
caugccccaa auuucuguga auaggcccug acuggcccag cuaagaucau gugacugcac 180
augaccaguc cacuuuggca uuaacaagcc uacugcagac ucuucccuug guguuggagu 240
cacuccuaga aaagagcaaa ucuuugugag ccaggcaguc aaccugcugg cagcuuccac 300

-continued

```
ucagccuugg aguuuuuucu auguguaacu uucauaaacu gagccuuauu uauuuauuuu    360
uugcacuauc aucucaugaa auauuauugc guaagcugag gaaacauguu auucaugaug    420
acuggaguuu caaguuuuaa uuguacaaug auuuaguuuu gaguuuggua gaaauaaaau    480
caaauuuaaa aaucagauau uuuucaucuu acauuaugau gucccaaaac ugccuuuaug    540
cuugugacau agauucauaa ugucuucuca uuccaccugu aaucacuguu ugaaauaaac    600
auaugucuaa ugauauauuu ggggacauuc uauuuucuuc agcuuguugc aagugaauug    660
auggugaucu uuugguauug guuucauuau caaauuuauc uccacuccaa aauuacagua    720
auuucaaagu aauuuagucu auauauuuuu ccauagcuuu ucuuccaaau agaaacugua    780
aaaaguuaua aauuacuucu cuccacuacu gaauuuuugu uugcagaaua acugauguaa    840
guagcagaau gccucuuccu aguucaaccc ucaggaauag aagugagaag aucuuuaaaa    900
cuucaccauu uuccuugacu uguuuauaau ucugaaugua aaugugaauu gauauggucu    960
aucgcuuaac accacaacuc uuaaucuaug ugcagggucg uagcucaaaa cuacugccag   1020
gaccacauca auuucauauu cacccugauc aauguguauu aauggugaua acuaugagaa   1080
ugaaauguac aguuaucagu aucauuuuug acucacuagg uauauccuca gaaauauaug   1140
aaaaaacuaa acacagcuuu uaguuugaca uaauuuuuaa acaacuggag uuaccuuggg   1200
agaaaaaucc uaccaaauau cuauaaauau gaaagaguaa aaaagaguua aauguccuua   1260
acaucauuaa ucauuaggga caugcaaauc aaaaccacag ugaaauacca ucucacaccc   1320
uuuaggaugg uggugauaag aagaaaaaca gagcauaaca aguguuggcc aggaugugga   1380
aaagcuggaa ccauugugca cugcugauug gaaaguacaa uggugcagcu gcuaagggaa   1440
auaguauggu aguucuucaa aaaauaaaca guuauaccau uugauucagc aguuucacuc   1500
cuagguauau accccaaaga auugaaagca gaaucucaaa uauuuguaca ccuauguuca   1560
uagcagcauu acucacaaua gccaaaaggu ggaaacaacc cgaaugaccc uggauggacg   1620
aauggauaaa caaaaugagg ucuauacuga caauaggaua uuaauugacc uuaaaaagga   1680
aagaaauucu ggccgggcac gguggcucac accuguaaua ccagcacuuu gggaggccaa   1740
ggcaggcaga ucaccugagg uugggaguuu gagaccagcc ugaccaacau ggagaaaccu   1800
cauaucuacu uaaaauacaa aaaaaaaaau uagccaagca ugguggcgcc ugccuguaau   1860
cccagguacu caguaggcug aggcaggaga aucgcuugaa caggaagcag agguugcaau   1920
gagcugagau ugcaccauca cacuccagcc ugggcaacaa gagugaaacu gcaucucaaa   1980
aaaaaaaaaa acaaaaaaaa caaaaaaaga aauucugaca caucugcuau ggucuaaauu   2040
auguguuccu cuaaaauuca uaaauugaaa uccuaacccc caaggugaug guauuaggag   2100
gugaggcuuu guggagguga uuaggucaug aggguacaac ccucgugaau gggacuagug   2160
cccucauaaa aagaagccca agagagaccc cuuuucccuu ccacuggaug aggucacacc   2220
aagaaguuac caucuacaug ucaggaaaua ggcccucacc agacaccaaa ucuauuggca   2280
ccuugaucuu ggacuuccca gccugcaaag cugugagaaa uaaguuccug uuguuuauaa   2340
accacccagu uuaugguauu uuguuauagc agcucaaaca gauuaagaug gcuugcuaca   2400
acauagauga acuuuaaaga uuaugcuuuu cuaugauucc acuuagaugg gguaccaaga   2460
guagucaagu ucauugagac agaaaauaga gugguuggca ggggcuaggg ggagggaacu   2520
cuggggaguu aguguuuaau ggauacagag uuucaguuuu gcaaaaugaa aaaguucuga   2580
agauggaugg ugcugauggc ugcacaauau gaauguauca acacuacuca acuguacacu   2640
```

-continued

```
uaaaauaagg uucaaaugau acauuuuauu ucaugugugu gucaaucuca acaaacagau   2700
uuguucaggc aaggaaacug guuagaugcg aauaauacua uuagagcauc aucaauugaa   2760
uauuaacaaa gugcucauag uuuaacuuuc uagcucaagg aagaauggac cauuuugaaa   2820
cuaugacaga acauuacuua uauagcugau gucuuuggga auuggaagga ggcauauucc   2880
uucaccagcu guggcucccc uucagcaacc ucauauacuc uccaagcuuc ucuuuccugg   2940
gucaccuguu uaaucacucc cgggacuuaa ucuuccaccu auauguugac cacucacaaa   3000
ucuaugucuc caucucacaa gcuuauucuu gacuccagac ccaaguauuc aacugccugc   3060
ugaauacgug uggucagaug ucauagaacu ucagcuucag uauaucaaau gcaaaccccu   3120
guucccccca acugccuccu acuccccacu ggccuuccuc uggcauuccc uccucaguua   3180
ugagcaccac cgucucacua gccagccagu caagccccaa acuccaucua gcugacuucu   3240
gccucuuccu caccacccuc uuccaguaac ucaucaggca cugcugugucu ucauuccuuc   3300
cuaucccucc agucccuccc cuucucucca ucauggcugu cacugcaugg uucaggcucu   3360
cuggcucccc ccaaaccacc cccacauugc ugccgaggug aacugacuac ucuuggcagc   3420
cacuggauua aaaucuuuca ucaucuucag caugauaaaa cccauauccu uuagcaugua   3480
acaaggucuu aaugauucug ccagagcuug cuugggggua gccugcacuu gugggccacu   3540
ccagucacuu cacaggugcu caguaaaucu caguugaauc agucaucauc aucaucauca   3600
ucaucaucau caucaucauc aucaauuuuu cagucugguu ccugucuccu uuuccagcau   3660
ccuccauuca uagccucaua gccuucacuc cagccauguu ucacuugugg uuuuccuggg   3720
caagauaagc uauuccuccc ugucuuugca gaguuuaaau gacucacuug uucaaguacc   3780
caccguugcc augugggacc gugagcaaag uacuuaaucu cacuaagcuu cacguuccuc   3840
aucuguaaaa cagcaaauau ggaccucaca aaauuguagu gaggcuaaaa ugaaauaaca   3900
uaugcaaaag caguuuauaa auaauaaacu uacuauaaaa uauuauuuug uaauucugca   3960
agcuugucuu aaaugccauc accuccaagg agccuuuuug ccaucauaag cagaaacuau   4020
cucucucuuc uuggaagcuc caccaugcac agccuauggg cccucaucac acuccuugag   4080
uuauucgagu ucaagucccg uguuuacaac cagaccgcaa acucuaugaa gucagcaucc   4140
auuccucucu gugguucucc cuccgcccca uccaggucuc aagggucuag agucuuucaa   4200
agagaacaca uucugagauu ugaggaggca gagacaaaaa guuccacugc gaagugccag   4260
ggaggcuucu guuuggggug ucccuuggga ucacagaucc cccaccuggu gaugagucaa   4320
cccagcacca ccccauugca gggcuggaau gacaguaaug ggcccaccug cugccucucc   4380
ucauacccgc accccaguca gacauugcaa gucagucacg gcucuguccu gcugggccug   4440
gaguguucca gugccuuuuc caucacagca ccaagcagcc acuacuaguc gaucaauuuc   4500
agcacaagag auaaacauca uuacccucug cuaagcucag agauaaccca acuagcugac   4560
cauaaugacu ucagucauua cggagcaaga uaaaagacua aaagagggag ggaucacuuc   4620
agaucugccg agugagucga uuggacuuaa agggccaguc aaacccugac ugccggcuca   4680
uggcaggcuc uugccgagga caaaugccca gccuauauuu augcaaagag auuuuguucc   4740
aaacuuaagg ucaaagauac cuaaagacau cccccucagg aaccccucuc auggaggaga   4800
gugccugagg gucuugguuu cccauugcau cccccaccuc aauuucccug gugcccagcc   4860
acuuguguc uuaggguucu cuuucucucc auaaaaggga gccaacacag ugucggccuc   4920
cucuccccaa cuaagggcuu auguguaauu aaaagggauu augcuuugaa ggggaaaagu   4980
agccuuuaau caccaggaga aggacacagc guccggagcc agaggcgcuc uuaacggcgu   5040
```

-continued

```
uuauguccuu ugcugucuga ggggccucag cucugaccaa ucuggucuuc guguggucau   5100
uagcaugggc uucgugagac agauacagcu uuugcucugg aagaacugga cccugcggaa   5160
aaggcaaaag guaacaguua cugucugugg uuuaaaaaug aggugugggag caaauaaaca   5220
gguuggaagu guggggguggg gugguggggu agggugguggg ggcagggugg ggggguuguga   5280
gcagucagug ggcuugucgc cgauuagcac ugaagcagug uuuagcugga cggccuuucu   5340
gugggccccu cugacagugc ccuucccagg aagauguguu ucucuguccu cagccacaug   5400
aaaaucuuuu gccuaccgug ccugucaauc cauugccugc ccgcccccucc cccaccccccc   5460
guuuuacacc ugccugucca gucuaccgcu cucuagggca uccacgcuga gcagugggaa   5520
gaacuuuaag cccugaagag caggccaaag gcaagcaaga accccccucga acagcuuccc   5580
agcuuaguga ggccuuauuu cauugauucu cugaggcaca uuguuuuuuc acauguuagc   5640
auuucugaaa uugggaugca gcucacgauc aagucacagu uuaacuggac acauuauuuu   5700
ucuuucuuag uggugcagaa aaguaacagu gugucuuaca auugacugcg ucccuagauuc   5760
ugugagaugc aauacguuau uaaccaucac gcacauuucc ugaacucuuu caaugagcag   5820
acaccagccu ggguuagacu ggagcccuaa aagcacgaca cagauuccac ccuggacugg   5880
cuucuguucu gccugggaaa acccaaagua cguuuggaga ccaagagcaa cauaaaguag   5940
cauaggugga auaguccaug agaagugcga gcaaaaggug ccggagauca gagaacacca   6000
agacuguacu uguaaaugac aacuggcuuu gugcaauuuu uucugggaaa ggauaaggag   6060
ugacuauaga acuguaaaga aagaaugcac uuugcuacag ccuugcagag uugugcaaau   6120
gccgaugacu aaaggagcug aaagaggaag gaggggauaa gggaugggggg cuggguaggg   6180
gugagauuag gacccuggga gcugcaagcc acuggagaga ucaggaggaa agggagggag   6240
accugcuuua ggcgagaaga gaacaguauu uguuccaaau cucgguucag aauaaguuca   6300
uguaggugau ggggccaacu ggaacaggug aaggccuaug aaugaguguc ucaguuaggg   6360
ucuccuuaga guuuaauaug aaaaggguguu agcuaaguac agagcuggua ccugagagag   6420
uaaaaggaaa cucuaaggua ucauggaggu agcaauugca ggacacagcu cccaccccua   6480
gggcugagag aaccaaggga agagacagga auuauuaaga cuuggagcau agaugagagg   6540
ucuguggagc ugacauuagg acuugggagg aaggcgugca uggaggcugc ugcuggaucu   6600
cugaaccuga ccucgggucu ggaccccuga ggagaaagcc cuggcagguu ggugcaugug   6660
gggccgaggg acaauagcuu aacaaccagc auaaaagaga gcagcauggg acacgcuuca   6720
accaugcgca uggauggcuc caaaaccugu guguggcugg cccaggacgc agggaggcug   6780
cagggggaag agacaaguua aaccugacuu gucugggaag caccauuguc cucaggucac   6840
uuuccucugu caagccuggu gcugaaguua ucuguugucu ccagggggcca aguauuaaga   6900
guaaucagaa acucagucccu uucuucuagg agcuucccuu cuugcaugaa aauccugaua   6960
aaacuggaaa aaaaaaccuc augauuaaau uuuuucaugu auucauucuu uccuucuauc   7020
aaaaaauaau cuccaggcac cgugcuaggu ucauugguau acaauggcaa caagaccucc   7080
cagccccugc cuaugugagg caucugugga cugcggagga aaauccaaua ugccauuguu   7140
cucucuuucc cauaagaaau uacaauucuc aguucauuuu auucucacug ugcucuuugu   7200
gacccucaaa gggggucaca ugauaacagg acuguagcug cuggccuaaa augagcccau   7260
uccuguggcg cucaugucgc ugugacagag aauaacccug uuuucagaau gcucuggugc   7320
ccucccucuc aaucuggccu uucgcuggca uggguggggcg acuccugcuc agggacucug   7380
```

-continued

```
ccuucuccac agugugcucc cagggagaug gagccacucg ggcugagggc cuuggccagg   7440
gcaccuccca gggcugggcc uggucugggc uggcguucac uggaugccau ccugauggcc   7500
uggaaauuga gauuucuguc uggcacgccu cccgauggcu ccccaccugc uaccacauuc   7560
caggagcuuc caggaugucu ggguaagaca gaggcacccc caacagauuc aguagcucug   7620
agagggaucu guggcuccuu ccuaagcuug cgguucuucu ggaaacuucu gccucuagaa   7680
gaugguccu cuaagaaaag uacaaccacc cagcccauaa uucagcuccc agguuuuccc   7740
ucaaaccucc augucuccug uaagcagagc aagaguaaaa ucagauacca aauuuccuca   7800
uuccucagcu cccaaucccu aagggcauaa gaugaaaauc uucagaucuc ugcuuuccuc   7860
ccucuuuuuu ucuuccucug uuaacauuug ucaaguguua cuaagugucu ggcacuguac   7920
uaagugcauc accucccuga acucuccgaa caguuccacg agagaggccu cucugugauc   7980
cccccgguac ugaugagguc acugaggcuc cagagaagga uuaguaacug gugggguugg   8040
accugggauu cacacccaug cugcgugacc caggacaggc aggcauggcc guuacaccac   8100
acugaccccc guggaucgag aucuauccaa uagucugguc acugauauca cuaagauaga   8160
guggccauau aauuuaucau ccaaucaggg caguuuugca agugaaaggg agcacuauua   8220
auaauugcac ugggacaaua aauguaaacc aacacuggac cuggaaaacu gggacgugug   8280
uuugcccuau accaagguaa gcuagacaca gccacugccu ucauggaguu cagaaccagg   8340
caggggcggc ucccacguau aauuacugug cagcacaacg uggagaccgu ggaguagaag   8400
gaaacacgga ugggagguga ggaggagguc ugugagcuca gaggaggcac cggggcugga   8460
gagggugaga gaagacuucc caaggaguuc auccugauaa cgugcauucc caaugacgag   8520
cgcucucucc acugcacaag acaaguauac aucugcccgu guuggcugug gaccuggcgc   8580
ugugucaggg aggguuuaug aagaucacua ggugggucuc uuggugucau cccuucaucc   8640
cagcuucugg guuaggaugg auaucugugg gggggccuga ggacucauga aaguggggcg   8700
cuaaucaugu uuuggacacc acacccugga gcaccuggga cagcuguggc cuuuguccug   8760
gguucagcau caagccgagg auguggcaag uaaagagagg cugggcacca acuccagugu   8820
acccaggcuc cgggucaugu uuguccaggc uaagaauucu guccugguuc ucagugcaga   8880
aggaagaauc auggggcuca uuuuaggccu uggcugccuu cuguuaaauu gaaaacagag   8940
caggaaggaa gaaaauuuaa caggcucagu ucuaaaacaa caagcacaac ugugcccuug   9000
ccagaaaccc cuccucccca uguugauuga augguaaaga gaggagggga ggugagaggg   9060
agagagagag agaggaagag agagagaaag gaaagaaagg aaagaagaag aaagaaagaa   9120
aaggaaagaa agaaagaaag aaagaaagaa agaaagaaag aaagaaagaa agaaagaaag   9180
agaaagaaag aaaggaggga gggagggaag gggaaaagaa aagaaaagaa aaagaaaaaa   9240
agaaggaaau accaguuugg gaaaaaagaa uuuuccacca gcccuucuga gccuuggcug   9300
ggcuuaauua aaguuacaga cauguguaaa gggcagggua gggggagucu gagcugcuga   9360
gaaaacaugu uuuuaauuau acuguggaau uucucccugg gguaugccug uacgcaguua   9420
agcgucaagg acagggaugc cgcucugggg aggggaagcu gagcaugauu uuggaagccg   9480
gcagaagagg cuauugugaa aaccagaccu gucaggcuag gaaaagaaug gcuggugguc   9540
uuugaccagg gagugacgcg ugaaaugcag caaccgcccc cgccccccgc caaaaacaaa   9600
cacacucuca cagaguuaga acaacaguga ccucucaaca aauauuuuuc aaagauuacc   9660
aaccaaccau uaccuagagc agcgguucuc aaccuuggcu gcacggugga acuaccugag   9720
acguguuaaa aagaagaacc cugaugucc augccccaag auucugaugu aguugaucug   9780
```

ggguaugauc ugagaccccg gcauguuuuc agccugcagc cacaugagaa gugcugaccu 9840
aaucaacagg ggugaugauu ugaggggcgg ggacuauagg caaaaaaaaa cagccuaauu 9900
caaggaugag aagagggcac aggugaggug ggaacagucc uagggccaga caaagaagga 9960
agggagaaag gaggugcuga ucccuccccu acuccugaga ggaggccuuu aagucaccgu 10020
gccuugugga gaccagauuc uucaaaaaua caagaaugag ugagugaggg agugggugga 10080
ugccaggaga gugcgugaca agccuugcaa gggaggauga caaugcacua gcuugguuug 10140
gaaauuuuac cccuggaaca ggcaggccaa gcuggcuggu ccccucccug auacacagcc 10200
cucccucuuu auauauggag caggggacgg uguguggcug guuucuuagc aagcaccaug 10260
guuccaaguu ggcaacuggg gaguucugaa uccaaaaagg agggagauga acguaagugg 10320
agggcaggcc uacaagguug cagauaagcu uaauucuguc ucccuuacucu ucugccuuug 10380
caacaacccu gugaucuugc gacaacccug uaaggcaaua acaaauggcu cauguuuauu 10440
gaguguuacc ucaugccaua uugugcuuuc guguuuaaca caauugucuc auuucacccu 10500
cacgacugcu cugggaggua gguccuggua ucacauccau uucacagaug agaccauuug 10560
gcacggaaga guugaguggg cugcccaagg ucacauagcu aagauggaac aggcuggaua 10620
ggaaccccag uaacuugacc ucagaguaac cuucucuuaa cccugagugu acacuguagg 10680
aaaaaugagc agucccauuu cagagaggac aaaacugaga cucagagguu aagcaagccc 10740
caaaguggu u guuaacccag aucuucccac uaacucccaa aucagcauca guguuuaacg 10800
uaccagaccu cucccagaua gauguugccg cauggaagac agccgaucua cgugauagaa 10860
agccaauauu gcaagcaguc gucuaaagga gucaaaugug uuggauuuga acuggauguc 10920
ucauuucuuu ggugaagaca cuggaaacaa cuuccagguu ucaucaauug cuccuaucac 10980
ucaacguugc uaucuuacug aacuuguucc ccagccuuac ccacugaugg aaugauccag 11040
aauggaagac aagacaccaa uguacaugac ccugggggag gcuguuucuu aaaucuacag 11100
acuguuggug accugagccc caugucacca aaggcuuucc uggagaagcc uccuagacca 11160
gucuugacaa aggcucacuc auuccgugga uauuuauugg gcaccuauua ugaguucugc 11220
cccaugaggg gugcuggaau cacaguagug acaacgacag augagguucc uguccucagg 11280
aagcuuacug cccuugaggg cuucacuuac uuggaggagu gaugaaccug aagugcggug 11340
uguguuaaga agcggaaguc cagggccagg cgcgguggcu cacgccugua aucccagcac 11400
uuugggaggc ugaggcaggc ggaucaccag gucaggagau cgagaccauc cuggcuaaca 11460
uggugaaacc ccgucucuac uaaaaauaca aaaaaauuag ccgggcaugg uggugggcac 11520
cugcaguccc agcuacucag gaggcugagg caggagagug gcgugaaccu gggaggcaga 11580
gcuugcagug agccaagauc gugccacugc acuccagccu gggcaacaga gugagacucc 11640
gucucaaaaa gaaaaaaaaa agugccucac ggagagucua uucuuuucuu cccauauugu 11700
gugugugugu gcgcgcuucc uccaacacau ccucccuaua uauauuuuga guaaaacauc 11760
uuguaaaaag uuacagcuac auaaucacca ccugucccua aauaguuuuu gcuuuuucuu 11820
ucuucaaugc acgaucauuu ucccccauca auuuauuuuu uaguuucuua uaaucuuguu 11880
gccaguaggc uguuuuuuaa aaagcagaac augguuuguu cuuacuagca ggaaaggagc 11940
auuuauugag ccucugcuau ggugucuuuu auuuugcuga gagccuauuu acauuucuuu 12000
gagaggaaaa caacaaaggg uuacaugaaa gaccauguga auagccccua gcugaucuau 12060
uaaacuugcu auuccccggc cagcugcuuc agaucuccuu cagaucuuau guguuuccuu 12120

-continued

```
ccuaaggucc cuggaguaag gguugcauag accuauucua cucuccaacu cacaugaccc  12180
ucucccucuu ccucuccaua auuccacauc uccaaccccc accccuaugu gcaaugccac  12240
agggugugga cugccacagc cacuggaucu gcuuuuggaa ucaagagucc uuaagcucca  12300
aauggaaccg aaauuuaaau accaacuuuc aaccauaugu uaacaucagc agccucuucc  12360
aauguaaaaa cccauggcag ugugcccugc uuuguuucuu uaagcaauag aaacuugaag  12420
gaagcauguu gguaggccag auuuuuguug gcuuugcaau ggaucacagu cauuuauuca  12480
cucauucauu cacugauuca uuaaaugacc acauuugcaa gggcaaggua augggggaggg  12540
ccagaaagga cacuggcccc agaaacagga ggcuggauuu ugguucugau gcugccacug  12600
cugaugugac acugcacagg ucaccugccu ccucugagcc ucuuuccuua acugcagagu  12660
gaguggcuac agagaaaucu uuacuaccug uuagaucagc auuaccuggg agcuuguuag  12720
aaaugcaagc ucuggugggg ccauacugaa cccaaaucug cauucaugug cauagugaca  12780
gcuaaaaugc acugaagcag augaucuuga ugauccuuua ugaaagucuc augcuaaugc  12840
aguuucuaa aauagaggca gaguggaacc cagauggaca caaaaucugg uugauauaau  12900
aaaacaaggu agagggugua ugguggggag gggguaaagg aaggaaacug uuuagguaaa  12960
gauaccacaa ccaaaguccu acugcacaca ugggaucuga ggagggcugu gucugcucug  13020
guuacguuuu cuauaaucuc uuagcaccac ugaacuuucu cucuuuuugu uuuguuuuuc  13080
cagauucgcu uuguggugga acucguguggg ccuuuaucuu uauuucuggu cuugaucugg  13140
uuaaggaaug ccaacccgcu cuacagccau caugaaugua agcauagcag gguagcuugg  13200
gcaagcccug aagagacuuu ggucugggcc uuuugucuag aaagaucuug gggugggagu  13260
guggggauca gaucugcuua ucaucauuuc augucuauga ugcauguaac agauuuauca  13320
auguuacaca aauuauaauu uuuaaaaagu cuuuagagac agggucucac ucuguugccg  13380
aggcuggagu acaguguuag gaccauggca cacugcagcu ucuaucucuu gggcucaagu  13440
gauccuccug ccugggcuuc caaagugcug gaauuauagg caugagccac ugcucccagc  13500
uaauuuuuuu guuuuuugug gagacagagu cacuacauug cccgggcugg ucuugaacuc  13560
cuggccucaa gugauccucc caccucagcg uucuaaagca cugggauuac aagcaugagc  13620
caccuugucc agcccaaauu uucauguuuu aauccuacac auucuaagca aauacuugug  13680
uguaguuacu aagggacugu gcacuuauuu uuguuugcuu uguuguugcu aguuuuuauu  13740
uuuuuauacc uaaacucucu cguuuuaaag agaacagauu uguagaugag uucucgaaaa  13800
uauuucagga aucaauauag agaauauguu auacauggug ccagagaaaa augaggacaa  13860
gagaugcuau acaaucguac ugaagaaaaa uuuuauuucu uggaccccug aggugucugc  13920
agaccugaaa ggaaccuagu gagagccucu uuuacacucu gccccugugg gaaagccuuc  13980
accugguuuc cggcccucua uguggugaau guggaagccu caagcguuau gcaaaucugc  14040
ccaguccucu auucuugauc uucaccuucu cguucaugag uuucaggccc caguucugaa  14100
ucagccuccu guccaucaga cucuucuuua ccucuccccg aggagcccau aaccugcagc  14160
ccuacugcau gcuuggggua ggugcucagu ucaccguggu ugaaggaaua gacgagcguc  14220
ugcucaagca gcagcagcaa cugcguggag ucuucuugaa cuaacacucc uaugccccuc  14280
ucggcacaaa augacguguc ccccuugcu uccccuucac auuuccaccc augccuauua  14340
caacauccgu cugucucccc acuacaccgg gagcuugaga gaagaggcca ugucucuagc  14400
acccagcaca gggacuggca cacaugagau gcuccugcuu cuuaaaugcu gagaaugaag  14460
gaggacauca gaggggcccg ggccccuucc caaaaaggcc aacuccuagg ucugcauccu  14520
```

-continued

```
gcuuggucuc caugacuaau cccgucuugu ccucauuuuc uguuuuaaag gccauuuccc  14580
caacaaggcg augcccucag caggaaugcu gccguggcuc caggggaucu ucugcaaugu  14640
gaacaauccc uguuuucaaa gccccacccc aggagaaucu ccuggaauug ugucaaacua  14700
uaacaacucc auguaagugu ugagaucccu accaugcagg ggaggaaguu gcacaccccu  14760
ucacgugcug aaaugcacac gugcgugcac ggagcaugga gcacugagug uucuuguggc  14820
uuugcugagc cccuaaccuc uuaggagcag agcagguuuc cucucuggaa cauucuguua  14880
acugucaggg cacuugggga gaaaucucca agcuaaggcc acgugcacaa aauuucuugg  14940
uccuuauauc cccagaaugu gaccuggagu cugauggcag cccgcugcag agaugugucc  15000
acugccuucu ggucauugac cugcuugggu ggagugaauc auuguaggag aaaaacucag  15060
uucccucacc cugaucaacc uggacagauc ucucuuccuu uaaaagcuuu cuuggacauc  15120
uaagggcuag gaaaaauguc agggagcauu gggaagguaa augaagucag guuuacaaag  15180
ucaaguuuac uucuugggag aaaaauacaa uuuccaaauc cucuguuaua auugccaucg  15240
gcccccugga guggugagau cucggaauau ggcucgggug caguggcucu ucacuguggg  15300
ccugcaggcu auucugaaaa gcugaugaaa accaaugacc ccucuuccaa gaaaaauggc  15360
cacauaccaa acauuacacu guacaucuga uuucagggaa uuguagaugc cagguuagua  15420
gccucagguc uagggucaaa auucaagucg aaucccacag gaagagggucugccuucgga  15480
auucccuuuc agagcauugg gagaacauca ugggagcaua uucuagagac agaggcuuag  15540
ggugugggaca gggccauccc ucacccacug ugcugaccuu aagcagcacc uugugcagcc  15600
cauaccugaa ggccaccagc aaaggccugu uggggagcag gcuuuacccg accuguauaa  15660
acaccaggcu aggugaaaac ugagauaccu gguuacuuua guuuuuuccu ugggggagcu  15720
caguaugauu cuuccaggag aagccugcuu uuagacuaaa aagaaaaaaa guuugauagg  15780
ucaaccuaau gauuggaggu ggccuucccc acugugaaca aacuauggcu gcaugugccc  15840
uacaauggca gaguugagua guugugauag agacuguaug aucuguaagc cuguaauuuu  15900
uauguuugcu gaccccugga uuaccagaug auagaagagg aaacaucugu cuuccuagca  15960
aagucaagga aguggcauuu agcaggacuc auauugcugc aagcacugcc uugcaguuuu  16020
aguuuacaac ugcacuuuca gcuuaagaaa caccugccca uccagagaga ucgugugggg  16080
ucacauggug ggaucaggga ggccugaaga cagcucagug gaggcugcau ggagcuuugg  16140
ugggaacggc ccuggcagug ucuauagaug uuauugcgga aacugaggg gugggaguug  16200
gagaaggggg cuccagacuc uagcuguacu uggcauuuga acccggaaag uuggguuuca  16260
uguuuugcac ucacauuaug agugaaauau uggcuuauuc aagguucuuu ugcuugcaag  16320
gcacggaaac ccauucaagc aaucuuaaac cccagaagga aaucuaugau uuggauacua  16380
gacauucuca cagagccaag ggcagcaagg cggggcucag gagaggcagg ccaagaccug  16440
gagagcuguc aggagcugcu ucccucaacuc ucuuccaucu gggccugcca gcccuggccu  16500
cuguaucuac uccauucacc ucucuccaug gaccagucuc cccugcuccu caaugccugg  16560
gcugccauug uucaugcaau ucacaauacc ucggccuggg caaucagaag cucaucucug  16620
aacaccaucc aaauuccugg gaacaaaucg gguugaccca gcuuuauucu cccugucca  16680
ucagccuugg cagaggcgug caugugcaug cgugccaaug ugugugugca gggagguccu  16740
uguggaugaa gcauggcugu cagagccuac cugcgugaau ggguggaagg gcaggucuca  16800
gagaauuggg uaaaaacugg auaaacccuc cagugauauc caccaauguc acccuguuua  16860
```

aggcuucucu gggcaagaga cacacagagc augggaccga gaggcgagca gacccugcca 16920
aaacugggag acugaauaga ucgcucacca uccuugucag uuagccuaua uguacaagga 16980
aguaaaauua ucucuuucuc cugccuuggc aguauuguaa ggauacucaa uguaguagcu 17040
aggccagaca cauaguaucu uuaaauauag caugagaugg ccaagcacgg uggcucaugc 17100
cuguaauccc agcacuuugg gaggcugagg cgggugga uc acgaggucag gagaucgaga 17160
ccauccuggc uaacacgaug aagccccguc ucuacuaaaa auauaaaaaa uuagcugggu 17220
gugguggcgg gcgccuguag ucccagcuac ucgggaggcu gaggcaggag aauagcguga 17280
acccgggggg cagagcuugc agugagccga gaucacgcca cugcacucca gccuggguga 17340
cagagcgaga uaaaaaaaaa aaauagcaug agauauuauu acuguuauaa aaauaacagc 17400
uauuuccuua uuaaugaggc uuuguccuua cagcuuggca aggguauauc gagauuuuca 17460
agaacuccuc augaaugcac cagagagcca gcaccuuggc cguauuugga cagagcuaca 17520
caucuugucc caauucaugg acacccuccg gacucacccg gagagaauug cagguaagca 17580
ugacugcagu gcucucaagc aucauuuccc ucaccuaugg agagacugaa gauauaggaa 17640
agaacaggga gaguugguga aaaauauacu agcggaggca ggaagggaug gggucuggag 17700
gcggcuugaa caucaccuug gugaagaugc cucuuccucc acagaagccu ggaagguagg 17760
aaguugggaa ggaaggcagg aaaggucuca uccacguuaa gucuagagac agaaagaaug 17820
cuaagagaga uggcacuaug ggaaguauga ggcuagguca agggcuagaa gcaggggaga 17880
cgaguuuaca gaguuucgua aagauauaga gcaacucuca cagaguucua gagcgagagc 17940
uaaccaggaa caugaagcag caaggccaac uaucauuaag gagccaggga ggucagagau 18000
cauguauuau caugacauaa auaugcauaa uuguacuauu ucucccagua auauuuagca 18060
cccaggcccc gaggcagagc aaguggagag ugggugaugc agggcugggg guguguaugg 18120
aggcaccaca gaaggucaac aggcagcggg cugaaggcag ggacuggacu acaugcauca 18180
aguccaggcu gcacgaggaa ggaugagaag gcagaugagc acggaaaugg acugggggaa 18240
augaagaggc aagggaauag aagucucagu gggugccaug acccuguuua agugauugag 18300
aaaaugaaca agaugaaaag guuaauggcu guggucagaa agugaaauau gugaauucag 18360
gauuucgaag guagggugg g ugaugacugg cccccagaug cggccauggu gaaguggggc 18420
aaaggugcag gugcauggug aggggaagga ggaaauggga ggugaugaug uuggccccac 18480
acggacacca cgguugugca ggaagauggc aggagcuggg caccagggug ggagccaccu 18540
ggagucagga agagugaaga gaaaggauga agaggcuccc ucuccugugu cucuccuccc 18600
caggagaaga acaagaaaca auccgaaagu aauaacacca augugccuuu acaaagugug 18660
agugggugu u gugugcuguc acguguguag uaggcuccuc uguggauggc uagagggacu 18720
ggacauggcc acuggauccc acuugcaaga gcagaggaaa agaguggucg ugaggaagua 18780
aagcccccca aaauccaggg guugcugcag cuuugggugu ggagcgugcc cucugaggaa 18840
aggcugcucu gggggagauu gcccaggaaa cggggcucag aggccacgaa agcagcuguu 18900
aggggcuucu gggagaugug ugcuccuagg auuagggagu ugacucuaag gaugaccuua 18960
gagguuaaca gggaugagaa aggggucacc aaggggucua ccaggggaau gggagaggcu 19020
guauugauag aacagcuucu gcugcagguu ccaaacaaga aaugugggag aaugguugaa 19080
aucagccccg ggggcaccuu cccgugcaug cgugcagcuc cuucaacauu cagucgaccu 19140
ucagugccuc cugugagcca ggcacugggc uagucucugg gggugggagag augagucagg 19200
caaaugccag cccucagagg gcucacaggg cagaagguga gagaugagug agcagaaaau 19260

-continued

```
gaccacagcg cgugugggc ccaguggagg gaaggagggg auucaggagc acaggagagu  19320
caacagggga aacuucuccg aggagaaucu gauccuccuc ccaucuggcc accuucugaa  19380
gcccucucuc cccauccaag ugagaaagga caggcguaug accagauugg uguaugaaga  19440
ugcugaauua cguucucauu guuucaaacu aguaaaccau agauuuuaug uaguaacuuc  19500
uacaaacugc auuacaaaca cuccauucuu uguugcccug gguagaaguu uauuuuagug  19560
agcccaaguu ugaggaaccu uauaugguau gaguacaauu accauuuuaa uaguaagaaa  19620
ucccccuucc ccuguguacc aaccagaagg uguuuuuuuc cuaauuuaaa caaacagaug  19680
cagacguggg cuguccagcu ccuggcggga ugacauaccu caugcaucca gugggguuuga  19740
ugaugaggca gacauuucac uuaagugccu gaucaucaga uugaguccug cugggaggaa  19800
gugugaagga aguaauuuca aaccacaguu ucucuguggc uuuuacaaug uggauaugag  19860
aaccaaaauc acuacuucuu aaccccagag caggacugau uuugaauugg uaugcaggcg  19920
guuccuucug caggcuucgg gcugugagaa gucccuaaca gagcaaaucu ggggacaagg  19980
gcucaggaaa gguuggccac ggcccccuag gaaugggggc ucugcaagau cccuggccuu  20040
agaggcugug agagggaaca ggggguccauc cccaaguaag ggacacgguc uuugaggaaa  20100
ucccaggcca gggccugaag ggcacuguca ggaacacagg cuguuucagu cuguugagau  20160
ucaccggggc gcugcucacu gugagcacgg acuccucagg ccaauguggc agaagagccc  20220
accuuugaaa gcgagcgggu gggggguggcg gggcuggugc uggugcgugc uucugcacag  20280
ccaccuggga agguaugccg cugguugacc caggcagagg uuuucuuuca uggcaaaccu  20340
gcaguacugc auucucagca gggaggauua augguaaaag accaggcaug gagcccccuu  20400
cccucucccu cgaagcaagc ucugugggucu cucaaucauc uuuaaaacac cuucuucccg  20460
ggagccuccu acauucuccu ggcuucccuc ccaccccac ccucagcucc uggggccuca  20520
gcagccccac ccccaagccu cuaaucuucc cagggaaggg aacaagaaga accacauuuu  20580
aaacgaaauu uauuuuucuu ucccucaggcu cccaguucac auuucucccu caggagucua  20640
gggaagcuuc ugucugguau cggccuccuc uucaccuggg cccccgcccu ccucaggugu  20700
accagaagcc agcacacucc cccuuccccc ccagagccac agcagcccug ucuccugggu  20760
ggucuugugu gccaagccug ggcaacauca cucccagcuu uucuuguuuu gccccuucuc  20820
cccagcaaga uauuuguaug uaaggucagg ugagugaguu aaagaauaac gaagagauaa  20880
acagucaaau ggaguccuga cugucagguc aagacaacag uuauuuacug aaugccucau  20940
gucauucaac agacauuuau ugagacucug auuggauguc agucuuuaau gcugggugugc  21000
agagagaggu gacuucaagg gcuugcaucu gugcacccag cauugcuagg uacaaugagg  21060
aguauaauaa aagcaggagc cauagccccc aacucucaag agaucuccca ugugugguaug  21120
ucugcauaug cgugcgugug caugugugcg caugugugca ugugugugug caugugugug  21180
caugcgugug ugugugcgug uguuggggau ggguguuggug gagugagagu guacaaggcu  21240
guguaugaag ggguaauugg gaaaagaaca auggagcugg cacccaggga caggaggaaa  21300
agcaggaggg cuggguuugg aagacagccg gauuuauguu uuugaagagg gaagacuaga  21360
auauaaggga gcagcccuuc ucagagcccu ccuccucccu ucgggcccug uguccagcuu  21420
ucccaaagu ccuuggaucu uuccuaugca aaggggagug acagugggca ccacucucag  21480
ggaacccauu acugugagag aagccacugu gccacugugu ggucgaacuu caagaccggc  21540
uuccccugcc ccagcugcau ggacaggccu gugggguugg cgcaagaccc uuccagagga  21600
```

-continued aacuagcugc aacauaaauc cggauauggu gcuguucagg gaaaggcaca accuggggau 21660
gagaagggug gcuguccagc acacaggggc aggccucuug gccacugggg gaggggagaa 21720
uuuggagagg aagaggaugg gaugccgugg aauugggacc aggaaagaau ggggacaugu 21780
gaugguuaaa gcuaguuaga gaagaacugg gagauaaaca gucacccaug ccccugaagc 21840
acucggggug aagagauugg cauuuucacg caccccagug cuuucccuuu guguugaagu 21900
cccuucguag acauccaggc ccauaaggcu cuucucuggc cagagccuca ugaacuauag 21960
cacuagcagg guugaggcca agcauuggcc cuggaagcca gccgaggagg agggugcuug 22020
ugugaaucuc ccaggagggg uaagaauuau auuaauucga ucauaaauaag cauuuauuga 22080 gugcuguuuu gaggccuggg agcuaagcac uucacauucc uuaccccgca ucaacaaucc 22140
uaugagguag auguggaaaa ugcagacacg gggacaggcu caaucacuug ccccaagguc 22200
accuuaacug uuagguguuc uuuaugccuc cuuauaaaga aacccugcuu cccacaggug 22260
uugagaggag cuggagggag cuugacuagg gcucaucagg caagccccgg caugugccug 22320
gcucuccucu uucuaccugg agcuuuuccu gcccuuaaug gccccaacuc auuucucuua 22380
guccauguca gugcccugag caucucagcc caagcugaga ugauagaaac acccagaggg 22440
guccucuacc cugugacagc ugcggugugg gaagagcacg ugucuccucc aauccuagac 22500
cagaguuucu cagccucagc aucacugaca cuuggggcua gauaauccuu ugugugggg 22560 agggaggagu gucuugggcc uugcaggaug uuuagcagca ucucuggccu cuacccacca 22620
gcaccucccc aguugugaca cccagaaaug ucuuuagauc uugccaaaua uuuccaggag 22680
gaugaaauuc cccuguuuca guuccccagc cccaccucaa ugagaagcac uguccuagac 22740
caaccccaca aagcaucuga cacccccauc cagcccuggc uaacuuuuuc caccuucuua 22800
cuaaauuggg cccagcugcu ucagcaguca auguguuggg ggcagcccac uggcaagagc 22860
cucaccucua ggggcuccca gagaccccaa gaacagaacc uuccucugag aguugaguua 22920
caaguguuuc caaucgacuc uggcuguuuu ccuuuuuuug acccauuucc ccuucaacac 22980
ccuguucuuu cucuuauuca uauguaggaa gaggaauacg aauaagggau aucuugaaag 23040
augaagaaac acugacacua uuucucauua aaaacaucgg ccugucugac ucaguggucu 23100
accuucugau caacucucaa guccguccag agcagguagg gggaugucac uggccagugg 23160
ucccuggagg ggagggaagc acccagccug agaaaggcaa gaaauauauu ggcuuuuuuc 23220
uucuuucuuc cuuguguuca cauucagaau ccaucacuua augccuugua uuuagaaaaa 23280
aaccggggga ucacuugaga ucgugaucau uuucaacaua ggauucgaag cuguacacau 23340
ccuggugacc uuaaaacauc ucagguuuuu auaacuggaa ggaaccuuag agaucauggg 23400
gcacaaccuu cucuuuauag augaggaaac agaaaucuau ucauuuauua cucaaauauu 23460
uagggacagu uguagguacu agaacacagu gugaaccaga caggcaaaac cccaggccag 23520
ggagcuucca uuccaguggg gccacaggcg augcucaggu aagcagagac uccgcugugu 23580
gacuucuggc ugugaugggu gcugcaagga aaauccggua gagucgaggg uuagagaggg 23640
acggaggggc agguuuaagg gggaugcuca ggaaggccuu ccugaggagg ugguauuuga 23700
gcagaguugu cugucagcca cacaguaagu gagaggggag uuccgggcuu ggaagcugcc 23760
agcacagugc uggcaagugc ugggguggcg ucccgaggcu acagaaccug agaugcugca 23820
gaagagccca cuucugcuuu ccuggaccac uuccuucuca gcaccaggca aacuccuucu 23880 ucuaucccu ggcacauuuc ugaccugugu auacgccccc aauuuaucua accccuuuaa 23940
auaaucuccu cuauuuaugc agagcauucu uaccacuaac ucacgacuug cacaucccuu 24000

-continued

```
agcucccuua cuccucacaa caauccugag augggucaga gaaggaggcu ugcgcgucug  24060
gugaugggu gauuugugca caguuacagg gcuagaaauu gucagagcca gauggaaucc  24120
agguccucuc aauccuaauc caguguuucu uacuucaguc cuguggcucu caaagcccag  24180
agaccagcag caucagcgau gccugggagc uuguuaggaa ugcaaauuau cagggcccac  24240
uccaggugaa cugggguccaa agcccuggga uaaggccuag caaucugugc uucacaagcc  24300
cuccaggua uuccgcaggc ucaggugugua gagcugcagc uguccucugg gccuucuggg  24360
cuccccgccc agcuucuuca gugugaugaa cacagcgaga augcuagauc ugcagcagcu  24420
gauaucccag acacccuccc gacuccccucc uggcuggguc ugauccuccu ccagacucca  24480
ggagagaacg agacauaaac agaacuucag agccuguguu aacccugaga ucaaggucug  24540
cacagggugc ugucugaguc cagaggagug agggacccca ccccaccugg ucagcaccag  24600
cuccuggaag cagguucuca cacugguucc cugcacaaug aaggagcuca uaccugcuuu  24660
ucuggcuucu cagacccuga gguuuucacc gaaacuagac aaggggaacc uagggucagc  24720
cuggaggcag ggugagcuug gcgccugcag ugcccaggcc cugggugug cggcuccggc  24780
caggcccugu uuagcuuccu cucccacccc cacagagggg gugcugucgg caccgauugc  24840
ucauuuuccc cuuugcuuuc ucuucagcuc guaaaacuca aguccugaca augccuugau  24900
gacuuccagu ugguaauaaa agggagauga agauaaggac aggaauuucg gggaaauuuc  24960
uuuccaguuc cuuacuaaug ugacauuuag aucucuagua cugugcuucu ggcaucagug  25020
ccaaggccuu ucauguugga gaauggaggc cggggucacc agguugugcc uuuauuucau  25080
guugcuggcu cugaugagcu gaugcucugc ugauuagcaa acgcugagcc aucugcgcuu  25140
cgcagaggca cguuccagcc aacccggccc ucccugccca cuucccagga ugcuuugccu  25200
ugugggcuca ccugucuucu agcuccugau cuguaucucc accuccaucc aguuccgggg  25260
cucccuuauca gcacuguucc cagaacuguc caucacgaug gcaacguucu cucugggcgc  25320
uguccaacau gggagcucgc cucuguguug ucacucaugc ucauugaaca uggauuugug  25380
ucccuuuacca ucaggacugg auaccccucc ugguccuuuc ugccuggggu cuuagcacag  25440
cucagaagga accucaccau ucccucucuc caucuaggga auuagaagau gacaggggca  25500
caguucucug gcucacccccc agcccaguaa acuccuggac augcuucaag gcccagcuca  25560
gauguugccu ccucagugaa auaauuuaua aacccacccu ucuuuguccu gccuucuccc  25620
ucuucccuac ucacuggaga guuaacaggu gaugguuaag cucuggguuc aaaucucaca  25680
aggccacaca cuuagcuaug ugacuucagg caaguuaauu aaccacucug ugccucucgu  25740
uuccucauuu guaaaaugga aauaguaaaa gugccuacca gcauggcagu ugaaguuaaa  25800
agaaauaaua uaugugaaca cuuggaaggg cgccugacac auaguaaacu cucaguaaau  25860
acuagcugcu uuuaguggcu auucuuaaca cacccucuuc agugcucugg uuucacuaug  25920
uuuuaugggu cccugagauc gaaagugucc acaccgacuc auggucagcu guaaccugug  25980
ccucgugugg ggaccaggcu gccaugugua gucuggacag uguaggaggu ggcagagcuc  26040
aggccuguuc ugcccuccag cccagagagc cacgucguua gaugucaugg gagacugugg  26100
ugccccggga aucucacgaa uuugcccacg guacucagug ucuguccaau gcuaugggag  26160
uccaggacuc uaggagccag uuaaggugcu ggguggccac agguccccugg ccaaggucca  26220
ggccucuccc cugccaccug auccucgaga ggccaucacg aggguuguac uucaagaacc  26280
acuauccuug agcuaccuag gagcugcaga augugcacuc ugcagggcuu agggccugca  26340
```

-continued

```
gacaagauag augcagggug ucuaguuaaa uucgaacuuc agauaaacaa caaauaauuu  26400
uuucaaauaa uuguguucua uucggucccu auuugggaca uauuuguacu aaaaaguauu  26460
cauuuaucug aaauucagau ucgacugggc aucuggugcu uuuguuugcu aaauccaaga  26520
gcaaauuugu ucuagcuacu ucucaacccc accuucagag aggaagccuu gaugguacug  26580
uaacaucaug cuguaagaag gggaucccuu gaauuguaaa uggcacucug auaagaugag  26640
guauggggau uguauugguu uccuguugcu gcugucauaa auuaccacaa acuuaguggc  26700
uucaaacaac acagaugcau uaucuuacag uucuggaggu cacaagucug aaaguuaggg  26760
caucagcagg acugcauucc uuacugcgga guucuagaga aaaauccauu uuccugccuc  26820
cuucagccuc cagagacacg ccacauucuu uggcuagugg ucugcuucca ucuccaaggc  26880
caguggggc uuaucaaguc uuucucacau cacaugacuc uguuucuucu gccucccucu  26940
ucuacauuua agggacccuu gugauuacac aggggcccac cuagaaaagc caaaauaauc  27000
uccuuauuuu aaaaucagcu aaucaguggc uuuaauccca ucugcgaucu uaauuccugu  27060
cgccauguaa cacaagguau ucccagguuc uguggguuag gacgugggug ucuuuccuac  27120
cacagggcag uuucuagugu ugccucuucu cccugcaguu cgcucaugga gucccggacc  27180
uggcgcugaa ggacaucgcc ugcagcgagg cccuccugga gcgcuucauc aucuucagcc  27240
agagacgcgg ggcaaagacg gugcgcuaug cccugugcuc ccucucccag ggcacccuac  27300
aguggauaga agacacucug uaugccaacg uggacuucuu caagcucuuc cgugugguaa  27360
gggaggggu uggcugcucg ccaauugcaa ggugauuccu gggguagcag agccucacga  27420
auugaccuug gggagggcgu gagccuggug uucuggacaa uccuugcaaa agcuccaggc  27480
ucccagggcu caaaaaauca caacugauag uauuucuaga acaguggccc agggacccag  27540
aagucacuau gagguucacc auuagguaug uggcuguggc auguuugugu ccacucuaaa  27600
ugugggaua aucccuuua ccuccucuaa cagaguggua aaggaaggag gaggccuggu  27660
uugacucccu gaccugcuau uuccuagcca ggugaucaug guaagauauu gaaccuuuuc  27720
uggucccagu acucaucuau aaaacaaaua uaauacuuua cagaguggua ggaauuauac  27780
aagaaaagua uacgcaaaac auuucauaaa uuuuaauaaa ugauggcccc augcuucuuc  27840
cucuggaaau ggucucaacc ucaaugguug guguuucuag agagaaaaaa cgacagagaa  27900
aguuucauag ucucaaaaau uuggaaagcc cugaucuagc ucaacccuuu guucuagaac  27960
ugcaucccag acagacugcu ugggaccuga aaauaucucc uccuuugcua gaaggauaag  28020
augagaagga auuagauaaa ggagguguag agcagagguu uucacacugc aaagugcaua  28080
aaaaccauca gagggccggg cgcaguggcu cacgccugua aucccagcac uuugggaggc  28140
cgaggcgggc ggaucaugag gucaggagau agagaccauc cuggcuaaca cggugaaacc  28200
ccgucucuac uaaaaaacac acacacacaa aaauuagcca ggugugguugg cgggcgccug  28260
uaaucccagc uacugaggag gcugaggccg gagaauggcg ugaacccggg aggcggagcu  28320
ugcagugagc cgagauugcg ccacugcacu ccagccuggg ugacagagca agacuccguc  28380
ucaauaaaaa caaacaaaca aacaaaccaa aaaaacccau cagagaaguu gguaaaagau  28440
gcaagugcua aauccccacc cccaaucacu gugauucaga agaaccaggc caggcccaga  28500
aucuauccug uuaccuuagg cgauucugau gaagaccauu guaggccaca cuuucagaaa  28560
cacucaaaau uagaauccuu cagagaaggu ggcauauaua auauuucuag cauggaauua  28620
uguuuuuuuu cuuuugccua cauuuuaauu ucuagaacug uguuguaggg aaugucaguc  28680
acuaagaacu ugauugagga acuguguuuu gucuguuuca ugacugcucu cucaaguccc  28740
```

-continued

```
aggaaacuca cuuucagcuu gucuuaaaaa gcaagcugaa ggcuuuuaaa aaugaagcaa  28800
caugaaauaa gacaccgcag uuucuggcac gguccacgcu uaauccccuu caauguguga  28860
cuuuccgugg aaaguuacuc uacgauuuuc ccagcucguc agggugggc cccagaguga  28920
guaugaaggg ucagagccua gggaugccac caucagugag agcccaggac cccagaaaag  28980
gucucuuggc ucaccacacu guaggaaaaa uaaaaagcaa uguaguccaa augucucuau  29040
ccaaaguuuc aaaaagaacu ugauuuuaga cacgcuccuu gacuuguuuu cagaaucaga  29100
cagaagagug aggcaacaaa gguccuuau uccaggcagc ugaauaccag cacagccagg  29160
aguccagugc ugguguuugc agagccacca gaggcucccu cucaggugug cagggcccgc  29220
augcuuugua gaaugggcag aaugagcaau gucugugcac cugggcuuug caggcagggc  29280
cuggguaccc agguucgugc aauccucucg ucaccaugaa gggagcagca ucauucuucc  29340
cuucuugaag caccuuggcc accaguauag guaaauuuac cucccaggac augaccauug  29400
auucugggau gucaaugcca gagauaguag gguaaaucgg caccugggua aaacuuucca  29460
uuggagacua gaaccaaaac ucaggacacu ggcuuccaaa uguuucuuua ucagacaaga  29520
aagaccaagu cuuuccuuac gucuucacau gcugccuugg caaaugcuag cauucacaaa  29580
cccugggcua ccuugaccug ucacccuugc agaccucaga cggguccugg gggcuugcuu  29640
ucucgguuuc uguaugcagg cacucaaacc ugcaucaggc accugugaag ggccgggcac  29700
ugugcugagg ccaaggcucc aaaugugaac cuuccacccu cacugaacuc acagccagac  29760
cagagacaag caaacaggac auuucacagc agugcagccu agaaagggcc aacaccagca  29820
gcauuugucc ccccgagcgg uagcuuuuag aagcuucccc agugauucaa uguguccuac  29880
aaaugccugg cccccacucc cagagauucu gagucagcug gccuagggug cagccuugac  29940
uucacugugu uaaaaagcuu cccagauaag uccaaugucc ggccaagauu gagaaucacu  30000
gaccuagagu uuaauuuacc accucagucu cuauagacca cgcauaauaa uaguacccca  30060
cacaccucug agggucaaa gaacuuucau uugaucaccc augagaccac cguggugugg  30120
agaugcuuuc ucucuccugu ucucuuaaca aagcugguga gcgacagagc cugcagugga  30180
ccgggagaug gcccagagga gaaagcucug ccguagucgg ccucaguuaa ccacggagca  30240
ccaccccuac cugcucuccu cucacuccug cuuccgucuc gguggagaaa gauccaaccg  30300
aagcaggaca caucuagucu ucuggugccu uuaaaaugua cuuuuccauu ugacaaaugg  30360
auuacacuaa aaacaaaaau uuacaaaaaa aaaaaaaaaa ccugaaagaa auugcaggca  30420
uuaaaauggg acuuugccuu uauugcuccu gggcccaucc uauuuggguu uuuagaaaaa  30480
caagccugag gcaggcccag aaaggcucag ggcagacccu ccgauccucu gaaaggagca  30540
ucaggcaggc aggggguugcu ccggggccag ggaaggggcc ccgcugggac gcggcuguua  30600
uugcagcugg uuggcgcgca gccaugcuua gcugcagugc gggaaugcug ggccuucugu  30660
ucugggcugu uucucauacg cacguaggcc aguguauaaa uaagguuuua uuaaaugcca  30720
aaugaguucu cauuaacaaa gaaagaggga aaaucucagu aaaccaccgu gacggcaucu  30780
acccacuuug agucaggagc uggggggugug agugcaaccu ccgagacaag ggaaccugug  30840
gagcccagag aaucggaggg gggcgcuggg guuagcaccg acugagacca gcuguguuuu  30900
cucucgguuc cuuggagauc agaagugagu guugucaucu ucaaacaauc caaaggcagu  30960
acccauggcc uuacuacauc ccucccacac caucccaccc auccccgcgc guacacucac  31020
acgcucauuu gcacacuauc gcacacgcuc acuugcgugc gcacacacag auuggugacc  31080
```

-continued

```
uagguggacu gggagagaaa uaagagccaa augacuggau uuucuccaag gaaauuuauu  31140
aauagccccu cuugguuuca ccugaaggag cuugucuuca ccugcggccu uugcaggcuu  31200
aacgccccca gcuugaaacc cagaagcuca gacuugggcc caagguauua uuagugccaa  31260
cacuaccuga aauguuucgc accucauaaa aauggugugu caguuucggg ugagagguug  31320
ggacgcuucc caucugauuu ggcccaaggc augcaugccc cuccuucucc uuccccuccu  31380
ccucccccuc uucccccuac cauccuuccu guuuucucuc caacucuggu gcacagcuuu  31440
gaaaucuugc ugagaagcaa aucugucccu ucugcuuuga auguuuauuu guggaaguuc  31500
ggcaggggaa ccgaggcggg ugccaagacc ugccaugcug cugggaaguc ugagucuccc  31560
ucccuucccc cuccuaaaug cuuguugaua gagaaaaguc agccuccucg gcauuugggc  31620
ucacgguuuu ccuuugaaaa ugcuuccagu guggcaugau ucagcuuucu uuucuguccc  31680
ccaaccacug cucuguuguc auuuuuacuu uucugauugc auuuuauccg ugucucuuug  31740
acuacggggu ggcuggacgu ugaguuccag gaagaaaagg gcccaaucuu gggguucuga  31800
cuacaugcgc ccaucaaugu ccuguuucau ucuuggcucu ggcucccuga auuccugagu  31860
cacuggggag aagcgugggu ggaccgcccc cuacccagug agaguugcca caguugcugc  31920
ucuccugggu cauugguugc agauuguuaa acuucaccua ugcauuucaa cuuucgggug  31980
gauauugcua cgucaagugu cugggaaagc ccccacagcu acaggauuuu acagugaggu  32040
cccacuaaug acuugauguc augacuuccu cauucuuucc aauuucuccc acuucuccau  32100
aaggguuuug ggaaggggag aagagaaagg agugauuccu gagugccagu accagggaac  32160
agcagggcug uugggaggaa acaaaacuaa aucaggaagg uuuuuguugu uguuuuuggg  32220
ggguuuuaug aaaauauuca agccacagca aauauauuug auuuauagca uuaguauuuu  32280
uucugccugc aucuacaaaa aucuuuaccu auuaccauca aaauauccuc ugggugaaug  32340
gauuucaaca aagaagaaau aaaaaugaaa uagaagagag gccccuucgu gcacauugag  32400
ccuacuggcu ggauugucac uugccugccu ugaugucuuu ucagcuccag gcaggcagua  32460
ggccagggcu uauuuucaug acagaucaga uguucuuuua uggauuuaca aagaaagaaa  32520
uacugagaag ucaaaacuga agucacuuaa gacaagagca ggccccuggg aaggcugcca  32580
uugaggauaa ugaguccugg gguccuggcc uuuguucagu aaauacgcac uaggcgccua  32640
caaugugugc accaaugugu gaggcgucag guucucucca gggucaguug guuuuaagaa  32700
agguuuuggc uucugauaug uuuuaucucu acagaacagu agcucuuaac cuuucuuaug  32760
gguuaggauu accuucgaga aucugacuac agcucuagac cuguucccua aagaaaacua  32820
aguucacagg gacacacagg augggggcuca uggagcagcu gaagccagac cccagguuaa  32880
uagccuuuac auuaaaaugu uuuucuaccu accacuaaua ugcauucuuu aguaagcggu  32940
cucaauauac accgauucuu ccuuaacucu guuuaugaag uauucagcau ccucccugcc  33000
cccuucagca uccucccugc cccugagcac aggauccaau ggcgugagga ccacaggccu  33060
gggcagcugc uggggcauac aggcaucucu uaguggcuga gagacugggc ccuggcucua  33120
uguuggcucc uaacuugcug ccauuuaaag gaaaucuuag ccucccaucc guaaaaucga  33180
gaaaauaaga cuuguccuac acagcucaug aaauaguaau gaaauucaca uuagagaaga  33240
gauggaaaaa cacuuugaac aaaaagcauu uugcucuuau aaaagcacag ccucuuuuga  33300
gaggcccuuu gcuccccauu ucuccuucuu cagaccccccc cagacuagga gaaggucugu  33360
cucauggagu gaccuuuugg cugccucuag auuccaagcu caguuuugcu uucauuaacc  33420
acagauacug ggacggacag aaaaagaccu aguuucuguu gagccaaaga gucucauaac  33480
```

uugucuguuc acauacccaa gagcccaccc ucuaguugag acacucaguu cccucucauu 33540
cugggagacu gcaugucucu gugaccuccu gguagagacc guuugacaug ucccccaacc 33600
ccccagugau ugagucugaa uucuccacug augacgcauu uccuagcacu cagggugucc 33660
ccuccugguu gcccccucac cacugaagcc cgcuuccucc cuuuucauuu gaugcuuaac 33720
aacugucagu uugcaagaaa caugcuucaa auccacauuc ucccaguugc cuagcaacaa 33780
cuucccuccc ggauaaaugu ggguuuccug uagcucagcc caggacugaa cacagcagca 33840
cacacuucug uccacugcuu caacugcuuu ucaccucugg ucugcaugcc uucaagacug 33900
cagcucaucc cucccuucag aaccuuccau agccugcaga ggccaugucu gccccaaaaa 33960
gacacauuga accugaggcu acuuauuuac ccuuguguua gguauauccu caacuuagaa 34020
auuaauacug uuuccagauu gucuucuuug aaucacagaa aguaaaacaa caaaacauuc 34080
aaugcuuaag acauuucaug ugcgguuggg ugacaucugu uugaugaaca cauuugaucc 34140
aaagcaucag aaauacuaug ccaacaagac uuuuuaggag gugauaaaca ugucuguucu 34200
accuuaagaa aaaaauauua cacaguccca agggagagac augguuuuga ucccagacaa 34260
cccaagcaga gaccucuuag ggccggaauc aucuuggcug cugccuagga ccuuauauca 34320
auuucuuaag cacaggauca aggccuaaag gccccuuaga cugaccucag uuaguagagg 34380
cagaucccuu cacagccuua ucuuccuuag aggucuaguc ugaccuugaa cuucggcugg 34440
cagugcuguc aguugugaug ugugacaugg aagaguuauu uguuacuugg aaaauuaaga 34500
gaacuuauuu ggcauaggaa auugugugug ugugugugug ugugugugug ugugugugug 34560
ugugugugug agaugauguu ugccauuuug aucugugacu uuuuuuucca gaaauaguuu 34620
cucaguucca uuccaacuaa acuuacaguc ucuuccgguu cuuugacaga aacaauucau 34680
gugaauuuga acagauaaua gggaaggggg aaccaaaaga agaggagagc ccugggaaag 34740
uuauuuuaua auuuauggca accucaguca ggcaacugug aacagguaca uauggagggc 34800
ucccucggga cuaggcagua uucagagaug uaagguguga ggaccggacc cucaucauuu 34860
accauuccca cuaaaaagag cugggaagga aauuguagcu guagcaccag gcacguaacu 34920
ggagcuuagu aacuauuugg ugaaggaaua uuauuaaauu auuaacaaga uggaaaaaag 34980
gguauuaacc acacaaaaau acaucucaag cuauuguuuc ucuguucccu uucccccaaa 35040
uuccuagucu ugcucuuauc uggcugucuc ucuagucacu cuuucuugcu gacucucuuc 35100
acguuccuuu cuccaccugg aauuccuggg cccuccccuu uuacugacag acacuguccu 35160
cacucucaca gucaucaguu ugucucuuua caaaccucag cucaaguguc acuuccccgu 35220
ccccagguga aacugacugc ucccucccug uaagucacca ugaugacugc uauauauagc 35280
ccucauggaa ccuaaaaccu caacagacac agucucuuuc cuacucuguu auaguuuauu 35340
uacucauuaa uuaccacaac acguauuauu gagcaccuac uguguaccau gcccagaaga 35400
uaaaagacaa acaaaauaaa accuauuccu augcuuaaug aguuuacagu cuaguggaga 35460
gauagauaca uuaaaaaaua acagcaaacc aaaauaaaag ugguaaauaa augcacugag 35520
aaagacagga auagcuagga ggggcaccua aucccuaggg aaggaaagcu ggaagagcau 35580
ggugaugggg gaagaaggcu uucuggagaa ggugagguag uuugaaauga guugacucug 35640
gccaguaggg guagagugag aaugggguga gacagggugg guuggucauu uugauccauu 35700
aguccucaaa gugauaggac uaguggcuaa ggacugcagg cuuuacagaa gccuacaaaa 35760
cuauuugaga uuugaaguuu uuuuuuuuuu uuaauuggcu ccaaaagaaa augaaaaaac 35820

-continued

```
uuuagaauua uaaugaauga auauuaaaug aauauuuaag gaagguaauu uuauucaacu  35880
ucauuguuaa auuuaguuaa aacaagcccu ugaguuucau ucaacacugu uuuaucauac  35940
cguugaugag agaaaacaaa acugauuccu ggccagggcc acugucagcg uggggguuugc  36000
acaucuuucc caugucugcu uggguuagcu ccagguacuc cuguuucccc cacaucccca  36060
agaugugccc auuaguggaa acggugugucugcaugauuc caacgugagu gagugugggu  36120
gugggaguga gugccccugc caugggaggg cauccugucc agguuagauu ccuaccuugu  36180
gcccugagcu gcugggaugg aauccagcca cccaugacuc ugaacugaaa uaauugggug  36240
aauaauuauc uuacuuuuua auuaaucuuu gaaaauguau guauaguuca cauguauuuc  36300
aauauuuaau auuagaagua uuuuagucuu uauuuugaag uuuggugauu uauuguaacc  36360
agaaacaagc uauagaaacu uaauuuuggg ccaagugcag uggcucacac cuauaauccc  36420
agcauuuugg gaggccgagg cagacgcauc acuugagguc cggaguucaa gaucagccug  36480
gccaacaugg uaaaacccug ucucuacuaa aaaauacaaa aauuagccag augugguggg  36540
caccuguagu cccagcuacu ugggguggcug aagcaggaga aucacuugaa cccgggaggc  36600
ggagcaguga gcagagaucg ugccacugca cucccaccua ggcgacagug ugacacucca  36660
ucucaaaaaa aaaaaaaaau agaaaagaaa gaaacuuaau ucugguuuau aucaauuagc  36720
cugugguaaa auugguuuca uuauagccau uucacuuagu ugaaguuucc aauaaccugu  36780
ggaugaauua agugaggauu uacuauauuc auaaaaucuu aaauuccaaa gccuguuugc  36840
aguucagguu uuuccacuuu acaaacacuu cuaaguauuc acaaugauug cuuaaaauuc  36900
auaccagaua aaucauuaaa uaaguuguuc aaagucaaau aauuucauaa guaaaaauua  36960
ggagcuuuua gaaaacuaua ccuacauaga ccuagaccua uagauagaca gagaucugaa  37020
uagauaugga cacagaugcu uuccaaagug uucaugugau guguggugga guuucaagac  37080
cagagugugc cuggggccug cagaaguaaa ggagagggga uggagagaag auuguccaca  37140
uggccauggg caaucuccca cccacacuca agugaggaag acaggaaaca aauucagaaa  37200
gaagagaaaa uaaucaaaac ugaugggagc uugugacuga uuuacuuaug cgcagccucc  37260
cuggagacau gagugugggcu guuccuuagg uugugccucu gggcuccuac ccccucuuag  37320
augccuuccu auuaucuagg accugguugc uuuuugucug cauagcuucu uuggauucca  37380
gucuuugaug ccagcuuccu ccuaaaguag ccuuucagau gucccuuggu uacccucugc  37440
uaucuaaggg cucauccuac cccacacuca uucccagcac caauuucugg aucuccaggc  37500
uggagauuua gacaauggga ugggaagaac ccaugauggg ucccagacag aaaguggugc  37560
cagccacaga aagggcacac aggcacagaa guugguuugg gguaagacga uguggucagu  37620
ucagaacacg cuggaucuag gcagaugccc agcagacagu uggauaugua agucugaagc  37680
ucuggggaga ggucuagguu ggagguacag auuuagaagu caucaacaaa aagguagcag  37740
auuaaaugau aaaggaaaug agacuauccg gggagugugc agagugagag gagcaaggga  37800
ggcccuuggg aaccucagca cuucagggga agguagaggu acaguugcug gugggaaagg  37860
cagagaagua gcaaagcaaa ccaggcaaaa gcagugucac agacgaccag ggaggaaaag  37920
gacaugauca aaauguugag aaaagcagag agguuugaaa auacaagaag caaaaauguc  37980
cacuagacuu aaaaaccagg agaaaacugg gggguucuug auaaagcauc uuaguaggau  38040
ggugagggua gaagccaggg aaguguuggu gaggaaguga agucacugau uacggacuau  38100
gcuuaaaaga augugggaau gaagggugga agagagaaau uagacuguag cuagggagac  38160
auaagcgauc agagguagau ucuuucucuc cugugggaga aucuugcacg uauacacagc  38220
```

augacgacag ugauggaagg gcuggcgaag ccucagggag acucuuggag guaaacccca 38280
ugaagggagg acuuuguuuc auucacugcc guguccccag caccuggcac aauagcagac 38340
acucaauaca uauuugucaa augugggauu uuaucauuua gaaacugcac cuggcuguga 38400
guaacaaaag ucagagaaac cgugggguuc auuuuucucc ccaggcagag ucuggagcug 38460
gguccuccaa gagggguuug gagcaccaca gguuuccuca agaccccccag gcugcccugu 38520 guuucccucc uucaucccca gcauaugccu gucaucuggu gaccuccaaa caccugugcu 38580
gccuccucca gcacauccau guugcaggca gggaccaggc aaagggcaga ggggccuacu 38640
ucaaaagacc auuuccagaa accccauccu augacuucuc cuggugucuu gguuaccauu 38700
gugccauagg cucacccugu augcauggga ggcugggcca ggcauuauga cuuuuagcaa 38760
uauugcauag auaagcauca aucuuuguca cugugacgaa gccuagucac ucagugcuag 38820
gcaagguuaa uggaaugggu uggugugugc auuauucuug aggucuuucu uaugcuucau 38880
guuauacauu uauuaggacg uuuaggcaac agggggauaa aaaugaagag gagaugcaug 38940
cuaugaucug aauguuugca uccuccccaa aauucauaug uugaaaucuu cauccccaag 39000
augauggcau uaggaggugg ggccuuucgg aggcaauuag gucaugacug ggauuagugc 39060
ccuuguaaaa ccccagaaag ccagcuugcc gcuuccacca uaugaagaca cagagagaag 39120
augccaucua cgaaucagga aaugagcccg caccaugcaa uaaaccugcu ggagccuuga 39180
ucuuagacuu cccagcugcc agaucugugg gaaauagauu ucuguuguuu acccagcuua 39240
ugguauuuug uuguagcagc cagagugaac uaagacagug cugaucucgu auucuuggag 39300
ggaacccuua gucuuuaggg aaagcaaagc caccauuugg ggcagggugu ucuccaagug 39360
cugccacaua ugcugaugug guuaaacugc aaacuauggu aaaaaugugg aggucugugg 39420
aauugucaau caggaaaaag auauaaaaag aaguuaaagu cuucgugcuu cuggaaggau 39480
augugccaaa uuguuaacau ugauuauccu uggguagaga ugugggggaag uuugcagaga 39540 caguuuugcc uuguacuuua uauaaguaaa cagcuacuac uucguugucu uaaaaaaaaa 39600
aaacagccua ugugcucuuc augugacuca gaacuaccua ggcaauacga uuaauugaau 39660
uaguaaaauu gagugauuau gaauuuucag gaagucauua auuuaccacu ucuuuauuac 39720
auccacuucu aacaggacuu caauauaggg gaauuugacu ucaagauaaa aagaccaaau 39780
uuauuuaccc uuuuaaaaaa agacaacuua aaagcagacu ugucuuacag aaccuuccuu 39840
aguuggacau cgaugagugu acagaaaaug caauggauaa aaagcuuggu gauacaaaga 39900
uaaaaagugg gguccugucc uuaaugaaca uaccauuuca uggaguauca gguguauaaa 39960
caauuauaau caaucugcuu guuauucuga uaagaucauu uacucacaca ucaaauacug 40020
agugcccacc acaugcccag cauaccuaga agucauccag uaugauuucu gucuacaugg 40080
agcauagagu cuuacagggg agauagauga caaguaaaca ccagaauaau uaccaauggu 40140
gaagagcaca aggaaggaaa cagaacuccu aaagagagcg uggcugggca ggggugagca 40200
agaggcauag aaaaaggggc aucuaaaucu acuugggagg aagcuguuuc ucacauaggu 40260
caucauguua ggaaugagac uugagggaug aguagaaguu ugccaggcaa agaaggaaug 40320
ggggggaaua gagagcagag cuaggggcag gagacagcug acgugugagc agacauaaaa 40380
agaaguccac uguggcagca gagaagcagg agagaaggca agugagggag ccaggcacca 40440
gcucacagag gucaugugug ucaaaacgua guaauggccu ucucuucugg agacaguagg 40500
gagccaugga agauguuuga gcagggaaag cgacaugacu ggauuggccu guuggguaac 40560

```
ucagaccaca augcauugga agggaggggg cuagaggcaa ggggacuggc aagaaggcca  40620
guccuuuuuc uaugccuauu uugaugaaau auucuagaag ggaagugaac aaagguaguc  40680
cuagagagga agaacaaaac agauaggaua cuuccuuagu auuugcucau ucgacaauuu  40740
auuuuugcau auacacuaaa accuuuuuua uuauuaaaac guuuuauugu aggaaaaaag  40800
uaugaaagua gagugaauaa uaaaaugagc ucccauggau cuaucaccca gcuucaacua  40860
uuaucaauau uuggcuguuc uuguuuuaac uguucuccac cuuuuuuucc ugaaguuuuu  40920
uugaagcaaa ucacagacaa cauaucauuu caccauaugu acuucccucu guaucucuaa  40980
cauguaagaa cuuguuuuaa caaaaucacc augcuaugau cauacccaac aaaauuuauc  41040
auaaugucuu aauaauaccu aauacccauu ucauguccac uuucccccaa uugcuacagc  41100
ugguuuguuc agaucagaau caaaauccac cuguggccau uuuacugcua ugucucucag  41160
gucucuuuuc aucucuaaua aucucagggg agacaggagg gaggacgggc aggacuuggg  41220
gcuaacuugc uuaucgacac acaguuuugc cuacuugcuu ccucccuuca cacccacucu  41280
ucuucucagc cccacccuug uauggaaaaa acagaaauua aagugcuuug cccagcaccc  41340
acugaagcua uuucgaagga guuugaagag uacucccggc aagacaaaug ccucggucca  41400
gugcucaggu caaagagggg agacgcuucu cagugaugug gugucaauag cagcuuaguu  41460
guucuuuccu cuggaaaauu cuacccaucu gcuuuguaac ucccauaccu aacaaggccu  41520
uuuauuucac aauuagaaaa uaagccugaa auaugaaugc ugccugagug uaccuacauu  41580
uauucuagag uuucaggguc aaaaagaaua caaggaccuc ugcaucuaca gccaagagga  41640
gaggggcaaa gacacacagc uacaaaugag aaccuggcug gucaaagccu aacuccaccu  41700
guuugucagc acugaugcaa guuaggucag cccaaugauc auuuaggaga acugugcugg  41760
caaauaaaaa gcagaggcuu uuggucccca gauacuugga ugagaauuac aaguccagcu  41820
gguuaaaagg cacaugccca gugcucacuu cacaccuacu caggaagcac acuugaguug  41880
gaaaaccacu gucuuuacac uuagaacuca guccuacaug acuccucuag gaucagugau  41940
uccaucaguu uugaaacaug aagcaugaag ucaaacagga caugaccuug guuuccagaa  42000
aaccagaugu ucacaucagu cucuggagcu uggaggcagc acaccugggg acuuccacau  42060
ccccugccga gguggcaaaa gcaggagcag uggugaguuc acaugggcug ggguuuccug  42120
aacacugcug gcaauuggag aaucugcaag ggaacuucuc cgacuccuac cagcagcugc  42180
uuuaaaauaa aggugaugua gcuggucaaa uccuccauga gagagcagug uugaauggag  42240
gaagagacac aaccugucug aaaauggcac aaaggaagaa agauguaaac aaugacgaga  42300
agacugcagu gucuacaaag cuccgaggug aacagauggg caccccaggc ccgcagcacu  42360
uccuucaguc ucugccagcu gcacucuguu uuccuuccuc caggaaucuu guuuggugug  42420
acuaaaacag caauuagaau cacuuugaaa uagugauagu auuuaauaua acuaugaaac  42480
uaucugugau ugacaagugc agcaaggagu cuuggaauga gagccuuuau uuuuucaauu  42540
aaauaaaaga guuuuuuguu ucuaaaagua aucuugcaga aaagauccug cgaucagaaa  42600
gaaggagggg gggaguuuuc aaacauauag gagaucagac ugugccuaug uguguauaua  42660
ccuacaaaca uauauauauu uaaaaaauug uuuuacuguc aauuacagcu ucccacacuc  42720
cuagacagcc guucucaagg uaucaaucug agaucuuggg gaggaauauu aucugauaug  42780
ucaccaagaa uucaagaggu gaguagccug augguaguaa uuauaauuuc auuaugucuu  42840
uccaccauuu accccacuua ugucaaauaa uuuaauugua uuucaaaccu guucaaggaa  42900
aaguacauuu gaucuuucca ucuagcaauu ucaaagcacc uguucacauc ccaaauuauc  42960
```

```
ugugcucuua aguaagaggc agaaagaaag gaaccacccu ucugauuuca caucaaaaaa  43020
gaaaugccac uggcaauaag caacuugccu ggugugggcau aaaucaucag aagacuuaca  43080
guugaaucua agucuuuuca guacugaggu gguucauuau ucuguuacag ucuuaaaauu  43140
cacauaaaua uauacugcca auaauaauag cauacaccuu uauagcuuac aggcacucuu  43200
cuucuaagug uuuuaccuau guuggcuuau uucaucauaa agaaaacaau ggacuuuugu  43260
guuguuuugu aaaaagaugc gcacauuuua auuaacaucu gauugcacaa gucuccuccc  43320
auauagaaau ggauucuucc acgcaauaga uaagaggugc uggggauaug augaugaaca  43380
cacagauuug gucaugaccc ugugggaaag agagauggga aaaaaacaau ucucuucaag  43440
ugugaugagu guuacgaaag ggagggaaaa guugaaacag guuuuuuucc aaacuuuucu  43500
cccuccauua uucgcagcug acuugggcuc caccaaccug gaaaacugca ugguuggaau  43560
cugucuuuau aaaacgcauc ucaaccuggg ccgaguaugc acacugaugu gggaaaguua  43620
gagaagagcc cauuguacua augcucaccu gcuacagugg gagucucugu uaaacagucu  43680
uuucuucaua gcauuaaaaa aauuuauauc acuacaauaa gguugaaauu gauagagaau  43740
guacaaacaa uccccaaagu auaucaacac ucuuaguucu gaguagaagu uccagaaggc  43800
uucuugacug ucuagauagc aagucuaauc auuugugaac uaaguuaaag cagaaggccc  43860
aguuuauaug aauugguauu acaccauuug accugagaac agccccuuca ucucugagug  43920
cuuugacuaa augagcaaca uaauaauagu aauaaccccu uacaagaugu cauaagacuc  43980
acuguuguug aagcaauuug agauuuugac uuuauugaag cauagauggu gauuauaggc  44040
augacucacu guguggauuc ucccugggcu caucaguuuc agagggcaag uguuggcaug  44100
uggacaaaga gagggaugac acguaaacau ggcuuauugc aaugggggaaa uauuuucagu  44160
cucacugauu gaauccuaau gguuuuauaa auuccccagu accacugaaa gcaaagcaag  44220
uaaucaggug uguuuuagga auaaaagcag cauuauuuua auuucguauu uuccccuaaa  44280
gcaaagccaa auggcauuau gggagccaag cuacuggcag cuccaccagc cuucuccuga  44340
guucucggca uuacagaucu acccucaaag gaugaggcca gcaagcacca cagggugccc  44400
acauggagaa gagaaggcca ccaaccuccu cuuagcuggc acagaauuga aaaaguguuu  44460
uuccaggaau ggauacuuca ucuguucugu auuugcuaga auuuuaaaac gcacacacag  44520
acacacacag gcgugcacac acacacgcac acacacacga gaaaaccaca aaccacacau  44580
uucaaggaaa uggaagaauu cauugguaaa auuaagcuaa uaagauuauu uuccaaauau  44640
aagaaacuaa auuuuagacu auuuagccaa agaaauuugc ucugaucuug cuuuucuaca  44700
acagaaucau uccccaauca uuuuauuucc cucuuuuucu ccccaguauc cccaucuugg  44760
ugggacaaca gaacccaaga acuggcuuaa caguaaaaua uuuucugcau uugcccaagg  44820
acacauuccc aacgaauuca aauaaaggag acuagaagaa gagaggcuau acuacagugc  44880
ucuagggguc acucugugau uuguuguugu uguuguuguu guuuugagac ggaguauugc  44940
ucagucgccc aggcuggagu gcaguggcac gaugucuacu cacuguaagc ucugcccccc  45000
agguucacgc cauucuccug ccucagccuc ccgaauagcu gggaguacag gggcccgcca  45060
ccauguccgg cuaauuuuuu uguauuuuua auagagacgg gguuucacca uguucgccag  45120
gauggucucg aucuccugac cucgugaucc gcccgccucg gccucccaaa gugcuaggau  45180
uacaggcaug agccacugcg cccggccacu cugugauuuu cuuuaaggcu cauccuagua  45240
uucuccuagu cccuaaguag auggcaguag guuuuguuuu uuguuuuucg cagcuggauu  45300
```

-continued

```
aaggauugcu gagaauauau ggauguuuuc uuuuaaaugu ggaagucaaa ccaaacguug  45360
gagcauuggc cucacagcag auuaugacuc uagcugccuu aaaauaaccu gaagacuuug  45420
ccuugcccua guuuauccau cggccgagua ugcaggacuu gcugugggug accaggcccc  45480
ucaugcagaa ugguggucca gagaccuuua caaagcugau gggcauccug ucugaccucc  45540
ugugugguca ccccgaggga gguggcucuc gggugcucuc cuucaacugg uaugaagaca  45600
auaacuauaa ggccuuucug gggauugacu ccacaaggaa ggauccuauc uauucuuaug  45660
acagaagaac aaguaaguuu ucugaguccu gcuuauaaau uggccucuca uguugguuaa  45720
guugaugguu uaacacuucu aggugaaacc aaaccugggg uugcaucugu cuugucuugc  45780
ugaguggccu uagguaaaga gacuucuccc agaaagucca cuuccccuug cagaaagggg  45840
gcauugcuua uaagcaauuc uggacaugaa ccacagaaag aacugaggcc cacuuggaaa  45900
gggaacagag gggccauuuc ccacugaugu aauugaacua gggcuaaguu caagaggaag  45960
agaaugaucc gcaaggaagc aacccagagu uccaggugaa gcucagguca gaagggcccu  46020
ggcaaguaaa cacggcugug ggaugcuuuu acaaacacaa uaucgugaaa aucuaugugu  46080
guaguacuga auuacauucc aaauggcaaa uuccuggcaa aucaucuucc ccaccuuuca  46140
cuauuuuuuu uuuuuuggcuc uucuaugggg uaaaggagga uggggugggg aagaaaugua  46200
acuggcugcc ccucuaguua aaaacugaaa agaggcagca agggacaugc caaaaguagu  46260
uggacucuaa gauagcuaca cacaacaaag cagcuaagca gcuaauugaa gggaaauuac  46320
ugaggcucaa gcugagauuc caagcggggg ccuuguuugg ccucucaguc ccuuucaucu  46380
gagaaaggcc ucaguuccua gcaguaauca gaggcaggcu ucucagccuc cuucuccuaa  46440
agcagaauaa accacagggc aagucgcauc cuuuguuucu cugaugaggc cauuacugag  46500
agucacugug gcauuuugcu acuaaugaug agcuuguuau uggugggua cagccuauua  46560
auuuagguua uucaucaaau ccuccagcau ggaguugaau gagacaugug auguggauac  46620
acuaaugacu auauugaguu acaagcaaug gggaguuucu guaaaaucug ucccuugucu  46680
ccuggcagca uccuuuugua augcauugau ccagagccug gagucaaauc cuuuaaccaa  46740
aaucgcuugg agggcggcaa agccuuugcu gaugggaaaa auccuguaca cuccugauuc  46800
accugcagca cgaaggauac ugaagaaugu aagaucccag cugggcuugc cuuguguacc  46860
cuggaccucc cagaagugug ugugugugug ugugugugug agagagaugu gccuuccugg  46920
uagcacaucu cauguuuguu uuuugcuaag uggacucuug cguuuccucc cccauccaca  46980
gucaucacug gaaugcuuug cuucagugcc ccugccuggg ccccuccccuc ucuacugcag  47040
ccuacaauga gguuuucuuu cccauugcuu gaauuauauc ccuaauggaa ggguucacaa  47100
uucucugaau ccuggcuacu cagauaaaga cagggaggaa gggaggaagg guauuuucuc  47160
ccaggggguc caaaucuagc uuuaacgagg gagguucuga gaaaauaaua ucaucaauau  47220
uacauggacu ucugagauac uaagaaauua gauucuguca gcccaggaag uugggagaug  47280
gugaauuguu cugggaaaua gcaauagacu gagaaaauaa aaacacuucc uugaaaagcc  47340
uuucccuaac acuaagugau aggggcagaa aagacacaac caaaaguucu cucucacuuu  47400
ucucucuguu cgugucucug ucuugaucuc ugucugguuu uaggccaacu caacuuuuga  47460
agaacuggaa cacguuagga aguuggucaa agccugggaa gaaguagggc cccagaucug  47520
guacuucuuu gacaacagca cacagaugaa caugaucaga guaagggggg uuggaggaug  47580
gggaggggag gggaggagga agcggugggg gcaagaaagu uccacuuguu uccuuuuccc  47640
aggaaagagu uaaucgcuau uggaguuaga ucaaaauaca acaagcaggc cccaaaggcc  47700
```

uucauuccaa gcagucacca agugggguca cugacuuugg augagaaaua uguuucuuga 47760
auucugggag aagucuaaaa gcugccacaa gaccaguggc uuccuggagu uuccuacuuu 47820
uaugaauuca cucaagggcc ucaaauucaa agaggcaucu ccccaagggg ccagcucugu 47880
aacuccaaag augguggaau guguuugucu ggucucauuu ucagcuuugc aaaaugaaga 47940
caagaguucu auauaucagg gacacucaaa agaaaacaaa aauauccaua agcaaaagaa 48000
agcuuuuuau acaccauauu caaugacccc caucuggccc cuccuuugcc ccuacacauc 48060
uucccucuau ucuagagacc cauggacuug gggaaauggg auauagauag guauguuuca 48120
uaguggaaca agcucaccag cucuucaggg agccuuagca ucucuauccu caaucacuaa 48180
aaauuagaaa uggcugaaga acaagaccaa agauccuaug gaauuucuaa gcagagcagu 48240
gacuguauuu cuucuuccca aggauacccu ggggaaccca acaguaaaag acuuuuugaa 48300
uaggcagcuu ggugaagaag guauuacugc ugaagccauc cuaaacuucc ucuacaaggg 48360
cccucgggaa agccaggcug acgacauggc caacuucgac uggagggaca uauuuaacau 48420
cacugaucgc acccuccgcc uggucaauca auaccuggag guaaggggcu gcaagcccca 48480 caguggggccc cuugaagaua gccccaugag uggggccaga gcucccuuag caagucaagu 48540
ggucuugaau uuaagcuuuc auuuucccca cugaagaaac aagaaucccu acaucccccug 48600 uacaguucuc auucucuaac agcuuaucca uacuuaaaac uuaucuaugc ugaaaacggu 48660
uuccucuuca caucuccuac uucucaugcu gggcaccucc uccuguagcc cccuuuaagc 48720
aucugugucu guccucaacc cucuucuguc ugacauugcu ugaguggcca ucuauggcca 48780
guguccccuc aaccccacag uccauugcuu gcuggacacu ccugcccuca aguucuacaa 48840
gcacaucagc cucaacaugu ccccuccaaa aacuguaugu ucuccuugcc cauagaacau 48900
auccuucucc uauauuuccu auccuaauua acguccucag cauuugcccg aauucucaag 48960
ugagggauuu cagggucauc ccuaauuuuc cuucuucacc cuccacacag uagcugucac 49020
uuacugagug uuacuuuaug ccaaguacug ugccaacugc uuuuacacac auaugcuuca 49080
uuuaauucuc acagcuccau gaggcuugca ccauuaucau ugccaauuug cagaugagaa 49140
gccagggcuu aaagagguua aauaagaucc cacgcaugac cauuaagagg agcgaacagg 49200
auccagcucu gggggugccu gaguucagag ccugccuuuc ugauuucucu uaccaagcuu 49260
ugucuccucu cccuccuaaa uaucucucaa cucugccucu ugcauuccag gcucucugag 49320
gacuagaggc cuugucaucu cugcgccagc ccauuccaag ggcuuccuuc cuggaaucca 49380
ggguccagcc ucuguuggcc caggcauuuc ucuacacugg caccagaguu acauuccgca 49440
caccugcuua cguugcucuc ucacuuaaaa ucuuaaugac ucgacccccca aauaacacag 49500 gucccuucca aaucuguccu accccaccuu cccagcccuu gcucaacucu gcuaccuggc 49560
ccuuucacgc cuacaggcau ucccauucca ugaccucuug ggauucuacc cuuugcaaau 49620
gcuguuuuca uugcccauuu auuagagcgc uuuuggucac aagcuuuuug cuuaaccaaa 49680
aagaaagcau uuauuggugg acauaaauaa ugaaguucag gaggauccaa gaguuggaag 49740
ccaccaugag accccugugu ccuuccaccu cacuuuucua cucgccucug cucagcuuca 49800
ucucuggcca ggcccucucc ucugcugaug cccuagcugc uuacagcccu uagcagucau 49860
cuauacacca aaaaucccuu ucccauagca gaagcaaugc uccuagagag uuucccuguu 49920
ggucuggcuc cuguacccac cccuguguac ucugauuggg aggccugggu cagcugccca 49980
ccauggggcc auuucuauga gcaggauuac ugugaagugg aggaagaugu uuccccaaaa 50040
gaagaaacac aagguagaaa aguguauguc caccaaugcc ugaaaugacu gucccuuucc 50100
ucaucugcug agcuucuacu cauucauucu uugagacuca gcacucagcu cuuaaauguc 50160
acuucugcuu ugauggaggu uuagucauuc acuccucugu gcuuccuggc ccucucuuca 50220
caccucucuc agaccccucu cccagauaga uuagaguugg cuguugacau guccaucucu 50280
ggcugggcag cuaaacugga guuauuuaga aucagggagc acaugucagu cauuuucaaa 50340
uucucaaccu cauacuccca guaaaugacu ccaucuaagg guggaccacu cuugcccaug 50400
ggccaggucu gggucugugu caucuagaac uguuggaagg uaggggcuuc ugugagcagu 50460
aggagaggga auaaacucga gggcccucgg gagcaugccc ucuugucuca gacuugugag 50520
uccugaggau aacaaacuag ugaagaaaag ccucguucua ucugucaccu ggugcucuug 50580
aggacuuucu guugcccugg ugccaccaca auuuuccaga gugugugacc cucgcucucc 50640
aaacucugga aguggcagcc gaggcucccc aguggccuuu cagaaggugc cagucaugac 50700
agcagcacca aacugcaggc aacuacuaag cgaucaccaa cuugucugaa gauaagaaug 50760
accuugaaug cauuuuauaa aacaggauuu uuuuuuuaau uuuuagauuu ucuuucuuua 50820
uuuuaccuua aguucuggga uacaagugca gaauguguag guuuguuaca uagguauaug 50880
ugugccaugg ugguuugcug cacuugucaa cccaucaucu agguuuuaag ccccacaugc 50940
auuagcuauu uguccuaaug cucucccucg ccucgccccu accccacccc aacaggcucc 51000
ggugugugau guuccccucc cuguguccau guguucucau uguucagcuu ccacuuacaa 51060
gugagaacau gugguguuua guuuucuguu ccuguguuag uuugcugagg augauggcuu 51120
ccagcuucuu ccaugucccu gcaaaggaca ugaucucauu ccuuuuuaug gcugcauagu 51180
auucuauggu guauauguac cauauuuucc uuauccagcc uaucacugau gggcauuugg 51240
auugguucca ugucuuugca auuguaaaca uacaugugca uguauuuuua uaguagaaug 51300
auuuauauuc cuuugguuau auacccagua augggauugc cuggucaaau uguauuucug 51360
guucuagauc cuugaggaau cacacuaucu uccacaaugg uugaacuaau uuacauuccc 51420
accaacagug uaaaagccuu ccuauuucuc aacagccuca ccagcaucua uuguuucuug 51480
acauuuuaau aaucaccauu cugacuggca ugagaugaua gauacccauu ugucagaugg 51540
guagauuaca aaaauuuucu cucauucugc agguugccug uucacgcuaa ugauaguuuc 51600
uuuugcugug cagaagcucu uuagccuaau uagauccauu uuucaauuuu ggcuuuuguu 51660
gcaauugcuu uugguguuuu agucaugaag ucuuugccca ugcguauguc cugaguggua 51720
uugccuaggc uuucuucuag uuuucaugau uuuagauuuu acauuuaagu cuuuaaucca 51780
gcuugaguua auuuuuguau aagguguaag gaagggaucc aguuuaaguu uucuacauau 51840
ggcuagccag uuuucccaac accauuuauu aaauagggaa uccuuucccc auugcuugug 51900
ugugucaggu uuggcaaaga ucaggugguu guagaugugu ggugcuauuu cugaagccuc 51960
uguucuguuc cauuggucua ugugucuguu uacaaaacag auucuuaagc aucaacccag 52020
aucgacuggc ucagaauuuc cagggaagag gccugguuau cugcauguuu acagaccuau 52080
uagauuugug ggaccugcag uucccuugua caguuaguua cucaauuaac aucucccucc 52140
ucucauggug ccucuaccug cuaagcccuu auucccagcc aggcccacca ccauccaccc 52200
acugcuguua uaacauaagc aggaccugug cgaggggggug uggacggagg agagaggcuc 52260
uguugcuuca uuugugcagc auggaguuca gugguucuca caauguuuuu gcaaaguaua 52320
uaaagaauac uccuugucua cuugacauuc guaucgugac auaaaugucu uguuuuccag 52380
aaggauuauu uuuuccaagc agcuuguucc uaaugcagcc ccaggcacca aacagauacu 52440

```
uaaaauauau uaauugcuua aaugguuaag aauucagucu cuggacccac acugccuggg  52500
uucaaauucc uauuaucugu gcccaguuuc caagucuaua aaauagggau auuaauagca  52560
cuuaccuaau aggcucguua ugagaauuaa augagcuaau ucaugcaaag cacugacaua  52620
uaguaagcac uuaauaaaua uuagcuuuuu aacaaaauac aagccaaaaa acacugcuua  52680
ggagaggaaa ugauguuagu gccuccugua aauaggccca gccuccaagc uggugcuccu  52740
cuaggaauca caacgcugca aaucacaucc uccggggccg ccaggacuuc acgagggccu  52800
cugagcagag ggguaugaug ggagcagaag cccagcagcu gugaugaugu gguuucugau  52860
cuuccugccc uuggggguggg ggaggaggaa agcaaggggc aaugaacaga aaggagaaga  52920
uagcggggag gaaaugugug aggaagaaac acaucacugu ggcuuguccu ggauuuuucu  52980
gcuucuguuc ucguguuuug ggaagucugg aggagacuug aaaaucauuc auguccccac  53040
ccugaggaug gcuuaguagc agagaggcca ugaaaacucu uugcugaugg cucugaaagc  53100
aaggauguug cuucacuggg cugcugaagg ccugccuggg gguucugagc agagaguaca  53160
ggccccuccc aggagggcgg ccuaaccacc augcuggcau uucuguggac cauggucugc  53220
ugucucagac ccccuccaca auagggucug caaucucauu caccccauaa auacauucug  53280
ucuuuccucu gauccccucc cauuagcagg gggaaauaaa uggaagucag acggcccagu  53340
uagaaggcag gcaguggagu aggaaaauag augauggugg uuuggggagc cucacaucac  53400
ucaugggggag acauucauuc ccaugggccu uccaaucacc cuuuucucca aaucuaagga  53460
cacaggacaa augggguccuc auacaggcaa auaucuuaaa cugguaugug uauucauuua  53520
uaguucuaau uuauaugugu cuuuauucac auauauuuug cuucuggaga aaagcucaau  53580
uagaaaaauu aauacauuau ucuucuuauu gcccuucagc uaaaacaagc auacacaccc  53640
cuccccuuug gauuuuuugu uuagcaaaag guuaggccug gcacagauga aauacuauuc  53700
agaguucaca guguauuuuc auuucauaau auauuugauu uucaggucuu gaauuucaca  53760
ucaggaagcu gauauaggaa gcugaauuca gccagauuuu aauacgaaaa uaccucugau  53820
caaggcauaa aauuguacuu uaaccaguaa ccacuguauu ucucuaagcu gugaaaaaac  53880
augcauucau uaacugcuuu uuccucugcu gucaacacag ucaauacaug ugcauaacuc  53940
cuuauugucu acaugggugau uaucuugcug augaauucuc aaaggccaga gauuuggacu  54000
auuuuuucuc uguaaccuug cauguuccug gccacaugcc accaccaccc aaacagaaug  54060
uacgcaggga auguauuuuu caggauaacc uaagaaaaaa uaggauuaag aagauaaagc  54120
ugcugaucau guaauguacu uuagacucag auauauaaau auuugugaau uaucugucccu  54180
auuucuuucu ucuauuaauu cauugacucu agaugugcau uggaaggcua gggagaaauc  54240
aggggaucgu gagaaagagc acagaagucu gcaucacaca aacaauauua uuucaagagc  54300
caugaacuag auccuaagca acucauaggc aaugaccuca uuucauaccu cuagucucua  54360
agaaacauau aacuggccug aggaaggaaa augugggcaa gggguagacc ggggucaugg  54420
guggaggucc aaauaguaau caauggagcu cauagggugg acugauauug aagcugcuau  54480
gagccagcca caugcugggc acuguuacau gucaucucau gcaauacucc caauuaccug  54540
ccuaguaagc auaauuguca uuuuauagaa uuaaaaacag acucaaagag guugacaguc  54600
uaauguaaca caacagcuaa auggggggauc uggaauuaua auccagagcu gccuggcucu  54660
gaugagaaag cucuuucugc ugucauaugc agcccacauu aauaggggggc ucagaaagua  54720
uucucuggau aaauuauaua augaauccaa ugaaggaaga cauuauuuua uaauaugcag  54780
```

-continued

```
cauaauaggc acuauuauga uuggauuuuc cugcuugaaa guagcuagau uagaguagga  54840
aaccaaaaag augugaauuc auucagucau ucaugcauuu gcauggauug agcuaccuac  54900
auuugaauaa augcuguuaa ucccugauuc cuuggaagcu cacauuggag agauaagcau  54960
gucauuaaau aaugccauaa uagugguauc ucagaggacu agcagaacau aauucaaucu  55020
gacagaguag aaacagauug uacaaaucca auucaaaaca ucauaaaucc ucuaagcacu  55080
gucaauucuu ccuccaaauu aucucugaaa uuccuccuuc uuucccauuu auggccucca  55140
uuuacagaag cguguacugu cucucuuagc uguuugccag gccgccaguc ucuugcuguu  55200
cagcucucaa cugcuuccag caagaucuuu cuaaaauccc aggcuugcca agacuuagcg  55260
cccacagcuc cacagugacu ccucauugcu guuaagguaa aggccuuccc agucuagccc  55320
uucaugcuuc uuccauguuc uaugggacug ccccaggcuu cccaccuggu accacugagc  55380
cuuuccaucc uucccccacu cgacugccag gucaacaccc acacccacgc uucaggacuc  55440
agguccuaug uuucgggccu ucuucugugc accauucccu ucccuguagc ccuugaucau  55500
gauuuguuua uacgccuccg caccuucaug gcccugaacc ccucaagggc cgaaacugcc  55560
uuacuuuucu uuuugacuuc ccaacuuacc uuaguggagc uguagucaca uagaauagac  55620
gcucauaaau gcuucucugg gcuguaaagg uugaauuuuc cagcuaagca aggaagaaag  55680
acaauuucag gcaggaggaa gggcauaagc aaagugcaga gaugugaagc ucaagagaaa  55740
uggaugggcu gggcagaggu guggcugcag caucagggga gaagaaguag ugccuggagu  55800
cagcaggcac ggcuugcaaa agcuucaccu auaggugaaa ggacaccauc ucuugcacca  55860
auaggcucug ugauuggagg caacuuugcu guuuuacugc cagaaaacug aggaugauaa  55920
cccaaacugc aguucaagug gcauucacug guguggcuga aaugggugguu uguggccaga  55980
auguggucug auuggucagu gcccagcucu guugauuagc agauguuuug aauauaguag  56040
cauccaugug cccaaguugu ugggaugauu caacaagaaa cuuuaagagc ucaagugccc  56100
ugcaguuguc agccagguga uucucuuccu uuggacccag uuagacgcag gcauuaccuc  56160
guggcuuugc cccaguguga aucuuugucc uccaacuuga ucuuuuuauu uguuucauua  56220
uuguauuuaa guuguuuauu uuagagacag acauuuuuua acagcugugc auuuccuguc  56280
ccuuuguuuu ccagucguca uguguuuccu uacucucugu gggugaacgu uucagauguc  56340
uguuugcggu gcccagcgug caagauaaaa uuuauugcag ugccuucggc cucuaacuca  56400
ccauuccaac caauucagau agcccaaggc uguuuuaucc aguggauuuu uccauguagu  56460
gggaaauaaa ucuugaaugu uacuguuuag auuagccagg aaacucauuc ugggauguuu  56520
gcccacaucc auuggcauuu cucaaaagga accccaggug ucuaccuuga caccagcagg  56580
gccacuugag cccuccgcug gcauucaucg cccgcuuugu ucucagccug aguuuaggag  56640
uuacagaugu gagaggcggg auuauacagc caacaucucu aagcgggcag uggcucccuu  56700
acccucgaag accucacucc uagcacgucc uggauguauu cgucaaaaua uguccucuua  56760
ugccacguca gcacaggguu gcuccccacu uugaucauca aguuuaaaca aaaggaaaga  56820
uuuucuuucu uucucugccu cuacuggaca ucauuuccca ccuaacagau aauuuaaugu  56880
aucuguuacu gaauguguuu gaauuacaga cagagagguc acaguuaaag aaggaagccu  56940
gcugcuacug cagcuugucc ucccaaggag guguuugauu uagcugugua aacaaaugac  57000
ugcauucucc agagguccug aacacagcug ccugcgcugg agagggcuca aaccucuucc  57060
gccaggguga acucugcuuc cuggugagug ccagcaaaac aaccaacaaa gagcuguagg  57120
acuugugugg acuucaaaug gugguggucc ugccacuugg gcucagccac agcaguuagg  57180
```

-continued

```
aaacuaaagg ggaggaggaa agcccuuucc uugcuuuauu gucauuggcu gucauagggc  57240
auuacaaugg uucucuuuga gauucugagc uccggcuaua acauuugccc agaaucugcc  57300
ucugaggccu uaagacacug uguuuuuauu cagcaaagau gcccuuugac uccuuuuccc  57360
acuaguggug cuagguuuga gcaccuuaca cuggccccuu acaauagcca guucuugucu  57420
accuacauuc uucccuaaca uucaugauug cauaguuacu cuuaguguag aagcagacag  57480
cuuuuacaca uagacuccau ggccguagcc ucauagaacc uacuauauuc uaacuugcaa  57540
gcuaaucaga ccaaauauau caaaaucaaa aaccucugcu gagaguuuau ucauucaucu  57600
cugucuccca aacguacuua uguacauacg ugcacuaaua uacaugucca uuagccaaga  57660
uuuugauuuc agggaucaaa gcaaguacca auagggaaug aggucacuug cugcauggca  57720
gguggcuucc ccaugagaau gcaaggccac cucaugacuc auacuucaga gggugaccca  57780
ggaacuucug auucaugucc aaagcagcuu cuacaauugc ucuaccuuga ucuagggaag  57840
augugggag gaugacauuc gggauuagcu uuauaaggcc uuccuguggg cagaguuguc  57900
ugacuuucac cuagugauca acaagcagcu agcaagcauc agugugugag gccccacgcc  57960
cucucagcuc cccuacugcc caccugggac augggcuuug gcaucugucc auagcauugu  58020
ucuaaccaaa ugagguguua uggaucagcu caggauggga uauguuccca gacauauuau  58080
uuaaagaaaa uagcucccuu ccuccccuga uaaacagcug ccauggcuaa aagguaaccu  58140
ggcuggggcu uaaaagucug uugacuuuca agauauuuug caaaaacagu cauaaaaaug  58200
guauuuauca gauccuaacu auuugugaga cgguuuggua uaccauagug guuaaaaaca  58260
caggcucuuu ccagaggagg uuuacuuugc uuagucgugu cuccuaagug aacuuggacc  58320
ucauaagguu guugugagaa ugaaaugggu gaauaugagu aaaguccuug gaccaguuuu  58380
ggccguauag uaagccuuca gcaagcaucu gcuuuuauuc cuacagggag gcaauuguaa  58440
gcccuucaca aacagcgucu aaugugaucc uuagaacaaa ccuaugagau agggcauauc  58500
ucaauuuugu agguagggaa acagaagcca cacaauuagg aaauggcaac agaucuguua  58560
gacucuuaaa cacuaugcua caccaauuug caaggcaagg aagacaaagc accuuugaaa  58620
augggucaga uguuuuaggg uaaaugaacg uuugagaauc uuuuaaguuu uuuuuccccc  58680
agagauuauc aagguaucau uguaggggga ugcaucagga aacaugacua ugaaucagcu  58740
gccugauaaa ccagccagga uggagcccac gucaucacag cagucagcaa ugccacugaa  58800
aaacaucagc ugcuuauucc cguauagauu uccccuuaag acaugaaaag ggaguucaaa  58860
gagaaugggc cagauaucuc ugagagucau auuacuaaaa uauauuuauu uuuacuagcu  58920
uuuuuguuuu aagagguaua cugucauuag cacuguagca aaaauucacg uuuuauuaau  58980
uucuccuagu uuaucaugug auucuagggu aggaugcaga guuauauuca aaauacacaa  59040
aucaacucaa cucaguaaac auauaucgag gcccuaucau gacaaaaugc uauucuagag  59100
accacggcga acaagccacg gccccagccu caaagaaugu acuaucuuug gaacugugcu  59160
ggccaauaca guaaccagca gccacgcagg gcuauuuaaa uuuaaauuaa uuaaaaguaa  59220
aaacacaaug ccucagaugc auuagccaca uuuuaagugu ucaauagaua uuuguggcuc  59280
cugccugcca uauuggacag ggcagauaua gaacaauucc aucacugcag aaaguucuac  59340
ugaacaaugc ugcucuggag cagaagaucu ucuuguucag ggauguuaca cccccgcuug  59400
uggcuagagu guggcuuauc cucagagcaa ggauagggga accauggcac ucugcaggcu  59460
cagcacugaa gacacggaug caggcucugc uucugaccua gauugaccuu gggcaaggcc  59520
```

-continued cuuugcuccu cugaucccaa uuucuucacc agccaaguaa gaacaucaga ccacaagccc 59580
ucuagggcuc uguccaaaug ccccaugacu gagugaacug guagaacauu cuaugugugu 59640
gucacaacau gaagagcaaa gacuuucauc uccccaaaua auuuuguuuu ucguuuuagg 59700
aauuaaauuu cagauucacu cuaauugcca auacuaaaau ucucuauaug caguucuaaa 59760
cuugacaaac caauaaaaaa agauuauuug acuacuuauc uuuguacaac auugaggucu 59820
cccuaaagca aauuuaaaug cauauuuuaa aaauguauuc uagcaguuca guucagaagc 59880
ccccuggccc aagcaucaca cugucaaucc uuuguccuca agcagcaugg uugggugggu 59940
uaaguacuga caaacacugg gugucaggcc cauggucagg gacugugcua acagucuaca 60000
uauuagaugc caccuacccc cacccucaac agacccaaac uauuuaucca auagcaaacc 60060
uugcauuauu ucuguccaga agaaacaaac auuuauugac aacuuuuggu gugugaccug 60120
uuuaaguccu acaucucauu uaaggacugg ucaauguuag gcuaggcaau gccuguuugu 60180
gagagaauca cugccuaaag aaaauucucc auuucccuua gcucuauggu gggugacuac 60240
acauacuggu auuucuuaaa gaaauaccaa uuccauuucc uuuuaacaua auuauuaaua 60300
ucucauuagc augguguca c ugaagccugg gcccaaagaa auaccaauuc cauaucauuu 60360
uaagaucauu auuaauaucu caucagcgug gugucacuua agccugggcc cuuuagaauu 60420
uuucauguac cuguguuccu cugcccauau cagcuggaac acuaauaguu uucuuccuuu 60480
uuaucuagaa gacugagaac auuacauggg accugccccc agggcaugga ggcugaggug 60540
ggacaguuua guucaggagg cccaagaagu guugggugug cagccccuug uucaaacaca 60600
gccucugaau cgccagaggc uuccggugca uacucugagg cgcaggugg g acucgggagu 60660
gagagguuuc ggcgaaugaa uugggauugc cuacuucuuc ccagugcagu ggagcuuggu 60720
ucugugguca gguccuuacg cccugucugc cuuucucguu ucuuuauuuc ucggguagua 60780
guuguggaau caaaugaccu gggguuugau accuacucua ccacgccucu gggggaguca 60840
cucagacucg uugaaccuaa guuccggggc ugccaaguga ggauaaguag uaauugcuga 60900
uccaccuacu ugacaagaua guagugaggg cccugagcgc caggcugugg auccagccuu 60960
ucccacgguu ccuggugugg caggaagaac ucuaggccug aaggugaaau uggggaggga 61020
gucccagcuc ugccacuguc ucucugggug accucaggca ggucuccuca aaaaaauaag 61080
auacuuuaua aagcucaguu uccucuucag uaaaaugagg auuccaggua acucacagau 61140
aguuuguggg gaugaaucug uuccuuaaag ccugcaguac aucaauaacc cagucuuccu 61200
gcuugcuuuc cccccucucc acuaccagug aucauagucu gaucccauag gugauauccc 61260
agcucaaaac ccuacauuag cuucuguggc uguuuaaggc cugcccagaa cuccccuggu 61320
cuuagcacug aaagcacgug uccggggaag cccugcauug gucguucaua cuacugaguc 61380
ccgcagggca aaccguccgg ucccacccuc cuuucuagug cugcugucac acucaccucc 61440
cuucacccua cacucccuuc ugugccuugc aauuaccuag ggaguuuuuu acaagauaug 61500
gaugcccugg cccugccacu agagauucug auuuaauugc uuggggguagg gccuggcaua 61560
gguaucuuuu aaagcuccgc agugguucua aagcacagcc acagauggga accacugauc 61620
uauucuugua gguccccaga uaccucaugu gcuguucccu gugccugagc ugaccuuucc 61680
cccacuuucc ucuccucggc uaauuccugc uuauccuccu acucaggagg cucuuccucc 61740
aggcagccuu cccugauccc uccaggaaga cuuagcugcg ucccuccgcu gggcuucccc 61800
aauacacugg gcuugcuuuc auuagaaccu gauccuucca cauuaugguu guugguuugc 61860
uccaauccuc ucccucauua gcucucaacu uucuuucagg aagagauguu uaucuuuccu 61920
ucuuguauuc cuagagucga ccaggcucug gcacauugca gauucucagu augcauucag 61980
ggaacaacuu aaucaagaca agaccaucug acuucuugug aguuacaugc uaagaaagaa 62040
augucgacac caauagcccu cacaaugaua ggaacaggag guuaaagaaa aggaaauaga 62100
ugcaaauagc aauauaagug cuuuaacaaa ucuauacagg aggacaacca ucauauucaa 62160
auuuucaaac auucuuaguu cugcucuuuu gugggguaaug guuuuuuuuu uuccucuucc 62220
aggagaagaa aagaggcaua uuauagaaau uccuccuccc ccagcauuac uugucacaga 62280
auuguaauug gaagugauuu cccugacuaa guuauuuugg cugucuguua uuuucucucu 62340
uccuccuugc ucuucccuca gcuggccauc cuguguguuu ggagagagcc agaaagguuc 62400
aaggcuagga auguuucucu cucucuuuaa agcucuuuaa ucgucaggcu uucugaucuu 62460
caaagcaggc uguagccagu gugaccccac ucccucgccu ccccaugcug gagaguaaaa 62520
gccuggagua uuuuugucau uuugaagacu ugcauauuug gacagccuug gacaucugga 62580
aagugugguc cucacuagcu cugcagggau aagagcacgu cagcacuucc aagcucucug 62640
gcgccccuac aucuggacac guugaaaaau uaacaccaga cucuggaguu aagcaaacau 62700
uaaguuuaua ggccuccuug cauuugacca uuuccuggga cagcagcccu uauccuguga 62760
cuuucugugu guagaguuga gucuuugcag uugguccucc ucacacucuc ucaacuuugu 62820
gacucucugc agugcuuggu ccuggauaag uuugaaagcu acaaugauga aacucagcuc 62880
acccaacgug cccucucucu acuggaggaa aacauguucu gggccggagu gguauucccu 62940
gacauguauc ccuggaccag cucucuacca ccccacguga aguauaagau ccgaauggac 63000
auagacgugg uggagaaaac caauaagauu aaagacaggu gauguuucag gaagggcucg 63060
cugcauuucu ccaaagucag ugggaaauua cauuugguag agagaaaggg auugagacug 63120
gacucauaaa ucaauaaaau uaaguuaaau aagaaaaaau aagauauuuu auaaagcuca 63180
acaaagaguc cuugaaugaa agcaauuaca gagucacauu guggcuaaua uucaaaacug 63240
agauuuaaac ugaggacuag gaaauagaau uggauccuuu ugaagcguuu aggagaaaga 63300
uuuuaagaga augaguuccg agucacccug uggucgggag gugugaguga gcuauccaag 63360
cccguuccca uccuuugucc cucugugucu ucucagguau ugggauucug gucccagagc 63420
ugaucccgug gaagauuucc gguacaucug gggcggguuu gccuaucugc aggacauggu 63480
ugaacagggg aucacaagga gccaggugca ggcggaggcu ccaguuggaa ucuaccucca 63540
gcagaugccc uaccccugcu ucguggacga uucgugaguc ugaaguucgc gauccuccuc 63600
caugacacgc uaaugggggu gcuggagugg gcuggggugg gcugggggug cccucaaggc 63660
uuccaugucu uuagagagag ccccagggac cagagccaaa uuggagagca uggagcucug 63720
acugaggaac cugcuucucc caagcuccag gcaggcacag augagucagu gcaguggugg 63780
gaaagggaaa agaguugaug uuguagcugg aaaagggaag gggaaaauua aagcaaggaa 63840
agugaggcug ggggagggga caaauucccc acuauguagu auguuuggua uguggaaggg 63900
uucuggucag aauguuugcc caaugauugc cacaucagca uucauuuugg acucuguaug 63960
gccaguaggu cugguuccug ggagcccugg aauaaugcag ccccuucccu aacuaacauu 64020
uccaugaugu augcucaaug acaaggcaga ggaauguguu ggaugagcuc aggaccugcc 64080
ucccuggaca cucccauccc aggccuguau aucuguugac caggaauaag ccaagcaagc 64140
agccuacugu uugacugaau auggauuugg gggguggguag agaaagggcc ggggguggagg 64200 guugggaggc ucauuuguca uuauagaugg ggucagacac acuaccaaaa cagcagcaga 64260

-continued gaucuacaau ugaguucacc uaaaacucag uguggacaca ggaaacccuc uuuuaauaac 64320
uguccaaugg guuuuccagc cucagcucua cagaaaacuu gagauaacag uggccagucu 64380
gcaguuaguu ugggguucgga caauaggcag agcugggaaa uggagccagg ggcgaaagcc 64440
cagguccacu uuaggaucag gacgggagug gcuggugggg aagugaggug ggugugggga 64500
ggcaauaggg agcuggguca uuugguaugg gagaguccuc ugguggcuag ucccagaagu 64560
gcaugcuuua cgaacauaug cuucucuccc uagggccacc uugagugaaa cccucccaug 64620
cuggaauugg gcccuuucag ugacaacaca caacaguuuu caauagauaa uaaucccaag 64680
ggcuuuacua gcacaugaaa cacagggaaa acguguaaag uucacaagaa agucguucca 64740
guguaucaaa ucuauccugu uugccaggug gauauaccag ggucuccucc accugugcau 64800
ggcugguggu ggguccagug gcuguuggau aacugaugua uugauggauc auucgccuuc 64860
ugaaagugcc aaacugauua guuauuuugu gugucuuuuu guguaacuag gguuugaccu 64920
uccagggcag acugugcugg ggcggcugac cccuugggga gccaaguuau ugcucuuacc 64980
accaccacuu gcccuuguca guccuccacc cucuuggguu ucagugucag cauguagcug 65040
ucuacucaga ucccauccac aucaucaagu cugcaguuuu uuccuugcaa ggccuuacag 65100
ggaagaucuu ugacauagag gauauaauuu uauugacaca uuuuacuugc agagcauuca 65160
cccgggcuaa ccagaaagcc agcacucugc uauaaacaaa aaauaaugcu ucagggcuaa 65220
cauggaaugu guuaaaagau uccagcccau uaaaugucca ggggagguuu uccuguuuuc 65280
cuuucccucc aucugggcuu uguucucaac acauucauuc aacaaacauu uauucugccu 65340
cuaccaggua cagagcacuc uacuauucug cuucucuccu uuugcuuuag uuucaugauc 65400
auccugaacc gcuguuuccc uaucuucaug gugcuggcau ggaucuacuc ugucuccaug 65460
acugugaaga gcaucgucuu ggagaaggag uugcgacuga aggagaccuu gaaaaaucag 65520
ggugucucca augcagugau uuggguguacc ugguuccugg acagcuucuc caucaugucg 65580
augagcaucu uccuccugac gauauucauc augguaagcc aaauggagaa ggcccagaaa 65640
aucuugaaua cuuugguucc uuuccccuuu ccuccuguuc augugccugg auuagucaug 65700
uggccaccaa ggagagcgug acaucuagcu ucccagcccu uccuuuuagc caacguggga 65760
gacacucaaa gagacgaaau cuccugaagg agccacugua ucacagcauc cucccaucuc 65820
ccacuuccug cccagggguc caugguccac acagacuucc caguccccauu ccgugaccau 65880 cuggagaagc ugcuauuagc agagcccugc acagggugau aguguaauua aaguggucuu 65940
cucuuuccaa acacagaaaa aaucaguuca gggaguguuu uccugggcuu acaauuuuaa 66000
cuacuggcua gaguugaaau ggggaaagcc uuuugccuuu ucaguagcag uaggggagga 66060
gaucuggauu auuuacuuau caucaucaug gucaccuccu acauggcuuc accaaaaaac 66120
auucugcugc cugaaaaagc uccaacaccu cucucucuuu uaaaggaugg aauuuggagu 66180
ccauccuucc ucagugauaa ggaguuuuua uagccacagg cagcaucuau uggucugucc 66240
ucugcaaacu ugcaacuccu cugagagcua gacuuggaaa ugaaacauua uuuugcaaug 66300
cgcugcuauc cuucauuuuu agcuccucca ccguagauga uaguuuguac uuguuaaaug 66360
auaaggauau aaauuuaggu cauuuuuuau auuuuauugg guggaauuug guauaauuuu 66420
uagacuucag gcuuuacagg cuccugagau ggacugauug agcuuguucu acuucuuccc 66480
caucaugaua ggaagugcug uaccacacua ggcagugugu guagugacca cagacuggcu 66540
gagugucucc caucccaugc uggcccauau cugguaccca ccugauccac aaauguucca 66600
ucagauccug uucaaacaac acaucuccag uuaagccaaa ucuugcccuu ucuccuuacg 66660

```
guaaaaugua cuaaaucuga agguuuuguc uuuuuaaugu ugcuccauga uccagugauc  66720
uguggccuug guuaugcucu gugcuagagu ccuaacaaga caaaugcuaa gguagagguc  66780
auucugcuca aacaaccuga ccccaccugg augugggcuu acauuugcaa agggcaccaa  66840
aguucuaaga gaugagggga ggagcugagc cccuuguccu uaucuagguu ucccuuguuc  66900
uuucccaucc cucagucugc uucuuuuccc aguaccaaca uguuuguguc cucagaauua  66960
aaggaguaaa aauguguaaa caucugacua gcaacagcca ugagauuuug ccuggcuugu  67020
ugauaagcag cauugagauc ugcccuccua agaaugggcc auuaggucuu caaagcuuuu  67080
acgaugugag guaaagaaug uucaccagga guuucaugca caaaaggguu ucucuuugug  67140
ggaacuagaa cauuguucca gugaugacgg aaacagggcu uuccauacca aaacaggguu  67200
uuccuuugaa ugacucuccc accuuucccu ugucucuucc uccccaccuc aacaacacag  67260
gaaagaagcu ggaagcaggg acaaugggaa ggucccuuug uuacucgagc uauuagaaac  67320
aaaaagaaaa guggccaucu gaggaagcca cagcugguga aacuguaggg ucacagagug  67380
aauuacaccu cuggcuuaag ucagugaaaa guccuagaag uuuguggucc uagaaguccu  67440
aaaaguuuau gggacuuugu uuugagcaag gauaagaaau ugauuucagg cugggcgugg  67500
uggcucacgc cuguaacccu aauacuuugg gagacagagg cagguggauc acuucagguc  67560
aggaguucca gagcagucug gccaacaugg cgaaacccug ccucuccuaa aaauacaaaa  67620
auuagccagg ugcgguggca caugccugua gucccggcua cucaggagac ugagcaagga  67680
gaaucccuug aacccaggag guggaggucu cagugagcug auaucauauc acugcacucu  67740
agccugggca acagagcaag acucugucua aaaaaauaaa uaaauaaaaa agaaauugau  67800
uucauucuuc ugagaacugc aacaacuacc uuaaagugau uccauccaaa acccacaugu  67860
ucagccaugg acuugcuuuu auggagcugc guguggguga cacacaaaau caggagcucu  67920
gaguccuaau uuagacuuuu auuuagauuu ccucaaauuu ggguuccagu uaagcguggg  67980
ucucuucugu gccccgcucc ccuuugccau uuguuuuauc uguucuucag ucuguucugu  68040
caguacccac aggcaggaga gcagaaagga gaaauggcag ccacagcaga caaauggcac  68100
auucguucca cucagcucuc gcaugcccau cacagauaca gcucauuggu cucuuuucua  68160
ugagaggaag ccagagcucc agggaacuac ugccaacuga ucagaacuca uuuaggacau  68220
ggaccuauuu guuccuuuau guuccuggga agagcacagg augaauucua uguacucauu  68280
uacguguuca gagaguaaag ugccucauag gaugccucca gcaaaagaua accaagaagg  68340
ucuaauaccu uugacaaucu caguuuaucc uauaguguaa uuggauagca guuccccuag  68400
caaaaguugc uaguuugguc cuauuuucua cauagccaaa gugauugauu cauugguuaa  68460
ugugaaaguu acugaguacu gccagcaggu ucuaggaaau auauuugugu gauauucaug  68520
gaugggg agg aucaauccac uuccaaguga uuuggauuaa uuacugguau uuucaccugu  68580
gugggguagca aaccucagaa aaucaaguau agaugacggc auaggacagg ccaggcccca  68640
ggcaaaaugu ugaagcuccu cuggaguucc cucccaucuc ccucuuuugu uuuccauaua  68700
ccugguuuau ccagggcccu ggagaugcuc caagaccccc uacccagguc uuccucccuu  68760
gucccagcua uauuucucca uauuaccacu cuucucaccg aggauuugcu uacuuaacac  68820
auaauaaaua cuauuaaaag agaaacuuag gcacauuaaa auguuagagu ugauuccagc  68880
aaacagugau ucacaggagg cuccagauca caagugguuc agggccccac ugaggggguag  68940
ggaagcaaga caaagaaaaa caaagcaaau auuugauugg uucaagugga aagucccuga  69000
```

-continued

```
uuacagguua gugggcaguu ugugauuagu uaaguuucuc uaaguugggu uuugguuugc  69060
ugauguagga acacagaaug cuggggccgu uucaaccuaa uggucuccca auuaauuuuu  69120
uuaacauuac ugaugacugu uaggagucua augugcuacu ccucccaggg aaaauggcau  69180
uccuaggauu aaaggaacuc agcacaugga gugugcguag aaauuuagac acuaacugca  69240
ggcugguggg agagagcccu uuagggcaga augagaaggc guccggccaa gggcaggagu  69300
uacugacgca uggccucuug guuucagcau ggaagaaucc uacauuacag cgacccauuc  69360
auccucuucc uguucuuguu ggcuuucucc acugccacca ucaugcugug cuuucugcuc  69420
agcaccuucu ucuccaaggc cagucuggca gcagccugua gugguguacu cuauuucacc  69480
cucuaccugc cacacauccu gugcuucgcc uggcaggacc gcaugaccgc ugagcugaag  69540
aaggcugugg ugaggcccuu gggcuggccc cuguccuaca acacguuucc uuggaagggu  69600
ccguagcagu ccuggaggcc cagccugccc ucugaggggg uccacuuugc cuuugaccua  69660
agguuaaaaa guucacguga ggcuaaaaug uacaggggca aaagugggag caguccucac  69720
cccgagcgau gcaacaguga cuccucacca cgccugcuug auucaucugc ccuggaaagu  69780
cauuaaaaaa ccaguucaac ucaugggucc cuuuauuuac ucacaagaga gagccagcag  69840
cccauuucac uaguuuuccu uuccuacucu uugagaagaa ucagaaggga gggagcuugc  69900
cacuuuacua ucugucuaaa gagauguuuc cauuaauuaa agguuuuugu uuugcuucaa  69960
aaaaacuuga auuggaguau uuccacaagu aucuuuaaca ugcucuacca auguuugcag  70020
aaagaagugc agaaaugaga cuguccacag agucaggcuc gcuggccagg agaggacucc  70080
cgaagcugac uucugauggc cugagaaacu uccuaguuca caauucccag acccagacaa  70140
agagcacugu cuuuucucua auuguuuuca aaugggccau uuccacccuc uaaucagccu  70200
cuggcccugg agggugcagu uccccuuguc cuccggaguc ucccugucuc ugugcuguag  70260
agucaagaag ggacaaccac cugcccucac ugggaaaaga cagaaagucu gacuuguucu  70320
cacgacucac acuuauuagg cuccagaggu gucagggcau cugccuuuca uuucuuaggu  70380
uaaauaagaa aucaauugcu gccauuugua guacccaauu uucuaaaaug aucacaaugg  70440
auaaguggca agaaauccuu augacucauc ugugggcaga guugggcuau uuugguaauc  70500
cuugaguagg cagauggaau uugaggccau cuucuugggu acauagauca cuaggaagcu  70560
auaggucuag caacugugga uuagggcugg gcugagaauu guuucauguu uuuugugacu  70620
guauagcuag agacucucuu guuugcagag agacacucug aacucccccu ggccgucaag  70680
ggaaagacug ccuucacccu ccugagcuga ccuuacacug agagacaaug gggacccucu  70740
uuuggcccuc cccucuaccu cgagggcauc ugggugcugu ugcauuggau aaaaggcacu  70800
gcucuuuuuc ugugcccucu ccgccucacu gcagagcuua cugucuccgg uggcauuugg  70860
auuuggcacu gaguaccugg uucgcuuuga agagcaaggc cuggggcugc aguggagcaa  70920
caucgggaac agucccacgg aaggggacga auucagcuuc cugcugucca ugcagaugau  70980
gcuccuugau gcugcugucu auggcuuacu cgcuugguac cuugaucagg uguuuccagg  71040
uaagcauccu ccucuauagg guaaagguaa uugaguucuu cagaucccca gcccucucca  71100
uucaucuagu uuaaauuuca uuucuuccaa gcucuuuguc agaaccagca uuugaaguuu  71160
aaaucuagaa guuaaaaauc caccagcaaa uccuacuggc ucuacuugag aaacaaaucc  71220
agaaucugau cucuugucac caccuccacc acaaccuucc caaugccagu cucuuccuuc  71280
cacuaccacc ucccaucagu ccauucugca cacuguauuc agggagaucc uuucagaauc  71340
aaggucaugu ggugucagcc cucucuguca aaugcuugca cuggcuuuuc cucucuuuca  71400
```

gaguaaaacc caguguccuca acccuggccu ccaagcugcu ucauuauccg gccuccaacu 71460
cucuucuuca ucuuacgauu uucccuacuc cuccauguuc cucugcucca gccacgucgg 71520
ccuccuuacu gacuguuuaa uacaccgagc gcauuuccuc uucagggccu uuccaccugc 71580
uguucucaug ccagaagcac auuucucucc ccacaaccug caacccgccc cucauaucug 71640
caggcuugcu uccuuacuuu guuaaggucu cuguucaaau gucccauuau cacagggauc 71700
uuuccagacu gaagagaucu acauaacuau ggcucuguaa acaacauucc uccaggguuc 71760
cuguccccuu acccuacuuu auuuuggggga acauucuuca ccaucugaua caaugaugua 71820
ucuuaugcau guauuuacug acucucugcc cuuaguagaa uaugagccca gagagcaugc 71880
auguggucua uuuuguuaac ugugacaguc ccagugccca gaauagugcc ugaccuuugg 71940
ugggcacuga auaaaauaucu aaguaaucug uagcauggaa aaucagcuuc ugaaaauugg 72000
cuguuugcac ggucguguau uugcuuggua gaaaaucaaa uuuuccuuca aauuagcauu 72060
uucugguaac uagagcugcc ccaucuuccu cugaguggguc uccaagucag ccaauagccu 72120
ugugcugugg cagccaugcc uggcucuuga ugcuguagcc aaaagcaggc aggggauggu 72180
gaggcugguc caguccaugg ggagggacaa acucacagcu cucagaucau cucagggcag 72240
ccuuuguugg cagaaauagg uaggcagcca cccugaauag gaggaaggcu ucuagacugg 72300
gucaggaggc cuggguuugc auccuagugg caagcgugca uucauuuacu agggcugcca 72360
uaacaaaaua ccacuaacug ggcagcuuag acaacagcca uuuauaucuc acagcucuga 72420
aggcuggaag uccaaaauca agguguuggc agggccaugc ucccucugaa accuguaggu 72480
gcuugggcac uccuugacuu guagaugcuu ccugcugauc cuucgucugc acauggcauu 72540
cugccugucu uacauggcca ucuuauaagg auaccaacug gauuggauua ggugccuacc 72600
uugcucccau gugaccucau cucaacuaau cacaucugca augacccugu uccuaaacaa 72660
ggccacauua ugagguaccu gggguuagca cucugguauc uuuuuucuug acagcacuuc 72720
ugacaccaaa ugugugguuuu gguuuuuugu uguuguuguu uuggcaccaa ccaauucucc 72780
uauauuaaug gguuguccaa gaauucaauu gaauucugac acuauccaga auucacacag 72840
acuccacggg uucagucccca caaggcuucc ccgucuucag augccagcug gaaauguggu 72900
gcccaggcua cccacacuuu ugccaaaauc cuguacuuac aaucacagcu uuaaaaugaa 72960
ggaugcagcu caggaacugc cacauggaag agaagcacag uaugggggucg ggggaagagu 73020 uucuaugcuc ucucuagacg caccacucuc ccagcaccuc aaaguguuca gcaacccaaa 73080
agcucuccaa aucuuguugu ucgagaguuu uuauaacccu aucuccagcu ccauacuccc 73140
ccauuggagg uugaggguug ggacugaaag uuccauucuu cacaugugug guguuucugg 73200
ugaccagucc ccagaaacug cagcuaucuu ggggcucuac ccugagucac aucauuagca 73260
uaaacucaga uguggguagag gaaggggcuu auuaugaaua aaaaaagaca cuccuuucug 73320
ccaggaaauu ccaaggguuu uaggagaucu gugcccugca caggagcugg ggacaaagac 73380
caaguauauu uuguguuaug ccacagaccc caacaugucu uuuuggaggg agaccaaauu 73440
caacccauga cagugacuuu gaacaagaca uuugaacuua gucuguuuuu ucuauccuac 73500
uagauuguug gaaacagaua uaauagauga aaauuaguug auuaaaauug aaauuugugc 73560
auaauucaaa aguuuuauuu uagccaagcu aaagcuuuca uuuauucaac agcuauuuac 73620
ugagcagcac cugugcauga ggcucagcag ggccagguuc ugggaacaga gcgguggaga 73680
uaaagaucca gaccugcccc gaggaauaga caguccagug gcagcaaagg ccaugaaaca 73740

-continued uacggcaacu cuuaaaaaaa gccgagacca ugauuuuaca aaaucaacau uuuguaggga 73800
gcagaacuuu caaagagaac uggacuagaa auuugggagu cuuuuucuug gaacccuggu 73860
agauccagua gaaugaggga ugggggugua ggguuaaaaa cacugacauu agaacuggau 73920
uaccuguguu ggaauuccua cauuucuguu ucacuaucug ugacgggggg cagauggcug 73980
aaucucagug ugccucuguu uccuuucuca caagaauaau auuacuaccu aucuccuggg 74040
guuguuuuga gguuuagauu auuuaacaca uggaaagcac ucacagcaau gccugccaca 74100
gaaagaauau ccaguacauc uuagugauga ucaccauuau uauuaucuga cuccuggaaa 74160
aggacuugau uuaauucucu caugaaacgu uuucuuggaa aacugauguc aaccaagauu 74220
auuggucuug cuguugcuua uaacacccca aaaacaugac uguguggaua aaaauauguu 74280
ggaaggggua gucuuucugg gagccugaga auagccaugu aauaauaacu gcaaauaucu 74340
auaguuacaa uuugagguuc agguaaauaa acucuagauc uuauagaacu gcgguaaggu 74400
aggauaggga gacuccuucg acuuucucug uuuauuuguc ucuauuuuua ggagacuaug 74460
gaaccccacu uccuugguac uuucuucuac aagagucgua uuggcuuggc ggugaaggug 74520
aguccuuuaa aacacaaauc uuaauguuug aaaucaacuc cuugggcucu gugcaagaug 74580
uauauggauc acagaggugg cccucuaugu aaacggugug auuccugaug agucagcugc 74640
cuccuggggc ucugccccuu gaugggcauu gcagcgucug ggggaccacc uuucacaagu 74700
ugcugggccc ugugugauca ugaauggcug aucauggaug aagcccuggg uccuguacac 74760
cuuguccagu agacuaaauu gcccuauuua aaaaaggcca agccacuuca ggguucaaag 74820
aacuuuugca gcuuuucagu auaaagcaga aauccaggga aucaugaagg aaccuuugca 74880
uucaucuccc auugccuucc uugugccuuu uuauucuucu cugccuuuuc aaaauauaaa 74940
uuaguuuauu cucccaagau gaagacuccu ccuggggcug aggcagagcu guuaucuuca 75000
gggcaauacc ucagauucuc cugguguuga ucuuucuuag gggugggg aa aaaggcugaa 75060
agggcauuug cccacaacac aucuuaggua aaaggcaccu uuacuacuga accaaacagg 75120
aggccuagcu agagaaaguu cuagaagcag ggaaaagcac agacucuuuu gugaggucug 75180
agaaagcaaa gaaauuccag ggugaaagcg ggggacuccc cuagagcuga aguacucucc 75240
caucuguuug uugcucaccu accuauucuu uacuuuguau uauugggccu gggccaggac 75300
uuauccugca agcacugaga uggauguuug uuuucucugg gggauuaguc uuuuuuuuuc 75360
uuuuuuucuu uuguuuuuug cuuuuguuuu cacuggguca aacaaacaac acuuuaacag 75420
cucaggauuu uuucauugua uugacuuguc uaccuguaaa cuuguuaauu uuuuacuaua 75480
auaaaauuau cauauaauaa augaaaaauu ucaacacagg gcuugugggc auuuuauuuu 75540
ucucuacaau cccaacagau acucugccuc uuaagaaaaa aagaaaucau aaggaaaaua 75600
ugcuccuuca aaagugaauc acaaauaugu uugccaacgg aaggcaaaua uuuuucaccu 75660
gucucauagg cuggacugaa auggauuucu aaaacucucu aaaaccagaa aagagcugag 75720
ugucuccacc caaccucccu ccuuucacag auuaaaaaau aaaaaaugga gcccaggaga 75780
cauccaguau cuuccccuau uggucaccug ggacaaaauc uggaacaugc acaugcauug 75840
ccuggcagga acucauucca gugauuaaac ucuucaggag gauguuuccu cuugcuauuu 75900
cauuaccuau uugugcaguu ugauagcuag uaaagugauc aaaggaacug uggggcauag 75960
auucaaaagu ccuucaggaa gcagaaauag aagaacagua cuagaggcag cagguccccug 76020
accagcaggc ccacuaccug cugcuccagc acacauccug cacauuuuca gaggguggggg 76080
gacagagggg cccugggugg cuguugcauu gagaaaucuc gcccugcucc uguaugugca 76140

-continued

```
cuugaggccg agagcccuug gaugccuggu gacagugguu uccuccugcc ccugccuucc  76200
ucucuggcag acugacuggc ccuucugcuc cucuuccccu uccaggaugu ccugauaucu  76260
uuuuaaacca aaugccaagu uugccaaaaa gugucuguuu gugugugugu gugugugugu  76320
guucaaugcg uguguuuaua ccacacuuca caauuugucc aggcuuguau uaauaccauc  76380
accaggcuca acccuggugu uaauuccaag auacuuaaau gcccaucuag gugaauuucu  76440
cagguaaacc auauauucaa gcuguaguuu aagcuggcug cccgucauag cacuuugaau  76500
agacuuuguu uuuguuuuug uuuuuugaga cagagucuca cucugucggc caggcuggag  76560
ugcaguggca cuaucucggc ucacugcaac cuccgccucc cggguucaag cgauucuccu  76620
gccucagccu ccuaaguagc ugggauuaca ggugagcgcc accccacccg gcuaauuuuu  76680
guauuuuuag uagauacggg guuucaccau guuggucaga cuggucucga acuccugacc  76740
ucaugauacg ccuacauugg ccucccaaag ugcugggauu acaggcguga gccaccacau  76800
ccggccccug aauagacuuu uacucaaggu ucaccaugac uuucacaugu uuuguauugg  76860
aguaaaaugu gccagugggug ggcuaaagaa aauuaacuca uuucaaauuc aaaccugguu  76920
uucuuaauuu uuuuaaaauc acaguuucug aaacuguggg cuccucaugg cacauugaga  76980
ggaggaggug aaacucucca agucugaagc uccuguuaua aaucuuccuc uggcaaagau  77040
ugugugauca ggcuugagua ccucacaguc cuagagcagg ucaaaggcug gcuaggaaac  77100
ucauuugcuc ccuguaccuc ucccccuccuu uccugccuuu gcucguucuc agcucccggu  77160
gguagaguaa cacuggcuuc ugauuggugc aggguguuca accagagaag aaagagcccu  77220
ggaaaagacc gagccccuaa cagaggaaac ggaggaucca gagcacccag aaggaauaca  77280
cgguaaaacc ccgauaaaga auacacagca gaggcgagga aaaggcucua agcacugcag  77340
agggccagag caaaacaucu cauggcaagg guggaaagaa gccuaggaaa cugacucucu  77400
cuguggacaa guguuaaacc agaucccuuc ucagaggucc aucugcaugu guguggaaug  77460
aaugguucag cccagacauu agcgcauauu uccuggagaa agcaaauacc aacuauguag  77520
ugugccugug cccuuguuag gcaaauccca agugaguugc acaaaugugc ugacuuccga  77580
ggauuuagca agaacaauaa cuuuggucac ugggacuuaa agcggauaug agcuauaagg  77640
aaagacaaaa auaaaugcuu cuguguccag ggggaaagag acuccagggg agcugacuac  77700
acuucacuua cggcuuacaa aucuagaagg ccauucauug aaaccaucag aagccuuucc  77760
ugacagugga aguuaccuaa uaaucccuaa acugacgacc cagauuuaca aguuuuguuu  77820
uccuggcuuu ugcugcccuc aucuucucuc uuaaacuagu ucuguauuuc ucccaaggcu  77880
uuucauuccc uaagcauacg cauuucucug uggccaaaau gcucuggguu uagacaggca  77940
gcacagcccc ugggcucugc cugacagggc aggagagggu cuggccuuua ucccuccagc  78000
ccaccccagg ggccauuuca uaaaacuaaa gccagagacc ugcagccccu cccagaguua  78060
gacugcagua caccaugccu cuggcaagau ccuccuccca caguggaaag ucuaagccaa  78120
aucaggaggc uggggacugg uuccaccuca guugcaggca aggccaggag gcacggauag  78180
aagaaacagu ggacuuuuuc ccccuaggga aagaaaugcu uagagcuaca guauuaagau  78240
gacaaauuaa gcugugccau auagggugaa augaagcagg gauagauggg aggucaggga  78300
gaagugagag cacucgguga gggucugcac uggaggggggc augggaggaa gaaggagggg  78360
agugggguuu gagggauggu gaugaggaag cguggacugc ccuacccacc uauuggaaaa  78420
ccugggaguu cugaggagca agaagccuua gucaaaguca acucaaagau ucaagccaag  78480
```

-continued gugacuaaga gaauggcggu ccagaaaagg ucaugggaga aucugaaggc agauguuguu 78540
uugggaagau gaagaaccua agccgcuucc agaaauucau gaggaaaugc cccguggacu 78600
guuggcaaug agggccuagg accaagguug agcuuggggc caacucuccc uauagacagu 78660
gagugcauuc ugacaagcau gggcucuggg uucaaauccc aacucugcca cucaugccua 78720
uguguccuua auaggacgcu ugaugucucu gugucuaagg uuuccuggac uauggaaaug 78780
agccuaauaa augucuaccc cuuaggacca uuguaagagu acauugaggu aauuugugua 78840
aagcagucga agcagugccu ggcauauagg aggugcugua uaaacguuug augcuaguau 78900
uacuauuauu auucuggagu cuuccuugca acggugauag ccgaagccac aggggcaggu 78960
gacguuauag gcagaauaca agggccugga gacagagccc uggggccaug uaauuaggca 79020
uuauguuuac aucauguuca uuuuuuuucc uccaagacuc cuucuuugaa cgugagcauc 79080 caggguggguu uccuggggua ugcgugaaga aucugguaaa gauuuuugag cccuguggcc 79140
ggccagcugu ggaccgucug aacaucaccu ucuacgagaa ccagaucacc gcauuccugg 79200
gccacaaugg agcugggaaa accaccaccu ugugagucuu ccagcagaga agcuggcugc 79260
caugcuagcc ugucauuucc uggcuuaguc uuucccuauc agcggcuguc uacucuuucc 79320
cacaaauuuu agugacaaau auuugcggcc ccaaaaaugu guaaaagcuu ucugcaguau 79380
ucaaagauca cuaauaugua uucucuugau ggggagguag aauacguuua uugccccuuu 79440
ugugugccgg ggaaguggac auucauucag agaguugaag ugacuuuccu gaagccacca 79500
aguugucaug gcucagcggg ggcaaaagcc aggcaccaca guugccucuu guuucucaca 79560
ccuugagucu uuccccccau cucaacaguc caugguggug aucaagucau ggccacuguc 79620
aucaugugca uggaagcuau agaguccucc uauuuccuuu cucuuuucuu uucuuuuuuu 79680
uuuuuuuuuu uuuugagaua guaaccauua cccaugcugg agggcagugg ugcgaucuug 79740
gcucacugca accuccgccu cccaggauca agcgauucuc ccaccucagc cucccaagua 79800 gguggggacua caggugcaua ccaccaugcc cagcuaauuu uuguauuuuu uuuuuuuuuu 79860
uuuuuuuuua guacagacag gguuucacca uguuggccag gcuggucucg aacuccugac 79920
cucaggugau cugcccgccu cagcuuccca aagugcuggg auuacaggcg ugagcgaccg 79980
caccaggccg aguccugcua uuuucaagga acauuccuuu uccuaccaau cauuaggcag 80040
gcuucaacau cagcugauga ggguuagugg ucguucugga gaaagugaaa aaagaaucag 80100
ucucuagagg ggcuugugga guaaccgccu gguaacagaa ggucagggca gggaaggcaa 80160
aggggcucug cgcggaucuc ucagcuccgc aggcgcccca cucuccucca agggacccga 80220
gcgccaucug cugagaggag aacacggccc gccaugguuu cccaaggagc agcagacacg 80280
gaccucgcag ggggcagcga acccacguga cacagucuuc aaguccuuug gagagcccca 80340
ggaaggaaca acagcgugua cacccuguga uggaauguuc ucuagggcgg uucaguguga 80400
auggaaugug gggccggugc cauucuaauu gguucuguuu cccucuagug guugaucgcg 80460
gagauuucgg cuucuccauc aggacaaguu cagauagccu gagaugguau cagaacucag 80520
ggacagagcu gggugugggcg gcccugcauc caucugcuuu cucuccaugc uaacugauau 80580
ggucagagag cuggaagcaa auuccaggac cccagggcuc cgcaaaggca aacacauuac 80640
uucaucggcu gcugacaugc aacuuccccc agggguuaaa acaauguuua auacuaacag 80700
uaauaauauu uuugaguuuu acuuuaugcu ggcgcuguuc uaauguugua aguguauuaa 80760
cucauuuaag ccuuacaaca accuaaggac augggaguca uaguucccau uuaaaaaaaa 80820
aaaaaaaaaa agcccaccau ugcucugagg cuuuuuaugu uuuggaucca aagcuaauau 80880

-continued uggugguggu aauucccaug ccuggcuucg aucaauuaau cagcaaaugc cuaggacugc 80940
uuaggguucu ggccuucauc aagaccuuac ccgggcuuua ugaugaugac accuggcuuu 81000
ucaauagcca ugacugcuca cccaggaggc aacgccucga gucaugcacc gaacaccuuu 81060
uauugauccu cuccaacacc aggcuccgug auggcugagc uggggacacc ugugacugca 81120
cgugaacauu uugaggcugg gaaucccaaa ggcccucggc guuggccugg gagcaccaug 81180
aaacaaguag aagcagagaa ggauggcaga gguggcccuc ugcauuaggg ccuggaugua 81240
uacacuggug cuaagggggc cccacagcua auaggggguuu gaguuugacu gacagcccca 81300
ggcaggaauc ugugagaguu cucacugaac cuggugaggg gguggcccuc cuaaggcaug 81360
uugcuaaagg ccaucucuuc ugccacugac gccuguguuc ugcaggucca uccugacggg 81420
ucuguugcca ccaaccucug ggacugugcu cguuggggga agggacauug aaaccagccu 81480
ggaugcaguc cggcagagcc uuggcaugug uccacagcac aacauccugu uccaccagua 81540
agcgacacag gaacugagac cgccccaucc ccucuccuca ccucugcccc cagcacacuu 81600
cucuagagcc cagcucaggg gugccaggcc ugggcacagg cagagauaca gacucuuauu 81660
ugguuucccc uauguuuaaa guccuuuguc cuacuugcag ugagaauugu cccugagaau 81720
augggacucu gccucugcug cucagagcug agggcuccuc ccucagaagg gugaggcugc 81780
cuucgcucug acagagcagc ugaucgaucc ccgagccccu ugugcagccc ugaaguacuu 81840
ccucucuggg accaaagaca ggagaaccau uguuccuuuu uccuguugaa gccacggccu 81900
gaaaggcaaa cuuuucaggg ggcuuuucag uuacuuuuuu uccccaauaa gauaucuuuu 81960
auuucuuauc uaagaagcua cgcauaguca uugugaaaga aaaaaaagga agggaggaag 82020
gaagggagga aggaaggaag gaaggaagga aggaaagaag ggagggaggg aggggagaag 82080
gaagcgaggg agggagggag gggagaagga agggaacagg agggaggaaa agggaagggg 82140
aaggaggaag gaaagggaag gagggaggaa guaaauauag guaaacaaaa aauugaaaau 82200
aaaagucacc uguaauuuca cuacucagag auaaccgcug aguuauaaca uugguauaua 82260
auuuuuuaga acuuucuccu auacauguau agauagauaa acacauauac uucaaaauga 82320
uaaagaauag uaaaacuaug cauacaauuu uauaaccuga cuuuuuuuuc aaaaaaaagg 82380
auugcuuuuu uaaacauaag auaucaggaa caucuuucau gucauuacau auucuucuau 82440
aaaauaauau uuaauguuua cagauuauuc cauuguaugc augaacuaug uaagccaucc 82500
ucuuauuaga uauuuaagca gggucugcua uuuuuguauu guaucauaaa caccaccaca 82560
gugagcaucu ugauugccaa aucaagaaua cuuguccuca auuauuucug uaagaucagc 82620
ugcuggaagu ggaagugcua agccacugcu uuucucguug ucccauccuc cuagccucac 82680
gguggcugag cacaugcugu ucuaugccca gcugaaagga aagucccagg aggaggccca 82740
gcuggagaug gaagccaugu uggaggacac aggccuccac cacaagcgga augaagaggc 82800
ucaggaccua ucaggugcuc agagcuggau ggagacaggg ccacagaugg caaauccaug 82860
gcuccccagu gcacccagga ggcaggggag gcuuggagca ggagagcuuc uaagggucggg 82920
aacaccucug ugaaguuaca ccaaaaaucu aagagcagcc cccagaucau uuucccugca 82980
gagcacuguc ucacagcagc cuggguuuua uuuguccuga gauugaugug cuugaacagu 83040
cuucaaaggg ucugauccga ggaggugagg guugcccuuu cugcauuuac aaagccugaa 83100
caguauuagg gcuuugaacg cuauaaacau cuaagaggca gcaccaaacc acugcugggu 83160
uaagguaccc ccacaaugcc acuugcccug ggccuuucuc uuccucaccc uccacagccc 83220

-continued

```
cuuaacucuc ccguccuucu ugugccucca gguggcaugc agagaaagcu gucgguugcc  83280
auugccuuug ugggagaugc caagguggug auucuggacg aacccaccuc ugggguggac  83340
ccuuacucga gacgcucaau cugggaucug cuccugaagu aucgcucagg uaacagcugc  83400
ugcucagucu ccugggcugg gcucucacug cagcccuagc uguggucccc acucucucac  83460
cugccauuuu guagcugagu acaggaacca caaugacuac acucagaagg ggguuuauca  83520
gugacuuggu gaaucuaagu uccagcuaaa gccuccugag guuuuuacaa auauaaacag  83580
agaaucacug augaugcaac cuacuuccca aaauauuuua gaaaauucuc uugaccugca  83640
gcccuucugu cuggaauaau ggaugcuacu cuaggugaau gucuucucug accaugggga  83700
cccaggucac cugcaaacau accuagaagc uccauagcug ucagaugacc acucaggacc  83760
agugugaggg ugaccugcug ggcauucagu gcuccagagg guggccacag auggaagugg  83820
cuccucuguc auggcaccuc ucagacaagg ggcucagauc agaagagaca gcaagcagag  83880
cugagugccc auagagguaa cagcacgguu caaccccgug gucaagccag agcuuucccc  83940
cuugcucuac ucacacagcg uugccccgug ccuuucucug aggguuuguc auccugaaau  84000
ccucauugcu auuuucuuuc uuucuuuucu uuuuuuuuuu uuuuuuuuuu ugagacagaa  84060
ucucgcucug ucgcgcaggc uggagugcag uggcgcaauc uccacucacu gcaagcuccg  84120
ccuccugggu ucgagccauu cuccugccuc agccuccuga guagcuggga cuacaggugc  84180
ccgccaccac gccuagcuaa uuguuuuugu auuuuuagua gagacggggu uucaccgugu  84240
uagccaggau ggucucgauc ucccgaccuc aggugauccu cccgccuugu ccucccaaag  84300
ugcugggauu acaggcauga gccaccgugc ccggccugcu guuuucuguu aaugacaucu  84360
ccaguuagug agaguaugca cgugugugu cuuuaugaag aguauaaauc cagagcuuaa  84420
ugauccagaa aauguacaua ugaaacuccc uagaugcuga ccauaauaca ugagccccua  84480
auauagagau uuauuugaau cagauccuau gcuggauaca gagacacugu guguggcaau  84540
gcuuuacagu auguaggaag cuaugaaaug uuaguuauua uuguccuaau augcuggaau  84600
uugcugcuga auuaguuccc uuggguuuuu uuuuuuaguu aacuccugau uuuugcaacu  84660
auauagccag gaaauugcug uacacccuuu accaacaaug cccaacccag ggcaggccug  84720
gugauugccc uggccccuac cuugcaggca gaaccaucau cauguccacu caccacaugg  84780
acgaggccga ccuccuuggg gaccgcauug ccaucauugc ccagggaagg cucuacugcu  84840
caggcacccc acucuuccug aagaacugcu uuggcacagg cuuguacuua accuuggugc  84900
gcaagaugaa aaacauccag agccaaagga aaggcaguga gguaggugucugcccaggga  84960
aggacccugg ccugggugag aaggagcaca cagcacgggg cugccacucc agacauggcu  85020
acucacacag gcucucgcca ccagaaucag ugucuuuguu cugggaccau uugcagaaga  85080
uuucgaugaa cacauucuga agccuccucc uacagagaug cuuuagccaa aaugaaacaa  85140
cuagcuuuaa auggucugca aguauuacau gccagauuac acaccaguuu ggugcgguuu  85200
ggugcaacau agaagugagu gucuuauucu guaagguuag gcuguuuuaa gagcaauugg  85260
uugagcuuca uuucaacauu aauauucccu aauuaaaccu gaauuucagu gguaagugaa  85320
aacuaagaag aggccuccuu gggugcuaua acauaaaaau gaugaaggca aaaaguacca  85380
accagcagag accacuucag cacaucagga gacccaguuu uaugucugug cugcgaagug  85440
aacaaacugu gucauccuag gcaaauuauu uaauuccucc uuuuuuuuag uauuuuuuuc  85500
uucuucacau ggaacaugaa gcuaaugacc ucugcuucua uuucuuaggg augugaagau  85560
aagugagaua aaguauuaua aaugugcucu gggcuucuua agaacaggca uugcucacau  85620
```

-continued

```
ucaaaugguc augauuauga uauggcagca uuauuuaugc cucugguuua agugucuggc  85680
ugccgcuggg guuuccuaug uccauccacg gggagggagg cacagaaugu cucccacagg  85740
cagaaccuac agcugccaca uaauugauga caagccaaag ggacccuugg agguucugcu  85800
ccucucugug ugugacucac acacucucua ggauaaaauc aagcgacuac acccucaaaa  85860
ugcucagaug aauuaacaga uuaaacagug aagaaaaaaa uguguugacu acacuuggca  85920
gugagaaaua aauaaagcgg gcggugacag cagcuggcau cagggagagg cugucaugga  85980
agggaugugc aucuugucag ucaucccauc caucuguugc aggggaccug cagcugcucg  86040
ucuaagggu ucuccaccac guguccagcc cacgucgaug accuaacucc agaacaaguc  86100
cuggauggua aggacuggac gggccauacu uggguuccgu cuggcagcca ucucccagua  86160
uugcugggug uguccuguug ugaugcauuu uaaugggagc aaagagaaca cuggguacuu  86220
cugcagguca cacaguuguu cuuuugcuuu gagcuucuuu cuccucuucc uucuuccuuc  86280
auucccaaag ggauuuuaaa agucaugcac cuaaaggccc ucucccuuua augaggaaua  86340
cacucugugc ucuuacccuu aguaagccau cauuccuggg guccccccugc ccuggcucca  86400
ggccacauuc cuuagugucu ggggagagcu ucuucuacau gugugccgug gcgcccucua  86460
guggaagcau ggugaugcac ggcucuucca gugaauucgu ggagucagag auugcacaug  86520
uggauggcaa gucuggaaau agcauacacc ccuguuauac uccugauucu ccccucagcu  86580
ucccaauuuc ccagugauuc ucccuuuaau uaggaugcac ugaagcucuc aggggugccc  86640
ccaucuccaa ggagcugcag uggagaggcu auccccucuc uaugugagag aaugugugag  86700
aagcguauuc ccacacagga gcaaaacuaa acuuacguac ugaugcaggu uaaugaaugg  86760
ggaaaguauc ugcuuaucaa agaaaaggca uauuuuucua uuuagcacaa acuuuuucaa  86820
auguuaagaa uuuacuaacu gaaaucuggu gaagcaagag aaccgggcaa uauuugcguu  86880
gucugaucau uacaacugga gggaacaugc ucagagaggc aucaucacug uucaugcacc  86940
ugcccucucu uuacacugag agacccugug augaacagaa aacaucuuuu uaggaugaca  87000
ucucugggue uuucuccuag ccugccuugc ugugguuacc uaucucccug cucucugaac  87060
cuuggucaag aaguuuauau uuguuuuaaa uugauacuaa uauguuaagu uacugugauu  87120
ugccaaaauc agauuggaaa cagggccugc auggcugaau gauucuuuuu uuuaaauuac  87180
uuuauuucua aauaaagguu uucuuuguau agaaucggga ugcugugaau ggugggaaau  87240
gcacuaaaua guuaugcccc aaauaagaaa gggaaaauca uuugaauccc caguuagcuc  87300
cuugaaaguc uuuucacuua aacacaccca cauaccacac acacacucac agaccucccu  87360
cccagaugcc caaagcccug cugaccuaca gagcuacuuc uggaaaggcu gacacaugcc  87420
uaagacacaa uuccugggaa uccagcagcu uuggguucaa uuuccuuccu aaaagaacaa  87480
ugaauaugac cccuggagag cuauuagggc agagcugcuu ccuuaacgua aaggacucuc  87540
cagccuccgu augaagucau cucagagcua aagacaauca aguccaacuu gcagauuuga  87600
cauaaagcaa gacuuccaau ccggcuaggc agaaggauuu ugguugaaaa ccaugaaauc  87660
ccuucauaug gaucauuuuu uaaacaacaa aaaaagaaaa gaaccuacug gguguccaca  87720
acucugagag cugcuuucug aagagucaug uuuugagucc uggaaucccu cucccuuuga  87780
ccugccucuc aagacaaugu gcgagagaac ucucucuuca agugcaugca agugagguuu  87840
ucacaguuag auuuuuaauu uuaaaguaau acacauuugu acauaaaauu caauucugac  87900
uguauacaug ugucagauaa acaguugaua ccugacacuu guucacaguc uaugauacgc  87960
```

-continued

```
accgcauauc cuacccucuc ccccagccuc ucuccauggc uucucaaccc ccccucugca  88020
uuuccuguga ccugaggauu caguuuuguu uguggaggca ggugcaaucc caagagaaac  88080
ugugcaaucu ucugagaagu uagaguaggc augugugugu gauuuaggga agguacuucu  88140
cacucagcuu ggucaccggu uccagguuug ugucuugggc aaguccccca uagcugguga  88200
cagaccagaa aaaugaaaac aacuuugacu uagcccucaa guuuucagug aaugagaaug  88260
aaaaacaacc augaguaaga gauuucuuac cgagaugaug uaaaggauaa uaauagcagc  88320
cagcacucac cuaugugcca gguauuucuc uaacugcuuu guguaguuug acucauccag  88380
uccucaaaaa caacaaugaa guggauacca guauuuuccc cuuuucacag augaggaaag  88440
ucuaauguga cccacccaac auaacauagu uugaggggac agagcauuuc guugaacaga  88500
ggaggaacug gcacaggaaa guugcaugac ccccccacca accuccgccc ccagguugca  88560
cagcuagcua gucgggagga cuuugcuucc guuucccucu gccucucaau gaugaucuca  88620
gggccaacua agcuaaaagc agacuugaug gagcaucagu ccucugaaag agucacugcc  88680
gagauacaaa auaccucuuc uucaaagggg aaguggagag aaguaggaaa ucuggguaac  88740
cucacagucu uccaguuucu ggaaaacaga gcuggcauca gucuuuuuuc uuguccuagg  88800
ggauguaaau gagcugaugg auguaguucu ccaccauguu ccagaggcaa agcuggugga  88860
gugcauuggu caagaacuua ucuuccuucu uccaaauaag aacuucaagc acagagcaua  88920
ugccagccuu uucagagagc uggaggagac gcuggcugac cuuggucuca gcaguuuugg  88980
aauuucugac acuccccugg aagagguaaa guagagauuc cagcugguuu cugucaagug  89040
ccagaagugg cgguucuuug aaaaagucua acauuagagc aaaguuuugu aaaagcaaaa  89100
agccaucguu ccccacccaa gcauagcaac uaucuuuauu uuuggcauag uucccccauc  89160
ucugcaugca uacaaauuuu auguacuugu gguuacugug ugcuuacguu uuuguauuua  89220
uagaagauga uguucucaga uagagucgua auggauuuuc uucccauuau gaagcaauac  89280
ccaacaaaac agagcuuggg uuagauuuuu cugagaauaa gaaugacuaa acaaaauucu  89340
cucuuuuuuu cuucuugaca gauuuuucug aaggucacgg aggauucuga uucaggaccu  89400
cuguuugcgg guauggugcu ggagccagug gcuuguuccc uuccuugccu cccucccaag  89460
uuccaucucg aaagucuaag gggcugggca caguggcuca ugccuguaau cccagcaauu  89520
ugggaggcca aggcagaugg accaccugag uucgagacca gccuggccaa cauggugaaa  89580
ccccaucugu acuaaaaaua caaaaauuag cuaggugugg uggcgcgcac cuguaauucc  89640
agcuacucgg gaggcugagg caggagaauc acuugaaccu gggaggcaga gguugcagug  89700
agcagagauu gugccacugc acugcagccu gagcgacaag agcaaaaucc aucucaaaaa  89760
aaaaaaaaag ucuaaggaaa aagucaugaa acaacaaagc aggcaaauac uccuccauag  89820
uaucugacuc cccaguagua ggcauuuugc auccuagaug gcuuugagug acaaaggaau  89880
aacagacuga guuaggucua gauggggaca cuuuggauga augaggauuc uuacggaggu  89940
cagguuggua gcuucauccc ucagcuccuc augcuguauc cccagucucu cggccugcca  90000
ugucaucauc cucaucuccu ccugucaucu ccaccaggcc ucugauccau cucugucugc  90060
augagugaca gcuggcagag uccuuaaugu uuaucaaaua caacucagac gucagucucc  90120
uggccccuuu gagaucaaca uaaaaucauu uugaacccuu auuuaguggu cuaugggcuu  90180
ugaaaacaug gggaccaaaa uuccugugga uucuagaagu cucucuucua caugugucag  90240
ccugggcacc aacuagcucc uuccaugaac uuuuaucaaa cccacagcca cacaaagcau  90300
gugugagugu agcagaguuu acagcagagg guggagggug gggagauaga uguguggaag  90360
```

-continued

```
gguuaccugc cacacaaaca gaaaccacuu cugauagaac acgaggugug cacccacacu  90420
guaaaauccu cuccugguac aggcaaagcu uugcagcgau ucuccuuugc ugccccuggg  90480
cuccuaacac cuccuaaacc accaguuacc uccuucuuuc caguguggca uauuucagug  90540
uuuuccuguu ggaguguuuc cuuucuaugu ggauucugga aucagcucuu aagauaacuu  90600
gguuuucauc uuucuucaua augaucccaa acaucuaucu acuaugccua gaacuaccaa  90660
uggacacaua uaccagccca gauaugcuuc agcccauccc aguacaucgc auggugacca  90720
aaagauguag ucguccuggc acagugggug uggggcagga agcaguccuc uccaggggac  90780
agcagcaauu caccacagaa cccaaguuuc uuucaagcuc ugcugacaca gaaauugaau  90840
aaucucagcu cacccaaugu caaagacuca uauuaaccaa gaccagaaug aaaauaugcu  90900
aauuuauauc agaagcuuug cuggauucaa gaguuagggc cuuuuaccug ugcagaauau  90960
uccuucuuga uaaauaggcc cucucaggag aauaaauuac acaucagagg acuguuuagu  91020
cagcauaggc auagaacagg auguuccaaa gauacaguca aggggagugg guaagagugu  91080
agccucugga gugaggccga ccaaauauca aaccugagcu ucauaauuug caaacuaacu  91140
ggcuuugggu aaguacauag ccucuuugua ccuguuuccc caucugcaaa auggagauaa  91200
uaauagcauc uaccuguagc auuguugaga gaauuaagug aguuaaugcu ugccgacuua  91260
uaacacagua uacgaucacu gauuaagacu uagcaacucu aaacuaaaug uuuacaaacc  91320
aucucuuacc ucaaagcacu uaacauccau ugucuuauuu gauuaucacu guaaucuuau  91380
gaagcaggca gggcaggggu cugccccauc ugggggggaac ugagcucaca gagguuggag  91440
gguuugccua aagucaccca ggccacuggg ucucacucuc uggucuuagc ucuguaaucu  91500
aggaugcuca augccacacu cucagccacu uuucagaugg cuaaguacau uuguuuugag  91560
uuagcucagu cucagaggau gacauuuucu gaucuugucu ccaguguuua aaugaaccug  91620
uagcugugca uuggggucac acaaugcgug gcauggagag ggucuguggc ugacugccac  91680
gguuacuacg ugaaaccauc auuacagcag uuacuacugu uacugccuga gaacaucauu  91740
acaagacuga acgaagggau caacauggaa augauaacaa aaaaaccaaa guaacuguuu  91800
uaaggaaagg cuagcaucgg gaagaagaag agagaagaag agaagaagaa aagggcuccc  91860
ugcuucuaau gaguaaaggc agcucccuaa gcuucugcag cccuucauua uuuauugggu  91920
aacaggagga aggagcagga gguaaugauu gggucagcug cuuaaaugau cacggguuca  91980
uguuguuacu gacagauuuc aauuaugccu aaucauaaga aacauuugug cagccuccaa  92040
caagggucaa ugccacuucu gaaggggugaa cucauaguca guaacuagaa agcagcagau  92100
agcuagggac aaacuggcga uucugaauag gccuggaacc cuuagcucug gccaggucag  92160
ugggcuccag ucaggaugga gccuucaggg agagaucaaa gcucagaggu uugagaugau  92220
aucagccagc aaagaggagg ggcaguaggg auccucccag agggagggcc agccauagaa  92280
gacaucaaau cugagcccgg aucaggagaa ggagccugca gaacuggggc ucuggcaccg  92340
agaaccugca gaacuucgcc ccucugagug caggugccag ggcuggggcu gccacccagc  92400
cuucgcaucc caggccuggc acgucauagg uaaauguagu ugaaaggaug acugagcuga  92460
uccaauuccc uuuacaacug uccuuguccu gggggacuug aggaggguua agaaagcagc  92520
uggggaccaa ccaacagucc ucuaggcucu ccauguccag caauaguugu ucagcaaaug  92580
agcauuaauc agugacuaua aacuguagcu ucaacauaac cgacaacuug caaugguuuc  92640
uagagcaugc ucccaugugu uaucucauuu aaauuuccaa accaauccug ugaaauguuc  92700
```

-continued uuuuuuuuuu ucuuuuuuuu uuuuuugaga uagaguuuug cucugucacc caggcuggaa 92760
uacagcggcu cgaucauagc ucacugcagc cuugaccucc ugggcccaag ggguccuccc 92820
accucagccu cccaaguagc ugggacuaca ggcacacgcc accgugccug gcuaauuucu 92880
uuucuaguug uuuguagaga cagggucucc cuauguugua caggcugauc ugaaacuccu 92940
ggggucaauc aauccuccug gcuuggccuc ccaaagugcu gggauuacag gcaugagcca 93000
ccaugccuuc auuuuacaga uaagaagucu gagaaaacuc agauuuaggc agauugaguc 93060
acuuccccaa auuuauguau cuuguaagaa uccauauuca aaccucaguc cccuaacucu 93120
uaguucauua cuuuuucuac cacuucucag uauccucuaa gaauucagaa agaaccacau 93180
cgacucugau uuuucauuug uuuaaguaca cagguaauag gugaauguau uuuguuguuu 93240
aaaaauucau auaauacaca aaaggcuaaa gucucgcuuc ccacuuccuc uccccuuucu 93300
acccaacucu gccuccccag ggagagcuuc ugcugacagu cgguggacau ucuuucagag 93360
uuuuacaauu augugugugu guguacauaa gaugucaguu uuucuuugug uaggauacau 93420
gaacaugaau uuuaaacaua aaugugagug uauuacacau auugaccagc accuuaguuu 93480
uuuuguuugu uuguuugguu uucuuugugc uguuugagaa ggagucuugc ucugucaccc 93540
aggcuggagu gcagucuugc aaucucggcu uacgcaaccu ccaccuccug gguucaagug 93600
auucuccugc cucagccucc cgaguaguug ggauuacagg ugccugccac caugccuggc 93660
uaauuuuugu auuuuuguag agaggggguu ucacuaugua ggucaagcug gucucaaacu 93720
gcugaccuca aaugauccau ccaccucagc cucccaaagu gcugagauga caggcgugag 93780
ccuccgugcc cagccaguuu uguuuuuuua uuaaccaagu uacguauuuu aaacuucucc 93840
augucaaugc uuuuagagcu auuuuguucu cuuuaauguu aauagagaau uuuaaggcaa 93900
uuucagguga aucuauacaa uuucucugua uaaguaauuu acacuagaaa uagauuuuua 93960
uaaagaugau uaagcuacca gccugguauu ucauugcuga cuuaaaugaa gaggaaaauc 94020
aaugcuguaa gggaaaaaaa aaauggcauu agagauccag accuuauagg cauuuuccaa 94080
auuauuaauu caaucucuca aaacaggugg cgcucagcag aaaagagaaa acgucaaccc 94140
ccgacacccc ugcuugggucc ccagagagaa ggcuggacag acaccccagg acuccaaugu 94200
cugcucccca ggggcgccgg cugcucaccc agagggccag ccucccccag agccagagug 94260
cccaggcccg cagcucaaca cggggacaca gcugguccuc cagcaugugc aggcgcugcu 94320
ggucaagaga uuccaacaca ccauccgcag ccacaaggac uuccuggcgc agguacuauu 94380
gucggucggu guuuagcuga gcucaguggc uccucuccca gccuuccccu ccucuccuga 94440
guguuccuuc aggcaugggu uauaacucag caaggagcac ccucuuuaga uucugcuggu 94500
uuuguuuccu gcuuuccaaa cccuuaucuu gauucuuggu aacaugaauc uucuuuguaa 94560
guuggaccuc cccuagcaaa gaaaauagaa uaauagugaa aauguuaaua uuguuuuuau 94620
uuuuacagug agggauaaag ucauguuuuc auucauuuuu gcagugaccc uacauaucaa 94680
aaucauugcc cucuuuuuuc uuuuaauguu guuuaauuua gaaaaagaag cucugguuua 94740
aagaacagug agucacguga cuugcucuuu gaaaugcccu uugaagucug gcugaacacu 94800
gggcugcauu cagauucuuc aguggccacc agaacauucu guuuucuucu gcacaucuua 94860
ccuuugcaca cccugcuuau uauguucccc cagaagccca acccucucca ccaggggcug 94920
auuaggaggc ugcaggauaa auguuuaaaa gaaugaagau gugugugcac gcgcacgugu 94980
gacaucucca ugccacaguc auguuuauuc cacgucuauu cucccacaga ucgugcuccc 95040
ggcuaccuuu guguuuuugg cucugaugcu uucuauuguu aucccuccuu uuggcgaaua 95100

```
ccccgcuuug acccuucacc ccuggauaua ugggcagcag uacaccuucu ucaggugcgc  95160
ggacucgggg ucaccauucu ccucuguggg uuuggggcac cugggucaca ugcugcuuag  95220
aagggcccug accuucccac uucacuggga ccuucaccaa ugagagaggg gaggggucuu  95280
ugggcugccu gcagaaagga acuuaaugua ucugccacug cuuggaaagg cgauccuagu  95340
ggacaggcag gacugcuugg gaaggccgaa uggggaaagg aaugcaaagc uuaggugaau  95400
ggguugaagc gccaucuuuu ugaggcauag gugacaugcc aucagaccac ugcgaguguu  95460
caggcagccu accgcacucc caggagagcu agcgccaucc caaggcagca uucggugccu  95520
ccaauacaua ccuggcacac agcagcuauc caguaaaggc ucugaguugc augauguugg  95580
cacgcgccug cucuguccca gucacauguc ucacucuguc uagcauggau gaaccaggca  95640
gugagcaguu cacgguacuu gcagacgucc uccugaauaa gccaggcuuu ggcaaccgcu  95700
gccugaagga aggguggcuu ccguaagugc cuacgcgccc cuguccuaag aagacuagcu  95760
ccccugggag gacccaacgg uggguucaag auggcaggcg uuggggaggc cccacucaau  95820
ccugcucugc uggucacuuc caugucucug accagcacuc ccccaaccuc uccuuccaca  95880
cuugugugca gggacauuca cuaccuccua ggaagccccc acaccacugg acagcucuau  95940
auuucucagc auagaaguuc uauguugagu ugacagauga uuccccauaa cuuauuugaa  96000
aggccucuga gcagggaggg agggaaauag gguuaugcua uugugugauu gggccuugaa  96060
uggcgugagu gacacagugg ccaguacuuu gugauaguug ugagucugga gaagggaguu  96120
agcgaaggcc auugacaucc accaggaauc cuaaaaguuc aauauaauuu uaacuuuucu  96180
cccucagucu uuuucaaagc ugucaauaag gaccaaaaca gacuaauuuc aaauuccucu  96240
ucugguugcu gugucucuca acagcuagag cugcuaggaa uaaaaaggga gacaaaacga  96300
uccacaagcu agagaugguu auuccccagc cccacaccua gucagucaca aaacccuagu  96360
uuugauauug cuugagcaga aaccagccuc caagagaaua agaagaaagg gccugggucu  96420
aaagaggagg aggaaagggu ugggcacaau uucuuaugcc uagggauuug ucagcaacuu  96480
ugaggcugau uauggaauau uuucuugucu uccaugaggg aguaccccug uggcaacuca  96540
acacccugga agacuccuuc ugugucccca aacaucaccc agcuguucca gaagcagaaa  96600
uggacacagg ucaacccuuc accauccugc aggugcagca ccagggagaa gcucaccaug  96660
cugccagagu gccccgaggg ugccgggggc cucccgcccc cccagguacc ugaccuccaa  96720
acaacggggc cccaggucug ccugccacag agggacuagg ggaguccugg guaucuccug  96780
agucucucac aaacuaacau uucaaacugg caguugagua ggggacuaaa ccaaacuccc  96840
ugcacccucu gggaggggcu ccccacaggg cgcuguggcu gccaacugga ggaagccacu  96900
caccaaaagc uucauuuucc accagauacu uccuauuuga ucuaguagaa aaaaugugu u  96960
uaagcacuaa aaaaaauuaa gucauaugug cucauuauag aaaaauuaga aaacacaggu  97020
aagucagaag gaaaaaaaau caucgcuugg auauaaacac agauaauguu ugguuugcag  97080
ccacccaaac agauuauauu ccaaauauug ucuuaaaauc ugauuuacug cauaauuuac  97140
uaggaacaug cauccauguc aauaaauaga caucugcauc acuuuuaaua ucuguauauu  97200
aucccauugu uugaauuucu uuuuuuuuuu uuuuuuuuuu uuugagacag agucucucuc  97260
ugucacccag guuggagugc agcgguguga ucucggcuca cugcaaccuc ugccucccag  97320
guucaauucu ugugccucag cccccccgag uaguggggau uacaggcaug caccaucaug  97380
cccgccuaau uuuuuuggua guuuuaguac agaugggguu uuaccauguu ggccaggcug  97440
```

guguugaacu ccuggccuca agugaucuac ccacuucugc cuaccagagu gcuaggauua 97500
caagcgucag ccacugcucc uggccuaaag uuacuuuaaa uuaacugauc ucccauuauu 97560
cgccacuuag guuuuuuagu uuucaccauu auaagcaaug cuaugaugua cauucaaaug 97620
gaaauguguu uacacacuua uuaacagucu uaauuaagaa gcucuccaug ugcugugucu 97680
cuaacaucug cagguaugua cacaaauaca ugcacagcca gcauccaucu uuugcaggga 97740
cauuaaugau cuuggcucug agcagcaccc uguccuggga guucuaaagu ccagaacaga 97800
uuacagugag caucuccugg gggauuuaga gacaucaaag aaggcugugu ccgugguuga 97860
uaaugggccu cccagcugac uugccagggc ugggccuuag acagcccugu ccaaugauuu 97920
gucaaugaau aaacuguucc caaacaggcu augcaguuca gugggaaagc acagguaugg 97980
gacacggaga gccccaggug gacuacuuga ccucucugag ccuuaauuuu aucaccugug 98040
aauugggaau aacugcuuau uucauaauau uauuaugagg auuuaaugaa aucauguggg 98100
caaggaauua uuuagaauua gauucaacuc aagugaugac aaccccaaac uaacagcaga 98160
uaaaacaaga cacaacuugu uucucacuca ucuaaaaguc uacgugggug gugcacgaug 98220
uucuauucuc uuucuccucc acacuaaaca ggccucagcc ucaucagcca auaaggcagg 98280
agcugccuuc caggcagcgg aauggaagaa ggaugaagca aaacagaggg cagagugugc 98340
acaugugcua uguuuaggga agguuuucug aaguucccac auaguacuuc cacuuacaaa 98400
cccaacaaaa aaggcuaugg cuaaggcagc agggaggagc aaauaauggg agcaacuaga 98460
uuuugccaca gcaccuauca cagucugguu uauaaauggu ucuaggccaa gaacacccga 98520
ucccugcucu uuuuuauauu cuaaagcaug uaucuuuaua uuucucaagc aauauuuucu 98580
cucuuugaau cacagcucau cugcugcauc auagggaucc caaaagaagg acccaaggaa 98640
cuugucucag uccucugugc cccaagagga agcuuugcuu guuugcuuug cugucaaugc 98700
ugagggcucc uguggcugcc uccacucaaa acccuccagc aucaggacgu caaggcugug 98760
auacuguacc cugagcucuu ggccagggcg agggagggga ggccaagccu accuacaugg 98820
uguuucauuu ccuaaacgaa cccuuacuuc cacgcggucu guccagcuua gaaacuuauu 98880
uucaguagug uugguccuug gucccuggac aaaauguaac agccaaaguc cuagaaaaag 98940
gcaagccagu uccugccauu uucuuucacu ucugcauuuc cucacuauua uacgugccuu 99000
ccauuggagc aaaacugaau gccacgcaua ugcacaggag cugugcgcgc ucugucucuc 99060
ucacucacuc uuuuucucuc ucucucuuuc ucucucaauc ucucugucuc uaucuaucuc 99120
uuacucuuua ucucucacuc ucucacucuu ucucacucuu ucucucaauc ucuuucucau 99180
ucucucucua ucuuucucuc ucucucucuu ucucacacac acacacucac aaacccacac 99240
ucuuauucac aucugcucac ccuagccacu caaacacaau cccucauuca gccuggaaua 99300
aguccagagg gcgugggccu gauucagaga caaucaguug uucucaucug ggaaaugggg 99360
caaugugguc aucucuaggg acccucccug cucuaacauu cuuugaaugu ggugggucc u 99420
gagguggaag cacucugucc cugacuucua guauaugugg agauaggguu acacaaauau 99480
uuuauugggc agaacuuuua uaaaacaauu uaucauaagc uaucgcagcc agcagcaauu 99540
uuuccaaccu ggauuccacc aggggagcuu ggccggugac ugagugccac uuucagcuug 99600
agaagcaggu gacucaguga aaagagcaag gaggagacag aggcagauuc aguuccuagg 99660
cccugggcca cccaccugca aguuugcagc ccagucagug caagucagcu aacuguucug 99720
aaccucaguu ucucugucug uaaauuaagc uaaaaauucu ucuuucaaag agugucagga 99780
ugaagugaga ucguguaugu agggcauuua acauagugcc cgacacacag ggagcauucg 99840
guaggugcca gcucuccucc uggcaggaga gagagaaaca aggugaaaag agugaauuaa 99900
agaagaggaa agucaaaugg gaaaacaggg ggaggagaua gaaaguguau gaaaaggaaa 99960
gaauggugcg caauaacggc gguguaaugc caccaaaauc cccucaacua cuucugggca 100020
gcacccuuga cagagugaau gcuuuuauga gaauguaagc ggaauguguu cccagauuug 100080
caguaauauu gccaccuggu ggacaaaccc augcaccuuu gaauuuucca aaauauuucg 100140
augaacuagc uuccaguccu agauguauuu ugaaagugau uuguaaauug uaaggaacua 100200
uucaaauucu uucauuaaug ucacaaauca acugugucau cuguaugcca cccacuauuc 100260
ugggugcugg ggacacaaca gcucacaaau caggcaaagu cccugcucuc accaaaauga 100320
uauccuacgg gggauuacag auacaaauac guaaacagau ccaucgggag gaaacucuca 100380
gauggaaaug agagcuauga agauaacaca acaguacaug acaauacaga gugacuggaa 100440
ccaggaacau uucuccgagg aauaaaauuu gaagcgagcc augagagggu cuacagguag 100500
aguucccagg cagagugaac agccaagcac aaagcugcac caggagagag aggugcucgc 100560
cgagagacag ggaggggagu guggcaggug agcucagaga ggggcagggc cacacacauc 100620
ggccacaugg gccuugguag ugagucgaga uuugauccca ggguuuauug gaguggauaa 100680
guaagcaagg ugacugaggu gcucggguuu acauuuuuau aguucaagcu ggcugcuggg 100740
uggaaaacgg aaguuggcag accaaggaca gaaucaggca gacccaugug gaaguuucuc 100800
uaguggucua ggugguggcu uggguagcgu ggcaguauug gagcuggaga aacgcagaug 100860
gauuggagau uuguuuugga gugacgccau ucugucuugu caauggauug gcgaaaaaag 100920
aggcaucaaa gaugaguuac acaucauuga agugagaacu agggagaugc caguacuuua 100980
uuuaguauuu ucucagcagc ucaauccaua aauaauuuuu ggaagacaac aagcaguuuc 101040
acaaacuacu uauaaguccu caaguuccaa gguaauuaac gugggugucu cauugccuca 101100
gagaacacag cgcagcacgg aaauucuaca agaccugacg gacaggaaca ucuccgacuu 101160
cuugguaaaa acguauccug cucuuauaag aagcagguaa gaagaaaucc uuuuaugcuu 101220
uuuauccugg cucccuguag aagauauuaa cuagggacag aagauaauuu ucucucucaa 101280
uuuauguaug aucagggcag uagauuuuuu ucuuuuuuau cugauuugag ggccccauuc 101340
aacauaaaaa gcaauugagg cacauacaag uaaaauguaa cuuaagauua auucuuuuuu 101400
uguuguuugu uuguuuguuu uuacauuuag ggcaagcagu cuuaaauuuu aacccacgua 101460
uuauuaaaag uuauaucaga agaccauaga aguuauucaa aaaugcagcc acauauuuua 101520
acuaguuaaa agagagagua aaaauuugga gggaggugga ggaguauagg ggaaaaggua 101580
gaagaaaaag agaaaauaag uaaguggcaa aaaagagaaa ggaaaaagau agggugggaa 101640
agaggcagcg ggacaguguc ugaguccagc acacgccagg gcgagccagg ucaacugcag 101700
cugucauauu cuaacuguga auuaucaucu uugaucacug cccuuugaga ugccaaugaa 101760
cuuuucaaga aauaucuagu ucucuuggcu cuccagcugu ucuuaucagc cccauccagg 101820
auggaacagc uuuggcagcc cguaucagaa caagcagcuu gacaggggca ugccaugcca 101880
ggagagagga uccuaaggaa gcguggucca guccgcacag gcucuggggc uuuaagauaa 101940
aaccuccugu cuaacuuuag uaggacuuuc uguugcuuca ccugccagag cccugaacga 102000
gggauaaauu gacuuaauua acuagaacac acugcaaaug gugaaagcau uuagcaaaac 102060
aaagaaugcc auccaagccc caaaauaaaa gcagaauaaa uagaaugcaa uaaacagcaa 102120
ccaucccaaa cugaguucuc agcagcaaau cuccaguaug aaauuuugga uuuugugcgu 102180

-continued gugugcuuaa agguggauga caaugacagu ucaugggauu gagcucuggg guccagaguu 102240
ggcaucuguu cauuucccau uuugucauuu uacccuugau ugacugaaug ucagugccuu 102300
aacuuugggc uguggaguga gucggaacuc ccccgaggug ugcaggugu uguuagaguc 102360 ucauuuuugc aggguggaag acaggagggc ugcagccuuc auuccacacu gacaugguca 102420
uugccgugug uucugggucc agaucaggca uauugaccug acauaugacc ugacaacagg 102480
accacucaga aaguccagca ugcgggauau gauuuggaga gccagugggg gaaaucauag 102540
guccuuucuc ugcaugugua uucaggcaau gucccagggc ugggcggcuu ccgcauugcu 102600
uggauaucgg aaaaugcaaa aaugccccug aagacugaga cuucagucuu caaaaugaau 102660
guuugggaaa gaaaguuaac ggcacugcug uacuuguggu auucauugca uuauuuuauu 102720
uuggcuuuca gcuuaaagag caaauucugg gucaaugaac agagguaaga aacuauuuuu 102780
aucagaauua aaaucucaga uugauucauu guugaaauaa uugcacacuu uuaaaaggca 102840
caccucacag ccaugaggag gggcuguucu guaggugcuc aggaagucac aagacacguc 102900
cugaagaaua uguggcuagg gacaucccag acucagaaga cacucagugg ugccucuucu 102960
uggaggacau aaguggggu ggcauucccu gauguggcgu uucagagcau ucucacccaa 103020
aaaaagcuuc uaaaaccucc aaguauauaa caguuuauaa uacuccaaca agagggccuu 103080
guagccuaaa cccgggacac uccuuggccc auuccuuuua agcuucaggg agugugggcc 103140
agccccagac ucaccccauu ccugaggcau ccuggagguu gaaauauuuc cagagguuua 103200
gaaccucacc aagugggacu cuaggagccu gcugccuccc agccucccuc aggaacugca 103260
ccuccagaac aggugcgggg cugacaugua ugugcuuucc ugggcagauu cuagaccgua 103320
cacaugaaau cuggcuuuca ggauugcucu ccagagggac cuguggggcc ucggcugaga 103380
cagagaguag gagugaggca gugauucaag gcccugagaa agagcuccuc cucugcuugg 103440
uauaaccagc uaauucauuc uguucuguug acuuuggcuu cugcccugcc uuugaagggu 103500
uugaggccag ggagugaugc acucagacug guguuuccac acagucacuu cagacuucca 103560
gggcaguaca ggagauagau cccagggcca gugaagaagc agagcacaag uccaggcagg 103620
agaggcuaag ggccucccug aacaggugug aggcacagaa gccccgagag guagggauga 103680
caggaugaag augggguccug ugcugcuaga aguaccugca aagcacagag guggcacaga 103740
aaaggagucc uuggcuggga ugggaggaga ugacauguga caugugaaag aggaccugga 103800
guuggcucga ugcucccaaa agggaaaggu gccgaggggga gcuagcagcc augcaaaggc 103860
agagacaugc aggcagucug ggccaugagg agcucuggaa gugacucgau auguccagaa 103920
uaggccacuc cagggaaggg cugaggaagg augaaguugg agaggggcac agaccagaug 103980
cagaagggcc ucagaggcca ggaugagggu uuggacuccu uccuggaggc agcagcagug 104040
ggaaaagagu uaaaagcugg uuuguaaagu ggagccaugu ugcucgcugg uccaggcaau 104100
ucccccgaaa guucauguuu cccuacaaaa cccgagagag cuacuaguag gcgugaaguu 104160
cguggcccug gucugaggau uuccuguuuc cuugucaggu auggaggaau uuccauugga 104220
ggaaagcucc cagucguccc caucacgggg gaagcacuug uuggguuuuu aagcgaccuu 104280
ggccggauca ugaaugugag cggggguaugu aaacagacug gagauuugag uaggauuuuu 104340
gacuugcuua acuaccauga augagaaacu cucaugagug auaacaggaa aaaaaaauua 104400
aaaccgucuu guuuguuugu uuacaugguu uuuagggccc uaucacuaga gaggccucua 104460
aagaaauacc ugauuuccuu aaacaucuag aaacugaaga caacauuaag guacuugacc 104520
uauguauaau cugcucugga gcuaaaaauu uaccugagcu gguuauuuua uuuuuacuuu 104580
ccuaccuuca uuaaauucca ucccuccucc ugcugaaauc uagcaaggaa ugucuuccag 104640
cuaccaaacc cuuccugcuu cucaaauuuc cuuuccuuca cugauuucug cuuuaacuag 104700
cuguuagugc agcgucucag auguccucuc cacccucuag gugugguuua auaacaaagg 104760
cuggcaugcc cuggucagcu uucucaaugu ggcccacaac gccaucuuac gggccagccu 104820
gccuaaggac aggagccccg aggaguaugg aaucaccguc auuagccaac cccugaaccu 104880
gaccaaggag cagcucucag agauuacagu guaagccacc acagccccag ccucaccacu 104940
uucuugucac cuucuccacu cuuugaacau ccugagagga uucucaccac cgcgaagugc 105000
ugauuuggau gguaaugcug uuuagucagg cacauaugaa cauccgacuu ucaaauaagu 105060
gccucacacu ucacauacca gaccucuugg ucauucuuuc uccccaacau uuauguggca 105120
aguaaguuua cauuugguuc cauucccuuu uggcuuuuga uagcaaguug cuccuggagc 105180
uuauacaauu auuaucuuug cuaugugcaa agcagcugcc aggaacuggc aaaguucagu 105240
aaaccuuuca gcucccucgg aguaauuauc uuagauucca ggaauuuccu cagaagagca 105300
uacuuuggag augucgacag agcuuugcua cccucaagcu gaggcucuuc uugcacaguu 105360
ucagccagug gagacagugg ccuugugcgu uuuguaguau guucacucua uuugaggccu 105420
acauggagga gggguuggua ggagcaccuu uguuagugca aacuucagca acguuguggg 105480
guccugauuu uacuauccua gcacacgcug agugccagug aacaugccca gggucaucca 105540
cuaaaaccug ggccuuggcu ccuuggugug uuccucugga cacccuaggg cccuagacug 105600
uccucuguua auucucacuc agccacacuu ucgugugucu ccuuccaguc auuuguucua 105660
agcuuacuac guguauggau gauaugaucu guaguuuuau caagguagug acuaccacau 105720
aggauaccuu uguggaaauu aguaaaaaug cucuuuucug cagguggaca cugucccaug 105780
ccagggguua uggcuuguac auaaaguuca ggcuggcuuu agccccaacu uaccccucag 105840
ccagaugccu ucuauuuguc cgaggaaaga auaaauagag ccaaguccu guacaacuug 105900
ccugcccucu uuucacuuaa auuuacauca ugaacauuuc cuuguguuac gauguacuuc 105960
uugaaaaugu gauuuaacaa gaugauuauu aacaaaagau aaaucucaca gaccguaugu 106020
cugucaacau agaaaauuca agagacucua uagacagauu auuagagcua augagagcau 106080
ugcaguacau aagauuaaua uaaacaucua uuucuauaca ccauaaaaau aauuagagaa 106140
uauaauaaaa agaaagguug ucuagaaaua uucacaugaa auagaaaggc aacccgcaaa 106200
uacccauuua accuuggucc auauggauua agacaguuua guggagugac agcuucaagg 106260
uagagaagag gaaccuggag gccacaccug ggcgggugua aggccuuccc aaagccugac 106320
uuuguaucuu cuccuccuuc ugcucuuccc ucuucaucgc ccucucccug ugucucuggc 106380
ccugcugcag gcugaccacu ucaguggaug cugugguugc caucugcgug auuuucucca 106440
uguccuucgu cccagccagc uuuguccuuu auuugaucca ggagcgggug aacaaaucca 106500
agcaccucca guuuaucagu ggagugagcc ccaccaccua cugggugacc aacuuccucu 106560
gggacaucgu aagugucagu uuacagcgcc ucccuccccu ccgugggccc aagguggagc 106620
uugugugugc ucugaaggac cagaccaaga ggggaggggu ucucacggug ccagggcugc 106680
ugaaaggcac ugggccaagg gccuugugua ucugcugucc cuugacaucu ucucagaaag 106740
gcacagaacu aggagcccga agcuaggaaa ggcugugggg ugcagcuuaa caacugguga 106800
acgggggcuc ucuauguccu gcacugaggg gucuucugac ccaucaaaua aucacugcac 106860
cgcaggcaug agucuggccu uccuggcauc agucuggcgc ugagaaggua auaugaaggg 106920

-continued gucuuucacc ccaagucccc uucucaaauc cugccccacc uucaaaaggg uaaagguaaa 106980
acuuucccug ugguagggug accagauaaa uacaggacac ccaguuaaau uuaauuucag 107040
augaugaaua auuuuuagua uaagcauaug cuacuucaaa uauugcacag gacauaucua 107100
cacuaaaaaa aaaaaaaaaa aaaaaaaaaa ccugguuguu uaucugaaac ucaaauuuca 107160
cuaggcaucc uagauuuuua uuugccaaau cuggcaaccc cagccagugg ccaaaauaau 107220
aagaccuuca cuuauuagau uaaccaccgc uacagggaaa aaugaagaaa aaauauuuau 107280
uaaaucaaua gcacacuacc accuuccuga caaccaaggu ugguggggu agggaggggu 107340 caggauagcg uacccuauua caggcugcag ggucaaagga auugguagua aaggccuagu 107400
uauaauguaa cagggaucau uaugacauca accccaauuu auucuaggug ucuugaguag 107460
uaaaaucuca acauuuuaag accaacauga gccuccauuu caugugauga uaagauauac 107520
caacugaugg agaccaacac aaaugaccuu cucauccaug guuuuuuaaa augaugguga 107580
auauuggaau uccugaagau augauuucua ucuuacucag cuuaguaagc agcuaucacu 107640
uaacaauaca aaaccagaga uuaucaguag caacuaaauu auuuccucuc ucuucugucu 107700
acacgaggaa acacucauaa augcacgggg aggaggucag aaccugaaag ccuuucuuug 107760
gauaagagca ucaacugcag guaccacauu ggcccuguga ugcuaauaua aaaggagcua 107820
ggcccaccgg uaccgaaaag uuacuuagaa aagugcggag gcuuuuaauu uuacuuuuuu 107880
uaaaagauaa gaaauagaau uuacacacuu ggggcuggcc cacguguuuc ugugugugug 107940
uaugugugca cgcacgcgcg ugugcgcuua cagggaucuc ugagccuaug gagagagaug 108000
uagcuaggau agaguggaca ucugaggugg gaggugauac uagcuggcag uccaaugaag 108060
ggguagaaga ugguaggcau cauguuagca ggcuuucuga ugcuccagaa uuuuaaagcu 108120
ggccuggaau cucaccuccg cgauccauca uuuuggaacu uaggaccacc auuagccagu 108180
ggcaaaaaaa aaguugaaug aaggaacaaa caauuauugc uuauguaauu cacuuagcac 108240
auauaugaug uuuuaaauuc uuauaugugu caucuauuuu ucuuuacuuu aaaauuuugc 108300
aacaguuaca gacuuaugga aaagucacaa guacaguuga aaccuuuuuu ucuuagucau 108360
uugaaaguaa cuucucagca agaugccccu ucucauuuau uucucucuuc cugucucucu 108420
cucucacacc ccucagcacg uccgauguau acuuccuaca aacgaggaua caccccauac 108480
aaccacaaca caaacuguca acaugaggaa accagcacug augugucauc accaccuaau 108540
ccucacaccc cacuccucuu ucgcccauug ccccagugau gucuuucaga aaaaaggauc 108600
uagcucagaa ucaugcauga cauuugauug ugcuguuucu uuagucucgu ucagccugga 108660
agaguuccac agucuuuugu uaacacucau ggucuugaca cuuugaggac ugcaggcugg 108720
uuauuuugca gaaugucccu uggucugagc uugucugagg uuuccucuug cccagguuga 108780
gggugugcau cuuggcagca guaucagcaa acagaugcug uguucucacu gcauccuauc 108840
agguggcuuc ugauuucaau uugcucuguu acugaugaug uucaauucgg ucacuuaaga 108900
aggugucugc ugagcuucuu cacuguaaaa uuacucuuuu ccccuuuaua auaaauacaa 108960
auuucaggua gaggcacuuc aaagauauau aaauauccua uucauuauac aauuuuccau 109020
uuauucaucc auuuauuuau cucuguaugc agucaugguu cauguguuaa ucaauggacu 109080
augauccaag acuaucauua uuuauuuuga uauucacauu auccccacug uggucagugg 109140
ggggccguug aagcuggcuu cuguaucguc uugacuuggg uccucaugcc ccuggaccuc 109200
cuccaugcuc aauggcacag caagauauuc caggcucauc cuuccauuau ccccauuccu 109260
acccucuccc caagaagccc ugguuccugc cagugggaag uggcccucag aagccaaggu 109320

-continued cugagugcua gauauguuca uugccucugg agcaccauug gucccaggcc uucucaguga 109380
uagaacuagg gaagauaugg auguacacac acagguaugc acacaccucu aucuauaguu 109440
cucuaucuac cuauacagug aacacuauga gcucuccaaa accaacucca cagggcucau 109500
ucuaguuuuu uuucuuucca caucuguaac ucccuucucc aacagugaga cgcuggcuuc 109560
ucucacuccc aacucauuua ucuaccggac cuauacaccu gaacagugcc caacucugcc 109620 accaucccu ccccaugugg augccguccu cucccugcuc cagcugccuc ugcugcaugc 109680
agguccuccu cguucugcuc uggcucugau acccugcacc agaucagccu ccuguaagga 109740
uaucuuucuc aucccguuga ggccuccaca ccccacggca gguugccccc ugaggaagcc 109800
cgucucuggu ucuugcccug cuccugauca ccauggcucc uccccuaacc ccacuguugc 109860
cguccccuuu cugugcccag uauaguggcu guaggacuaa auuguuuaaa aaggguauca 109920
uuauuuauuu gagcuuugug aagccaagaa cuaggcuuua aguuuuucug aauucugaag 109980
acaugcuuag aaagaagaau caacaaaacu uuaugaccaa auagaaagag ugagagacca 110040
ggcagaauuu uguaauugau ccuuucaaaa gauacaaacu aaagguuccc uuggcaggga 110100
gguagggcau gggguggggu aggaggacua gugacagcuu aacauauguu ugccaaccaa 110160
gaacuguuua aaaagcaagu cgaaucagaa ucccagaccc uacgagcugg aggagccugg 110220
ccccaccccu cauuuugcag agcuggcagc aggucugaga gguuaaguga cuugcucucc 110280
ucuucucuuu ccgagaugaa uuauuccgug agugcugggc ugguggugg caucuucauc 110340 ggguuucaga agaaagccua cacuucucca gaaaaccuuc cugcccuugu ggcacugcuc 110400
cugcuguaug gguaagccgu uugggccauu agcuaaugcc ucugaagaga agccuggugg 110460 ugggggugg ggaucaucuc cugacagaaa accugggcug uccugugug guagcaccca 110520 caaguuuagc uuccggcccc agguagggguc ugaagcugau aaccagggau cugucuggcu 110580
ucugauucug acuccacuga cagagguauc ucugaggccu gguccuguca gugacaauga 110640
gagaaguccc acaugaucug aaucuccuac ucaaacugag gccuugacca aagccugggg 110700
gcagccauuc cccaaccccu cacccagcuc ugacucucac ucaucugugg ccaaucuguc 110760
caccucagug uccccaugug aacuggccaa gaguuaccgc ccacaguaga agacuccggc 110820
caaaaagcuc cuccugaguc agggacagag gaugacacag ggguuacauc agcagaguua 110880
cagggcccag caugcaacuu ucuuucccac guguguaaau uugaaugagu aauucaucca 110940
ucucggccuc aguuuccuca ucuguaaaag aaaauaguga uccuggcccu uccucugugg 111000
gccaguagag ccuugccaaa gcauuguucu ccacaucuuu cucuuggaaa uagagaauuu 111060
gggaaccaac cugacuauaa gcugugaaga ugagcucacu gggcucaucu gagaugaccu 111120
cagcugggcu uugcugaccc aggcuagagu gggaggu guu gcaggcugga gaacccuccu 111180
augaauugua cagggcuuug uaguuuacag aguauauaca cagcuagcag cccauuugcu 111240
ccucacaaaa ccccaugaag uggucaaggc aggcaucauu aucuccauuu aaaguugagg 111300
cacagagacc aacaaaugga guaucucucu gguccccugg gacucuggcc aguucacaca 111360
caucaccuca gguguaaggg gagugcauua uauccagacg uauuguaggu ggaauggaau 111420
guggaacucc aucacucuga guugucucau uucacacaga ugggcgguca uucccaugau 111480
guacccagca uccuuccugu uugaugucc cagcacagcc uauguggcuu uaucuugugc 111540
uaaucuguuc aucggcauca acagcagugc uauuaccuuc aucuuggaau uauuugagaa 111600
uaaccgggug agcauaacuu ucuuggcuuu uuuguuugau uaguaggaua guagaguaug 111660
uguuggucga gcagagccag gggcaagcau cguacaugua gcagcuguau gcggaugagu 111720
gccacuuucu uccucccuac ccccgacccu gccuccuuuc cuuccuuccu uccucccauc 111780
cuuccuuccu cuuuccuucu ucuccucccu ccucccuccu ucccccgucc cuccuuccuu 111840
ccuuuuucau ugcuuccuuc cuuccuucgu cccuccuucc cuuccucuuu ccuucugccc 111900
ucucucccuu uuuccuuuca ucccucccuc aucccucccu ccauccuucc uucuuucuuc 111960
cuucuuuccu uccuauaagc accuuuuuca uuucugugcu cugaaugaaa ugguuuucug 112020
uguuuauucu gcaagcaaaa cuugauucuu gcaauaaacu uuaagcuuug cuuacucuuu 112080
cagaaagguu uucucaggga cuuugggugu uggguuuuac acacacacac aucaauacau 112140
uuggguaauu ucaaaaucua aaaggaacaa aaaggcauac aaugaaaaaa ucuccuuccu 112200
accccuguuu cccacucaug caguucucuu cuccagaggc aaacucuuac uugaguuucc 112260
ugugugcucu ggagacacau cagcagaucc cuauacgguc uuucucccgc uuucuuaugg 112320
aaauuguaac acucugacau auacuauucc uugggcaagu uaaucuugau gaagagacug 112380
gguguucucc augcugaaug ccucacuuuu augagcugcc aagcccaguu gucccuucca 112440
ccugaccucc cccuguccag agacagaugg ccaaacugaa ucauaaaaag agggggaaaa 112500
aaagaaggca gucgcugcag ggcugucuuu acuccacacu ccacacuccc aguccccacc 112560
gcugugucug aguccuggcu guggcugucc uuggaacauu ugccucacca cgugccugug 112620
uccccaggcg ccucaaccuu uccucuccuc auuagcucuu cccaguucag agggugggac 112680
cggccagcac aucugcacug cugcccugcc acacccaccu ccaccugccu cugggcccca 112740
cuggggaaca caggacaaau cugugcggag gccccaccau gaaccgccca gacccgugga 112800
ccccugagac ugacucuuuc cagaucuugu uaggguuucg uggcugcuag gcaaguaacg 112860
aagccucauc ugucccauga augauaagaa auucagcaug ucagagucag acucuggaaa 112920
ggcgggggga uaagaacaca gccccagcag auggccagag cacccaggug acugaaagug 112980
cugcuuugca gagcuguguu ugccacaggc ucacagccca cuaagucuua agacaguuuu 113040
ccuucagaau aauuaaauag ccagcuuaaa gcaacucaga acauuuuccc cucugaggcu 113100
gcacccauuu agccaacauu ugcuaagcac ccgccuucaa aaaccuggua uuuucaugua 113160
aauuauccga uacacagcug cuauggaaac ccccaguauc ccacaggaag cuccccagcu 113220
cccagcagcu gccggcccgu gugagaucag gaggucuuua ccagcugaac accacgugcc 113280
gggugugugc ugauauaaac aagcguggcc cacucguccu gcccuccaga ggcucccguu 113340
ccagucggaa aaggaccugc ccacgaaguu ugcaacgaua uaagccacag uguaugaucc 113400
uccauaauac agcgugugac agagcagcag aggagcgagg cagauaacau gcugcaggcc 113460
agaggcagcg ggaagagcca ggcugcaggg gcugggggag ccgugguгga ggaaguucaa 113520 uuucagccug uagauuucua uuagcccauu uaauaaauaa ugaagugccu acucugagcu 113580
aaucauugug cagguauuua ggaaggacaa aaaaauaauu aggacucagu gcccacccuc 113640
caggggccca cugacuagua gagaaaguag gcagauuuuu aaaaaauuaa ucaugggaau 113700
gugauaagug cugggagaga ggaauggaua cuuucucaug ggaaucuugg aaggcuugua 113760
agggaaggca cucucugagc cagcugucua aagaagaaca ggaaucuuua agaaagcaga 113820
agggaaaaga gcauucuuuc cugcuuggag caauagguaa cagccugcac augcccaggc 113880
cuagaggcca aagagcacag ugauuccaga aagagugggg agaaagggua ggcagggaag 113940
gaugagguaa ugugggcgca ggguguggagg cuggagaggg aggagguugu gggacuggga 114000
ggagccagau ggaauggaca gcaguggccc agccaggagc uaugcuggcc ucguacgccu 114060
cgaugucccu ucuauuuucu caggggaggc ucugcccaac augccaaguc cgaccacuug 114120
aaaacaaguc ccuggcuuaa cacagacccc agagagaguc uccaacccuc cucucccuag 114180
acaaugguag uugcccugug aggggcugaa aagcagagcu ggagauggcu cagggccugg 114240
uguuaacaaa ugccuugagg gcuccuguug uuucaaagug agucugcagg gagagcuccc 114300
uaaguggaca gcaggagggc ugcagcuucu cugcacauuc cugcugucac ccccagaguc 114360
accuagggga ggggaagga caguaaugca gguuccucac aguuagccuc ggugcccaca 114420
ugguacugag cauaguaaau guuuagaaga ugcugccugg cuagacaaag gggaagcucc 114480
cgcccacuag aaacuugcag ggagccccag uccuugauug gucauuuaau ugauuagcuc 114540
cuuggccugg ccuugaggca cugcuuguaa guacuucaug accuccauug caaacccaug 114600
augcucugcu ggacaaaucc cuccaguggc cagucuggcu gcaaggacuc ucugucugca 114660
ggccuugccc ugugcugucc ugugagagca ucugggcccc accugcugaa gagagggggg 114720
gugggguuug ccccguuucc aacaguccua cuucucuguu ucagacgcug cucagguuca 114780
acgccgugcu gaggaagcug cucauugucu ucccccacuu cugccugggc cggggccuca 114840
uugaccuugc acugagccag gcugugacag augucuaugc ccgguuuggu gggugguagc 114900
cgaggcccau ggagcauggg cccugggucc aaagcuggga ggguuaccgg gggggcuccu 114960
gcaucagacu guggcagggg cuggugcuag gaggggaccu uguugggcug gaggugucu 115020 gccagcugga gaggauuagg gugccucugu uuccauggcu ggggagccac aggagggaug 115080
gagggcagcc cuuaugaggc ggguguuugg cucuugcuca guucccacau aaggccuggu 115140
cuagugggcc cugugcugug gccaggucug uggggugagc uggggcggcu gaaguggacu 115200
caauuccugu ugaugcccag gugaggagca cucugcaaau ccguuccacu gggaccugau 115260
ugggaagaac cuguuugcca ugguggugga aggggugug uacuuccucc ugacccugcu 115320
gguccagcgc cacuucuucc ucucccaaug guacguccau gccacacccu gggccagugg 115380
gcagcucagg gcauccagaa cuggaccuua uacccacaug gucauuucuu ucccucaggag 115440 ccccacucca caauguuuuu ucuacauucu caaagccugg cuuuucucca auaauacaag 115500
uagaggaucg gguuaaaaua ggcacauuca aauaugugaa gagcauccac uuuaaaauau 115560
uuaaaaugca gugcuauuaa uuucaauugc ugauauuuaa uccuucucau uuaauuacca 115620
aauguguauu uugauuagau gauaguauug caaauaacaa ugguuacagg guauccaaag 115680
uacuaggaaa uagacuaaug uauuuaugag agaaaggaca cagcaggccc cuuugcuaau 115740
uagagauuug ggagcauggg aguaauaugg gagccaugug gaggggugcg ggcagugauc 115800 acgaccccccc acuccuggag gaaggugggu agcugccaac ccugacuuuu gaccagggcu 115860
ucucaaaugc cagguuagcu ggcaauugcc auucuuccgc aggcucuucc ugaagcuggg 115920
ugggccccug ccucacuccc cucugcaauc caguccuacc uuuauugucc ucacccaggg 115980
gccugaauug ccaagcagca gcccuuccua gcaagcuuuc cccaauagug uuuuguuucu 116040
uaacuuuucc ucccucucagg cugagugugg ucaccuguaa auagauucca aggacuuggu 116100
uuuauguuuu gauccacagg gaauugauuu auuggaaaug aaucugccuu ucuacucaca 116160
ggacugugag aggugaauga gaucacaggu gucaacacac gccugaugaa acaggauaca 116220
caagcaguuc uaguuauggg agacagugc aggaauuguu guccuuggca cccucagccc 116280
cugcagaccc uuucugcagc cuuggccaua ccuuuuagag gcuuuugugu gggagagagc 116340
aggucaggag guugacuacc caaauugacu cauuagcuuc aaacucugau gucaacacau 116400
uugaaugagu ccugccugcu uuagggccua aagaggacca gagaaguaca ccauaguccc 116460
uggcuuccag aaggucaggg aggguuucaa agaagaggcu gugucuuuaa gaaugggggaa 116520 gauuccauuu gguggggcag gaggaggaga acauugaggg acuggaaaca caugcggagg 116580
cugggagacg ggaaugacca auaggacugg gaaccagggg gagaugccaa uugcugacag 116640
aggaguuagu gcaagaggua agugagaagg guaggugggg cuggauugca gggcuguaac 116700
uacagcugca gagggagggc uucaaccuac agcugauggg gaacaacaga agguuuugag 116760
gcaugaggug gccugaugac aacucuguuu uggaaaggug gaguuggcag ggcagacugg 116820
aggaaguggg aggcucggag guuaguaacu accccuuacu gagugcuugc uguagaggaa 116880
gcauuuuagu ccugacggug aucccaggcc cugagucuuu acucugugcc aggcacugug 116940
cugaguucau cuucagcaca auccuaugag acagguauug uuacccuccu ccucaucaca 117000
ugguugaagu aggcaagguu cagagagguc caaugcccaa gaucacacau gaggaggcca 117060
ggacuggaac ccaaggcuga cucuggacau gagcaccuga ccucucuacc uaaugccuaa 117120
ugccucuccu gcugggagcc cuuuuuagaa uuuaagucuu aaaggaugga agcccagaag 117180
gaagcagaag caaggaagug gaagagaggu cccauggaaa ggacagugcc aaggacacug 117240
uacagccagc ccaauccuga ccccuuuucu ucaucuagga uugccgagcc cacuaaggag 117300
cccauuguug augaagauga ugauguggcu gaagaaagac aaagaauuau uacuggugga 117360
aauaaaacug acaucuuaag gcuacaugaa cuaaccaagg uaagggaaug gguaugaguu 117420
uggaggugcu gguuagaucc acaguuggca ugauguugcc auuuuccuuc uauagaacaa 117480
uugauaugcu uaugcaagca auuugguucc caguuuuaug uagggucauc aucccugugu 117540
uauaacucgu cuuccaagag caucuaauuc caaugugugu ucccugcuau ucaucucggg 117600
cacugacaca gggccucagu gagaaucacu ccagcugagc aucauucccu uuucuguguu 117660
cuguuucugc agagcauggg ucagccucga gaugucucag uacucaccac accucugugc 117720
cugcccaugu caauauguaa ccuccuagug cugguaguuu ucuccuaaac cauccuuugc 117780
ucuuuguucc cucuuccccu ccuugcucuc acccugucuc aguucucagu ccgguuucuu 117840
cguaucuugc agauuuaucc aggcaccucc agcccagcag uggacaggcu gugugucgga 117900
guucgcccug gagaggugg uacucugcag accacgugug aaaggcuucc gaacaucagc 117960
ucuugugccu gccucuccuc cccauaaggc agagcuauuc aauaggaaca uaaugccaua 118020
augcaaguca cauauguaau uuuaaaucuu ccacuagcca caugagaaaa guaaaaagaa 118080
aauagguaaa auuaauuuca uuaguauuuu uuauuuuacu caauauaacc aaaauauuau 118140
uucaaaaugu aauuaauaga aaaccuuauu aaugaaauau uugacaauuu cucguuguuu 118200
uuaagucuuu gaaucuuuac acucagggcc cgugucaacu gggacuuaga uguguuucaa 118260
gugcuuagua gccacauaug gcucguggcc ucugauggca gcccaggucu aaaauuccuc 118320
ccccagcuca cacacacacu uacccugggg ccugacauuu uagaccuucu ugaucucuag 118380
ggccaggcua gcucuguguu uucuccuagu gcuuuggccu ccugggagug aauggugccg 118440
gcaaaacaac cacauucaag augcucacug gggacaccac agugaccuca ggggaugcca 118500
ccguagcagg caagagguga guauccugcu ccuccugucu cagggagucu cucacagguc 118560
cugugagaag aauaggaagg gugaucauca gacccuauag uagggugggcu cugaggcccu 118620 gaaagaucug uacagagaag gaggccuccc agagagcaug gcccaaaaag cccaacacau 118680
agacccaaug gaaaagugaa cugaauugug auaguuaaga gauuccucug uugggaugga 118740
uucuuggaaa gaccugggaa gcacuaagug uguggguucuu aaucucuuag aggucacgga 118800
accuuuuaag caucugauga auauuuguag ccuauuccua uaaaaaugca ccauugcuuc 118860
ccauuaccuc ccuccacaca uuuuuacaaa acguuucagg gaguuuacug agccccaggu 118920
cacauuuaug auccugcagg agcucuugaa ucccagguua agaaccccug ugaugaauga 118980
agaauccuuc cucuggguug aguuucuaga uaggggcuca ugcaugggcc uuuggggguag 119040 ccuaaccugc auuggcuauu uguaggcuga uauuuggcuu ugccagacca aggagcauag 119100
agggaaaacu ggcgugugcc cuuggauucu ggagggugac ugcugcucuc uguaauaaaa 119160
uguguuuaaa cagacugguc cccuaugggc aggacagaga ggaugagcuc ucacucaucu 119220
gccucuuucc uggcugcagg aaaagcuuga acaguaaaac uucagcacac acaauagagg 119280
ugcccagagg aagccucugc ccugguuuau aaguggaguu aggugcugcu gacaucuguc 119340
cagcaucugc uugacugggg ccucuuccuc ucuccugaaa gccauccuca gcauggccca 119400
augcccagug ggcaggacga guccugagca cgcuucacug gcucagacag gaugaauuug 119460
auucuuuggc cuccauagcc agcccuacug gguuuacaga aaagggacag gcaggggguga 119520 agccagguca uggcugaguc caucucaaca gauccagcuu caccugcaag ugaccacgca 119580
ggugacuucc ucauggugac aaaaggaguc auggcagggu agagauauca uaccauggca 119640
ggggaaagau aucauagaau uuuccaugag cacauuuaug agacaucaag uuacaacugu 119700
guccaaguga ggcacagucu gacauccaga agguaaaacu gagcuggacg cuagaaagaa 119760
acuauaggcu uaagacacag aauugggauu auaugguagg guagcuccca cuaauuugga 119820
aacguacccu acuugcuucc cugaguaguu uuaauuggcc cagccaugcc uuuggguggcu 119880 uuugucauug uggggaacug uaauggucuc ucuguaccau ccuauaucau ccauccuuua 119940
uucauagacc cuaagcuaua agaagaaaag gaugagauua gacuaaaugu cuauguauag 120000
uuuauuuucc aucuuggcaa uauauuuuuu aguggggggug aauauauuag ccaaagggag 120060
uugguggaac ccaacucacu cuaccccugc ucccugcagg ccucucgcug uggguaguua 120120
ucugacuggc uccucuuuca uugcuaucuu ugccaauaaa uacagauaga gaaguuuacu 120180
uccaucggga cacaugcauc uuuucuaguu acuucccaaa ugucugaaaa uuauugauaa 120240
aucaugaauc auuuucuuaa accugaucuu cccucuguuu uuaaacucac augugaggug 120300
aucugaucca aaaugaaagc ugacuuuugg cguaacaggg auucaauuaa uccuagacau 120360
ggaaacaugg aagaaucuga caggauucag uuucuaaccg aagggccccu guuuugauuc 120420
ccaaauaucc caugcauuuc ugaagccaaa uaggagaaga gaagaagcag cuuccuuuuc 120480
ccguuggcag aagcuucucc agcccuagcu cuauggucau cccuccacuc cuugaaggau 120540
acucaguaau ugcuuuuuuu cuugcaguau uuuaaccaau auuucugaag uccaucaaaa 120600
uaugggcuac uguccucagu uugaugcaau ugaugagcug cucacaggac gagaacaucu 120660
uuaccuuuau gcccggcuuc gaggguguacc agcagaagaa aucgaaaagg ugaaaaaugu 120720
uuuguugugg ccacauagga gucugguuaa uuacaagccu guuucaugag agugcauucu 120780
cuuggagaug agaaacugaa gcgugcuauu cauucauuca uuccaacaaa uguuuacuau 120840
gugucuacug ugugccaagu acuguucuag aaaccaggag uauagcagug aacaagacag 120900
acaaaaaaaa auccccacuc ucauaucuaa caaaauguug uaugcauuua uccucugacu 120960
cagcaaucac acgucuaaga guuuauccug aagaugcauc ucccacagug caaaaugaau 121020
auguauaagg ugauccauug cauuuguaau ugcaaaaugc uggaaguuac cuaaauguuu 121080
agucauugua gauuggcuga auaaauuuaug guacagacac acaauaaagu cuuacgcaac 121140

-continued uauaaaaaag aagaagaaaa gucucaguaa acugauaugg agauauuucc aguaaauacu 121200
guuaaaugau aaaaagcaaa guggaaaaca gaacauagag aacgcuacuu uguauguaag 121260
aaagaaggaa aaacaagaaa guaaacguau gucugcuuac cuuugcaaau agaacguaga 121320
aaggauaaac cagaaaacaa ugaauuuggu gaucaacaag aagaaaaugg gaagaaagaa 121380
aaaugggagg aaacaguacu ucuggggaua uauuuuugua uaguuuuaau uuuuggaagc 121440
auguuaaugu uccacauauu caaaaaaaau caguaagaau gggaaguagg caaaaaugaa 121500
aacaaaaaga aaaccuaaca cugacagcaa acuaaauaaa guaacccaau uuuauuucaa 121560
auaaauauca uaaucuugca aaagggggau agagcuaaca caaacaacug cugaacacag 121620
uguuugacuc uauauccuca uucuugggca ggguggagcg ggggagaaga acuacaaaua 121680
auuucugagu ucuuuuuagu uuguuuuuua uaguugguaua ggcaaaguga uucugaaaau 121740
uuuagaugug uuacaggauu aaauaaauua auaaaauguu ugauguuauu gggacccaga 121800
auucucaccg uggaagaagg gacuuacaaa uauggaaaag ggaaaagcaa gaaagaacug 121860
ugaggucaug gauaggaacc ggagguagca cugggaauuc aggaauauuu auaugcuugu 121920
guuugugggu gcaugcagau guguucaugu uucaugcaca uaggcaugua uauauagaca 121980
uauauuugca ugugugua uc ugucuucga aaggcucaag aagcaaaaac accccaguag 122040
ccaugagcac acuuagcacu caggcuuuug ucuuaauaac auuccccacu aaaaguaacc 122100
cugauuccuc caauaaauga uaaguuccag ggcuggaaug gcauagguau aaaaugaacc 122160
uggaauaucu uaugccagaa aguaaggaag ugcuuuuaaa aaaaaaauaa ggggcugggc 122220
augguggcuc acaccuguaa ucgcagcacu uugggaggcc aagguaggaa gaucgcuuga 122280
gcccaggagu uccagauuag ccugugcaac auagggagac ccugucucua caaaaaauua 122340
gcaaacaaau uagcugggcc ugguggugca cgccuauagu cccagcuacu cagguggcug 122400
aggugggagg aaugcuugag cccaggaggu ugaggcugca gugagcugug aucaagccac 122460
ugcucuccag ccugggaaac agagcaagac ucugucucuu aaaauaauaa uaauauaauu 122520
uuaaagaaau aaaaguaacu cuguacagau ugcuuauugg uuacauggga gaaacauaau 122580
aauuuuacaa uggagaaauu agacagcacc uuaacugggu gaucaaaauu aaccauaagg 122640
ggcagaugga caucucaugc cccgagaugu gauacccugu gaaggacaca auuucacuua 122700
uguagaaucc agauuggaga uauguaaccu gaaucuuauc augaggaaac aucugacaag 122760
cuccaaagaa ggaauauucc uuaaaaaaaa aaaaaggaga cuguauucuu caaaaacaua 122820
agagucauaa aagacaaaga aagagcuaug gaaauaucuc ugaucgcagg aggcuaaaca 122880
ggcauaauga cugaauagca gacaauagac uacaucuugu gcagaagaga aaaaaaauga 122940
uagaaggaua uuauuggacc aacugacaaa acugaacuau gaacaguaga uuagguaaau 123000
guaucauaac auuaaguuua cugacauuga uaauguacug ugguuaugua agagaagauc 123060
ucuauucuua ggaaauaugc ccugaaguau uuaggaguga agggcuguga ugaguaauuu 123120
acccucaaau gggucacaaa aaauugugug ugagagagag aaggguuuua uuaguuaaua 123180
auucuaugaa cuauuuuuau uccuauaugu uugugugagu uugaaacuau uuccaaauaa 123240
aaaguuaaaa auggagauua cauucuagug ggagggauag acgaucugua gauaaaauagg 123300
uaaaauaucc aguacauuag agagugaaaa guccucaggg aaaaguaacg cagggaggaa 123360
cugcuggggc aggguuugca uuuugaggua ggguggccca gggagagccu gcagaggaga 123420
gaaccugaau gaagaacuag aggugagaga aggagccacg ugcacaccua gggaggaaca 123480
uuccaggcac gggggacuag uauagaaggc agaagcaugg ugagcuuguc uccaguggcu 123540
ucccuagauc cccuccugcg caugugcaca cacaccuggu gucucuguca ucguucccuc 123600
acagcacugu cacgaucugc caguauucug uuuauuuuga cugccacccuc cccgcagucu 123660
gaggauagca gcaauggcug uguucacauu guucuccagu gccugguuca gugccuggcg 123720
uauggucagu gcuccauagg uaugugucgg augcacaagg cuuugggugu aacccucuug 123780
acgggugggga ucaacagguc ugggacucac caucuucuca aacagagccu uccuccucca 123840
cugcuagcca ugguccagga cgcugggcga gacccacugu cuugcucuuu guaaggcuga 123900
aguccauuuc ccaggcggcu acacccaaca gaugcugagc aggcugggcc acccugggau 123960
ccaagacaca gagagaaaga gccccugucu ggcgccugaa gcacaugcca gaggacagga 124020
gccagcagga gccuguuuca gccuagcugg ggauuucauu cuggaggcgu gagaucuggg 124080
agcccaaggc uuugaacugg gggagguuug ggguguuugc uugucuucuc caaauggcau 124140
uucuuucucu ucccuagguu gcaaacugga guauuaagag ccugggccug acugucuacg 124200
ccgacugccu ggcuggcacg uacagugggg gcaacaagcg gaaacucucc acagccaucg 124260
cacucauugg cugcccaccg cuggugcugc ugguaacugc gggcuugggc cgcaccaagg 124320
gcuuaaacca agugcugggu cucuuggguu ggggaaauag guucugggguc ggcagauuua 124380
gaaacugcag caguuuggcu uuagucugga cuguuuccug uguugcucau uuugagcgau 124440
cagcccagug uuugguucac acagcuccgg agaaaaacaa gucacggcac agccuugacu 124500
ugggacugcg cacauccugc guucccagga ugucuccugu ggggccaucg gcucacagcc 124560
gggaaguuca gcccacucug cggccugucg gugucugguc cccauacagg agcacugagc 124620
ugggucaaag gcuccugagc ugagccaggc caggccugag gccaugccca cgcagcccaa 124680
ggaucaugag ggcacaggac auagcgggaa ccaaggaagu gaccugagug accucccugc 124740
cuucugacaa auguauuugc aggauuuucu uuuuuugagg agaauucugu cauugccuua 124800
auccacuuua auccccucgu gggcugaaau gggcccagga uggacgccac gcuucuuuac 124860
ucuuggaucc accuccugcc uucccuaccc uacaccaggg uaccccuguc uugcucaagu 124920
gaggggagug acugugugcg ccuucuguca gcucauccuc cacaggggag ccagcccagg 124980
gggaagcagu aaucagaagg gccagcuccc agccugugcc cccaaccuuc ucuccacccc 125040
ccaggaugag cccaccacag ggauggaccc ccaggcacgc cgcaugcugu ggaacgucau 125100
cgugagcauc aucagagaag ggagggcugu gguccucaca ucccacaggc aagagauucc 125160
cagggcuggg gaagguggggu gggaauccuc uccugcucac cuccucucuc cugccccaca 125220
gcauggaaga augugaggca cuguguaccc ggcuggccau caugguaaag ggcgccuuuc 125280
gauguauggg caccauucag caucucaagu ccaaguaagc agaugguggg gcgugccccu 125340
uguugccuuc uguggaucca ccuggauccu guguucucca uugacacuug gaagaguccu 125400
gcugcuccgu cauccccugg ggcagaggca gguggugggcu gggccucauu cuccagcagc 125460
agauggagaa ggccaucaug cugauaagaa acuccucuau auuggccuaa uuuccugugg 125520
ucgaagacuc gcccaagucu cuggaugggg caucugauca ggaugcaugc agagccuggc 125580
ugggaugagg gagggcugcu accacugccu caauauuuca ccacuuaucu caacagaucc 125640
gggaccugug gccuauuuac uaagagucca cuccaaugua ggaaugguua ggagaccaac 125700
ugacuugagg acccaucuuu guuuuuagaa uauuguaugc uuuugaguuu gaaaaaagac 125760
cauauguuau augacaaacc aacaauggca guaaucuuga auaggauuau ccuuauccug 125820
uacccacaca uuguaaacua uuguagauaa uuccuuauua uuaagaguuu gcaugccaaa 125880
gcuaacaguu uaagauuauc agcauauugc cgugcucauu cacguucuga uaugcuuuau 125940
aaccuagaaa agagcagagu uacaauuacu cauuuauuua acaaacacuu auuaagagcu 126000
cagaauauaa gucacuaagc ugguuggugg gaggaacagc acauaaccca ccuuaucuau 126060
gcugaggugc auaauccuga ugcacccaca ggaggguguu acacagaaga ugucauccuu 126120
ucauaugugu cagagcagau aaauaauuga gagaaagguc uaauagauua gcugcuugug 126180
gcaaguggac guuugaccca ugauuuauug agcaacuaca acuuggacac ugcauagaua 126240
ucuauagaaa uagcagcaug ucaggucacc agaccugugu cagcaacuuc cuguguccaa 126300
cugcuggaga aagggaaguc uccuauuccu uucccuccag cuccuuaaua ucuccaugau 126360
agagggggug agaggggagu guucccugug uggagggaug gugaguuuuc uggagcugaa 126420
agguaaacag ccuuucuccu cugcaucuua cugcagagga gaacagcccu agacugugga 126480
ggaagcuuug gagucaguua ugacugacac aggauaccag ggcauagggu acugacaccc 126540
gcuagccgug cacacacucu cugguggacc aucacucauc caagagaggg uaaccagcca 126600
uccugcugaa ggagaaagaa agcaccaaug gcccaagccc uagcagcucc auuguuucag 126660
gaagcuuccu cagggaagug cugccuuccc gagccuuugc ucccaccugg cccaucagcc 126720
cuuaccacca cucaguaugc acugguccac gugucuuuau gggcagucuu gggaucccca 126780
cacugggcua aaacuaccuu ugacggccag gugcaguggc uuacaccugu aauccuauca 126840
cuuugggaag cugaggcagg uggaucacuu gaggucagga guucgagacc agccuggcca 126900
acacggugaa acccugucuc uacuaaaaau acaaaaauua gaugggcaug gugguaugca 126960
ccuguaaucc caccuacucg ggaaacugag gcacaagaau ugcuugaacu cagaaggcag 127020
agguugcagu gaaucgagau cacaccacug cacuccagcc ugggugaaac agcaagacuc 127080
ugucucaaaa aauaaaauag gcugggcgug guggcucaug ccuguaaucc cagcacuuug 127140
ggaggccaag gcgggcggau cacuugaggu caggaguuua agaccagccu ggccaacaua 127200
gugaaacccu gucucuacua aaaauacaaa aaaaaaaaaa aaaauuagcc gaguguggug 127260
gcaggugccu guaguuccag ccucucagga gacugaggca ggagaauugc uugaacccag 127320
gaggcggagg uugcagugag ccaagaucau gccacuguac uccagccugg gcaacgguga 127380
gacugucuca aauaaaauaa aauaaaauaa aauaaaauaa aauaaaauaa aauaaauaaa 127440
auaaaauaaa uaaaacuacc uuugacuuca gcaaguacga uuaucccaca uuaccaugca 127500
gacauuugau cucuaaaaac ugguaucaaa ugauuucucc agggacuacc augguuuuuc 127560
ucuccuaguu uucaguaugu acacaggucu augguauggg ccuuuaaucc ccaguauuuc 127620
uuuuuuuguu guucuuguuu ggguuuguuu cuuguuuuuc gguuuuuuug agacaggguc 127680
ucacucuguc acccaggcug gagugcagug gcaugaucau ggcucacugu agccuugacc 127740
uccuaugcuc aagugauccu cccgccucag ccucccaagu agcugggacc acaggcaugu 127800
gccaccaugc ccugcuaauu uucguagaga cagggucuuu cuuguugccc aggcuuaucu 127860
uacauuccug agcucaagug auccucccac cucuaccucc caaauugcug ggauuucagg 127920
ugugagccac caagcugagc uuaaucccca aaauuucuga ugagucuacu ccuuauuuug 127980
ggauuaccuu aggcccaacc acuaacagag gccuguccug cacugugugc auccccuaga 128040
uuuggagaug gcuauaucgu cacaaugaag aucaaauccc cgaaggacga ccugcuuccu 128100
gaccugaacc cuguggagca guucuuccag gggaacuucc caggcagugu gcagagggag 128160
aggcacuaca acaugcucca guuccagguc uccuccuccu cccuggcgag gaucuuccag 128220
cuccuccucu cccacaagga cagccugcuc aucgaggagu acucagucac acagaccaca 128280

-continued cuggaccagg caaguuggcc cuggggcacc gagagcugag caaagacugg uccagaacac 128340 ccagugugggg uuggaauugc cauaagaggg aggcauaaca uucccgauuu uuaacaaacu 128400
cuugcccucu guuuauuggg guaaaagcug auauaucaga aauuguuuuc uaacaauauu 128460
uuuuagucau caggaaacuu cauugauucu uuuuuuuaca uuuuccuucc cugugaugcu 128520 auggugugu auuucauucu ugcucguuug ugguggugu uuuuccuuca aaucagcuuu 128580
auugaugugu aauuaacaua cgaugaaaca cagguucuuu gggaggccaa ggcaggagga 128640
ucacuugagc ccaggaguuu aagacaggcc cauguaacaa agugagacuu ugucucuaca 128700
gaaaaaaaaa aaaaaaauca gaaaauuagc caggcguggu ggugcaugcc uguggucca 128760 ucuacauggg agguugagga aggaagauug cuggagccca ggaggucaag gcugcaauga 128820
gcuguguuca uaccacugca cucuagucug ggugacagag caagccccug ucucaaaaaa 128880
gcaaaacaaa acaaaaacac cuauuuuaaa uguacaguuu agugaguuuu gauaaacgug 128940
cauuccaugu gugguuuuua aaaauguaau cacauuuuuu auugcgguaa aauauaauaa 129000
cauaaaauug accaugccaa ccauguuuaa gugcacagug caguggcacu aaguacauuu 129060
acauuguugu gcaaccguua ccaccauccc cgauagaacu cuuucaucuu gcuucaguga 129120
aaaucugugc ccauuaaaca cuaacucacc acuuacugcc ccccucgccc uuggcaacua 129180
cuguucuacu uucugucucu aaggcucuga cuacuauaga uaccucauau aaguggaauc 129240
auacaguguu uguccuuuug ugucuggcuu auuaugcgag gacuuagcau aauguccuca 129300
agguucaucc guguuguauc augugccaga auuuccuucc uuuuucaggc cgaauaaauau 129360 uccuuuguac guauaugugc uacauuuugu ucauccaucu auucauucau ugauagacau 129420 uuggguugu ucuggguuuu guguuuuuau auauguuuuu uuaaaaauaa acaucuuuag 129480
agacaguuca guaaagcagu ggaaacaggg aagucuccau uuaaccccug aggaucuggc 129540
ucaccugcac cuucucauca gcauuaagca gagggaggca cgagcaggag ccaccugcac 129600
acucaaugag gagcugaaca gggaucaauu accuuuuuuu uuaguuauua ggaugcugcu 129660
agcugagaau cugccuugcc uugauuaccc caaugucugg ugcccaaguc ccuugagucc 129720
uccagcagga acuccugugg caucacucag gagucuaguc uaagaagcua gcucugacca 129780
gggcaguggu ggccaggcuu cugugagugg gccagccucc cccggguagg acacaagcca 129840
uaccagcagg gcuguaugug aacuguggaa aauagagagc aaagugggua ggugggugua 129900
gggugcuguu uuccuggaaa uaucuaccua aucucgcucu ucucuuaccu cuaggugguu 129960
guaaauuuug cuaaacagca gacugaaagu caugaccucc cucugcaccc ucgagcugcu 130020
ggagccaguc gacaagccca gguaccccug cugcuuaugc aguccacagc uugaggcagu 130080
uccuuggcuc agagcccagc ugguucacug ggcuugaguu gcuccaaggc ucagauaugc 130140
cuccuacaga gagccccacc cacaccacgg ucccuaccaa guccccacca cauccucauc 130200
acauccuugc uaagucccug ccacugugug uucugugcug aagaacuuuu cauucaguag 130260
uuguaggggu uccuauugua aucaggaaac caucuggaua gcaugggaga gcauuuuuga 130320
aaagaacuuu cccauguuuu ugcuuacagc aaaaaagcuu ggauuugggg aauaaggagc 130380
agagaaggua auagagaaua uuagaauguu uugggugcuu gacaucuaug ucuggacaug 130440
uguuugaguu ucaagggaag ggacuuaacu ggcacaucau uucaguguca gacacauuug 130500
guuagaucaa ggaauagcau cuguuguagg aagagggcuc uuuguucuuu auaaaaaauua 130560 caagaagaug gagaaagaag caauaggagg uaugucuccu ggcuugugau aacucuugga 130620

-continued auaggugcuu guagguuccu gcccuggcac agugccccau guaaggagca caccacccaa 130680
gaaggagaga gcuagagcaa guacuggagg aggcaccagc aucccaaugc cuuggcuuaa 130740
gccugggauu guagagggau gaauuagcca cucucuucug acuuaccugg agaguaaauc 130800
aaaucaaauc aagaagcaag gauaugcaaa aaccuuauuu ccccauaaag uuuuuauucu 130860
gcccaguuuc uggauugcaa gaaaaaccaa auacagcuaa ugauugaaac acugcugucu 130920
aaagcagugc uugugaugaa uuuuuucccu uccucuugac cagcagagac cuaauggcua 130980
cuuggcaaaa cugacuuugu cuucccaccc cuuaccugcc agagggccca gaaaugccua 131040
aggcuccuuu aguuacagaa aguuugcuuu uacugagauc uuccagccac ugauucccau 131100
uuauagaucu ggugauugcu guugacauca guugaaaauu auuuuuaaaa accacuugca 131160
guugcaaauc cuuuuuauaa cucuguaacu cagaauauag aauugggguag caaaauuguu 131220 ucccagaauu accaaugguc uccccacccc ugccuggcau guucccucuu aaaggacuaa 131280
ucccaccaca ucaccucugg gccaggcaga acaucagggg ugcugauguu cugugaucua 131340
cagcaguuaa uuccaaacuu uucucccuua uuggaugaga ucauuuuucu auuguguuuu 131400
uuacauuuuu guucacaaag auuagaaaac cugcaacaca cuuauuggca uauuuuucug 131460
auaauuuuca uccaaaaccu aauucugacu uuacaacaua cuaucuuuac aaagguuugc 131520
aaaaauucuu ucauauagca uuguauaugu cugucaugaa auaauaguaa guauauuauu 131580
guuuacauua uaccacuuca aaauaauuuc cuuuaaagua uucuucaaac aagaaaaagg 131640
caauuucucu caagaaguuu uagagagaau uuacaacuug cuccuaagca aaugugagaa 131700
cuucaggagg uucaucuggc cauuggcuuu acaacuccaa auugugagcc aggaccacac 131760
agauauuucu cuagaaauca gcguuugcuu accaagaaca uuuuuacucu ccaaaggacu 131820
ccauccugga aaacauguuu ugggauaagg ucuuaugcaa ucuuauacuc uguuauuaaa 131880
accagugagg gucaaggugu uaauagauua aguagugaca gaugaucaga caacuuagaa 131940
acauccuaaa uagguuaaua auuaugugac caucgcaugu gcauucccaa auuaggaaca 132000
acucagauca auuucuaauc cuuauucuua cacuguucca guucccccau auaacucgua 132060
ucuuuguguu aguuucagaa guuucugaag uacccucagc cuugaugggg auccucgcac 132120
caccucaaau ccuguucuca gcccuaagaa cuguguuagu cauccucuua agaggaugug 132180
ugauuuuaaa ucagauaaug ggauaaacca cauuucgucu agacugguca ggccuuuguc 132240
caguccccuc cucgcccaca cuaccccagc uccacagcgg gcauugguuc aggaauucaa 132300
cccacacuuu auaacuggag acaguaucuc uccaguuaaa aaggucaccu ugguguccgc 132360
uucucaagga acauggacau cuuuauuaau caaagcccaa gcuuugaucu ggagccuaau 132420
auccugcacu ccagcucuca ucucuccccu cccccaguca cacuuucaug cuucccagag 132480
ccaccccuac aggaaguggu caagggaauu cuauaccuca gggcugaccu aaauuaggau 132540
uucuuggcuu uuaagauaau gguaacuuuc uuaagcuaaa aaagccccaa aagacccugu 132600
aagagcccuu ggaaacagca ccaugggugu agcuuccccc caggauguaa gcauguaugc 132660
acacaucucg uaugugugc uuuguaacaa augccuggau cuuaguacca gggagaccug 132720
auucauagau uucauagaga aggagagaaa gauggcccau aaccugggug aucugacaga 132780
aucacagugc ccucagcuga gugcccuuca gaaauugauu gacaacuguu uagcuuuuga 132840
aaucuaaaag uaguacagca ucucagaaaa ccaagaugac gcgaguccau gugaucuccu 132900
uccacaggac ugaucuuuca caccgcucgu uccugcagcc agaaaggaac ucugggcagc 132960
uggaggcgca ggagccugug cccauauggu cauccaaaug gacuggccag cguaaaugac 133020
cccacugcag cagaaaacaa acacacgagg agcaugcagc gaauucagaa agaggucuuu 133080
cagaaggaaa ccgaaacuga cuugcucacc uggaacaccu gauggugaaa ccaaacaaau 133140
acaaaauccu ucuccagacc ccagaacuag aaaccccggg ccaucccacu agcagcuuug 133200
gccuccauau ugcucucauu ucaagcagau cugcuuuucu gcauguuugu cugugugucu 133260
gcguugugug ugauuuucau ggaaaaauaa aaugcaaaug cacucaucac aaacuauccu 133320
aauucacagu cucccuggug ugcaccaccu aguauaguuu uagacauucu uuagaugggu 133380
gcauagcucc uugucagucc caugcacuuc ugugaguguu acugccucag gacugcucgu 133440
ucuggcaaga uucugcaaca cuagguugga agugaaugga cuagucuuaa uguuccaugu 133500
caagucuuug uagaguuuga agaaaacacc caacuaguaa ugccuguaaa cauuauccau 133560
ugucagcugg guauuacuga cuuuaaguuu cgugucuguu ugcccagcuu auuugagugu 133620
uuaccucaca aguguaauua ggacaggaga caaagaggca ugcacaggcg agaguugguc 133680
cuugguugga cgugagaccc gacaggacuu uguaaccauu ugaagagguc aggaccucau 133740
ucucaugcug cugugccuuu ucugcagugc uaccaugugc aucuucugca gugguguuag 133800
aagggaauga aggccgggcg caguagcuca cgccuguaau cccagcacuu ugggagccug 133860
aggugggcag aucacaagau cagaagauca agaccauccu gacuaacaca gugagacccc 133920
gugucuacua aaacuaugaa aaauuagcug agcauggugg cacaugccug uagucccagc 133980
uacucaggag gcugaggcag gagaaucgcu ugaacccagg aggcagaggu ugcagugagc 134040
ugagauugug ccacugcaca ccagccuggc gacagagcaa gacuccaucu aaaaauaaau 134100
aaauaaauaa aaaggaauga agauggacau cuaguucaca uaaaugcuca ucaagauuca 134160
gaaaauaaua auuuuaaacc aaacauuucc agagacugug gaugaggaga acaagugggu 134220
uuccuuguca gggcagucuc cccuccauga ccuagagaug ggcuucgucg uaaacaugcu 134280
uucauuauac ugaggauaga cuccagaguc ggggugaggc aagaggaaaa ggggagagau 134340
gcugaggccc aggaacuguu gcugagaaga ggaugagaaa gaaagugagc acaaggugcu 134400
aaaauuuuug uuucagcugu gcuuguuuag aggcagacag agggcaaggg cuacacaacu 134460
uuaaguccug cacaccuccu ggcuugccac uuugcaccuu cuagaugcua ggcaaacaac 134520
ugcccauaga gacuauaaaa cuacuuuggu aaccccgcag cuucaucugg uguugacuuu 134580
uucuuuuaag uuaccaagga ccaaaacugu aagaccauuu uagcuagggc uaggauagag 134640
guugggaaag cccagcacac ugcuugcauc acacugcugc acccuggcug guuucauaau 134700
uuaaauuagc aacugcaaua ucacaggaaa gaagacuaca cucuucgggg cugcuuagga 134760
aaagaaaacu aaaaaaagac uauguagggg aggugguuua gcagccauuc uguuuggcug 134820
ugaggguuuc ggaaaggcau caugaacugg gaagagucga ugcagguaaa aucugcacac 134880
ccccuuaagg aaaaaucuca guuuaccuuu ugucuccacu acaccugagg ucugugucuu 134940
uucauccugu uuuuuccagc uccuggcaca cagaaaaugu ucaacuaaua cccaccaaac 135000
ugaaaaccca gcaaacuaug aaaacucagc aagaaaaaua gacagaaaag aaguggguccc 135060
aagaaaauga ugccuccaaa aagcagcaaa gggcaagugg agcaggagga ugccgugcuu 135120
uaaaaacagc cacaggccgg guguggugge ucacgucuaa uccuagcacu uugggaggcc 135180
gaggcgggcg gauugccuga gcucaggagu ucgagaccag cuggccaaug uggugaaagc 135240
ccgucucuau uaaaauacaa aaaaaaaaaa aagaaagaaa gaaaauuagc caggcguggu 135300
ggugggugcc ugu 135313

<210> SEQ ID NO 7
<211> LENGTH: 7913
<212> TYPE: RNA
<213> ORGANISM: Homo sapiens

<400> SEQUENCE: 7
guaacaguua cugucugugg uuuaaaaaug aggugugggag caaauaaaca gguuggaagu 60 guggggguggg guggugggggu aggguggugg ggcagggugg gggguuguga gcagucagug 120
ggcuugucgc cgauuagcac ugaagcagug uuuagcugga cggccuuucu gugggccccu 180
cugacagugc ccuucccagg aagaugugu ucucugcccu cagccacaug aaaaucuuuu 240
gccuaccgug ccugucaauc cauugccugc ccgcccccucc cccacccccc guuuuacacc 300
ugccugucca gucuaccgcu cucuagggca uccacgcuga gcaguggggaa gaacuuuaag 360 cccugaagag caggccaaag gcaagcaaga accccccucga acagcuuccc agcuuaguga 420
ggccuuauuu cauugauucu cugaggcaca uuguuuuuuc acauguuagc auuucugaaa 480
uugggaugca gcucacgauc aagucacagu uuaacuggac acauuauuuu ucuuucuuag 540
uggugcagaa aaguaacagu gugucuuaca auugacugcg uccuagauuc ugugagaugc 600
aauacguuau uaaccaucac gcacauuucc ugaacucuuu caaugagcag acaccagccu 660
ggguuagacu ggagcccuaa aagcacgaca cagauuccac ccuggacugg cuucuguucu 720
gccugggaaa acccaaagua cguuuggaga ccaagagcaa cauaaaguag cauaggugga 780
auaguccaug agaagugcga gcaaaaggug ccggagauca gagaacacca agacuguacu 840
uguaaaugac aacuggcuuu gugcaauuuu uucugggaaa ggauaaggag ugacuauaga 900
acuguaaaga aagaaugcac uuugcuacag ccuugcagag uugugcaaau gccgaugacu 960
aaaggagcug aaagaggaag gaggggauaa gggaugggggg cuggguaggg gugagauuag 1020
gacccuggga gcugcaagcc acuggagaga ucaggaggaa agggagggag accugcuuua 1080
ggcgagaaga gaacaguauu uguuccaaau cucgguucag aauaaguuca uguaggugau 1140
ggggccaacu ggaacaggug aaggccuaug aaugagugucc ucaguuaggg ucuccuuaga 1200
guuuaauaug aaaaggugu agcuaaguac agagcuggua ccugagagag uaaaaggaaa 1260
cucuaaggua ucauggaggu agcaauugca ggacacagcu cccaccccua gggcugagag 1320
aaccaaggga agagacagga auuauuaaga cuuggagcau agaugagagg ucuguggagc 1380
ugacauuagg acuugggagg aaggcgugca uggaggcugc ugcuggaucu cugaaccuga 1440
ccucgggucu ggaccccuga ggagaaagcc cuggcagguu ggugcaugug gggccgaggg 1500
acaauagcuu aacaaccagc auaaaagaga gcagcauggg acacgcuuca accaugcgca 1560
uggauggcuc caaaaccugu guguggcugg cccaggacgc agggaggcug caggggggaag 1620 agacaaguua aaccugacuu gucugggaag caccauuguc cucaggucac uuuccucugu 1680
caagccuggu gcugaaguua ucuguugucu ccaggggcca aguauuaaga guaaucagaa 1740
acucaguccu uucuucuagg agcuucccuu cuugcaugaa aauccugaua aaacuggaaa 1800
aaaaaaccuc augauuaaau uuuuucaugu auucauucuu uccuucuauc aaaaaauaau 1860
cuccaggcac cgugcuaggu ucauugguau acaauggcaa caagaccucc cagccccugc 1920
cuaugugagg caucugugga cugcggagga aaauccaaua ugccauuguu cucucuuucc 1980
cauaagaaau uacaauucuc aguucauuuu auucucacug ugcucuuugu gacccucaaa 2040
gggggucaca ugauaaacagg acuguagcug cuggccuaaa augagcccau uccuguggcg 2100
cucaugucgc ugugacagag aauaacccug uuucagaau gcucuggugc ccucccucuc 2160
aaucuggccu uucgcuggca ugggugggcg acuccugcuc agggacucug ccuucuccac 2220
agugugcucc cagggagaug gagccacucg ggcugagggc cuuggccagg gcaccuccca 2280
gggcugggcc uggucugggc uggcguucac uggaugccau ccugauggcc uggaaauuga 2340
gauuucuguc uggcacgccu cccgauggcu ccccaccugc uaccacauuc caggagcuuc 2400
caggaugucu ggguaagaca gaggcacccc caacagauuc aguagcucug agagggaucu 2460
guggcuccuu ccuaagcuug cgguucuucu ggaaacuucu gccucuagaa gauggucccu 2520
cuaagaaaag uacaaccacc cagcccauaa uucagcuccc agguuuuccc ucaaaccucc 2580
augucuccug uaagcagagc aagaguaaaa ucagauacca aauuuccuca uuccucagcu 2640
cccaaucccu aagggcauaa gaugaaaauc uucagaucuc ugcuuuccuc ccucuuuuuu 2700
ucuuccucug uuaacauuug ucaaguguua cuaagugucu ggcacuguac uaagugcauc 2760
accucccuga acucuccgaa caguuccacg agagaggccu cucugugauc cccccgguac 2820
ugaugagguc acugaggcuc cagagaagga uuaguaacug guggggguugg accugggauu 2880
cacacccaug cugcgugacc caggacaggc aggcauggcc guuacaccac acugaccccc 2940
guggaucgag aucuauccaa uagucugguc acugauauca cuaagauaga guggccauau 3000
aauuuaucau ccaaucaggg caguuuugca agugaaaggg agcacuauua auaauugcac 3060
ugggacaaua aauguaaacc aacacuggac cuggaaaacu gggacgugug uuugcccuau 3120
accaagguaa gcuagacaca gccacugccu ucauggaguu cagaaccagg caggggcggc 3180
ucccacguau aauuacugug cagcacaacg uggagaccgu ggaguagaag gaaacacgga 3240
ugggagguga ggaggagguc ugugagcuca gaggaggcac cggggcugga gagggugaga 3300
gaagacuucc caaggaguuc auccugauaa cgugcauucc caaugacgag cgcucucucc 3360
acugcacaag acaaguauac aucugcccgu guuggcugug gaccuggcgc ugugucaggg 3420
aggguuuaug aagaucacua ggugggucuc uuggugucau cccuucaucc cagcuucugg 3480
guuaggaugg auaucugugg gggggccuga ggacucauga aaguggggcg cuaaucaugu 3540
uuuggacacc acacccugga gcaccuggga cagcuguggc cuuuguccug gguucagcau 3600
caagccgagg auguggcaag uaaagagagg cugggcacca acuccagugu acccaggcuc 3660
cgggucaugu uuguccaggc uaagaauucu guccugguuc ucagugcaga aggaagaauc 3720
auggggcuca uuuuaggccu uggcugccuu cuguuaaauu gaaaacagag caggaaggaa 3780
gaaaauuuaa caggcucagu ucuaaaacaa caagcacaac ugugcccuug ccagaaaccc 3840
cuccucccca uguugauuga augguaaaga gaggagggga ggugagaggg agagagagag 3900
agaggaagag agagagaaag gaaagaaagg aaagaagaag aaagaaagaa aaggaaagaa 3960
agaaagaaag aaagaaagaa agaaagaaag aaagaaagaa agaaagaaag agaaagaaag 4020
aaaggaggga gggagggaag gggaaaagaa aagaaaagaa aaagaaaaaa agaaggaaau 4080
accaguuugg gaaaaaagaa uuuuccacca gcccuucuga gccuuggcug ggcuuaauua 4140
aaguuacaga cauguguaaa gggcagggua gggggagucu gagcugcuga gaaaacaugu 4200
uuuuaauuau acuguggaau uucucccugg gguaugccug uacgcaguua agcgucaagg 4260
acagggaugc cgcucugggg aggggaagcu gagcaugauu uuggaagccg gcagaagagg 4320
cuauugugaa aaccagaccu gucaggcuag gaaaagaaug gcuggugguc uuugaccagg 4380
gagugacgcg ugaaaugcag caaccgcccc cgcccccgc caaaaacaaa cacacucuca 4440
cagaguuaga acaacaguga ccucucaaca aauauuuuuc aaagauuacc aaccaaccau 4500

-continued uaccuagagc agcgguucuc aaccuuggcu gcacggugga acuaccugag acguguuaaa 4560
aagaagaacc cugaugucce augccccaag auucugaugu aguugaucug ggguaugauc 4620
ugagaccccg gcauguuuuc agccugcagc cacaugagaa gugcugaccu aaucaacagg 4680
ggugaugauu ugaggggcgg ggacuauagg caaaaaaaaa cagccuaauu caaggaugag 4740
aagagggcac aggugaggug ggaacagucc uagggccaga caaagaagga agggagaaag 4800
gaggugcuga ucccuccccu acuccugaga ggaggccuuu aagucaccgu gccuugugga 4860
gaccagauuc uucaaaaaua caagaaugag ugagugaggg agugggugga ugccaggaga 4920
gugcgugaca agccuugcaa gggaggauga caaugcacua gcuugguuug gaaauuuuac 4980
cccuggaaca ggcaggccaa gcuggcuggu ccccucccug auacacagcc cucccucuuu 5040
auauauggag caggggacgg ugugugcug guuucuuagc aagcaccaug guuccaaguu 5100
ggcaacuggg gaguucugaa uccaaaaagg agggagauga acguaagugg agggcaggcc 5160
uacaagguug cagauaagcu uaauucuguc uccuuacucu ucugccuuug caacaacccu 5220
gugaucuugc gacaacccug uaaggcaaua acaaauggcu cauguuuauu gaguguuacc 5280
ucaugccaua uugugcuuuc guguuuaaca caauugucuc auuucacccu cacgacugcu 5340
cugggaggua gguccuggua ucacauccau uucacagaug agaccauuug gcacggaaga 5400
guugaguggg cugcccaagg ucacauagcu aagauggaac aggcuggaua ggaaccccag 5460
uaacuugacc ucagaguaac cuucucuuaa cccugagugu acacuguagg aaaaaugagc 5520
agucccauuu cagagaggac aaaacugaga cucagagguu aagcaagccc caaagugguu 5580
guuaacccag aucuucccac uaacucccaa aucagcauca guguuuaacg uaccagaccu 5640
cucccagaua gauguugccg cauggaagac agccgaucua cgugauagaa agccaauauu 5700
gcaagcaguc gucuaaagga gucaaaugug uuggauuuga acuggauguc ucauuucuuu 5760
ggugaagaca cuggaaacaa cuuccagguu ucaucaauug cuccuaucac ucaacguugc 5820
uaucuuacug aacuuguucc ccagccuuac ccacugaugg aaugauccag aauggaagac 5880
aagacaccaa uguacaugac ccugggggag gcuguuucuu aaaucuacag acuguuggug 5940
accugagccc caugucacca aaggcuuucc uggagaagcc uccuagacca gucuugacaa 6000
aggcucacuc auuccgugga uauuuauugg gcaccuauua ugaguucugc cccaugaggg 6060
gugcuggaau cacaguagug acaacgacag augagguucc uguccucagg aagcuuacug 6120
cccuugaggg cuucacuuac uuggaggagu gaugaaccug aagugcggug uguguuaaga 6180
agcggaaguc cagggccagg cgcgguggcu cacgccugua aucccagcac uuugggaggc 6240
ugaggcaggc ggaucaccag gucaggagau cgagaccauc cuggcuaaca uggugaaacc 6300
ccgucucuac uaaaaauaca aaaaaauuag ccgggcaugg uggugggcac cugcaguccc 6360
agcuacucag gaggcugagg caggagagug gcgugaaccu gggaggcaga gcuugcagug 6420
agccaagauc gugccacugc acuccagccu gggcaacaga gugagacucc gucucaaaaa 6480
gaaaaaaaaa agugccucac ggagagucua uucuuuucuu cccauauugu gugugugugu 6540
gcgcgcuucc uccaacacau ccucccuaua uauauuuuga guaaaacauc uuguaaaaag 6600
uuacagcuac auaaucacca ccugucccua aauaguuuuu gcuuuuucuu ucuucaaugc 6660
acgaucauuu ucccccauca auuuauuuuu uaguuucuua uaaucuuguu gccaguaggc 6720
uguuuuuuaa aaagcagaac augguuuguu cuuacuagca ggaaaggagc auuuauugag 6780
ccucugcuau ggugucuuuu auuuugcuga gagccuauuu acauuucuuu gagaggaaaa 6840
caacaaaggg uuacaugaaa gaccauguga auagccccua gcugaucuau uaaacuugcu 6900
auuccccggc cagcugcuuc agaucucccuu cagaucuuau guguuucccuu ccuaaggucc 6960 cuggaguaag gguugcauag accuauucua cucuccaacu cacaugucccc ucuccccucuu 7020 ccucuccaua auuccacauc uccaaccccc accccuaugu gcaaugccac agggugugga 7080
cugccacagc cacuggaucu gcuuuuggaa ucaagagucc uuaagcucca aauggaaccg 7140
aaauuuaaau accaacuuuc aaccauaugu uaacaucagc agccucuucc aauguaaaaa 7200
cccauggcag ugugcccugc uuuguuucuu uaagcaauag aaacuugaag gaagcauguu 7260
gguaggccag auuuuuguug gcuuugcaau ggaucacagu cauuuauuca cucauucauu 7320
cacugauuca uuaaaaugacc acauuugcaa gggcaaggua auggggaggg ccagaaagga 7380
cacuggcccc agaaacagga ggcuggauuu ugguucugau gcugccacug cugaugugac 7440
acugcacagg ucaccugccu ccucugagcc ucuuuccuua acugcagagu gaguggcuac 7500
agagaaaucu uuacuaccug uuagaucagc auuaccuggg agcuuguuag aaaugcaagc 7560
ucuggugggg ccauacugaa cccaaaucug cauucaugug cauagugaca gcuaaaaugc 7620
acugaagcag augaucuuga ugauccuuua ugaaagucuc augcuaaugc aguuuucuaa 7680
aauagaggca gaguggaacc cagauggaca caaaaucugg uugauauaau aaaacaaggu 7740
agagggugua uggugggggag gggguaaagg aaggaaacug uuuagguaaa gauaccacaa 7800
ccaaaguccu acugcacaca ugggaucuga ggagggcugu gucugcucug guuacguuuu 7860
cuauaaucuc uuagcaccac ugaacuuucu cucuuuuugu uuuguuuuuc cag 7913

<210> SEQ ID NO 8
<211> LENGTH: 1393
<212> TYPE: RNA
<213> ORGANISM: Homo sapiens

<400> SEQUENCE: 8
guaagcauag cagggguagcu ugggcaagcc cugaagagac uuuggucugg gccuuuuguc 60
uagaaagauc uuggggguggg agugugggga ucagaucugc uuaucaucau uucaugucua 120
ugaugcaugu aacagauuua ucaauguuac acaaauuaua auuuuuaaaa agucuuuaga 180
gacagggucu cacucuguug ccgaggcugg aguacagugu uaggaccaug gcacacugca 240
gcuucuaucu cuugggcuca agugauccuc cugccugggc uuccaaagug cuggaauuau 300
aggcaugagc cacugcuccc agcuaauuuu uuuguuuuuu guggagacag agucacuaca 360
uugcccgggc uggucuugaa cuccuggccu caagugaucc ucccaccuca gcguucuaaa 420
gcacugggau uacaagcaug agccaccuug uccagcccaa auuuucaugu uuuaauccua 480
cacauucuaa gcaaauacuu guguguaguu acuaagggac ugugcacuua uuuuuguuug 540
cuuuguuguu gcuaguuuuu auuuuuuuau accuaaacuc ucucguuuua aagagaacag 600
auuuguagau gaguucucga aaauauuuca ggaaucaaua uagagaauau guuauacaug 660
gugccagaga aaaaugagga caagagaugc uauacaaucg uacugaagaa aaauuuuauu 720
ucuuggaccc cugaggugucc ugcagaccug aaaggaaccu agugagagcc ucuuuuacac 780
ucugccccug ugggaaagcc uucaccuggu uuccggcccu cuauguggug aauguggaag 840
ccucaagcgu uaugcaaauc ugcccagucc ucuauucuug aucuucaccu ucucguucau 900
gaguuucagg ccccaguucu gaaucagccu ccuguccauc agacucuucu uuaccucucc 960
ccgaggagcc cauaaccugc agcccuacug caugcuuggg guaggugcuc aguucaccgu 1020
gguugaagga auagacgagc gucugcucaa gcagcagcag caacugcgug gagucuucuu 1080
gaacuaacac uccuaugccc cucucggcac aaaaugacgu guccccccuu gcuuccccuu 1140
cacauuucca cccaugccua uuacaacauc cgucugucuc cccacuacac cgggagcuug 1200
agagaagagg ccaugucucu agcacccagc acagggacug gcacacauga gaugcuccug 1260
cuucuuaaau gcugagaaug aaggaggaca ucagaggggc ccgggccccu ucccaaaaag 1320
gccaacuccu aggucugcau ccugcuuggu cuccaugacu aaucccgucu uguccucauu 1380
uucuguuuua aag 1393

<210> SEQ ID NO 9
<211> LENGTH: 2721
<212> TYPE: RNA
<213> ORGANISM: Homo sapiens

<400> SEQUENCE: 9
guaaguguug agaucccuac caugcagggg aggaaguugc acaccccuuc acgugcugaa 60
augcacacgu gcgugcacgg agcauggagc acugaguguu cuuguggcuu ugcugagccc 120
cuaaccucuu aggagcagag cagguuuccu cucuggaaca uucuguuaac ugucagggca 180
cuuggggaga aaucuccaag cuaaggccac gugcacaaaa uuucuugguc cuuauauccc 240
cagaauguga ccuggagucu gauggcagcc cgcugcagag augugucca c ugccuucugg 300 ucauugaccu gcuugggugg agugaaucau uguaggagaa aaacucaguu cccucacccu 360
gaucaaccug gacagaucuc ucuuccuuua aaagcuuucu uggacaucua agggcuagga 420
aaaaugucag ggagcauugg gaagguaaau gaagucaggu uuacaaaguc aaguuuacuu 480
cuugggagaa aaauacaauu uccaaauccu cuguuauaau ugccaucggc ccccuggagu 540
ggugagaucu cggaauaugg cucgggugca guggcucuuc acugugggcc ugcaggcuau 600
ucugaaaagc ugaugaaaac caaugacccc ucuuccaaga aaaauggcca cauaccaaac 660
auuacacugu acaucugauu ucagggaauu guagaugcca gguuaguagc cucaggucua 720
gggucaaaau ucaagucgaa ucccacagga agaggggucug ccuucggaau ucccuuucag 780
agcauuggga gaacaucaug ggagcauauu cuagagacag aggcuuaggg uguggacagg 840
gccaucccuc acccacugug cugaccuuaa gcagcaccuu gugcagccca uaccugaagg 900
ccaccagcaa aggccuguug gggagcaggc uuuacccgac cuguauaaac accaggcuag 960
gugaaaacug agauaccugg uuacuuuagu uuuuuccuug ggggagcuca guaugauucu 1020
uccaggagaa gccugcuuuu agacuaaaaa gaaaaaaagu uugauagguc aaccuaauga 1080
uuggaggugg ccuuccccac ugugaacaaa cuauggcugc augugcccua caauggcaga 1140
guugaguagu ugugauagag acuguaugau cuguaagccu guaauuuuua uguuugcuga 1200
ccccuggauu accagaugau agaagaggaa acaucugucu ucccuagcaaa gucaaggaag 1260 uggcauuuag caggacucau auugcugcaa gcacugccuu gcaguuuuag uuuacaacug 1320
cacuuucagc uuaagaaaca ccugcccauc cagagagauc gugugggguc acaugguggg 1380
aucagggagg ccugaagaca gcucagugga ggcugcaugg agcuuuggug ggaacggccc 1440
uggcaguguc uauagauguu auugcggaaa acugaggggu gggaguugga gaagggggcu 1500
ccagacucua gcuguacuug gcauuugaac ccggaaaguu ggguuucaug uuuugcacuc 1560
acauuaugag ugaaaauaug gcuuauucaa gguucuuuug cuugcaaggc acggaaaccc 1620
auucaagcaa ucuuaaaccc cagaaggaaa ucuaugauuu ggauacuaga cauucucaca 1680
gagccaaggg cagcaaggcg gggcucagga gaggcaggcc aagaccugga gagcugucag 1740
gagcugcuuc cucaacucuc uuccaucugg gccugccagc ccuggccucu guaucuacuc 1800
cauucaccuc ucuccaugga ccagucuccc cugcuccuca augccugggc ugccauuguu 1860
caugcaauuc acaauaccuc ggccugggca aucagaagcu caucucugaa caccauccaa 1920
auuccuggga acaaaucggg uugacccagc uuuauucucc cugucccauc agccuuggca 1980
gaggcgugca ugugcaugcg ugccaaugug ugugugcagg gagguccuug uggaugaagc 2040
auggcuguca gagccuaccu gcgugaaugg guggaagggc aggucucaga gaauugggua 2100
aaaacuggau aaacccucca gugauaucca ccaaugucac ccuguuuaag gcuucucugg 2160
gcaagagaca cacagagcau gggaccgaga ggcgagcaga cccugccaaa acugggagac 2220
ugaauagauc gcucaccauc cuugucaguu agccuauaug uacaaggaag uaaaauuauc 2280
ucuuucuccu gccuuggcag uauuguaagg auacucaaug uaguagcuag gccagacaca 2340
uaguaucuuu aaauauagca ugagauggcc aagcacggug gcucaugccu guaaucccag 2400
cacuuuggga ggcugaggcg gguggaucac gaggucagga gaucgagacc auccuggcua 2460
acacgaugaa gccccgucuc uacuaaaaau auaaaaaauu agcugggugu gguggcgggc 2520
gccuguaguc ccagcuacuc gggaggcuga ggcaggagaa uagcgugaac ccgggggca 2580 gagcuugcag ugagccgaga ucacgccacu gcacuccagc cugggugaca gagcgagaua 2640
aaaaaaaaaa auagcaugag auauuauuac uguuauaaaa auaacagcua uuuccuuauu 2700
aaugaggcuu uguccuuaca g 2721

<210> SEQ ID NO 10
<211> LENGTH: 5434
<212> TYPE: RNA
<213> ORGANISM: Homo sapiens

<400> SEQUENCE: 10
guaagcauga cugcagugcu cucaagcauc auuucccuca ccuauggaga gacugaagau 60
auaggaaaga acagggagag uuggugaaaa auauacuagc ggaggcagga agggaugggg 120
ucuggaggcg gcuugaacau caccuuggug aagaugccuc uuccuccaca gaagccugga 180
agguaggaag uugggaagga aggcaggaaa ggucucaucc acguuaaguc uagagacaga 240
aagaaugcua agagagaugg cacuauggga aguaugaggc uaggucaagg gcuagaagca 300
ggggagacga guuuacagag uuucguaaag auauagagca acucucacag aguucuagag 360
cgagagcuaa ccaggaacau gaagcagcaa ggccaacuau cauuaaggag ccagggaggu 420
cagagaucau guauuaucau gacauaaaua ugcauaauug uacuauuucu cccaguaaua 480
uuuagcaccc aggccccgag gcagagcaag uggagagugg gugaugcagg gcugggggug 540
uguauggagg caccacagaa ggucaacagg cagcgggcug aaggcaggga cuggacuaca 600
ugcaucaagu ccaggcugca cgaggaagga ugagaaggca gaugagcacg gaaauggacu 660
gggggaaaug aagaggcaag ggaauagaag ucucaguggg ugccaugacc cuguuuaagu 720
gauugagaaa augaacaaga ugaaaagguu aauggcugug gucagaaagu gaaauaugug 780
aauucaggau uucgaaggua gggugggguga ugacuggccc ccagaugcgg ccauggugaa 840
guggggcaaa ggugcaggug cauggugagg ggaaggagga aaugggaggu gaugauguug 900
gccccacacg gacaccacgg uugugcagga agauggcagg agcugggcac cagggugga 960 gccaccugga gucaggaaga gugaagagaa aggaugaaga ggcucccucu ccugugucuc 1020
uccuccccag gagaagaaca agaaacaauc cgaaaguaau aacaccaaug ugccuuuaca 1080
aagugugagu ggguguugug ugcugucacg uguguaguag gcuccucugu ggauggcuag 1140
agggacugga cauggccacu ggaucccacu ugcaagagca gaggaaaaga guggucguga 1200
ggaaguaaag ccccccaaaa uccaggggguu gcugcagcuu ugggugugga gcgugcccuc 1260
ugaggaaagg cugcucuggg ggagauugcc caggaaacgg ggcucagagg ccacgaaagc 1320
agcuguuagg ggcuucuggg agaugugugc uccuaggauu agggaguuga cucuaaggau 1380
gaccuuagag guuaacaggg augagaaagg ggucaccaag gggucuacca ggggaauggg 1440
agaggcugua uugauagaac agcuucugcu gcagguucca aacaagaaau gugggagaau 1500
gguugaaauc agccccgggg gcaccuuccc gugcaugcgu gcagcuccuu caacauucag 1560
ucgaccuuca gugccuccug ugagccaggc acugggcuag ucucuggggg uggagagaug 1620
agucaggcaa augccagccc ucagagggcu cacagggcag aaggugagag augagugagc 1680
agaaaaugac cacagcgcgu guggggccca guggagggaa ggaggggauu caggagcaca 1740
ggagagucaa caggggaaac uucuccgagg agaaucugau ccuccuccca ucuggccacc 1800
uucugaagcc cucucucccc auccaaguga gaaaggacag gcguaugacc agauuggugu 1860
augaagaugc ugaauuacgu ucucauuguu ucaaacuagu aaaccauaga uuuuauguag 1920
uaacuucuac aaacugcauu acaaacacuc cauucuuugu ugcccugggu agaaguuuau 1980
uuuagugagc ccaaguuuga ggaaccuuau augguaugag uacaauuacc auuuuaauag 2040
uaagaaaucc cccuuccccu guguaccaac cagaaggugu uuuuuuccua auuuaaacaa 2100
acagaugcag acgugggcug uccagcuccu ggcgggauga cauaccucau gcauccagug 2160
gguuugauga ugaggcagac auuucacuua agugccugau caucagauug aguccugcug 2220
ggaggaagug ugaaggaagu aauuucaaac cacaguuucu cuguggcuuu uacaaugugg 2280
auaugagaac caaaaucacu acuucuuaac cccagagcag gacugauuuu gaauugguau 2340
gcaggcgguu ccuucugcag gcuucgggcu gugagaaguc ccuaacagag caaaucuggg 2400
gacaagggcu caggaaaggu uggccacggc ccccuaggaa ugggggcucu gcaagauccc 2460
uggccuuaga ggcugugaga gggaacaggg guccaucccc aaguaaggga cacggucuuu 2520
gaggaaaucc caggccaggg ccugaagggc acugucagga acacaggcug uuucagucug 2580
uugagauuca ccggggcgcu gcucacugug agcacggacu ccucaggcca auguggcaga 2640
agagcccacc uuugaaagcg agcggguggg gguggcgggg cuggugcugg ugcgugcuuc 2700
ugcacagcca ccugggaagg uaugccgcug guugacccag gcagagguuu ucuuucaugg 2760
caaaccugca guacugcauu cucagcaggg aggauuaaug guaaaagacc aggcauggag 2820
cccccuuccc ucucccucga agcaagcucu guggucucuc aaucaucuuu aaaacaccuu 2880
cuucccggga gccuccuaca uucuccuggc uucccuccca cccccacccu cagcuccugg 2940
ggccucagca gccccacccc caagccucua aucuucccag ggaagggaac aagaagaacc 3000
acauuuuaaa cgaaauuuau uuuucuuucc ucaggcuccc aguucacauu ucucccucag 3060
gagucuaggg aagcuucugu cugguaucgg ccuccucuuc accugggccc ccgcccuccu 3120
cagguguacc agaagccagc acacuccccc uuccccccca gagccacagc agcccugucu 3180
ccugggugguu cuugugugcc aagccugggc aacaucacuc ccagcuuuuc uuguuuugcc 3240
ccuucucccc agcaagauau uuguauguaa ggucagguga gugaguuaaa gaauaacgaa 3300
gagauaaaca gucaaaugga guccugacug ucaggucaag acaacaguua uuuacugaau 3360
gccucauguc auucaacaga cauuuauuga gacucugauu ggaugucagu cuuuaaugcu 3420
gggugucaga gagaggugac uucaagggcu ugcaucugug cacccagcau ugcuaggwac 3480
aaugaggagu auaauaaaag caggagccau agcccccaac ucucaagaga ucucccaugu 3540

```
guguaugucu gcauaugcgu gcgugugcau gugugcgcau gugugcaugu gugugugcau   3600

gugugugcau gcgugugugu gugcgugugu uggggauggu guugguggag ugagagugua   3660

caaggcugug uaugaagggg uaauugggaa aagaacaaug gagcuggcac ccagggacag   3720

gaggaaaagc aggagggcug gguuuggaag acagccggau uuauguuuuu gaagagggaa   3780

gacuagaaua uaagggagca gcccuucuca gagcccuccu ccucccuucg ggcccugugu   3840

ccagcuuucc ccaaaguccu uggaucuuuc cuaugcaaag gggagugaca gugggcacca   3900

cucucaggga acccauuacu gugagagaag ccacugugcc acuguguggu cgaacuucaa   3960

gaccggcuuc cccugcccca gcugcaugga caggccugug ggguuggcgc aagacccuuc   4020

cagaggaaac uagcugcaac auaaauccgg auauggugcu guucagggaa aggcacaacc   4080

uggggaugag aagggugcu guccagcaca caggggcagg ccucuuggcc acuggggggag   4140

gggagaauuu ggagaggaag aggaugggau gccguggaau ugggaccagg aaagaauggg   4200

gacaugugau gguuaaagcu aguuagagaa gaacugggag auaaacaguc acccaugccc   4260

cugaagcacu cggggugaag agauuggcau uuucacgcac cccagugcuu ucccuuugug   4320

uugaaguccc uucguagaca uccaggccca uaaggcucuu cucuggccag agccucauga   4380

acuauagcac uagcaggguu gaggccaagc auuggcccug gaagccagcc gaggaggagg   4440

gugcuugugu gaaucuccca ggaggggguaa gaauuauauu aauucgauca uaauaagcau   4500

uuauugagug cuguuuugag gccugggagc uaagcacuuc acauuccuua ccccgcauca   4560

acaauccuau gagguagaug uggaaaaugc agacacgggg acaggcucaa ucacuugccc   4620

caaggucacc uuaacuguua gguguucuuu augccuccuu auaaagaaac ccugcuuccc   4680

acagguguug agaggagcug gagggagcuu gacuagggcu caucaggcaa gccccggcau   4740

gugccuggcu cuccucuuuc uaccuggagc uuuuccugcc cuuaauggcc ccaacucauu   4800

ucucuuaguc caugucagug cccugagcau cucagcccaa gcugagauga uagaaacacc   4860

cagaggggguc cucuacccug ugacagcugc gguguggggaa gagcacgugu cuccuccaau   4920

ccuagaccag aguuucucag ccucagcauc acugacacuu ggggcuagau aauccuuugu   4980

guggggggagg gaggagugucu uugggccuug caggauguuu agcagcaucu cuggccucua   5040

cccaccagca ccuccccagu ugugacaccc agaaaugucu uuagaucuug ccaaauauuu   5100

ccaggaggau gaaauucccc uguuucaguu ccccagcccc accucaauga gaagcacugu   5160

ccuagaccaa ccccacaaag caucugacac ccccauccag cccuggcuaa cuuuuuccac   5220

cuucuuacua aauugggccc agcugcuuca gcagucaaug uguuggggggc agcccacugg   5280

caagagccuc accucuaggg gcucccagag accccaagaa cagaaccuuc cucugagagu   5340

ugaguuacaa guguuuccaa ucgacucugg cuguuuuccu uuuuuugacc cauuuccccu   5400

ucaacacccu guucuuucuc uuauucauau guag                               5434
```

<210> SEQ ID NO 11
<211> LENGTH: 4023
<212> TYPE: RNA
<213> ORGANISM: Homo sapiens

<400> SEQUENCE: 11

```
guagggggau gucacuggcc aguggucccu ggaggggagg gaagcaccca gccugagaaa     60

ggcaagaaau auauuggcuu uuuucuucuu ucuuccuugu guucacauuc agaauccauc    120

acuuaaugcc uuguauuuag aaaaaaaccg ggggaucacu ugagaucgug aucauuuuca    180
```

-continued

```
acauaggauu cgaagcugua cacauccugg ugaccuuaaa acaucucagg uuuuuauaac    240
uggaaggaac cuuagagauc augggggcaca accuucucuu uauagaugag gaaacagaaa    300
ucuauucauu uauuacucaa auauuuaggg acaguuguag guacuagaac acagugugaa    360
ccagacaggc aaaaccccag gccagggagc uuccauucca guggggccac aggcgaugcu    420
cagguaagca gagacuccgc ugugugacuu cuggcuguga ugggugcugc aaggaaaauc    480
cgguagaguc gaggguuaga gagggacgga ggggcagguu uaagggggau gcucaggaag    540
gccuuccuga ggaggguggua uuugagcaga guugucuguc agccacacag uaagugagag    600
gggaguuccg ggcuuggaag cugccagcac agugcuggca agugcugggg uggcgucccg    660
aggcuacaga accugagaug cugcagaaga gcccacuucu gcuuuccugg accacuuccu    720
ucucagcacc aggcaaacuc cuucuucuau ccccuggcac auuucugacc uguguauacg    780
cccccaauuu aucuaacccc uuuaaauaau cuccucuauu uaugcagagc auucuuacca    840
cuaacucacg acuugcacau cccuuagcuc ccuuacuccu cacaacaauc cugagauggg    900
ucagagaagg aggcuugcgc gucuggugau ggggugauuu gugcacaguu acagggcuag    960
aaauugucag agccagaugg aauccagguc cucucaaucc uaauccagug uuucuuacuu   1020
caguccugug gcucucaaag cccagagacc agcagcauca gcgaugccug ggagcuuguu   1080
aggaaugcaa auuaucaggg cccacuccag gugaacuggg uccaaagccc ugggauaagg   1140
ccuagcaauc ugugcuucac aagcccucca ggugauuccg caggcucagg ugugagagcu   1200
gcagcugucc ucugggccuu cugggcuccc cgcccagcuu cuucagugug augaacacag   1260
cgagaaugcu agaucugcag cagcugauau cccagacacc cucccgacuc ccuccuggcu   1320
gggucugauc cuccuccaga cuccaggaga gaacgagaca uaaacagaac uucagagccu   1380
guguuaaccc ugagaucaag gucugcacag ggugcugucu gaguccagag gagugaggga   1440
ccccacccca ccuggucagc accagcuccu ggaagcaggu ucucacacug guucccugca   1500
caaugaagga gcucauaccu gcuuuucugg cuucucagac ccugagguuu ucaccgaaac   1560
uagacaaggg gaaccuaggg ucagccugga ggcaggguga gcuuggcgcc ugcagugccc   1620
aggcccuggg uggugcggcu ccggccaggc ccuguuuagc uuccucuccc acccccacag   1680
agggggugcu gucggcaccg auugcucauu uuccccuuug cuuucucuuc agcucguaaa   1740
acucaagucc ugacaaugcc uugaugacuu ccaguuggua auaaaaggga gaugaagaua   1800
aggacaggaa uuucggggaa auuucuuucc aguuccuuac uaaugugaca uuuagaucuc   1860
uaguacugug cuucuggcau cagugccaag gccuuucaug uuggagaaug gaggccgggg   1920
ucaccagguu gugccuuuau uucauguugc uggcucugau gagcugaugc ucugcugauu   1980
agcaaacgcu gagccaucug cgcuucgcag aggcacguuc cagccaaccc ggcccucccu   2040
gcccacuucc caggaugcuu ugccuugugg gcucaccugu cuucuagcuc cugaucugua   2100
ucuccaccuc cauccaguuc cggggcuccu uaucagcacu guucccagaa cuguccauca   2160
cgauggcaac guucucucug ggcgcugucc aacaugggag cucgccucug uguugucacu   2220
caugcucauu gaacauggau uuguguccuu uaccaucagg acuggauacc ccuccugguc   2280
cuuucugccu ggggucuuag cacagcucag aaggaaccuc accauucccu cucuccaucu   2340
agggaauuag aagaugacag gggcacaguu cucuggcuca cccccagccc aguaaacucc   2400
uggacaugcu ucaaggccca gcucagaugu ugccuccuca gugaaauaau uuauaaaccc   2460
acccuucuuu guccugccuu cucccucuuc ccuacucacu ggagaguuaa caggugaugg   2520
uuaagcucug gguucaaauc ucacaaggcc acacacuuag cuaugugacu ucaggcaagu   2580
```

uaauuaacca cucugugccu cucguuuccu cauuuguaaa auggaaauag uaaaagugcc 2640
uaccagcaug gcaguugaag uuaaaagaaa uaauauaugu gaacacuugg aagggcgccu 2700
gacacauagu aaacucucag uaaauacuag cugcuuuuag uggcuauucu uaacacaccc 2760
ucuucagugc ucugguuuca cuauguuuua ugggucccug agaucgaaag uguccacacc 2820
gacucauggu cagcuguaac cugugccucg uguggggacc aggcugccau guguagucug 2880
gacaguguag gagguggcag agcucaggcc uguucugccc uccagcccag agagccacgu 2940
cguuagaugu caugggagac uguggugccc cgggaaucuc acgaauuugc ccacgguacu 3000
cagugucugu ccaaugcuau gggaguccag gacucuagga gccaguuaag gugcugggug 3060
gccacagguc ccuggccaag guccaggccu cuccccugcc accugauccu cgagaggcca 3120
ucacgagggu uguacuucaa gaaccacuau ccuugagcua ccuaggagcu gcagaaugug 3180
cacucugcag ggcuuagggc cugcagacaa gauagaugca gggugucuag uuaaauucga 3240
acuucagaua aacaacaaau aauuuuuuca aauaauugug uucuauucgg ucccuauuug 3300
ggacauauuu guacuaaaaa guauucauuu aucugaaauu cagauucgac ugggcaucug 3360
gugcuuuugu uugcuaaauc caagagcaaa uuuguucuag cuacuucuca accccaccuu 3420
cagagaggaa gccuugaugg uacuguaaca ucaugcugua agaaggggau cccuugaauu 3480
guaaauggca cucugauaag augagguaug gggauuguau ugguuuccug uugcugcugu 3540
cauaaauuac cacaaacuua guggcuucaa acaacacaga ugcauuaucu uacaguucug 3600
gaggucacaa gucugaaagu uagggcauca gcaggacugc auuccuuacu gcggaguucu 3660
agagaaaaau ccauuuuccu gccuccuuca gccuccagag acacgccaca uucuuuggcu 3720
aguggucugc uuccaucucc aaggccagug ggggcuuauc aagucuuucu cacaucacau 3780
gacucuguuu cuucugccuc ccucuucuac auuuaaggga cccuugugau uacacagggg 3840
cccaccuaga aaagccaaaa uaaucuccuu auuuuaaaau cagcuaauca guggcuuuaa 3900
ucccaucugc gaucuuaauu ccugucgcca uguaacacaa gguauuccca gguucugugg 3960
guuaggacgu gggugucuuu ccuaccacag ggcaguuucu aguguugccu cuucucccug 4020
cag 4023

<210> SEQ ID NO 12
<211> LENGTH: 15352
<212> TYPE: RNA
<213> ORGANISM: Homo sapiens

<400> SEQUENCE: 12
guaagggagg gguuuggcug cucgccaauu gcaaggugau uccuggggua gcagagccuc 60
acgaauugac cuuggggagg gcgugagccu gguguucugg acaauccuug caaaagcucc 120
aggcucccag ggcucaaaaa aucacaacug auaguauuuc uagaacagug gcccagggac 180
ccagaaguca cuaugagguu caccauuagg uauguggcug uggcauguuu guguccacuc 240
uaaaaugugg gauaaucccc uuuaccuccu cuaacagagu gguaaaggaa ggaggaggcc 300
ugguuugacu cccugaccug cuauuuccua gccaggugau caugguaaga uauugaaccu 360
uuucuggucc caguacucau cuauaaaaca aauauaauac uuuacagagu gguaggaauu 420
auacaagaaa aguauacgca aaacauuuca uaaauuuuaa uaaaugaugg ccccaugcuu 480
cuuccucugg aaauggucuc aaccucaaug guugguguuu cuagagagaa aaaacgacag 540
agaaaguuuc auagucucaa aaauuuggaa agcccugauc uagcucaacc cuuuguucua 600

-continued gaacugcauc ccagacagac ugcuugggac cugaaaauau cuccuccuuu gcuagaagga 660
uaagaugaga aggaauuaga uaaaggaggu guagagcaga gguuuucaca cugcaaagug 720
cauaaaaacc aucagagggc cgggcgcagu ggcucacgcc uguaauccca gcacuuuggg 780
aggccgaggc gggcggauca ugaggucagg agauagagac cauccuggcu aacacggaga 840
aaccccgucu cuacuaaaaa acacacacac acaaaaauua gccaggugug guggcgggcg 900
ccuguaaucc cagcuacuga ggaggcugag gccggagaau ggcgugaacc cgggaggcgg 960
agcuugcagu gagccgagau ugcgccacug cacuccagcc ugggugacag agcaagacuc 1020
cgucucaaua aaaacaaaca aacaaacaaa ccaaaaaaac ccaucagaga aguugguaaa 1080
agaugcaagu gcuaaauccc cacccccaau cacugugauu cagaagaacc aggccaggcc 1140
cagaaucuau ccuguuaccu uaggcgauuc ugaugaagac cauuguaggc cacacuuuca 1200
gaaacacuca aaauuagaau ccuucagaga agguggcaua uauaauauuu cuagcaugga 1260
auuauguuuu uuuucuuuug ccuacauuuu aauuucuaga acuguguugu agggaauguc 1320
agucacuaag aacuugauug aggaacugug uuuugucugu uucaugacug cucucucaag 1380
ucccaggaaa cucacuuuca gcuugucuua aaaagcaagc ugaaggcuuu uaaaaaugaa 1440
gcaacaugaa auaagacacc gcaguuucug gcacggucca cgcuuaaucc ccuucaaugu 1500
gugacuuucc guggaaaguu acucuacgau uuucccagcu cgucagggug gggccccaga 1560
gugaguauga agggucagag ccuagggaug ccaccaucag ugagagccca ggaccccaga 1620
aaaggucucu uggcucacca cacuguagga aaaauaaaaa gcaauguagu ccaaaugucu 1680
cuauccaaag uuucaaaaag aacuugauuu uagacacgcu ccuugacuug uuuucagaau 1740
cagacagaag agugaggcaa caaagguccc uuauuccagg cagcugaaua ccagcacagc 1800
caggagucca gugcuggugu uugcagagcc accagaggcu cccucucagg uguccagggc 1860
ccgcaugcuu uguagaaugg gcagaaugag caaugucugu gcaccugggc uuugcaggca 1920
gggccugggu acccagguuc gugcaauccu cucgucacca ugaagggagc agcaucauuc 1980
uucccuucuu gaagcaccuu ggccaccagu auagguaaau uuaccuccca ggacaugacc 2040
auugauucug ggaugucaau gccagagaua guaggguaaa ucggcaccug gguaaaacuu 2100
uccauuggag acuagaacca aaacucagga cacuggcuuc caaauguuuc uuuaucagac 2160
aagaaagacc aagucuuucc uuacgucuuc acaugcugcc uuggcaaaug cuagcauuca 2220
caaacccugg gcuaccuuga ccugucaccc uugcagaccu cagacggguc cuggggggcuu 2280 gcuuucucgg uuucuguaug caggcacuca aaccugcauc aggcaccugu gaagggccgg 2340
gcacugugcu gaggccaagg cuccaaaugu gaaccuucca cccucacuga acucacagcc 2400
agaccagaga caagcaaaca ggacauuuca cagcagugca gccuagaaag ggccaacacc 2460
agcagcauuu gucccccega gcgguagcuu uuagaagcuu ccccagugau ucaaugugue 2520 cuacaaaugc cuggccccca cucccagaga uucugaguca gcuggccuag ggugcagccu 2580
ugacuucacu guguuaaaaa gcuucccaga uaaguccaau guccggccaa gauugagaau 2640
cacugaccua gaguuuaauu uaccaccuca gucucuauag accacgcaua auaauaguac 2700
cccacacacc ucugaggguc caaagaacuu ucauuugauc acccaugaga ccaccguggu 2760
guggagaugc uuucucucuc cuguucucuu aacaaagcug gugagcgaca gagccugcag 2820
uggaccggga gauggcccag aggagaaagc ucugccguag ucggccucag uuaaccacgg 2880
agcaccaccc cuaccugcuc uccucucacu ccugcuuccg ucucggugga gaaagaucca 2940
accgaagcag gacacaucua gucuucuggu gccuuuaaaa uguacuuuuc cauuugacaa 3000

-continued auggauuaca cuaaaaacaa aaauuuacaa aaaaaaaaaa aaaaccugaa agaaauugca 3060
ggcauuaaaa ugggacuuug ccuuuauugc uccugggccc auccuauuug gguuuuuaga 3120
aaaacaagcc ugaggcaggc ccagaaaggc ucagggcaga cccuccgauc cucugaaagg 3180
agcaucaggc aggcaggggu ugcuccgggg ccagggaagg ggccccgcug ggacgcggcu 3240
guuauugcag cugguuggcg cgcagccaug cuuagcugca gugcgggaau gcugggccuu 3300
cuguucuggg cuguuucuca uacgcacgua ggccagugua uaaauaaggu uuuauuaaau 3360
gccaaaugag uucucauuaa caaagaaaga gggaaaaucu caguaaacca ccgugacggc 3420
aucuacccac uuugagucag gagcuggggg ugugagugca accuccgaga caagggaacc 3480
uguggagccc agagaaucgg aggggggcgc uggggguuagc accgacugag accagcugug 3540
uuuucucucg guuccuugga gaucagaagu gaguguuguc aucuucaaac aauccaaagg 3600
caguacccau ggccuuacua caucccuccc acaccauccc acccaucccc gcgcguacac 3660
ucacacgcuc auuugcacac uaucgcacac gcucacuugc gugcgcacac acagauuggu 3720
gaccuaggug gacugggaga gaaauaagag ccaaaugacu ggauuuucuc caaggaaauu 3780
uauuaauagc cccucuuggu uucaccugaa ggagcuuguc uucaccugcg gccuuugcag 3840
gcuuaacgcc cccagcuuga aacccagaag cucagacuug ggcccaaggu auuauuagug 3900
ccaacacuac cugaaauguu ucgcaccuca uaaaaauggu gugucaguuu cgggugagag 3960
guugggacgc uucccaucug auuuggccca aggcaugcau gccccuccuu cuccuucccc 4020
uccuccuccc ccucuucccc cuaccauccu uccuguuuuc ucuccaacuc uggugcacag 4080
cuuugaaauc uugcugagaa gcaaaucugu cccuucugcu uugaauguuu auuuguggaa 4140
guucggcagg ggaaccgagg cgggugccaa gaccugccau gcugcuggga agucugaguc 4200
ucccucccuu cccccuccua aaugcuuguu gauagagaaa agucagccuc cucggcauuu 4260
gggcucacgg uuuuccuuug aaaaugcuuc caguguggca ugauucagcu uucuuuucug 4320
ucccccaacc acugcucugu ugucauuuuu acuuuucuga uugcauuuua uccgugucuc 4380
uuugacuacg ggguggcugg acguugaguu ccaggaagaa aagggcccaa ucuuggggguu 4440 cugacuacau gcgcccauca auguccuguu ucauucuugg cucuggcucc cugaauuccu 4500
gagucacugg ggagaagcgu ggguggaccg cccccuaccc agugagaguu gccacaguug 4560
cugcucuccu gggucauugg uugcagauug uuaaacuuca ccuaugcauu ucaacuuucg 4620
gguggauauu gcuacgucaa gugucuggga aagcccccac agcuacagga uuuuacagug 4680 agguccacu aaugacuuga ugucaugacu uccucauucu uuccaauuuc ucccacuucu 4740
ccauaagggu uuugggaagg ggagaagaga aaggagugau uccugagugc caguaccagg 4800
gaacagcagg gcuguuggga ggaaacaaaa cuaaaucagg aagguuuuug uuguuguuuu 4860
ugggggguuu uaugaaaaua uucaagccac agcaaauaua uuugauuuau agcauuagua 4920
uuuuuucugc cugcaucuac aaaaaucuuu accuauuacc aucaaaauau ccucugggug 4980
aauggauuuc aacaaagaag aaauaaaaau gaaauagaag agaggccccu ucgugcacau 5040
ugagccuacu ggcuggauug ucacuugccu gccuugaugu cuuuucagcu ccaggcaggc 5100
aguaggccag ggcuuauuuu caugacagau cagauguucu uuuauggauu uacaaagaaa 5160
gaaauacuga gaagucaaaa cugaagucac uuaagacaag agcaggcccc ugggaaggcu 5220
gccauugagg auaaugaguc cuggggucu ggccuuuguu caguaaauac gcacuaggcg 5280
ccuacaaugu gugcaccaau gugugaggcg ucagguucuc uccaggguca guugguuuua 5340

-continued

```
agaaagguuu uggcuucuga uauguuuuau cucuacagaa caguagcucu uaaccuuucu   5400
uaugggguuag gauuaccuuc gagaaucuga cuacagcucu agaccuguuc ccuaaagaaa   5460
acuaaguuca cagggacaca caggaugggg cucauggagc agcugaagcc agaccccagg   5520
uuaauagccu uuacauuaaa auguuuuucu accuaccacu aauaugcauu cuuuaguaag   5580
cggucucaau auacaccgau ucuuccuuaa cucuguuuau gaaguauuca gcauccuccc   5640
ugccccccuuc agcauccucc cugccccuga gcacaggauc caauggcgug aggaccacag   5700
gccugggcag cugcuggggc auacaggcau cucuuagugg cugagagacu gggcccuggc   5760
ucuauguugg cuccuaacuu gcugccauuu aaaggaaauc uuagccuccc auccguaaaa   5820
ucgagaaaau aagacuuguc cuacacagcu caugaaauag uaaugaaauu cacauuagag   5880
aagagaugga aaaacacuuu gaacaaaaag cauuuugcuc uuauaaaagc acagccucuu   5940
uugagaggcc cuuugcuccc cauuucuccu ucuucagacc cccccagacu aggagaaggu   6000
cugucucaug gagugaccuu uuggcugccu cuagauucca agcucaguuu ugcuuucauu   6060
aaccacagau acugggacgg acagaaaaag accuaguuuc uguugagcca aagagucuca   6120
uaacuugucu guucacauac ccaagagccc acccucuagu ugagacacuc aguucccucu   6180
cauucuggga gacugcaugu cucugugacc uccugguaga gaccguuuga caugucccccc   6240
aacccccccag ugauugaguc ugaauucucc acugaugacg cauuuccuag cacucagggu   6300
gucccccuccu gguugccccc ucaccacuga agcccgcuuc cucccuuuuc auuugaugcu   6360
uaacaacugu caguuugcaa gaaacaugcu ucaaauccac auucucccag uugccuagca   6420
acaacuuccc ucccggauaa augugggguuu ccuguagcuc agcccaggac ugaacacagc   6480
agcacacacu ucuguccacu gcuucaacug cuuuucaccu cuggucugca ugccuucaag   6540
acugcagcuc aucccucccu ucagaaccuu ccauagccug cagaggccau gucugcccca   6600
aaaagacaca uugaaccuga ggcuacuuau uuacccuugu guuagguaua uccucaacuu   6660
agaaauuaau acuguuucca gauugucuuc uuugaaucac agaaaguaaa acaacaaaac   6720
auucaaugcu uaagacauuu caugugcggu ugggugacau cuguuugaug aacacauuug   6780
auccaaagca ucagaaauac uaugccaaca agacuuuuua ggaggugaua aacaugucug   6840
uucuaccuua agaaaaaaau auuacacagu cccaagggag agacaugguu uugaucccag   6900
acaacccaag cagagaccuc uuagggccgg aaucaucuug gcugcugccu aggaccuuau   6960
aucaauuucu uaagcacagg aucaaggccu aaaggccccu uagacugacc ucaguuagua   7020
gaggcagauc ccuucacagc cuuaucuucc uuagaggucu agucugaccu ugaacuucgg   7080
cuggcagugc ugucaguugu gaugugugac auggaagagu uauuuguuac uuggaaaauu   7140
aagagaacuu auuuggcaua ggaaauugug ugugugugug ugugugugug ugugugugug   7200
ugugugugug ugugagauga uguuugccau uuugaucugu gacuuuuuuu uccagaaaua   7260
guuucucagu uccauuccaa cuaaacuuac agucucuucc gguucuuuga cagaaacaau   7320
ucaugugaau uugaacagau aauagggaag ggggaaccaa aagaagagga gagcccuggg   7380
aaaguuauuu uauaauuuau ggcaaccuca gucaggcaac ugugaacagg uacauaugga   7440
gggcucccuc gggacuaggc aguauucaga gauguaaggu gugaggaccg gacccucauc   7500
auuuaccauu cccacuaaaa agagcuggga aggaaauugu agcuguagca ccaggcacgu   7560
aacuggagcu uaguaacuau uuggugaagg aauauuauua aauuauuaac aagauggaaa   7620
aaaggguauu aaccacacaa aaauacaucu caagcuauug uuucucuguu cccuuucccc   7680
caaauuccua gucuugcucu uaucuggcug ucucucuagu cacucuuucu ugcugacucu   7740
```

-continued cuucacguuc cuuucuccac cuggaauucc ugggcccucc ccuuuuacug acagacacug 7800
uccucacucu cacagucauc aguuugucuc uuuacaaacc ucagcucaag ugucacuucc 7860
ccguccccag gugaaacuga cugcucccuc ccuguaaguc accaugauga cugcuauaua 7920
uagcccucau ggaaccuaaa accucaacag acacagucuc uuuccuacuc uguuauaguu 7980
uauuuacuca uuaauuacca caacacguau uauugagcac cuacugugua ccaugcccag 8040
aagauaaaag acaaacaaaa uaaaaccuau uccuaugcuu aaugaguuua cagucuagug 8100
gagagauaga uacauuaaaa aauaacagca aaccaaaaua aaagugguaa auaaaugcac 8160
ugagaaagac aggaauagcu aggaggggca ccuaaucccu agggaaggaa agcuggaaga 8220
gcauggugau gggggaagaa ggcuuucugg agaaggugag guaguuugaa augaguugac 8280
ucuggccagu aggguagag ugagaauggg gugagacagg gugguuggu cauuuugauc 8340 cauuaguccu caaagugaua ggacuagugg cuaaggacug caggcuuuac agaagccuac 8400
aaaacuauuu gagauuugaa guuuuuuuuu uuuuuuaauu ggcuccaaaa gaaaaugaaa 8460
aaacuuuaga auuauaauga augaauauua aaugaauauu uaaggaaggu aauuuuauuc 8520
aacuucauug uuaaauuuag uuaaaacaag cccuugaguu ucauucaaca cuguuuuauc 8580
auaccguuga ugagagaaaa caaaacugau uccuggccag ggccacuguc agcguggggu 8640
uugcacaucu uucccauguc ugcuuggguu agcuccaggu acuccuguuu cccccacauc 8700
cccaagaugu gcccauuagu ggaaacggug ugucugcaug auuccaacgu gagugagugu 8760 gggugugggga gugagugccc cugccauggg agggcauccu guccagguua gauuccuacc 8820
uugugcccug agcugcuggg auggaaucca gccacccaug acucugaacu gaaauaauug 8880
ggugaauaau uaucuuacuu uuuaauuaau cuuugaaaau guauguauag uucacaugua 8940
uuucaauauu uaauauuaga aguauuuuag ucuuuauuuu gaaguuuggu gauuuauugu 9000
aaccagaaac aagcuauaga aacuuaauuu ugggccaagu gcaguggcuc acaccuauaa 9060
ucccagcauu uugggaggcc gaggcagacg caucacuuga gguccggagu ucaagaucag 9120
ccuggccaac augguaaaac ccugucucua cuaaaaaaua caaaaauuag ccagaugugg 9180
ugggcaccug uagucccagc uacuugggug gcugaagcag gagaaucacu ugaacccggg 9240
aggcggagca gugagcagag aucgugccac ugcacuccca ccuaggcgac agugugacac 9300
uccaucucaa aaaaaaaaaa aaauagaaaa gaaagaaacu uaauucuggu uuauaucaau 9360
uagccugugg uaaaauuggu uucauuauag ccauuucacu uaguugaagu uuccaauaac 9420
cuguggauga auuaagugag gauuuacuau auucauaaaa ucuuaaauuc caaagccugu 9480
uugcaguuca gguuuuucca cuuuacaaac acuucuaagu auucacaaug auugcuuaaa 9540
auucauacca gauaaaucau uaaauaaguu guucaaaguc aaauaauuuc auaaguaaaa 9600
auuaggagcu uuuagaaaac uauaccuaca uagaccuaga ccuauagaua gacagagauc 9660
ugaauagaua uggacacaga ugcuuuccaa aguguucaug ugaugugugg uggaguuuca 9720
agaccagagu gugccugggg ccugcagaag uaaaggagag gggauggaga gaagauuguc 9780
cacauggcca ugggcaaucu cccacccaca cucaagugag gaagacagga aacaaauuca 9840
gaaagaagag aaaauaauca aaacugaugg gagcuuguga cugauuuacu uaugcgcagc 9900
cucccuggag acaugagugu ggcuguuccu uagguugugc cucugggcuc cuacccccuc 9960
uuagaugccu uccuauuauc uaggaccugg uugcuuuuug ucugcauagc uucuuuggau 10020
uccagucuuu gaugccagcu uccuccuaaa guagccuuuc agaugucccu ugguuacccu 10080

-continued

```
cugcuaucua agggcucauc cuaccccaca cucauuccca gcaccaauuu cuggaucucc  10140
aggcuggaga uuuagacaau gggaugggaa gaacccauga ugggucccag acagaaagug  10200
gugccagcca cagaaagggc acacaggcac agaaguuggu uuggggguaag acgauguggu  10260
caguucagaa cacgcuggau cuaggcagau gcccagcaga caguuggaua uguaagucug  10320
aagcucuggg gagaggucua gguuggaggu acagauuuag aagucaucaa caaaaaggua  10380
gcagauuaaa ugauaaagga aaugagacua uccggggagu gugcagagug agaggagcaa  10440
gggaggcccu ugggaaccuc agcacuucag gggaagguag agguacaguu gcuggugggga  10500
aaggcagaga aguagcaaag caaaccaggc aaaagcagug ucacagacga ccagggagga  10560
aaaggacaug aucaaaaugu ugagaaaagc agagagguuu gaaaauacaa gaagcaaaaa  10620
uguccacuag acuuaaaaac caggagaaaa cugggggguu cuugauaaag caucuuagua  10680
ggauggugag gguagaagcc agggaagugu uggugaggaa gugaagucac ugauuacgga  10740
cuaugcuuaa aagaaugugg gaaugaaggg uggaagagag aaauuagacu guagcuaggg  10800
agacauaagc gaucagaggu agauucuuuc ucuccugugg gagaaucuug cacguauaca  10860
cagcaugacg acagugaugg aagggcuggc gaagccucag ggagacucuu ggagguaaac  10920
cccaugaagg gaggacuuug uuucauucac ugccgugucc ccagcaccug gcacaauagc  10980
agacacucaa uacauauuug ucaaaugugg gauuuuauca uuuagaaacu gcaccuggcu  11040
gugaguaaca aaagucagag aaaccguggg uuucauuuuu cuccccaggc agagucugga  11100
gcuggguccu ccaagagggg uuuggagcac cacagguuuc cucaagaccc ccaggcugcc  11160
cuguguuucc cuccuucauc cccagcauau gccugucauc uggugaccuc caaacaccug  11220
ugcugccucc uccagcacau ccauguugca ggcagggacc aggcaaaggg cagaggggcc  11280
uacuucaaaa gaccauuucc agaaacccca uccuaugacu ucuccuggug ucuugguuac  11340
cauugugcca uaggcucacc cuguaugcau gggaggcugg gccaggcauu augacuuuua  11400
gcaauauugc auagauaagc aucaaucuuu gucacuguga cgaagccuag ucacucagug  11460
cuaggcaagg uuaauggaau ggguuggugu gugcauuauu cuugaggucu uucuuaugcu  11520
ucauguuaua cauuuauuag gacguuuagg caacaggggg auaaaaauga agaggagaug  11580
caugcuauga ucugaauguu ugcauccucc ccaaaauuca uauguugaaa ucuucauccc  11640
caagaugaug gcauuaggag gugggggccuu ucggaggcaa uuaggucaug acugggauua  11700
gugcccuugu aaaaccccag aaagccagcu ugccgcuucc accauaugaa gacacagaga  11760
gaagaugcca ucuacgaauc aggaaaugag cccgcaccau gcaauaaacc ugcuggagcc  11820
uugaucuuag acuucccagc ugccagaucu gugggaaaua gauuucuguu guuuacccag  11880
cuuaugguau uuuguuguag cagccagagu gaacuaagac agugcugauc ucguauucuu  11940
ggagggaacc cuuagucuuu agggaaagca aagccaccau uuggggcagg guguucucca  12000
agugcugcca cauaugcuga uguggguuaaa cugcaaacua ugguaaaaau guggaggucu  12060
guggaauugu caaucaggaa aaagauauaa aaagaaguua aagucuucgu gcuucuggaa  12120
ggauaugugc caaauuguua acauugauua uccuugggua gagaugugggg gaaguuugca  12180
gagacaguuu ugccuuguac uuuauauaag uaaacagcua cuacuucguu gucuuaaaaa  12240
aaaaaaacag ccuaugugcu cuucauguga cucagaacua ccuaggcaau acgauuaauu  12300
gaauuaguaa aauugaguga uuaugaauuu ucaggaaguc auuaauuuac cacuucuuua  12360
uuacauccac uucuaacagg acuucaauau aggggaauuu gacuucaaga uaaaaagacc  12420
aaauuuauuu acccuuuuaa aaaaagacaa cuuaaaagca gacuugucuu acagaaccuu  12480
```

ccuuaguugg acaucgauga guguacagaa aaugcaaugg auaaaaagcu uggugauaca 12540
aagauaaaaa gugggguccu guccuuaaug aacauaccau uucauggagu aucaggugua 12600
uaaacaauua uaaucaaucu gcuuguuauu cugauaagau cauuuacuca cacaucaaau 12660
acugagugcc caccacaugc ccagcauacc uagaagucau ccaguaugau uucugucuac 12720
auggagcaua gagucuuaca ggggagauag augacaagua aacaccagaa uaauuaccaa 12780
uggugaagag cacaaggaag gaaacagaac uccuaaagag agcguggcug ggcaggggug 12840
agcaagaggc auagaaaaag gggcaucuaa aucuacuugg gaggaagcug uuucucacau 12900
aggucaucau guuaggaaug agacuugagg gaugaguaga aguuugccag gcaaagaagg 12960
aauggggggg aauagagagc agagcuaggg gcaggagaca gcugacgugu gagcagacau 13020
aaaaagaagu ccacuguggc agcagagaag caggagagaa ggcaagugag ggagccaggc 13080
accagcucac agaggucaug ugugucaaaa cguaguaaug gccuucucuu cuggagacag 13140
uagggagcca uggaagaugu uugagcaggg aaagcgacau gacuggauug gccuguuggg 13200
uaacucagac cacaaugcau uggaagggag ggggcuagag gcaaggggac uggcaagaag 13260
gccaguccuu uuucuaugcc uauuuugaug aaauauucua gaagggaagu gaacaaaggu 13320
aguccuagag aggaagaaca aaacagauag gauacuuccu uaguauuugc ucauucgaca 13380
auuuauuuuu gcauauacac uaaaaccuuu uuuauuauua aaacguuuua uuguaggaaa 13440
aaaguaugaa aguagaguga auaauaaaau gagcucccau ggaucuauca cccagcuuca 13500
acuauuauca auauuuggcu guucuuguuu uaacuguucu ccaccuuuuu uuccugaagu 13560
uuuuuugaag caaaucacag acaacauauc auuucaccau auguacuucc cucuguaucu 13620
cuaacaugua agaacuuguu uuaacaaaau caccaugcua ugaucauacc caacaaaauu 13680
uaucauaaug ucuuaauaau accuaauacc cauuucaugu ccacuuuccc ccaauugcua 13740
cagcugguuu guucagauca gaaucaaaau ccaccugugg ccauuuuacu gcuaugucuc 13800
ucaggucucu uuucaucucu aauaaucuca ggggagacag gagggaggac gggcaggacu 13860
uggggcuaac uugcuuaucg acacacaguu uugccuacuu gcuuccuccc uucacaccca 13920
cucuucuucu cagccccacc cuuguaugga aaaaacagaa auuaaagugc uuugcccagc 13980
acccacugaa gcuauuucga aggaguuuga agaguacucc cggcaagaca aaugccucgg 14040
uccagugcuc aggucaaaga ggggagacgc uucucaguga ugugguguca auagcagcuu 14100
aguuguucuu uccucuggaa aauucuaccc aucugcuuug uaacucccau accuaacaag 14160
gccuuuuauu ucacaauuag aaaauaagcc ugaaauauga augcugccug aguguaccua 14220
cauuuauucu agaguuucag ggucaaaaag aauacaagga ccucugcauc uacagccaag 14280
aggagagggg caaagacaca cagcuacaaa ugagaaccug gcuggucaaa gccuaacucc 14340
accuguuugu cagcacugau gcaaguuagg ucagcccaau gaucauuuag gagaacugug 14400
cuggcaaaua aaaagcagag gcuuuugguc cccagauacu uggaugagaa uuacaagucc 14460
agcugguuaa aaggcacaug cccagugcuc acuucacacc uacucaggaa gcacacuuga 14520
guuggaaaac cacugucuuu acacuuagaa cucaguccua caugacuccu cuaggaucag 14580
ugauuccauc aguuuugaaa caugaagcau gaagucaaac aggacaugac cuugguuucc 14640
agaaaaccag auguucacau cagucucugg agcuuggagg cagcacaccu ggggacuucc 14700
acaucccug ccgagguggc aaaagcagga gcagugguga guucacaugg gcuggggauu 14760
ccugaacacu gcuggcaauu ggagaaucug caagggaacu ucuccgacuc cuaccagcag 14820

-continued cugcuuuaaa auaaagguga uguagcuggu caaauccucc augagagagc aguguugaau 14880
ggaggaagag acacaaccug ucugaaaaug gcacaaagga agaaagaugu aaacaaugac 14940
gagaagacug cagugucuac aaagcuccga ggugaacaga ugggcacccc aggcccgcag 15000
cacuuccuuc agucucugcc agcugcacuc uguuuuccuu ccuccaggaa ucuuguuugg 15060
ugucacuaaa acagcaauua gaaucacuuu gaaauaguga uaguauuuaa uauaacuaug 15120
aaacuaucug ugauugacaa gugcagcaag gagucuugga augagagccu uuauuuuuuc 15180
aauuaaauaa aagaguuuuu uguuucuaaa aguaaucuug cagaaaagau ccugcgauca 15240
gaaagaagga ggggggagu uuucaaacau auaggagauc agacugugcc uaugugugua 15300
uauaccuaca aacauauaua uauuuaaaaa auuguuuuac ugucaauuac ag 15352

<210> SEQ ID NO 13
<211> LENGTH: 2633
<212> TYPE: RNA
<213> ORGANISM: Homo sapiens

<400> SEQUENCE: 13
gugaguagcc ugaugguagu aauuauaauu ucauuauguc uuuccaccau uuaccccacu 60
uaugucaaau aauuuaauug uauuucaaac cuguucaagg aaaaguacau uugaucuuuc 120
caucuagcaa uuucaaagca ccuguucaca ucccaaauua ucugugcucu uaaguaagag 180
gcagaaagaa aggaaccacc cuucugauuu cacaucaaaa aagaaaugcc acuggcaaua 240
agcaacuugc cuggugugge auaaaucauc agaagacuua caguugaauc uaagucuuuu 300
caguacugag gugguucauu auucuguuac agucuuaaaa uucacauaaa uauauacugc 360
caauaauaau agcauacacc uuuauagcuu acaggcacuc uucuucuaag uguuuuaccu 420
auguuggcuu auuucaucau aaagaaaaca auggacuuuu guguuguuuu guaaaaagau 480
gcgcacauuu uaauuaacau cugauugcac aagucuccuc ccauauagaa auggauucuu 540
ccacgcaaua gauaagaggu gcuggggaua ugaugaugaa cacacagauu uggucaugac 600
ccugugggaa agagagaugg gaaaaaaaca auucucuuca agugugauga guguuacgaa 660
agggagggaa aaguugaaac agguuuuuuu ccaaacuuuu cucccuccau uauucgcagc 720
ugacuugggc uccaccaacc uggaaaacug caugguugga aucugucuuu auaaaacgca 780
ucucaaccug ggccgaguau gcacacugau gugggaaagu uagagaagag cccauuguac 840
uaaugcucac cugcuacagu gggagucucu guuaaacagu cuuuucuuca uagcauuaaa 900
aaaauuuaua ucacuacaau aagguugaaa uugauagaga auguacaaac aauccccaaa 960
guauaucaac acucuuaguu cugaguagaa guuccagaag gcuucuugac ugucuagaua 1020
gcaagucuaa ucauuuguga acuaaguuaa agcagaaggc ccaguuuaua ugaauuggua 1080
uuacaccauu ugaccugaga acagccccuu caucucugag ugcuuugacu aaaugagcaa 1140
cauaauaaua guaauaaccc cuuacaagau gucauaagac ucacuguugu ugaagcaauu 1200
ugagauuuug acuuuauuga agcauagaug gugauuauag gcaugacuca cugugugau 1260 ucucccuggg cucaucaguu ucagagggca aguguuggca uguggacaaa gagagggaug 1320
acacguaaac auggcuuauu gcaaugggga aauauuuuca gucucacuga uugaauccua 1380
augguuuuau aaauuccccca guaccacuga aagcaaagca aguaaucagg uguguuuuag 1440
gaauaaaagc agcauuauuu uaauuucgua uuuuccccua aagcaaagcc aaauggcauu 1500
augggagcca agcuacuggc agcuccacca gccuucuccu gaguucucgg cauuacagau 1560
cuacccucaa aggaugaggc cagcaagcac cacagggugc ccacauggag aagagaaggc 1620
caccaaccuc cucuuagcug gcacagaauu gaaaaagugu uuuuccagga auggauacuu 1680
caucuguucu guauuugcua gaauuuuaaa acgcacacac agacacacac aggcgugcac 1740
acacacacgc acacacacac gagaaaacca caaaccacac auuucaagga aauggaagaa 1800
uucauuggua aaauuaagcu aauaagauua uuuuccaaau auaagaaacu aaauuuuaga 1860
cuauuuagcc aaagaaauuu gcucugaucu ugcuuuucua caacagaauc auuccccaau 1920
cauuuuauuu cccucuuuuu cuccccagua uccccaucuu gguggggacaa cagaacccaa 1980 gaacuggcuu aacaguaaaa uauuuucugc auuugcccaa ggacacauuc ccaacgaauu 2040
caaauaaagg agacuagaag aagagaggcu auacuacagu gcucuagggg ucacucugug 2100
auuuguuguu guuguuguug uuguuuugag acggaguauu gcucagucgc ccaggcugga 2160
gugcaguggc acgaugucua cucacuguaa gcucugcccc ccagguucac gccauucucc 2220
ugccucagcc ucccgaauag cugggaguac aggggcccgc caccaugucc ggcuaauuuu 2280
uuuguauuuu uaauagagac gggguuucac cauguucgcc aggauggucu cgaucuccug 2340
accucgugau ccgcccgccu cggccuccca aagugcuagg auuacaggca ugagccacug 2400
cgcccggcca cucugugauu uucuuuaagg cucauccuag uauucuccua gucccuaagu 2460
agauggcagu agguuuuguu uuuuguuuuu cgcagcugga uuaaggauug cugagaauau 2520
auggauguuu ucuuuuaaau guggaaguca aaccaaacgu uggagcauug gccucacagc 2580
agauuaugac ucuagcugcc uuaaaauaac cugaagacuu ugccuugccc uag 2633

<210> SEQ ID NO 14
<211> LENGTH: 1016
<212> TYPE: RNA
<213> ORGANISM: Homo sapiens

<400> SEQUENCE: 14
guaaguuuuc ugaguccugc uuauaaauug gccucucaug uugguuaagu ugaugguuua 60
acacuucuag gugaaaccaa accuggggguu gcaucugucu ugucuugcug aguggccuua 120
gguaaagaga cuucucccag aaaguccacu uccccuugca gaaagggggc auugcuuaua 180
agcaauucug gacaugaacc acagaaagaa cugaggccca cuuggaaagg gaacagaggg 240
gccauuuccc acugauguaa uugaacuagg gcuaaguuca agaggaagag aaugauccgc 300
aaggaagcaa cccagaguuc caggugaagc ucaggucaga agggcccugg caaguaaaca 360
cggcuguggg augcuuuuac aaacacaaua ucgugaaaau cuaugugugu aguacugaau 420
uacauuccaa auggcaaauu ccuggcaaau caucuucccc accuuucacu auuuuuuuuu 480
uuuuggucuu cuaugggggua aaggaggaug gggugggggaa gaaauguaac uggcugcccc 540
ucuaguuaaa aacugaaaag aggcagcaag ggacaugcca aaaguaguug gacucuaaga 600
uagcuacaca caacaaagca gcuaagcagc uaauugaagg gaaauuacug aggcucaagc 660
ugagauucca agcgggggcc uuguuuggcc ucucaguccc uuucaucuga gaaaggccuc 720
aguuccuagc aguaaucaga ggcaggcuuc ucagccuccu ucuccuaaag cagaauaaac 780
cacagggcaa gucgcauccu uuguuucucu gaugaggcca uuacugagag ucacuguggc 840
auuuugcuac uaaugaugag cuuguuauug gugggguaca gccuauuaau uuagguuauu 900
caucaaaucc uccagcaugg aguugaauga gacaugugau guggauacac uaaugacuau 960
auugaguuac aagcaauggg gaguuucugu aaaaucuguc ccuugucucc uggcag 1016

<210> SEQ ID NO 15

<211> LENGTH: 615
<212> TYPE: RNA
<213> ORGANISM: Homo sapiens

<400> SEQUENCE: 15
guaagauccc agcugggcuu gccuugugua cccuggaccu cccagaagug ugugugugug 60
ugugugugug ugagagagau gugccuuccu gguagcacau cucauguuug uuuuuugcua 120
aguggacucu ugcguuuccu cccccaucca cagucaucac uggaaugcuu ugcuucagug 180
ccccugccug ggcccucccc ucucuacugc agccuacaau gagguuuucu uucccauugc 240
uugaauuaua ucccuaaugg aaggguucac aauucucuga auccuggcua cucagauaaa 300
gacagggagg aagggaggaa ggguauuuuc ucccaggggg uccaaaucua gcuuuaacga 360
gggagguucu gagaaaauaa uaucaucaau auuacaugga cuucugagau acuaagaaau 420
uagauucugu cagcccagga aguugggaga uggugaauug uucugggaaa uagcaauaga 480
cugagaaaau aaaaacacuu ccuugaaaag ccuuucccua acacuaagug auaggggcag 540
aaaagacaca accaaaaguu cucucucacu uuucucucug uucgugucuc ugucuugauc 600
ucugucuggu uuuag 615

<210> SEQ ID NO 16
<211> LENGTH: 702
<212> TYPE: RNA
<213> ORGANISM: Homo sapiens

<400> SEQUENCE: 16
guaagggggg uuggaggaug gggaggggag gggaggagga agcggugggg gcaagaaagu 60
uccacuuguu uccuuuuccc aggaaagagu uaaucgcuau uggaguuaga ucaaaauaca 120
acaagcaggc cccaaaggcc uucauuccaa gcagucacca agugggguca cugacuuugg 180
augagaaaua uguuucuuga auucugggag aagucuaaaa gcugccacaa gaccaguggc 240
uuccuggagu uuccuacuuu uaugaauuca cucaagggcc ucaaauucaa agaggcaucu 300
ccccaagggg ccagcucugu aacuccaaag augguggaau guguuugucu ggucucauuu 360
ucagcuuugc aaaaugaaga caagaguucu auauaucagg gacacucaaa agaaaacaaa 420
aauauccaua agcaaaagaa agcuuuuuau acaccauauu caaugacccc caucuggccc 480
cuccuuugcc ccuacacauc uucccucuau ucuagagacc cauggacuug gggaaauggg 540
auauagauag guauguuuca uaguggaaca agcucaccag cucuucaggg agccuuagca 600
ucucuauccu caaucacuaa aaauuagaaa uggcugaaga acaagaccaa agauccuaug 660
gaauuucuaa gcagagcagu gacuguauuu cuucuuccca ag 702

<210> SEQ ID NO 17
<211> LENGTH: 14372
<212> TYPE: RNA
<213> ORGANISM: Homo sapiens

<400> SEQUENCE: 17
guaaggggcu gcaagcccca caguggcccc cuugaagaua gccccaugag uggggccaga 60
gcucccuuag caagucaagu ggucuugaau uuaagcuuuc auuuucccca cugaagaaac 120
aagaaucccu acaucccug uacaguucuc auucucuaac agcuuaucca uacuuaaaac 180
uuaucuaugc ugaaaacggu uuccucuuca caucuccuac uucucaugcu gggcaccucc 240
uccuguagcc cccuuuaagc aucugugucu guccucaacc cucuucuguc ugacauugcu 300
ugaguggcca ucuauggcca guguccccuc aaccccacag uccauugcuu gcuggacacu 360
ccugcccuca aguucuacaa gcacaucagc cucaacaugu ccccuccaaa aacuguaugu 420
ucuccuugcc cauagaacau auccuucucc uauauuuccu auccuaauua acguccucag 480
cauuugcccg aauucucaag ugagggauuu cagggucauc ccuaauuuuc cuucuucacc 540
cuccacacag uagcugucac uuacugagug uuacuuuaug ccaaguacug ugccaacugc 600
uuuuacacac auaugcuuca uuuaauucuc acagcuccau gaggcuugca ccauuaucau 660
ugccaauuug cagaugagaa gccagggcuu aaagagguua aauaagaucc cacgcaugac 720
cauuaagagg agcgaacagg auccagcucu gggggugccu gaguucagag ccugccuuuc 780
ugauuucucu uaccaagcuu ugucuccucu cccuccuaaa uaucucucaa cucugccucu 840
ugcauuccag gcucucugag gacuagaggc cuugucaucu cugcgccagc ccauuccaag 900
ggcuuccuuc cuggaaucca ggguccagcc ucuguuggcc caggcauuuc ucuacacugg 960
caccagaguu acauuccgca caccugcuua cguugcucuc ucacuuaaaa ucuuaaugac 1020 ucgacccca aauaacacag gucccuucca aaucugucc accccaccuu cccagcccuu 1080
gcucaacucu gcuaccuggc ccuuucacgc cuacaggcau ucccauucca ugaccucuug 1140
ggauucuacc cuuugcaaau gcuguuuuca uugcccauuu auuagagcgc uuuuggucac 1200
aagcuuuuug cuuaaccaaa aagaaagcau uuauuggugg acauaaauaa ugaaguucag 1260
gaggauccaa gaguuggaag ccaccaugag accccugugu ccuuccaccu cacuuuucua 1320
cucgccucug cucagcuuca ucucuggcca ggcccucucc ucugcugaug cccuagcugc 1380
uuacagcccu uagcagucau cuauacacca aaaaucccuu ucccauagca gaagcaaugc 1440
uccuagagag uuucccuguu ggucuggcuc cuguacccac cccuguguac ucugauuggg 1500
aggccugggu cagcugccca ccaugggggcc auuucuauga gcaggauuac ugugaagugg 1560
aggaagaugu uuccccaaaa gaagaaacac aagguagaaa aguguauguc caccaaugcc 1620
ugaaaugacu gucccuuucc ucaucugcug agcuucuacu cauucauucu uugagacuca 1680
gcacucagcu cuuaaauguc acuucugcuu ugauggaggu uuagucauuc acuccucugu 1740
gcuuccuggc ccucucuuca caccucucuc agaccccucu cccagauaga uuagaguugg 1800
cuguugacau guccaucucu ggcugggcag cuaaacugga guuauuuaga aucagggagc 1860
acaugucagu cauuuucaaa uucucaaccu cauacuccca guaaaugacu ccaucuaagg 1920
guggaccacu cuugcccaug ggccaggucu gggucugugu caucuagaac uguuggaagg 1980
uaggggcuuc ugugagcagu aggagaggga auaaacucga gggcccucgg gagcaugccc 2040
ucuugucuca gacuugugag uccugaggau aacaaacuag ugaagaaaag ccucguucua 2100
ucugucaccu ggugcucuug aggacuuucu guugcccugg ugccaccaca auuuuccaga 2160
gugugugacc cucgcucucc aaacucugga aguggcagcc gaggcucccc aguggccuuu 2220
cagaaggugc cagucaugac agcagcacca aacugcaggc aacuacuaag cgaucaccaa 2280
cuugucugaa gauaagaaug accuugaaug cauuuuauaa aacaggauuu uuuuuuuaau 2340
uuuuagauuu ucuuucuuua uuuuaccuua aguucuggga uacaagugca gaauguguag 2400
guuuguuaca uagguauaug ugugccaugg ugguuugcug cacuugucaa cccaucaucu 2460
agguuuuaag ccccacaugc auuagcuauu uguccuaaug cucucccucg ccucgccccu 2520
accccacccc aacaggcucc ggugugugau guuccccucc cuguguccau guguucucau 2580
uguucagcuu ccacuuacaa gugagaacau gugguguuua guuucuguu ccuguguuag 2640 uuugcugagg augauggcuu ccagcuucuu ccaugucccu gcaaaggaca ugaucucauu 2700

-continued

```
ccuuuuuaug gcugcauagu auucuauggu guauauguac cauauuuucc uuauccagcc   2760
uaucacugau gggcauuugg auugguucca ugucuuugca auuguaaaca uacaugugca   2820
uguauuuuua uaguagaaug auuuauauuc cuuugguuau auacccagua augggauugc   2880
cuggucaaau uguauuucug guucuagauc cuugaggaau cacacuaucu uccacaaugg   2940
uugaacuaau uuacauuccc accaacagug uaaaagccuu ccuauuucuc aacagccuca   3000
ccagcaucua uuguuucuug acauuuuaau aaucaccauu cugacuggca ugagaugaua   3060
gauacccauu ugucagaugg guagauuaca aaaauuuucu cucauucugc agguugccug   3120
uucacgcuaa ugauaguuuc uuuugcugug cagaagcucu uuagccuaau uagauccauu   3180
uuucaauuuu ggcuuuuguu gcaauugcuu uugguguuuu agucaugaag ucuuugccca   3240
ugcguauguc cugaguggua uugccuaggc uuucuucuag uuuucaugau uuuagauuuu   3300
acauuuaagu cuuuaaucca gcuugaguua auuuuuguau aagguguaag gaagggaucc   3360
aguuuaaguu uucuacauau ggcuagccag uuuucccaac accauuuauu aaauagggaa   3420
uccuuucccc auugcuugug ugugucaggu uuggcaaaga ucaggugguu guagaugugu   3480
ggugcuauuu cugaagccuc uguucuguuc cauuggucua ugugucuguu uacaaaacag   3540
auucuuaagc aucaacccag aucgacuggc ucagaauuuc cagggaagag gccugguuau   3600
cugcauguuu acagaccuau uagauuugug ggaccugcag uucccuugua caguuaguua   3660
cucaauuaac aucucccucc ucucauggug ccucuaccug cuaagcccuu auucccagcc   3720
aggcccacca ccauccaccc acugcuguua uaacauaagc aggaccugug cgaggggggug   3780
uggacggagg agagaggcuc uguugcuuca uuugugcagc auggaguuca gugguucuca   3840
caauguuuuu gcaaaguaua uaaagaauac uccuugucua cuugacauuc guaucgugac   3900
auaaaugucu uguuuuccag aaggauuauu uuuuccaagc agcuuguucc uaaugcagcc   3960
ccaggcacca aacagauacu uaaaauauau uaauugcuua aaugguuaag aauucagucu   4020
cuggacccac acugccuggg uucaaauucc uauuaucugu gcccaguuuc caagucuaua   4080
aaauagggau auuaaauagca cuuaccuaau aggcucguua ugagaauuaa augagcuaau   4140
ucaugcaaag cacugacaua uaguaagcac uuaauaaaua uuagcuuuuu aacaaaauac   4200
aagccaaaaa acacugcuua ggagaggaaa ugauguuagu gccuccugua aauaggccca   4260
gccuccaagc uggugcuccu cuaggaauca caacgcugca aaucacaucc uccggggccg   4320
ccaggacuuc acgagggccu cugagcagag ggguaugaug ggagcagaag cccagcagcu   4380
gugaugaugu gguuucugau cuucccugccc uugggguggg ggaggaggaa agcaaggggc   4440
aaugaacaga aaggagaaga uagcggggag gaaaugugug aggaagaaac acaucacugu   4500
ggcuuguccu ggauuuuucu gcuucuguuc ucguguuuug ggaagucugg aggagacuug   4560
aaaaucauuc auguccccac ccugaggaug gcuuaguagc agagaggcca ugaaaacucu   4620
uugcugaugg cucugaaagc aaggauguug cuucacuggg cugcugaagg ccugccuggg   4680
gguucugagc agagaguaca ggccccuccc aggagggcgg ccuaaccacc augcuggcau   4740
uucuguggac cauggucugc ugucucagac ccccuccaca auagggucug caaucucauu   4800
caccccauaa auacauucug ucuuuccucu gaucccccucc cauuagcagg gggaaauaaa   4860
uggaagucag acggcccagu uagaaggcag gcaguggagu aggaaaauag augauggugg   4920
uuuggggagc cucacaucac ucauggggag acauucauuc ccaugggccu uccaaucacc   4980
cuuuucucca aaucuaagga cacaggacaa augggguccuc auacaggcaa auaucuuaaa   5040
cugguaugug uauucauuua uaguucuaau uuauaugugu cuuuauucac auauauuuug   5100
```

cuucuggaga aaagcucaau uagaaaaauu aauacauuau ucuucuuauu gcccuucagc 5160
uaaaacaagc auacacaccc cuccccuuug gauuuuuugu uuagcaaaag guuaggccug 5220
gcacagauga aauacuauuc agaguucaca guguauuuuc auuucauaau auauuugauu 5280
uucaggucuu gaauuucaca ucaggaagcu gauauaggaa gcugaauuca gccagauuuu 5340
aauacgaaaa uaccucugau caaggcauaa aauuguacuu uaaccaguaa ccacuguauu 5400
ucucuaagcu gugaaaaaac augcauucau uaacugcuuu uuccucugcu gucaacacag 5460
ucaauacaug ugcauaacuc cuuauugucu acauggugau uaucuugcug augaauucuc 5520
aaaggccaga gauuuggacu auuuuuucuc uguaaccuug cauguuccug gccacaugcc 5580
accaccaccc aaacagaaug uacgcaggga auguauuuuu caggauaacc uaagaaaaaa 5640
uaggauuaag aagauaaagc ugcugaucau guaauguacu uuagacucag auauauaaau 5700
auuugugaau uaucuguccu auuucuuucu ucuauuaauu cauugacucu agaugugcau 5760
uggaaggcua gggagaaauc aggggaucgu gagaaagagc acagaagucu gcaucacaca 5820
aacaauauua uuucaagagc caugaacuag auccuaagca acucauaggc aaugaccuca 5880
uuucauaccu cuagucucua agaaacauau aacuggccug aggaaggaaa augugggcaa 5940
gggguagacc ggggucaugg guggagaucc aaauaguaau caauggagcu cauagggugg 6000
acugauauug aagcugcuau gagccagcca caugcugggc acuguuacau gucaucucau 6060
gcaauacucc caauuaccug ccuaguaagc auaauuguca uuuuauagaa uuaaaaacag 6120
acucaaagag guugacaguc uaauguaaca caacagcuaa augggggauc uggaauuaua 6180
auccagagcu gccuggcucu gaugagaaag cucuuucugc ugucauaugc agcccacauu 6240
aauagggggc ucagaaagua uucucuggau aaauuauaua augaauccaa ugaaggaaga 6300
cauuauuuua uaauaugcag cauaauaggc acuauuauga uuggauuuuc cugcuugaaa 6360
guagcuagau uagaguagga aaccaaaaag augugaauuc auucagucau ucaugcauuu 6420
gcauggauug agcuaccuac auuugaauaa augcuguuaa ucccugauuc cuuggaagcu 6480
cacauuggag agauaagcau gucauuaaau aaugccauaa uagugguauc ucagaggacu 6540
agcagaacau aauucaaucu gacagaguag aaacagauug uacaaaucca auucaaaaca 6600
ucauaaaucc ucuaagcacu gucaauucuu ccuccaaauu aucucugaaa uuccuccuuc 6660
uuucccauuu auggccucca uuuacagaag cguguacugu cucucuuagc uguuugccag 6720
gccgccaguc ucuugcuguu cagcucucaa cugcuuccag caagaucuuu cuaaaauccc 6780
aggcuugcca agacuuagcg cccacagcuc cacagugacu ccucauugcu guuaagguaa 6840
aggccuuccc agucuagccc uucaugcuuc uuccauguuc uaugggacug ccccaggcuu 6900
cccaccuggu accacugagc cuuuccaucc uucccccacu cgacugccag gucaacaccc 6960
acacccacgc uucaggacuc agguccuaug uuucgggccu ucuucugugc accauucccu 7020
ucccuguagc ccuugaucau gauuuguuua uacgccuccg caccuucaug gcccugaacc 7080
ccucaagggc cgaaacugcc uuacuuuucu uuuugacuuc ccaacuuacc uuaguggagc 7140
uguagucaca uagaauagac gcucauaaau gcuucucugg gcuguaaagg uugaauuuuc 7200
cagcuaagca aggaagaaag acaauuucag gcaggaggaa gggcauaagc aaagugcaga 7260
gaugugaagc ucaagagaaa uggaugggcu gggcagaggu guggcugcag caucagggga 7320
gaagaaguag ugccuggagu cagcaggcac ggcuugcaaa agcuucaccu auaggugaaa 7380
ggacaccauc ucuugcacca auaggcucug ugauuggagg caacuuugcu guuuuacugc 7440

-continued

```
cagaaaacug aggaugauaa cccaaacugc aguucaagug gcauucacug guguggcuga   7500
aaugggugu ugugggccaga auguggucug auuggucagu gcccagcucu guugauuagc   7560
agauguuuug aauauaguag cauccaugug cccaaguugu ugggaugauu caacaagaaa   7620
cuuuaagagc ucaagugccc ugcaguuguc agccaggugg uucucuuccu uuggacccag   7680
uuagacgcag gcauuaccuc guggcuuugc cccaguguga aucuuugucc uccaacuuga   7740
ucuuuuuauu uguuucauua uuguauuuaa guuguuuauu uuagagacag acauuuuuua   7800
acagcugugc auuuccuguc ccuuuguuuu ccagucguca uguguuuccu uacucucugu   7860
gggugaacgu uucagauguc uguuugcggu gcccagcgug caagauaaaa uuuauugcag   7920
ugccuucggc cucuaacuca ccauuccaac caauucagau agcccaaggc uguuuuaucc   7980
aguggauuuu uccauguagu gggaaauaaa ucuugaaugu uacuguuuag auuagccagg   8040
aaacucauuc ugggauguuu gcccacaucc auuggcauuu cucaaaagga accccaggug   8100
ucuaccuuga caccagcagg gccacuugag cccuccgcug gcauucaucg cccgcuuugu   8160
ucucagccug aguuuaggag uuacagaugu gagaggcggg auuauacagc caacaucucu   8220
aagcgggcag uggcucccuu acccucgaag accucacucc uagcacgucc uggauguauu   8280
cgucaaaaua uguccucuua ugccacguca gcacaggguu gcuccccacu uugaucauca   8340
aguuuaaaca aaaggaaaga uuuucuuucu uucucugccu cuacuggaca ucauuuccca   8400
ccuaacagau aauuuaaugu aucuguuacu gaauguguuu gaauuacaga cagagagguc   8460
acaguuaaag aaggaagccu gcugcuacug cagcuugucc ucccaaggag guguuugauu   8520
uagcugugua aacaaaugac ugcauucucc agagguccug aacacagcug ccugcgcugg   8580
agagggcuca aaccucuucc gccaggguga acucugcuuc cuggugagug ccagcaaaac   8640
aaccaacaaa gagcuguagg acuugugugg acuucaaaug guggugguc c ugccacuugg   8700
gcucagccac agcaguuagg aaacuaaagg ggaggaggaa agcccuuucc uugcuuuauu   8760
gucauuggcu gucauagggc auuacaaugg uucucuuuga gauucugagc uccggcuaua   8820
acauuugccc agaaucugcc ucugaggccu uaagacacug uguuuuuauu cagcaaagau   8880
gcccuuugac uccuuuuccc acuaguggug cuagguuuga gcaccuuaca cuggccccuu   8940
acaauagcca guucuugucu accuacauuc uucccuaaca uucaugauug cauaguuacu   9000
cuuaguguag aagcagacag cuuuuacaca uagacuccau ggccguagcc ucauagaacc   9060
uacuauauuc uaacuugcaa gcuaaucaga ccaaauauau caaaaucaaa aaccucugcu   9120
gagaguuuau ucauucaucu cugucuccca aacguacuua uguacauacg ugcacuaaua   9180
uacaugucca uuagccaaga uuuugauuuc agggaucaaa gcaaguacca auagggaaug   9240
aggucacuug cugcauggca gguggcuucc ccaugagaau gcaaggccac cucaugacuc   9300
auacuucaga gggugaccca ggaacuucug auucaugucc aaagcagcuu cuacaauugc   9360
ucuaccuuga ucuagggaag auguggggag gaugacauuc gggauuagcu uuauaaggcc   9420
uuccuguggg cagaguuguc ugacuuucac cuagugauca acaagcagcu agcaagcauc   9480
agugugugag gccccacgcc cucucagcuc cccuacugcc caccugggac augggcuuug   9540
gcaucugucc auagcauugu ucuaaccaaa ugagguguua uggaucagcu caggauggga   9600
uauguuccca gacauauuau uuaaagaaaa uagcuccuu ccucccccuga uaaacagcug   9660
ccauggcuaa aagguaaccu ggcuggggcu uaaaagucug uugacuuuca agauauuuug   9720
caaaaacagu cauaaaaaug guauuuauca gauccuaacu auuugugaga cgguuuggua   9780
uaccauagug guuaaaaaca caggcucuuu ccagaggagg uuuacuuugc uuagucgugu   9840
```

```
cuccuaagug aacuuggacc ucauaagguu guugugagaa ugaaaugggu gaauaugagu   9900
aaaguccuug gaccaguuuu ggccguauag uaagccuuca gcaagcaucu gcuuuuauuc   9960
cuacagggag gcaauuguaa gcccuucaca aacagcgucu aaugugaucc uuagaacaaa  10020
ccuaugagau agggcauauc ucaauuuugu agguagggaa acagaagcca cacaauuagg  10080
aaauggcaac agaucuguua gacucuuaaa cacuaugcua caccaauuug caaggcaagg  10140
aagacaaagc accuuugaaa augggucaga uguuuuaggg uaaaugaacg uuugagaauc  10200
uuuuaaguuu uuuuuccccc agagauuauc aagguaucau uguaggggga ugcaucagga  10260
aacaugacua ugaaucagcu gccugauaaa ccagccagga uggagcccac gucaucacag  10320
cagucagcaa ugccacugaa aaacaucagc ugcuuauucc cguauagauu uccccuuaag  10380
acaugaaaag ggaguucaaa gagaaugggc cagauaucuc ugagagucau auuacuaaaa  10440
uauauuuauu uuuacuagcu uuuuuguuuu aagagguaua cugucauuag cacuguagca  10500
aaaauucacg uuuuauuaau uucuccuagu uuaucaugug auucuagggu aggaugcaga  10560
guuauauuca aaauacacaa aucaacucaa cucaguaaac auauaucgag gcccuaucau  10620
gacaaaaugc uauucuagag accacggcga acaagccacg gccccagccu caaagaaugu  10680
acuaucuuug gaacugugcu ggccaauaca guaaccagca gccacgcagg gcuauuuaaa  10740
uuuaaauuaa uuaaaaguaa aaacacaaug ccucagaugc auuagccaca uuuuaagugu  10800
ucaauagaua uuuguggcuc cugccugcca uauuggacag ggcagauaua gaacaauucc  10860
aucacugcag aaaguucuac ugaacaaugc ugcucuggag cagaagaucu ucuuguucag  10920
ggauguuaca cccccgcuug uggcuagagu guggcuuauc cucagagcaa ggauagggga  10980
accauggcac ucugcaggcu cagcacugaa gacacggaug caggcucugc uucugaccua  11040
gauugaccuu gggcaaggcc cuuugcuccu cugaucccaa uuucuucacc agccaaguaa  11100
gaacaucaga ccacaagccc ucuagggcuc uguccaaaug ccccaugacu gagugaacug  11160
guagaacauu cuaugugugu gucacaacau gaagagcaaa gacuuucauc uccccaaaua  11220
auuuuguuuu ucguuuuagg aauuaaauuu cagauucacu cuaauugcca auacuaaaau  11280
ucucuauaug caguucuaaa cuugacaaac caauaaaaaa agauuauuug acuacuuauc  11340
uuuguacaac auugaggucu cccuaaagca aauuuaaaug cauauuuuaa aaauguauuc  11400
uagcaguuca guucagaagc ccccuggccc aagcaucaca cugucaaucc uuuguccuca  11460
agcagcaugg uuggguggu uaaguacuga caaacacugg gugucaggcc cauggucagg  11520
gacugugcua acagucuaca uauuagaugc caccuacccc cacccucaac agacccaaac  11580
uauuuaucca auagcaaacc uugcauuauu ucuguccaga agaaacaaac auuuauugac  11640
aacuuuuggu gugugaccug uuuaaguccu acaucucauu uaaggacugg ucaauguuag  11700
gcuaggcaau gccuguuugu gagagaauca cugccuaaag aaaauucucc auuucccuua  11760
gcucuauggu gggugacuac acauacuggu auuucuuaaa gaaauaccaa uuccauuucc  11820
uuuuaacaua auuauuaaua ucucauuagc augguguacac ugaagccugg gcccaaagaa  11880
auaccaauuc cauaucauuu uaagaucauu auuaauaucu caucagcgug gugucacuua  11940
agccugggcc cuuuagaauu uuucauguac cuguguuccu cugcccauau cagcuggaac  12000
acuaauaguu uucuuccuuu uuaucuagaa gacugagaac auuacauggg accugccccc  12060
agggcaugga ggcugaggug ggacaguuua guucaggagg cccaagaagu guugggugug  12120
cagccccuug uucaaacaca gccucugaau cgccagaggc uuccggugca uacucugagg  12180
```

-continued

```
cgcaggguggg acucgggagu gagagguuuc ggcgaaugaa uugggauugc cuacuucuuc  12240
ccagugcagu ggagcuuggu ucuguggguca gguccuuacg cccugucugc cuuucucguu  12300
ucuuuauuuc ucggguagua guuguggaau caaaugaccu gggguuugau accuacucua  12360
ccacgccucu gggggagguca cucagacucg uugaaccuaa guuccggggc ugccaaguga  12420
ggauaaguag uaauugcuga uccaccuacu ugacaagaua guagugaggg cccugagcgc  12480
caggcugugg auccagccuu ucccacgguu ccuggugugg caggaagaac ucuaggccug  12540
aaggugaaau uggggaggga gucccagcuc ugccacuguc ucucugggug accucaggca  12600
ggucuccuca aaaaaauaag auacuuuaua aagcucaguu ucccucuucag uaaaaugagg  12660
auuccaggua acucacagau aguuugguggg gaugaaucug uuccuuaaag ccugcaguac  12720
aucaauaacc cagucuuccu gcuugcuuuc cccccucucc acuaccagug aucauagucu  12780
gaucccauag gugauauccc agcucaaaac ccuacauuag cuucuguggc uguuuaaggc  12840
cugcccagaa cuccccuggu cuuagcacug aaagcacgug uccggggaag cccugcauug  12900
gucguucaua cuacugaguc ccgcagggca aaccguccgg ucccacccuc cuuucuagug  12960
cugcugucac acucaccucc cuucacccua cacucccuuc ugugccuugc aauuaccuag  13020
ggaguuuuuu acaagauaug gaugcccugg cccugccacu agagauucug auuuaauugc  13080
uugggguagg gccuggcaua gguaucuuuu aaagcuccgc agugguucua aagcacagcc  13140
acagauggga accacugauc uauucuugua gguccccaga uaccucaugu gcuguucccu  13200
gugccugagc ugaccuuucc cccacuuucc ucuccucggc uaauuccugc uuauccuccu  13260
acucaggagg cucuuccucc aggcagccuu cccugauccc uccaggaaga cuuagcugcg  13320
ucccuccgcu gggcuucccc aauacacugg gcuugcuuuc auuagaaccu gauccuucca  13380
cauuaugguu guugguuugc uccaauccuc ucccucauua gcucucaacu uucuuucagg  13440
aagagauguu uaucuuuccu ucuuguauuc cuagagucga ccaggcucug gcacauugca  13500
gauucucagu augcauucag ggaacaacuu aaucaagaca agaccaucug acuucuugug  13560
aguuacaugc uaagaaagaa augucgacac caauagcccu cacaaugaua ggaacaggag  13620
guuaaagaaa aggaaauaga ugcaaauagc aauauaagug cuuuaacaaa ucuauacagg  13680
aggacaacca ucauauucaa auuuucaaac auucuuaguu cugcucuuuu gugguguaaug  13740
guuuuuuuuu uuccucuucc aggagaagaa aagaggcaua uuauagaaau uccuccuccc  13800
ccagcauuac uugucacaga auuguaauug gaagugauuu cccugacuaa guuauuuugg  13860
cugucuguua uuuucucucu ucccucuugc ucuucccuca gcuggccauc cugugguguuu  13920
ggagagagcc agaaagguuc aaggcuagga auguuucucu cucucuuuaa agcucuuuaa  13980
ucgucaggcu uucugaucuu caaagcaggc uguagccagu gugaccccac ucccucgccu  14040
ccccaugcug gagaguaaaa gccuggagua uuuuugucau uuugaagacu ugcauauuug  14100
gacagccuug gacaucugga aagugugguc cucacuagcu cugcagggau aagagcacgu  14160
cagcacuucc aagcucucug gcgccccuac aucuggacac guugaaaaau uaacaccaga  14220
cucuggaguu aagcaaacau uaaguuuaua ggccuccuug cauuugacca uuuccuggga  14280
cagcagcccu uauccuguga cuuucugugu guagaguuga gucuuugcag uugguccucc  14340
ucacacucuc ucaacuuugu gacucucugc ag                                14372
```

<210> SEQ ID NO 18
<211> LENGTH: 358
<212> TYPE: RNA
<213> ORGANISM: Homo sapiens

<400> SEQUENCE: 18
gugauguuuc aggaagggcu cgcugcauuu cuccaaaguc agugggaaau uacauuuggu 60
agagagaaag ggauugagac uggacucaua aaucaauaaa auuaaguuaa auaagaaaaa 120
auaagauauu uuauaaagcu caacaaagag uccuugaaug aaagcaauua cagagucaca 180
uuguggcuaa uauucaaaac ugagauuuaa acugaggacu aggaaauaga auuggauccu 240
uuugaagcgu uuaggagaaa gauuuuaaga gaaugaguuc cgagucaccc uguggucggg 300
aggugugagu gagcuaucca agcccguucc cauccuuugu cccucugugu cuucucag 358

<210> SEQ ID NO 19
<211> LENGTH: 1817
<212> TYPE: RNA
<213> ORGANISM: Homo sapiens

<400> SEQUENCE: 19
gugagucuga aguucgcgau ccuccuccau gacacgcuaa ugggggugcu ggagugggcu 60 gggguggggcu gggggugccc ucaaggcuuc caugucuuua gagagagccc cagggaccag 120
agccaaauug gagagcaugg agcucugacu gaggaaccug cuucucccaa gcuccaggca 180
ggcacagaug agucagugca gugguggggaa agggaaaaga guugauguug uagcuggaaa 240
agggaagggg aaaauuaaag caaggaaagu gaggcugggg gaggggacaa auuccccacu 300
auguaguaug uuugguaugu ggaaggguuc uggucagaau guuugcccaa ugauugccac 360
aucagcauuc auuuuggacu cuguauggcc aguaggucug guuccuggga gcccuggaau 420
aaugcagccc cuucccuaac uaacauuucc augauguaug cucaaugaca aggcagagga 480
auguguugga ugagcucagg accugccucc cuggacacuc ccaucccagg ccuguauauc 540
uguugaccag gaauaagcca agcaagcagc cuacuguuug acugaauaug gauuuggggg 600
gugguagaga aagggccggg guggagguu gggaggcuca uuugucauua uagauggggu 660
cagacacacu accaaaacag cagcagagau cuacaauuga guucaccuaa aacucagugu 720
ggacacagga aacccucuuu uaauaacugu ccaauggguu uuccagccuc agcucuacag 780
aaaacuugag auaacagugg ccagucugca guuaguuugg guucggacaa uaggcagagc 840
ugggaaaugg agccaggggc gaaagcccag guccacuuua ggaucaggac gggaguggcu 900
gguggggaag ugaggugggu gugggggaggc aauagggagc ugggucauuu gguaugggag 960
aguccucugg uggcuagucc cagaagugca ugcuuuacga acauaugcuu cucucccuag 1020
ggccaccuug agugaaaccc ucccaugcug gaauugggcc cuuucaguga caacacacaa 1080
caguuuucaa uagauaauaa ucccaagggc uuuacuagca caugaaacac agggaaaacg 1140
uguaaaguuc acaagaaagu cguuccagug uaucaaaucu auccuguuug ccagguggau 1200
auaccagggu cuccuccacc ugugcauggc ugguggugggg uccaguggcu guuggauaac 1260
ugauguauug auggaucauu cgccuucuga aagugccaaa cugauuaguu auuuugugug 1320
ucuuuuugug uaacuagggu uugaccuucc agggcagacu gugcuggggc ggcugacccc 1380
uuggggagcc aaguuauugc ucuuaccacc accacuugcc cuugucaguc cuccacccuc 1440
uuggguuuca gugucagcau guagcugucu acucagaucc cauccacauc aucaagucug 1500
caguuuuuuc cuugcaaggc cuuacaggga agaucuuuga cauagaggau auaauuuuau 1560
ugacacauuu uacuugcaga gcauucaccc gggcuaacca gaaagccagc acucugcuau 1620
aaacaaaaaa uaaugcuuca gggcuaacau ggaauguguu aaaagauucc agcccauuaa 1680
auguccaggg gagguuuucc uguuuuccuu ucccuccauc ugggcuuugu ucucaacaca 1740
uucauucaac aaacauuuau ucugccucua ccagguacag agcacucuac uauucugcuu 1800
cucuccuuuu gcuuuag 1817

<210> SEQ ID NO 20
<211> LENGTH: 3714
<212> TYPE: RNA
<213> ORGANISM: Homo sapiens

<400> SEQUENCE: 20
guaagccaaa uggagaaggc ccagaaaauc uugaauacuu ugguuccuuu ccccuuuccu 60
ccuguucaug ugccuggauu agucaugugg ccaccaagga gagcgugaca ucuagcuucc 120
cagcccuucc uuuuagccaa cgugggagac acucaaagag acgaaaucuc cugaaggagc 180
cacuguauca cagcauccuc ccaucuccca cuuccugccc aggggucca u gguccacaca 240 gacuucccag ucccauuccg ugaccaucug gagaagcugc uauuagcaga gcccugcaca 300
gggugauagu guaauuaaag uggucuucuc uuuccaaaca cagaaaaaau caguucaggg 360
aguguuuucc ugggcuuaca auuuuaacua cuggcuagag uugaaauggg gaaagccuuu 420
ugccuuuuca guagcaguag gggaggagau cuggauuauu uacuuaucau caucaugguc 480
accuccuaca uggcuucacc aaaaaacauu cugcugccug aaaaagcucc aacaccucuc 540
ucucuuuuaa aggauggaau uuggagucca uccuuccuca gugauaagga guuuuuauag 600
ccacaggcag caucuauugg ucuguccucu gcaaacuugc aacuccucug agagcuagac 660
uuggaaauga aacauuauuu ugcaaugcgc ugcuauccuu cauuuuuagc uccuccaccg 720
uagaugauag uuuguacuug uuaaaugaua aggauauaaa uuuaggucau uuuuuauauu 780
uuauugggug gaauuuggua uaauuuuuag acuucaggcu uuacaggcuc cugagaugga 840
cugauugagc uuguucuacu ucuuccccau caugauagga agugcuguac cacacuaggc 900
agugugugua gugaccacag acuggcugag ugucucccau cccaugcugg cccauaucug 960
guacccaccu gauccacaaa uguuccauca gauccuguuc aaacaacaca ucuccaguua 1020
agccaaaucu ugcccuuucu ccuuacggua aaauguacua aaucugaagg uuuugucuuu 1080
uuaauguugc uccaugaucc agugaucugu ggccuugguu augcucugug cuagaguccu 1140
aacaagacaa augcuaaggu agaggucauu cugcucaaac aaccugaccc caccuggaug 1200
ugggcuuaca uuugcaaagg gcaccaaagu ucuaagagau gaggggagga gcugagcccc 1260
uuguccuuau cuagguuucc cuuguucuuu cccaucccuc agucugcuuc uuuucccagu 1320
accaacaugu uuguguccuc agaauuaaag gaguaaaaau guguaaacau cugacuagca 1380
acagccauga gauuuugccu ggcuuguuga uaagcagcau ugagaucugc ccuccuaaga 1440
augggccauu aggucuucaa agcuuuuacg augugaggua aagaauguuc accaggaguu 1500
ucaugcacaa aaggguuucu cuuuguggga acuagaacau uguuccagug augacggaaa 1560
cagggcuuuc cauaccaaaa caggguuuuc cuuugaauga cucucccacc uuucccuugu 1620
cucuuccucc ccaccucaac aacacaggaa agaagcugga agcagggaca augggaaggu 1680
cccuuuguua cucgagcuau uagaaacaaa aagaaaagug gccaucugag gaagccacag 1740
cuggugaaac uguaggguca cagagugaau uacaccucug gcuuaaguca gugaaaaguc 1800
cuagaaguuu gugguccuag aaguccuaaa aguuuauggg acuuuguuuu gagcaaggau 1860
aagaaauuga uuucaggcug ggcguggugg cucacgccug uaacccuaau acuuugggag 1920
acagaggcag guggaucacu ucaggucagg aguuccagag cagucuggcc aacauggcga 1980
aacccugccu cuccuaaaaa uacaaaaauu agccaggugc gguggcacau gccuguaguc 2040
ccggcuacuc aggagacuga gcaaggagaa ucccuugaac ccaggaggug gaggucucag 2100
ugagcugaua ucauaucacu gcacucuagc cugggcaaca gagcaagacu cugucuaaaa 2160
aaauaaauaa auaaaaaaga aauugauuuc auucuucuga gaacugcaac aacuaccuua 2220
aagugauucc auccaaaacc cacauguuca gccauggacu ugcuuuuaug gagcugcgug 2280
ugggugacac acaaaaucag gagcucugag uccuaauuua gacuuuuauu uagauuuccu 2340
caaauuuggg uuccaguuaa gcgugggucu cuucugugcc ccgcuccccu uugccauuug 2400
uuuuaucugu ucuucagucu guucugucag uacccacagg caggagagca gaaaggagaa 2460
auggcagcca cagcagacaa auggcacauu cguuccacuc agcucucgca ugcccaucac 2520
agauacagcu cauuggucuc uuuucuauga gaggaagcca gagcuccagg gaacuacugc 2580
caacugauca gaacucauuu aggacaugga ccuauuuguu ccuuuauguu ccugggaaga 2640
gcacaggaug aauucuaugu acucauuuac guguucagag aguaaagugc cucauaggau 2700
gccuccagca aaagauaacc aagaaggucu aauaccuuug acaaucucag uuuauccuau 2760
aguguaauug gauagcaguu ccccuagcaa aaguugcuag uuuggucoua uuuucuacau 2820 agccaaagug auugauucau ugguuaaugu gaaaguuacu gaguacugcc agcagguucu 2880
aggaaauaua uuugugugau auucauggau ggggaggauc aauccacuuc caagugauuu 2940
ggauuaauua cugguauuuu caccugugug gguagcaaac cucagaaaau caaguauaga 3000
ugacggcaua ggacaggcca ggccccaggc aaaauguuga agcuccucug gaguucccuc 3060
ccaucucccu cuuuuguuuu ccauauaccu gguuuaucca gggcccugga gaugcuccaa 3120 gaccccuac ccaggucuuc cucccuuguc ccagcuauau uucuccauau uaccacucuu 3180
cucaccgagg auuugcuuac uuaacacaua auaaauacua uuaaaagaga aacuuaggca 3240
cauuaaaaug uuagaguuga uuccagcaaa cagugauuca caggaggcuc cagaucacaa 3300
gugguucagg gccccacuga gggguaggga agcaagacaa agaaaaacaa agcaaauauu 3360
ugauugguuc aaguggaaag ucccugauua cagguuagug ggcaguuugu gauuaguuaa 3420
guuucucuaa guuggguuuu gguuugcuga uguaggaaca cagaaugcug gggccguuuc 3480
aaccuaaugg ucucccaauu aauuuuuuua acauuacuga ugacuguuag gagucuaaug 3540
ugcuacuccu cccagggaaa auggcauucc uaggauuaaa ggaacucagc acauggagug 3600
ugcguagaaa uuuagacacu aacugcaggc ugguggggaga gagcccuuua gggcagaaug 3660
agaaggcguc cggccaaggg caggaguuac ugacgcaugg ccucuugguu ucag 3714

<210> SEQ ID NO 21
<211> LENGTH: 1285
<212> TYPE: RNA
<213> ORGANISM: Homo sapiens

<400> SEQUENCE: 21
gugaggcccu ugggcuggcc ccuguccuac aacacguuuc cuuggaaggg uccguagcag 60
uccuggaggc ccagccugcc cucugagggg guccacuuug ccuuugaccu aagguuaaaa 120
aguucacgug aggcuaaaau guacaggggc aaaaguggga gcaguccuca ccccgagcga 180
ugcaacagug acuccucacc acgccugcuu gauucaucug cccuggaaag ucauuaaaaa 240
accaguucaa cucaugggguc ccuuuauuua cucacaagag agagccagca gcccauuuca 300
cuaguuuucc uuuccuacuc uuugagaaga aucagaaggg agggagcuug ccacuuuacu 360
aucugucuaa agagauguuu ccauuaauua aagguuuuug uuuugcuuca aaaaaacuug 420
aauuggagua uuuccacaag uaucuuuaac augcucuacc aauguuugca gaaagaagug 480
cagaaaugag acuguccaca gagucaggcu cgcuggccag gagaggacuc ccgaagcuga 540
cuucugaugg ccugagaaac uuccuaguuc acaauuccca gacccagaca aagagcacug 600
ucuuuucucu aauuguuuuc aaaugggcca uuuccacccu cuaaucagcc ucuggcccug 660
gagggugcag uuccccuugu ccuccggagu cucccugucu cugugcugua gagucaagaa 720
gggacaacca ccugcccuca cugggaaaag acagaaaguc ugacuuguuc ucacgacuca 780
cacuuauuag gcuccagagg ugucagggca ucugccuuuc auuucuuagg uuaaauaaga 840
aaucaauugc ugccauuugu aguacccaau uuucuaaaau gaucacaaug gauaaguggc 900
aagaaauccu uaugacucau cugugggcag aguugggcua uuuugguaau ccuugaguag 960
gcagauggaa uuugaggcca ucuucuuggg uacauagauc acuaggaagc uauaggucua 1020
gcaacugugg auuagggcug ggcugagaau uguuucaugu uuuuugugac uguauagcua 1080
gagacucucu uguuugcaga gagacacucu gaacuccccc uggccgucaa gggaaagacu 1140
gccuucaccc uccugagcug accuuacacu gagagacaau ggggacccuc uuuuggcccu 1200
ccccucuacc ucgagggcau cugggugcug uugcauugga uaaaaggcac ugcucuuuuu 1260
cugugcccuc uccgccucac ugcag 1285

<210> SEQ ID NO 22
<211> LENGTH: 3412
<212> TYPE: RNA
<213> ORGANISM: Homo sapiens

<400> SEQUENCE: 22
guaagcaucc uccucuauag gguaaaggua auugaguucu ucagaucccc agcccucucc 60
auucaucuag uuuaaauuuc auuucuucca agcucuuugu cagaaccagc auuugaaguu 120
uaaaucuaga aguuaaaaau ccaccagcaa auccuacugg cucuacuuga gaaacaaauc 180
cagaaucuga ucucuuguca ccaccuccac cacaaccuuc ccaaugccag ucucuuccuu 240
ccacuaccac cucccaucag uccauucugc acacuguauu cagggagauc cuuucagaau 300
caaggucaug uggugucagc ccucucuguc aaaugcuugc acuggcuuuu ccucucuuuc 360
agaguaaaac ccagugucuc aacccuggcc uccaagcugc uucauuaucc ggccuccaac 420
ucucuucuuc aucuuacgau uuucccuacu ccuccauguu ccucugcucc agccacgucg 480
gccuccuuac ugacuguuua auacaccgag cgcauuuccu cuucagggcc uuuccaccug 540
cuguucucau gccagaagca cauuucucuc cccacaaccu gcaacccgcc ccucauaucu 600
gcaggcuugc uuccuuacuu uguuaagguc ucuguucaaa ugucccauua ucacagggau 660
cuuuccagac ugaagagauc uacauaacua uggcucugua aacaacauuc cuccaggguu 720
ccuguccccu uacccuacuu uauuuugggg aacauucuuc accaucugau acaaugaugu 780
aucuuaugca uguauuuacu gacucucugc ccuuaguaga auaugagccc agagagcaug 840
cauguggucu auuuuguuaa cugugacagu cccagugccc agaauagugc cugaccuuug 900
gugggcacug aauaaauauc uaaguaaucu guagcaugga aaaucagcuu cugaaaauug 960
gcuguuugca cggucgugua uuugcuuggu agaaaaucaa auuuuccuuc aaauuagcau 1020
uuucugguaa cuagagcugc cccaucuucc ucugaguggu cuccaaguca gccaauagcc 1080
uugugcugug gcagccaugc cuggcucuug augcuguagc caaaagcagg caggggaugg 1140
ugaggcuggu ccaguccaug ggagagggaca aacucacagc ucucagauca ucucagggca 1200

-continued

```
gccuuuguug gcagaaauag guaggcagcc acccugaaua ggaggaaggc uucuagacug   1260

ggucaggagg ccuggguuug cauccuagug gcaagcgugc auucauuuac uagggcugcc   1320

auaacaaaau accacuaacu gggcagcuua gacaacagcc auuuauaucu cacagcucug   1380

aaggcuggaa guccaaaauc aaggguuugg cagggccaug cucccucuga aaccuguagg   1440

ugcuugggca cuccuugacu uguagaugcu uccugcugau ccuucgucug cacauggcau   1500

ucugccuguc uuacauggcc aucuuauaag gauaccaacu ggauuggauu aggugccuac   1560

cuugcuccca ugugaccuca ucucaacuaa ucacaucugc aaugacccug uuccuaaaca   1620

aggccacauu augagguacc ugggguuagc acucugguau cuuuuuucuu gacagcacuu   1680

cugacaccaa auguguguuu ugguuuuuug uuguuguugu uuuggcacca accaauucuc   1740

cuauauuaau ggguugucca agaauucaau ugaauucuga cacuauccag aauucacaca   1800

gacuccacgg guucaguccc acaaggcuuc cccgucuuca gaugccagcu ggaaaugugg   1860

ugcccaggcu acccacacuu uugccaaaau ccuguacuua caaucacagc uuuaaaauga   1920

aggaugcagc ucaggaacug ccacauggaa gagaagcaca guaugggguc gggggaagag   1980

uuucuaugcu cucucuagac gcaccacucu cccagcaccu caaaguguuc agcaacccaa   2040

aagcucucca aaucuuguug uucgagaguu uuuauaaccc uaucuccagc uccauacucc   2100

cccauuggag guugaggguu gggacugaaa guuccauucu ucacaugugu gguguuucug   2160

gugaccaguc cccagaaacu gcagcuaucu uggggcucua cccugaguca caucauuagc   2220

auaaacucag augugguaga ggaaggggcu uauuaugaau aaaaaaagac acuccuuucu   2280

gccaggaaau uccaaggguu uuaggagauc ugugcccugc acaggagcug gggacaaaga   2340

ccaaguauau uuuguguuau gccacagacc ccaacauguc uuuuuggagg gagaccaaau   2400

ucaacccaug acagugacuu ugaacaagac auuugaacuu agucuguuuu uucuauccua   2460

cuagauuguu ggaaacagau auaauagaug aaaauuaguu gauuaaaauu gaaauuugug   2520

cauaauucaa aaguuuuauu uuagccaagc uaaagcuuuc auuuauucaa cagcuauuua   2580

cugagcagca ccugugcaug aggcucagca gggccagguu cugggaacag agcgguggag   2640

auaaagaucc agaccugccc cgaggaauag acaguccagu ggcagcaaag gccaugaaac   2700

auacggcaac ucuuaaaaaa agccgagacc augauuuuac aaaaucaaca uuuuguaggg   2760

agcagaacuu ucaaagagaa cuggacuaga aauuugggag ucuuuuucuu ggaacccugg   2820

uagauccagu agaaugaggg auggggggugu aggguuaaaa acacugacau uagaacugga   2880

uuaccugugu uggaauuccu acauuucugu uucacuaucu gugacggggg gcagauggcu   2940

gaaucucagu gugccucugu uuccuuucuc acaagaauaa uauuacuacc uaucuccugg   3000

gguuguuuug agguuuagau uauuuaacac auggaaagca cucacagcaa ugccugccac   3060

agaaagaaua uccaguacau cuuagugaug aucaccauua uuauuaucug acuccuggaa   3120

aaggacuuga uuuaauucuc ucaugaaacg uuuucuugga aaacugaugu caaccaagau   3180

uauuggucuu gcuguugcuu auaacacccc aaaaacauga cuguguggau aaaaauaugu   3240

uggaaggggu agucuuucug ggagccugag aauagccaug uaauaauaac ugcaaauauc   3300

uauaguuaca auuugagguu cagguaaaua aacucuagau cuuauagaac ugcgguaagg   3360

uaggauaggg agacuccuuc gacuuucucu guuuauuugu cucuauuuuu ag           3412
```

<210> SEQ ID NO 23
<211> LENGTH: 2675
<212> TYPE: RNA

<213> ORGANISM: Homo sapiens

<400> SEQUENCE: 23

```
gugaguccuu uaaaacacaa aucuuaaugu uugaaaucaa cuccuugggc ucugugcaag     60
auguauaugg aucacagagg uggcccucua uguaaacggu gugauuccug augagucagc    120
ugccuccugg ggcucugccc cuugaugggc auugcagcgu cugggggacc accuuucaca    180
aguugcuggg cccuguguga ucaugaaugg cugaucaugg augaagcccu ggguccugua    240
caccuugucc aguagacuaa auugcccuau uuaaaaaagg ccaagccacu ucaggguuca    300
aagaacuuuu gcagcuuuuc aguauaaagc agaaauccag ggaaucauga aggaaccuuu    360
gcauucaucu cccauugccu uccuugugcc uuuuuauucu ucucugccuu uucaaaauau    420
aaauuaguuu auucucccaa gaugaagacu ccuccugggg cugaggcaga gcuguuaucu    480
ucagggcaau accucagauu cuccuggugu ugaucuuucu uaggggugg gaaaaaggcu    540
gaaagggcau uugcccacaa cacaucuuag guaaaaggca ccuuuacuac ugaaccaaac    600
aggaggccua gcuagagaaa guucuagaag cagggaaaag cacagacucu uuugugaggu    660
cugagaaagc aaagaaauuc cagggugaaa gcgggggacu ccccuagagc ugaaguacuc    720
ucccaucugu uuguugcuca ccuaccuauu cuuuacuuug uauuauuggg ccugggccag    780
gacuuauccu gcaagcacug agauggaugu uuguuuucuc ugggggauua gucuuuuuuu    840
uucuuuuuuu cuuuuguuuu uugcuuuugu uuucacuggg ucaaacaaac aacacuuuaa    900
cagcucagga uuuuuucauu guauugacuu gucuaccugu aaacuuguua auuuuuuacu    960
auaauaaaau uaucauauaa uaaaugaaaa auuucaacac agggcuugug ggcauuuuau   1020
uuuucucuac aaucccaaca gauacucugc cucuuaagaa aaaaagaaau cauaaggaaa   1080
auaugcuccu ucaaaaguga aucacaaaua uguuugccaa cggaaggcaa auauuuuuca   1140
ccugucucau aggcuggacu gaaauggauu ucuaaaacuc ucuaaaacca gaaaagagcu   1200
gagugucucc acccaaccuc ccuccuuuca cagauuaaaa aauaaaaaau ggagcccagg   1260
agacauccag uaucuucccc uauuggucac cugggacaaa aucuggaaca ugcacaugca   1320
uugccuggca ggaacucauu ccagugauua aacucuucag gaggauguuu ccucuugcua   1380
uuucauuacc uauuugugca guuugauagc uaguaaagug aucaaaggaa cugugggggca   1440
uagauucaaa aguccuucag gaagcagaaa uagaagaaca guacuagagg cagcaggucc   1500
cugaccagca ggcccacuac cugcugcucc agcacacauc cugcacauuu ucagagggug   1560
ggggacagag gggcccuggg uggcuguugc auugagaaau cucgcccugc uccuguaugu   1620
gcacuugagg ccgagagccc uuggaugccu ggugacagug guuuccuccu gccccugccu   1680
ucccucuggg cagacugacu ggcccuucug cuccucuucc ccuuccagga uguccugaua   1740
ucuuuuuaaa ccaaaugcca aguuugccaa aaagugucug uuugugugug ugugugugug   1800
uguguucaau gcguguguuu auaccacacu ucacaauuug uccaggcuug uauuaauacc   1860
aucaccaggc ucaacccugg uguuaauucc aagauacuua aaugcccauc uaggugaauu   1920
ucucagguaa accauauauu caagcuguag uuuaagcugg cugcccguca uagcacuuug   1980
aauagacuuu guuuuuguuu uuguuuuuug agacagaguc ucacucuguc ggccaggcug   2040
gagugcagug gcacuaucuc ggcucacugc aaccuccgcc ucccggguuc aagcgauucu   2100
ccugccucag ccuccuaagu agcugggauu acaggugagc gccaccccac ccggcuaauu   2160
uuuguauuuu uaguagauac gggguuucac cauguugguc agacuggucu cgaacuccug   2220
accucaugau acgccuacau uggccuccca aagugcuggg auuacaggcg ugagccacca   2280
```

cauccggccc cugaauagac uuuuacucaa gguucaccau gacuuucaca uguuuuguau 2340
uggaguaaaa ugugccagug gugggcuaaa gaaaauuaac ucauuucaaa uucaaaccug 2400
guuuucuuaa uuuuuuuaaa aucacaguuu cugaaacugu gggcuccuca uggcacauug 2460
agaggaggag gugaaacucu ccaagucuga agcuccuguu auaaaucuuc cucuggcaaa 2520
gauuguguga ucaggcuuga guaccucaca guccuagagc aggucaaagg cuggcuagga 2580
aacucauuug cucccuguac cucuccccuc cuuuccugcc uuugcucguu cucagcuccc 2640
ggugguagag uaacacuggc uucugauugg ugcag 2675

<210> SEQ ID NO 24
<211> LENGTH: 1774
<212> TYPE: RNA
<213> ORGANISM: Homo sapiens

<400> SEQUENCE: 24
guaaaacccc gauaaagaau acacagcaga ggcgaggaaa aggcucuaag cacugcagag 60
ggccagagca aaacaucuca uggcaagggu ggaaagaagc cuaggaaacu gacucucucu 120
guggacaagu guuaaaccag aucccuucuc agagguccau cugcaugugu guggaaugaa 180
ugguucagcc cagacauuag cgcauauuuc cuggagaaag caaauaccaa cuauguagug 240
ugccugugcc cuuguuaggc aaaucccaag ugaguugcac aaaugugcug acuuccgagg 300
auuuagcaag aacaauaacu uuggucacug ggacuuaaag cggauaugag cuauaaggaa 360
agacaaaaau aaaugcuucu guguccaggg ggaaagagac uccaggggag cugacuacac 420
uucacuuacg gcuuacaaau cuagaaggcc auucauugaa accaucagaa gccuuuccug 480
acaguggaag uuaccuaaua aucccuaaac ugacgaccca gauuuacaag uuuuguuuuc 540
cuggcuuuug cugcccucau cuucucucuu aaacuaguuc uguauuucuc ccaaggcuuu 600
ucauucccua agcauacgca uuucucugug gccaaaaugc ucuggguuua gacaggcagc 660
acagccccug ggcucugccu gacagggcag gagagggucu ggccuuuauc ccuccagccc 720
accccagggg ccauuucaua aaacuaaagc cagagaccug cagccccucc cagaguuaga 780
cugcaguaca ccaugccucu ggcaagaucc uccucccaca guggaaaguc uaagccaaau 840
caggaggcug gggacugguu ccaccucagu ugcaggcaag gccaggaggc acggauagaa 900
gaaacagugg acuuuuuccc ccuagggaaa gaaaugcuua gagcuacagu auuaagauga 960
caaauuaagc ugugccauau agggugaaau gaagcaggga uagaugggag gucagggaga 1020
agugagagca cucggugagg gucugcacug gagggggcau gggaggaaga aggaggggag 1080
ugggguuuga gggauggugu ugaggaagcg uggacugccc uacccaccua uuggaaaacc 1140
ugggaguucu gaggagcaag aagccuuagu caaagucaac ucaaagauuc aagccaaggu 1200
gacuaagaga auggcggucc agaaaagguc augggagaau cugaaggcag auguuguuuu 1260
gggaagauga agaaccuaag ccgcuuccag aaauucauga ggaaaugccc cguggacugu 1320
uggcaaugag ggccuaggac caagguugag cuuggggcca acucucccua uagacaguga 1380
gugcauucug acaagcaugg gcucuggguu caaaucccaa cucugccacu caugccuaug 1440
uguccuuaau aggacgcuug augucucugu gucuaagguu uccuggacua uggaaaugag 1500
ccuaauaaau gucuaccccu uaggaccauu guaagaguac auugagguaa uuuguguaaa 1560
gcagucgaag cagugccugg cauauaggag gugcuguaua aacguuugau gcuaguauua 1620
cuauuauuau ucuggagucu uccuugcaac ggugauagcc gaagccacag gggcagguga 1680
cguuauaggc agaauacaag ggccuggaga cagagcccug gggccaugua auuaggcauu 1740
auguuuacau cauguucauu uuuuuuccuc caag 1774

<210> SEQ ID NO 25
<211> LENGTH: 2174
<212> TYPE: RNA
<213> ORGANISM: Homo sapiens

<400> SEQUENCE: 25
gugagucuuc cagcagagaa gcuggcugcc augcuagccu gucauuuccu ggcuuagucu 60
uucccuauca gcggcugucu acucuuuccc acaaauuuua gugacaaaua uuugcggccc 120
caaaaaugug uaaaagcuuu cugcaguauu caaagaucac uaauauguau ucucuugaug 180
gggagguaga auacguuuau ugccccuuuu gugugccggg gaaguggaca uucauucaga 240
gaguugaagu gacuuuccug aagccaccaa guugucaugg cucagcgggg gcaaaagcca 300
ggcaccacag uugccucuug uuucucacac cuugagucuu uccccccauc ucaacagucc 360
auggugguga ucaagucaug gccacuguca ucaugugcau ggaagcuaua gaguccuccu 420
auuuccuuuc ucuuuucuuu ucuuuuuuuu uuuuuuuuuu uuugagauag uaaccauuac 480
ccaugcugga gggcaguggu gcgaucuugg cucacugcaa ccuccgccuc ccaggaucaa 540
gcgauucucc caccucagcc ucccaaguag gugggacuac aggugcauac caccaugccc 600
agcuaauuuu uguauuuuuu uuuuuuuuuu uuuuuuuuag uacagacagg guuucaccau 660
guuggccagg cuggucucga acuccugacc ucaggugauc ugcccgccuc agcuucccaa 720
agugcuggga uuacaggcgu gagcgaccgc accaggccga guccugcuau uuucaaggaa 780
cauuccuuuu ccuaccaauc auuaggcagg cuucaacauc agcugaugag gguuaguggu 840
cguucuggag aaagugaaaa aagaaucagu cucuagaggg gcuuguggag uaaccgccug 900
guaacagaag gucagggcag ggaaggcaaa ggggcucugc gcggaucucu cagcuccgca 960
ggcgccccac ucuccuccaa gggacccgag cgccaucugc ugagaggaga acacggcccg 1020
ccaugguuuc ccaaggagca gcagacacgg accucgcagg gggcagcgaa cccacgugac 1080
acagucuuca aguccuuugg agagccccag gaaggaacaa cagcguguac acccugugau 1140
ggaauguucu cuagggcggu ucagugugaa uggaaugugg ggccggugcc auucuaauug 1200
guucuguuuc ccucuagugg uugaucgcgg agauuucggc uucuccauca ggacaaguuc 1260
agauagccug agaugguauc agaacucagg gacagagcug ggugugggcgg cccugcaucc 1320 aucugcuuuc ucuccaugcu aacugauaug gucagagagc uggaagcaaa uuccaggacc 1380
ccagggcucc gcaaaggcaa acacauuacu ucaucggcug cugacaugca acuuccccca 1440
gggguuaaaa caauguuuaa uacuaacagu aauaauauuu uugaguuuua cuuuaugcug 1500
gcgcuguucu aauguuguaa guguauuaac ucauuuaagc cuuacaacaa ccuaaggaca 1560
ugggagucau aguucccauu uaaaaaaaaa aaaaaaaaaa gcccaccauu gcucugaggc 1620
uuuuuauguu uuggauccaa agcuaauauu ggugguggua auucccaugc cuggcuucga 1680
ucaauuaauc agcaaaugcc uaggacugcu uaggguucug gccuucauca agaccuuacc 1740
cgggcuuuau gaugaugaca ccuggcuuuu caauagccau gacugcucac ccaggaggca 1800
acgccucgag ucaugcaccg aacaccuuuu auugauccuc uccaacacca ggcuccguga 1860
uggcugagcu ggggacaccu gugacugcac gugaacauuu ugaggcuggg aaucccaaag 1920 gccccucggcg uuggccuggg agcaccauga aacaaguaga agcagagaag gauggcagag 1980
guggcccucu gcauuagggc cuggauguau acacuggugc uaagggggcc ccacagcuaa 2040

```
uaggggguuug aguuugacug acagccccag gcaggaaucu gugagaguuc ucacugaacc   2100

uggugugggg guggcccucc uaaggcaugu ugcuaaaggc caucucuucu gccacugacg   2160

ccuguguucu gcag                                                     2174
```

<210> SEQ ID NO 26
<211> LENGTH: 1137
<212> TYPE: RNA
<213> ORGANISM: Homo sapiens

<400> SEQUENCE: 26

```
guaagcgaca caggaacuga gaccgcccca uccccucucc ucaccucugc ccccagcaca     60

cuucucuaga gcccagcuca ggggugccag gccugggcac aggcagagau acagacucuu    120

auuugguuuc cccuauguuu aaaguccuuu guccuacuug cagugagaau ugucccugag    180

aauaugggac ucugccucug cugcucagag cugagggcuc cucccucaga agggugaggc    240

ugccuucgcu cugacagagc agcugaucga uccccgagcc ccuugugcag cccugaagua    300

cuuccucucu gggaccaaag acaggagaac cauuguuccu uuuuccuguu gaagccacgg    360

ccugaaaggc aaacuuuuca ggggggcuuuu caguuacuuu uuuuccccaa uaagauaucu    420

uuuauuucuu aucuaagaag cuacgcauag ucauugugaa agaaaaaaaa ggaagggagg    480

aaggaaggga ggaaggaagg aaggaaggaa ggaaggaaag aagggaggga gggaggggag    540

aaggaagcga gggagggagg gaggggagaa ggaagggaac aggagggagg aaaagggaag    600

gggaaggagg aaggaaaggg aaggagggag gaaguaaaua uagguaaaca aaaaauugaa    660

aauaaaaguc accuguaauu ucacuacuca gagauaaccg cugaguuaua acauugguau    720

auaauuuuuu agaacuuucu ccuauacaug uauagauaga uaaacacaua uacuucaaaa    780

ugauaaagaa uaguaaaacu augcauacaa uuuuauaacc ugacuuuuuu uucaaaaaaa    840

aggauugcuu uuuuaaacau aagauaucag gaacaucuuu caugucauua cauauucuuc    900

uauaaaauaa uauuuaaugu uuacagauua uuccauugua ugcaugaacu auguaagcca    960

uccucuuauu agauauuuaa gcagggucug cuauuuuugu auuguaucau aaacaccacc   1020

acagugagca ucuugauugc caaaucaaga auacuugucc ucaauuauuu cuguaagauc   1080

agcugcugga aguggaagug cuaagccacu gcuuuucucg uugucccauc cuccuag      1137
```

<210> SEQ ID NO 27
<211> LENGTH: 437
<212> TYPE: RNA
<213> ORGANISM: Homo sapiens

<400> SEQUENCE: 27

```
gugcucagag cuggauggag acagggccac agauggcaaa uccauggcuc cccagugcac     60

ccaggaggca ggggaggcuu ggagcaggag agcuucuaag ggugggaaca ccucugugaa    120

guuacaccaa aaaucuaaga gcagccccca gaucauuuuc ccugcagagc acugucucac    180

agcagccugg guuuuauuug uccugagauu gaugugcuug aacagucuuc aaagggucug    240

auccgaggag gugaggguug cccuuucugc auuuacaaag ccugaacagu auuagggcuu    300

ugaacgcuau aaacaucuaa gaggcagcac caaaccacug cuggguuaag guaccccccac   360

aaugccacuu gcccugggcc uuucucuucc ucacccucca cagccccuua acucuccccgu   420

ccuucuugug ccuccag                                                   437
```

<210> SEQ ID NO 28

<211> LENGTH: 1358
<212> TYPE: RNA
<213> ORGANISM: Homo sapiens

<400> SEQUENCE: 28
guaacagcug cugcucaguc uccugggcug ggcucucacu gcagcccuag cuguggaccc 60
cacucucuca ccugccauuu uguagcugag uacaggaacc acaaugacua cacucagaag 120
gggguuuauc agugacuugg ugaaucuaag uuccagcuaa agccuccuga gguuuuuaca 180
aauauaaaca gagaaucacu gaugaugcaa ccuacuuccc aaaauauuuu agaaaauucu 240
cuugaccugc agcccuucug ucuggaauaa uggaugcuac ucuaggugaa ugucuucucu 300
gaccaugggg acccagguca ccugcaaaca uaccuagaag cuccauagcu gucagaugac 360
cacucaggac cagugugagg gugaccugcu gggcauucag ugcuccagag gguggccaca 420
gauggaagug gcuccucugu cauggcaccu cucagacaag gggcucagau cagaagagac 480
agcaagcaga gcugagugcc cauagaggua acagcacggu ucaaccccgu ggucaagcca 540
gagcuuuccc ccuugcucua cucacacagc guugccccgu gccuuucucu gaggguuugu 600
cauccugaaa uccucauugc uauuuucuuu cuuucuuuuc uuuuuuuuuu uuuuuuuuuu 660
uugagacaga aucucgcucu gucgcgcagg cuggagugca guggcgcaau cuccacucac 720
ugcaagcucc gccuccuggg uucgagccau ucuccugccu cagccuccug aguagcuggg 780
acuacaggug cccgccacca cgccuagcua auuguuuuug uauuuuuagu agagacgggg 840
uuucaccgug uuagccagga uggucucgau cucccgaccu caggugaucc ucccgccuug 900
uccucccaaa gugcugggau uacaggcaug agccaccgug cccggccugc uguuuucugu 960
uaaugacauc uccaguuagu gagaguaugc acgugugugu ucuuuaugaa gaguauaaau 1020
ccagagcuua augauccaga aaauguacau augaaacucc cuagaugcug accauaauac 1080
augagccccu aauauagaga uuuauuugaa ucagauccua ugcuggauac agagacacug 1140
uguguggcaa ugcuuuacag uauguaggaa gcuaugaaau guuaguuauu auuguccuaa 1200
uaugcuggaa uuugcugcug aauuaguucc cuuggguuuu uuuuuuuagu uaacuccuga 1260
uuuuugcaac uauauagcca ggaaauugcu guacacccuu uaccaacaau gcccaaccca 1320
gggcaggccu ggugauugcc cuggccccua ccuugcag 1358

<210> SEQ ID NO 29
<211> LENGTH: 1081
<212> TYPE: RNA
<213> ORGANISM: Homo sapiens

<400> SEQUENCE: 29
guaggugucu gcccagggaa ggacccuggc cugggugaga aggagcacac agcacggggc 60
ugccacucca gacauggcua cucacacagg cucucgccac cagaaucagu gucuuuguuc 120
ugggaccauu ugcagaagau uucgaugaac acauucugaa gccuccuccu acagagaugc 180
uuuagccaaa augaaacaac uagcuuuaaa uggucugcaa guauuacaug ccagauuaca 240
caccaguuug gugcgguuug gugcaacaua gaagugagug ucuuauucug uaagguuagg 300
cuguuuuaag agcaauuggu ugagcuucau uucaacauua auauucccua auuaaaccug 360
aauuucagug guaagugaaa acuaagaaga ggccuccuug ggugcuauaa cauaaaaaug 420
augaaggcaa aaaguaccaa ccagcagaga ccacuucagc acaucaggag acccaguuuu 480
augucugugc ugcgaaguga acaaacugug ucauccuagg caaauuauuu aauuccuccu 540
uuuuuuuagu auuuuuuucu ucuucacaug gaacaugaag cuaaugaccu cugcuucuau 600
uucuuaggga ugugaagaua agugagauaa aguauuauaa augugcucug ggcuucuuaa 660
gaacaggcau ugcucacauu caaaugguca ugauuaugau auggcagcau uauuuaugcc 720
ucugguuuaa gugucuggcu gccgcugggg uuuccuaugu ccauccacgg ggagggaggc 780
acagaauguc ucccacaggc agaaccuaca gcugccacau aauugaugac aagccaaagg 840
gacccuugga gguucugcuc cucucugugu gugacucaca cacucucuag gauaaaauca 900
agcgacuaca cccucaaaau gcucagauga auuaacagau uaaacaguga agaaaaaaau 960
guguugacua cacuuggcag ugagaaauaa auaaagcggg cggugacagc agcuggcauc 1020
agggagaggc ugucauggaa gggaugugca ucuugucagu caucccaucc aucuguugca 1080
g 1081

<210> SEQ ID NO 30
<211> LENGTH: 2692
<212> TYPE: RNA
<213> ORGANISM: Homo sapiens

<400> SEQUENCE: 30
guaaggacug gacgggccau acuuggguuc cgucuggcag ccaucuccca guauugcugg 60 gugugugccug uugugaugca uuuuaauggg agcaaagaga acacugggua cuucugcagg 120
ucacacaguu guucuuuugc uuugagcuuc uuucuccucu uccuucuucc uucauuccca 180
aagggauuuu aaaagucaug caccuaaagg cccucucccu uuaaugagga auacacucug 240
ugcucuuacc cuuaguaagc caucauuccu ggggucccc ugcccuggcu ccaggccaca 300
uuccuuagug ucuggggaga gcuucuucua caugugugcc guggcgcccu cuaguggaag 360
cauggugaug cacggcucuu ccagugaauu cguggaguca gagauugcac auguggaugg 420
caagucugga aauagcauac accccuguua uacuccugau ucuccccuca gcuucccaau 480
uucccaguga uucucccuuu aauuaggaug cacugaagcu cucaggggug cccccaucuc 540
caaggagcug caguggagag gcuaucccccu cucuauguga gagaaugugu gagaagcgua 600
uucccacaca ggagcaaaac uaaacuuacg uacugaugca gguuaaugaa uggggaaagu 660
aucugcuuau caaagaaaag gcauauuuuu cuauuuagca caaacuuuuu caaauguuaa 720
gaauuuacua acugaaaucu ggugaagcaa gagaaccggg caauauuugc guugucugau 780
cauuacaacu ggagggaaca ugcucagaga ggcaucauca cuguucaugc accugcccuc 840
ucuuuacacu gagagacccu gugaugaaca gaaaacaucu uuuuaggaug acaucucugg 900
gucuuucucc uagccugccu ugcugugggu accuaucucc cugcucucug aaccuugguc 960
aagaaguuua uauuuguuuu aaauugauac uaauauguua aguuacugug auuugccaaa 1020
aucagauugg aaacagggcc ugcauggcug aaugauucuu uuuuuuaaau uacuuuauuu 1080
cuaaauaaag guuuucuuug uauagaaucg ggaugcugug aaugguggga aaugcacuaa 1140
auaguuaugc cccaaauaag aaagggaaaa ucauuugaau ccccaguuag cuccuugaaa 1200
gucuuuucac uuaaacacac ccacauacca cacacacacu cacagaccuc ccucccagau 1260
gcccaaagcc cugcugaccu acagagcuac uucuggaaag gcugacacau gccuaagaca 1320
caauuccugg gaauccagca gcuuuggguu caauuuccuu ccuaaaagaa caaugaauau 1380
gaccccugga gagcuauuag ggcagagcug cuuccuuaac guaaaggacu cuccagccuc 1440
cguaugaagu caucucagag cuaaagacaa ucaaguccaa cuugcagauu ugacauaaag 1500
caagacuucc aauccggcua ggcagaagga uuuugguuga aaaccaugaa aucccuucau 1560

-continued

```
auggaucauu uuuuaaacaa caaaaaaaga aaagaaccua cugggugucc acaacucuga   1620

gagcugcuuu cugaagaguc auguuuugag uccuggaauc ccucucccuu ugaccugccu   1680

cucaagacaa ugugcgagag aacucucucu ucaagugcau gcaagugagg uuuucacagu   1740

uagauuuuua auuuuaaagu aauacacauu uguacauaaa auucaauucu gacuguauac   1800

augugucaga uaaacaguug auaccugaca cuuguucaca gucuaugaua cgcaccgcau   1860

auccuacccu cucccccagc cucucuccau ggcuucucaa cccccccucu gcauuuccug   1920

ugaccugagg auucaguuuu guuuguggag gcaggugcaa ucccaagaga aacugugcaa   1980

ucuucugaga aguuagagua ggcaugugug ugugauuuag ggaagguacu ucucacucag   2040

cuuggucacc gguuccaggu uugugucuug ggcaaguccc ccauagcugg ugacagacca   2100

gaaaaaugaa aacaacuuug acuuagcccu caaguuuuca gugaaugaga augaaaaaca   2160

accaugagua agagauuucu uaccgagaug auguaaagga uaauaauagc agccagcacu   2220

caccuaugug ccagguauuu cucuaacugc uuuguguagu uugacucauc caguccucaa   2280

aaacaacaau gaaguggaua ccaguauuuu ccccuuuuca cagaugagga aagucuaaug   2340

ugacccaccc aacauaacau aguuugaggg gacagagcau uucguugaac agaggaggaa   2400

cuggcacagg aaaguugcau gaccccccca ccaaccuccg cccccagguu gcacagcuag   2460

cuagucggga ggacuuugcu uccguuuccc ucugccucuc aaugaugauc ucagggccaa   2520

cuaagcuaaa agcagacuug auggagcauc aguccucuga aagagucacu gccgagauac   2580

aaaauaccuc uucuucaaag gggaagugga gagaaguagg aaaucugggu aaccucacag   2640

ucuuccaguu ucuggaaaac agagcuggca ucagucuuuu uucuuguccu ag           2692
```

<210> SEQ ID NO 31
<211> LENGTH: 356
<212> TYPE: RNA
<213> ORGANISM: Homo sapiens

<400> SEQUENCE: 31

```
guaaaguaga gauuccagcu gguuucuguc aagugccaga aguggcgguu cuuugaaaaa     60

gucuaacauu agagcaaagu uuuguaaaag caaaaagcca ucguucccca cccaagcaua    120

gcaacuaucu uuauuuuugg cauaguuccc ccaucucugc augcauacaa auuuuaugua    180

cuugugguua cugugugcuu acguuuuugu auuuauagaa gaugauguuc ucagauagag    240

ucguaaugga uuuucuuccc auuaugaagc aauacccaac aaaacagagc uuggguuaga    300

uuuuucugag aauaagaaug acuaaacaaa auucucucuu uuuuucuucu ugacag        356
```

<210> SEQ ID NO 32
<211> LENGTH: 4696
<212> TYPE: RNA
<213> ORGANISM: Homo sapiens

<400> SEQUENCE: 32

```
guauggugcu ggagccagug gcuuguuccc uuccuugccu cccucccaag uuccaucucg     60

aaagucuaag gggcugggca caguggcuca ugccuguaau cccagcaauu ugggaggcca    120

aggcagaugg accaccugag uucgagacca gccuggccaa cauggugaaa ccccaucugu    180

acuaaaaaua caaaaauuag cuaggugugg uggcgcgcac cuguaauucc agcuacucgg    240

gaggcugagg caggagaauc acuugaaccu gggaggcaga gguugcagug agcagagauu    300

gugccacugc acugcagccu gagcgacaag agcaaaaucc aucucaaaaa aaaaaaaaag    360

ucuaaggaaa aagucaugaa acaacaaagc aggcaaauac uccuccauag uaucugacuc    420
```

cccaguagua ggcauuuugc auccuagaug gcuuugagug acaaaggaau aacagacuga 480
guuaggucua gauggggaca cuuuggauga augaggauuc uuacggaggu cagguuggua 540
gcuucauccc ucagcuccuc augcuguauc cccagucucu cggccugcca ugucaucauc 600
cucaucuccu ccugucaucu ccaccaggcc ucugauccau cucugucugc augagugaca 660
gcuggcagag uccuuaaugu uuaucaaaua caacucagac gucagucucc uggccccuuu 720
gagaucaaca uaaaaucauu uugaacccuu auuuaguggu cuaugggcuu ugaaaacaug 780
gggaccaaaa uuccugugga uucuagaagu cucucuucua caugugucag ccugggcacc 840
aacuagcucc uuccaugaac uuuuaucaaa cccacagcca cacaaagcau gugugagugu 900
agcagaguuu acagcagagg guggagggug gggagauaga ugugugggaag gguuaccugc 960 cacacaaaca gaaaccacuu cugauagaac acgagguguc cacccacacu guaaaauccu 1020
cuccugguac aggcaaagcu uugcagcgau ucuccuuugc ugccccuggg cuccuaacac 1080
cuccuaaacc accaguuacc uccuucuuuc caguguggca uauuucagug uuuuccuguu 1140
ggaguguuuc cuuucuaugu ggauucugga aucagcucuu aagauaacuu gguuuucauc 1200
uuucuucaua augaucccaa acaucuaucu acuaugccua gaacuaccaa uggacacaua 1260
uaccagccca gauaugcuuc agcccauccc aguacaucgc auggugacca aaagauguag 1320
ucguccuggc acagugggug uggggcagga agcaguccuc uccaggggac agcagcaauu 1380
caccacagaa cccaaguuuc uuucaagcuc ugcugacaca gaaauugaau aaucucagcu 1440
cacccaaugu caaagacuca uauuaaccaa gaccagaaug aaaauaugcu aauuuauauc 1500
agaagcuuug cuggauucaa gaguuagggc cuuuuaccug ugcagaauau uccuucuuga 1560
uaaauaggcc cucucaggag aauaaauuac acaucagagg acuguuuagu cagcauaggc 1620
auagaacagg auguuccaaa gauacaguca aggggagugg guaagagugu agccucugga 1680
gugaggccga ccaaauauca aaccugagcu ucauaauuug caaacuaacu ggcuuugggu 1740
aaguacauag ccucuuugua ccuguuuccc caucugcaaa auggagauaa uaauagcauc 1800
uaccuguagc auuguugaga gaauuaagug aguuaaugcu ugccgacuua uaacacagua 1860
uacgaucacu gauuaagacu uagcaacucu aaacuaaaug uuuacaaacc aucucuuacc 1920
ucaaagcacu uaacauccau ugucuuauuu gauuaucacu guaaucuuau gaagcaggca 1980
gggcaggggu cugccccauc uggggggaac ugagcucaca gagguuggag gguuugccua 2040
aagucaccca ggccacuggg ucucacucuc uggucuuagc ucuguaaucu aggaugcuca 2100
augccacacu cucagccacu uuucagaugg cuaaguacau uuguuuugag uuagcucagu 2160
cucagaggau gacauuuucu gaucuugucu ccaguguuua aaugaaccug uagcugugca 2220
uuggggucac acaaugcgug gcauggagag ggucuguggc ugacugccac gguuacuacg 2280
ugaaaccauc auuacagcag uuacuacugu uacugccuga gaacaucauu acaagacuga 2340
acgaagggau caacauggaa augauaacaa aaaaaccaaa guaacuguuu uaaggaaagg 2400
cuagcaucgg gaagaagaag agagaagaag agaagaagaa aagggcuccc ugcuucuaau 2460
gaguaaaggc agcucccuaa gcuucugcag cccuucauua uuuauugggu aacaggagga 2520
aggagcagga gguaaugauu gggucagcug cuuaaaugau cacggguuca uguuguuacu 2580
gacagauuuc aauuaugccu aaucauaaga aacauuugug cagccuccaa caagggucaa 2640
ugccacuucu gaagggguga cucauaguca guaacuagaa agcagcagau agcuagggac 2700
aaacuggcga uucugaauag gccuggaacc cuuagcucug gccaggucag ugggcuccag 2760

-continued ucaggaugga gccuucaggg agagaucaaa gcucagaggu uugagaugau aucagccagc 2820
aaagaggagg ggcaguaggg auccucccag agggagggcc agccauagaa gacaucaaau 2880
cugagcccgg aucaggagaa ggagccugca gaacuggggc ucuggcaccg agaaccugca 2940
gaacuucgcc ccucugagug caggugccag ggcuggggcu gccacccagc cuucgcaucc 3000
caggccuggc acgucauagg uaaauguagu ugaaaggaug acugagcuga uccaauuccc 3060
uuuacaacug uccuuguccu gggggacuug aggaggguua agaaagcagc uggggaccaa 3120
ccaacagucc ucuaggcucu ccauguccag caauaguugu ucagcaaaug agcauuaaauc 3180 agugacuaua aacuguagcu ucaacauaac cgacaacuug caaugguuuc uagagcaugc 3240
ucccaugugu uaucucauuu aaauuuccaa accaauccug ugaaauguuc uuuuuuuuuu 3300
ucuuuuuuuu uuuuuugaga uagaguuuug cucugucacc caggcuggaa uacagcggcu 3360
cgaucauagc ucacugcagc cuugaccucc ugggcccaag ggguccuccc accucagccu 3420
cccaaguagc ugggacuaca ggcacacgcc accgugccug gcuaauuucu uuucuaguug 3480
uuuguagaga cagggucucc cuauguugua caggcugauc ugaaacuccu ggggucaauc 3540
aauccuccug gcuuggccuc ccaaagugcu gggauuacag gcaugagcca ccaugccuuc 3600
auuuuacaga uaagaagucu gagaaaacuc agauuuaggc agauugaguc acuuccccaa 3660
auuuauguau cuuguaagaa uccauauuca aaccucaguc cccuaacucu uaguucauua 3720
cuuuuucuac cacuucucag uauccucuaa gaauucagaa agaaccacau cgacucugau 3780
uuuucauuug uuuaaguaca cagguaauag gugaauguau uuuguuguuu aaaaauucau 3840
auaauacaca aaaggcuaaa gucucgcuuc ccacuuccuc uccccuuucu acccaacucu 3900
gccuccccag ggagagcuuc ugcugacagu cgguggacau ucuuucagag uuuuacaauu 3960
augugugugu guguacauaa gaugucaguu uuucuuugug uaggauacau gaacaugaau 4020
uuuaaacaua aaugugagug uauuacacau auugaccagc accuuaguuu uuuuguuugu 4080
uuguuugguu uucuuugugc uguuugagaa ggagucuugc ucugucaccc aggcuggagu 4140
gcagucuugc aaucucggcu uacgcaaccu ccaccuccug gguucaagug auucuccugc 4200
cucagccucc cgaguaguug ggauuacagg ugccugccac caugccuggc uaauuuuugu 4260
auuuuuguag agaggggguu ucacuaugua ggucaagcug gucucaaacu gcugaccuca 4320
aaugauccau ccaccucagc cucccaaagu gcugagauga caggcgugag ccuccgugcc 4380
cagccaguuu uguuuuuuua uuaaccaagu uacguauuuu aaacuucucc augucaaugc 4440
uuuuagagcu auuuuguucu cuuuaauguu aauagagaau uuuaaggcaa uuucagguga 4500
aucuauacaa uuucucugua uaaguaauuu acacuagaaa uagauuuuua uaaagaugau 4560
uaagcuacca gccugguauu ucauugcuga cuuaaaugaa gaggaaaauc aaugcuguaa 4620
gggaaaaaaa aaauggcauu agagauccag accuuauagg cauuuuccaa auuauuaauu 4680
caaucucuca aaacag 4696

<210> SEQ ID NO 33
<211> LENGTH: 657
<212> TYPE: RNA
<213> ORGANISM: Homo sapiens

<400> SEQUENCE: 33
guacuauugu cggucggugu uuagcugagc ucaguggcuc cucucccagc cuuccccucc 60
ucuccugagu guuccuucag gcaugggguua uaacucagca aggagcaccc ucuuuagauu 120
cugcugguuu uguuuccugc uuuccaaacc cuuaucuuga uucuugguaa caugaaucuu 180
cuuuguaagu uggaccuccc cuagcaaaga aaauagaaua auagugaaaa uguuaauauu 240
guuuuuauuu uuacagugag ggauaaaguc auguuuucau ucauuuuugc agugacccua 300
cauaucaaaa ucauugcccu cuuuuuucuu uuaauguugu uuaauuuaga aaaagaagcu 360
cugguuuaaa gaacagugag ucacgugacu ugcucuuuga aaugcccuuu gaagucuggc 420
ugaacacugg gcugcauuca gauucuucag uggccaccag aacauucugu uuucuucugc 480
acaucuuacc uuugcacacc cugcuuauua uguuccccca gaagcccaac ccucuccacc 540
aggggcugau uaggaggcug caggauaaau guuuaaaaga augaagaugu gugugcacgc 600
gcacguguga caucuccaug ccacagucau guuuauucca cgucuauucu cccacag 657

<210> SEQ ID NO 34
<211> LENGTH: 469
<212> TYPE: RNA
<213> ORGANISM: Homo sapiens

<400> SEQUENCE: 34
gugcgcggac ucggggucac cauucuccuc uguggguuug gggcaccugg gucacaugcu 60
gcuuagaagg gcccugaccu ucccacuuca cugggaccuu caccaaugag agagggggagg 120 ggucuuuggg cugccugcag aaaggaacuu aauguaucug ccacugcuug gaaaggcgau 180
ccuaguggac aggcaggacu gcuugggaag gccgaauggg gaaaggaaug caaagcuuag 240
gugaaugggu ugaagcgcca ucuuuuugag gcauagguga caugccauca gaccacugcg 300
aguguucagg cagccuaccg cacucccagg agagcuagcg ccaucccaag gcagcauucg 360
gugccuccaa uacauaccug gcacacagca gcuauccagu aaaggcucug aguugcauga 420
uguuggcacg cgccugcucu gucccaguca caugucucac ucugucuag 469

<210> SEQ ID NO 35
<211> LENGTH: 796
<212> TYPE: RNA
<213> ORGANISM: Homo sapiens

<400> SEQUENCE: 35
guaagugccu acgcgccccu guccuaagaa gacuagcucc ccugggagga cccaacggug 60
gguucaagau ggcaggcguu ggggaggccc cacucaaucc ugcucugcug gucacuucca 120
ugucucugac cagcacuccc ccaaccucuc cuuccacacu ugugugcagg gacauucacu 180
accuccuagg aagcccccac accacuggac agcucuauau uucucagcau agaaguucua 240
uguugaguug acagaugauu ccccauaacu uauuugaaag gccucugagc agggagggag 300
ggaaauaggg uuaugcuauu gugugauugg gccuugaaug gcgugaguga cacaguggcc 360
aguacuuugu gauaguugug agucuggaga agggaguuag cgaaggccau ugacauccac 420
caggaauccu aaaaguucaa uauaauuuua acuuuucucc cucagucuuu uucaaagcug 480
ucaauaagga ccaaaacaga cuaauuucaa auuccucuuc ugguugcugu gucucucaac 540
agcuagagcu gcuaggaaua aaaagggaga caaaacgauc cacaagcuag agaugguuau 600
uccccagccc cacaccuagu cagucacaaa acccuaguuu ugauauugcu ugagcagaaa 660
ccagccucca agagaauaag aagaaagggc cugggucuaa agaggaggag gaaaggguug 720
ggcacaauuu cuuaugccua gggauuuguc agcaacuuug aggcugauua uggaauauuu 780
ucuugucuuc caugag 796

<210> SEQ ID NO 36

<211> LENGTH: 4396
<212> TYPE: RNA
<213> ORGANISM: Homo sapiens

<400> SEQUENCE: 36
guaccugacc uccaaacaac ggggccccag gucugccugc cacagaggga cuaggggagu 60
cccugguauc uccugagucu cucacaaacu aacauuucaa acuggcaguu gaguagggga 120
cuaaaccaaa cucccugcac ccucugggag gggcuccccca cagggcgcug uggcugccaa 180
cuggaggaag ccacucacca aaagcuucau uuuccaccag auacuuccua uuugaucuag 240
uagaaaaaau guguuuaagc acuaaaaaaa auuaagucau augugcucau uauagaaaaa 300
uuagaaaaca cagguaaguc agaaggaaaa aaaaucaucg cuuggauaua aacacagaua 360
auguuugguu ugcagccacc caaacagauu auauuccaaa uauugucuua aaaucugauu 420
uacugcauaa uuuacuagga acaugcaucc augucaauaa auagacaucu gcaucacuuu 480
uaauaucugu auauuauccc auuguuugaa uuucuuuuuu uuuuuuuuuu uuuuuuuuga 540
gacagagucu cucucuguca cccagguugg agugcagcgg ugugaucucg gcucacugca 600
accucugccu cccagguuca auucuugugc cucagccccc ccgaguagug gggauuacag 660
gcaugcacca ucaugcccgc cuaauuuuuu ugguaguuuu aguacagaug ggguuuuacc 720
auguuggcca ggcugguguu gaacuccugg ccucaaguga ucuacccacu ucugccuacc 780
agagugcuag gauuacaagc gucagccacu gcuccuggcc uaaaguuacu uuaaauuaac 840
ugaucuccca uuauucgcca cuuagguuuu uuaguuuuca ccauuauaag caaugcuaug 900
auguacauuc aaauggaaau guguuuacac acuuauuaac agucuuaauu aagaagcucu 960
ccaugugcug ugucucuaac aucugcaggu auguacacaa auacaugcac agccagcauc 1020
caucuuuugc agggacauua augaucuugg cucugagcag cacccugucc ugggaguucu 1080
aaaguccaga acagauuaca gugagcaucu ccuggggggau uuagagacau caaagaaggc 1140
uguguccgug guugauaaug ggccucccag cugacuugcc agggcugggc cuuagacagc 1200
ccuguccaau gauuugucaa ugaauaaacu guucccaaac aggcuaugca guucaguggg 1260
aaagcacagg uaugggacac ggagagcccc agguggacua cuugaccucu cugagccuua 1320
auuuuaucac cugugaauug ggaauaacug cuuauuucau aauauuauua ugaggauuua 1380
augaaaucau gugggcaagg aauuauuuag aauuagauuc aacucaagug augacaaccc 1440
caaacuaaca gcagauaaaa caagacacaa cuuguuucuc acucaucuaa aagucuacgu 1500 gggugguggca cgauguucua uucucuuucu ccuccacacu aaacaggccu cagccucauc 1560
agccaauaag gcaggagcug ccuuccaggc agcggaaugg aagaaggaug aagcaaaaca 1620
gagggcagag ugugcacaug ugcuauguuu agggaagguu uucugaaguu cccacauagu 1680
acuuccacuu acaaacccaa caaaaaaggc uauggcuaag gcagcaggga ggagcaaaua 1740
augggagcaa cuagauuuug ccacagcacc uaucacaguc ugguuuauaa augguucuag 1800
gccaagaaca cccgaucccu gcucuuuuuu auauucuaaa gcauguaucu uuauauuucu 1860
caagcaauau uuucucucuu ugaaucacag cucaucugcu gcaucauagg gaucccaaaa 1920
gaaggaccca aggaacuugu cucaguccuc ugugccccaa gaggaagcuu ugcuuguuug 1980
cuuugcuguc aaugcugagg gcuccugugg cugccuccac ucaaaacccu ccagcaucag 2040
gacgucaagg cugugauacu guacccugag cucuuggcca gggcgaggga ggggaggcca 2100
agccuaccua cauggguguuu cauuuccuaa acgaacccuu acuuccacgc ggucugucca 2160
gcuuagaaac uuauuuucag uaguguuggu ccuuggucccc uggacaaaau guaacagcca 2220

```
aaguccuaga aaaaggcaag ccaguuccug ccauuuucuu ucacuucugc auuuccucac   2280
uauuauacgu gccuuccauu ggagcaaaac ugaaugccac gcauaugcac aggagcugug   2340
cgcgcucugu cucucucacu cacucuuuuu cucucucucu cuuucucucu caaucucucu   2400
gucucuaucu aucucuuacu cuuuaucucu cacucucuca cucuuucuca cucuuucucu   2460
caaucucuuu cucauucucu cucuaucuuu cucucucucu cucuuucuca cacacacaca   2520
cucacaaacc cacacucuua uucacaucug cucacccuag ccacucaaac acaaucccuc   2580
auucagccug gaauaagucc agagggcgug ggccugauuc agagacaauc aguuguucuc   2640
aucugggaaa uggggcaaug uggucaucuc uagggacccu cccugcucua acauucuuug   2700
aauguggugg guccugaggu ggaagcacuc ugucccugac uucuaguaua uguggagaua   2760
ggguuacaca aauauuuuau ugggcagaac uuuuauaaaa caauuuauca uaagcuaucg   2820
cagccagcag caauuuuucc aaccuggauu ccaccagggg agcuuggccg gugucugagu   2880
gccacuuuca gcuugagaag caggugacuc agugaaaaga gcaaggagga gacagaggca   2940
gauucaguuc cuaggcccug ggccacccac cugcaaguuu gcagcccagu cagugcaagu   3000
cagcuaacug uucugaaccu caguuucucu gucuguaaau uaagcuaaaa auucuucuuu   3060
caaagagugu caggaugaag ugagaucgug uauguagggc auuuaacaua gugcccgaca   3120
cacagggagc auucgguagg ugccagcucu ccuccuggca ggagagagag aaacaaggug   3180
aaaagaguga auuaaagaag aggaaaguca aaugggaaaa caggggggagg agauagaaag   3240
uguaugaaaa ggaaagaaug gugcgcaaua acggcggugu aaugccacca aaaucccc uc  3300
aacuacuucu gggcagcacc cuugacagag ugaaugcuuu uaugagaaug uaagcggaau   3360
guguucccag auuugcagua auauugccac cugguggaca aacccaugca ccuuugaauu   3420
uuccaaaaua uuucgaugaa cuagcuucca guccuagaug uauuuugaaa gugauuugua   3480
aauuguaagg aacuauucaa auucuuucau uaaugucaca aaucaacugu gucaucugua   3540
ugccacccac uauucugggu gcuggggaca caacagcuca caaaucaggc aaagucccug   3600
cucucaccaa aaugauaucc uacgggggau uacagauaca aauacguaaa cagauccauc   3660
gggaggaaac ucucagaugg aaaugagagc uaugaagaua acacaacagu acaugacaau   3720
acagagugac uggaaccagg aacauuucuc cgaggaauaa aauuugaagc gagccaugag   3780
agggucuaca gguagaguuc ccaggcagag ugaacagcca agcacaaagc ugcaccagga   3840
gagagaggug cucgccgaga gacagggagg ggagugugc aggugagcuc agagaggggc    3900
agggccacac acaucggcca caugggccuu gguagugagu cgagauuuga ucccaggguu   3960
uauuggagug gauaaguaag caaggugacu gaggugcucg gguuuacauu uuuauaguuc   4020
aagcuggcug cuggguggaa aacggaaguu ggcagaccaa ggacagaauc aggcagaccc   4080
auguggaagu uucucuagug gucuaggugg uggcuugggu agcguggcag uauuggagcu   4140
ggagaaacgc agauggauug gagauuuguu uuggagugac gccauucugu cuugucaaug   4200
gauuggcgaa aaaagaggca ucaaagauga guuacacauc auugaaguga gaacuaggga   4260
gaugccagua cuuuauuuag uauuuucuca gcagcucaau ccauaaauaa uuuuuggaag   4320
acaacaagca guuucacaaa cuacuuauaa guccucaagu uccaagguaa uuaacguggg   4380
ugucucauug ccucag                                                   4396
```

<210> SEQ ID NO 37
<211> LENGTH: 1535
<212> TYPE: RNA

<213> ORGANISM: Homo sapiens

<400> SEQUENCE: 37
guaagaagaa auccuuuuau gcuuuuuauc cuggcucccu guagaagaua uuaacuaggg 60
acagaagaua auuuucucuc ucaauuuaug uaugaucagg gcaguagauu uuuuucuuuu 120
uuaucugauu ugagggcccc auucaacaua aaaagcaauu gaggcacaua caaguaaaau 180
guaacuuaag auuaauucuu uuuuuguugu uuguuuguuu guuuuuacau uuagggcaag 240
cagucuuaaa uuuuaaccca cguauuauua aaaguuauau cagaagacca uagaaguuau 300
ucaaaaaugc agccacauau uuuaacuagu uaaaagagag aguaaaaauu uggagggagg 360
uggaggagua uaggggaaaa gguagaagaa aaagagaaaa uaaguaagug gcaaaaaaga 420
gaaaggaaaa agauagggug ggaaagaggc agcgggacag ugucugaguc cagcacacgc 480
cagggcgagc caggucaacu gcagcuguca uauucuaacu gugaauuauc aucuuugauc 540
acugcccuuu gagaugccaa ugaacuuuuc aagaaauauc uaguucucuu ggcucuccag 600
cuguucuuau cagccccauc caggauggaa cagcuuuggc agcccguauc agaacaagca 660
gcuugacagg ggcaugccau gccaggagag aggauccuaa ggaagcgugg uccaguccgc 720
acaggcucug gggcuuuaag auaaaaccuc cugucuaacu uuaguaggac uuucuguugc 780
uucaccugcc agagcccuga acgagggaua aauugacuua auuaacuaga acacacugca 840
aauggugaaa gcauuuagca aaacaaagaa ugccauccaa gccccaaaau aaaagcagaa 900
uaaauagaau gcaauaaaca gcaaccaucc caaacugagu ucucagcagc aaaucuccag 960
uaugaaauuu uggauuuugu gcgugugugc uuaaaggugg augacaauga caguucaugg 1020
gauugagcuc uggggguccag aguuggcauc uguucauuuc ccauuuuguc auuuuacccu 1080
ugauugacug aaugucagug ccuuaacuuu gggcugugga gugagucgga acucccccga 1140
ggugugcagg ugguuguuag agucucauuu uugcagggug gaagacagga gggcugcagc 1200
cuucauucca cacugacaug gucauugccg uguguucugg guccagauca ggcauauuga 1260
ccugacauau gaccugacaa caggaccacu cagaaagucc agcaugcggg auaugauuug 1320
gagagccagu gggggaaauc auagguccuu ucucugcaug uguauucagg caaugucca 1380 gggcugggcg gcuuccgcau ugcuuggaua ucggaaaaug caaaaaugcc ccugaagacu 1440
gagacuucag ucuucaaaau gaauguuugg gaaagaaagu uaacggcacu gcuguacuug 1500
ugguauucau ugcauuauuu uauuuuggcu uucag 1535

<210> SEQ ID NO 38
<211> LENGTH: 1434
<212> TYPE: RNA
<213> ORGANISM: Homo sapiens

<400> SEQUENCE: 38
guaagaaacu auuuuuauca gaauuaaaau cucagauuga uucauuguug aaauaauugc 60
acacuuuuaa aaggcacacc ucacagccau gaggaggggc uguucuguag gugcucagga 120
agucacaaga cacguccuga agaauaugug gcuagggaca ucccagacuc agaagacacu 180
caguggugcc ucuucuugga ggacauaagu gggggguggca uucccugaug uggcguuuca 240
gagcauucuc acccaaaaaa agcuucuaaa accuccaagu auauaacagu uuauaauacu 300
ccaacaagag ggccuuguag ccuaaacccg ggacacuccu uggcccauuc cuuuuaagcu 360
ucagggagug ugggccagcc ccagacucac cccauuccug aggcauccug gagguugaaa 420
uauuuccaga gguuuagaac cucaccaagu gggacucuag gagccugcug ccucccagcc 480

```
ucccucagga acugcaccuc cagaacaggu gcggggcuga cauguaugug cuuuccuggg    540

cagauucuag accguacaca ugaaaucugg cuuucaggau ugcucuccag agggaccugu    600

ggggccucgg cugagacaga gaguaggagu gaggcaguga uucaaggccc ugagaaagag    660

cuccuccucu gcuugguaua accagcuaau ucauucuguu cuguugacuu uggcuucugc    720

ccugccuuug aaggguuuga ggccagggag ugaugcacuc agacuggugu uuccacacag    780

ucacuucaga cuuccagggc aguacaggag auagauccca gggccaguga agaagcagag    840

cacaagucca ggcaggagag gcuaagggcc ucccugaaca ggugugaggc acagaagccc    900

cgagagguag ggaugacagg augaagaugg guccugugcu gcuagaagua ccugcaaagc    960

acagaggugg cacagaaaag gaguccuugg cugggauggg aggagaugac augugacaug   1020

ugaaagagga ccuggaguug gcucgaugcu cccaaaaggg aaaggugccg aggggagcua   1080

gcagccaugc aaaggcagag acaugcaggc agucugggcc augaggagcu cuggaaguga   1140

cucgauaugu ccagaauagg ccacuccagg gaagggcuga ggaaggauga aguuggagag   1200

gggcacagac cagaugcaga agggccucag aggccaggau gaggguuugg acuccuuccu   1260

ggaggcagca gcagugggaa aagaguuaaa agcugguuug uaaaguggag ccauguugcu   1320

cgcuggucca ggcaauuccc ccgaaaguuc auguuucccu acaaaacccg agagagcuac   1380

uaguaggcgu gaaguucgug gcccuggucu gaggauuucc uguuuccuug ucag         1434
```

<210> SEQ ID NO 39
<211> LENGTH: 131
<212> TYPE: RNA
<213> ORGANISM: Homo sapiens

<400> SEQUENCE: 39

```
guauguaaac agacuggaga uuugaguagg auuuuugacu ugcuuaacua ccaugaauga     60

gaaacucuca ugagugauaa caggaaaaaa aaauuaaaac cgucuuguuu guuuguuuac    120

augguuuuua g                                                         131
```

<210> SEQ ID NO 40
<211> LENGTH: 230
<212> TYPE: RNA
<213> ORGANISM: Homo sapiens

<400> SEQUENCE: 40

```
guacuugacc uauguauaau cugcucugga gcuaaaaauu uaccugagcu gguuauuuua     60

uuuuuacuuu ccuaccuuca uuaaauucca ucccuccucc ugcugaaauc uagcaaggaa    120

ugucuuccag cuaccaaacc cuuccugcuu cucaaauuuc cuuuccuuca cugauuucug    180

cuuuaacuag cuguuagugc agcgucucag auguccucuc cacccucuag               230
```

<210> SEQ ID NO 41
<211> LENGTH: 1480
<212> TYPE: RNA
<213> ORGANISM: Homo sapiens

<400> SEQUENCE: 41

```
guaagccacc acagccccag ccucaccacu uucuugucac cuucuccacu cuuugaacau     60

ccugagagga uucucaccac cgcgaagugc ugauuuggau gguaaugcug uuuagucagg    120

cacauaugaa cauccgacuu ucaaauaagu gccucacacu ucacauacca gaccucuugg    180

ucauucuuuc uccccaacau uuauguggca aguaaguuua cauuugguuc cauucccuuu    240
```

-continued uggcuuuuga uagcaaguug cuccuggagc uuauacaauu auuaucuuug cuaugugcaa 300
agcagcugcc aggaacuggc aaaguucagu aaaccuuuca gcucccucgg aguaauuauc 360
uuagauucca ggaauuuccu cagaagagca uacuuuggag augucgacag agcuuugcua 420
cccucaagcu gaggcucuuc uugcacaguu ucagccagug gagacagugg ccuugugcgu 480
uuuguaguau guucacucua uuugaggccu acauggagga ggggguuggua ggagcaccuu 540 uguuagugca aacuucagca acguuguggg guccugauuu uacuauccua gcacacgcug 600
agugccagug aacaugccca gggucaucca cuaaaaccug ggccuuggcu ccuuggugucc 660 uuccucugga cacccuaggg cccuagacug uccucuguua auucucacuc agccacacuu 720
ucgugugucu ccuuccaguc auuuguucua agcuuacuac guguauggau gauaugaucu 780
guaguuuuau caagguagug acuaccacau aggauaccuu uguggaaauu aguaaaaaug 840
cucuuuucug cagguggaca cugucccaug ccaggggguua uggcuuguac auaaaguuca 900
ggcuggcuuu agccccaacu uaccccucag ccagaugccu ucuauuuguc cgaggaaaga 960
auaaauagag ccaagucccu guacaacuug ccugcccucu uuucacuuaa auuuacauca 1020
ugaacauuuc cuuguguuac gauguacuuc uugaaaaugu gauuuaacaa gaugauuauu 1080
aacaaaagau aaaucucaca gaccguaugu cugucaacau agaaaauuca agagacucua 1140
uagacagauu auuagagcua augagagcau ugcaguacau aagauuaaua uaaacaucua 1200
uuucuauaca ccauaaaaau aauuagagaa uauaauaaaa agaaagguug ucuagaaaua 1260
uucacaugaa auagaaaggc aacccgcaaa uacccauuua accuuggucc auauggauua 1320
agacaguuua guggagugac agcuucaagg uagagaagag gaaccuggag gccacaccug 1380
ggcgggugua aggccuuccc aaagccugac uuuguaucuu cuccuccuuc ugcucuuccc 1440
ucuucaucgc ccucucccug ugucucuggc ccugcugcag 1480

<210> SEQ ID NO 42
<211> LENGTH: 3727
<212> TYPE: RNA
<213> ORGANISM: Homo sapiens

<400> SEQUENCE: 42
guaaguguca guuuacagcg ccucccuccc cuccgugggc ccaaggugga gcuugugugu 60
gcucugaagg accagaccaa gaggggaggg guucucacgg ugccagggcu gcugaaaggc 120
acugggccaa gggccuugug uaucugcugu cccuugacau cuucucagaa aggcacagaa 180
cuaggagccc gaagcuagga aaggcugugg ggugcagcuu aacaacuggu gaacgggggc 240
ucucuauguc cugcacugag gggucuucug acccaucaaa uaaucacugc accgcaggca 300
ugagucuggc cuuccuggca ucagucuggc gcugagaagg uaauaugaag gggucuuuca 360
ccccaagucc ccuucucaaa uccugcccca ccuucaaaag gguaaaggua aaacuuuccc 420
ugugguaggg ucaccagaua aauacaggac acccaguuaa auuuaauuuc agaugaugaa 480
uaauuuuuag uauaagcaua ugcuacuuca aauauugcac aggacauauc uacacuaaaa 540
aaaaaaaaaa aaaaaaaaaa aaccugguug uuuaucugaa acucaaauuu cacuaggcau 600
ccuagauuuu uauuugccaa aucuggcaac cccagccagu ggccaaaaua auaagaccuu 660
cacuuauuag auuaaccacc gcuacaggga aaaaugaaga aaaaauauuu auuaaaucaa 720
uagcacacua ccaccuuccu gacaaccaag guuggugggg guagggaggg gucaggauag 780
cguacccuau uacaggcugc agggucaaag gaauugguag uaaaggccua guuauaaugu 840
aacagggauc auuaugacau caaccccaau uuauucuagg ugucuugagu aguaaaaucu 900
caacauuuua agaccaacau gagccuccau uucaugugau gauaagauau accaacugau 960
ggagaccaac acaaaugacc uucucaucca ugguuuuuua aaaugauggu gaauauugga 1020
auuccugaag auaugauuuc uaucuuacuc agcuuaguaa gcagcuauca cuuaacaaua 1080
caaaaccaga gauuaucagu agcaacuaaa uuauuuccuc ucucuucugu cuacacgagg 1140
aaacacucau aaaugcacgg ggaggagguc agaaccugaa agccuuucuu uggauaagag 1200
caucaacugc agguaccaca uuggcccugu gaugcuaaua uaaaaggagc uaggcccacc 1260
gguaccgaaa aguuacuuag aaaagugcgg aggcuuuuaa uuuuacuuuu uuuaaaagau 1320
aagaaauaga auuuacacac uuggggcugg cccacguguu ucugugugug uguaugugug 1380
cacgcacgcg cgugugcgcu uacagggauc ucugagccua uggagagaga uguagcuagg 1440
auagagugga caucugaggu gggaggugau acuagcuggc aguccaauga agggguagaa 1500
gaugguaggc aucauguuag caggcuuucu gaugcuccag aauuuuaaag cuggccugga 1560
aucucaccuc cgcgauccau cauuuuggaa cuuaggacca ccauuagcca guggcaaaaa 1620
aaaaguugaa ugaaggaaca aacaauuauu gcuuauguaa uucacuuagc acauauauga 1680
uguuuuaaau ucuuauaugu gucaucuauu uuucuuuacu uuaaaauuuu gcaacaguua 1740
cagacuuaug gaaaagucac aaguacaguu gaaaccuuuu uuucuuaguc auuugaaagu 1800
aacuucucag caagaugccc cuucucauuu auuucucucu uccugucucu cucucucaca 1860
ccccucagca cguccgaugu auacuuccua caaacgagga uacaccccau acaaccacaa 1920
cacaaacugu caacaugagg aaaccagcac ugauguguca ucaccaccua auccucacac 1980
cccacuccuc uuucgcccau ugccccagug augucuuuca gaaaaaagga ucuagcucag 2040
aaucaugcau gacauuugau ugugcuguuu cuuuagucuc guucagccug gaagaguucc 2100
acagucuuuu guuaacacuc augggcuuuga cacuuugagg acugcaggcu gguuauuuug 2160
cagaaugucc cuuggucuga gcuugucuga gguuuccucu ugcccagguu gagggugugc 2220
aucuuggcag caguaucagc aaacagaugc uguguucuca cugcauccua ucagguggcu 2280
ucugauuuca auuugcucug uuacugauga uguucaauuc ggucacuuaa gaaggugucu 2340
gcugagcuuc uucacuguaa aauuacucuu uuccccuuua uaauaaauac aaauuucagg 2400
uagaggcacu ucaaagauau auaaauaucc uauucauuau acaauuuucc auuuauucau 2460
ccauuuauuu aucucuguau gcagucaugg uucauguguu aaucaaugga cuaugaucca 2520
agacuaucau uauuuauuuu gauauucaca uuauccccac uguggucagu ggggggccgu 2580
ugaagcuggc uucuguaucg ucuugacuug gguccucaug ccccuggacc uccuccaugc 2640
ucaauggcac agcaagauau uccaggcuca uccuuccauu auccccauuc cuacccucuc 2700
cccaagaagc ccugguuccu gccaguggga aguggcccuc agaagccaag gucugagugc 2760
uagauauguu cauugccucu ggagcaccau uggucccagg ccuucucagu gauagaacua 2820
gggaagauau ggauguacac acacagguau gcacacaccu cuaucuauag uucucuaucu 2880
accuauacag ugaacacuau gagcucucca aaaccaacuc cacagggcuc auucuaguuu 2940
uuuuucuuuc cacaucugua acucccuucu ccaacaguga gacgcuggcu ucucucacuc 3000
ccaacucauu uaucuaccgg accuauacac cugaacagug cccaacucug ccaccauccc 3060
cuccccaugu ggaugccguc cucucccugc uccagcugcc ucugcugcau gcagguccuc 3120
cucguucugc ucuggcucug auacccugca ccagaucagc cuccuguaag gauaucuuuc 3180
ucaucccguu gaggccucca caccccacgg cagguugccc ccugaggaag cccgucucug 3240

-continued

```
guucuugccc ugcuccugau caccauggcu ccuccccuaa ccccacuguu gccguccccu   3300

uucugugccc aguauagugg cuguaggacu aaauuguuua aaaaggguau cauuauuuau   3360

uugagcuuug ugaagccaag aacuaggcuu uaaguuuuuc ugaauucuga agacaugcuu   3420

agaaagaaga aucaacaaaa cuuuaugacc aaauagaaag agugagagac caggcagaau   3480

uuuguaauug auccuuucaa aagauacaaa cuaaagguuc ccuuggcagg gagguagggc   3540

augggguggg guaggaggac uagugacagc uuaacauaug uuugccaacc aagaacuguu   3600

uaaaaagcaa gucgaaucag aaucccagac ccuacgagcu ggaggagccu ggccccaccc   3660

cucauuuugc agagcuggca gcaggucuga gagguuaagu gacuugcucu ccucuucucu   3720

uuccgag                                                             3727
```

<210> SEQ ID NO 43
<211> LENGTH: 1048
<212> TYPE: RNA
<213> ORGANISM: Homo sapiens

<400> SEQUENCE: 43

```
guaagccguu ugggccauua gcuaaugccu cugaagagaa gccugguggu gggggugggg     60

gaucaucucc ugacagaaaa ccugggcugu ccugugugg uagcacccac aaguuuagcu    120

uccggcccca gguagggucu gaagcugaua accagggauc ugucuggcuu cugauucuga    180

cuccacugac agagguaucu cugaggccug guccugucag ugacaaugag agaaguccca    240

caugaucuga aucuccuacu caaacugagg ccuugaccaa agccuggggg cagccauucc    300

ccaaccccuc acccagcucu gacucucacu caucuguggc caaucugucc accucagugu    360

ccccauguga acuggccaag aguuaccgcc cacaguagaa gacuccggcc aaaaagcucc    420

uccugaguca gggacagagg augacacagg gguuacauca gcagaguuac agggcccagc    480

augcaacuuu cuuucccacg uguguaaauu ugaaugagua auucauccau cucggccuca    540

guuuccucau cuguaaaaga aaauagugau ccugguccuu ccucuguggg ccaguagagc    600

cuugccaaag cauuguucuc cacaucuuuc ucuuggaaau agagaauuug ggaaccaacc    660

ugacuauaag cugugaagau gagcucacug ggcucaucug agaugaccuc agcugggcuu    720

ugcugaccca ggcuagagug ggagguguug caggcuggag aacccuccua ugaauuguac    780

agggcuuugu aguuuacaga guauauacac agcuagcagc ccauuugcuc cucacaaaac    840

cccaugaagu ggucaaggca ggcaucauua ucuccauuua aaguugaggc acagagacca    900

acaaauggag uaucucucug guccccuggg acucuggcca guucacacac aucaccucag    960

guguaagggg agugcauuau auccagacgu auuguaggug gaauggaaug uggaacucca   1020

ucacucugag uugucucauu ucacacag                                      1048
```

<210> SEQ ID NO 44
<211> LENGTH: 3157
<212> TYPE: RNA
<213> ORGANISM: Homo sapiens

<400> SEQUENCE: 44

```
gugagcauaa cuuucuuggc uuuuuuguuu gauuaguagg auaguagagu auguguuggu     60

cgagcagagc caggggcaag caucguacau guagcagcug uaugcggaug agugccacuu    120

ucuuccuccc uacccccgac ccugccuccu uuccuuccuu ccuuccuccc auccuuccuu    180

ccucuuuccu ucuucuccuc ccuccucccu ccuucccccg ucccuccuuc cuuccuuuuu    240

cauugcuucc uuccuuccuu cguccuccu ucccuuccuc uuuccuucug cccucucucc    300
```

-continued cuuuuuccuu ucauccuccc uccaucccuc ccuccauccu uccuucuuuc uuccuucuuu 360
ccuuccuaua agcaccuuuu ucauuucugu gcucugaaug aaaugguuuu cuguguuuau 420
ucugcaagca aaacuugauu cuugcaauaa acuuuaagcu uugcuuacuc uuucagaaag 480
guuuucucag ggacuuuggg uguuggguuu uacacacaca cacaucaaua cauuugggua 540
auuucaaaau cuaaaaggaa caaaaaggca uacaaugaaa aaaucuccuu ccuaccccug 600
uuucccacuc augcaguucu cuucuccaga ggcaaacucu uacuugaguu uccugugugc 660
ucuggagaca caucagcaga ucccuauacg gucuuucucc cgcuuucuua uggaaauugu 720
aacacucuga cauauacuau ucccuugggca aguuaaucuu gaugaagaga cuggguguuc 780
uccaugcuga augccucacu uuuaugagcu gccaagccca guugucccuu ccaccugacc 840
ucccccuguc cagagacaga uggccaaacu gaaucauaaa aagaggggga aaaaaagaag 900
gcagucgcug cagggcuguc uuuacuccac acuccacacu cccagucccc accgcugugu 960
cugaguccug gcuguggcug uccuuggaac auuugccuca ccacgugccu guguccccag 1020
gcgccucaac cuuuccucuc cucauuagcu cuucccaguu cagagggugg gaccggccag 1080
cacaucugca cugcugcccu gccacaccca ccuccaccug ccucugggcc ccacugggga 1140
acacaggaca aaucugugcg gaggccccac caugaaccgc ccagacccgu ggaccccuga 1200
gacugacucu uuccagaucu uguuaggguu ucguggcugc uaggcaagua acgaagccuc 1260 aucugucca ugaaugauaa gaaauucagc augucagagu cagacucugg aaaggcgggg 1320
ggauaagaac acagccccag cagauggcca gagcacccag gugacugaaa gugcugcuuu 1380
gcagagcugu guuugccaca ggcucacagc ccacuaaguc uuaagacagu uuuccuucag 1440
aauaauuaaa uagccagcuu aaagcaacuc agaacauuuu ccccucugag gcugcaccca 1500
uuuagccaac auuugcuaag cacccgccuu caaaaaccug guauuuucau guaaauuauc 1560
cgauacacag cugcuaugga aacccccagu aucccacagg aagcucccca gcucccagca 1620
gcugccggcc cgugugagau caggaggucu uuaccagcug aacaccacgu gccgggugug 1680
ugcugauaua aacaagcgug gcccacucgu ccugcccucc agaggcuccc guuccagucg 1740
gaaaaggacc ugcccacgaa guuugcaacg auauaagcca caguguauga uccuccauaa 1800
uacagcgugu gacagagcag cagaggagcg aggcagauaa caugcugcag gccagaggca 1860
gcgggaagag ccaggcugca ggggcugggg gagccguggu ggaggaaguu caauuucagc 1920
cuguagauuu cuauuagccc auuuaauaaa uaaugaagug ccuacucuga gcuaaucauu 1980
gugcagguau uuaggaagga caaaaaaaua auuaggacuc agugcccacc cuccaggggc 2040
ccacugacua guagagaaag uaggcagauu uuuaaaaaau uaaucauggg aaugugauaa 2100
gugcugggag agaggaaugg auacuuucuc augggaaucu uggaaggcuu guaagggaag 2160
gcacucucug agccagcugu cuaaagaaga acaggaaucu uuaagaaagc agaagggaaa 2220
agagcauucu uuccugcuug gagcaauagg uaacagccug cacaugccca ggccuagagg 2280
ccaaagagca cagugauucc agaaagagug gggagaaagg guaggcaggg aaggaugagg 2340
uaaugugggc gcaggugugg aggcuggaga gggaggaggu ugugggacug ggaggagcca 2400
gauggaaugg acagcagugg cccagccagg agcuaugcug gccucguacg ccucgauguc 2460
ccuucuauuu ucucagggga ggcucugccc aacaugccaa guccgaccac uugaaaacaa 2520
gucccuggcu uaacacagac cccagagaga gucuccaacc cuccucuccc uagacaaugg 2580
uaguugcccu gugaggggcu gaaaagcaga gcuggagaug gcucagggcc ugguguuaac 2640

-continued

```
aaaugccuug agggcuccug uuguuucaaa gugagucugc agggagagcu cccuaagugg   2700

acagcaggag ggcugcagcu ucucugcaca uuccugcugu cacccccaga gucaccuagg   2760

ggaggggaa ggacaguaau gcagguuccu cacaguuagc cucggugccc acaugguacu   2820

gagcauagua aauguuuaga agaugcugcc uggcuagaca aaggggaagc ucccgcccac   2880

uagaaacuug cagggagccc caguccuuga uuggucauuu aauugauuag cuccuuggcc   2940

uggccuugag gcacugcuug uaaguacuuc augaccucca uugcaaaccc augaugcucu   3000

gcuggacaaa ucccuccagu ggccagucug gcugcaagga cucucugucu gcaggccuug   3060

cccugugcug uccugugaga gcaucugggc cccaccugcu gaagagaggg ggggugggu   3120

uugccccguu uccaacaguc cuacuucucu guuucag                            3157
```

<210> SEQ ID NO 45
<211> LENGTH: 332
<212> TYPE: RNA
<213> ORGANISM: Homo sapiens

<400> SEQUENCE: 45

```
gugggguggua gccgaggccc auggagcaug ggcccugggu ccaaagcugg gaggguuacc     60

gggggggcuc cugcaucaga cuguggcagg ggcuggugcu aggaggggac cuuguugggc    120

uggaggguguc cugccagcug gagaggauua gggugccucu guuuccaugg cuggggagcc    180

acaggaggga uggagggcag cccuuaugag gcgggguguu ggcucuugcu caguucccac    240

auaaggccug gucuaguggg cccugugcug uggccagguc ugugggguga gcuggggcgg    300

cugaagugga cucaauuccu guugaugccc ag                                  332
```

<210> SEQ ID NO 46
<211> LENGTH: 1928
<212> TYPE: RNA
<213> ORGANISM: Homo sapiens

<400> SEQUENCE: 46

```
guacguccau gccacacccu gggccagugg gcagcucagg gcauccagaa cuggaccuua     60

uacccacaug gucauuucuu uccucaggag ccccacucca caauguuuuu ucuacauucu    120

caaagccugg cuuuucucca auaauacaag uagaggaucg gguuaaaaua ggcacauuca    180

aauaugugaa gagcauccac uuuaaaauau uuaaaaugca gugcuauuaa uuucaauugc    240

ugauauuuaa uccuucucau uuaauuacca aauguguauu uugauuagau gauaguauug    300

caaauaacaa ugguuacagg guauccaaag uacuaggaaa uagacuaaug uauuuaugag    360

agaaaggaca cagcaggccc cuuugcuaau uagagauuug ggagcauggg aguaauaugg    420

gagccaugug gaggggugcg ggcagugauc acgacccccc acuccuggag gaaggugggu    480

agcugccaac ccugacuuuu gaccagggcu ucucaaaugc cagguuagcu ggcaauugcc    540

auucuuccgc aggcucuucc ugaagcuggg ugggccccug ccucacuccc cucugcaauc    600

caguccuacc uuuauugucc ucacccaggg gccugaauug ccaagcagca gcccuuccua    660

gcaagcuuuc cccaauagug uuuuguuucu uaacuuuucc uccucucagg cugagugugg    720

ucaccuguaa auagauucca aggacuuggu uuuauguuuu gauccacagg gaauugauuu    780

auuggaaaug aaucugccuu ucuacucaca ggacugugag aggugaauga gaucacaggu    840

gucaacacac gccugaugaa acaggauaca caagcaguuc uaguuauggg agacaguguc    900

aggaauuguu guccuuggca cccucagccc cugcagaccc uuucugcagc cuuggccaua    960

ccuuuuagag gcuuuugugu gggagagagc aggucaggag guugacuacc caaauugacu   1020
```

```
cauuagcuuc aaacucugau gucaacacau uugaaugagu ccugccugcu uuagggccua   1080

aagaggacca gagaaguaca ccauaguccc uggcuuccag aaggucaggg aggguuucaa   1140

agaagaggcu gugucuuuaa gaaugggggaa gauuccauuu gguggggcag gaggaggaga   1200

acauugaggg acuggaaaca caugcggagg cugggagacg ggaaugacca auaggacugg   1260

gaaccagggg gagaugccaa uugcugacag aggaguuagu gcaagaggua agugagaagg   1320

guaggugggg cuggauugca gggcuguaac uacagcugca gagggagggc uucaaccuac   1380

agcugauggg gaacaacaga agguuuugag gcaugaggug gccugaugac aacucuguuu   1440

uggaaaggug gaguuggcag ggcagacugg aggaaguggg aggcucggag guuaguaacu   1500

accccuuacu gagugcuugc uguagaggaa gcauuuuagu ccugacggug aucccaggcc   1560

cugagucuuu acucugugcc aggcacugug cugaguucau cuucagcaca auccuaugag   1620

acagguauug uuacccuccu ccucaucaca ugguugaagu aggcaagguu cagagagguc   1680

caaugcccaa gaucacacau gaggaggcca ggacuggaac ccaaggcuga cucuggacau   1740

gagcaccuga ccucucuacc uaaugccuaa ugccucuccu gcugggagcc cuuuuuagaa   1800

uuuaagucuu aaaggaugga agcccagaag gaagcagaag caaggaagug gaagagaggu   1860

cccauggaaa ggacagugcc aaggacacug uacagccagc ccaauccuga ccccuuuucu   1920

ucaucuag                                                             1928
```

<210> SEQ ID NO 47
<211> LENGTH: 453
<212> TYPE: RNA
<213> ORGANISM: Homo sapiens

<400> SEQUENCE: 47

```
guaagggaau ggguaugagu uuggaggugc ugguuagauc cacaguuggc augauguugc     60

cauuuuccuu cuauagaaca auugauaugc uuaugcaagc aauuugguuc ccaguuuuau    120

guagggucau caucccugug uuauaacucg ucuuccaaga gcaucuaauu ccaaugugug    180

uucccugcua uucaucucgg gcacugacac agggccucag ugagaaucac uccagcugag    240

caucauuccc uuuucugugu ucuguuucug cagagcaugg gucagccucg agaugucuca    300

guacucacca caccucugug ccugcccaug ucaauaugua accuccuagu gcugguaguu    360

uucuccuaaa ccauccuuug cucuuuguuc ccucuucccc uccuugcucu cacccugucu    420

caguucucag uccgguuucu ucguaucuug cag                                 453
```

<210> SEQ ID NO 48
<211> LENGTH: 494
<212> TYPE: RNA
<213> ORGANISM: Homo sapiens

<400> SEQUENCE: 48

```
gugggguacuc ugcagaccac gugugaaagg cuuccgaaca ucagcucuug ugccugccuc     60

uccuccccau aaggcagagc uauucaauag gaacauaaug ccauaaugca agucacauau    120

guaauuuuaa aucuuccacu agccacauga gaaaaguaaa aagaaaauag guaaaauuaa    180

uuucauuagu auuuuuuauu uuacucaaua uaaccaaaau auuauuucaa aauguaauua    240

auagaaaacc uuauuaauga aauauuugac aauuucucgu uguuuuuaag ucuuugaauc    300

uuuacacuca gggcccgugu caacugggac uuagaugugu uucaagugcu uaguagccac    360

auauggcucg uggccucuga uggcagccca ggucuaaaau uccuccccca gcucacacac    420
```

acacuuaccc uggggccuga cauuuuagac cuucuugauc ucuagggcca ggcuagcucu 480
guguuuucuc cuag 494

<210> SEQ ID NO 49
<211> LENGTH: 2051
<212> TYPE: RNA
<213> ORGANISM: Homo sapiens

<400> SEQUENCE: 49
gugaguaucc ugcuccuccu gucucaggga gucucucaca gguccuguga gaagaauagg 60
aagggugauc aucagacccu auaguagggu ggcucugagg cccugaaaga ucuguacaga 120
gaaggaggcc ucccagagag cauggcccaa aaagcccaac acauagaccc aauggaaaag 180
ugaacugaau ugugauaguu aagagauucc ucuguuggga uggauucuug gaaagaccug 240
ggaagcacua agugugugu ucuuaaucuc uuagagguca cggaaccuuu uaagcaucug 300
augaauauuu guagccuauu ccuauaaaaa ugcaccauug cuucccauua ccucccucca 360
cacauuuuua caaaacguuu cagggaguuu acugagcccc aggucacauu uaugauccug 420
caggagcucu ugaaucccag guuaagaacc ccugugauga augaagaauc cuuccucugg 480
guugaguuuc uagauagggg cucaugcaug ggccuuuggg guagccuaac cugcauuggc 540
uauuuguagg cugauauuug gcuuugccag accaaggagc auagagggaa aacuggcgug 600
ugcccuugga uucuggaggg ugacugcugc ucucuguaau aaaaugugu uaaacagacu 660 gguccccuau gggcaggaca gagaggauga gcucucacuc aucugccucu uuccuggcug 720
caggaaaagc uugaacagua aaacuucagc acacacaaua gaggugccca gaggaagccu 780
cugcccuggu uuauaagugg aguuaggugc ugcugacauc uguccagcau cugcuugacu 840
ggggccucuu ccucucuccu gaaagccauc cucagcaugg cccaaugccc agugggcagg 900
acgaguccug agcacgcuuc acuggcucag acaggaugaa uuugauucuu uggccuccau 960
agccagcccu acuggguuua cagaaaaggg acaggcaggg gugaagccag gucauggcug 1020
aguccaucuc aacagaucca gcuucaccug caagugacca cgcaggugac uuccucaugg 1080
ugacaaaagg agucauggca ggguagagau aucauaccau ggcaggggaa agauaucaua 1140
gaauuuucca ugagcacauu uaugagacau caaguuacaa cuguguccaa gugaggcaca 1200
gucugacauc cagaagguaa aacugagcug gacgcuagaa agaaacuaua ggcuuaagac 1260
acagaauugg gauuauaugg uaggguagcu cccacuaauu uggaaacgua cccuacuugc 1320
uucccugagu aguuuuaauu ggcccagcca ugccuuuggu ggcuuuuguc auuguggga 1380 acuguaaugg ucucucugua ccauccuaua ucauccaucc uuuauucaua gacccuaagc 1440
uauaagaaga aaaggaugag auuagacuaa augucuaugu auaguuuauu uuccaucuug 1500
gcaauauauu uuuuaguggg ggugaauaua uuagccaaag ggaguuggug gaacccaacu 1560
cacucuaccc cugcucccug caggccucuc gcuguggua guuaucugac uggcuccucu 1620
uucauugcua ucuuugccaa uaaauacaga uagagaaguu uacuuccauc gggacacaug 1680 caucuuucu aguuacuucc caaaugucug aaaauuauug auaaaucaug aaucauuuuc 1740
uuaaaccuga ucuucccucu guuuuuaaac ucacauguga ggugaucuga uccaaaauga 1800
aagcugacuu uuggcguaac agggauucaa uuaaauccuag acauggaaac auggaagaau 1860
cugacaggau ucaguuucua accgaagggc cccuguuuug auucccaaau aucccaugca 1920
uuucugaagc caaauaggag aagagaagaa gcagcuuccu uuucccguug gcagaagcuu 1980
cuccagcccu agcucuaugg ucaucccucc acuccuugaa ggauacucag uaauugcuuu 2040
uuuucuugca g 2051

<210> SEQ ID NO 50
<211> LENGTH: 3448
<212> TYPE: RNA
<213> ORGANISM: Homo sapiens

<400> SEQUENCE: 50
gugaaaaaug uuuuguugug gccacauagg agucugguua auuacaagcc uguuucauga 60
gagugcauuc ucuuggagau gagaaacuga agcgugcuau ucauucauuc auuccaacaa 120
auguuuacua ugugucuacu gugugccaag uacuguucua gaaaccagga guauagcagu 180
gaacaagaca gacaaaaaaa aaucccccacu cucauaucua acaaaauguu guaugcauuu 240
auccucugac ucagcaauca cacgucuaag aguuuauccu gaagaugcau cuccccacagu 300 gcaaaaugaa uauguauaag gugauccauu gcauuuguaa uugcaaaaug cuggaaguua 360
ccuaaauguu uagucauugu agauuggcug aauaauuuau gguacagaca cacaauaaag 420
ucuuacgcaa cuauaaaaaa gaagaagaaa agucucagua aacugauaug gagauauuuc 480
caguaaauac uguuaaauga uaaaaagcaa aguggaaaac agaacauaga gaacgcuacu 540
uuguauguaa gaaagaagga aaaacaagaa aguaaacgua ugucugcuua ccuuugcaaa 600
uagaacguag aaaggauaaa ccagaaaaca augaauuugg ugaucaacaa gaagaaaaug 660
ggaagaaaga aaaaugggag gaaacaguac uucuggggau auauuuuugu auaguuuuaa 720
uuuuuggaag cauguuaaug uuccacauau ucaaaaaaaa ucaguaagaa ugggaaguag 780
gcaaaaauga aaacaaaaag aaaaccuaac acugacagca aacuaaauaa aguaacccaa 840
uuuuauuuca aauaaauauc auaaucuugc aaaagggggga uagagcuaac acaaacaacu 900
gcugaacaca guguuugacu cuauauccuc auucuugggc agggugggagc gggggagaag 960 aacuacaaau aauuucugag uucuuuuuag uuuguuuuuu auaguggaau aggcaaagug 1020
auucugaaaa uuuuagaugu guuacaggau uaaauaaauu aauaaauguu uugauguuau 1080
ugggacccag aauucucacc guggaagaag ggacuuacaa auauggaaaa gggaaaagca 1140
agaaagaacu gugaggucau ggauaggaac cggagguagc acugggaauu caggaauauu 1200
uauaugcuug uguuuguggg ugcaugcaga uguguucaug uuucaugcac auaggcaugu 1260
auauauagac auauauuugc augugugauu cugucuuccg aaaggcucaa gaagcaaaaa 1320
caccccagua gccaugagca cacuuagcac ucaggcuuuu gucuuaauaa cauuccccac 1380
uaaaaguaac ccugauuccu ccaauaaaug auaaguucca gggcuggaau ggcauaggua 1440
uaaaaugaac cuggaauauc uuaugccaga aaguaaggaa gugcuuuuaa aaaaaaaaua 1500
aggggcuggg cauggugggcu cacaccugua aucgcagcac uuugggaggc caagguagga 1560
agaucgcuug agcccaggag uuccagauua gccugugcaa cauagggaga cccugucucu 1620
acaaaaaauu agcaaacaaa uuagcugggc cuggugggugc acgccuauag ucccagcuac 1680
ucagguggcu gaggugggag gaaugcuuga gcccaggagg uugaggcugc agugagcugu 1740
gaucaagcca cugcucucca gccugggaaa cagagcaaga cucugucucu uaaaauaaua 1800 auaaauauaau uuuaaagaaa uaaaaguaac ucuguacaga uugcuuauug guuacauggg 1860
agaaacauaa uaauuuuaca auggagaaau uagacagcac cuuaacuggg ugaucaaaau 1920
uaaccauaag gggcagaugg acaucucaug ccccgagaug ugauacccug ugaaggacac 1980
aauuucacuu auguagaauc cagauuggag auauguaacc ugaaucuuau caugaggaaa 2040
caucugacaa gcuccaaaga aggaauauuc cuuaaaaaaa aaaaaaggag acuguauucu 2100
ucaaaaacau aagagucaua aaagacaaag aaagagcuau ggaaauaucu cugaucgcag 2160
gaggcuaaac aggcauaaug acugaauagc agacaauaga cuacaucuug ugcagaagag 2220
aaaaaaaaug auagaaggau auuauuggac caacugacaa aacugaacua ugaacaguag 2280
auuagguaaa uguaucauaa cauuaaguuu acugacauug auaauguacu gugguuaugu 2340
aagagaagau cucuauucuu aggaaauaug cccugaagua uuuaggagug aagggcugug 2400
augaguaauu uacccucaaa ugggucacaa aaaauugugu gugagagaga gaaggguuuu 2460
auuaguuaau aauucuauga acuauuuuua uuccuauaug uuugugugag uuugaaacua 2520
uuuccaaaua aaaaguuaaa aauggagauu acauucuagu gggagggaua gacgaucugu 2580
agauaaauag guaaaauauc caguacauua gagagugaaa aguccucagg gaaaaguaac 2640
gcagggagga acugcugggg caggguuugc auuuugaggu aggguggccc agggagagcc 2700
ugcagaggag agaaccugaa ugaagaacua gaggugagag aaggagccac gugcacaccu 2760
agggaggaac auuccaggca cgggggacua guauagaagg cagaagcaug gugagcuugu 2820
cuccaguggc uucccuagau ccccuccugc gcaugugcac acacaccugg ugucucuguc 2880
aucguucccu cacagcacug ucacgaucug ccaguauucu guuuauuuug acugccaccu 2940
ccccgcaguc ugaggauagc agcaauggcu guguucacau uguucuccag ugccugguuc 3000
agugccuggc guauggucag ugcuccauag guaugugucg gaugcacaag gcuuugggug 3060
uaacccucuu gacggguggg aucaacaggu cugggacuca ccaucuucuc aaacagagcc 3120
uuccuccucc acugcuagcc augguccagg acgcugggcg agacccacug ucuugcucuu 3180
uguaaggcug aaguccauuu cccaggcggc uacacccaac agaugcugag caggcugggc 3240
cacccuggga uccaagacac agagagaaag agccccuguc uggcgccuga agcacaugcc 3300
agaggacagg agccagcagg agccuguuuc agccuagcug gggauuucau ucuggaggcg 3360
ugagaucugg gagcccaagg cuuugaacug ggggagguuu ggggguguug cuugucuucu 3420
ccaaauggca uuucuuucuc uucccuag 3448

<210> SEQ ID NO 51
<211> LENGTH: 752
<212> TYPE: RNA
<213> ORGANISM: Homo sapiens

<400> SEQUENCE: 51
guaacugcgg gcuugggccg caccaagggc uuaaaccaag ugcugggucu cuuggguugg 60
ggaaauaggu ucugggucgg cagauuuaga aacugcagca guuuggcuuu agucuggacu 120
guuuccugug uugcucauuu ugagcgauca gcccaguguu ugguucacac agcuccggag 180
aaaaacaagu cacggcacag ccuugacuug ggacugcgca cauccugcgu ucccaggaug 240
ucuccugugg ggccaucggc ucacagccgg gaaguucagc ccacucugcg gccugucggu 300 gucuggucc cauacaggag cacugagcug ggucaaaggc uccugagcug agccaggcca 360
ggccugaggc caugcccacg cagcccaagg aucaugaggg cacaggacau agcgggaacc 420
aaggaaguga ccugagugac cucccugccu ucugacaaau guauuugcag gauuuucuuu 480
uuuugaggag aauucuguca uugccuuaau ccacuuuaau ccccucgugg gcugaaaugg 540
gcccaggaug gacgccacgc uucuuuacuc uuggauccac cuccugccuu cccuacccua 600
caccagggua ccccugucuu gcucaaguga ggggagugac ugugugcgcc uucugucagc 660
ucauccucca caggggagcc agcccagggg gaagcaguaa ucagaagggc cagcucccag 720
ccugugcccc caaccuucuc uccaccccc ag 752

<210> SEQ ID NO 52
<211> LENGTH: 73
<212> TYPE: RNA
<213> ORGANISM: Homo sapiens

<400> SEQUENCE: 52
gcaagagauu cccagggcug gggaaggugg gugggaaucc ucuccugcuc accuccucuc 60
uccugcccca cag 73

<210> SEQ ID NO 53
<211> LENGTH: 2725
<212> TYPE: RNA
<213> ORGANISM: Homo sapiens

<400> SEQUENCE: 53
guaagcagau gguggggcgu gccccuuguu gccuucugug gauccaccug gauccugugu 60
ucuccauuga cacuuggaag aguccugcug cuccgucauc cccuggggca gaggcaggug 120
guggcugggc cucauucucc agcagcagau ggagaaggcc aucaugcuga uaagaaacuc 180
cucuauauug gccuaauuuc cuguggucga agacucgccc aagucucugg auggggcauc 240
ugaucaggau gcaugcagag ccuggcuggg augagggagg gcugcuacca cugccucaau 300
auuucaccac uuaucucaac agauccggga ccuguggccu auuuacuaag aguccacucc 360
aauguaggaa ugguuaggag accaacugac uugaggaccc aucuuuguuu uuagaauauu 420
guaugcuuuu gaguuugaaa aaagaccaua uguuauauga caaaccaaca auggcaguaa 480
ucuugaauag gauuauccuu auccuguacc cacacauugu aaacuauugu agauaauucc 540
uuauuauuaa gaguuugcau gccaaagcua acaguuuaag auuaucagca uauugccgug 600
cucauucacg uucugauaug cuuuauaacc uagaaaagag cagaguuaca auuacucauu 660
uauuuaacaa acacuuauua agagcucaga auauaaguca cuaagcuggu uggugggagg 720
aacagcacau aacccaccuu aucuaugcug aggugcauaa uccugaugca cccacaggag 780
gguguuacac agaagauguc auccuuucau augugucaga gcagauaaau aauugagaga 840
aaggucuaau agauuagcug cuuguggcaa guggacguuu gacccaugau uuauugagca 900
acuacaacuu ggacacugca uagauaucua uagaaauagc agcaugucag gucaccagac 960
cugugucagc aacuuccugu guccaacugc uggagaaagg gaagucuccu auuccuuucc 1020
cuccagcucc uuaauaucuc caugauagag ggggugagag gggaguguuc ccugugugga 1080
gggaugguga guuuucugga gcugaaaggu aaacagccuu ucuccucugc aucuuacugc 1140
agaggagaac agcccuagac uguggaggaa gcuuuggagu caguuaugac ugacacagga 1200
uaccagggca uaggguacug acacccgcua gccgugcaca cacucucugg uggaccauca 1260
cucauccaag agaggguaac cagccauccu gcugaaggag aaagaaagca ccaauggccc 1320
aagcccuagc agcuccauug uuucaggaag cuuccucagg gaagugcugc cuucccgagc 1380
cuuugcuccc accuggccca ucagcccuua ccaccacuca guaugcacug guccacgugu 1440
cuuuaugggc agucuuggga ucccacacu gggcuaaaac uaccuuugac ggccaggugc 1500
aguggcuuac accuguaauc cuaucacuuu gggaagcuga ggcaggugga ucacuugagg 1560
ucaggaguuc gagaccagcc uggccaacac ggugaaaccc ugucucuacu aaaaauacaa 1620
aaauuagaug ggcauggugg uaugcaccug uaaucccacc uacucgggaa acugaggcac 1680
aagaauugcu ugaacucaga aggcagaggu ugcagugaau cgagaucaca ccacugcacu 1740
ccagccuggg ugaaacagca agacucuguc ucaaaaaaua aaauaggcug ggcguggugg 1800
cucaugccug uaaucccagc acuuugggag gccaaggcgg gcggaucacu ugaggucagg 1860
aguuuaagac cagccuggcc aacauaguga aacccugucu cuacuaaaaa uacaaaaaaa 1920
aaaaaaaaaa uuagccgagu gugguggcag gugccuguag uuccagccuc ucaggagacu 1980
gaggcaggag aauugcuuga acccaggagg cggagguugc agugagccaa gaucaugcca 2040
cuguacucca gccugggcaa cggugagacu gucucaaaua aaauaaaaua aaauaaaaua 2100
aaauaaaaua aaauaaaaua aauaaaauaa aauaaaauaa acuaccuuug acuucagcaa 2160
guacgauuau cccacauuac caugcagaca uuugaucucu aaaaacuggu aucaaaugau 2220
uucuccaggg acuaccaugg uuuuucucuc cuaguuuuca guauguacac aggucuaugg 2280
uaugggccuu uaaucccag uauuucuuuu uuuguuguuc uuguuugggu uuguuucuug 2340
uuuuucgguu uuuuugagac agggucucac ucugucaccc aggcuggagu gcaguggcau 2400
gaucauggcu cacuguagcc uugaccuccu augcucaagu gauccucccg ccucagccuc 2460
ccaaguagcu gggaccacag gcaugugcca ccaugcccug cuaauuuucg uagagacagg 2520
gucuuucuug uugcccaggc uuaucuuaca uuccugagcu caagugaucc ucccaccucu 2580
accucccaaa uugcugggau uucaggugug agccaccaag cugagcuuaa uccccaaaau 2640
uucugaugag ucuacuccuu auuuugggau uaccuuaggc ccaaccacua acagaggccu 2700
guccugcacu gugugcaucc ccuag 2725

<210> SEQ ID NO 54
<211> LENGTH: 1665
<212> TYPE: RNA
<213> ORGANISM: Homo sapiens

<400> SEQUENCE: 54
gcaaguuggc ccuggggcac cgagagcuga gcaaagacug guccagaaca cccagugugg 60
guuggaauug ccauaagagg gaggcauaac auucccgauu uuuaacaaac ucuugcccuc 120
uguuuauugg gguaaaagcu gauauaucag aaauuguuuu cuaacaauau uuuuuaguca 180
ucaggaaacu ucauugauuc uuuuuuuuac auuuuccuuc ccugugaugc uauggugugu 240
uauuucauuc uugcucguuu gugguggugg uuuuuccuuc aaaucagcuu uauugaugug 300
uaauuaacau acgaugaaac acagguucuu ugggaggcca aggcaggagg aucacuugag 360
cccaggaguu uaagacaggc ccauguaaca aagugagacu uugucucuac agaaaaaaaa 420
aaaaaaaauc agaaaauuag ccaggcgugg uggugcaugc cuguggcccc aucuacaugg 480
gagguugagg aaggaagauu gcuggagccc aggaggucaa ggcugcaaug agcuguguuc 540
auaccacugc acucuagucu gggugacaga gcaagccccu gucucaaaaa agcaaaacaa 600
aacaaaaaca ccuauuuuaa auguacaguu uagugaguuu ugauaaacgu gcauuccaug 660
ugugguuuuu aaaaauguaa ucacauuuuu uauugcggua aaauauaaua acauaaaauu 720
gaccaugcca accauguuua agugcacagu gcaguggcac uaaguacauu uacauuguug 780
ugcaaccguu accaccaucc ccgauagaac ucuuucaucu ugcuucagug aaaaucugug 840
cccauuaaac acuaacucac cacuuacugc cccccucgcc cuuggcaacu acuguucuac 900
uuucugucuc uaaggcucug acuacuauag auaccucaua uaaguggaau cauacagugu 960
uuguccuuuu gugucuggcu uauuaugcga ggacuuagca uaauguccuc aagguucauc 1020
cguguuguau caugugccag aauuuccuuc cuuuuucagg ccgaauaaua uuccuuugua 1080
cguauaugug cuacauuuug uucauccauc uauucauuca uugauagaca uuuggguugu 1140
uucuggguuu uguguuuuua uauauguuuu uuuuaaaaua aacaucuuua gagacaguuc 1200
aguaaagcag uggaaacagg gaagucucca uuuaaccccu gaggaucugg cucaccugca 1260
ccuucucauc agcauuaagc agagggaggc acgagcagga gccaccugca cacucaauga 1320
ggagcugaac agggaucaau uaccuuuuuu uuuaguuauu aggaugcugc uagcugagaa 1380
ucugccuugc cuugauuacc ccaaugucug gugcccaagu cccuugaguc cuccagcagg 1440
aacuccugug gcaucacuca ggagucuagu cuaagaagcu agcucugacc agggcagugg 1500
uggccaggcu ucugugagug ggccagccuc ccccggguag gacacaagcc auaccagcag 1560
ggcuguaugu gaacugugga aaauagagag caaagugggu aggugggugu agggugcugu 1620
uuuccuggaa auaucuaccu aaucucgcuc uucucuuacc ucuag 1665

<210> SEQ ID NO 55
<211> LENGTH: 2866
<212> TYPE: RNA
<213> ORGANISM: Homo sapiens

<400> SEQUENCE: 55
guaccccugc ugcuuaugca guccacagcu ugaggcaguu ccuuggcuca gagcccagcu 60
gguucacugg gcuugaguug cuccaaggcu cagauaugcc uccuacagag agccccaccc 120
acaccacggu cccuaccaag uccccaccac auccucauca cauccuugcu aagucccugc 180
cacugugugu ucugugcuga agaacuuuuc auucaguagu uguaggggguu ccuauuguaa 240 ucaggaaacc aucuggauag caugggagag cauuuuugaa aagaacuuuc ccauguuuuu 300
gcuuacagca aaaaagcuug gauuugggga auaaggagca gagaagguaa uagagaauau 360
uagaauguuu ugggugcuug acaucuaugu cuggacaugu guuugaguuu caagggaagg 420
gacuuaacug gcacaucauu ucagugucag acacauuugg uuagaucaag gaauagcauc 480
uguuguagga agagggcucu uuguucuuua uaaaaauuac aagaagaugg agaaagaagc 540
aauaggaggu augucuccug gcuugugaua acucuuggaa uaggugcuug uagguuccug 600
cccuggcaca gugccccaug uaaggagcac accacccaag aaggagagag cuagagcaag 660
uacuggagga ggcaccagca ucccaaugcc uuggcuuaag ccugggauug uagagggaug 720
aauuagccac ucucuucuga cuuaccugga gaguaaauca aaucaaauca agaagcaagg 780
auaugcaaaa accuuauuuc cccauaaagu uuuuauucug cccaguuucu ggauugcaag 840
aaaaaccaaa uacagcuaau gauugaaaca cugcugucua aagcagugcu ugugaugaau 900
uuuuucccuu ccucuugacc agcagagacc uaauggcuac uuggcaaaac ugacuuuguc 960
uucccacccc uuaccugcca gagggcccag aaaugccuaa ggcuccuuua guuacagaaa 1020
guuugcuuuu acugagaucu uccagccacu gauucccauu uauagaucug gugauugcug 1080
uugacaucag uugaaaauua uuuuuaaaaa ccacuugcag uugcaaaucc uuuuuauaac 1140
ucuguaacuc agaauauaga auuggguagc aaaauuguuu cccagaauua ccaauggucu 1200
ccccaccccu gccuggcaug uucccucuua aaggacuaau cccaccacau caccucuggg 1260
ccaggcagaa caucaggggu gcugauguuc ugugaucuac agcaguuaau uccaaacuuu 1320
ucucccuuau uggaugagau cauuuuucua uuguguuuuu uacauuuuug uucacaaaga 1380
uuagaaaacc ugcaacacac uuauuggcau auuuuucuga uaauuuucau ccaaaaccua 1440
auucugacuu uacaacauac uaucuuuaca aagguuugca aaaauucuuu cauauagcau 1500

```
uguauauguc ugucaugaaa uaauaguaag uauauuauug uuuacauuau accacuucaa   1560

aauaauuucc uuuaaaguau ucuucaaaca agaaaaaggc aauuucucuc aagaaguuuu   1620

agagagaauu uacaacuugc ucccuaagcaa auguggagaac uucaggaggu ucaucuggcc   1680

auuggcuuua caacuccaaa uugugagcca ggaccacaca gauauuucuc uagaaaucag   1740

cguuugcuua ccaagaacau uuuuacucuc caaaggacuc cauccuggaa aacauguuuu   1800

gggauaaggu cuuaugcaau cuuauacucu guuauuaaaa ccagugaggg ucaaggugu u   1860

aauagauuaa guagugacag augaucagac aacuuagaaa cauccuaaau agguuaauaa   1920

uuaugugacc aucgcaugug cauucccaaa uuaggaacaa cucagaucaa uuucuaaucc   1980

uuauucuuac acuguuccag uucccccaua uaacucguau cuuuguguua guuucagaag   2040

uuucugaagu acccucagcc uugaugggga uccucgcacc accucaaauc cuguucucag   2100

cccuaagaac uguguuaguc auccucuuaa gaggaugugu gauuuuaaau cagauaaugg   2160

gauaaaccac auuucgucua gacuggucag gccuuugucc aguccccucc ucgcccacac   2220

uaccccagcu ccacagcggg cauugguuca ggaauucaac ccacacuuua uaacuggaga   2280

caguaucucu ccaguuaaaa aggucaccuu gguguccgcu ucucaaggaa cauggacauc   2340

uuuauuaauc aaagcccaag cuuugaucug gagccuaaua uccugcacuc cagcucucau   2400

cucuccccuc ccccagucac acuuucaugc uucccagagc caccccuaca ggaagugguc   2460

aagggaauuc uauaccucag ggcugaccua aauuaggauu ucuuggcuuu uaagauaaug   2520

guaacuuucu uaagcuaaaa aagccccaaa agacccugua agagcccuug gaaacagcac   2580

caugggugua gcuucccccc aggauguaag cauguaugca cacaucucgu augugugucu   2640

uuguaacaaa ugccuggauc uuaguaccag ggagaccuga uucauagauu ucauagagaa   2700

ggagagaaag auggcccaua accuggguga ucugacagaa ucacagugcc cucagcugag   2760

ugcccuucag aaauugauug acaacuguuu agcuuuugaa aucuaaaagu aguacagcau   2820

cucagaaaac caagaugacg cgaguccaug ugaucuccuu ccacag                     2866
```

```
<210> SEQ ID NO 56
<211> LENGTH: 738
<212> TYPE: PRT
<213> ORGANISM: Artificial Sequence
<220> FEATURE:
<223> OTHER INFORMATION: Synthetic Construct

<400> SEQUENCE: 56

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540
```

```
Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 57
<211> LENGTH: 4393
<212> TYPE: DNA
<213> ORGANISM: Artificial Sequence
<220> FEATURE:
<223> OTHER INFORMATION: Synthetic Construct

<400> SEQUENCE: 57

```
cagagaggga gtggccaact ccatcactag gggtagcgcg aagcgcctcc cacgctgccg     60

cgtcagcgct gacgtaaatt acgtcatagg ggagtggtcc tgtattagct gtcacgtgag    120

tgcttttgcg gcattttgcg acaccacgtg gccatttgag gtatatatgg ccgagtgagc    180

gagcaggatc tccattttga ccgcgaaatt tgaacgagca gcagccatgc cgggcttcta    240

cgagatcgtg atcaaggtgc cgagcgacct ggacgagcac ctgccgggca tttctgactc    300

gtttgtgaac tgggtggccg agaaggaatg ggagctgccc ccggattctg acatggatcg    360

gaatctgatc gagcaggcac ccctgaccgt ggccgagaag ctgcagcgcg acttcctggt    420

ccaatggcgc cgcgtgagta aggccccgga ggccctcttc tttgttcagt tcgagaaggg    480

cgagagctac tttcacctgc acgttctggt cgagaccacg gggtcaagt ccatggtgct     540

aggccgcttc ctgagtcaga ttcgggaaaa gcttggtcca gaccatctac ccgcggggtc    600

gagccccacc ttgcccaact ggttcgcggt gaccaaagac gcggtaatgg cgccggcggg    660

ggggaacaag gtggtggacg agtgctacat ccccaactac ctcctgccca agactcagcc    720

cgagctgcag tgggcgtgga ctaacatgga ggagtatata agcgcgtgct tgaacctggc    780

cgagcgcaaa cggctcgtgg cgcagcacct gacccacgtc agccagacgc aggagcagaa    840

caaggagaat ctgaacccca attctgacgc gcccgtgatc aggtcaaaaa cctccgcgcg    900

ctatatggag ctggtcgggt ggctggtgga ccggggcatc acctccgaga agcagtggat    960
```

-continued

```
ccaggaggac caggcctcgt acatctcctt caacgccgcc tccaactcgc ggtcccagat   1020
caaggccgcg ctggacaatg ccggcaagat catggcgctg accaaatccg cgcccgacta   1080
cctggtgggg ccctcgctgc ccgcggacat tacccagaac cgcatctacc gcatcctcgc   1140
tctcaacggc tacgaccctg cctacgccgg ctccgtcttt ctcggctggg ctcagaaaaa   1200
gttcgggaaa cgcaacacca tctggctgtt tggacccgcc accaccggca agaccaacat   1260
tgcggaagcc atcgcccacg ccgtgccctt ctacggctgc gtcaactgga ccaatgagaa   1320
ctttcccttc aatgattgcg tcgacaagat ggtgatctgg tgggaggagg gcaagatgac   1380
ggccaaggtc gtggagtccg ccaaggccat tctcggcggc agcaaggtgc gcgtggacca   1440
aaagtgcaag tcgtccgccc agatcgaccc cacccccgtg atcgtcacct ccaacaccaa   1500
catgtgcgcc gtgattgacg ggaacagcac caccttcgag caccagcagc ctctccagga   1560
ccggatgttt aagttcgaac tcacccgccg tctggagcac gactttggca aggtgacaaa   1620
gcaggaagtc aaagagttct tccgctgggc cagtgatcac gtgaccgagg tggcgcatga   1680
gttttacgtc agaaagggcg gagccagcaa aagacccgcc cccgatgacg cggataaaag   1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gacccttcaa cggactcgac aagggggagc ccgtcaacgc ggcggacgca gcggccctcg   2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
cagactcctc tacgggcatc ggcaagaaag gccaacagcc cgccagaaaa agactcaatt   2640
ttggtcagac tggcgactca gagtcagttc cagaccctca acctctcgga gaacctccag   2700
cagcgccctc tggtgtggga cctaatacaa tggctgcagg cggtggcgca ccaatggcag   2760
acaataacga aggcgccgac ggagtgggta gttcctcggg aaattggcat tgcgattcca   2820
catggctggg cgacagagtc atcaccacca gcacccgaac ctgggccctg cccacctaca   2880
acaaccacct ctacaagcaa atctccaacg ggacatcggg aggagccacc aacgacaaca   2940
cctacttcgg ctacagcacc ccctgggggt attttgactt taacagattc cactgccact   3000
tttcaccacg tgactggcag cgactcatca acaacaactg gggattccgg cccaagagac   3060
tcagcttcaa gctcttcaac atccaggtca aggaggtcac gcagaatgaa ggcaccaaga   3120
ccatcgccaa taacctcacc agcaccatcc aggtgtttac ggactcggag taccagctgc   3180
cgtacgttct cggctctgcc caccagggct gcctgcctcc gttcccggcg gacgtgttca   3240
tgattcccca gtacggctac ctaacactca acaacggtag tcaggccgtg ggacgctcct   3300
```

-continued

```
ccttctactg cctggaatac tttccttcgc agatgctgag aaccggcaac aacttccagt   3360

ttacttacac cttcgaggac gtgcctttcc acagcagcta cgcccacagc cagagcttgg   3420

accggctgat gaatcctctg attgaccagt acctgtacta cttgtctcgg actcaaacaa   3480

caggaggcac ggcaaatacg cagactctgg gcttcagcca aggtgggcct aatacaatgg   3540

ccaatcaggc aaagaactgg ctgccaggac cctgttaccg ccaacaacgc gtctcaacga   3600

caaccgggca aaacaacaat agcaactttg cctggactgc tgggaccaaa taccatctga   3660

atggaagaaa ttcattggct aatcctggca tcgctatggc aacacacaaa gacgacgagg   3720

agcgtttttt tcccagtaac gggatcctga tttttggcaa acaaaatgct gccagagaca   3780

atgcggatta cagcgatgtc atgctcacca gcgaggaaga aatcaaaacc actaaccctg   3840

tggctacaga ggaatacggt atcgtggcag ataacttgca gcagcaaaac acggctcctc   3900

aaattggaac tgtcaacagc caggggggcct tacccggtat ggtctggcag aaccgggacg  3960

tgtacctgca gggtcccatc tggccaaga ttcctcacac ggacggcaac ttccacccgt   4020

ctccgctgat gggcggcttt ggcctgaaac atcctccgcc tcagatcctg atcaagaaca   4080

cgcctgtacc tgcggatcct ccgaccacct tcaaccagtc aaagctgaac tctttcatca   4140

cgcaatacag caccggacag gtcagcgtgg aaattgaatg ggagctgcag aaggaaaaca   4200

gcaagcgctg gaaccccgag atccagtaca cctccaacta ctacaaatct acaagtgtgg   4260

actttgctgt taatacagaa ggcgtgtact ctgaaccccg ccccattggc acccgttacc   4320

tcacccgtaa tctgtaattg cctgttaatc aataaaccgg ttgattcgtt tcagttgaac   4380

tttggtctct gcg                                                      4393
```

<210> SEQ ID NO 58
<211> LENGTH: 738
<212> TYPE: PRT
<213> ORGANISM: Artificial Sequence
<220> FEATURE:
<223> OTHER INFORMATION: Synthetic Construct

<400> SEQUENCE: 58

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
```

```
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Pro Glu Arg Thr Ala Met
            580                 585                 590
```

```
Ser Leu Pro Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 59
<211> LENGTH: 2214
<212> TYPE: DNA
<213> ORGANISM: Artificial Sequence
<220> FEATURE:
<223> OTHER INFORMATION: Synthetic Construct

<400> SEQUENCE: 59

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacatcggg aggagccacc aacgacaaca cctacttcgg ctacagcacc    840

ccctgggggt attttgactt taacagattc cactgccact tttcaccacg tgactggcag    900

cgactcatca acaacaactg gggattccgg cccaagagac tcagcttcaa gctcttcaac    960

atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200
```

```
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgtttttt tcccagtaac   1620
gggatcctga tttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgcc tgagcggacg gcgatgagtc ttccgggaac tgtcaacagc   1800
caggggggcct tacccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctg         2214
```

<210> SEQ ID NO 60
<211> LENGTH: 565
<212> TYPE: RNA
<213> ORGANISM: Homo sapiens

<400> SEQUENCE: 60

```
gugggguggau ccuuguaagc aggauuagcg agucacucca cgcucagguu cuuuagccug     60
agggcccgug ugccacagca uagcuacccc gcccuuccag ccucgggucc cuaauacugc    120
cuugcuucgg uuccaguuuc cgccgcacaa cuucacucau uccaaauguu aauuucugcg    180
uuuuuuuuca gccccaauuc uguuucucca aaucagggau gauugucggc cuuccacaga    240
cccucgcgcu ugccaggauu agggguuucg cgcgcauugu ggguaggggu guggaggaag    300
ggauccagaa aucuuaagua uuaacuuaga uuaguguuag caaggaagcc gucacauuuu    360
auuuagccgg gacacucuga caguuugugc cgacugcuau uuuugaucaa ggcuauuuug    420
cccacuuguc uauuuugugg cccaauuguc uguuuugcua acaucagaaa guuauaauga    480
aauaaucugc aaaaaaugua aggugcuaga aaaccaauaa uacuguguac cuugaaaaug    540
cuaauauaca ccuguuuugu uacag                                         565
```

<210> SEQ ID NO 61
<211> LENGTH: 172
<212> TYPE: RNA
<213> ORGANISM: Homo sapiens

<400> SEQUENCE: 61

```
gugcuuaauu ggucaauaau aauagauaua uacauuaacu uaugauuaau uuauuaauaa     60
aauaugaauu uauuuuuuuc agggacaacu auaauuguca caaucuggaa guguucuuau    120
auuuugcuug aagguuauaa aauauaaaac aguugcuuuu cuguuuacuu ag           172
```

<210> SEQ ID NO 62

<211> LENGTH: 1391
<212> TYPE: RNA
<213> ORGANISM: Homo sapiens

<400> SEQUENCE: 62
guuuguaugu aguagguuuu aacuauaggu uuggcuauua guggaacuau aaaaaucugu 60
ucuuauauaa gguaaucuuu gugaaaauac cugguaauau cuacaucacc acuaaaaaau 120
gcaauauauu uaaaugugaa uuaaguauuu uaguguauaa aacauugcua guuucuacuu 180
aaaguuucua aaagggugug uaggggaaau agaaugagua uguugaaaag uaacauaagg 240
aaauauaucu ugagguccaa augacaaaug cagacaauga cugcuauagg gauuuguuaa 300
gaggggaaau gauuuaagag augucagaag acuucacaaa ggaucaauac ugaggaguag 360
uguuagauaa guggaaggca augcaguggu aagauaguaa gggaauucua gagcuguugg 420
uuaccauaaa uaaauacuga gaacaggaaa uauguuuauu cuuuauauuu gaggaaacaa 480
ggugcagcaa guuuguagca gacuguagag aaaacaaauc uuggguaagu acuuugagau 540
agguuguuga gggccuuaaa gguguauuuu augcuaucag caauugagaa ggcaguaaag 600
guuuucgaaa cacaauugau agguacaaaa auacaccuua agaaggcaaa acugaguaua 660
uuauguagga caaacugaag gaaauuggag cuuuguagac aucacauuau agcggaguuu 720
aaaccugaaa uuauggauua gaauaauagc aauuggaaca gaaaaaaagu aguggaaaga 780
cauuacaaag ggagauguug cauuacugga uauaagacuu gaggacuuga gguaaaaagg 840
agaaucaaaa auguuucaug cuauuaaaaa ucuagaaauu guagucuuaa guaagaaaau 900
ugccuggcau gguggcucac gucuguaauc ccagcacuuu gggaggccaa ggcaggagga 960
uugcuugagc cugggaguuc aagacuagcc uggauaauau agugaguccu ugccuguacg 1020
aaaaaauuug ccgagcauga uggcacacca agcaugaugg cacgccaagc augauggcau 1080
gcaccuguag ucccagcuac ucaggagacu gagaugggaa gauugcuuga gcccaggagg 1140
caggagguug cagugagcug agauugugcc acugcacucc agccugggug acaaagugag 1200
gcccuaucuc aaaagcaaaa aaaacaaaaa caaaaaccaa aaacuauuua uucagcaaau 1260
auuuacugaa cgucuccaug ugccagccau ugcuggcacu aaggaucaua acaaauaaaa 1320
cagaauuuuu auuuucagug cuuacauucc aguauaaagg cauauugaaa uaaccuuuuu 1380
uuaauguuua g 1391

<210> SEQ ID NO 63
<211> LENGTH: 303
<212> TYPE: RNA
<213> ORGANISM: Homo sapiens

<400> SEQUENCE: 63
guaagcaccu uggaaaaagu uuauuauggu auuaaauaau gaauuccauu uguucauuaa 60
acuguagaaa auuaaauuau auucuauaaa auauauauau ucaguuuauu uuuaauauau 120
aacauuuaau aauaaauauu ucuagacucc uauuuuaugg aucugccaua uaauacuuuu 180
uguuaccuua uaaucaugau ggacucuuuu aaaagaauua auuuuguuau ugaaauuuau 240
uuaaaaguuu guuuuguggu aacuaaucaa uuaaaacguu uuucuuuuuu uuuaaaaaaa 300
uag 303

<210> SEQ ID NO 64
<211> LENGTH: 2358
<212> TYPE: RNA
<213> ORGANISM: Homo sapiens

<400> SEQUENCE: 64

```
guaugucuuu uuguauuccc uaggauguaa uugucauuaa uuuuauuuug aauuguuuuc      60
aaauuuuaaa auuauuguug gcuggaaaaa uuauaaggau gauuguaauc augguuauuu     120
guuuauucug uauauguucu acaugccuau uaugugccuu auauaguacu aaggacugag     180
cauaugguug ugaacaaaau aagaaguuaa cugcuggaug gagcuuauag ucuugggaaa     240
uauacagaaa gauuacuagu aacugaggug gaggguggu ggggauuuga ggaauaguga     300
cgaaagggug uuauagaagu aauuuuugac aaagcugaag gcuaaaauau gaauguauug     360
uugaagaaca aaauacauug agauuccuga gaagguagga augugauaca aauggaucag     420
ccuuugaaag gaggaauacc cuuuuccuuu guguuaggag aggaggauga guggaugagc     480
gugggaagag uggauguguu uagaggcuuu uauguuugua ggcauaaugc uuggaaguug     540
agggguuggu gaugacaucu ucuguuaaaa agagugggaa augguguggu cacauuuuaa     600
ggaaauuagg uaaaauuuga aauauauugg agacaggacu ggagaguugg ggaucuggag     660
ucagacagau uugaguucua guccugauuc uucuacucgu uaacucucug aacuuggaug     720
accuauuguu uuugauugua uauccagcuc cugggaaaau gccaagcacu uucaauaaau     780
acuaaaugaa uuauggaguu ggaucaguuc uguguuagug uuuagcuagg uagcugcugu     840
agaauagaag gguagcacag uugaagauau ugguaggaaa gugguugaag ugaugauuau     900
gaagucuuaa cugaauagau aaaaucaaga uuggggguugg gugggcagaa ggguagggau     960
auggagggag aagaugaggg guuagagugu ccugugaggu cgaaggacag gcauaguggg    1020
aauaauugaa agaauguucu gguuggacaa ggaucugaug ugggugugg agugagagac    1080
uauagugaau ucaagaaaaa aauagacuag aacaaaaguu auguggagau ugcuuagugg    1140
gcauuugaua gacaucugug ggccacaugc uuaaauuccc agugcauuuu gcggaguuac    1200
uggaagguug guggcuuguu ucuaccauga guagguaaag auggagagca ggauauuuug    1260
ugagaaagca gcugaaguuu cuauaggaug auggaggaau gauaggaaug aucaccugaa    1320
guugcagggu gggguaaacc uagaagcacc aacaccuucu ucugacccuc auguauuugg    1380
aaucugaaag aaugagcacc uuccaauuga aagaguucca agggcauuag uauacuaaag    1440
gauccaaauu gcagcuaagc caaggagaug gaaaggagga uucaguaaag aaucugagga    1500
ugugaaauau uaauuuaucu uggaagagaa uuuuagagag cacaauggaa ugcuuuuugg    1560
aggagagaaa gaguaagaac aauuugguua agguagagga auaacagaac uauaaggua     1620
agaaaugaau gugagacaca uuagaugacc aaaugauuug auguucuugg ccaugaccug    1680
aauuaacaag acugugaggu aaaauggauu uaaucggcua caaaucuuaa gauaaccaaa    1740
accugagcug uuuaauaugg uagcacuagc acuaaccacu uguagcuauu uauauuuaca    1800
uugguuaaaa uuaaaaugaa aaauuuaguu cuucaguugc acuagccaca cuucaaaugc    1860
ccgaacauag cuacauguag cgaguggcua uugaacugga cagcacugac agcaugucca    1920
uuaugcuaga aaguccuaug ggacagcacu ggucuaaaca gugcauggua ugagagaaag    1980
ggcagguuaa ggcacucagc uucacugacu gggguggaga uucugauggu uuguacucag    2040
guuccagauc ccugaggcuc aggaaccuuu gcaguuuagu cugguuaccu guggcccagu    2100
gguuacaaca gaaugauuaa cagucaauuc uuugcaucuc uggguggcuc aggaaaaauu    2160
uaaggaguua uuagcuguga acuaaccuua aguaaguuaa auuaaaaaaa aaaaaguucu    2220
uaagcuaaua ugauuuuaaa uaucugcacu gaaguauaau gcaaauuuaa auucagcaua    2280
```

auuauuugcu uguuguugac ucauuugaac cucaaaauau aaugggauua auuuauacuu 2340
uggguuuauu acuuuaag 2358

<210> SEQ ID NO 65
<211> LENGTH: 5424
<212> TYPE: RNA
<213> ORGANISM: Homo sapiens

<400> SEQUENCE: 65
guaaagcacu uuuuuuuucc augaaucuuc acuguucaag uuaccuggcu uuuuauuauu 60
auugguaaca auaucaauuu uuauauugua uguuauauuu gaaaaaugau guacacuuau 120
cucuaagguu uuauaucacu guucauuuug ucaucaccaa uuuuaaaaua uaaugguacu 180
ucuagugaau augacuugaa gauuaauucu uuauauuugg aaguacauuu uucucaggac 240
aucaaacuug uuaccuaaaa uuaaugcuuu ugucuggaag auugguauca aguaacuaau 300
agauuuucau aaagaaguga ucuuucuagu gccauaguuu auuuugggua aaaguuauau 360
uuguucauuu caaguauuu auaugauuag uagauucgca aaugaaucuu ucgauauauu 420
caauaauggu uaauuaaaua ucuuguuuuu gguuguaccu uauuuuaugu gagauauaua 480
uauauaugua uaguuuuuga aaaguugugu ucaugucagc aguuuauaaa ucacauauuu 540
aaaauaacau uuuuaaugca uaguuuuuau uaccucguua uuccuuguua uaaacuaaua 600
auucuugcag uguucacuug aauuuaguuu uaggaaaaaa guuuuuugca gaucaacuug 660
uauuuccugg aagaaaauuu ccuauuuuac cucagcuucc uauuuaaugu auuauuuauu 720
uauuuacuua acauuuauuu guuuuuuauu ucaccugaac uguuaguaaa cuuaguaaaa 780
uuuggugccu acauguggua acuguccugu cccuuauacu cagaaacguu uuccaccuuu 840
guguccuuua ggucauuguu guguuauauu ccauuuauuu uauuuugucc auuguucucu 900
cagaaauuga gggucauaca uuuuaagaaa acaaugauau gcuauuuaag agaauguauc 960 auaaaauugau uuguaaggaa aaguaucccc auucuucaug uauguauuuu acucuaaaau 1020
guugaagaau cauauagaag uuagcuauga aaacaaugug guagagaaag uauggaucga 1080
ugccacuuaa auguuaggaa gaagcucuua gagcauuauc uguuuagcua acugcaaaac 1140
auagcagaca uguggauuuu uuaauaguca ucaaggaucu aacuuauaau auacacuggu 1200
agaauugcuu agggggaugu cugugguuuu cuggacuuuu guucuucuau auagaccugu 1260
aucaguugac uuaucauuca uaccacacac ccuuagcuaa ucagaacuac cuuguccauu 1320
uauaucuuag acuauugucu uuuuucauag ucacacacag agaaaacuug aauauauggc 1380
cuguguuccu uuuuggcugc ucaauuccuu gagaugaaau augguaugg guugcuuugg 1440 caauuacuuc uuugccguua accagucauu caguuuuauu gagucuuuac agcauaccag 1500
aggcugcuag uuacuaguga uauaguggc aacuauguuc ugguucucaa gaauauucau 1560
agucaauaau aagcauaaca uagugauaau augauacuua gggagauaca uaaggucaua 1620
uucuggcaua cucuggagag agauaccgua aucagccuug aggugcagga ugugaucugu 1680
aaacugagac cugaaguaua guuagacugg uaagaggaau gaggauauau augguguua 1740 auaaaagaac auucugggua gaagauauag cauuugcuaa gaccuagagg uaagagaugu 1800
uauggaguau uuaggaaacu acaguuauuc auuuugacug aaauauaagu gaaaauagcu 1860
uucauagagu ccuuacuaug ugccaggcac uucauaugca uuaauucauu auugcuuauu 1920
ugauacuugu cauaugagau aguugucauu ucugccauga uacagaugaa gaaauggaga 1980
cacagaaaga guaauugccc augguugcac agcuuauaaa ugguaaaggu aggauuugaa 2040

-continued

```
aacagucuua cucaagaguc ugugcuaucu ugccuuccca guuuuauuuu uuaugauccu   2100
cuggagagau aagcaagggc caguuccuaa ugaauuuggu ucuuuuccug aaaggagcca   2160
gugaagaguu uugagcacag gauaucauga ucagaucuau acuuuaaaag uuuacuguac   2220
uuuguagaga guggauugaa aagggccaag acuaguaagg aaacauuugu guuaauucag   2280
ggaagugcua augauggcau uugccugaga aagacaagug ugagagaagu agauguaauu   2340
ggauguggug aauguaauug guuguuggag gagagggagg auggagaguc ugccuaauuu   2400
ugugggguugg gccacuaaau agguagauag ugccauucau uaaggaggaa cacaagagga   2460
auuuggaaag cuugagauua uuucaguuuu guagauguug aguuugaggu ucuucugggc   2520
auauucaaaa aggguaucug uggauaugga auucacaaga gacccuguac agaugaugag   2580
gauuuaugaa ucaucaaugu agacauuauu gaagccagag aagugauugu aaggcacguc   2640
ucugagaaau gucuaauaaa gcaaugaaau aggaagagug cuucaaggaa aagcucaaga   2700
aaggagaaac agagugugau guuugagaag acaagggaaa aaaacauuaa uagcauuaaa   2760
ugcuuuagca uuaaguucuu ggcuucucuu cuuguaaaaa uuucccaauu cagaacacag   2820
ugggauuauu aacuuucaau ugauaauaau aaugauaggc aaacuucuaa aauuuguauu   2880
guaguuugca uuuuauuaua aacuuucuuu aaauuuuuau uuugaaaaau gucauaucuu   2940
cauaaagauu guaagaaaca cacuguuggu guuaauguaa auuaguucaa ccauuguggg   3000
agacagugug gcaauuccuc gaagaucuag aagcagaaau accacuugac ccagcaaucc   3060
cauuacuggg uauauaccca aaagaauaua aaucauuuuc uuauaaagau acuugcacac   3120
auauguucau ugcagcacua uucacaauag caaagacaug gaaucaaccc aaaugcucau   3180
caaugauaga cuggauaaug aaaaugugga acauauacau cauagaauac uaugcagcca   3240
ucaaaagaga augagagguc aagcguggug acucaugccu acagucccag cacuuuggga   3300
ggccgaggca ggcagaucac uugaggucag gaguucaaga ccagccuggc caguauggug   3360
aaaccccauc ucuacaaaaa caaaacaaaa caaacaaaaa uuaacugguc augguacugu   3420
augccugcag ucccagcuac uugggaggcu gaggcaggag aaugacuuga acccagaagg   3480
cagagguugc agugagcuga gaucgcacca cuggacucua gccuuagcaa caaaacuaga   3540
guuugucuca aaaaaaaaaa aaaaaaaaaa ccggaacaag aucauguccu uugcagggac   3600
augggaugga gguggaagcc auuauccuca gcaaacucac acaggaacag aaaaccaaac   3660
acugcauguu cucacuuaua agugggagcu gaacaaugag aacacaugga cacauggugg   3720
ggaacaacac acacugggac ccgucaaggg gucggggugg gagaacauca ggaagaauag   3780
cuaauggaug cugggcuuaa uaucuagguu augguugau cugugcagca agccaccauu   3840
guacacauuu accuaaguaa caaaccugca caucuuacac auguacccca gaacuuaaaa   3900
guugauggga aaaagaaaaa caauaaccac ccacauaccc uucauauaga uucaccaguu   3960
cuuaauguug ugccaacuuu gcuuuaucuu uuugucagua uuuuuacaca cacauguauu   4020
ucucugucuc uuguuuguuc aaucacauuu uuugcugagu cauuuaagag cuaauugcag   4080
auaugauacu uugcacuuaa auauuucagc uugucuguuu gaaaaagaaa gauguucucc   4140
uacaaugaac acaauauaau ugucaugcuc aggaauuuua auauugauuc aacaccauua   4200
ucuaguccau aaugagauuu cuucuaaugg cccaauaaua uccuucaguc uccccaccuc   4260
caauauccaa aguucuguca aggaucacau acuacauuug guucuuuauu auagacuuuu   4320
uaaauaucgu uguauaccau ugugauucua ucgucuccuu uaauaaagag gagaaccaga   4380
```

-continued

```
aaaaugaaag gucauaagag gaaugagguu uggagaauag gugaaaaaag gcaucauaau   4440

guuuauaaua auguuugccu guucagagaa acaagaauca cagauaaagu cacuuauaug   4500

uagauaagag aaugcuguau uacuuuuugc uauucuauuc acugaucauu uuucuaagaa   4560

cucuguaugc uucuuguuua acucuuaugu cagcauguau gagaaaacug aguuaaagag   4620

auguuaagua acucauucau gcuuuacuag aaauugguug augagggaca uaaaccuagg   4680

ccggugugau uuuagauugc uucuuuuaac cauuguguug uauugccuua uauuucuaag   4740

uaauuuaugu ucacugagag caaauaauag ucuagcuaug acuuagaaaa guaaaauaaa   4800

gauguugggc agaaaaccau uuuauuaggg guuuuuuugg aggagcagau uaauuuguuu   4860

cuguauucuu ugguuaguuu gugugugugu ucuuuuuaau ucuuuaaaau gaaacuguuu   4920

aauccuuaaa uccuuaaguu uugaaaauuu uggccuauua uuuauguguu agguugauau   4980

uaaauccuua auagcuuuaa cauuuucuac uuuguuagag aggauuuaaa auuuaaguag   5040

auaagcugaa uaucuggcuu uauauuaaau uacugcugau ggccaggcac aguggcucau   5100

gucugaaauc cuagcacuuu gggagguuga ggcagaugga ucacuugagg ccaggaguuc   5160

aagaccagcc uggcuaacac agugaaaccc cgucucuacu aaaaauacaa aaauuagcca   5220

guuaugguaa ugcaugccag uaauuccagc uacucgguag gcugaggugg gagaauugcu   5280

ugaaccggga ggcagagguu gcagugagcc gagaucgcac cacuguacuc cagccuaggc   5340

gacaaagacu uugucucaaa aaaaaaaaaa auuacugcug aauuuuaucu ucuucuuauu   5400

uauuuuuuuu uuuuacuauu uuag                                         5424
```

```
<210> SEQ ID NO 66
<211> LENGTH: 599
<212> TYPE: RNA
<213> ORGANISM: Homo sapiens

<400> SEQUENCE: 66

guaaaaaauu uuaguaguug uggugguuca acaaagguac uuauuaaaau aaguaccuaa     60

guuuacauaa auuuauauuu uaaccaggac uggagucuuc uaaguaacug auguuuucag    120

acugauuuua ugguaugacu uugucucagg gaaauagaaa acaaagcaaa augugaggcc    180

auuaaguauu acauucaucu caggucuaug cggguaaauc uuuuuuuguu guuuuauaag    240

ccauucuuug cuaguuuucu aauugaauag augacuggau uucuauucuu auuucucuua    300

cccagaaucc uuuaaaauuu uuuguuacuu guggaaucuu auaaauucug auuaucauuu    360

gguucuacug agccaaauaa uguuuguaca uuguuuauuc ugauagaagu ucuuaaguuu    420

cuaacauaau ugaaauauua uuuguuuugg uagauaauua guauucuuuc uuugguuauu    480

caagauaaua ugcaucauuu ucccaaaauu uuuuuguuuu cuuuaguuuc ugauuauuau    540

uuuuaauuau guauuaccuu ucucauuucu aauuaccguu uuccuguccu uuucuguag     599
```

```
<210> SEQ ID NO 67
<211> LENGTH: 124
<212> TYPE: RNA
<213> ORGANISM: Homo sapiens

<400> SEQUENCE: 67

gugaggcuuu aaguguggug aaaucuuggg aauuuaaaau auguugugag agcacuauuu     60

agaggauaug auuuuguuau ucugaauagu uuuguaauug aauguugugu uugguuaccu    120

ucag                                                                 124
```

<210> SEQ ID NO 68
<211> LENGTH: 391
<212> TYPE: RNA
<213> ORGANISM: Homo sapiens

<400> SEQUENCE: 68
guaaaauggc uagaagucaa uucagagcaa ugguuccuaa aaacuuuaau uucauuacaa 60
uguaaauaua auauuuagcc cuacauguaa auucccuggu auaaaucugu cacuauguac 120
uuguaaaaug ugaaauaaau uacaucuuug aaguugcaac uuuuuagcca uuuuuauauu 180
ugccugucuu ggucauuaag aacaauugag guccuuaugu acuauuuucu ugauucaauu 240
ugauuuaauu ggucaaugcc aauuaguaaa ggucuauaaa gaauucucuu uuuuucuaga 300
ggacacuuau ggcugcguuu aauuuuaauu ugguuuaaau uucaguuuuu uuaaaauuac 360
uuuuuaauua uagugucuuu aacuuuuuua g 391

<210> SEQ ID NO 69
<211> LENGTH: 658
<212> TYPE: RNA
<213> ORGANISM: Homo sapiens

<400> SEQUENCE: 69
guaagaauua cuuuuagaau aacuuauuua uucagacuuc auauuaucuc auuacuauuu 60
auuugacacu agaaaguacu uuuucuagga ugugaauuuu ugucugucuu uuuaauagug 120
uaauaucuug ucauguuggu auauuugucc auauguguuu cuccaaucac cucacaaaca 180
cuaauuuuug caauuuagga uauauaaaug auacuugaau gaauguguag auagcaguca 240
uuaugggguu uucuauaaaa gacuacugaa aauccugugg aucauaacau uucauuuuau 300
cuuaaaauaa auacauuaua aauguauuag aaaccaauac auuguucagu auuuaugugg 360
auuaaauuug uuuaaaaggu agaauaaugu uuaaaaauaa aauuuucuag uaaugaaaga 420
uaauuaugca auuauaagau gcagaaacua uuaaauguca ccuauaauuc caggaugacu 480
ucaaugauaa auacacauau guaauguaau guauccguau guauguguau auaaguauga 540
auacguaugu guguguaugu agauauauuu auauauauaa uguauaugua aauaugcaca 600
gguguaaaua uauguuacau caguuugcaa caacucuuga aauaacuuug ucuuuuag 658

<210> SEQ ID NO 70
<211> LENGTH: 2507
<212> TYPE: RNA
<213> ORGANISM: Homo sapiens

<400> SEQUENCE: 70
guauuuuuuu ucaauugaca uaauaacuuu uucuuuuugu auuuuagauu uaaauuuuag 60
ucuuauuuuu cuuuaaaugu cuuauacugg uuuauaacac guuuauuagg guuuuuaaac 120
auaaguuuau uuuauuuauu gguuagaaaa gcucuagaac uguccuuuuu gaucucuagc 180
uaauuuguua uugaaugacc ucuuucacau caaugaguuu aacuuuaaac uuuuugauag 240
aagucuaacu ccaaaauaua uuuggcaucu aaaauauaua auucgaaaua uaauuuaaau 300
uuuuuuacuu aacucauagu uaccuuauau acauuaguua aauaguugca gguuuaauuu 360
uaguuuuucu aacuaaaugu cagguucauc agugggaaug ggaauaagca aagggaucag 420
aauaacuugg gaagccuuuu caaaauacac uuuucuuccu caccaccacu cuccaaccuu 480
aaccaaauug ucaggccuua ccauauuaga agcugggauu augaugguug uauacuugaa 540
aaacaucaga gauuauucug aaugaauaau ucuaauuuua aaaacuauca cuucuagagu 600

```
cauugcuuuc uaguaugguu cacauaaauc uugugggcag uuuggaacug guuagcaucu    660
agggagcuca gauaaccuau auuuuaaaca aaagcauuag caauggaaau aaggccuaua    720
gaaucaguca ugucuccaua aacuuuauau aaagggccag acagugaaua uuuuagacca    780
ccuggucucu gcuauaacua aacucugcuu auagcaugaa agcagccauu gacaauacgu    840
aaaugaguga gcaagguggu uuuccgguaa aauuuuauuu acaaaagcag augggaggcc    900
agauuugacc uuugggccau agucuaccaa ccccuggaaa aaacaguugu cuuuaccaga    960
uugaauguug gcaggguaaa uggugacaug uuauauguau ucuguacuuu guuuugacuu   1020
aauaccauuu cauaauuauu uuauaucagu acguauagua uugcuguucu uuuuaaaggc   1080
uauguaauuu uucuuuuuau acagguguua auuugauaau uugugaaguu uaugaaguuu   1140
ccaauuuugg gguuguaaac uguuuuaaug aauauccuua uauauguuau uuugcaaaug   1200
uacaaguaua ucuguggaau aaaauugcugc aaguguugua auugucaugu auguugcaaa   1260
uacauucuaa caguuuguca cuuuuuuugc uuuauggcau uuuuugcugu gaaauauuuc   1320
uuuuuaugcu uaguuaaauu uauuauuuuu uaaugacuuu ugacauuugu uauaaugaga   1380
aaggcuucug aguauaaacu uguuuucuca ucuuuucucc uaauaucuug uuuuguuuuu   1440
guuuuuguuu uuguuuuuga gacagagucu cacucaguug cuuaggcugg agugcaaugg   1500
uacaaucuca gcucacugca aaugccaccu ccuggguuca gguguucuu gugccucagc   1560
cuccugagua gcugggauua caggcaugug ccgccaugcg cagcuaauuu uuguaguuuu   1620
aguagacaug gggucacacu guguuggcca ggcuggucuu gaaccccugg ccucaaguga   1680
uccuccugcc ugggccuccc aaagugcugg aauuacaggu gugacucugc cuggccuuuu   1740
uuuacauuua aaucuucgaa acauauaauu cauuuugaug uaaggaguau cauguggauu   1800
caacagagcu acucuguugu ccaaacaucu uuuauugauu auuucaucuu uuauugaauu   1860
gauugaucua uuuucuagca guguauacuu guuuuaauuu guguauguuu uaauaucuaa   1920
aaacguuauu auuuuucugc uuuuagacuu cuuuaugaau auuuuuaaug ugaauuauag   1980
aacuggcuug uccaguucuu aaaaaauauc uuguggauuu uuauugggua uguguuaaag   2040
uuauaaauug uuuuauagau ugauuuagga uaaaccuuuu uauguuauuu gguccuucua   2100
gcuaaagaac acaagauacc uuuucuuuca uucauucaag auauuuuaug ccucuugguu   2160
gcauuuuaau gcauacuuca uaaagaucaa uuguauaaaa cuuuucacag uuguauggaa   2220
guacuucuug uuuauaaaug aguuuugaaa gguugaaaua uuuuuaaaga uugaauuaua   2280
aaaaaagaaa auucgguaua uauuuuaaaa ucauuuucua uuugaauuuc agguuguaua   2340
uacaaaagga acagagauua ugccaguagu ugcucauacu uucucauuuc aaauaauuuu   2400
uauuuucugu aucauaaauc uacuaacggu guuuauuauu uaugauaaug aagaauguuu   2460
uauuaacuuu ccuuuugcau aacagauucu auuguguuua uuucuag                 2507
```

<210> SEQ ID NO 71
<211> LENGTH: 946
<212> TYPE: RNA
<213> ORGANISM: Homo sapiens

<400> SEQUENCE: 71

```
guaaaaucuu aacagaauuu uguuuaucaa ccaguuuuau uacaguugga acucugaacg     60
augucuuuua uuuauuauau caucagugcc uaguguagcg gcugguacua ccaaguguau    120
aauaaugucu uuugaaauuu cuucuaccac cuggucccaa uaaaaaauua gaauuaaguu    180
uagaucacgg auuagacuua gaacuagagu uacuguguuu auuuuucuau guuuaugugg    240
```

```
auaguacaca cauuguuuug guuagaaauu auuuaacaag aaaugauuaa aaacuuuuag    300

aaauuuaaaa uaauuuuaua cucuuuuaag guuuauuuua cuguaucuua guccuaacau    360

acccuauaca augugaaaua agcuaaaagc augguuauaa uuugacugug cuaccuauuu    420

uauuuuuagu gaaaauaacc caaauaaaag gaaguaauac uuuuauuauu ugugcuguag    480

uuauagucca caaguaagaa gaugauuuga aaaguguaug cugaauaaga acaauuacag    540

gggacaacau uuuuuaauaa aguacgaaag gggaaaaagc uaaguugaau aaaagagaaa    600

gcacagagca aaacagaaac auacaaaaug guaaaaaggu ggaauugaau ggaggaugag    660

gaaaguaaca uauaaggaag uauagaagcc auaaacauua gggaguucug gaaauccuau    720

uuuccagagu guuagccauu auauccaucu uucaguauug gaguaacagc aguguaccua    780

ucauugugua uuacaguuga aguguacaaa augguaaaag gcauacuugu acccacaaga    840

aaauauguuc uacagucuug uugaaaaaaa ucagacguac uuuuuuccuu accuuuuuag    900

guuaauauuc augaagggau auauauuguu uuaaaaauau uuauag                   946
```

<210> SEQ ID NO 72
<211> LENGTH: 4079
<212> TYPE: RNA
<213> ORGANISM: Homo sapiens

<400> SEQUENCE: 72

```
guauuuuuau aaauauauag uuauuuuaua uacaauuaug uuuuuaacga cuuuauuuuu     60

auuaaaauaa aaugucaagu caauauugag uuuucuccau uugaauuuua uauuuucaaa    120

aaauuguaca agauauuuau uauuauacuu auauuacuag ugcuuacauu uguaaaugau    180

ggaugcauuu ucuauuauuu uucuccucug gugaaaauua cauuaacguu uauuaccagg    240

ucacugguau gaaagaaaug aaaaauugug auacaauuau uuuuauuuaa cuuuuuauaa    300

uuaacaaaga auggaagaua auaaaauuuu gaccagugua acagcauugc agauaguuuu    360

cagagguaau uucacauuaa ucuuacccaa auuaauguuu caucauauuc uccuuacccu    420

gagccauauu accuuuuuua acacaucaaa uucuaugaau auaaguucuu acaauaucug    480

uguuguuaua uuuccauagc acuacauacu auaguuaugc cagggcacac uagugcgaac    540

uguucauggg aaauucaugg acauguuuau uauaauuggu gacuauguau auauguauac    600

acuacauuua uacacacgcg cauggaauca cuauuucuuc uucaugucau auauauauac    660

auauauacac auauauauac augucauaug ugugugugua uauauauaua uuuguauaua    720

ugacaugaag aagaaauagu gauuccgugc acauaugugu guguaagugu agugaugugu    780

uugcagguac gguuguaauu ucaaaaauga agcaaaagcc uugcucagga gauaauugaa    840

ccaauacuua aaggaaguaa aggagugaaa caugcagaug gcucuaagca gugggaauaa    900

guucaaaggc aguaaagcag gaguguacca aucaugucug agaacaacaa agaagucuuu    960

uuggcuggag uagagucagc aagugaggca gugauaagac cagagaggua aacagaggcc   1020

auaucauaug gggccuuaua guucauugug cagacuuggc uuuuaaguga gaagggacac   1080

cggggaaagu uucugaagau agaaaugaua uaauuugacu uaggcugugu uugcaguaga   1140

cuguaggagu gguaaauaag aaucagggag accuguuaga agacuauugc aauaaaucugg  1200

agaaaaguga ugguguuuug gggcauggug guagcagugg aguuacugga ugcagcaguu   1260

cuggauguau uuugaaagug auaaaaaugg aauuugcuaa cagaucagau guaggaugug   1320

agagagagag aacucuuggu cugaaccaaa aguuuugguc auggugggu ugugggaaga   1380
```

-continued

```
gcagguugag agauaaucag guacuuaauu uuagacaugu uagguuugag augcuuauua   1440
gacauucaag ugaagguguu aaguaggcac uuguauauaa aaguuuaagg uuuaggacaa   1500
caaucuaggc uaaagauaug uuugguaacu gucucuguaa aaguaauuga aauaaugagg   1560
cuggcuaaga ucaccaaggg aguaaaugua gguuaagaag aaaaaucuaa agagcuucua   1620
cuuuagcagc uggggagaua aaaaggagcu accaaaggag acugaaaagg aaagcccaga   1680
gagcuaggag gaaaagcagg aguauggaga gcccugaaaa ccacaugagg aauguaacca   1740
aggaagaaga aacaacugcu uucagagcug uguucauugc ugcugauagg ucaagaugau   1800
cacuaaaagu ugacuauugg acuuagcaau ggucauuuuu gguucaagag aaaaugggua   1860
gagaggaaau guaauaaaga aauauaggaa cccuuuucca ggacuguuuc uauaaagaga   1920
aggagaaaac aaggugguag cuugagggga aagagggauu aagaaaacau uuuucucuuu   1980
aagauggaag aaauaacuca ugauuuuagg uuaauaggag agcuccauua aagaagaaac   2040
auuaaugaau caaugaagug gagagagaga acuucuggaa caauaaauau uuuaagaaug   2100
caaugggaug ggauccuagu gugccaguga agagguuggc cuuaacuagg aacacagagu   2160
ucauccauaa uuguagaaaa gaagguagag uguauagaua ucgauguagg uggcuuggua   2220
gacauccugg uaaugggaau uuguggaagu ucuaaacugg uugcugcuuu uuucucagug   2280
aacaagggag caagguucuu agcugaaggu gaggauagga gaagauguuu cauaaguuug   2340
aggagaaaga agagaaguga aaguauaaaa uggucaucug aaagauugaa gacguggaga   2400
auguggguaug acuguugagu aacuucaaga gcccacgaua uauauaugua uuucuauuua   2460
uguguuuauu auauuuguau cagaacacuu ugaaaguagu uuaaacugcu uuaaaaggau   2520
gacuaauagu auggauugug cguauucuaa uuacuaggag aaaaaguggc aauugaucuc   2580
ugcugucaaa uaaggaaaag gacuuaucug auaacacuuu agucaguccg uaguuauaua   2640
aucccuaaag cucacagaag guguguguac uagacuguac ucuacaucuu gaacuuaacu   2700
uguaaaacgu aauggcuaau gguauucuuc cuucauaaga uuaggauuag guuuaguuau   2760
caggaacaga gagcugaaga auaauggcaa aaucaagaua gacauuuauu ucucaucuau   2820
guaauggccu agaauuaagc auuccagggu guugccuuca ucugccccau ccaaaaugga   2880
uggaaugcag cuuuaucuca ugucuguguc ccaaacagca agacagagga agaggggcaa   2940
gaguuaaaag caugugcuga aggauaggca gguaaauaua guguuuauug uguagggcca   3000
uguggaagaa ugauaggaga auagauaugu ggauggaagg gagaauagau acugggggac   3060
aacucagccu gugucauguu ccacagcuua gauguuagcu ccagacagcu gugcucauuu   3120
cuuaaaaacu uuugugaucu caaacguacu aguuuuaugc cuaaguccaa uauuaaauau   3180
auaaccuaua uauuaguaaa ugcuuauaau gaaugagugu gagaaugauc ugucaaucaa   3240
uuuuggaaug auagcaauau uauguuuugg ucuuuuaaca auuuaguaag auauuacaag   3300
uaggcauuua ggaaguuuuu agcuuaguuu ggauuaaauu uagcugcaag ugacagaaaa   3360
aucaagcaua auacaauaau uuaaacaaga uagaaauuua uuucucuaua auauagacaa   3420
aguugaagca acuagggcag gauuugugug acagaugcuc aaauaucccc uaucaggaac   3480
ccugucucuu guugcugugc cuaucucaac augugguuuc uaacucaugu gaaguugcca   3540
cccucauauc cauguggauu ucagcuagca ggaaggagga aagagaagag agauuacucc   3600
uuuauuuuaa aaacauuuuu uuuuuuuuuu uugaaauuca cauaugaacu uugcguuuau   3660
auuccauuac ugacaugacc acacauagcu gcuugugugu aaguggaaau uuaguucuuu   3720
auuucaaaug gccacguguc aagcuaaaaa uccauaguuu uaguacagug gacaaaaggg   3780
```

agguuaaaua uuaggaacag cuagcagucu guaucacaau gaucauuuuu uguaaagcag 3840
uauuuugcaa ccuuuuaaaa uccauacccc uucagcuaag aagguuuuac ugaacuucag 3900
uuuuuuagua aauuguauua guaaaaccaa aacaaaacuu ucaucuuaca aauauaaaau 3960
gacaacuuua aaggauuuuu uuuuaauggc auaccacuuu ucuugccacc auguugggau 4020
cacugauuug aaggaauaag uagucaauuc aauucaugau uuuuguuuuu acucuguag 4079

<210> SEQ ID NO 73
<211> LENGTH: 720
<212> TYPE: RNA
<213> ORGANISM: Homo sapiens

<400> SEQUENCE: 73
guauguauuu uuaucuuguc auucaaggag cuuagaauua uucuugccau ucacagacua 60
uucugugcua uuuacugcau accauuuaaa aaacauucca uaaguaucuu uugauaaaga 120
uuauccucau uaauuuauac uaaacuauug aaaccuuuga gcauuuacuu uuugccagaa 180
uuguuuucaa acuuuugauc acagugauuu guccaaauaa ucaguuuugg ugaagcagca 240
ggauuacuuu uuuuuauuau cuguguucau ugggccacca uguagaugug acaccacugg 300
ccaauuugac agaauuuaug acaggaacau acugugucaa uacaaccugc ucuccacuuu 360
uuauacuuuu ucauugguua caacuaauuc aagcaacuaa ugacuuacuu auucuacugg 420
uauugcugau uugcuuuuac uaauucuuuu aguauuuugg uaaguguuuu uuauauguaa 480
ugcauauuca gagucacuuu gccuuuagga uauuauacug gaaaguuuua acuguugcau 540
auuacaucau uauuauuacu ggauuugguu uauaaaagca caauaaaaaa ccaguguaau 600
gauauaaauu auaggcauau guacauuuuc cuuuagacuu aguaaaaaaa aaaucaugaa 660
cuugauaaau uuauucaagu aaaccauguu auauuuuaaa uuaaauugga uauuuuucag 720

<210> SEQ ID NO 74
<211> LENGTH: 1370
<212> TYPE: RNA
<213> ORGANISM: Homo sapiens

<400> SEQUENCE: 74
guaagccaug uuuuaaguua cauaguuugc gcaaccugau uuacaagucu uuuuuuuuaa 60
uuuaaauuuu guuuauuauu auuuauuaag uaguuuaaug cuuuuuucaa augcuuuuau 120
aaaacauuua auacaaauaa aaguggagcu aaccugauug aaguggaauc agauuuuaug 180
ggguuggagu ggugggu ggg cagggcugga acauugcuuu auuuggucua gcaucuccuc 240
aguaauagcu gcuuguuuaa aaagaugaaa guuuauuaau accacauauc agagauuaac 300
cuuuuuuuuu cccaacaaaa guagggucug uauuacccau guuuguuugc aaaaugcucu 360
uguaacagau gagauauuua aacuucuugc ucuguguugu gauucuccug ccucugccuc 420
cugaguagcu gggauuacag gugugcacca cuaugcccgg cuaauuuuug uauuuuuggu 480
agagauggga uuucaccaug uuggcuaggc uggucuccaa cuccugaccu uaagugaucc 540
acccgccuug gccucccaaa gugcugggau aauaggcaug agccaccgcg ccuggccugu 600
uaaaaucuuu uaaagauuuu uaaguacuug auuuuuauaa uuuagacuac uuacguuuua 660
cuuuguucga guauuuuaag gaguaauuag uaauauagcu ugagaguuua uauauuuauu 720
uuaauaaaua gccuauuagu uaauauuacu aauuugagug uuaugauagu gcagacuaag 780
uugcugcuuu aaaaugaaaa uaaauaucua aauaucaauu ucauuauugc uaaauuucau 840
uuaaugcuuu cuuaguuaaa aaugaucauu uguaaaaacu auuaucuaaa gaaaagacaa 900
auagacaaau aaguauuuua uacagauaua uaugugugaa aaguaucuaa cuuggauccg 960
uaguugugcu aggaccccaa auuagacuuc ugaucaacuu ggacuaucag aucacagccu 1020
ucugaucaac uuggacuauc agaucacagc caagaaucug gaaguuccua aagaugacuu 1080
cuggcccguc uagguagcug ucauagacau cauauuuucu gugcuuaaaa agcuccaaau 1140
cuugguuuau aauuucauuu agguuuuugu uaggauuucc auuaauaauu gugauaaaau 1200
uuuaacuugg guuacaguuu aaauaucugg aaaauucuuu cacagaaagu uaccucauuc 1260
uucagugaua cuggcuaagu gaauuauaac caguugcuug augguauaug acauuuuugc 1320
agcuuauuug aauguuuuua aguuuuuaau uauauugcuu ucuauuguag 1370

<210> SEQ ID NO 75
<211> LENGTH: 72
<212> TYPE: RNA
<213> ORGANISM: Homo sapiens

<400> SEQUENCE: 75
gcaagugugg uagucaguug auuauuuucu uggcugaacu auagagaaau acuaauaauu 60
uauacuuugc ag 72

<210> SEQ ID NO 76
<211> LENGTH: 1337
<212> TYPE: RNA
<213> ORGANISM: Homo sapiens

<400> SEQUENCE: 76
guauacucag uuauucuaaa ccuuuaaaaa gaauuauuga uaagugaguu gucuggauau 60
gaaauuauuu gugucuuagc uguuuuugcu guucuauugu ggaucugcua caaauuuaau 120
aaaugacaau aauaaccuga aggagauaag ugagugucag uggguucagu ccugaaucug 180
aaauagacaa aaacaaaaca aaacaaaaua acaaaaacca agcaaacaaa aaagaaaaaa 240
accuuagaau uauggaauuu uugaaaaguu uuauaguaua guauuuuaau uucuagacag 300
caccaauaug uuguuauuaa uaauaauaaa acuuaguagu uuuuauguua auauauguua 360
cucaacauuu ucccuuuccu uaaggacuau gcauugaaaa gcuuuucuug uaaguuauua 420
uuauuauuau uauuauuaau auuugagaug gagucugucu uguucuauug cccaggcugg 480
agugcacugg ugcgaucuug cucauugcaa ccuccgccuc ccggguucua gugauucuug 540
ugcuucagcc uccugaguag uugagacuac aggcgugagc caccacgccu gacuuauuuu 600
uguauuuuua guagaaacag gguuucacca uguuggccca ggcuggucuu gaacuccuga 660
ccucaaguga uccauccacu uuggcucccc aaagugcugg aauuauaggc gugagccacc 720
augccuggcc uuaaauuauu cuuuucuaag ugaaaguaau guuuuauuga auauaaauua 780
acaucuuucu uggguuuauu uuacuugagc uaaagagaac aguugguuaa guuuuauaau 840
agccauugca gugcuuuuuu guaagaagac cacacagaag gacugucuuu uucacuugcc 900
ccaaaucccc aagcacguau augaguaaua gcagaguggu ucuuuuuagc auuaugauuu 960
cuauaauaca uccaaaacuu ucucaagaaa aaacuucaug auuuauuagu acaauaauca 1020
guuuacucau uacucaucau uuauauuuac uuuauauguc uuuuaacugg ugcuuauuaa 1080
guagcacuuu aauauagaau aggcaaagaa ugguagagaa gaugaaauuc aaaaauuagg 1140
uucucacauu auuaauaguu cauuaaaagu gagcuaaaug agaagcuugu auuggcuaug 1200
uagaauuuug gagggauuuu ggaaacaauu auucuaccuu ugcauuaaaa cuugauugua 1260
gguuuuaaga auuaaagugu uggaauagua ggaggguuau uuuaauguuu uuaguuuguu 1320
aauucucuua uauauag 1337

<210> SEQ ID NO 77
<211> LENGTH: 1850
<212> TYPE: RNA
<213> ORGANISM: Homo sapiens

<400> SEQUENCE: 77
guaauaguaa aguauugcaa agagaguaaa ggaaaauauu uuuuuuuuuu uuuuuuuuug 60
agacggaguc ucgcucuguc ucccaggcug gagugcagug gcgcgaucuc ggcucacugc 120
aagcuccgcc ucccggguuc augccauucu ccugccucag ccucccaagu agcugggacu 180
acaggcgccc gccaccacgc ccggcuaauu uuuuguauuu uuaguagaga cgggguuuca 240
ccguuuuagc cgggaugguc ucgaucuucu gaccucguga uccgcccgcc ucggccuccc 300
aaagugcugg gauuacaggc gugagccacc gcgcccggcc aggaaaauau uuuuauuugug 360 uuuucauuuc uucccccuuu aucucauucu ugaacaucua aucuuauuau uguuguuaaa 420
uaaguagagg gaaauauuug cuuauuuaac cuguugauuc aaagauugau uaaugagaca 480
uuauuuacuc ugaauacaga uuaggaguuc agauaaagca gagcugcugc auaggagauc 540
aucauucaau accccacagu cagaucagaa ugagacagaa gagaauauga ccauaggauc 600
auuaucaaga auguuaucug aaauucacca uaguguagaa aguggaaugc auccuuuugu 660
cccuuuaacu agacuuucuu cauccaugca aguuaaagag aauucaacuc cagaaacuau 720
uacaauaaga gagauuuuua aagcaccaug ucugcagucu ucaagaaauc uagaaucguu 780
agucagcacc uuuaguaggg aaagccauga agaaauaaau gacauaugcc uuuuuucuga 840
ugacuguaug aagaaggugu caagaagcca ucaagcacua gagaagacua guuuuguaca 900
aaaaagcaau ucaucuuuuc auggcuuauc aacagcuuca gacauaaugc agaaguuauc 960
acuuaggcaa aaaucugcaa uauuuuguca acaaauucau gaaaauagag cugacaugga 1020
uaaaucacaa guagcaacau uagaagaaga acagguucau ucccaaguaa aguaugcuga 1080
uaucaauuug aaagaagaua uaauaaaaag ugaaguaccc uuacagacag agauauugaa 1140
aaauaagcuu aagguuaauc uuccagaccc ugugucuauu acugcacaau caaaauuauc 1200
ucagauaaau ucucuugaaa aucuuauaga acaguuacgg agagagcuag uauuucuuag 1260
aucucaggug aguuuuucuc caaauuauau uucugugguu guucuuuuau gacgucucua 1320
acaaaguucu guaacaauua uaguuagaau auuuuuguuu gcacuuuaac aucaguuaua 1380
cacauuguac uuuuuaaaau cuaaaaugca guacauugau augaacucau ugacuugucu 1440
aauuuauuaa auuuuucuuu agaaugaaau cauagcacag gaauucuuga ucaaagaagc 1500
agaguguaga aaugcagaua uagagcuuga acaucacaga agccaggcag aacagguagu 1560
guaaaggcag aacauuaaaa gagaugauug ugguacuaaa gacaaaaacc guuauaucuu 1620
uuugccucuu accauggaug uugggagagg gagaaagugg gauuaagauc accaucugcu 1680
uuacuguuua gauuuuaguu uauuuuuaug auugcugcua ugucuucaua gcucguuuuu 1740
uuuguuuugu uuuguuauac uuaauugauc aaacuuuucu uaacuugaaa auuauagacu 1800
ugugauauuu uguugaaaaa aaucaauuuu auucucucug cuuuuuucag 1850

<210> SEQ ID NO 78
<211> LENGTH: 535
<212> TYPE: RNA

<213> ORGANISM: Homo sapiens

<400> SEQUENCE: 78
guaaguuaca auuaucuuuu acuuuucugu ucuuauuuuu ccuauacuua aaaucauggg 60
ccuaaaaggg cguuaacaca uucucuguuu ucuaaucugc uuuacuccua auuaccucug 120
uacuguauau acuucagucu gucacuaucc aguugauuug ccuugcuguu uucauuguga 180
gagaauguua cuaauaugaa uuuuuuguga gaauauauaa cuccuuuuuc uugugugu uc 240 uucaaucaaa augaaguuag aacaccaaau uuaaaauacu uuaauauaaa gcauaguuua 300
aguuaaggca gaaguaugcc uuauauacgu guguauaugc acgugauaua aauaggucug 360
ucauuuaacu caacuauuca cguuggauuu auaguugaau uuuuuuguau guuuauuuac 420
auuuggauuu uuccaaugau gucuuuggua uaugugaaau auuugucauc uguauagcau 480
aguguaaauu gugaaaaaga ucugaucauc caaugagaaa acuguguaau uacag 535

<210> SEQ ID NO 79
<211> LENGTH: 2561
<212> TYPE: RNA
<213> ORGANISM: Homo sapiens

<400> SEQUENCE: 79
guaaguuauu uuuuucaugu uaauguuuuu ccccuaucac uuuagagaga uuuucugcug 60
uguacagauc uccauaguuu cugaugagau auuuuuaguc auuugaauca uuguuucccu 120
guauguaaag uguaguuuuu cuugagcugc uuucaauacu uuucuucuac caauuggaua 180
auuguuauua aucugucuuc aaguucacug acauuuuccu cuuuaucugu guucuuuugg 240
uucaaggguc agcuugagac cuugaggagu uuuuuacacc gacuuuggag cucguuuuug 300
cugacucuuu ucuuauuggg auuuuccuuu cacuuauccc auggcuuugg gcuguauccu 360
gugguuuucu agaugagaaa gaugauagau cucugcaauu gcacccugcc cuaugacuaa 420
aucuuuaaaa auggcaaagu caaucuuugc ugguccuguc uuccguauuu gaggggguuuu 480 uucccaaaau cugcuugcuu uuguucauuu ucuagaacau cuagguaguu uuuuuucauu 540
cauuuuuuau uuaugggagu guagaucucu uaggaacuua ugccaucaga aguauuauga 600
aauggcuuua uucuaaaugu uuaaagauuu acucauugcu acaagaaaga uuuagccauc 660
acuaauauuc uauauauauu uaccauauag ggacuugaga auuucacagg auucaguauc 720
uguauauaaa cuugaauaau auacacauuu uagauuguua auauuuaagu auaugucauu 780
uauguuaucu gaacauauuu agcguacauu gucauauuau uucccaaauu ugugcuugau 840
uucaaauggg aaaaaaauuc uuauuauuua uugaauuguu uuuuuaaaaa aaucaugauu 900
aaucaguaau uggauacuuu uuaaaauaac acuauaauug uuaacagaga augagaguga 960
uacugguaug uuaaaaacuu ccugaggcaa gaaaauaauu ugauucccau uauaucuuuc 1020
ucauacugac uuuccuucuc ugauugguga uuuuguuuug ccucugccac uuugaauguc 1080
uaaaaugauu cuuuaugcuu uuuuuaugug aacaucuuuu guccgugaug augcccacua 1140
cugauacugu gucccagauc aaacuuaauu uuccaagggc agcucuacuu agugaccaaa 1200
ugaaaacaca gugaauagcc caagaaaucc uaacuucuau uuauguugac aaucucugga 1260
ccuuccugaa gccacuguuu gcauagacuu cauuuacuuu uauccgggau ugucauuguu 1320
uuuucagauu cauaggcccu aucugaaauu cacaaaucac cuagcaauac uucucuaaga 1380
aaucuucaga auccaugaca auuuagacca gacaaugcug gauuaugcac uucaguucac 1440
uuuuuguuac uacaagguau uuuucagugc ccccaacagc uaucuuaacu cauucucauu 1500
uuaccaaagu ccauguagac acggcacuau uccucaauga gacaacuaac uagaccaccu 1560
uguugucagu cagaguaccu uccucuaccu acuuuuaucu uccuuauauc cucuuugagu 1620
uaguauaagu uauuacucug caugaccugc ucuaaucucc uucaggggaa ggcuuuuaca 1680
aaucuacuac cuagaguuaa accccagauc accuuccuga guaggagauu gcauuugguu 1740
cuauucauuu uaccuuauuu ggcuucuacc uucacuuuuu aagacuuacu uugccuuuaa 1800
caguuuuuuc cauacaguuc aucuaaaguc caaauauauu uauuagaugu gugcauugug 1860
uguauauacu uagauaugcc acuguuggag auuucgggcc agugaugcca cucugauaau 1920
auuuuaauau uugacauauu auuuuugcuu acucauuauu cuuagauaau aucauguuau 1980
gauaccuugc cuuuauuuuu auuuaugcuu caacuaugug gagaggaagc acugaaaaau 2040
ucacuuaauu gaauguugua uugaucaauu guucaauauu guauuccauu ccuuugcgca 2100
ugcuuugaau gcaggugcua uauaauuuca gagaaaaaua ccucauuuug acuguacaaa 2160
aaccccaugu agggagcaga gcucacauug uuuuccccuu uuagagacaa gaaaacuaag 2220
auacagagaa uuuaagucac uugcccagcu guuaagugac ugauuaaaau uugaacccug 2280
gucaucuuau ucccgucugg uuguuuuucu agucuaccag ucuauuaaga uuagcuaggu 2340
guuuuuuaau uguuuuaaug aaguaauuac uaugcuuggu aauguaaaug aaaguuuuau 2400
agauucauaa auaagaauuu gaauuggcau acuuuauuau caugcuuggc aaugaaaaua 2460
ggaaaaugcu uaaaugucca uuuuauuuaa agacagacug uuuuuuacua ugauuuuacu 2520
guuuuucucc acauuucuaa uauauaauau aaauuugcua g 2561

<210> SEQ ID NO 80
<211> LENGTH: 342
<212> TYPE: RNA
<213> ORGANISM: Homo sapiens

<400> SEQUENCE: 80
gugagaauuu uauuaaauaa aagaaaaugc uaaacauaag aauguagauu uaauaggaaa 60
uuuuuaauuu uuuaaaaaga augcuuuaug agaaaaugcc ccuugaauua auucuuucaa 120
uauuaagaaa cuggauuucu cuuauaaaau uauaagugga aaauaagugc cuuauaagau 180
ugaaaagaau acaaaaaauc uaaaucucau accuaggcau uucuaagcag aaacugaagu 240
augguugagg uaaaauuccu ggcagggcau ucacauaucu gucaauuugu cuuucuuugg 300
guguaagagu ugugauucuc auugcuggau uuuuuuuucc ag 342

<210> SEQ ID NO 81
<211> LENGTH: 2020
<212> TYPE: RNA
<213> ORGANISM: Homo sapiens

<400> SEQUENCE: 81
guauugaaaa uuuuguuaca gguauugaaa auuuuacaug ugaauaacaa aaaucauugg 60
uaguauguuu cuuuauguuu uuauuuuuau uuuacuuuau uuuaauuuuu ccaucaccaa 120
agcaugcaga uaguacuuuu cucaauauuu agucuucaug uauuccugag uucucaaaau 180
aguaacagug aaauauauuu uuuauggauu uugauguuag auggauuaua aauaaaagca 240
auuuauacca uucauuccau ucaucugcau gagcagcaug uucauacauc uuguucgcac 300
accugucauu caugugaaau auaugguuca caagcagaac aacaagcagc uauuauaaag 360
caguguuaag uaaaugagca cuuuuauuuc uugcugggug gaaaacaaaa gaauaaaguc 420
ugucaaggcu uuuuagugug augauagaau uguuccccuu uuugcauuca caaguaaaaa 480
cuacuuuuuu uuugagacag agccucacuc ugucacucag gcuggagugc aguugcgcua 540
ucuuggcuca cugcaacuuc caccuccuga guuuaaguga uucucaugcc ucagccuccu 600
gaguagcugg gacuacaggc augcaucccu ggcuaauuuu uguauuuuuu uuuaguagag 660
auggugugug gucauauugg ccaggcuggu cucaaacucc uggucucaag ugauucgccu 720
gccuuggccu cccaaggugc uaggguuaca gacgugagcc acugcacaca gccauaagca 780
aaaacuucua aaccaaauua uucuucaucu uugucuuccc uuuacgcaau aaaauguuaa 840
ucuaccacca aagaggaaag gguacucuac uauacuaccu gcccuggguu ucucaguuuu 900
gcugucuaua uaauggucgu uaugaauguc cuaaugacag auccuuuuca uuauuuuauu 960
ugaaauuuga cuaucuauaa caucacauac auuauaaaua uaauuacaaa uauauguuca 1020
gaaucaauga aaauauauuu uugauuauau gggccacuau uucucucugc uaggugaucc 1080
auuugugagu auacuugagu uauaauuauu aaguacucau uuuuauuuug gaaauuacag 1140
uaauucaucu uuuucucaau auugggauuu uuauuauuau uuuauguugu cuaaggacag 1200
ccuuaacuac uuauuagaau auugcuuugu augugauauu auuauuuuua aauguauaau 1260
uuuaacauua uuauuucucu uauuuaccug agguauagga acacuaucag caaauauugg 1320
uaguauggca uugucguauu uuuugagaua aaauucauga uuuuuaaucu uuguauaaga 1380
aauauaucag aaguuuguag uagauuagag aguaccaacu gggagucuga aaagcugucc 1440
aaaguggcaa aacagguacu uagacucuca auccuaaggc uguauagagc uauaaacgug 1500
gcaagaccuu uggagucaga cagacccaaa cucaaauguu ggauccaugu auauggaaag 1560
caccugacaa caagccuagc auauguacuu gguaaaaaug auugccaagu guaguguuaa 1620
ugaguuuuug gauauugagu aaguuauuua aauuucaauu ucaucuuuaa aaugaaauaa 1680
uuggaaagga uaauuugagu gaggguauga aauuaugugu ucauaagaga ggguaugugg 1740
ccgagugacu agaggcgagu uuauaacuau ucuaucuaau aaaacuuugu aaucugguaa 1800
uuugugugcu aaaaauaacu uuaccuguug uauaguacuc uuuuuuuaug ccuuaaacua 1860
aaguguucaa aauaucaugg aaaaaugauc uguguugcuu acagauuugg ugacuuuuaa 1920
cuuuccuaua auguugucag aauaugaauu uauacuuuca aauucagcau uuauucuauu 1980
guguuuuuuu uugcauucuu auuucuaaac cacuuuucag 2020

<210> SEQ ID NO 82
<211> LENGTH: 1967
<212> TYPE: RNA
<213> ORGANISM: Homo sapiens

<400> SEQUENCE: 82
guauagguau uagcaaaacu auaaauauaa uugcaguaua uucuuguuaa uugugaaagu 60
aacguaagaa uaauuuaugu uuuguucuuc ccuucuucuu cuuccuuugc aauuguauuu 120
uuuuuuacuc ugguaacuac uguuaggaac uuauuuaugg agacagugua gcuuaaugau 180
uacauuaagc cugggauuau ccugccuggg uuugagucau uuaacguuug cuuuuuguaa 240
gagcuugagc aagucaucuu accuaucugu gucucaguuu ccuuaucugu aaguuacuuu 300
guaaguaaua cccuuuucau aggauuauug uaaaacguaa augaauuauu agaugaaaau 360
gcucggacua gugugugca cauaugaaca guuuguaaau guuagcuguu guuagcauca 420
uucaucauca ucacaaucau cauuguucau auauguuuau agggaacuaa cauauuucuc 480
cuuauuucug ucaucucauc uaaaucaaua gaaugauuuc cuuaauagga auuagaauac 540
cuaaucaaag gugauuuaaa cacuaagaau aauuauuauc ugaccuaacc agaaccacaa 600
agcuaguugu agggcagguc auauuugaag guuguuguua ucgccuauga ugguuguaaa 660
auagcugcau gaauucaaga aagaugaugu gcccauugaa gaagaggagc auuuuuuucu 720
acauagcuuu uauuuuuaaa uaaacauuuu uuucugguga uaccuggcag acauugacuc 780
cgaucucauu ugcuagaauu ggaucacaug uccaagucug aaccauucag uugcaaagag 840
aaugauaccg cuauacuggg uuuaugccaa gaacauuaca cauguuugug gaaugcucau 900
guguagacaa cagugucuua cacaacuuca aaaaaauaau uuauauauaa auauguuuua 960
aauuacuuuu uaaauucaca agaauuuaug guauacaaca ugguguucua uauauguaua 1020
uacuaugcua uacaacaugg uguucuauau auguauauac uaugcuauac aacauggugu 1080
ucuauauaug uauauacugu ggaauggcua aaucaagcua cuuaacauau guauuaccuc 1140
gcauacuuuu uuuuuuuuuu ccuugagaca gagucuugcu cugucaccca ggcuggagug 1200
caguggcgcu aucuuggcuc acugcaaccu cugccuccug gguccaaguu auuuucuugc 1260
cucagccucc caaguagcug agauuacagg caugugccac cacgccuggc uaauuuuugu 1320
auuuuuggua aagacggagu uuugccauau uguccacgcu agucucaaaa uuccuagccu 1380
caagcaaucu gcccaccuug gccucccaaa gugcugggau uacagcauac uucuucuuau 1440
uuuuuuuuuu uuuugcacua agaacacuua aaauuuacuc ucuuagcaau uuuaaaguau 1500
auaauauacu guuauuaacu uuggucacua uuuuaauuag acuuaagaug uguuuguauu 1560
caaauuauuu uguaagcauu uaacacccaa auuugagagu ggggucagaa uguuggaauu 1620
ugauuucuag aauuaguaua ggguauuauu uuccuacuuu uuuucugugu ucaauaaaau 1680
guuuauaaga uucagcuuca auuauauuau aacccauuua guggugaauc agggaagaau 1740
gaaaauaauu ugauaacuuu guugccuugc auuuauuuaa aaaauuuuua auucuaggcu 1800
aaacccuuuu uaaaugaaag uuuaacuucu uguguuuuca gauacugaau agcuaugaua 1860
ccucuugugu ugagaaaacu uuaaauuugc auaaucugaa guuaucuuuu cuuauaaaca 1920
uuuuauuagg uuuacaguau ugucuuuuug uuuuguuuug uuuuuag 1967

<210> SEQ ID NO 83
<211> LENGTH: 90
<212> TYPE: RNA
<213> ORGANISM: Homo sapiens

<400> SEQUENCE: 83
guaaguaaaa cauuuuuaac auuaguaugc aauauuguac aaaguaggau agcuagauuc 60
aacaaguaau auggaugugu cuuugugcag 90

<210> SEQ ID NO 84
<211> LENGTH: 3663
<212> TYPE: RNA
<213> ORGANISM: Homo sapiens

<400> SEQUENCE: 84
guacaucuga uucuuauuuu gcuuuuucug acuaugaaaa auuucaaaua ugcagaagau 60
aggaugguau caauaaugcu caucaccuga auuaaauaguu aacauuuauu aacauuuugu 120
cauaauugcu ucuucugauu uuugugggau guuugaauug cagacauucc uccccuaaau 180
auuuaaugua cccuuuugaa aaaggcuuuu uucuuuaacu aaccauagua acuuuauuau 240
accuaacaaa augacaguaa uuuucuaaua ucgccuaaua cccugauuau agucacauuu 300

-continued

```
uuuacauuuu uugaucaaag aauaagcauu uggauguuac aucucauaaa ucuuuuuaau    360
auagaauccc cuugguuuuc uuuuucucca aaaaauguuu gaagauguau cuaacuuuug    420
ugugugugucauuuuacuug uuccugugucccuuguauua cuaaaaguua ggucagaacc    480
cuaaguuaca uucagguuua aacauuuuug gcaagaauac uucauaagua guguucuaua    540
cuuuauauug caucacuuca agaguaucug guuguuccau guuuuguaau ugauuacucu    600
guuaaggaaa agacaagcag accaaguaug guggcucaug ccuauaauuc caacauuuug    660
gaaggcccag gcaggaaaau uuccugagcc cagaccagcc uaggcaauau agugagacuc    720
cgucucuaca aaaaauguuu uuuuuuuugu uuguuuguuu uuaauuagcu ugguguagug    780
gcacaugcuu guaaucccag cuaccuggga cauugaggug ggaggaucgc uugagcccag    840
gaaguugggg gcugcaguga gcugugauca ugugccacug aucuccagcc uaugugccug    900
uauaacagag cgagucucuc ucuuaaaaga aaaaaagaag aagaagaaga agaaaagaua    960
accauauacc uccauuauua agcaauuuag cuaacuggug auauuuuggu accauacaaa   1020
uaacaaauua uuugucaguc cuaaugauuu uagcaucugc ugaugauugu ugccuaaccc   1080
aauuauuaaa aguugcaaac aucauaauuu ucuaguuaua uuaugcacuu acauuuauua   1140
acagacaugc uuuuguaaaa uaaauagcgu uuccucauua gcccaggcua uuuguuuauc   1200
uugaaguuua gcuccuacua caaaggcaag auaaaugcuu uucucuuuaa uuaccaguuu   1260
ucagaauaca cacuuggugu acucugcacu accugcuuuu uuugucccccu ccgcuuucuc   1320
uuuuuuaagu aucagauuag acucacagau uuuuaaauau uccauguguu uuaguuggag   1380
ucauauucuu uugucucaac uuuagccaaa gagaguccuu uaaaguugac ucuuauauug   1440
ucuugacaaa aauucauuag ucuuuugaac gaagccucaa agcuugacuu guuuucuagc   1500
auaagauguc uuagacuuac cuacauacuu caugcccaua cuuggaauaa accauuucuu   1560
uaaagagccc agguuccuuu uaguggggaa ggcauuuaga uaccaaaaac uggccacugg   1620
gcaucauugc ucucagagua ucauugccac uagucucuca guagacaagu uagaaaaaua   1680
uguauauauu uaaaccauga guucauauug uuauuuccag uuuaauuaua acauuauggg   1740
guaaguaaau aguaucggau uuuuacuaag cuucuuugau uuugcacuug uauuuuuuuc   1800
uuacauagaa aaccuuuauu auuaacauua aaauauuugu uuuauccuac aauauacaua   1860
caauaauuug aaaaauaaua cuugaauuga uauuaauagu aacaacaaca gcacugcugc   1920
caaacauagu uuaaaguuuu auuucagguc uuauuuucuu cagaauauau cuugcugaga   1980
auguauaggc aaaguauucu acacuuacuu gaaauaauug ucuucaugcg guuauguuau   2040
acauuugaua uauaguuagg cucauuuguu uuucauuuuu uuuauuuuag ggauuuuuuu   2100
ccuuuauuga auuuuaauau auacaauauu uauauaugca aaauauuuaa ucagagaaau   2160
cuuaauucug gucuuacgcc uuucauauua uucugcucca cccucuguag guaacuuauu   2220
aucuuucuca uguuuccuuu uuggaaacau aaacaaagac aagacagguu acaugacaug   2280
uauacccuuc ugcaccuagu uuuauaccuu accuuguagu uuauuuuuaa gcauguaaau   2340
guucaauguu caugacuaaa uuuggacagg aucauaggaa cacagaauuc aaagugaaau   2400
uaaaaugggc uuggguucuu uacuuuccac uuuaaagguu guaaugggug augucaggcu   2460
aauaaaccua uuuucagcuu gaucuaaagc uuaauacuga gcaucaagaa auucuuuaau   2520
aaauauaagu gauauuuauu cagacaugua auaaggaaau guucaugucu uauuuuugug   2580
uuagauuuuu uuagaaucua cuuuuguuag aguuuuauaa auacaguuag uguuugagau   2640
agaaagagaa aagaauuagu uuucuuccuc uucuaccugc ucaugaacuu gauuuuuuuc   2700
```

```
ucccaacaau ugaagagcca agaaaaaggg agauucuuaa gagaugggaa auagaaucuc   2760
aucuaccccu guuuccccca gaacagugaa acugaaucuu aaggguaaga uagaauagug   2820
uguacuuaac uuagauggag aagaaaggcu gccaaaauga gaucugaagc gcuauuacaa   2880
auauuuccau cguuacugua cuucagaaug aauuacaacc guaaguuuuu uuacuuccuc   2940
auucauaaau uugauuauuc cuuauaccac uucucagcuu ucaucauucu uuauuguacu   3000
uuucuaugua auguuugccu auuauacagc aacuuaagag aacuguaagu uuggacauuu   3060
cauuuuggug uugauaauag aauaucuuug aauaguucua uaguugauga guagaaccau   3120
gaaccaagua acuuaaaguc cuugauguua uuuauuacag agaacuauaa uagaagcucu   3180
cccgcuaaug uuuccaucau guguacaaaa aguuuucuug uuauuaaagc uaguccguuu   3240
aacuuacaau aagcauaaau agcuaagcug ugaaaguuac cugugauaau gcuaauuuuc   3300
ccauuuauua aaaggcaagu uguuuuccga ucauaagaaa uuuagaaaag ccauccaaag   3360
auaaauuccg agugauauau uccugcuguu uguuauguuu ucucaaauua auugaguuuu   3420
auuuuacaau gacaggaguu auuaaaguau uuuauuuuua uuaugauuaa gauuuucaaa   3480
guaacauuuc uuauaugaaa gaaauuaugu uaaugcaugu uuuucuuaca ugggaaauca   3540
uauauuuuaa aaaugauuuu aaaauucguu uuacuuuaag uuguauuauc uuucucaaaa   3600
guggcuagug cuugaccaga aaaaaagaca ccagcauaac ucaguguauc uuuauuuaca   3660
uag                                                                 3663
```

<210> SEQ ID NO 85
<211> LENGTH: 5838
<212> TYPE: RNA
<213> ORGANISM: Homo sapiens

<400> SEQUENCE: 85

```
guaaguuugu gugauucuug aaccuuguga aauuagccau uuuucuucaa uauuuuugug     60
uuuggggga uuuggcagau uuuaauuaaa guuugccugc auuuauauaa auuuaacaga    120
gauauaauua uccauauuau ucauucaguu uaguuauaaa uauuuuguuc ccacauaaca    180
cacacacaca cacacaauau auuaucuauu uauaguggcu gaaugacuuc ugaaugauua    240
ucuagaucau ucuccuuagg ucacuugcau gauuuagcug aaucaaaccu cuuuuaacca    300
gacaucuaag agaaaaagga gcaugaaaca gguagaauau uguaaucaaa ggagggaagc    360
acucauuaag ugcccauccc uuucucuuac cccuguaccc agaacaaacu auucucccau    420
gguccuggc uuuuguuccu uggaauggau guagccaaca guagcugaaa uauuaagggc    480
ucuuccugga ccauggaugc acucuguaaa uucucaucau uuuuuauugu agaauaaaug    540
uagaauuuua auguagaaua aauuuauuua auguagaaua aaaaauaaaa aaacuagagu    600
agaauaucau aaguuacaau cugugaauau ggaccagacc cuuuguaguu aucuuacagc    660
cacuugaacu cuauaccuuu uacugaggac agaacaagcu ccugauuugu ucaucuuccu    720
caucagaaau agaggcuuau ggauuuugga uuauucuuau cuaagauccu uucacaggag    780
uagaauaaga ucuaauucua uuagcucaaa agcuuuugcu ggcucauaga gacacauuca    840
guaaaugaaa acguuguucu gaguagcuuu caggauuccu acuaaauuau gagucauguu    900
uaucaauauu auuuagaagu aaucauaauc aguuugcuuu cugcugcuuu ugccaaagag    960
aggugauuau guuacuuuuu auagaaaauu augccuauuu agugugguga uaauuuauuu   1020
uuuuccauuc uccauguccu cuguccuauc cucuccagca uuagaaaguc cuaggcaaga   1080
```

-continued

```
gacaucuugu ggauaaugua ucaaugagug auguuuaacg uuaucauuuu cccaaagagu   1140
auuuuucauc uuuccuaaag auuuuuuuuu uuuuuuuuug agauggaguu ucauucuguc   1200
acccaggcug agugcagugg cacgaucucg gcuuaacgcu uacugcaucc ucugccuccc   1260
agauucaagc aguucuccug ccucagccuc ugaguagcug ggauuacagg ugugcaccac   1320
cacaccagcu aauuuuuuuu uuuuuuuuuu uuuuuuugag gcagagucuc gcucugucac   1380
ccaggcugga gugcaguggc gccaucuugg cucacugcaa gcuccaccuc ccggguucag   1440
gccguucucc ugccucagcc uccugaguag cugguaccac aggcacccac caucaugccc   1500
ggcuaauuuu uuguauuuuu aguagagaug ggguuucacc uuguuagcca ggauggugug   1560
gaucuccuga acucgugauc cacccgccuc ggccuccuaa agugcuggga uuacagaugu   1620
gagccaccgc accuggcccc aguuguaauu gugaauaucu cauaccuauc ccuauuggca   1680
gugucuuagu uuuauuuuuu auuaucuuua uuguggcagc cauuauuccu gucucuaucu   1740
ccagucuuac auccuccuua cugccacaag aaugaucauu cuaaacauga auccuacccu   1800
gugacuccca ugugacuccc cgccuuaaaa acugucaaaa gcuaccgguu accugaaggg   1860
uaaaagucaa guccccuacu uaccucaugu caucuagagc aagagaugaa cuagcugagu   1920
uuucugacca caguguucuu ucuuauguau guucuuuugu acgugcucuu uucuauauau   1980
agggaaccau uucucucuuc caguuguuuu gcucagugaa uuucuauucc uguuucaaaa   2040
cuuguucagg cauuaccuuu uuuuucuuaa gcauacuuuu uuuaauggaa caaagucacu   2100
ccugucuaca cuaguucugc aucuuauaca uagguuuugu acauaguaca uauuuauauc   2160
acaucaaauu auauguguuu acauaucugu cuuccuuaau ggaauauaag ucuuuugaua   2220
uaaggaacua uuuaauuugu uucugugugu ugaguaucuc cuguuuggca cagaguucaa   2280
gcuaauacau gagagugauu aguggugqag agccacagug cauguggugu caaauauggu   2340
gcuuaggaaa uuauuguugc uuuuugagag guaaagguuc augagacuag aggucacgaa   2400
aaucagauuu caugugugaa gaauggaaua gauaauaagg aaauacaaaa acuggauggg   2460
uaauaaagca aaagaaaaac uugaaauuug auaguagaag aaaaaagaaa uagauguaga   2520
uugagguaga aucaagaaga ggauucuuuu uuuguuguuu uuuuuuuuga aacagagucu   2580
cacuguguug cccaggcugg agugcagugg agugaucuug gcuuacugca accucugccu   2640
cccagguuca agcgauucuu cugcuucagu cucccgagua gcuggaauua caggugccca   2700
ccagcacggc cggcuaauuu aguagagaca ggguuuugcc auguuggccg ggcuggucuc   2760
aaacuuugga ucucagguaa uccgccagcc ucaacuuccc aaagugcugg gauuacaggc   2820
augagccacu gugcccagcc uguuuuuuuu uuuuuaaagg agaccaguga aguuucagga   2880
ggagggaaag aaaauuuaga guuacuaggg agagagugau gaagauaaga gaugaaagug   2940
guaauaaggg aaauagcaaa auaucagggu aggugggaga aaaagagauu uguaacaaac   3000
aauaggauua uccugugaaa aaggaugaaa ggaagaaaaa aauggauaga aagauauuua   3060
aaacacccuc agccuccugu uuucccuccu guguauucau aguauauaaa acuauaauua   3120
uguacuuuac uuaaaaaaua uauuauuauu accuuaucgu gcuuauuuaa ucauagcaug   3180
uccucuuuuu agucucauua cccuguuugu auuauucuuc auaacacuua auaccugaca   3240
uuguauuaua uauuggcuua uuuuccaggu acuccacuca aauauaaguu cuaggauaua   3300
auuuauuuau cacugaaauc cauugcuuag aguaccuggc auguaguaaa uaggcauucu   3360
guuuuuucaa auaaaaaaua aaggaacuua agauauauau uuauguuaua ucgccagccu   3420
uuuuccucac agcucuauuc uguuguacag aauuaccuac uuuacaauuc cuguguuuca   3480
```

```
aggggaucuc aaauuuaacg uguccacaau gaacuccuga uuucuguuuc ucuccuaguc   3540
auucuuauuu caauauaugu ucaguuaccu aaccagcuag ucaaggcaga uacuuuagag   3600
uuauucugua gucauucuuu uucccuacca uuuuuguuuu ccaaauguaa uuuaugugug   3660
ucuucuucau ccucgcagcu cuaacccuug uccaaaccag caucaucacu caucuggagu   3720
uccacaaugu cuuucuggcu aguuucccug auuucucuau ugaccccuuu auucuccaca   3780
gugcagccag aaugauuguu uaaaacuucc uccuuaaaau cuuuaaauug uuuucuuuua   3840
uacguuaagu uaaauuccag uuccuugucu uggcaugcca ugcccugccu ggugugggccc   3900
cugaugucu cuccaacuuc auguuuuacu acuauugacu cuuauuuuug cuuacucugc   3960
uugggugcuc caguccucca aaucauuucc ugcuccaauc auuucaauca uuuuuuccuc   4020
ucagaucuua uaguauucca aaugcuuucu uccuuuggag caucuggguu uacuaauaaa   4080
uacuucguac cucacaguuc agcuuaaaua ucaauuauuu ggugguuaag acauccuuca   4140
accgcucuau cuaaauguuc cuuucuauua uucacuggcu caguacucug uuuuuauuuu   4200
cuuucuaaau gucaacuuuu uuuuuuuuga gucagggucu cacuguugcc caggcucgag   4260
ugcaguugca caaucauagc ucauugcagc cuugcccucc ugggaucaag uaauucuccc   4320
accucagccu ccaaaauagc ugggauuaca gguaugcauc accaugcuca gcuaauuuuu   4380
uguguuuuuu uguagagaug aggucucacu uuguugccca ggcuggucuc aaacuccugg   4440
acucaaguga uucucccacc ucagccuccc aaagugcugg gguuacaggu gugagccacu   4500
gcaccugguc gauacugacu uuuuuuuuuu uuugagaugg aguuuugcuc uguugcccag   4560
gcuagagcgc agugguguga ucucagcuca cugcaaccuc caccucccag guuaaaggga   4620
uucuucugcc ucagucuccu gaguagcugg gauuacaggc aagugccauc augacuggcu   4680
aauuuuugua uuuuuagcac uauguuuagu acuguguugg ccaggcuugu cucgaacucc   4740
ugaccucaag ugauccaccc accucagccu cccaaagugc ugggauuaca ggugugagcc   4800
accguaaucg gccaacauug acauuuuuag uagacuuuuu guuuguuuac uugcuuauua   4860
ucugcugccu uccacacucu ggcgaaaucc ugccacccac ccacacacac auaggcacug   4920
aaugggcaga acucugaagg ccagaauuuu auauuucuuu ucacuguaaa caucaucauc   4980
ugucacugau ggcacacuag gaugcucagc aacugugugc augaaggaag uaagcacuag   5040
uuugugaagg cugcaaaacu cuugaguauu cuaagaguuu uggccaaaau gaauguacag   5100
cuuuaguggc agaagcuaau acucagaaau ugaggccgua uauuggauaa cacaggauuu   5160
ggaugauuau uuuaaaauaa uauuuuacau uguauauaug ugugugugug ugugugugug   5220
ugugugguaug ugugugugug uguauauaua uauguaugua uguguauuag uccguucuca   5280
ugcugcuaug aagaaauacc ugagacuggg uaauuuauaa aggaaagagg uuuaauugac   5340
ucacaguucc acagagcugg ggaggccuca gaaaacuuaa caguuauggc agaaggggaa   5400
gcaaacacau uuuucuucac augguggccg gaauuagaag aaugugagcc gagcaaaggg   5460
gaaagccccu uauaaaacca ucagacaucg ugagaacuua cuauuaugag aauagcgugg   5520
gggaaaccac ccccacgauu caauuaccuc ccaccaaauc ccucccauga cauaugagga   5580
uuaugggaac uaugauucaa gaugagauuu ggguagggac acagccaaac cauaucagua   5640
uguauaugua uacaaguauu auauauauau guauguguuu guaugcauac auguauuaua   5700
uauggaggaa auucuaauuu uguaaaaaac uggauuguga guuuuaagga gauguuauau   5760
aaaguuaaga caaugucauu uugugguauu ggucugaauu acaauguagu uucuuaguga   5820
```

uauuuuuccu uuauucag 5838

<210> SEQ ID NO 86
<211> LENGTH: 2912
<212> TYPE: RNA
<213> ORGANISM: Homo sapiens

<400> SEQUENCE: 86
guaaguuuua ugacucugau aauauaaaau gauuaacauc uaauaaugaa uauuucuuau 60
uuaaaguucc uuuuuuaugc uagauuaaaa ggaaguauuu ugacuaaaaa aagaaagaac 120
uuucugccua auaauuuaac uuaggcagau gaauaaaucu guacuuaacc ccaccaaagu 180
uuaguuuuca guccuuaagu uagauuuguu ucuaaugaaa ucauauaugu uaaaaauuua 240
ugacuaagua uuagcuacuu ugaaccguuu aacaauuaaa acugaugaua uuuuauuaau 300
gguauuauga guucuuucac ugagugcaag uuauauuagu uauauaucac uugauauuuu 360
uaaauuaaaa gauaccagga aacagcaaag aaaaugugaa aagaaguugu auuucucaua 420
guuuuacuac uauauuacug uauauuuuug cuccuauaug cuuacauauu uuauauauuu 480
uaaauuauua uaaacauggu uuuauacugu auuuagauag uaauaucaaa aauauuuuua 540
uggccggcgc aguggcucac accuguaauu ccagcacuug ggaggcugag gagagcagau 600
ccccuggggu caggaguucg agaccagccu ggccaacaug gcaaaacccc aucucuacua 660
aaaguacaaa aauuagccag gcguggugge aguugccugu aauuccaucu acucaggagg 720
cugaggcagg agaauugcuu gaaccuagga gucagagguu gcagugagcc aagaucauac 780
cacagcacuc cagccuaggc gauaagagug agacuccguc ucaaaaaaaa aaaaaaauuu 840
guuuuauuca ucauacuuau aaauacuuau acaauagccu aauguguuug agugauuaaa 900
ucacuagcuu uuuauauuuu ugcuauugcu uauagugcca cagugaacau uuucauguau 960
aucuaacaga gauauuacug ucucagaagg uauugaaauc uuuguugcuc ucauuagagu 1020
uuuccauauu aauuuuucaa acaguuauau aguuuauaag auuuucauaa uuuuaucuca 1080
uauauugugc uucauaauuu ucaaauaaau uugcugcuuu cgauaaugua uuuucaugua 1140
uuuguuuccu agacguuaga gcuauucaag guuuuuauua cuaaauagag cuguucucuu 1200
aaauugguaa ugagauacuu gguuuagaga agccuaacac ugggaaaucu uacauaagcu 1260
acuuuuagaa auguaauuuu uagcucaaua agagauuaaa uaugaauuga cuuuugugua 1320
guauuugcau ggaagaaggu accauuuaaa ugaagacaug agaguauuac guacaauuuu 1380
aguagguucu uuuuauuuua ucaucuuuau uuuuaauaaa ugcugaauuc ccuacagaaa 1440
uucuuuaauu uuuacauauc uugaucucuu ucauauaugg auuuauauca ccgaaguuuu 1500
aagaguguuu cccuauuccc uguugcccuu auaucuuugu uuaaaaaugu cacaucauua 1560
gcuuuuuuuc aucuaggaau uuguuagugu ugggcuguug ugcucuaccc ucucuuuaag 1620
aaaacuccaa acccaaaaac auacaagaug gcuagucugc uucagccuuu gugaugugcu 1680
uuucucuucu aaucagaguu uagcacaaua cagaauggag aaggacuccu uuauauauug 1740
guauuuauug caguauuuuu cuacauggug ccuaagguua cuugaaugag ucuuuauucc 1800
auaaugaacu gauuuacuaa ugcuuuuagc accuguuagu gauccauuau uguuaguuac 1860
uugauuacug cuugccacag cuauucuaaa auaauacauu uuaaagauaa auacagaaca 1920
uaaugaagua cuuuuuaaaa cugagauaga gaccaauuuu uuuuucagga aauguauauu 1980
acuuugagaa aacucaguua uaaaacuuga acuuaugaag cuggaaaaac aggagggggc 2040
auuauuggua uuguaaaagg cuguuuacaa agugaguugc ugcuuaguuc cuuuaaguaa 2100

```
uuggcuaccc uaaacacauc aguuuuaagu ugcugaaaag caaaacacuc uaccaaauuu   2160

uguuuuuuuu cuagaccaug uuuacaaagc aaaaguaugu uuucuucccc cccccucaaa   2220

aaaugacuaa ugacacuccu augcgaugcc uuuuuauggu aaauugaggc uuuuaguucu   2280

cuuuccauuu agccacagac uuuugugucc aaagacaagc ugcguaacug cauauauaag   2340

guuaaggcau aacuacuaau aaaagaaugu aaaauauuug auauuagguc uguacaaaga   2400

ccaaauaaua cucaugauua gacaagauua uauuugguag aaucuaucca ucauauggcu   2460

ucagauuuua cuuuucagcu uggcuuugug agacuuuaaa aaucaaguca uugcacuuau   2520

auucacaaag ucacauugcu uuacugcauu gcuucucaua caguuuaucu ccuuucagua   2580

aaauguuuac uugccauuuu uaaaauuucu uauaugugac acuucuacac uaaguccuuu   2640

auguuguuag uuccacaauu cugugaggaa uagguuuuuu uuuuuaauca uuugauugau   2700

gaagaacauu aaguuccaca gagauuaaau gguacaggca ucacacaggc aggaaguaac   2760

agagcuaaga uuagagucca ggucugaugg aauucagaaa gcuaaugugc uuuccaugga   2820

acuauaaugc uuucuaauau acagcaucua aaauaucuga gguaauuuua auauaaacag   2880

caugagauug acuuaaauau uauugcaugu ag                                 2912
```

<210> SEQ ID NO 87
<211> LENGTH: 937
<212> TYPE: RNA
<213> ORGANISM: Homo sapiens

<400> SEQUENCE: 87

```
guuugauauu auaaguuuua ucauacaauu auagaauaaa gaauuaguuu ugguagacau     60

uguauuauug uuaagugguu ugucuggauc ucugaaauau cuuauuaaua uagugccuau    120

guuuugugua auaaauaaau aaaagauuua aaucugaauu guuuaaaagg aaagcagaua    180

uuucuguaag uuuuucucac caauguuaua uuauuagauu uaauuuauga aauguuauuu    240

acuaaacaau ggaauugccu uucaccacca ucccuucauu uaacaaauau uuauucauug    300

ccuauuacau gucagacccu guguugggac uggcaguaua gcaagaaaca aaauagacaa    360

uaaucucuac uuucagggac uuuacauucu aauuggugu uuuauauauu uuugaugugg    420

ucagaaucau uaaacugugu ggcaguaaau auaguuugca aguauuuaac aauuuaugau    480

uaaacacaac ucuuacagug uuugcuuacc uugagauuua auauauuuuc aaagcauuua    540

uaucauuuuu guuuuaacua ugucacuaaa ucuauaugag uaagauuuua uuaacucauu    600

uggauuuauu uauagaugau acaauugaag uaaaauauaa ugagcagauu gcauucuaag    660

caaaguaaga auauugcaag uucagauauu auuagauaau gaguugccua auaaaaauga    720

cuuuuggugg auuggaauau aaccagaguu uccauaguuu guuucugauu cuuucauauu    780

uuuuacccuc cuucagucug uucuuaacac uucacacuua auauaauaug ugaacuaagg    840

ccaaguaaag aggauugcag uacuuuaaaa gcuaaauuac aaagaaaacc ucaccaaaaa    900

uugauguauc ugaacauuuu uuguuacauu uccuuag                            937
```

<210> SEQ ID NO 88
<211> LENGTH: 1841
<212> TYPE: RNA
<213> ORGANISM: Homo sapiens

<400> SEQUENCE: 88

```
guaagugcau auaagcauuu uagccauuug acuagaugua ucuucuuuaa uuugucuuua     60
```

```
agaaacccaa uuacagguau acaauucuua guaguaauug auacugauuu cuuuuuauaa    120
gaacaggauu aaguaauauu aagaucgguu uuaacagggu uaaauaauaa uauugacgag    180
aauaauauug uuaaagagga agugaccucu caagauuugc auuuuuuaga guucaggaau    240
auuauugcag aaagguccag uuccuccaca uauugauuuu uuggggaagg ggugauggag    300
gaggaauggu uguuuauugu auuuaaacuu aaguuucuuc auuuuaauaa gggaguaaua    360
guaccucuuc uaccuguuuc auaagguugc uguaagaaua uaauaaaaaa uucagauuuu    420
gauuuaguuu acauuuaucg ggcaucuacu auguacuagu cacggugcaa gguauuaaac    480
auauauugac uuguacaauu auacuuaacc uugagguuau auuuuuguuu ucauuuuaca    540
ugaagaaaua ugcccagcua guuuagaaca caaaauauau auaaggagua aauacugcgu    600
gcuggcuggg cguggugaca ugugccugua gccccagcua cucgggaggc agaggcagga    660
gaaucgcuug aucccgggag guggagguug cagugagccg agaucgcgcc acugcacucc    720
ugccugguga cagagcgaga cucugucaaa caaacaaaca aacaaagaaa aacaaaacaa    780
aaaaaccgug ugccagcuau augcuguauu uucauucucu uuuguaauua ggugauauuu    840
caguagaaaa guauaaggag cacuuaguua aucugucaag cauaaauagu aaaaauauuu    900
uauggccuac ucauaaaaau auaaccauuc cuuuggagcc uugauaguuc ucuugggaau    960
aucaguuuuu gacaucuuuu ucacuaugaa agacccuuuu uuuuaaaaaa auugauccuu   1020
ucuucucaug gaccucuuuu gauauaaacu aacuuauaau aguucauuuu aaucauauuu   1080
uguuaaucau gcaacuggca augagagccu cucaucagua ugaggaaacc ugccuuaucu   1140
auaauacuga acuaaaauua uucuaaccca aagcaaagaa acuuuacauu uugcuuugcc   1200
uguauuagcu uaucacagua uucaugaggg aauuugaagg acuuauuacc auuaggcuau   1260
cucuuuuuuu uuuuuuuugu aauuuuauua aaugcauguu uuguuucuuu ucacauuacu   1320
gauaacuugu agauuaaaac aaaucaaaac augcauuaau ccaucuaagg auccuagaaa   1380
uuuuacauuu cuguguucuu aacuguguga uggucuuaga uaaauguacu aaauaccuua   1440
uccuagcaua uuccaaauua ugacaauaaa uguuuuaugg aaaaaaguau gggaacagaa   1500
guucuuuggc uauauacauu uggaaaauac uauauaguaa guaugauuug agauaauuau   1560
auaugauaga accucuggga gcacugaaua uauguuagga auauucaaga gggaggaggg   1620
auguugagaa ugaaguuuuu uuuauauagc aaacaugaua accucugaug gaauuauguu   1680
ucaugaaaca guuuaggaaa uccuguuuua auauuucaua caaagaagag auagaugcug   1740
aaaacgaaug gcuuuuugaa aaagggucua gaaauuuuga auuuuggcau uuacuuagaa   1800
aguguacuua auuguuccug aaauaccuua ucauuuccua g                       1841
```

<210> SEQ ID NO 89
<211> LENGTH: 1240
<212> TYPE: RNA
<213> ORGANISM: Homo sapiens

<400> SEQUENCE: 89

```
guaugugcag uauuggcucu ucuacauaga auccacuuuu uucccuaaau uuacauuaga     60
uguugggagu gggauauguu auacuuuuug uuuguuucga gauagggucu cauucuguug    120
cccagggugg agugcagugg uacauucaag gcucauugca gccuucacca ccuggguuca    180
ggugauccuc ccaccucagc cucuuagaca gcugggacua caggcacgug ccaccacacc    240
uaauuuuuuu gcauuuuuug uagagacagg guuucaccau guugccuagg cuggucccaa    300
acuccugggu uaaaaugauc ugcccaccuu gacuucccag aaugcuggga uuacagguau    360
```

```
gagccaccau gcugggccau uguuacauuu uuaaucaaaa gauauaccaa ccagaggcug    420

uuauucuugu uaguuggaac cugauuagaa agcucuuuaa uuugaaauau uguucaguaa    480

uccaguacag cauuuaaaug ccuauagaug aauuaugcug cugaucaaaa uuaggacacu    540

gagaauugua guuaguaaau cuuuaauaac aauauuuucu cuuguauuua uauguaacuu    600

uuuacauauu cuuacguuau auauguuggg aauuauaaaa acauacacau uguccugauc    660

aguauuaugu uacuugcaau ggagguuaaa aaaaaacugu aacagucagg cauggugcu     720

cacgccugua aucccagcac ucugggaggc cgaggcaggc ggaucacgag gucaggaguu    780

cgagaccagc cugaccaaua uggugaaacc ccgucccuac uaaaaauaca aaaguuagcc    840

aggcguggug gcaugugccu guaaucccag cuacccagga ggcugaggca ggagaauugc    900

uugaacccgg gagguggagg uugcagugag ccaaaaucac gccauugcac uccagcuugg    960

gugacagagu gaaacucugu cucaaaaaaa aaaaaaaaaa acaccaguaa cauacccacu   1020

guuauucagu uacauuugga uuuuaaguuu guuugauucu agguuuuuuc uuuuacaguu   1080

cuuugguaau uauuuguauu aaagcaaagu uacauuuuug uagaucucau gugccacugu   1140

guuaaaacuu ugcuuaguaa auugugaauu uuaaaucugu gauaacuuuc acuggaaaaa   1200

uuugaaacuu acuacaaaua uauauuuuuu uuaauaucag                         1240
```

<210> SEQ ID NO 90
<211> LENGTH: 1087
<212> TYPE: RNA
<213> ORGANISM: Homo sapiens

<400> SEQUENCE: 90

```
guaaacauuu aaacuugauu uuuuuuuuua agagacagua ucuugaucug uuucccaggc     60

uggaguucag uggugcaaac auagcuggaa cuccugggcu caagggacuc ucuagccuca    120

gccuccugag uaguuguagc uggcaguaca ggugcacacc accauaccua ccuaauuuuu    180

uaaaauuuuu aaauuuuuuu guagagacaa ggucucacuu ugucacccag gcuggccuug    240

aacuccuggc uucaaguaau ccuccugcuu uggucucuca aaagugcuga gauuacaggc    300

augagccacu gugcccagcc aauuuuaaau ucauuaucuu caaaagaguu acaugauaau    360

uucuuaauau augccuauau gaaaaaugcu uaagauacaa auuccaauua ugauucauua    420

auuuagauuu uauaacuuag caguguuggc uauuugaaug ucuauuauac guaaaaauaa    480

aauuaggcuu uucuaaccaa agauuuuagu gggaauguuc agauuguaua auagcaaaga    540

auuuuaauua cuauaggaaa auuuauauua auuaaacacu aauuauuaua uuuaaacauu    600

guaguaguua ucaguugauu ucuacuguuc auaauuaucu uugaucuaca aguagugggc    660

ccacauuuac uuuuaauaug guuuaaucuu cauuuagaaa gaauuaaaug aaaaauaauu    720

aucuugcaac uacauccugu ucucuaggcu agaaacauuu aggauuucug uuuuugaaag    780

uaauaccaaa guuccaauga ccugcuuaua gucaguguuc aauaaacgua uaacaaauga    840

aagugaauau uagugauguc cauuccaaca uaauuugaag auuuuuauug uaaaaauccca   900

cauauuugua gaaaagucua uggaaauccu aaauaagauu uugucaugua guuugacaaa    960

agauaacauu gugucuuauu uuauuuuaga auggccauua cuuucaauua aaaucauuau   1020

caucaaugga ggaauguuau uuguuaauau agcauuuaua uuuguguaua uaaauuguaa   1080

aucuuag                                                             1087
```

<210> SEQ ID NO 91

<211> LENGTH: 1281
<212> TYPE: RNA
<213> ORGANISM: Homo sapiens

<400> SEQUENCE: 91
guuuuauuuu auauuuauuu cauuuuuuuc ccuaaguuuu uuuuuuuuuu uuuuuuuuuu 60
gagauggagu cucacucugu cgcccagacu ggagugcagu ggcgugaucu cggcucacug 120
caagcucugc cucccggguu caugccauuc uccugccuca gccucccaag uagcugggac 180
uacaggcacc cgccaccgug ccuggcuaau uuuuuguauu uuuaguagag acgggguuuc 240
accauauuag ccaggauggu cuugaucucc ugaccucaug auccgcccgc cucggccucc 300
caaagugcug ggauuacagg cgugagcccc uaagauuuua aacaagaaua uugcacaaau 360
gacuauguua uccuucuaau uaagugcacc uuccauuacu aauugauuau auaauaauuu 420
guuuuuuauu uucuaaacua uucuaaaaau ucauauuuau uuagcuuuua uaacaguagu 480
cuuaaucuua aaaacggcaa uacauaagca accucauuug guaaguuaau uuuuauuuug 540
auauugguua uuugacuuuu cacaguucca cguuucuacu ggcucucacu gauagaguaa 600
gaagucagcu ucuuauagaa uaaaguauau acuucagaga cagaugaaau ucgucaaaca 660
uaugacuguc ucagagauug uucccccugc uuaaaauguu cuuacccuag auaccuuugg 720
uauuuacacu gucagugccu gcaggucuua gcucaaaugu cuuaccuuau caguguaucc 780
uucaccagcc accuaauaua caacaguaaa uccuacuauc cagauuccua aauagagauu 840
aauuaacuua auuuuucucc aaagugcuug uaaccuucug acguauuaca uacuuacugg 900
uuuauuauug acugucuuuc cuucgccaga augcaaguuc cguggugaca cggacuuggu 960
uuuguuuacu gccauguuug uauuuccuag aaugaugcuu ggcacauaau auaugucauc 1020
aaauaucuuu cguauagcug aacggaugga uggauggaug gauggaugga uggauagacu 1080
gaaauccuua cuucacaucu gccuuuguga ucuuacacaa guuacuucac cucucugagu 1140
uuguauuuuu uuccauaaaa ggaaaauaau uacaguuucu ucaauguguu gugaggauua 1200
gauaagaaaa uauauauaaa augccuguua ugugccugau gucuucgugu augugucuga 1260
cacaaauugu ccuuuuuuua g 1281

<210> SEQ ID NO 92
<211> LENGTH: 217
<212> TYPE: RNA
<213> ORGANISM: Homo sapiens

<400> SEQUENCE: 92
guaugaauga uuaaucuugu uuguuacucu guagcauagu cuagaguguu aacucacaga 60
aauauuuccu guaucagaug uaauuuuaau ugauguuaua uuguauauuu aaaauauaag 120 aggguuuaa ucuauguuuu aucauacagc uguaaaaauu aauaguuacu cucaaugcug 180
caacugcuuu uuuaaaaaac auacuauuuc uuaauag 217

<210> SEQ ID NO 93
<211> LENGTH: 1186
<212> TYPE: RNA
<213> ORGANISM: Homo sapiens

<400> SEQUENCE: 93
guaauuagaa gaauuugcau uuugauuagu guauuauuug guauguuugg ggggcuuucu 60
aaauaauauu ucuuuaugag ggcaaugcau agaaugauga aucuauugcu aauuucacua 120
uuuuucuauu cuccuauaau guuucuaaua gccaauaaug aacagcagau auaguuaauu 180

```
ugaauucacu auuuaauuau uaguugguac cuuucgguac acugaauaug aaaggaaaua    240

aaaagcauuu aauuguaguu cuaugagcaa uauauucucu uauaugaucu cuuuauucuu    300

acuuuuuugg uuuuauuuug aagugcaugu uacauaaucu augaaucaau uuucaguuca    360

uugccuuuaa ugcaugguua aaggguugaa gguaaauuag aaauuacuuu cuguuuuaac    420

cuagaucuug aauuugauua guaggugauc aaaucuguca ucuucauuaa auuauucaga    480

aaauaaugua aacugaaugu guuuucauuu uaguuuucau cuaaauaaac ugcaaauaca    540

uuuaaaauau acauaaagaa guuuuucaag uaaaacugua cauuuuuaau cauuucagga    600

aacguagauu uucuucagua auuuuaagau uugucauuua ugugaauugc cauugaauua    660

cuuaauuuaa aauacucacc uuaauccucu ugaagaguaa aaauuuuucu guuuuuuucu    720

cuuuguuuua auaagcugcg gauuuuauau ucguaauuua uugaguuggg ccucuaaaau    780

uccaguuuug uacuuaacug acuuauagau uagucuccua augcucugcu agucaaugga    840

ccaaaauaaa agaaauaauu uauuacauau ucuuccuaaa ucuaguacca ccauacaugu    900

auaauucuaa acuguaauau cucaauaaag uaccuuaauu aaauuuuaug uucaucauaa    960

caaugaaguu ucuagcauau guaauagucu uauaaauaag caugcaaaua acugcuguca   1020

auuagaauua gucaguuuaa ccuuauuaag uaucaaaugg cuauuguaca uaugauguga   1080

aaaauaaagu gaauuuuuuu uggcuaauaa cuaaucuaaa auucagauga agcauuuuaa   1140

agggaaaaag auacuuuaau gauuuauuau aauuuaauca uugcag                  1186
```

<210> SEQ ID NO 94
<211> LENGTH: 631
<212> TYPE: RNA
<213> ORGANISM: Homo sapiens

<400> SEQUENCE: 94

```
guauuuuauu auauuaugag uuaugcuguu auccauuagu uuuuuuaagc aaaugcuaaa     60

uauuauuuua cccuaaagug guauuucuuu ucuugcuuuc aaaugauucu auuuaagaau    120

uguuacuugc augugauugg auuacaccuc ugucaguaaa acuggaaguu uguguacaug    180

uaucuuucua uuauacacug acuaaaccac gaguagcuau cauggugaaa ucauaugauu    240

uugaaaaaua uuuuaauuga guuuauaggu gaggauugag gcaauagggu ggaaugaaau    300

auaucacacc gguaaucagu agaaaucaga uuuguuagaa cuucgugggg gaaagcuaac    360

auuuaauuuu uucuagaagu aaguuaaaag augauagaua caugucauuc uaauguuaag    420

aauaaauuau gaacugaggc ugggcuuguc aacuugaaca uugucugagg ggacaugcau    480

accagucuag auacauacau auauggagau acuguuucuu ccucaucuca aaggaauuuu    540

agaagauuga agagaaaaua uauaaggucu ucaaaaugug aauuuguuuu aaucacaauu    600

uaagauauag uuucgauuuu cuguaaaaca g                                   631
```

<210> SEQ ID NO 95
<211> LENGTH: 616
<212> TYPE: RNA
<213> ORGANISM: Homo sapiens

<400> SEQUENCE: 95

```
guaagauucu aagaacuuug uuccauucuu uauugauuuu ugugaccaug uaaauuaaaa     60

uucagcucuc uucuuuuuug gaauggaagu uacccuuuuu guugccaaaa uaaucuucug    120

aaaacauagc ucugaucauu cuuccuccug uagcucaccg cuguucacaa aauuauauuu    180
```

```
auaauucuua gccauguacu caaucugcua ugaaccuacc ugccuuucuu uucaaauucu    240

acucacugug aguuuagcua uaucuaacuu ccagaauuca gcucauauuu gccucuuuug    300

accauucugu uccauaugua ugaaaugaca ugucuuucau cuuuuaaugu guaaccuuag    360

cauauuugag cauuaccucg uuaauucggu caacacuuau ugaucuccug cuacgugcag    420

acauuuugcu agcuauugua aauacaaaua auaaagucug cauuuccugu cuucuuuaag    480

ccuucauugc cuauuaaauc auuacauuuu agauuagaua uuauauuuug aucauuugag    540

gaaccaaauu aaaaauaugg aauaaguaug gcauugaauu auacaugccu auugcuaaua    600

uauucauauu uuauag                                                    616
```

<210> SEQ ID NO 96
<211> LENGTH: 2635
<212> TYPE: RNA
<213> ORGANISM: Homo sapiens

<400> SEQUENCE: 96

```
guaagucuuc gaaauguauu guaaaaauag gcaaaugaua agugauauaa ugaagauaaa     60

cauaaguguu ugcuaugcca ggcacuguuc uaagacuuuu aaguauauug ucucauuuuu    120

auccucagga cugcugguua cauauguuau cauuuucccc auuuuaaaga gaggauaugg    180

ccucaggaau gcuuaauagc augucugggg guagaugggga aagccauaau uugaaacuag    240

ucagucugac ucaaaagcca auacaaauuc uuuuccagaa ucucauuuuu accuucuuug    300

agccucaguu ucaucuuauu uauuuauuuu uauuuuugag acaaggucug gcucuauuuc    360

cuaggcugga gugcagugac auaaucucag cucacugcaa ccuugaccuu ccaggcucaa    420

accaucuucc caccucagcc ugcagaguag cuggcacuac aggcaggugc caccacaccu    480

ggguaguuuu uuuguauuuu uguagagaca agguuucucc auguugccca ggcuggucuu    540

gaacucguga gcucaaguga uccgcccacu ucggccuccc aaagugcugg gauuacaggc    600

cugagccauu gcacccagcc ucaucaucuu uaaaauggaa auaauaauac uuacccuggc    660

ccuuucaggg ugguuauaug aaggucaaau uauaccgugu augaaaguaa uuugaaaacu    720

guaaaauaac auacagauag aaaacuuuug auuacacacu uauaagagug ucugucauau    780

aauagagauu cuaaacauug uucaaccacu uuaucagaac guagauuuua aacucaaaau    840

agguuuauag uuagguaguu ucuaaucauu auaauauuau cucuaugggc cuaaauuuua    900

uuaucugaaa aaacaugaga aaauugaacu gcuugacuua uaauuccauu ucagcucuca    960

agccccugcu agagucuuug auucuuuacu cacuuauuca aaugccucug acagaauuaa   1020

cacuauuuuu gcuuugcuaa ggagcugcca cuguuaagaa auuacucucu aaaagaaaga   1080

aaauuggcaa cagcauaugu guauuuucag ucucuuuucc ucacucuauu aaauuuugua   1140

caagagaugu uauuuuuggu cuaguaaauu ucugucaugu uuuggaguau aaaauuacuu   1200

gugcuuuugc aucuaauuug ugggguguaga aaaucauaau cuuuugaaau accuuauaua   1260

auacauuuuu uugccacagg aaauacuuga aguuauuguu guguaccuua cgucauuuua   1320

guccaaaauu auacuugugu ucucugugug cauauuuuga uauguauuag gagauuaugg   1380

aucugugugua uuucuuaagu aaauccugau auuuucacaa uuugaugaug acucuuuaaa   1440

guuagacuua aguuuugcca aaagcaagaa gccucaaaga guaacauuug uucaugucuu   1500

aacacuaucu cccucuuauu ggucagaauc ucaguaugga ugcagugucc auaugcacaa   1560

caauauauua auucaguuua acagacuuaa ugcugaauaa gcaauaagau uaauugaauu   1620

aacuaaaucu uuugauagua uccacuucca uauauauagu uauagauaua augcuaguga   1680
```

auuugaacca uaaacaaauu aauaauacau gugauuucug ugaaaauuua uauuagucuu 1740
uucaauaugu caauauaggg caguauuucu caaauauaga ggaucaguuu uucaccauug 1800
ucccucuugg ggacauuugg cgaugucugg agacauuuuu gauugucaug gcucgggggu 1860
gcuacuggua uccagugggu agaaucaaaa gaugcugcua aacauccuau caugcacaag 1920
gcagccccac caccaacaaa gaauuaucca gucaaaaaug uuacuaguag uaugguuagg 1980
aaacuaucau auagaggaag caaucacauu uuacaagagc cauaauauuu aaaaugccuu 2040
uuuguucauu cucuguauau uugacuagag ucacaaaaua acuugauaag auuguugcca 2100
aaaauauuag aaacuagaag aaaaaugugu uguuaagucu aagaguaguu aaaugaaaua 2160
aagaauuauu cuucuuugga uuuggaugcc ugcaucaaga uuuagauugu aaggauacuu 2220
aggacugaac auuugcucua uaugaaauuu guauuaauca agguaugaau ugcagcaacc 2280
acucuauuaa uuacauaugu uuggccaggu gugguggcuc acaccuguaa ucccagcaau 2340
uugggaugcc aaagcgggcu uaucaccuga ggucaugcgu ucaaacuggc cuggccaaca 2400
uggugaaacc ccaucucuac uaaaaauaca aaaauuagcu gggccugaug gugcacgccc 2460
guagucccag cuacucagga aguugaggca aaaaaaucac uugaaucugg gaggcagagg 2520
uugcagucag ccgagauugc gcugcugcac uccagccugg gugacagagu gagacugggu 2580
cucaaaaaaa uuaaaaauua aaaaacacac acacacauau guuuauuuac aucag 2635

<210> SEQ ID NO 97
<211> LENGTH: 952
<212> TYPE: RNA
<213> ORGANISM: Homo sapiens

<400> SEQUENCE: 97
guaaguaaca acagaaaauu aucaacauuu aggaaaaaua uguggguagau ugcuuuuaga 60 gaagauuugu aaauuuauaa aagaugguag uauaaaucuc cguguuguaa uaaaaaguau 120
gagcuuuauc uuaugcuguu aaacaaggua uuuuagacaa ugcuguuuuu gugggcagau 180
auaguccaau uuaucuuuuu auguuuucgu caaucugauu ugugaauuau cuauaugaag 240
uuaggaaaaa ucuuaaugua cauuacaaaa auauaauaua uauuacauug uauuuucuuu 300
uuuucuacug gaauuuuaug cuacugaggc uauuuuuaac aaaugaacaa uuuugaacaa 360
uuugagggau ugagggaagu augauaauga caaaaaggga ugaaaaaagg gggucauaga 420
gauguuuuug ugagaaggag uuggucagug uauucugauu uauuaggguu uuuuuuaguu 480
uaucucagau uugaucuauu uaaauuguuu uagaagaugc ugguguuuuu cugugcuagc 540
uaugaaauuu augguaaac uuuaagccuu uccuaguccu uuuguugucu accuaaauuc 600
aauuaauuuc auauggaagg auguaguaag ugaguaauau aaauaucuaa aauuggaugu 660
uugaaaacaa aacauaccug uuuuuuguaa uagcuugauu uaaugcugag uucucaaaau 720
cauuauuaag auuugaacu uucacauuca augugggaaag aauugagugu aauuacaaaa 780
gauuuauuug aaaaaguuga guuguuaauu ugugaaauau guuccauuaa acucauaaua 840
uuuuagaaaa auaguaggaa guaauaaagc uuguuuauuu uuuauaucau auauucauau 900
aaaaugucag uuuuccuuua aaaauuacau uuuuuuuuug guuaauuuuu ag 952

<210> SEQ ID NO 98
<211> LENGTH: 1173
<212> TYPE: RNA
<213> ORGANISM: Homo sapiens

<400> SEQUENCE: 98
gugaacauca acacguguua auguaacaaa auuucugaua auuccuauug gaagagaauu 60
cacuaugaua uauaguaauu uuguugauga auagggaauu uauaaugcac uguuggugge 120 uagacauaga cacacacaug cauuuuucaa caauaagucu cuuuaugaua cucauuuacu 180
gauuaucauc uuggggauua ggaaaggaua ggccauuaug aacuacuguu ucuaaugaaa 240
uuaaauuuaa gaaauauuuu acuuaggauu uuuuuuaaga cuuuauuauu uuuuuagagc 300
aauuuuaggu ucacagcaaa auugagagga agguacagag auuuccugua uaucuccuac 360
ccugaaagug guacauuugu uaaaaauugau gaaccuauau ugauacauca uaaucaccca 420
aaguccaagu uuaccucuau uuuagcucuu gguauuuuac acucugugug uuuagacaaa 480
uguauaauga uauguaucca ucauuauagu auuauacagg guauuuucac ugcccuaaaa 540
aucuucugug ccucucuucu ucauuccuuc cucugcaccu caccaaaccc cuggcaacca 600
gugaucuuuu uacugucucc auaguuucac cuuuuccaga auauguuaua gauggaaaca 660
uacagugugu ccccaucauu cucaccauag gacagcuagg aacuccuuuc uaguggcaua 720
cauauugucu aguauuguaa guuacccuuu uauaucuuau cuuuguaaac uagguuagaa 780
auuacuucaa gucagagauu uguucuguac uacucuuaug cuucauagug uuuaaaacgu 840
ugucauauau auuguuauau acuuguuugu uuaauuaauu cagccaaaau gaaacgugca 900
uauuugauaa aauuuuguuu gugggguguuu guugaagaug aauugcuuua cacuaguuuu 960
uuuuuuuuuu cucaaagucg acuuuuuucc ucaagguaga cuugacauga auauggaaaa 1020
auauauguag uuuguggua uuuuuuuucu cuuguguacu uaaaaauuca gacugaauuu 1080
uucuuauaau gguauauuuu cuguuuuaug uuccuuuuau cauugauacu ucuugaagag 1140
ucaugaauaa uaccuuucuu uuucucuuau uag 1173

<210> SEQ ID NO 99
<211> LENGTH: 352
<212> TYPE: RNA
<213> ORGANISM: Homo sapiens

<400> SEQUENCE: 99
guaauuuuau auuuaacucu gauaaugucu gauuuacaau auagagguag uaguuuauuu 60
cuacuuuauc auuuuaucua ugguauuugu uaaaacugac uuucaaauca cuuugauuaa 120
uguaauuaau uucuuuugug acuucuauug uguuuauagu ucuagaguag cauauuagua 180
uguuguauua aaaugcagaa gcagcuacca gauuaucuua uguauuaagu gucauuuaga 240
aaguaugguc agugauagcu ucagaaaguu gcuauuauau aauugaaaua uuuacugucu 300
auuuuguuuu acauuuauuu guaaaaauau aaaguuacau uuuauuuuuu ag 352

<210> SEQ ID NO 100
<211> LENGTH: 5295
<212> TYPE: RNA
<213> ORGANISM: Homo sapiens

<400> SEQUENCE: 100
guaugugaag aaacauacug acuuauaugc uuaagguagu gacagaguaa guuaaauaca 60
uagcugauua acaguuaaua uacugccuua auuugaugac cuggcuguau uaauucugua 120
uuaauuuuga ggacuauaag caguauugaa uaacguagaa aagucuaagu uucuguucug 180
uaggaauuua gagucuacuu gaggagauac cuauaaugua acucuuauuu ggaaauuacu 240
acaucaauuu cauucaucuu ucugacauua gaguaccucu gaaguuccuu cacaccuuaa 300
cauauucaac uguguaucau uucucuccaa aguaaucauu uacacagguu ggugcuuuug 360
acuuuuggga cagaaagaua gacauuuuaa gauaccccac uuugacccaa auagguccuu 420
uuuaauccuu caggagacua ggcuguuauu ucagauagca aaguuauuug gaauaucuuc 480
aguauuugca guaauaauca guaaccaauc ugcucauaga uuaauucugu gggagaaauu 540
gcuuaaaauu uuauaguuca uaguaaacug uuuuguaaua aaaauuacug auugaaauaa 600
ccccaaaaaa aacuaaaauu ggcuaaaaug cguguaauua aauuuguuau ggacaauaaa 660
uuggagauaa cuuguuggua acauucaaaa uaucgaaagu gaacugggaa auguugaugu 720
uagcaguaau auuugccauu gaagaaaauc aguauggagg agcuaugguu aggaaaauuu 780
uuauuauaaa auuuacccag aaaauauuua augucuauaa aauaauuuca aucacaugaa 840
aauggaaaag aaaauucugu cuuuaaaggc auugaauaga aaauagguaa uggaauucaa 900
auuucuuaau agaguaugcu cccaaaauua uuuucuauga aaauucauua augucagugu 960
aauuuauuga cacuauuugc guggagucac aacaugcuug cugucagaag cuuugcuggu 1020
gaaaacugua agaucaaagu guccuuaauc uuuuggauuu ccaucuuucu aacucccuaa 1080
uuggggauag gccugaucuu aucccuaaau ggggauaggu uagaaacugg uauguuuguu 1140
ccuaacuggu guguuucuau accaguuucu aaccugauuc cuaucagaau guuuuaagag 1200
ccuuguggcu uugccuggac ucuucuaugc uacaguuuau uuaguuuauu uauucaguuu 1260
auuccuccuu aaagugggaa uaauacuauc uguauugcca guuucucagg auuauuuuac 1320
auaaaaugau augauaugcg gaagucuuuu guaagccauc acauccauag caguauaaga 1380
uauuacuacu aacuagaaag agaaaacagg ggucuaugcc caguauuaaa auuggcauuc 1440
aggaaucuag ugagaauauu uuuucagguu cauugcuugg gcauuucuaa uuuauacuca 1500
agaaaugcuu ucauauuguu uggaaauuuu aguacccuuu ucucuguaaa cagaauuugu 1560
agucuaccua uguaacaaaa cccaccccug ugccuugcau uucauucucc uuagcauuua 1620
uuacuaucuu aacauacuag acauguacuu gucuuuuguu caucuuuuuu uuuucuuuuu 1680
uuauuagacc auaaacuuug auggcaggaa cuuugccuau uuuauuuauu auuguauucc 1740
cagcaccuag aacaaucgcu ggcacauagu agaugcucag uauuuguuga augaauauaa 1800
auuuuuaaau guuauaauaa uauuauucug aaaucuaugc auacgaagcu uuugguacag 1860
aaaacaugaa aagagaacua cugccuuauc auccagucuu cuucccucuu cucauucagu 1920
cuagaacaua accuguuuug gaaaaaguuc ucaaaccaua uguuuaucuu gcccucaaac 1980
cauaacaaca aucaaugcaa aagacuucug ugacccccag aauauguggg gauuucucca 2040
caucagcaag caagcaguug guuuuguagc agacaccaac ugggugucgu ccaauucaau 2100
ucaucaucua ccuggagaua gugucagauc ccacagauau cuuacuucga ucaaaucaca 2160
aguccaggcc uccgugacuu ccgaaguucc cacaucccca gcccccagcu uuggguuuga 2220
uuaauuuccu ggaguggcuc acagaacuca gggaaacauu uacuuacauu uaccaguuua 2280
uaauaaaggu uauuacaaag gauacagguu aagagaugug uaagaagaga uaugggggaa 2340
gggguggga ccuuccaugc cuuucugggg ugccaccuuc cucuagaaac cuccacaugu 2400
ucaguucucc agaaccucuc ugaacccagu ccucuugguu uuuagggaag cuucaugaca 2460
ucaguauuuc uucuccuagg guauggggca ggacccccuc guauuagggu uuuaagaccc 2520
acagucagaa aggcagggga agauuacagu ccugccuuag ggcaggugaa aggaggaugg 2580
gagaagguca gagagacucu uuucugaggu gugcucggaa ggccuaacac acucaauauu 2640

-continued auaacuaaag augaggacaa gggcuaugag aguuauaagc caggaaccau ggaaaaaagc 2700
cuauauguaa uaacaccaca auacccaugg uaccauucac guuuguuguu uuucuguuuu 2760
ucaauuguuc uuucagucuu gguucccuua aucuuaauuu agcaaguaau gccaggaggg 2820
auaaaaauugc ccaaacccaa caaaguacug ugugcugcag gauuauuuaa ugacauaccu 2880
uauguccccc acuaguauuu acauuucugg gaguacagaa aaauucuugu acauauuuca 2940
gaaaaaauga aauuaauaac uaucaaccac uuagugaagu uuuuacuuuu uuuuuugaga 3000
uggaguuuua uucuugucac ccaggcugga gugcaauggc gcaaucucag cucacugcaa 3060
ccuccgccuc cuggguucaa gugauucucc ugcaucaacc ucccaaguag cugggauuac 3120
aggugccugg caccacgacu ggcuaauuuu ugaauuuuua guaaagaugg gguuucacca 3180
uguuggccag gcuagucuca aacuccugac cucaggugau cugcccgccu uggcccccca 3240
aagugcugga uuacagguau gagccaccac acccagacug aaguuuuuac auuuuuuaaa 3300
gggcacuuau uagcugaauu aaauaaggua aaaaauugac uaguauuaga gacaagaauu 3360
ggagaauaua guucucuagu auucgagaaa gucguuuuga uaggacaacu aaucuuagug 3420
agaauuuggc uuuauuucau auuuuuuuaa uuuuuugaga ugacgucuua cuauguugcc 3480
cuggcugguc uuugaacucu gggcucaaac aaucuuccug ccucggccuc ccaaagugcu 3540
gagauuauaa gcaugagcca ucuccccagg aauuugacuu uaaaccaugg uucucaaccc 3600
uuucagauuc aacauucccu uuaauaaaaa auauaauguu ucauaauuuc cccuuuacua 3660
uuauaauuga aaugcauagu uaacauaaac ucuaccuacu uacauaauuu caaaaauguc 3720
auuaugaaug uccuaaauga aauauauagg gggaacauaa aaggaauauu cauauuucaa 3780
cauguaaaug cuuuggcaug acuccauugg aaaauauaau gaacuaguca ugugcuugca 3840
ccuucauuaa ugugaguuca aagcuacgau ugcagacuga cacaaaugug uucuauuggc 3900
aacugauggg ucaugauggu auugccauuu guaauuugau uuccaaaaug guaaacaaau 3960
uguuggugca guucucagca aaacaauguc uauaaucuua ccuuuuauaa gacuguugua 4020
uuccuagaaa acuuagugua uaguaaaacc auuaaaaaau uacuuagugu gaauauguua 4080
guuggagaua aauucuuagc ucagaccagu guaagcagaa uuuuuuacug uauuaauauc 4140
caguagaaca uuugaaaguu guucagugca ugagacuauu cugcauugga uaggcuuucu 4200
uuggcuccuu uaucauaguu auaauaaacc augacaccua ccccugaaau gcccuaauuc 4260
ccuuccguuu cuuuuucuuu uuucuuuuua gcacuuaaaa cuagcuaacu uacuacaaaa 4320
uagauuuaga uuuauuucuu guuuuguuau cuguaucguu ugcucccuuc uccccaaucu 4380
aucuaaccaa cuaguauaaa cuagauagua agauucauga agauacacuu uuuuaucuga 4440
uuuuauucau uuguucuauu ccuauugccu cuagaguagu acuuggcaca ugguuagcac 4500
uaaauaagua ccugucaaau gagugaagua augugcauug aagacuugaa ggggcucuga 4560
ugcuaggaaa uugucauggg auaauagaug agguuggucg uuuguacaga ggauucuugu 4620
uagaagcuua cucuagucau gauuguauua gaaucuucau uuaaaggcuc cugaagggug 4680
uuggcauuag ucagaacugu cucccagaau uuuauuuguc uugugauaga auaaagcaua 4740
guuagccuaa agagcaguuu uccuaauagc ucggcaugcc caaagauucu aggaguuaua 4800
cagguugaac aucuaaucca aaaaucugaa augcuccaag auacaaaauu uuuugagcac 4860
caauaugaug ccacaagugg aaaauucuga ugugaccuca uaugaugagu cacagucaaa 4920
acacagucaa aacuuuguuu cauguacaaa auuauuaaaa aauauuguau aauacuaccu 4980
ccaagcuaug uguagaaggu guaugugaaa cauaagugaa uuuuguguuu ggacuuggga 5040
cccaucccua agauaucuca uuauguauau gcaaauauuc caaaaauauu uuuuaaaaaa 5100
auccaaauuc uaaaacacgg cugguuccaa gcguuucgua agggauacuc aaccuguaua 5160
gcaaaaugaa cauauuuaca uauucucuag gaaauauuag uuuacaauuu uucuaggcaa 5220
auuauaauug auaaaucaua aagaaaauuu aaaauaacac ugguaauuuu ccuaccuccu 5280
ucguuauugu uacag 5295

<210> SEQ ID NO 101
<211> LENGTH: 331
<212> TYPE: RNA
<213> ORGANISM: Homo sapiens

<400> SEQUENCE: 101
gugaguuuaa auaucauuau aaaacuaauu auguguaaaa ucccuuuagug accuggaaau 60 uauauagcuu uaucauaguu gauaaauauga gaaauggucu aguuuaaaug aucauuuauu 120
aucuaugauu uacuuacuuu uuauuuucuu uaaaaucugu uuuaaauaua uuguaacaau 180
uauagaugga uuuuccugug aucucguugu aaauuagcuu augacaaaua uagggguguua 240 caauuauugu aauuugguuu gguaaugagu augcaauuga aaagccaaac acugaauggu 300
auauuucaug auucuauauu aaauuccaca g 331

<210> SEQ ID NO 102
<211> LENGTH: 2648
<212> TYPE: RNA
<213> ORGANISM: Homo sapiens

<400> SEQUENCE: 102
guaagcuauu auguggaaau gugccaccca uuguaaugaa aaacugguug accccuagaa 60
auugaaauaa uaaaugugug uugucuuaag cuuggguuau guuuucuuuu cccaugugaa 120
uugagauauu ccugguucuu cauaugccac auaaauuugg uguauuuuug aucuuuugaa 180
uauuauauug ugagacucug guucuuguuu aaauucuaug ggaaaaugua gauacuuuug 240
uuuuagcaug caaucggucu aauuagguuc aggccacaag uuccaaccuc auuucuuggg 300
cugugguucc auuuuucaaa gccuuuucaa uacucuucag aucuguccug ccuguguacc 360
ucacaauagg ugaucuggua ugugagcuau guaccauuag uucaguucuu agaaacuuug 420
guauucugau uaggaucgau ccauacauuu gcagcucaag agugagccca gaaguucaua 480
aacaacuuua uagggucccu uucuugagcu ccucccucuu ugccaucucu cugauacuuu 540
guuucccuag ggauuuccau uuggggcuuu aguuacccag ugaugccaug uacuucagga 600
auugcacacu ucugcagcca agcaagcaag aggagaguag aaagaggaag aaaaaaacga 660
cuuuuaccuu acccucuuag uaucauagcu cuaccaauug gagauuuccc ucccaaaaaa 720
uauuagcuuc ugugaguucc cauugcagcc ucuauuacca cugcuauggg auggcuuaag 780
gguuggggca ugaaagaaca gauagaagaa aaaaaaagug agguguuuuc auauugucuc 840
uugaguguua aaagauuccc uuucucuuua cucgagcuag aauuagaagg uuuaccugga 900
gcucucucug ucagugcaga cacccaucuu cagguuucaa auaaauguugu cuucagggca 960 ggcaguaaca gaauaaaaga aaagguaaau ucaucaccug uuugcugcua cuuuaagucc 1020
ugguauucua uuguaaucug ccuucuacuc cuuugcaaag uccucaaaug guugcuccau 1080
gcauuuagga gagagaagau ugaauguauu uacuccauug uaccuggaac cagaugcccu 1140
ugcccugcau caccccaugu cauuucuuag cagagccuuu gagauuuuug ugugugugug 1200
cuuuacaauc ucuuuccaag uuauaucuuc ugauacaguc auggucguga aaagcaaaau 1260
aaaaucaugu guuaacauuu aaaacuuuuu aauuuuauuc ugacaacagc uaaaacuauu 1320
uaaucuucug uuucgcucau uucuuccaag guaaacuuca guugguuuua cgugauuugc 1380
uauuucuucu ucuuugcauu uacaaaugau cugugaucau auuacugauc uuuguaaagg 1440
gcuaauaucu accugcaaca uuuggauaug acaguauuua cccuuuguaa auacacauuu 1500
ucuauuuauc uucaaaaauu accauucauu agucuguguu aaugucuguu uacuauugug 1560
ucauuaugaa ugugauguga acauacgaag uugaacuuau uuaaacgaac acucucauga 1620
gcuucuaauc cacauuccuu ccuuuuccuu cuaaguuacc auuucuuaaa aaucuuuuag 1680
aaguuuccuu gauagggaaa acacaaauua uugaggaauu uuucuuucuc uugacaucug 1740
uuuauaguua cucucuuguu ccagcagugg auauuucccc uccauguuuu ucuuugucua 1800
aacauauguu caaaacaaaa cacuuuuauu cuucuuugca gguuuuacaa ggaucaacuu 1860
uuaguuuuga aaccugcuau uacuuuuaga ggccauuuuu uuuuucucua auaaugugag 1920
uucaugcggg cugaaguaau uggaauacuu uauagaaaag auugaauuug ucuucucucu 1980
gaacucuagu uugaauuucu aaauuuuaug aaucaucuag auauuaaaga ggaggggcau 2040
aucaaagagg agaacccuag cagagauaag aggcaagagu aaauguuuca uguaugggua 2100
agaguggauu uguauuuacc uaaguaaagg uagacccugg acaauaaggu uggauagaug 2160
uggagguggc aaaccaugga gggucuugua ggucaagugg auguuuuuag acuugaagug 2220
uuaaauuauu aucugaaauc auuaagaguc uuuuuagauc cuugagcuuc uugagaagac 2280
cauggauauu augcaguuau uauauaaugu uuuaaaauag uaaguauuuu aguuuaacug 2340
ucuuauguaa uuccauauaa auggaugcau guucuuuaaa aauguuaaug uauuucagua 2400
aaucaaaaua uacuuuuuga cucaucauuu aaaggaggcc uucagugaau gcucuguaga 2460
ggauuauuuu auaauacuaa uuuugauauc cuaauuuauu uguuauaaag uuuagaaggu 2520
uugaagaauu uaaaauauag uguuaauaaa cacacugaac uuuucuuuuu uuaucuugua 2580
uuuuuauaua guacaacaga aaaaagauga aaugugaaua guaaagaguc ugugauuguu 2640
guucauag 2648

<210> SEQ ID NO 103
<211> LENGTH: 4406
<212> TYPE: RNA
<213> ORGANISM: Homo sapiens

<400> SEQUENCE: 103
guaaguguau aucuuuuauu auuuuuuucu uuuuuccaug uuaaaaugca ugaaagugaa 60
aucaacuucu uucuuaaucu ggccaaaagc auuacaucuu ucucauuaau aguaauacag 120
uaaauucaac uuuuauuuuu aacagguagu gauguguaau aauuuauuua auccuuuuua 180
acauaauaac aguaaacuua agauucuuaa gcuuuucaua aagcucauaa augauuucua 240
gaaauuuuaa auauguaguu aucauuaugu auuuugcugu agcagcagua uacaguuaaa 300
uaaaauagga aaacauguuc caagacuguu uucauucaaa uauuuaugcu auauuuuuag 360
cuuauaaaaa cucauuaauc auuaauguaa aauuauuugu uggauuuuuu aaauauuuag 420
uguauuauuu uuguuucuuu uuucuuucca uguuucuuca uucuuccacc uuaagcagaa 480
ucaggugugu gacacaacua uguuucuauu ccuuguuacc auuauuaaua aauacaaggg 540
caugauauuu uucacaaaag aaacacuuug uucagaacca aaaaagauca uggcaacagu 600
cagaauuaaa aaugguaaaa gacuaggugc caaagaugac uuacauaauu ggguaccuag 660

-continued

```
aaauauucua ugguauuaca guaaugauga aaaauacaaa uuagaacaca uuuuagaucc    720
uauugaguua aauaaaucag agucaagacc aaacaauaaa uaaagucaau uuacgucaac    780
aaaugguaag uuggcagauu uuaacucccu uuuugaaaau gaaccaugau ccuaagguug    840
guaaaauuaa ucaagaaugu ugucaaaaug auaaagauaa aaaugaggaa gagaauaaga    900
uaggcaagag ugagaaagga aagagacaca uagcugaaaa ugugagucac aacaacuaca    960
uagauccgua gaaucugcua uggaggacug ugauuaugug acaguugcug augccguggc   1020
uuagugagcu gagggugaug cacaggcagg cgauguaacu gaugcgucag uccagccaag   1080
aaaggacgcg ucccugguuu ggcuacgugg ccguccuuua uuucuuuguu aacugaauuu   1140
ucuuauagua aguagcuuac guacauauau agugcaaaug ggaaagugug uaagauuuag   1200
aaaaagcauu aacuauuagu aaacuuuauc uuaagcucua acuuuugauu aguuccuaca   1260
aaaauuagug aauaugcauu uucuaauuua gugcuuuuuu uuuuuuuaca auuggguguuc   1320
acuuaauguu auauuagaua aaugaauagc aaaaauaagg uacuuuagag uugauuguuu   1380
ugccuuacaa acuucuaauc cauccagcug uauuuagaag uaagaucuca cuacagcgaa   1440
uuauaucagu aaaauuuugu uacaguguug ugcagugucc uaagauguau acuaaguucc   1500
uucaguggcu uuuuuugcca uguuuuauaa cagauaauuu uguuauaaug agaaaaggaa   1560
acuuggaugu guugcugucu auauuguguu aggcucaggc aggaugcugu ggcuuacuca   1620
uuuaaucacu uugggaggca ggggcaggaa gauugcuuga ggccaagagu uugagaucag   1680
cuugggcagc auagccagac ccugucucua caaaaaauuu agacagaugu gguggaacac   1740
auuuguaguc cuagcuauua gggaggcugu ggugggagga ucauuugagc ccaggaguuu   1800
gauguuacau ugcccuauug cacuccagac ugggcaacag agugagaccu gucucuaaaa   1860
uaauaauaau gauaaugaua aagguguuaa ggcucugugc cuaaguauau uuuucacaua   1920
ggcugguaa aguggcucau gccugcaauc ccagcacuuu gggaggccaa ggcagcagga   1980
gcauuugagg ccaggaguca aagaccagcc uugagagacc ccaucucuac cagaaaaaaa   2040
aaaaaaaaga aacaauuagc uggguguggau ugugcacacc uguaguccua gcuacucggg   2100
aggcagaggu gggcagauca cuugagccca ggaguuugag guuauaguga gcuaagauug   2160
ugccacugca cuccagacug ggcaacagag caagacuguc ucaaacaaaa acaaacaaac   2220
aaaaagcacu uugcagaaua ucagucuaac ucuacaguuu auggacuuuu uauguacgua   2280
cuacuuuugg cuagcuuaca uugagauaca gaauaaaagu uuguucauag cauuuaucgu   2340
uuuuuucuuu auacugucca ccugagauau uccagucacc uaagucaugg aaacaucaac   2400
uaaaauuaaa uaucuauguu aagagaaaau ggcugaaagu gauuuaauuc auaacacuuu   2460
uuuucacaug cuaauaaaua agaguuugag acuuccacua ggcauuaucu cuaacuccua   2520
uccacuaaga auuugauuuu aaguaguuga uggcuuuuaa ccggauuauu cuucuguaag   2580
aguuuggaag ucucgugaag uucguuauac aagaauucug uuuacaagag agcauuacau   2640
uagaauuugu uuuucagaaa uuuggacuau cucaacgaau accuuuaguu uuauuauuuc   2700
aaaaugcaag ggaaaaaaug agccauaauc acuaauagua acugcaucau auuuuaguga   2760
gaaauguguu aaaaauaucc ucaugugaga ucuuccuuag auagaauuac ccucuacucu   2820
aauauuuaau auauuuuaua ucuaccaauc agugauauua auaggugguuu aucauuugcu   2880
gaaucaaaua gguacaacag aagacaggaa guuugggaga uagaagagcu cagggacagg   2940
aaaucacaga uguccauauc ugaaauaacc uuaaaaguua uccugucuaa ugccuucacu   3000
```

uauaaacugu agugguagaa uuugccuagu auuaaccuaa uagugguaga uuugaaugua 3060
uacuugggcu uucuuauuaa guggaaaugu auuccuguga uuuacauaua ucaacaaaaa 3120
uguuugucuu cuuuuuuuug cuacgacaua ugugcaugug cacacacauc uccucaaaca 3180
aaaaucagau ggacacaugc agucauugga ucuaaaagau guuauaaagu uguguauaau 3240
agguauuuua uaauaauaua uuuuaagacc cauaaugucg guggaguaac ugacuuuaca 3300
gcccaucaag ccaauagaga gagaaaggag aaaaaaauga aaguugugcu gaauaauuaa 3360
aaaaaauuau uuccuaugau gcuuauaaca guccuaugag guagguggua uucuaauuua 3420
uagaaaaaau gcauagaaaa auauaauuaa gcacaguuaa aaaaaauaaa guuuagaaug 3480
agaaguaaca acauaaauaa ugacccaaug uagauucagg ucaaaagaaa ugaaaauaua 3540
auauuaaugg uuuucaaaga gggaaccauu acuuuagcuc aaagaaugaa ggagggcuuu 3600
ccgaaggagu aaagaauuau ggcaguucuu uuguagccua guguauucau uugcuaaggu 3660
ggcuguaaca gacuacuaca gauuuggugg cuuaaacaau agaaauuuau ggucuuaguu 3720
cuggagaccu agaaguccaa aaucaagaca ucagcagggu ugauuuccuc ugcacaauca 3780
gagggaaaga ucuuucccaa uccucucucc uuggcuuaua aauguccaug uuuucccugu 3840
uucuuuuuau caucuuccuu cuguacaugu cucugugucu aaauccccaa auuuucucuu 3900
uucauaagga uaccagucac agucgaauag gguuuacccu gaaaucucau uuuaacuuga 3960
auaccucugu aaagacccag ucuccaaaua aagucacauu cugagguacu ggaaauuaug 4020
acuuuaauau auaaaugugg aggguaaggg gaacacaguu caacccauaa cgguuagaua 4080
acaaucgugc uuuauuuugg acuaguaaaa ccaccauaga ucaguuuaac cauuaugaaa 4140
uuauacauga aggcauuaua uguauggaca uuauuaaguc auacuugcuu ugcuuccauu 4200
guaauuaaaa caaaccauac uaccuuuguu cugcaaguuu uguauucuaa cuuauuuauu 4260
uuuggcuuuc accagaacac uccgauuuuc ucauauuccu uugaggaaaa aaaguuaccu 4320
uuugacagua uuuucuuauc caguaugucu uuuauggcuu uuauuuauua aacuuuaaaa 4380
auauuccuaa uuucauuucc cugaag 4406

<210> SEQ ID NO 104
<211> LENGTH: 1202
<212> TYPE: RNA
<213> ORGANISM: Homo sapiens

<400> SEQUENCE: 104
gugaauuuaa uguuuuuuau uaggaaaucu aaugccuaaa acuccuuccu uaguuguuau 60
guuuacuuuu auuagcuuau uaagaaguca aaaaugcaua uuccuaauau aucaugguga 120
ugguauacuu uauacauuug cucuuuagca uuuauuuguu gaaggccuac uuuauauuaa 180
acacuccucc agaugcuggg aaacagcagu caaaaaauuc cuuauacuca uaggacuuac 240
guucuagugg agaagacuga caauaaacaa gucacuaaau aguaugucau cugauguuag 300
ugcuaaggag agaaauaaag caugauuggu guaaagagua uggggagaga gaaggggugu 360
aacugaaaau agaguaguaa gggaggucuu ccuuaauaag augauauaug aacagagagc 420
uaaggagggg uaaaggaagu gagucauaca gauacuagaa aaauaauuac agacaacaga 480
aauagcaagu ucagaugucc uaagguggga ggaugcgugg uauauuucau uaaaaaauuau 540 cacacuguaa aauauaagaa uaauuuguuu cuuuuagaaa uuuuacuuua uucugauauu 600 aauaaaugauu uuuuaaucuu ugguuuucca agucuuaccc uauuuauggg aaucuuuuuu 660
uucuuuuggc uagcuaauug cuucaguuuu guuuucuaau cuagaauguu agcaaucugu 720
uaauuccacu gguaaugaua uaguuaagcu augucuugcu ucucacacuu uauuuauuua 780
uuuacucagg gcacuaaucu gccauuuuuu cgcacuuuuu uuccuuuuuu uuuuuuuugg 840
uacugcuucu uauucugguu uuuacauuga uagaaccaau guuagacguu cauuugccuu 900
uugcugugua uauuugggua aggaucuaua ugugcaauau augggacagu uaaaaucaga 960
auucuaaauu uguauuauug caucaggcaa uaauguggga aauaccuuga cauuucauau 1020
acacaauauu cuuguauuaa uuuaacgucu uaguucaaaa ucuuccuugu uaauauagag 1080
acccuauuau uugguuuggc aauacaguug aagagauuga ugguucuuau gaauuguuug 1140
ccuuuucuuu ucaauggcug uagcuauguu aaauuauuac auguuugcuu guuaucuuuc 1200
ag 1202

<210> SEQ ID NO 105
<211> LENGTH: 1697
<212> TYPE: RNA
<213> ORGANISM: Homo sapiens

<400> SEQUENCE: 105
guaugugaga auuuaccaua cauuuguuuu gguuucagca gugauaagcc agaaaugaaa 60
aguuuagaua uguuguaaaa guacugauau gccucuacaa gugcccugua guuucagugu 120
uuauucugca ucuguaauau aaaacaguaa gcauuucuau gugucucaaa guauuuuauc 180
aucuguuaua ccuuacauac uuucaucucu cuuuuuauug aauaugccuc cauaccuuga 240
aaacauuuaa cuuccaggaa uccuuuuguu uauggaggua acugcuaacu gguccuuggu 300
ccaaugcugc cauuuuguaa ccauuuguua ugauaucuuc ccagcuuggu auaauguuuu 360
auaauuacau uguuccuccc ccucuuuuuu uguguucuug uaauuuucuc ccuauguuau 420
uuuguauuca uuuuauauaa ugaauaaaug uugcuuauga ggucaaggcc aaagacuuaa 480
gcuccuguug auuucauguu gcugaguguc auaaaauggaa gcaaucauaa ugcagaguca 540
uucugguagu aauauuaaau auaugaugga uucagugaaa auauuaugug uuauuagaaa 600
aauauucaga acaggccggg ggcaguggcu cacaccugua aucccagcaa uuugggaggc 660
cgaggcgggc agaucacugg aagucaggag uucaagacca gccuggccga cauggugaaa 720
ccccaucucu acuaaaaaua ugaaaauuag cugggcaugg uggcucaugc cuguaauccu 780
agcuacucag gagguugagg caggagaauu gcuugaaccu ggcaggcgga gguuacagug 840
agccaugguc acacaacugu acuccagccu gggcgacaga gcgagacucc aucuuuuaaa 900
acaaaaaaaa aaaaggaaaa auauucagaa caguaucuug cuggcagcaa cauuuguuuc 960
aucaaugaaa auauguguua auuugaccuu uucuaucuaa guuaauuaug aaagugcaua 1020
cuaaaaugau guaaaaguuu auauuucagg auuauucuua uucauggaug auuaacuaaa 1080
augcaaaaag aaauuaagca uacuguuugg cuaaacuguu aaaaauuauu uuuauuuuaa 1140
augauaagca guuaaacuua uuaagugaug acucaucucu gcugauauau uuaugcaagg 1200
uuuuuuauuu cagauaacuc uucuauuuau auuaaacaga aacuguauuu cuaagcaaua 1260
gcauuucuua gagaaaauug ccucuauuau guugcaauua aaauuuaauu acucaugagc 1320
ucuuuaaaga cacaauuucu cuuguguggu uuuauuucau auaaagaaaa acucugauau 1380
acuggagaga acauuagcua aauagacuau uuagacuuaa ucauuuugau cagacaucaa 1440
ggcuagacua uuuaagcugu uacuuauuag cugcaugauu uuaggaaugu caaauuuccu 1500
aagucuuggu uuucuuguau uuaaaaugga aauuauaauu ccuaucucau agaauuguuu 1560
uaaggaugaa uugaauuaau acaguuuuga cuucaaauau uaggaauuau ugaguauaau 1620
aagccuguug uauuguuggu acuucguauu auacuuacua aaauauuuga uuaaagauuu 1680
aacauauucu uucguag 1697

<210> SEQ ID NO 106
<211> LENGTH: 809
<212> TYPE: RNA
<213> ORGANISM: Homo sapiens

<400> SEQUENCE: 106
guaauuuuuu uuaaugugau cauuuuuagg ggaauauuuu acguuuuguu acuauuuagg 60
aaaauuucaa auaugcucau uacuauauaa aauggcuuua augaauacaa uacauauuuu 120
auaaauauag aaaaaaacuu augagaggca aggcuaaggg uuauagagua ggucuaccug 180
aucuuucuug uuauuucaag accaauacuu uucacuuuuc ucucugacag cauagauuaa 240
uuaccugugu cucucuuuuu uuuuucuuuu gagauggagu acugcuuugu cacccaggcu 300
ggaaugcagu ggugcaaucu ugacucacug caagcucugc cucccggguu caugccauuc 360
uccugccuca gccuccccca guagcuggga cuacaggugc ccaccaccac gccuggcuaa 420
cuuuucguau uuuuaguaga gauggggguuu caccauguua accaggacug ucucgaucuc 480
cugaccucgu gauccgccca cugcggccuc ugugucucuu ugugaaaaua cagaugccca 540
agcucccauc ccugaaauug auuuaauuau uuuagggugg guccugacac agauauguau 600
guuguuguua uuuuaaguca ucaauuuauu cuaauaugua gccaacguug ggaacuucgu 660
ucucacuaau auucaaauga agacuuuaau ucuaaucaua ucaaauaugg uuucuaaaac 720
uacuuugaag auuuaugagu uuauaagauu aucuuuuauu uccuuguuuu gauaauguau 780
acuuuuuauu uuguuuguuu uuuuacuag 809

<210> SEQ ID NO 107
<211> LENGTH: 877
<212> TYPE: RNA
<213> ORGANISM: Homo sapiens

<400> SEQUENCE: 107
guaugacuuu uaugacugau uauaacuuuu gauuuuuauu uuacuuaaua ccucuuggaa 60
aaacuggaag uagauccuug augagagugu cuguaaaggu agauauuaag agauugagga 120
auuguguuuc uaugccugcu gucaucacau uccaccauga aaaacauuga uaauaaaagu 180
uaauacauuu aggcugggca cgguggcuca cgccuguaau cccagcacuu ugggaggcca 240
aggcgggugg aucacgaggu caggagaucg agaccauccu ggcuaacacg gugaaacccc 300
gucucuacua aaaauacaaa aaauuagccg ggcguggugg cgggcgccug uagucccagc 360
uacucgggaa gcugaggcag gagaaucgcu ugaacccggg aggcagaggu ugcagugagc 420
cgagaucgca ccacuacacu ccagccuggg caacagagcg agacuccauc ucaaacaaac 480
aaaaaaaaga aaugaucuac guugcuuaca cauaccuuau gcuuauagcu aggucucgua 540
agcauuagga agucaaaaca aagaaucuuu uacaugugua aagguauaaa cuaucccauu 600
uuucuaaaaa uauagaggaa caaaguguca aauuuaaagu aaucacuagu aacuaaauau 660
auuccucuga ccucauuuuc gugaucuguu guucuaauua uuauuggcca uauugcugcu 720
uuaaaggaga gauguugaau uuguugaaau uuuaaucagc auuuagagcc ccagguuauu 780
uuuguuuucc aauuuguaau gauaauuuug aauacacuga aucuaugaga acaguauuau 840 guuucucau aaaauacuaa uuagcauuua augauag 877

<210> SEQ ID NO 108
<211> LENGTH: 3130
<212> TYPE: RNA
<213> ORGANISM: Homo sapiens

<400> SEQUENCE: 108
guaggaacag aguuuuaaac uuguacaaag uuuaaucauu ucaaauuuug gcauuguuuu 60
aaaagacaac acuauucugg auaaccuggu uucuuccuga ugaacaguuu guuugguugu 120
uguuuuaaca uaauacuuuu uuucuguugu aguauuguug gagacuuuuu cuuccuugaa 180
auguuuaacu uguuuaaccu uguuugggug gcagggcaug gaacagugua gagcuggggc 240
ugggcgaagg aguuggagcu gugugugcgu caugaagcug ucaucagcua ugagccuggg 300
cugaggcugc ucagcuucuc cugggugcua uuuuucucca acugcagcuu cagcuucuug 360
auuguauaau uugcuuccuc aaguaugagc caggaauaau ugagcugucu ugucacaaug 420
uguggcauac uggaucuagg cugugcugca augcuuuuag aguuauaucc ugggcaacuu 480
ucucuucaga uagccccaag agaugaauuc agcaccagcu uugauguuuu acuagcuucu 540
gcuuucuggu acuugauuuu cucccacccc gaacacaugg gauuccaacc ugugaaacua 600
auuuuugugg cuaugaaaga gguaguggua guuuaugagu aaacauucag ucuguugcca 660
cuaucaucau gugugguuca ucaugacugu gaugaguagg uaaaaggcuc uuugugucau 720
ucucauuucc aauuuuaagc agcugcuuca aggagucugg aagucauuga ccagugggau 780
ccugccugug ucuuuuccca uuaaagccau ccuguaugaa gugguauccu uuaccaucua 840
gcacaucugc cgcccccauu ucaaaaggca uacucaucuu uaucucaaca uucucauaca 900
guuccuuaug uccaugcacc uccaaugucc ccuuugaugu cuuugagguu uucaucuucc 960
augucugcua uuuggaaugg ucuugauggg aggcaagaua gugaucacua caacuaggau 1020
gggagucuua guaccgugag gcuacagcaa gucccacaga gggccugcug cacuguacuu 1080
gccucuguca accaagucua aggagaaaga uuaagcaggc auauuaaagg acagcccaga 1140
uggacaugaa guccuggagg aggccuuggu uccuguccua auacuaaacc uagaguaccc 1200
agaauccaca cuucuccacu cuagcucuca cuuuucccau cuacacacug ggaaaaauua 1260
uucugucaga aagccagugu caaggugaga acaaauaaca aaugugauga uauggagugg 1320
gagaaggggu cucuucuacu gucuuauugg acccuagcag uggcucugag ccagcagucc 1380
ugucaguuga uuucuugguc guuccuuugu uuucuucuau aaucacaugu ggacucagaa 1440
ugaauuuuga guuacucuga aaucuauuua uucaacagau auuuacuuag uaccuccuau 1500
ugccagacuc ugcuuuaugu uggauauuau uuuuuaaaag cccaccuugc cuagauuucc 1560
ucaaaggacc agguggcuuc ccugguuuug aaagacccua auucuuacua ugaucuuaag 1620
uaaauuauau ccuuucugug ggcucaaguu cuuucuaaga gggcucuuug gggcuacaaa 1680
agaaauuguu agugcaaaaa gaguuuauaa gguuuauaaa ugguuaguag aggugaugau 1740
gauauuuaac cauaauugaa gaugacuuug cauuuuagau cauauacgug uuuuucgucu 1800
gagaacgaua caggucacug agcauaccau aagccuucag uaaaucauuu gcagaagaca 1860
uugcagaaga cauaagucua aguagaaauc ucuugacaga gagaaggcuc guuuugaucc 1920
uugaccucaa auuuagguuc ccuaaaucca uuaaaaaaga gaaagaaaaa gaaaaaaagu 1980
uacuaaaguu uaaaucuggg aggauuauau acccuucuca auaaagcagu uuagagagau 2040
cucuuuuggg acccaugaca caggucuugc ucaugcugac aucuuuauag uugcuuuauu 2100
auuuauucaa caaacuuagu aacacguauu cuaugucagg ccuuuuccug acuacuggga 2160
caaaccaggg ugaugugggg gcuguuuuag auagggugau cagaggaggc cucucuguuu 2220 gggugcuuu ugaauagaaa auuagaugaa gugaaggagu aagcuucuga uauuucacug 2280
uuuacuugug guagaucugu gauaaucucu gucagguuaa aaacauuccc uucuaaucua 2340
aguuucuaag aucuaucaaa agcuguuuga auauauuuag acaaucauaa uuuuccuuuc 2400
uuguauuauc cuagcagauu uuguugccaa agcuauacug gccauuuuaa cuuagaaugc 2460
agucuuucua uucauuucuc uggaaaaguu uggauauugu aagcauuauu uuucuuuagg 2520
uaugaugaac cugcagaacu guuugguuca auuaugaauu uuuuuuuucu ggagucugua 2580
uuuuuuugaa cuauuaauca uuucuuuaau gauuauaaau cuauucagau uuuuacaagc 2640
uuuaucccuc ucccaucaua cacuauuuuu cuuacccaug cuuuugcaca auuuuuuccu 2700
cucccuuagu guuuuccuac cuagauaccu ccuaugugug ucuguguaug ugagaaaagc 2760
uuuuuauuug ccaucuuuau auuucuaaga auaucuagua auacagaauu uuauauucug 2820
aagaauuuua cuuugcauuu ucuuauuuug ugauugaaaa aagguauuaa uuuuaaaaug 2880
gucaaaucag gcuccauccu uggaaaauac ccaaauccuu uauuuugauu gggccaucug 2940
uuaauuaggg auaccuuauc ucuugccacc acuuuuuaau gcuaaauaaa uauguagcua 3000
aaacuuugac uagaagaaac aguaaaauaa gauauucuug cuuauuuuua guacaguuau 3060
uugaacugac uuuuaaauca gugacauaaa uuauuugcca ugucuauacu uuuuuuccuu 3120
auacuuuuag 3130

<210> SEQ ID NO 109
<211> LENGTH: 1162
<212> TYPE: RNA
<213> ORGANISM: Homo sapiens

<400> SEQUENCE: 109
guaaguaacg uaauuuuucu uuacaugaua aaauaaugca uaauaucgca agauguuccu 60
ugcauugucu uauauagaua aaaauggacu cuauuaagaa gacccaucua acugaagggc 120
accccauuca cccauuugcu uaagccagaa acuuuggauc aucaacgacu ucauucuuuu 180
cauucuccac auuuucuauc auuaaaucau gucagcucua uuuucaaacu auauccuaaa 240
uaugaccacu ucuugguauc uugagacauc acuaccaguc uuguccaagc uauuguuuua 300
uaccugaaua acugcaauaa uuuccaagcu gguaucucag cuuccacucu uggauuauuu 360
cacccuauuu cuauuucugg gcugucucca cacaguugcc agguaacccu uuuaaaacau 420
aaagcacauc acaaagcaca aaguccuauc cucagaaucu uccagugguu cuccaucacc 480
cuaaaauaaa acuuaaaagu ucuuuucaua ucccaaaaca acauaugagg ucuggcaccc 540 aguuucuuc ccaaucucau cuucuacuac uuuucccuuc auuucauuca caauguuuua 600
accacaguaa ccuucuuuca guacuuuaaa caauccaaac ucguuuaagc gucaaguccu 660
uauacuuguu uccuuuguuu agaauacugu ucacccaaau auucucauag cuugcuccca 720
gacuucaugu cucugcugaa auagaggcuc cuuagagaga ccuucccuaa cccuaacccu 780
aacccuauac uacuugccau cacucuuuau ccucuuaccc uggauuauuu uuucuugaua 840
gcucuuccua ccaucuggca cuauauuaca ucauaucaua uuaaacacac auucuuugug 900
cuuccccacu aaacaaggac caugcaagau ggaacauugc cauuuuguuc acugcuguua 960
gccucugugc cuaggacaau gccaguuaug caguaguuac ucaauacuug uugaaugaau 1020
ggugaauaga acauagaaau uugccuaugc gugcuuuuga aaaccauauu uuaauauuac 1080
gcuuuguuaa aaauguguau cuuuauaaau ccucauauuu ccauggcaaa ccuuaucuuc 1140
uaacuuuuca uuguccucaa ag 1162

<210> SEQ ID NO 110
<211> LENGTH: 593
<212> TYPE: RNA
<213> ORGANISM: Homo sapiens

<400> SEQUENCE: 110
guacaucaug uauucauaug acuacuuugu uuuuuucuuu aaaaaaaaaa uuauuaguuu 60
uuauauacuc cgaauugcua caacuagaga caagcauuuu ucgacuuuac ugccuaacag 120
gcuuauuagg uccuuauuuc uucccucuaa ugcuaaucac ucuuuuucau aauacacacu 180
agaaaaaaag gauaaaccca acucuaaguu uccaguuugu aauuuaguuu aaacuuuucu 240
aagagcauag aaugaguuaa accuuagcuu cccagaggaa aauacuaaug aaagagaaca 300
aguaauuuuu uuacuuucag gggucucugu agccugcuuu cauuaagcuc cucuuauaac 360
gaaaccacac uugcaaaugc caucagguca gauauuaaga aaaacgugaa ggcuuuugua 420
uuccaggcuu uuuguuugag aauggugaca uuguagcauu gagaguaaau guuuacuucg 480
auaaaggcua gcuuguucug auuacuguac aucacuaguu cauaagaaau gcccauauau 540
uuuaugaagc aauaucugcu uuauuuuuuu aacacauuau cauuguguuc uag 593

<210> SEQ ID NO 111
<211> LENGTH: 3218
<212> TYPE: RNA
<213> ORGANISM: Homo sapiens

<400> SEQUENCE: 111
guaauguauu uuaaaaaaca uguuagcuac ccccaaguuu uugaauuugg guuugccuuu 60
uuuuuuuuuu uuuggcucag auuucugauc auugucuccc uguaaaaucg aauuccugau 120
aagcuuuggg ucuuuugucu cucugugcua uuaauauaaa aauauuccca uuuuucucuu 180
uguguuguuu auacuauaga guagcaagua cccaaguguu cuucucuuug uucuccaucu 240 gggguguuaca gauuuaauca caauacagug cuaagcaaug aauacuaaau cuguugcuuc 300
caguuucuaa guauaggcuc uuucaagucc ucugaacauu uuuaaaaacu gcaaauaagu 360
aaauacugcc uauauuuuuu uccguuuaca aaguaaaaag aaaaucuuuc ugcucccuuc 420
cauucccauu caaaagugau uacuaaucau uccucauucc ugcauauaca uacacacaua 480
uuuuguauac auauauauca cacauaugca uacauguguu uguauguuca uauguacaau 540
guacauaucc ucauuauuug uggauucugu auuuucuaaa ucaccuccuc acuaaagugu 600
guauguaauc ccaaaucaac acucgcagca cauuugcaaa cauccacaga gccuuggaaa 660
guuugaauaa uccaaccuac augucccag cagaagucca acaaggcagu gcucaguauc 720
cucauuucag uuuucauaga gaaaugagca gaggauggag acaguagagg gcagcacagc 780
auagugcaag aagcuguggc ucuggggccu gguggaaggg auuugaaucc caauucugag 840
gcuuguuacu gcucuagccu uaggagaguc auguaacacu ucugaaucuu guuuucuuau 900
guaaauaaau agaauuuacc aggaugaguu aucuuuagga uuuaagauua ucaucugugu 960
gagauaugua gguguaugua uauauaugcg uguauguaua uauaugcgug uauguauaua 1020
uaugcauguc uguacauauu ucccguagca gcagugguuu gauauucacu aauugggcua 1080
acuuuauaga ccaaaacuac uauggauaga gaauacuuug uuugcauuua cguauauaua 1140

-continued

```
uuuucuuggc aaguaacaua aaauugaacu aauacuauac acauuucuag cauauuugcc   1200

uuuaacaguu uaucauggac aucuuuugag gucuguucau aaauuaucuc auccauuuaa   1260

uaauuccaua guguauuauu gcauguauaa gcacaucgaa ccauuuaugu uuugauggau   1320

auuuaguuug cuuccaaguu ucugcuucua uaaaauauga uuaaucuauu gaccuaauua   1380

ugccauugug auaggaugau agagaugcca uucucuccaa aggauuauac caauuuauau   1440

cugaacuauc uuugacuauc ucuuguagcu uuuucaguau gcuauguagu ccuauuacua   1500

auuuguaaua aaagccauca ugugugaguu guacuagaca cuaugcuaau ugccuuacaa   1560

gcauucuaua uuuacaacca uauaugauag guauuacugu cuccauuuua ugugauaaac   1620

aaauucaaag ugguuaagua accauucccu aagccagcua ggaaauagag gcaggauuaa   1680

aaucuaaaug uaugaaacuc cacagcuccu uggcauuccu aguccuuaac ccgcuaugcu   1740

augcuacguc uugguaacua aaaguacaua uuaaauacuc ucaaaauaug ucucauagca   1800

gccagcuugg uauguacacu agacacagua uuaaugcugu ugaugugagg aaaauuuuau   1860

aauuuuccuu ccauccauau acuaaccagg cccaacagug cuuagcuucu gagaucagag   1920

aucaggugca ugugcauuaa gggucauaug gccauagaua guucucuaau cuuuccauuc   1980

cucaguuucu uaagggaauu ucugaacccu caaaauuccu uauuuccuaa guagacagau   2040

uaccugucau uuuucaaaga uuaaggcuua agaucaaacc agaacuguuu uggaaauucu   2100

aaaucacugu cuauauaaau ggcaagauaa cuuuuaagau auuuauacca agcccaguac   2160

aguagcacac cacaccugua aucccagcac uuugggaggc ugaagugggu ggaucacaug   2220

aggucaggag uucgagacca cucuggccaa cauggugaaa cccugucucu acuaaaaaua   2280

uaaaaauuag ccaggcaugg uggcacuugc cuguuauccc agcuacaagg gaggcuaagg   2340

caggagaauc gcuuuaaccu gggaggcagu gguuguugca gugagccaag auugcaccac   2400

ugcacucuag ccugggcgac agagugagac ugucucaaaa aaaaaaaaaa aaaaaaagau   2460

acuuguccca gccaugaaaa uguuugcugc cccuuacuuu cgcaaacuuu uaguauuuua   2520

uuauuuuuca auggcuguaa aauaugacuu auuaaaugua guauaauaua aagaaaagag   2580

auaucuagca aagauagcau uaaagcaaaa auccuauuug ccugcugaua aaguuagagg   2640

uguuaacuug gagggugaau ccaauaaauu agaacuuuug ugcuauauuu ggagacuuuu   2700

guuuuccuac caaaguauca gggcuauguc uuacuuaucu uuguauuaca cagccugcau   2760

gacacguuuu gcacauagua auugcacagu aaauguguaa uaaccuacau ggaauagcca   2820

guguuguguu ggauagcggg agcauuuggc uagcuuaugg uuauaguccc uuacccaaca   2880

gucugcuuuu cuucuguugu acuuuuagua ccuaacaagu uucccuggcu uuaggauuuu   2940

uuccauguaa aauuucuauc augugaagaa aaaauaacuu ggccuacacu ucuaauaccu   3000

agcacauacc ucuuucugcc ugcuaugaaa uuauaauacu ugauggaggg aggcagcauu   3060

aaguguuuac auccugaagu auuucagcca uaacauccag uguuuuccag guucuagguu   3120

ucauaaaaug uaucucuguu cucuagaaca aauccauuac cuugaacuca uucguagugg   3180

gaaaaagcug agucuaauuu guaugacuuu uucaacag                           3218
```

<210> SEQ ID NO 112
<211> LENGTH: 939
<212> TYPE: RNA
<213> ORGANISM: Homo sapiens

<400> SEQUENCE: 112

```
guaauauuua auuauauuuu aguaucguuu ugugaaaaca gcuguugaaa acuauuuuca     60
```

uuaccaucuu uaacuacgua uccuaaaaaa uucaguaaua acaucuuaua uuugaccuuu 120
auauugcaaa guuaauuaug uucaucugac uauuccuaac auauuagagu uaacaaaaaa 180
uucagacuca acauaggauu aaguaguaaa uuuauuuuuu aauuguaaca aauauaugcc 240
auuaguaugu ucuuaaguuu ugggucacau uggcaacagu gucuuuauuu uuuuuuugaa 300
auucuuuuca ggaauccuaa gguuauaguu cccuuaaaaa aauauuugcu guuuuaccuc 360
uuuuaagacu guaaacagga caaaaaggca uggauaugag aauuagcuag ugaucacugg 420
cuauucuaaa uagucacuaa ggcuugaauu gucucuucac cagaugccug ucagaagucc 480
caaagguuuc ccugaucaua uuaauaacuu uauaaaaaau ugaucauuau ucauuaaaua 540
uuagauauua guaaggaaaa uauaaaugaa gucuaaacca aaacucuuaa ccagacuaac 600
uucaauguua ugaaucacaa aaucuuuuug auugauugcu cuauugacaa gcucuuauau 660
gcuuuuagag aaagauuaag ucccauuaua agagaugaua aauuuuaguc aaagacuaga 720
acacaacuua cagaauacau aacuggacuu gacaguuaac aacuuaguua uuuacacugu 780
acaauggaac aaagaaaaau cuuaauucuu cugccuuuau ugcuguauuu gaccauucag 840
gaauacuuug gcuuucauau uuacaauuaa aucuccuugu ucaaacguaa aauauguaua 900
uuuccuauau gcaacuuuua aagauaaugu uuccauuag 939

<210> SEQ ID NO 113
<211> LENGTH: 100204
<212> TYPE: RNA
<213> ORGANISM: Homo sapiens

<400> SEQUENCE: 113
auacuuggga acaacuuaug uaucuaauuu uuagaguacu ugcaauguuu aagagaaucu 60
aacauccugg agacuugaua cauuagcugu uaaauuauug uuaaauuaaa uaauuuaaaa 120
uaaauuaaau aauuuaaaaa uauauaaaaa uauacaauaa uaugcauaau aaacaauauu 180
aaauuaugca ucugauuuuu uagaguaacu gcaaccuuua agagaaucug acauccugga 240
gacuuugaua uauuagcugc auaacuauaa uuuuaaaaua uacaauaaua cguauaaauaa 300 acauauuaaa cauaauaaac auauuaaacu acugacuaug uaguuucugg auucacaacu 360
auaguugaaa aguauaauaa uuagcuaaau acacaaauag uauuggaauu uuuauaagaa 420
cuugggauuu gcuauaguuu caaguuuuau uuccuaaauu uaaucaguua uuuaaguacu 480
gagaaaguuu ucuuuguuaa guuaggcauc ugaaguacuu aaaaaugaau acauucaaaa 540
uaauucaauu cuucaauaua ucuuuauuuu acauauauau acauauauau guauauauau 600
auauacacac acacacacac acacaaauau auagguaugu auaugguucu ucuguuaguu 660
gugccugggg ucacucaugu gcuuauaguu auccaguggc uugauuaggg cuggauggcu 720
uuuaaagggu agauuucuca gcuuugaaaa cuagucucug cuacuuauua acacauccuc 780
uaauagguua ucuuaggcuu cuuaaaugau gaucucagga caacaggagg gcaagguuca 840
augcacaagc ucuuuauaag gcucuauuua gugcguauuu uaaaaauuau uauucaagca 900
agguacaucc ugaaucaaug gggaagaagu uauaaaaggg ccaagauaac agaauuuuua 960
agauucccca agggagcaua guaugagaga aagggagaga gagcauguua cgagcucagu 1020
uguggaguca ucuuagguua cuuccaagag ccaccugcaa aguagagguu gcagggaagg 1080
gacagauuua cacaaaggca uaggcagacg gggaccugac ucacuggggg ccauuauugc 1140
aaacauguaa cacacuauuc uuguuaguug ugagaacuuc uaauuuuucc uaggcacaga 1200

```
agcagacuua cagaugcagu uuaaguggau gggaugacug auuucuguuu gcuuacaaaa 1260
auggggguguu acuauauaug ugcacaaaau ccaagugcaa uuggaaaugu gaaaggaaaa 1320
uaaaacuugg gaucucaauu cauuaugucu auaagaaaaa auuagggugu aagcugaguc 1380
augcaagaaa cugcucuccu uuuguucuua gcagacagcu acacaucaaa uguuaaauau 1440
cuccacaggu agcuacuuua ggacauucau cuuaucucac guaaagugcu gauuuaccac 1500
cccacgugaa uacauaauau cuauuucccu cucugcucuu uuucucuugc aacacauaga 1560
uuaccauauc uacccuuuuu cucuuccaau ggauuuuucc ccuuuaaaua cugaagcccu 1620
caaaaucauc uuagagaaag gaagagacua cagacuguuu cugugauuca guguuuauuu 1680
cuuuucggca ugucccuaac cuuggcaaaa uaaacuucua aauugauuga gacccgucuu 1740
agacacuuuu ugguucacaa agacuucuca ugagcuacau uauagauaua caaaacuaaa 1800
uacaaucccu ucaauaaaac uguaaauugu auuaaggcaa auuguuuugc cuuaauuuca 1860
uggacaagaa ugagugugca gcaagcagau acuugucuuc cuucaacaug aggaaacugg 1920
aaagaucagu agggagucag ugugaauuaa gccauuaacc auggcuuaau uugccaugaa 1980
gauaaggcaa aacaaaaugu uuaggacaca caauggauac aaaauggcca ugcuuuguuu 2040
uagagaucgg agaaguaagc uacuaugacu uuucuuggua agucagcaaa aaggaacuag 2100
aaguaacauc caaggaauau aaauucauug cuacagagaa caaagguaag caauaauaaa 2160
aggugaggcc uucuugugaa gugauuuugg ucagauaaaa cuguucacaa aagccuaggg 2220
cagaaagaag gcagguccag acaaguguuc uuauaacaag gccacuuaca acauugucac 2280
auaaguccca uuucuugaug aaaacugaca ggugcagaaa aucugacgaa aaauaauagu 2340
uuugccaauu uuccucaaaa auauacagug aguuauugaa cuagaaccug aguuaaauuu 2400
ccugacucac acuuagguac agacgacaau gcauaaaaac uuaguugacu uguucaagcc 2460
agagcugacu uguucacugc uguaucccca gugccuagca caggaaacag gauaaaaaau 2520
acuguuagaa ugaguuaaag aauaaaauuu agguaagauu uugcuuuuag uuacaauugu 2580
cacugagauc uagguuacaa ucuuagcuuc aucaauuauu acuuaacuuc uaugaacuug 2640
uucucacuuc ugaaaaauua gaauaaaauu uaccauuaga gaccaggcac cuugaguuua 2700
ugaaugugag caagagggug guggcagaag gguagaaaag aguaauacag acaaacgaaa 2760
cuuguaagug aauacauaaa aauaaguuau aacgaaugaa aaaaaaaaca gaagaaaagg 2820
uguuagagaa aacagacuuc uauuaugaaa acaaacacgc aguagucagc auaguguaug 2880
acauaacaug ugcucaguaa cuauuaaauu ucauuccuac cauugucaga gguauuugaa 2940
ucacaacaac uccaucuuga auaggggcug gguaaaauaa gggugagacc uacugggcug 3000
cauucucagg augucuguca gucauucuaa gucacaggau gagauaggag gugggcacaa 3060
gauacugauc auaaagacuu ugcugauaaa acagcaugca guaaagaagc cagccaaauc 3120
ccaccaaauc caagauggcg agaaaggugg gacgucugcu cguucucacu gcucauuaua 3180
cacuaauuau aaugcauuag cauccuaaaa gacacuccca ccagugcuau gacaguuuac 3240
agaugccaug gcaaugugaa gaaguuacuc uauauagucu aaaaagggga ggaacacuca 3300
gaucuaggaa uggccuaccc ucuucccaga aaacucauga auaacccacc ccuuguuuag 3360
cauauaauca agaaauaacu auaacaaucc uuagucuacc accuccaaug gggguguaug 3420
caccuccaau ucuuucuugg cgagauccag gagcccucuc cuggggucca gaucagaaca 3480
ccuuuccaga aacaccaucc cauguuaaau uaugaauuaa gaacacugaa caugaagaau 3540
guuuaauuca aauuauugag uaaacacuua caaaauuaaa auauaacauu uaauaaaaau 3600
```

-continued agcaagauug aggaacaagc acuucacaaa uauugguuuc ccagaauguc ugaggaggug 3660
uauagaaguu aagaauaugu ccuccagcca gagagaucug uguucaauca cacuauuuaa 3720
guuacuuagc uucuccaagc cucaguuucu uaacucagau ggaaaaugag gacaauguaa 3780
gcaccuauuu cacuggauug uaaggaagaa uaaacaagau aaugaauagu auuuggcaua 3840
uaaucuuuca gaaaaguagu aaaauuguca uuccuauaaa ucuaacuaau gucuuuaaaa 3900
uucaucucac aaaaucagua ucuuuuuauu uuguacugag cuacuuauuu uacccaaauu 3960
gggggguuaa aaagaaacuc auuacuuauu uucgaaagga aaauuuacug ucaaguacag 4020
uaauuuuuuu uuuaaagcag cguuuaaaaa aaaaaaaaga caaagcacug guccagauag 4080
uuggaaaugu cauuuagauu uaagucuaca gcuucuuagg aaaguuaggu agagauguau 4140
cauacuccag caugauugug agcagacgag caggaugagc aaaacuugca cgaguaagag 4200
ugguaaacac cagagaaggc gcuuucaugg aagggcaccc uagguaacca agcaaguggc 4260
aacaauagua caggugaguc cuuggauccc uucucucucc acccccggca gugguccgga 4320
caaguacuaa ccucuccucu cuagagccuu gacuuuauac uagcuccaca accaucaagc 4380
cccacgaucc gcgaaaggaa uggugcuaca gguaaggcgg gcggggucgg gaugccgaga 4440
ccucuuguca auucuucgcu cgcccccaaa cgaggaucac ggcugcgcgg cucucacucu 4500
aacuaucaag acagauucug auacuaaaca aggcuaaaac uuuuuguuuu uuccuucuua 4560
cagaaggcac uacccuggac gccgcuugca aacgccugaa gagaaggcag ggguguuccca 4620
cuuuuucaga augggaccag gcccuacggc cccaauagca gaagcuucuc uaacccagga 4680
cugcuccccu caauuccucc caauaugcug accgacagcu cgaccucacc uggggggcggu 4740
uccgccaggg gauggcuuag gaaaaccuca ggaagagcag cccagcgagu gacgccacug 4800
aaaccacagu cauggucuac cucguucagg ccaccaguuu gcaggcgccu gagccgcugc 4860
uccucccgcc ucucgguccu uccccgccgc cccgguaccg ucgcagucuu acgcguugca 4920
ugccgggagc gccuuaccuc cucuucucag ggacuucagu ucccagcaug cagaagccuc 4980
aggcagaacu gcacucuggg auuugaaguc cucguuccac gccuucucau cauccugaac 5040
accgagcucu gggacuccgg cggagaaucu aaacguaaag caucacccac ggucgugaac 5100
uguaggcucu ccuggcaucc gggaucuuau ucuggccuug gcggaguugg ggaugguguc 5160
gccuagcagc cgcugccgcu uuggcuugcu cgggaccauu uggcuggacc cagaguccgc 5220
guggaaccgc gauagggauc ugucagggcc cgcggccggg uccagcuugg ugguugcggu 5280
agugagaggc cuccgcuggu ugccaggcuu ggucuaggug gguggauccu uguaagcagg 5340
auuagcgagu cacuccacgc ucagguucuu uagccugagg gcccgugugc cacagcauag 5400
cuaccccgcc cuuccagccu cggguccua auacugccuu gcuucgguuc caguuuccgc 5460
cgcacaacuu cacucauucc aaauguuaau uucugcguuu uuuuucagcc ccaauucugu 5520
uucuccaaau cagggaugau ugucggccuu ccacagaccc ucgcgcuugc caggauuagg 5580
guguucgcgc gcauuguggg uaggggugug gaggaaggga uccagaaauc uuaaguauua 5640
acuuagauua guguuagcaa ggaagccguc acauuuuauu uagccgggac acucugacag 5700
uuugugccga cugcuauuuu ugaucaaggc uauuuugccc acuugucuau uuuguggccc 5760
aauugucugu uuugcuaaca ucagaaaguu auaaugaaau aaucugcaaa aaauguaagg 5820
ugcuagaaaa ccaauaauac uguguaccuu gaaaaugcua auauacaccu guuuuguuac 5880
agagguggag cacagugaaa gaauucaaga ugccaccuaa uauaaacugg aaagaaauaa 5940

-continued

```
ugaaaguuga cccagaugac cugccccguc aagaagaacu ggcagauaau uuauugauuu   6000
ccuuauccaa ggugcuuaau uggucaauaa uaauagauau auacauuaac uuaugauuaa   6060
uuuauuaaua aaauaugaau uuauuuuuuu cagggacaac uauaauuguc acaaucugga   6120
aguguucuua uauuuugcuu gaagguuaua aaauauaaaa caguugcuuu ucuguuuacu   6180
uagguggaag uaaaugagcu aaaaagugaa aagcaagaaa augugauaca ccuuuucaga   6240
auuacucagu cacuaaugaa gguuuguaug uaguagguuu uaacuauagg uuuggcuauu   6300
aguggaacua uaaaaaucug uucuuauaua agguaaucuu ugugaaaaua ccugguaaua   6360
ucuacaucac cacuaaaaaa ugcaauauau uuaaauguga auuaaguauu uuaguguaua   6420
aaacauugcu aguuucuacu uaaaguuucu aaaagggugu guaggggaaa uagaaugagu   6480
auguugaaaa guaacauaag gaaauauauc uugaggucca aaugacaaau gcagacaaug   6540
acugcuauag ggauuuguua agaggggaaa ugauuuaaga gaugucagaa gacuucacaa   6600
aggaucaaua cugaggagua guguuagaua aguggaaggc aaugcagugg uaagauagua   6660
agggaauucu agagcuguug guuaccauaa auaaauacug agaacaggaa auauguuuau   6720
ucuuuauauu ugaggaaaca aggugcagca aguuuguagc agacuguaga gaaaacaaau   6780
cuuggguaag uacuuugaga uagguuguug agggccuuaa agguguauuu uaugcuauca   6840
gcaauugaga aggcaguaaa gguuuucgaa acacaauuga uagguacaaa aauacaccuu   6900
aagaaggcaa aacugaguau auuauguagg acaaacugaa ggaaauugga gcuuuguaga   6960
caucacauua uagcggaguu uaaaccugaa auuauggauu agaauaauag caauuggaac   7020
agaaaaaaag uaguggaaag acauuacaaa gggagauguu gcauuacugg auauaagacu   7080
ugaggacuug agguaaaaag gagaaucaaa aauguuucau gcuauuaaaa aucuagaaau   7140
uguagucuua aguaagaaaa uugccuggca ugguggcuca cgucuguaau cccagcacuu   7200
ugggaggcca aggcaggagg auugcuugag ccugggaguu caagacuagc cuggauaaua   7260
uagugagucc uugccuguac gaaaaaauuu gccgagcaug auggcacacc aagcaugaug   7320
gcacgccaag caugauggca ugcaccugua gucccagcua cucaggagac ugagauggga   7380
agauugcuug agcccaggag gcaggagguu gcagugagcu gagauugugc cacugcacuc   7440
cagccugggu gacaaaguga ggcccuaucu caaaagcaaa aaaaacaaaa acaaaaacca   7500
aaaacuauuu auucagcaaa uauuuacuga acgucuccau gugccagcca uugcuggcac   7560
uaaggaucau aacaaauaaa acagaauuuu uauuuucagu gcuuacauuc caguauaaag   7620
gcauauugaa auaaccuuuu uuuaauguuu agaugaaagc ucaagaagug gagcuggcuu   7680
uggaagaagu agaaaaagcu ggagaagaac aagcaaaauu ugguaagcac cuuggaaaaa   7740
guuuauuaug guauuaaaua augaauucca uuuguucauu aaacuguaga aaauuaaauu   7800
auauucuaua aaauauauau auucaguuua uuuuuaauau auaacauuua auaauaaaua   7860
uuucuagacu ccuauuuuau ggaucugcca uauaauacuu uuuguuaccu uauaaucaug   7920
auggacucuu uuaaaagaau uaauuuuguu auugaaauuu auuuaaaagu uuguuuugug   7980
guaacuaauc aauuaaaacg uuuuucuuuu uuuuuaaaaa aauagaaaau caauuaaaaa   8040
cuaaaguaau gaaacuggaa aaugaacugg agguaugucu uuuuguauuc ccuaggaugu   8100
aauugucauu aauuuuauuu ugaauuguuu ucaaauuuua aaauuauugu uggcuggaaa   8160
aauuauaagg augauuguaa ucaugguuau uuguuuauuc uguauauguu cuacaugccu   8220
auuaugugcc uuauauagua cuaaggacug agcauauggu ugugaacaaa auaagaaguu   8280
aacugcugga uggagcuuau agucuuggga aauauacaga aagauuacua guaacugagg   8340
```

-continued

```
uggagggugg guggggauuu gaggaauagu gacgaaaggg uguuauagaa guaauuuuug   8400
acaaagcuga aggcuaaaau augaauguau uguugaagaa caaaauacau ugagauuccu   8460
gagaagguag gaaugugaua caaauggauc agccuuugaa aggaggaaua cccuuuuccu   8520
uuguguuagg agaggaggau gaguggauga gcgugggaag aguggaugug uauagaggcu   8580
uuuauguuug uaggcauaau gcuuggaagu ugaggggguug gugaugacau cuucuguuaa   8640
aaagaguggg aaauggugug gucacauuuu aaggaaauua gguaaaauuu gaaauauauu   8700
ggagacagga cuggagaguu ggggaucugg agucagacag auuugaguuc uaguccugau   8760
ucuucuacuc guuaacucuc ugaacuugga ugaccuauug uuuuugauug uauauccagc   8820
uccugggaaa augccaagca cuuucaauaa auacuaaaug aauuauggag uuggaucagu   8880
ucuguguuag uguuuagcua gguagcugcu guagaauaga aggguagcac aguugaagau   8940
auugguagga aagugguuga agugaugauu augaagucuu aacugaauag auaaaaucaa   9000
gauuggggguu gggugggcag aaggguaggg auauggaggg agaagaugag ggguuagagu   9060
guccugugag gucgaaggac aggcauagug ggaauaauug aaagaauguu cugguuggac   9120
aaggaucuga ugugggugug ggagugagag acuauaguga auucaagaaa aaaauagacu   9180
agaacaaaag uuauguggag auugcuuagu gggcauuuga uagacaucug ugggccacau   9240
gcuuaaauuc ccagugcauu uugcggaguu acuggaaggu ugguggcuug uuucuaccau   9300
gaguagguaa agauggagag caggauauuu ugugagaaag cagcugaagu uucuauagga   9360
ugauggagga augauaggaa ugaucaccug aaguugcagg guggggguaaa ccuagaagca   9420
ccaacaccuu cuucugaccc ucauguauuu ggaaucugaa agaaugagca ccuuccaauu   9480
gaaagaguuc caagggcauu aguauacuaa aggauccaaa uugcagcuaa gccaaggaga   9540
uggaaaggag gauucaguaa agaaucugag gaugugaaau auuaauuuau cuuggaagag   9600
aauuuuagag agcacaaugg aaugcuuuuu ggaggagaga aagaguaaga acaauuuggu   9660
uaagguagag gaauaacaga acuauaaggu gaagaaauga augugagaca cauuagauga   9720
ccaaaugauu ugauguucuu ggccaugacc ugaauuaaca agacugugag guaaaaugga   9780
uuuaaucggc uacaaaucuu aagauaacca aaaccugagc uguuuaauau gguagcacua   9840
gcacuaacca cuuguagcua uuuauauuua cauugguuaa aauuaaaaug aaaaauuuag   9900
uucuucaguu gcacuagcca cacuucaaau gcccgaacau agcuacaugu agcgaguggc   9960
uauugaacug gacagcacug acagcauguc cauuaugcua gaaaguccua ugggacagca  10020
cuggucuaaa cagugcaugg uaugagagaa agggcagguu aaggcacuca gcuucacuga  10080
cuggggugga gauucugaug guuuguacuc agguuccaga ucccugaggc ucaggaaccu  10140
uugcaguuua gucugguuac cuguggccca gugguuacaa cagaaugauu aacagucaau  10200
ucuuugcauc ucuggguggc ucaggaaaaa uuuaaggagu uauuagcugu gaacuaaccu  10260
uaaguaaguu aaauuaaaaa aaaaaaaguu cuuaagcuaa uaugauuuua aauaucugca  10320
cugaaguaua augcaaauuu aaauucagca uaauuauuug cuuguuguug acucauuuga  10380
accucaaaau auaaugggau uaauuuauac uuuggguuua uuacuuuaag auggcucagc  10440
agucugcagg uggacgagau acucgguuuu uacguaauga aauuugccaa cuugaaaaac  10500
aauuagaaca aaaagauaga gaauuggagg acauggaaaa ggaguuggag aaagagaaga  10560
aaguuaauga gcaaguaaag cacuuuuuuu uuccaugaau cuucacuguu caaguuaccu  10620
ggcuuuuuau uauuauuggu aacaauauca auuuuuauau uguauguuau auuugaaaaa  10680
```

ugauguacac uuaucucuaa gguuuuauau cacuguucau uuugucauca ccaauuuuaa 10740
aauauaaugg uacuucuagu gaauaugacu ugaagauuaa uucuuuauau uuggaaguac 10800
auuuuucuca ggacaucaaa cuuguuaccu aaaauuaaug cuuuugucug gaagauuggu 10860
aucaaguaac uaauagauuu ucauaaagaa gugaucuuuc uagugccaua guuuauuuug 10920
gguaaaaguu auauuuguuc auuucaaugu auuuauauga uuaguagauu cgcaaaugaa 10980
ucuuucgaua uauucaauaa ugguuaauua aauaucuugu uuuugguugu accuuauuuu 11040
augugagaua uauauauaua uguauaguuu uugaaaaguu guguucaugu cagcaguuua 11100
uaaaucacau auuuaaaaua acauuuuuaa ugcauaguuu uuauuaccuc guuauuccuu 11160
guuauaaacu aauaauucuu gcaguguuca cuugaauuua guuuuaggaa aaaaguuuuu 11220
ugcagaucaa cuuguauuuc cuggaagaaa auuuccuauu uuaccucagc uuccuauuua 11280
auguauuauu uauuuauuua cuuaacauuu auuuguuuuu uauuucaccu gaacuguuag 11340
uaaacuuagu aaaauuuggu gccuacaugu gguaacuguc cugucccuua uacucagaaa 11400
cguuuuccac cuuugugucc uuuaggucau uguuguguua uauuccauuu auuuuauuuu 11460
guccauuguu cucucagaaa uugaggguca uacauuuuaa gaaaacaaug auaugcuauu 11520
uaagagaaug uaucauaaau ugauuuguaa ggaaaaguau ccccauucuu cauguaugua 11580
uuuuacucua aaauguugaa gaaucauaua gaaguuagcu augaaaacaa ugugguagag 11640
aaaguaugga ucgaugccac uuaaauguua ggaagaagcu cuuagagcau uaucuguuua 11700
gcuaacugca aaacauagca gacaugugga uuuuuuaaua gucaucaagg aucuaacuua 11760
uaauauacac ugguagaauu gcuuaggggg augucugugg uuuucuggac uuuuguucuu 11820
cuauauagac cuguaucagu ugacuuauca uucauaccac acacccuuag cuaaucagaa 11880
cuaccuuguc cauuuauauc uuagacuauu gucuuuuuuc auagucacac acagagaaaa 11940
cuugaauaua uggccugugu uccuuuuugg cugcucaauu ccuugagaug aaauaugggu 12000
augguugcu uuggcaauua cuucuuugcc guuaaccagu cauucaguuu uauugagucu 12060
uuacagcaua ccagaggcug cuaguuacua gugauauagu gggcaacuau guucugguuc 12120
ucaagaauau ucauagucaa uaauaagcau aacauaguga uaauaugaua cuuagggaga 12180
uacauaaggu cauauucugg cauacucugg agagagauac cguaaucagc cuugaggugc 12240
aggaugugau cuguaaacug agaccugaag uauaguuaga cugguaagag gaaugaggau 12300
auauauggug guuaauaaaa gaacauucug gguagaagau auagcauuug cuaagaccua 12360
gagguaagag auguuaugga guauuuagga aacuacaguu auucauuuug acugaaauau 12420
aagugaaaau agcuuucaua gaguccuuac uaugugccag gcacuucaua ugcauuaauu 12480
cauuauugcu uauuugauac uugucauaug agauaguugu cauuucugcc augauacaga 12540
ugaagaaaug gagacacaga aagaguaauu gcccaugguu gcacagcuua uaaaugguaa 12600
agguaggauu ugaaaacagu cuuacucaag agucugugcu aucuugccuu cccaguuuua 12660
uuuuuuauga uccucuggag agauaagcaa gggccaguuc cuaaugaauu ugguucuuuu 12720
ccugaaagga gccagugaag aguuuugagc acaggauauc augaucagau cuauacuuua 12780
aaaguuuacu guacuuugua gagaguggau ugaaaagggc caagacuagu aaggaaacau 12840
uuguguuaau ucagggaagu gcuaaugaug gcauuugccu gagaaagaca agugugagag 12900
aaguagaugu aauuggaugu ggugaaugua auugguuguu ggaggagagg gaggauggag 12960
agucugccua auuuuguggg uugggccacu aaauagguag auagugccau ucauuaagga 13020
ggaacacaag aggaauuugg aaagcuugag auuauuucag uuuuguagau guugaguuug 13080
agguucuucu gggcauauuc aaaaagggua ucuguggaua uggaauucac aagagacccu 13140
guacagauga ugaggauuua ugaaucauca auguagacau uauugaagcc agagaaguga 13200
uuguaaggca cgucucugag aaaugucuaa uaaagcaaug aaauaggaag agugcuucaa 13260
ggaaaagcuc aagaaaggag aaacagagug ugauguuuga gaagacaagg gaaaaaaaca 13320
uuaauagcau uaaaugcuuu agcauuaagu ucuuggcuuc ucuucuugua aaaauuuccc 13380
aauucagaac acagugggau uauuaacuuu caauugauaa uaauaaugau aggcaaacuu 13440
cuaaaauuug uauuguaguu ugcauuuuau uauaaacuuu cuuuaaauuu uuauuuugaa 13500
aaaugucaua ucuucauaaa gauuguaaga aacacacugu ugguguuaau guaaauuagu 13560
ucaaccauug ugggagacag uguggcaauu ccucgaagau cuagaagcag aaauaccacu 13620
ugacccagca aucccauuac uggguauaua cccaaaagaa uauaaaucau uuucuuauaa 13680
agauacuugc acacauaugu ucauugcagc acuauucaca auagcaaaga cauggaauca 13740
acccaaaugc ucaucaauga uagacuggau aaugaaaaug uggaacauau acaucauaga 13800
auacuaugca gccaucaaaa gagaaugaga ggucaagcgu ggugacucau gccuacaguc 13860
ccagcacuuu gggaggccga ggcaggcaga ucacuugagg ucaggaguuc aagaccagcc 13920
uggccaguau ggugaaaccc caucucuaca aaaacaaaac aaaacaaaca aaaauuaacu 13980
ggucauggua cuguaugccu gcagucccag cuacuuggga ggcugaggca ggagaaugac 14040
uugaacccag aaggcagagg uugcagugag cugagaucgc accacuggac ucuagccuua 14100
gcaacaaaac uagaguuugu cucaaaaaaa aaaaaaaaaa aaaaccggaa caagaucaug 14160
uccuuugcag ggacauggga uggaggugga agccauuauc cucagcaaac ucacacagga 14220
acagaaaacc aaacacugca uguucucacu uauaaguggg agcugaacaa ugagaacaca 14280
uggacacaug gugggggaaca acacacacug ggacccguca aggggucggg gugggagaac 14340
aucaggaaga auagcuaaug gaugcugggc uuaauaucua gguuaugggu ugaucugugc 14400
agcaagccac cauuguacac auuuaccuaa guaacaaacc ugcacaucuu acacauguac 14460
cccagaacuu aaaaguugau gggaaaaaga aaaacaauaa ccacccacau acccuucaua 14520
uagauucacc aguucuuaau guugugccaa cuuugcuuua ucuuuuuguc aguauuuuua 14580
cacacacaug uauuucucug ucucuuguuu guucaaucac auuuuuugcu gagucauuua 14640
agagcuaauu gcagauauga uacuuugcac uuaaauauuu cagcuugucu guuugaaaaa 14700
gaaagauguu cuccuacaau gaacacaaua uaauugucau gcucaggaau uuuaauauug 14760
auucaacacc auuaucuagu ccauaaugag auuucuucua auggcccaau aauauccuuc 14820
agucucccca ccuccaauau ccaaaguucu gucaaggauc acauacuaca uuugguucuu 14880
uauuauagac uuuuuaaaua ucguuguaua ccauugugau ucuaucgucu ccuuuaauaa 14940
agaggagaac cagaaaaaug aaaggucaua agaggaauga gguuuggaga auaggugaaa 15000
aaaggcauca uaauguuuau aauaauguuu gccuguucag agaaacaaga aucacagaua 15060
aagucacuua uauguagaua agagaaugcu guauuacuuu uugcuauucu auucacugau 15120
cauuuuucua agaacucugu augcuucuug uuuaacucuu augucagcau guaugagaaa 15180
acugaguuaa agagauguua aguaacucau ucaugcuuua cuagaaauug guugaugagg 15240
gacauaaacc uaggccggug ugauuuuaga uugcuucuuu uaaccauugu guuguauugc 15300
cuuauauuuc uaaguaauuu auguucacug agagcaaaua auagucuagc uaugacuuag 15360
aaaaguaaaa uaaagauguu gggcagaaaa ccauuuuauu aggggguuuuu uuggaggagc 15420 agauuaauuu guuucuguau ucuuugguua guuugugugu guguucuuuu uaauucuuua 15480
aaaugaaacu guuuaauccu uaaauccuua aguuuugaaa auuuuggccu auuauuuaug 15540
uguuagguug auauuaaauc cuuaauagcu uuaacauuuu cuacuuuguu agagaggauu 15600
uaaaauuuaa guagauaagc ugaauaucug gcuuuauauu aaauuacugc ugauggccag 15660
gcacaguggc ucaugucuga aauccuagca cuuugggagg uugaggcaga uggaucacuu 15720
gaggccagga guucaagacc agccuggcua acacagugaa accccgucuc uacuaaaaau 15780
acaaaaauua gccaguuaug guaaugcaug ccaguaauuc cagcuacucg guaggcugag 15840
gugggagaau ugcuugaacc gggaggcaga gguugcagug agccgagauc gcaccacugu 15900
acuccagccu aggcgacaaa gacuuugucu caaaaaaaaa aaaaauuacu gcugaauuuu 15960
aucuucuucu uauuuauuuu uuuuuuuuac uauuuuaguu ggcucuucga aaugaggagg 16020
cagaaaauga aaacagcaaa uuaagaagag agguaaaaaa uuuuaguagu uguggugguu 16080
caacaaaggu acuuauuaaa auaaguaccu aaguuuacau aaauuuauau uuuaaccagg 16140
acuggagucu ucuaaguaac ugauguuuuc agacugauuu uaugguauga cuuugucuca 16200
gggaaauaga aaacaaagca aaaugugagg ccauuaagua uuacauucau cucaggucua 16260
ugcggguaaa ucuuuuuuug uuguuuuaua agccauucuu ugcuaguuuu cuaauugaau 16320
agaugacugg auuucuauuc uuauuucucu uacccagaau ccuuuaaaau uuuuuguuac 16380
uuguggaauc uuauaaauuc ugauuaucau uugguucuac ugagccaaau aauguuugua 16440
cauuguuuau ucugauagaa guucuuaagu uucuaacaua auugaaauau uauuuguuuu 16500
gguagauaau uaguauucuu ucuuugguua uucaagauaa uaugcaucau uuucccaaaa 16560
uuuuuuuguu uucuuuaguu ucugauuauu auuuuuaauu auguauuacc uuucucauuu 16620
cuaauuaccg uuuuccuguc cuuuucugua gaacaaacgu cuaaagaaaa aggugaggcu 16680
uuaagugugg ugaaaucuug ggaauuuaaa auauguugug agagcacuau uuagaggaua 16740
ugauuuuguu auucugaaua guuuuguaau ugaauguugu guuugguuac cuucagaaug 16800
aacaacuuug ucaggauauu auugacuacc agaaacaaau agauucacag aaagaaacac 16860
uuuuaucaag aagaggggaa gacagugacu accgaucaca guugucuaaa aaaaacuaug 16920
agcuuaucca auaucuugau gaaauucagg uaaaauggcu agaagucaau ucagagcaau 16980
gguuccuaaa aacuuuaauu ucauuacaau guaaauauaa uauuuagccc uacauguaaa 17040
uucccuggua uaaaucuguc acuauguacu uguaaaaugu gaaauaaauu acaucuuuga 17100
aguugcaacu uuuuagccau uuuuauauuu gccugucuug gucauuaaga acaauugagg 17160
uccuuaugua cuauuuucuu gauucaauuu gauuuaauug gucaaugcca auuaguaaag 17220
gucuauaaag aauucucuuu uuuucuagag gacacuuaug gcugcguuua auuuuaauuu 17280
gguuuaaauu ucaguuuuuu uaaaauuacu uuuuaauuau agugucuuua acuuuuuuag 17340
acuuuaacag aagcuaauga gaaaauugaa guucagaauc aagaaaugag aaaaaauuua 17400
gaagagucug uacaggaaau ggagaagaug acugaugaau auaauagaau gaaagcuauu 17460
gugcaucaga cagauaaugu aauagaucag uuaaaaaaag aaaacgauca uuaucaacuu 17520
caaguaagaa uuacuuuuag aauaacuuau uuauucagac uucauauuau cucauuacua 17580
uuuauuugac acuagaaagu acuuuuucua ggaugugaau uuuugucugu cuuuuuaaua 17640
guguaauauc uugucauguu gguauauuug uccauaugug uuucuccaau caccucacaa 17700
acacuaauuu uugcaauuua ggauauauaa augauacuug aaugaaugug uagauagcag 17760
ucauuauggg guuuucuaua aaagacuacu gaaaauccug uggaucauaa cauuucauuu 17820
uaucuuaaaa uaaauacauu auaaauguau uagaaaccaa uacauuguuc aguauuuaug 17880
uggauuaaau uuguuuaaaa gguagaauaa uguuuaaaaa uaaaauuuuc uaguaaugaa 17940
agauaauuau gcaauuauaa gaugcagaaa cuauuaaaug ucaccuauaa uuccaggaug 18000
acuucaauga uaaauacaca uauguaaugu aauguauccg uauguaugug uauauaagua 18060
ugaauacgua ugugugugua uguagauaua uuuauauaua uaauguauau guaaauaugc 18120
acagguguaa auauauguua caucaguuug caacaacucu ugaaauaacu uugucuuuua 18180
ggugcaggag cuuacagauc uucugaaauc aaaaaaugaa gaagaugauc caauuauggu 18240
agcugucaau gcaaaaguag aagaauggaa gguauuuuuu uucaauugac auaauaacuu 18300
uuucuuuuug uauuuuagau uuaaauuuua gucuuauuuu ucuuuaaaug ucuuauacug 18360
guuuauaaca cguuuauuag gguuuuuaaa cauaaguuua uuuuauuuau ugguuagaaa 18420
agcucuagaa cuguccuuuu ugaucucuag cuaauuuguu auugaaugac cucuuucaca 18480
ucaaugaguu uaacuuuaaa cuuuuugaua gaagucuaac uccaaaauau auuuggcauc 18540
uaaaauauau aauucgaaau auaauuuaaa uuuuuuuacu uaacucauag uuaccuuaua 18600
uacauuaguu aaauaguugc agguuuaauu uuaguuuuuc uaacuaaaug ucagguucau 18660
cagugggaau gggaauaagc aaagggauca gaauaacuug ggaagccuuu ucaaaauaca 18720
cuuuucuucc ucaccaccac ucuccaaccu uaaccaaauu gucaggccuu accauauuag 18780
aagcugggau uaugaugguu guauacuuga aaaacaucag agauuauucu gaaugaauaa 18840
uucuaauuuu aaaaacuauc acuucuagag ucauugcuuu cuaguauggu ucacauaaau 18900
cuugugggca guuuggaacu gguuagcauc uagggagcuc agauaaccua uauuuuaaac 18960
aaaagcauua gcaauggaaa uaaggccuau agaaucaguc augucuccau aaacuuuaua 19020
uaaagggcca gacagugaau auuuuagacc accuggucuc ugcuauaacu aaacucugcu 19080
uauagcauga aagcagccau ugacaauacg uaaaugagug agcaaggugg uuuuccggua 19140
aaauuuuauu uacaaaagca gaugggaggc cagauuugac cuuugggcca uagucuacca 19200
accccuggaa aaaacaguug ucuuuaccag auugaauguu ggcaggguaa auggugacau 19260
guuauaugua uucuguacuu uguuuugacu uaauaccauu ucauaauuau uuuauaucag 19320
uacguauagu auugcuguuc uuuuuaaagg cuauguaauu uuucuuuuua uacagguguu 19380
aauuugauaa uuugugaagu uuaugaaguu uccaauuuug ggguuguaaa cuguuuuaau 19440
gaauauccuu auauauguua uuuugcaaau guacaaguau aucuguggaa uaaauugcug 19500
caaguguugu aauugucaug uauguugcaa auacauucua acaguuuguc acuuuuuuug 19560
cuuuauggca uuuuuugcug ugaaauauuu cuuuuuaugc uuaguuaaau uuauuauuuu 19620
uuaaugacuu uugacauuug uuauaaugag aaaggcuucu gaguauaaac uuguuuucuc 19680
aucuuuucuc cuaauaucuu guuuuguuuu uguuuuuguu uuuguuuuug agacagaguc 19740
ucacucaguu gcuuaggcug gagugcaaug guacaaucuc agcucacugc aaaugccacc 19800 uccugguuc agguguucu ugugccucag ccuccugagu agcugggauu acaggcaugu 19860
gccgccaugc gcagcuaauu uuuguaguuu uaguagacau ggggucacac uguguuggcc 19920
aggcuggucu ugaaccccug gccucaagug auccuccugc cugggccucc caaagugcug 19980
gaauuacagg ugugacucug ccuggccuuu uuuuacauuu aaaucuucga aacauauaau 20040
ucauuuugau guaaggagua ucauguggau ucaacagagc uacucuguug uccaaacauc 20100
uuuuauugau uauuucaucu uuuauugaau ugauugaucu auuuucuagc aguguauacu 20160

-continued

```
uguuuuaauu uguguauguu uuaauaucua aaaacguuau uauuuuucug cuuuuagacu  20220
ucuuuaugaa uauuuuuaau gugaauuaua gaacuggcuu guccaguucu uaaaaaauau  20280
cuuguggauu uuuauugggu auguguuaaa guuauaaauu guuuuauaga uugauuuagg  20340
auaaaccuuu uuauguuauu ugguccuucu agcuaaagaa cacaagauac cuuuucuuuc  20400
auucauucaa gauauuuuau gccucuuggu ugcauuuuaa ugcauacuuc auaaagauca  20460
auuguauaaa acuuuucaca guuguaugga aguacuucuu guuuauaaau gaguuuugaa  20520
agguugaaau auuuuuaaag auugaauuau aaaaaaagaa aauucgguau auauuuuaaa  20580
aucauuuucu auuugaauuu cagguuguau auacaaaagg aacagagauu augccaguag  20640
uugcucauac uuucucauuu caaauaauuu uuauuuucug uaucauaaau cuacuaacgg  20700
uguuuauuau uuaugauaau gaagaauguu uuauuaacuu uccuuuugca uaacagauuc  20760
uauuguguuu auuucuagcu aauuuugucu ucuaaagaug augaaauuau ugaguaucag  20820
caaauguuac auaaccuaag ggagaaacuu aagaaugcuc agcuugaugc ugauaaaagu  20880
aauguuaugg cucuacagca gguaaaaucu uaacagaauu uuguuuauca accaguuuua  20940
uuacaguugg aacucugaac gaugucuuuu auuuauuaua ucaucagugc cuaguguagc  21000
ggcugguacu accaagugua uaauaauguc uuuugaaauu ucuucuacca ccuggucca  21060
auaaaaaauu agaauuaagu uuagaucacg gauuagacuu agaacuagag uuacuguguu  21120
uauuuuucua uguuuaugug gauaguacac acauuguuuu gguuagaaau uauuuaacaa  21180
gaaaugauua aaaacuuuua gaaauuuaaa auaauuuuau acucuuuuaa gguuuauuuu  21240
acuguaucuu aguccuaaca uacccuauac aaugugaaau aagcuaaaag caugguuaua  21300
auuugacugu gcuaccuauu uuauuuuuag ugaaaauaac ccaaauaaaa ggaaguaaua  21360
cuuuuauuau uugugcugua guuauagucc acaaguaaga agaugauuug aaaaguguau  21420
gcugaauaag aacaauuaca ggggacaaca uuuuuuaaua aaguacgaaa ggggaaaaag  21480
cuaaguugaa uaaaagagaa agcacagagc aaaacagaaa cauacaaaau gguaaaaagg  21540
uggaauugaa uggaggauga ggaaaguaac auauaaggaa guauagaagc cauaaacauu  21600
agggaguucu ggaaauccua uuuuccagag uguuagccau uauauccauc uuucaguauu  21660
ggaguaacag caguguaccu aucauugugu auuacaguug aaguguacaa aaugguaaaa  21720
ggcauacuug uacccacaag aaaauauguu cuacagucuu guugaaaaaa aucagacgua  21780
cuuuuuuccu uaccuuuuua gguuaaauau caugaaggga uauauauugu uuuaaaauau  21840
uuuauagggu auacaggaac gagacaguca aauuaagaug cucaccgaac aaguagaaca  21900
auauacaaaa gaaauggaaa agaauacuug uauuauugaa gauuugaaaa augagcucca  21960
aagaaacaaa gguauuuuua uaaauauaua guuauuuuau auacaauuau guuuuuaacg  22020
acuuuauuuu uauuaaaaua aaaugucaag ucaauauuga guuuucucca uuugaauuuu  22080
auauuuucaa aaaauuguac aagauauuua uuauuauacu uauauuacua gugcuuacau  22140
uuguaaauga uggaugcauu uucuauuauu uuucuccucu ggugaaaauu acauuaacgu  22200
uuauuaccag gucacuggua ugaaagaaau gaaaaauugu gauacaauua uuuuuauuua  22260
acuuuuuaua auuaacaaag aauggaagau aauaaaauuu ugaccagugu aacagcauug  22320
cagauaguuu ucagagguaa uuucacauua aucuuaccca aauuaauguu ucaucauauu  22380
cuccuuaccc ugagccauau uaccuuuuuu aacacaucaa auucuaugaa uauaaguucu  22440
uacaauaucu guguuguuau auuuccauag cacuacauac uauaguuaug ccagggcaca  22500
cuagugcgaa cuguucaugg gaaauucaug gacauguuua uuauaauugg ugacuaugua  22560
```

-continued uauauguaua cacuacauuu auacacacgc gcauggaauc acuauuucuu cuucauguca 22620
uauauauaua cauauauaca cauauauaua caugucauau gugugugugu auauauauau 22680
auuuguauau augacaugaa gaagaaauag ugauuccgug cacauaugug uguguaagug 22740
uagugaugug uuugcaggua cgguuguaau uucaaaaaug aagcaaaagc cuugcucagg 22800
agauaauuga accaauacuu aaaggaagua aaggagugaa acaugcagau ggcucuaagc 22860
agugggaaua aguucaaagg caguaaagca ggaguguacc aaucaugucu gagaacaaca 22920
aagaagucuu uuuggcugga guagagucag caagugaggc agugauaaga ccagagaggu 22980
aaacagaggc cauaucauau ggggccuuau aguucauugu gcagacuugg cuuuuaagug 23040
agaagggaca ccggggaaag uuucugaaga uagaaaugau auaauuugac uuaggcugug 23100
uuugcaguag acuguaggag ugguaaauaa gaaucaggga gaccuguuag aagacuauug 23160
caauaaucug gagaaaagug augguggguuu ggggcauggu gguagcagug gaguuacugg 23220
augcagcagu ucuggaugua uuuugaaagu gauaaaaaug gaauuugcua acagaucaga 23280
uguaggaugu gagagagaga gaacucuugg ucugaaccaa aaguuuuggu cauggugggg 23340
uugugggaag agcagguuga gagauaauca gguacuuaau uuuagacaug uuagguuuga 23400
gaugcuuauu agacauucaa gugaaggugu uaaguaggca cuuguauaua aaaguuuaag 23460
guuuaggaca acaaucuagg cuaaagauau guuugguaac ugucucugua aaaguaauug 23520
aaauaaugag gcuggcuaag aucaccaagg gaguaaaugu agguuaagaa gaaaaaucua 23580
aagagcuucu acuuuagcag cuggggagau aaaaaggagc uaccaaagga gacugaaaag 23640
gaaagcccag agagcuagga ggaaaagcag gaguauggag agcccugaaa accacaugag 23700
gaauguaacc aaggaagaag aaacaacugc uuucagagcu guguucauug cugcugauag 23760
gucaagauga ucacuaaaag uugacuauug gacuuagcaa uggucauuuu ugguucaaga 23820
gaaaaugggu agagaggaaa uguaauaaag aaauauagga acccuuuucc aggacuguuu 23880
cuauaaagag aaggagaaaa caaggugua gcuugagggg aaagagggau uaagaaaaca 23940
uuuuucucuu uaagauggaa gaaauaacuc augauuuuag guuaauagga gagcuccauu 24000
aaagaagaaa cauuaaugaa ucaaugaagu ggagagagag aacuucugga acaauaaauau 24060 uuuuaagaau gcaaugggau gggauccuag ugugccagug aagagguugg ccuuaacuag 24120
gaacacagag uucauccaua auuguagaaa agaagguaga guguauagau aucgauguag 24180
guggcuuggu agacauccug guaaugggaa uuuguggaag uucuaaacug guugcugcuu 24240
uuuucucagu gaacaaggga gcaagguucu uagcugaagg ugaggauagg agaagauguu 24300
ucauaaguuu gaggagaaag aagagaagug aaaguauaaa auggucaucu gaaagauuga 24360
agacguggag aauguggua gacuguugag uaacuucaag agcccacgau auauauaugu 24420
auuucuauuu auguguuuau uauauuugua ucagaacacu uugaaaguag uuuaaacugc 24480
uuuaaaagga ugacuaauag uauggauugu gcguauucua auuacuagga gaaaaagugg 24540
caauugaucu cugcugucaa auaaggaaaa ggacuuaucu gauaaacacu uagucagucc 24600
guaguuauau aaucccuaaa gcucacagaa ggugugugua cuagacugua cucuacaucu 24660
ugaacuuaac uuguaaaacg uaauggcuaa ugguauucuu ccuucauaag auuaggauua 24720
gguuuaguua ucaggaacag agagcugaag aauaauggca aaaucaagau agacauuuau 24780
uucucaucua uguaauggcc uagaauuaag cauuccaggg uguugccuuc aucugcccca 24840
uccaaaaugg auggaaugca gcuuuaucuc augucugugu cccaaacagc aagacagagg 24900

-continued aagaggggca agaguuaaaa gcaugugcug aaggauaggc agguaaauau aguguuuauu 24960
guguagggcc auguggaaga augauaggag aauagauaug uggauggaag ggagaauaga 25020
uacuggggga caacucagcc ugugucaugu uccacagcuu agauguuagc uccagacagc 25080
ugugcucauu ucuuaaaaac uuuugugauc ucaaacguac uaguuuuaug ccuaagucca 25140
auauuaaaua uauaaccuau auauuaguaa augcuuauaa ugaaugagug ugagaaugau 25200
cugucaauca auuuuggaau gauagcaaua uuauguuuug gucuuuuaac aauuuaguaa 25260
gauauuacaa guaggcauuu aggaaguuuu uagcuuaguu uggauuaaau uuagcugcaa 25320
gugacagaaa aaucaagcau aauacaauaa uuuaaacaag auagaaauuu auuucucuau 25380
aauauagaca aaguugaagc aacuagggca ggauuugugu gacagaugcu caaauauccc 25440
cuaucaggaa cccugucucu uguugcugug ccuaucucaa cauguggguuu cuaacucaug 25500
ugaaguugcc acccucauau ccauguggau uucagcuagc aggaaggagg aaagagaaga 25560
gagauuacuc cuuuauuuua aaaacauuuu uuuuuuuuuu uuugaaauuc acauaugaac 25620
uuugcguuua uauuccauua cugacaugac cacacauagc ugcuugugug uaaguggaaa 25680
uuuaguucuu uauuucaaau ggccacgugu caagcuaaaa auccauaguu uuaguacagu 25740
ggacaaaagg gagguuaaau auuaggaaca gcuagcaguc uguaucacaa ugaucauuuu 25800
uuguaaagca guauuuugca accuuuuaaa auccauaccc cuucagcuaa gaagguuuua 25860
cugaacuuca guuuuuuagu aaauuguauu aguaaaacca aaacaaaacu uucaucuuac 25920
aaauauaaaa ugacaacuuu aaaggauuuu uuuuuaaugg cauaccacuu uucuugccac 25980
cauguuggga ucacugauuu gaaggaauaa guagucaauu caauucauga uuuuuguuuu 26040
uacucuguag gugcuucaac ccuuucucaa cagacucaua ugaaaauuca gucaacguua 26100
gacauuuuaa aagagaaaac uaaagaggcu gagagaacag cugaacuggc ugaggcugau 26160
gcuagggaaa aggauaaaga auuaguugag gcucugaaga gguuaaaaga uuaugaaucg 26220
guauguauuu uuaucuuguc auucaaggag cuuagaauua uucuugccau ucacagacua 26280
uucugugcua uuuacugcau accauuuaaa aaacauucca uaaguaucuu uugauaaaga 26340
uuauccucau uaauuuauac uaaacuauug aaaccuuuga gcauuuacuu uuugccagaa 26400
uuguuuucaa acuuuugauc acagugauuu guccaaauaa ucaguuuugg ugaagcagca 26460
ggauuacuuu uuuuuauuau cuguguucau ugggccacca uguagaugug acaccacugg 26520
ccaauuugac agaauuuaug acaggaacau acugugucaa uacaaccugc ucuccacuuu 26580
uuauacuuuu ucauugguua caacuaauuc aagcaacuaa ugacuuacuu auucuacugg 26640
uauugcugau uugcuuuuac uaauucuuuu aguauuuugg uaaguguuuu uuauauguaa 26700
ugcauauuca gagucacuuu gccuuuagga uauuauacug gaaaguuuua acuguugcau 26760
auuacaucau uauuauuacu ggauuugguu uauaaaagca caauaaaaaa ccaguguaau 26820
gauauaaauu auaggcauau guacauuuuc cuuuagacuu aguaaaaaaa aaaucaugaa 26880
cuugauaaau uuauucaagu aaaccauguu auauuuuaaa uuaaauugga uauuuuucag 26940
ggaguauaug guuuagaaga ugcugucguu gaaauaaaga auuguaaaaa ccaaauuaaa 27000
auaagagauc gagagauuga aauauuaaca aaggaaauca auaaacuuga auugaagauc 27060
agugauuucc uugaugaaaa ugaggcacuu agagagcgug uggguaagcc auguuuuaag 27120
uuacauaguu ugcgcaaccu gauuuacaag ucuuuuuuuu uaauuuaaau uuuguuuauu 27180
auuauuuauu aaguaguuua augcuuuuuu caaaugcuuu uauaaaacau uuaauacaaa 27240
uaaaagugga gcuaaccuga uugaagugga aucagauuuu augggguugg aguggugggu 27300
gggcagggcu ggaacauugc uuuauuuggu cuagcaucuc cucaguaaua gcugcuuguu 27360
uaaaaagaug aaaguuuauu aauaccacau aucagagauu aaccuuuuuu uuucccaaca 27420
aaaguagggu cuguauuacc cauguuuguu ugcaaaaugc ucuuguaaca gaugagauau 27480
uuaaacuucu ugcucugugu ugugauucuc cugccucugc cuccugagua gcugggauua 27540
caggugugca ccacuaugcc cggcuaauuu uuguauuuuu gguagagaug ggauuucacc 27600
auguuggcua ggcuggucuc caacuccuga ccuuaaguga uccacccgcc uuggccuccc 27660
aaagugcugg gauaauaggc augagccacc gcgccuggcc uguuaaaauc uuuuaaagau 27720
uuuuaaguac uugauuuuua uaauuuagac uacuuacguu uuacuuuguu cgaguauuuu 27780
aaggaguaau uaguaauaua gcuugagagu uuauauauuu auuuuaauaa auagccuauu 27840
aguuaauauu acuaauuuga guguuaugau agugcagacu aaguugcugc uuuaaaauga 27900
aaauaaauau cuaaauauca auuucauuau ugcuaaauuu cauuuaaugc uuucuuaguu 27960
aaaaaugauc auuuguaaaa acuauuaucu aaagaaaaga caaauagaca aauaaguauu 28020
uuauacagau auauaugugu gaaaaguauc uaacuuggau ccguaguugu gcuaggaccc 28080
caaauuagac uucugaucaa cuuggacuau cagaucacag ccuucugauc aacuuggacu 28140
aucagaucac agccaagaau cuggaaguuc cuaaagauga cuucuggccc gucuagguag 28200
cugucauaga caucauauuu ucugugcuua aaaagcucca aaucuugguu uauaauuuca 28260
uuuagguuuu uguuaggauu uccauuaaua auugugauaa aauuuuaacu uggguuacag 28320
uuuaaaauauc uggaaaauuc uuucacagaa aguuaccuca uucuucagug auacuggcua 28380
agugaauuau aaccaguugc uugaugguau augacauuuu ugcagcuuau uugaauguuu 28440
uuaaguuuuu aauuauauug cuuucuauug uaggccuuga accaaagaca augauugauu 28500
uaacugaauu uagaaauagc aaacacuuaa aacagcagca guacagagcu gaaaaccaga 28560
uucuuuugaa agaggcaagu gugguaguca guugauuauu uucuuggcug aacuauagag 28620
aaauacuaau aauuuauacu uugcagauug aaagucuaga ggaagaacga cuugaucuga 28680
aaaaaaaaau ucgucaaaug gcucaagaaa gaggaaaaag aagugcaacu ucagguauac 28740
ucaguuauuc uaaaccuuua aaaagaauua uugauaagug aguugucugg auaugaaauu 28800
auuugugucu uagcuguuuu ugcuguucua uuguggaucu gcuacaaauu uaauaaauga 28860
caauaaauaac cugaaggaga uaagugagug ucagugggu caguccugaa ucugaaauag 28920
acaaaaacaa aacaaaacaa aauaacaaaa accaagcaaa caaaaaagaa aaaaaccuua 28980
gaauuaugga auuuuugaaa aguuuuauag uauaguauuu uaauuucuag acagcaccaa 29040
uauguuguua uuaauaauaa uaaaacuuag uaguuuuuau guuaauauau guuacucaac 29100
auuuucccuu uccuuaagga cuaugcauug aaaagcuuuu cuuguaaguu auuauuauua 29160
uuauuauuau uaauauuuga gauggagucu gucuuguucu auugcccagg cuggagugca 29220
cuggugcgau cuugcucauu gcaaccuccg ccucccgggu ucuagugauu cuugugcuuc 29280
agccuccuga guaguugaga cuacaggcgu gagccaccac gccugacuua uuuuuguauu 29340
uuuaguagaa acaggguuuc accauguugg cccaggcugg ucuugaacuc cugaccucaa 29400
gugauccauc cacuuuggcu ccccaaagug cuggaauuau aggcgugagc caccaugccu 29460
ggccuuaaau uauucuuuuc uaagugaaag uaauguuuua uugaauauaa auuaacaucu 29520
uucuuggguu uauuuuacuu gagcuaaaga gaacaguugg uuaaguuuua uaauagccau 29580
ugcagugcuu uuuuguaaga agaccacaca gaaggacugu cuuuuucacu ugccccaaau 29640
ccccaagcac guauaugagu aauagcagag ugguucuuuu uagcauuaug auuucuauaa 29700
uacauccaaa acuuucucaa gaaaaaacuu caugauuuau uaguacaaua aucaguuuac 29760
ucauuacuca ucauuuauau uuacuuuaua ugucuuuuaa cuggugcuua uuuaaguagca 29820
cuuuaauaua gaauaggcaa agaaugguag agaagaugaa auucaaaaau uagguucuca 29880
cauuauuaau aguucauuaa aagugagcua aaugagaagc uuguauuggc uauguagaau 29940
uuuggaggga uuuuggaaac aauuauucua ccuuugcauu aaaacuugau uguagguuuu 30000
aagaauuaaa guguuggaau aguaggaggg uuauuuuaau guuuuuaguu uguuaauucu 30060
cuuauauaua ggauuaacca cugaggaccu gaaccuaacu gaaaacauuu cucaaggaga 30120
uagaauaagu gaaagaaaau uggauuuauu gagccucaaa aauaugagug aagcacaauc 30180
aaagguaaua guaaaguauu gcaaagagag uaaaggaaaa uauuuuuuuu uuuuuuuuuu 30240
uuugagacgg agucucgcuc ugucucccag gcuggagugc aguggcgcga ucucggcuca 30300
cugcaagcuc cgccucccgg guucaugcca uucuccugcc ucagccuccc aaguagcugg 30360
gacuacaggc gcccgccacc acgcccggcu aauuuuuugu auuuuuagua gagacggggu 30420
uucaccguuu uagccgggau ggucucgauc uucugaccuc gugauccgcc cgccucggcc 30480
ucccaaagug cugggauuac aggcgugagc caccgcgccc ggccaggaaa auauuuuuau 30540
uguguuuuca uuucuucccc cuuuaucuca uucuugaaca ucuaaucuua uuauuguugu 30600
uaaauaagua gagggaaaua uuugcuuauu uaaccuguug auucaaagau ugauuaauga 30660
gacauuauuu acucugaaua cagauuagga guucagauaa agcagagcug cugcauagga 30720
gaucaucauu caauacccca cagucagauc agaaugagac agaagagaau augaccauag 30780
gaucauuauc aagaauguua ucugaaauuc accauagugu agaaagugga augcauccuu 30840
uugucccuuu aacuagacuu ucuucaucca ugcaaguuaa agagaauuca acuccagaaa 30900
cuauuacaau aagagagauu uuuaaagcac caugucugca gucuucaaga aaucuagaau 30960
cguuagucag caccuuuagu agggaaagcc augaagaaau aaaugacaua ugccuuuuuu 31020
cugaugacug uaugaagaag gugucaagaa gccaucaagc acuagagaag acuaguuuug 31080
uacaaaaaag caauucaucu uuucauggcu uaucaacagc uucagacaua augcagaagu 31140
uaucacuuag gcaaaaaucu gcaauauuuu gucaacaaau ucaugaaaau agagcugaca 31200
uggauaaauc acaaguagca acauuagaag aagaacaggu ucauucccaa guaaaguaug 31260
cugauaucaa uuugaaagaa gauauaauaa aaagugaagu acccuuacag acagagauau 31320
ugaaaaauaa gcuuaagguu aaucuuccag acccugugu cuauuacugca caaucaaaau 31380
uaucucagau aaauucucuu gaaaaucuua uagaacaguu acggagagag cuaguauuuc 31440
uuagaucuca ggugaguuuu ucuccaaauu auauuucugu gguuguucuu uuaugacguc 31500
ucuaacaaag uucuguaaca auuauaguua gaauauuuuu guuugcacuu uaacaucagu 31560
uauacacauu guacuuuuua aaaucuaaaa ugcaguacau ugauaugaac ucauugacuu 31620
gucuaauuua uuaaauuuuu cuuuagaaug aaaucauagc acaggaauuc uugaucaaag 31680
aagcagagug uagaaaugca gauauagagc uugaacauca cagaagccag gcagaacagg 31740
uaguguaaag gcagaacauu aaaagagaug auuguggguac uaaagacaaa aaccguuaua 31800
ucuuuuugcc ucuuaccaug gauguuggga gagggagaaa gugggauuaa gaucaccauc 31860
ugcuuuacug uuuagauuuu aguuuauuuu uaugauugcu gcuaugucuu cauagcucgu 31920
uuuuuuuguu uuguuuuguu auacuuaauu gaucaaacuu uucuuaacuu gaaaauuaua 31980
gacuugugau auuuuguuga aaaaaaucaa uuuuauucuc ucugcuuuuu ucagaaugaa 32040

-continued uuucuuucaa gagaacuaau ugaaaaagaa agagauuuag aaaggaguag gacagugaua 32100
gccaaauuuc agaauaaaug uaaguuacaa uuaucuuuua cuuuucuguu cuuauuuuuc 32160
cuauacuuaa aaucaugggc cuaaaagggc guuaacacau ucucuguuuu cuaaucugcu 32220
uuacuccuaa uuaccucugu acuguauaua cuucagucug ucacuaucca guugauuugc 32280
cuugcuguuu ucauugugag agaauguuac uaauaugaau uuuuugugag aauauauaac 32340
uccuuuuucu uguguguucu ucaaucaaaa ugaaguuaga acaccaaauu uaaaauacuu 32400
uaauauaaag cauaguuuaa guuaaggcag aaguaugccu uauauacgug uguauaugca 32460
cgugauauaa auaggucugu cauuuaacuc aacuauucac guuggauuua uaguugaauu 32520
uuuuuguaug uuuauuuaca uuuggauuuu uccaaugaug ucuuugguau augugaaaua 32580
uuugucaucu guauagcaua guguaaauug ugaaaaagau cugaucaucc aaugagaaaa 32640
cuguguaauu acaguaaaag aauuaguuga agaaaauaag caacuugaag aagguaugaa 32700
agaaauauug caagcaauua aggaaaugca gaaagauccu gauguuaaag gaggagaaac 32760
aucucuaauu aucccuagcc uugaaagacu aguuaaugua aguuauuuuu uucauguuaa 32820
uguuuuuccc cuaucacuuu agagagauuu ucugcugugu acagaucucc auaguuucug 32880
augagauauu uuuagucauu ugaaucauug uuucccugua uguaaagugu aguuuuucuu 32940
gagcugcuuu caauacuuuu cuucuaccaa uuggauaauu guuauuaauc ugucuucaag 33000
uucacugaca uuuuccucuu uaucuguguu cuuuugguuc aagggucagc uugagaccuu 33060
gaggaguuuu uuacaccgac uuuggagcuc guuuuugcug acucuuuucu uauugggauu 33120
uuccuuucac uuaucccaug gcuuugggcu guauccugug guuuucuaga ugagaaagau 33180
gauagaucuc ugcaauugca cccugcccua ugacuaaauc uuuaaaaaug gcaaagucaa 33240
ucuuugcugg uccugucuuc cguauuugag ggguuuuuuc ccaaaaucug cuugcuuuug 33300
uucauuuucu agaacaucua gguaguuuuu uuucauucau uuuuuauuua ugggagugua 33360
gaucucuuag gaacuuaugc caucagaagu auuaugaaau ggcuuuauuc uaaauguuua 33420
aagauuuacu cauugcuaca agaaagauuu agccaucacu aauauucuau auauauuuac 33480
cauauaggga cuugagaauu ucacaggauu caguaucugu auauaaacuu gaauaaauaa 33540
cacauuuuag auuguuaaua uuuaaguaua ugucauuuau guuaucugaa cauauuuagc 33600
guacauuguc auauuauuuc ccaaauuugu gcuugauuuc aaaugggaaa aaaauucuua 33660
uuauuuauug aauuguuuuu uuaaaaaaau caugauuaau caguaauugg auacuuuuua 33720
aaauaacacu auaaauugua acagagaaug agagugauac ugguauguua aaaacuuccu 33780
gaggcaagaa aauaauuuga uucccauuau aucuuucuca uacugacuuu ccuucucuga 33840
uuggugauuu uguuuugccu cugccacuuu gaaugucuaa aaugauucuu uaugcuuuuu 33900
uuaugugaac aucuuuuguc cgugaugaug cccacuacug auacuguguc ccagaucaaa 33960
cuuaauuuuc caagggcagc ucuacuuagu gaccaaauga aaacacagug aauagcccaa 34020
gaaauccuaa cuucuauuua uguugacaau cucuggaccu uccugaagcc acuguuugca 34080
uagacuucau uuacuuuuau ccgggauugu cauuguuuuu ucagauucau aggcccuauc 34140
ugaaauucac aaaucaccua gcaauacuuc ucuaagaaau cuucagaauc caugacaauu 34200
uagaccagac aaugcuggau uaugcacuuc aguucacuuu uuguuacuac aagguauuuu 34260
ucagugcccc caacagcuau cuuaacucau ucucauuuua ccaaagucca uguagacacg 34320
gcacuauucc ucaaugagac aacuaacuag accaccuugu ugucagucag aguaccuucc 34380

-continued

```
ucuaccuacu uuuaucuucc uuauauccuc uuugaguuag uauaaguuau uacucugcau  34440
gaccugcucu aaucuccuuc aggggaaggc uuuuacaaau cuacuaccua gaguuaaacc  34500
ccagaucacc uuccugagua ggagauugca uuugguucua uucauuuuac cuuauuuggc  34560
uucuaccuuc acuuuuuaag acuuacuuug ccuuuaacag uuuuuuccau acaguucauc  34620
uaaaguccaa auauauuuau uagaugugug cauugugugu auauacuuag auaugccacu  34680
guuggagauu ucgggccagu gaugccacuc ugauaaauau uuaauauuug acauauuauu  34740
uuugcuuacu cauuauucuu agauaaauauc auguuaugau accuugccuu uauuuuuauu  34800
uaugcuucaa cuauguggag aggaagcacu gaaaaauuca cuuaauugaa uguuguauug  34860
aucaauuguu caauauugua uuccauuccu uugcgcaugc uuugaaugca ggugcuauau  34920
aauuucagag aaaaauaccu cauuuugacu guacaaaaac cccauguagg gagcagagcu  34980
cacauuguuu uccccuuuua gagacaagaa aacuaagaua cagagaauuu aagucacuug  35040
cccagcuguu aagugacuga uuaaaauuug aacccugguc aucuuauucc cgucugguug  35100
uuuuucuagu cuaccagucu auuaagauua gcuaggugu uuuuaauugu uuuaaugaag  35160
uaauuacuau gcuugguaau guaaaugaaa guuuuauaga uucauaaaua agaauuugaa  35220
uuggcauacu uuauuaucau gcuuggcaau gaaaauagga aaaugcuuaa auguccauuu  35280
uauuuaaaga cagacuguuu uuuacuauga uuuuacuguu uuucuccaca uuucuaauau  35340
auaauauaaa uuugcuaggc uauagaauca aagaaugcag aaggaaucuu ugaugcgagu  35400
cugcauuuga aagcccaagu ugaucagcuu accggaagaa augaagaauu aagacaggag  35460
cucagggaau cucggaaaga ggcuauaaau uauucacagc aguuggcaaa agcuaauuua  35520
aaggugagaa uuuuauuaaa uaaaagaaaa ugcuaaacau aagaauguag auuuaauagg  35580
aaauuuuuaa uuuuuuaaaa agaaugcuuu augagaaaau gccccuugaa uuaauucuuu  35640
caauauuaag aaacuggauu ucucuuauaa aauuauaagu ggaaaauaag ugccuuauaa  35700
gauugaaaag aauacaaaaa uucuaaaucu cauaccuagg cauuucuaag cagaaacuga  35760
aguaugguug agguaaaauu ccuggcaggg cauucacaua ucugucaauu ugucuuucuu  35820
uggguguaag aguugugauu cucauugcug gauuuuuuuu uccagauaga ccaucuugaa  35880
aaagaaacua gucuuuuacg acaaucagaa ggaucgaaug uuguuuuuaa aggaauugac  35940
uuaccugaug ggauagcacc aucuagugcc aguaucauua auucucagaa ugaauauuua  36000
auacauuugu uacagguauu gaaaauuuug uuacagguau ugaaaauuuu acaugugaau  36060
aacaaaaauc auugguagua uguuucuuua uguuuuuauu uuuauuuuac uuuauuuuaa  36120
uuuuuccauc accaaagcau gcagauagua cuuuucucaa uauuuagucu ucauguauuc  36180
cugaguucuc aaaauaguaa cagugaaaua uauuuuuuau ggauuuugau guuagaugga  36240
uuauaaauaa aagcaauuua uaccauucau uccauucauc ugcaugagca gcauguucau  36300
acaucuuguu cgcacaccug ucauucaugu gaaauauaug guucacaagc agaacaacaa  36360
gcagcuauua uaaagcagug uuaaguaaau gagcacuuuu auuucuugcu ggguggaaaa  36420
caaaagaaua aagucuguca aggcuuuuua gugucaugau agaauuguuc cccuuuuugc  36480
auucacaagu aaaaacuacu uuuuuuuuga gacagagccu cacucuguca cucaggcugg  36540
agugcaguug cgcuaucuug gcucacugca acuuccaccu ccugaguuua agugauucuc  36600
augccucagc cuccugagua gcugggacua caggcaugca ucccuggcua auuuuuguau  36660
uuuuuuuuag uagagauggu gugucgucau auuggccagg cuggucucaa acuccugguc  36720
ucaagugauu cgccugccuu ggccucccaa ggugcuaggg uuacagacgu gagccacugc  36780
```

```
acacagccau aagcaaaaac uucuaaacca aauuauucuu caucuuuguc uucccuuuac  36840
gcaauaaaau guuaaucuac caccaaagag gaaaggguac ucuacuauac uaccugcccu  36900
ggguuucuca guuuugcugu cuauauaaug gucguuauga auguccuaau gacagauccu  36960
uuucauuauu uuauuugaaa uuugacuauc uauaacauca cauacauuau aaauauaauu  37020
acaaauauau guucagaauc aaugaaaaua uauuuuugau uauaugggcc acuauuucuc  37080
ucugcuaggu gauccauuug ugaguauacu ugaguuauaa uuauuaagua cucauuuuua  37140
uuuuggaaau uacaguaauu caucuuuuuc ucaauauugg gauuuuuauu auuauuuuau  37200
guugucuaag gacagccuua acuacuuauu agaauauugc uuuguaugug auauuauuau  37260
uuuuaaaugu auaauuuuaa cauuauuauu ucucuuauuu accugaggua uaggaacacu  37320
aucagcaaau auugguagua uggcauuguc guauuuuuug agauaaaauu caugauuuuu  37380
aaucuuugua uaagaaauau aucagaaguu uguaguagau uagagaguac caacugggag  37440
ucugaaaagc uguccaaagu ggcaaaacag guacuuagac ucucaauccu aaggcuguau  37500
agagcuauaa acguggcaag accuuuggag ucagacagac ccaaacucaa auguuggauc  37560
cauguauaug gaaagcaccu gacaacaagc cuagcauaug uacuugguaa aaaugauugc  37620
caaguguagu guuaaugagu uuuuggauau ugaguaaguu auuuaaauuu caauuucauc  37680
uuuaaaauga aauaauugga aaggauaauu ugagugaggg uaugaaauua uguguucaua  37740
agagagggua uguggccgag ugacuagagg cgaguuuaua acuauucuau cuaauaaaac  37800
uuuguaaucu gguaauuugu gugcuaaaaa uaacuuuacc uguuguauag uacucuuuuu  37860
uuaugccuua aacuaaagug uucaaaauau cauggaaaaa ugaucugugu ugcuuacaga  37920
uuuggugacu uuuaacuuuc cuauaauguu gucagaauau gaauuuauac uuucaaauuc  37980
agcauuuauu cuauuguguu uuuuuuugca uucuuauuuc uaaaccacuu uucaggaacu  38040
agaaaauaaa gaaaaaaagu uaaagaauuu agaagauucu cuugaagauu acaacagaaa  38100
auuugcugua auucgucauc aacaaaguuu guuguauaaa gaauaccuaa gguauaggua  38160
uuagcaaaac uauaaauaua auugcaguau auucuuguua auugugaaag uaacguaaga  38220
auaauuuaug uuuuguucuu cccuucuucu ucuuccuuug caauuguauu uuuuuuuacu  38280
cugguaacua cuguuaggaa cuuauuuaug gagacagugu agcuuaauga uuacauuaag  38340
ccugggauua uccugccugg guuugaguca uuuaacguuu gcuuuuugua agagcuugag  38400
caagucaucu uaccuaucug ugucucaguu uccuuaucug uaaguuacuu uguaaguaau  38460
acccuuuuca uaggauuauu guaaaacgua aaugaauuau uagaugaaaa ugcucggacu  38520
agugugugge acauaugaac aguuuguaaa uguuagcugu uguuagcauc auucaucauc  38580
aucacaauca ucauuguuca uauauguuua uagggaacua acauauuucu ccuuauuucu  38640
gucaucucau cuaaaucaau agaaugauuu ccuuaaauagg aauuagaaua ccuaaucaaa  38700
ggugauuuaa acacuaagaa uaauuauuau cugaccuaac cagaaccaca aagcuaguug  38760
uagggcaggu cauauuugaa gguuguuguu aucgccuaug augguuguaa aauagcugca  38820
ugaauucaag aaagaugaug ugcccauuga agaagaggag cauuuuuuuc uacauagcuu  38880
uuauuuuuaa auaaacauuu uuuucuggug auaccuggca gacauugacu ccgaucucau  38940
uugcuagaau uggaucacau guccaagucu gaaccauuca guugcaaaga gaaugauacc  39000
gcuauacugg guuuaugcca agaacauuac acauguuugu ggaaugcuca uguguagaca  39060
acagugucuu acacaacuuc aaaaaaauaa uuuauauaua aauauguuuu aaauuacuuu  39120
```

-continued uuaaauucac aagaauuuau gguauacaac augguguucu auauauguau auacuaugcu 39180
auacaacaug guguucuaua uauguauaua cuaugcuaua caacauggug uucuauauau 39240
guauauacug uggaauggcu aaaucaagcu acuuaacaua uguauuaccu cgcauacuuu 39300
uuuuuuuuuu uccuugagac agagucuugc ucugucaccc aggcuggagu gcaguggcgc 39360
uaucuuggcu cacugcaacc ucugccuccu ggguccaagu uauuuucuug ccucagccuc 39420
ccaaguagcu gagauuacag gcaugugcca ccacgccugg cuaauuuuug uauuuuuggu 39480
aaagacggag uuuugccaua uuguccacgc uagucucaaa auuccuagcc ucaagcaauc 39540
ugcccaccuu ggccucccaa agugcuggga uuacagcaua cuucuucuua uuuuuuuuuu 39600
uuuuugcacu aagaacacuu aaaauuuacu cucuuagcaa uuuuaaagua uauaauauac 39660
uguuauuaac uuuggucacu auuuuaauua gacuuaagau guguuuguau ucaaauuauu 39720
uuguaagcau uuaacaccca aauuugagag uggggucaga auguuggaau uugauuucua 39780
gaauuaguau aggguauuau uuuccuacuu uuuuucugug uucaauaaaa uguuuauaag 39840
auucagcuuc aauuauauua uaacccauuu aguggugaau cagggaagaa ugaaaauaau 39900
uugauaacuu uguugccuug cauuuauuua aaaaauuuuu aauucuaggc uaaacccuuu 39960
uuaaaugaaa guuuaacuuc uuguguuuuc agauacugaa uagcuaugau accucuugug 40020
uugagaaaac uuuaaauuug cauaaucuga aguuaucuuu ucuuauaaac auuuuauuag 40080
guuuacagua uugucuuuuu guuuuguuuu guuuuuagug aaaaggagac cuggaaaaca 40140
gaaucuaaaa caauaaaaga ggaaaagaga aaacuugagg aucaagucca acaagaugcu 40200
auaaaaguaa aagaauauaa uguaaguaaa acauuuuuaa cauuaguaug caauauugua 40260
caaaguagga uagcuagauu caacaaguaa uauggaugug ucuuugugca gaauuugcuc 40320
aaugcucuuc agauggauuc ggaugaaaug aaaaaaauac uugcagaaaa uaguaggaaa 40380
auuacuguuu ugcaagugaa ugaaaaauca cuuauaaggc aauauacaac cuuaguagaa 40440
uuggagcgac aacuuagaaa agaaaaugag aagcaaaaga augaauuguu gucaauggag 40500
gcugaaguuu gugaaaaaau ugggugguug caaagauuua agguacaucu gauucuuauu 40560
uugcuuuuuc ugacuaugaa aaauuucaaa uaugcagaag auaggauggu aucaauaaug 40620
cucaucaccu gaauuaauag uuaacauuua uuaacauuuu gucauaauug cuucuucuga 40680
uuuuuguggg auguuugaau ugcagacauu ccuccccuaa auauuuaaug uacccuuuug 40740
aaaaaggcuu uuuucuuuaa cuaaccauag uaacuuuauu auaccuaaca aaaugacagu 40800
aauuuucuaa uaucgccuaa uacccugauu auagucacau uuuuuacauu uuuugaucaa 40860
agaauaagca uuuggauguu acaucucaua aaucuuuuua auauagaauc cccuugguuu 40920
ucuuuuucuc caaaaaaugu uugaagaugu aucuaacuuu ugugugugug ucauuuuacu 40980
uguuccugug ucccuuguau uacuaaaagu uaggucagaa cccuaaguua cauucagguu 41040
uaaacauuuu uggcaagaau acuucauaag uaguguucua uacuuuauau ugcaucacuu 41100
caagaguauc ugguuguucc auguuuugua auugauuacu cuguuaagga aaagacaagc 41160
agaccaagua ugguggcuca ugccuauaau uccaacauuu uggaaggccc aggcaggaaa 41220
auuuccugag cccagaccag ccuaggcaau auagugagac uccgucucua caaaaaaugu 41280
uuuuuuuuuu guuuguuugu uuuuaauuag cuuggugaug uggcacaugc uuguaauccc 41340
agcuaccugg gacauugagg ugggaggauc gcuugagccc aggaaguugg gggcugcagu 41400
gagcugugau caugugccac ugaucuccag ccuaugugcc uguauaacag agcgagucuc 41460
ucucuuaaaa gaaaaaaaga agaagaagaa gaagaaaaga uaaccauaua ccuccauuau 41520

-continued uaagcaauuu agcuaacugg ugauauuuug guaccauaca aauaacaaau uauuugucag 41580
uccuaaugau uuuagcaucu gcugaugauu guugccuaac ccaauuauua aaaguugcaa 41640
acaucauaau uuucuaguua uauuaugcac uuacauuuau uaacagacau gcuuuuguaa 41700
aauaaauagc guuuccucau uagcccaggc uauuuguuua ucuugaaguu uagcuccuac 41760
uacaaaggca agauaaaugc uuuucucuuu aauuaccagu uuucagaaua cacacuuggu 41820
guacucugca cuaccugcuu uuuuuguccc cuccgcuuuc ucuuuuuuaa guaucagauu 41880
agacucacag auuuuuaaau auuccaugug uuuuaguugg agucauauuc uuuugucuca 41940
acuuuagcca aagagagucc uuuaaaguug acucuuauau ugucuugaca aaaauucauu 42000
agucuuuuga acgaagccuc aaagcuugac uuguuuucua gcauaagaug ucuuagacuu 42060
accuacauac uucaugccca uacuuggaau aaaccauuuc uuuaaagagc ccagguuccu 42120
uuuagugggg aaggcauuua gauaccaaaa acuggccacu gggcaucauu gcucucagag 42180
uaucauugcc acuagucucu caguagacaa guuagaaaaa uauguauaua uuuaaaccau 42240
gaguucauau uguuauuucc aguuuaauua uaacauuaug ggguaaguaa auaguaucgg 42300
auuuuuacua agcuucuuug auuuugcacu uguauuuuuu ucuuacauag aaaaccuuua 42360
uuauuaacau uaaaauauuu guuuuauccu acaauauaca uacaauaauu ugaaaaauaa 42420
uacuugaauu gauauuaaua guaacaacaa cagcacugcu gccaaacaua guuuaaaguu 42480
uuauuucagg ucuuauuuuc uucagaauau aucuugcuga gaauguauag gcaaaguauu 42540
cuacacuuac uugaaauaau ugucuucaug cgguuauguu auacauuuga uauauaguua 42600
ggcucauuug uuuuucauuu uuuuuauuuu agggauuuuu uuccuuuauu gaauuuuaau 42660
auauacaaua uuuauauaug caaaauauuu aaucagagaa aucuuaauuc uggucuuacg 42720
ccuuucauau uauucugcuc cacccucugu agguaacuua uuaucuuucu cauguuuccu 42780
uuuuggaaac auaaacaaag acaagacagg uuacaugaca uguauacccu ucugcaccua 42840
guuuuauacc uuaccuugua guuuauuuuu aagcauguaa auguucaaug uucaugacua 42900
aauuuggaca ggaucauagg aacacagaau ucaaagugaa auuaaaaugg gcuuggguuc 42960
uuuacuuucc acuuuaaagg uuguaauggg ugaugucagg cuaauaaacc uauuuucagc 43020
uugaucuaaa gcuuaauacu gagcaucaag aaauucuuua auaaauauaa gugauauuua 43080
uucagacaug uaauaaggaa auguucaugu cuuauuuuug uguuagauuu uuuuagaauc 43140
uacuuuuguu agaguuuuau aaauacaguu aguguuugag auagaaagag aaaagaauua 43200
guuuucuucc ucuucuaccu gcucaugaac uugauuuuuu ucucccaaca auugaagagc 43260
caagaaaaag ggagauucuu aagagauggg aaauagaauc ucaucuaccc cuguuucccc 43320
cagaacagug aaacugaauc uuaaggguaa gauagaauag uguguacuua acuuagaugg 43380
agaagaaagg cugccaaaau gagaucugaa gcgcuauuac aaauauuucc aucguuacug 43440
uacuucagaa ugaauuacaa ccguaaguuu uuuuacuucc ucauucauaa auuugauuau 43500
uccuuauacc acuucucagc uuucaucauu cuuuauugua cuuuucuaug uaauguuugc 43560
cuauuauaca gcaacuuaag agaacuguaa guuuggacau uucauuuugg uguugauaau 43620
agaauaucuu ugaauaguuc uauaguugau gaguagaacc augaaccaag uaacuuaaag 43680
uccuugaugu uauuuauuac agagaacuau aauagaagcu cucccgcuaa uguuuccauc 43740
auguguacaa aaaguuuucu uguuauuaaa gcuaguccgu uuaacuuaca auaagcauaa 43800
auagcuaagc ugugaaaguu accugugaua augcuaauuu ucccauuuau uaaaaggcaa 43860

-continued guuguuuucc gaucauaaga aauuuagaaa agccauccaa agauaaauuc cgagugauau 43920
auuccugcug uuuguuaugu uuucucaaau uaauugaguu uuauuuuaca augacaggag 43980
uuauuaaagu auuuuauuuu uauuaugauu aagauuuuca aaguaacauu ucuuauauga 44040
aagaaauuau guuaaugcau guuuuucuua caugggaaau cauauauuuu aaaaaugauu 44100
uuaaaauucg uuuuacuuua aguuguauua ucuuucucaa aaguggcuag ugcuugacca 44160
gaaaaaaaga caccagcaua acucagugua ucuuuauuua cauaggaaau ggccauuuuc 44220
aagauugcag cucuccaaaa aguuguagau aauaguguuu cuuugucuga acuagaacug 44280
gcuaauaaac aguacaauga acugacugcu aaguacaggg acaucuugca aaaagauaau 44340
augcuuguuc aaagaacaag uaacuuggaa caccuggagg uaaguuugug ugauucuuga 44400
accuugugaa auuagccauu uuucuucaau auuuuugugu uuggggggau uuggcagauu 44460
uuaauuaaag uuugccugca uuuauauaaa uuuaacagag auauaauuau ccauauuauu 44520
cauucaguuu aguuauaaau auuuuguucc cacauaacac acacacacac acacaauaua 44580
uuaucuauuu auaguggcug aaugacuucu gaaugauuau cuagaucauu cuccuuaggu 44640
cacuugcaug auuuagcuga aucaaaccuc uuuuaaccag acaucuaaga gaaaaaggag 44700
caugaaacag guagaauauu guaaucaaag gagggaagca cucauuaagu gcccaucccu 44760
uucucuuacc ccuguaccca gaacaaacua uucucccaug gucccuggcu uuuguuccuu 44820
ggaauggaug uagccaacag uagcugaaau auuaagggcu cuuccuggac cauggaugca 44880
cucuguaaau ucucaucauu uuuuauugua gaauaaaugu agaauuuuaa uguagaauaa 44940
auuuauuuaa uguagaauaa aaaauaaaaa aacuagagua gaauaucaua aguuacaauc 45000
ugugaauaug gaccagaccc uuuguaguua ucuuacagcc acuugaacuc uauaccuuuu 45060
acugaggaca gaacaagcuc cugauuuguu caucuucuc aucagaaaua gaggcuuaug 45120
gauuuuggau uauucuuauc uaagauccuu ucacaggagu agaauaagau cuaauucuau 45180
uagcucaaaa gcuuuugcug gcucauagag acacauucag uaaaugaaaa cguuguucug 45240
aguagcuuuc aggauuccua cuaaauuaug agucauguuu aucaauauua uuuagaagua 45300
aucauaauca guuugcuuuc ugcugcuuuu gccaaagaga ggugauuaug uuacuuuuua 45360
uagaaaauua ugccuauuua guguggugau aauuuauuuu uuuccauucu ccauguccuc 45420
uguccuaucc ucuccagcau uagaaagucc uaggcaagag acaucuugug gauaauguau 45480
caaugaguga uguuuaacgu uaucauuuuc ccaaagagua uuuuucaucu uuccuaaaga 45540
uuuuuuuuuu uuuuuuuuga gauggaguuu cauucuguca cccaggcuga gugcaguggc 45600
acgaucucgg cuuaacgcuu acugcauccu cugccuccca gauucaagca guucuccugc 45660
cucagccucu gaguagcugg gauuacaggu gugcaccacc acaccagcua auuuuuuuuu 45720
uuuuuuuuuu uuuuuugagg cagagucucg cucugucacc caggcuggag ugcaguggcg 45780
ccaucuuggc ucacugcaag cuccaccucc cggguucagg ccguucuccu gccucagccu 45840
ccugaguagc ugguaccaca ggcacccacc aucaugcccg gcuaauuuuu uguauuuuua 45900
guagagaugg gguuucaccu uguuagccag gauggugucg aucuccugaa cucgugaucc 45960
acccgccucg gccuccuaaa gugcugggau uacagaugug agccaccgca ccuggcccca 46020
guuguaauug ugaauaucuc auaccuaucc cuauuggcag ugucuuaguu uuauuuuuua 46080
uuaucuuuau uguggcagcc auuauuccug ucucuaucuc cagucuuaca uccuccuuac 46140
ugccacaaga augaucauuc uaaacaugaa uccuacccug ugacucccau gugacucccc 46200
gccuuaaaaa cugucaaaag cuaccgguua ccugaagggu aaaagucaag uccccuacuu 46260

```
accucauguc aucuagagca agagaugaac uagcugaguu uucugaccac aguguucuuu  46320
cuuauguaug uucuuuugua cgugcucuuu ucuauauaua gggaaccauu ucucucuucc  46380
aguuguuuug cucagugaau uucuauuccu guuucaaaac uuguucaggc auuaccuuuu  46440
uuuucuuaag cauacuuuuu uuaauggaac aaagucacuc cugucuacac uaguucugca  46500
ucuuauacau agguuuugua cauaguacau auuuauauca caucaaauua uauguguuua  46560
cauaucuguc uuccuuaaug gaauauaagu cuuuugauau aaggaacuau uuaauuuguu  46620
ucuguguguu gaguaucucc uguuuggcac agaguucaag cuaauacaug agagugauua  46680
guggugggaga gccacagugc auguggguc aaauauggug cuuaggaaau uauuguugcu  46740
uuuugagagg uaaagguuca ugagacuaga ggucacgaaa aucagauuuc augugugaag  46800
aauggaauag auaauaagga aauacaaaaa cuggaugggu aauaaagcaa aagaaaaacu  46860
ugaaauuuga uaguagaaga aaaaagaaau agauguagau ugagguagaa ucaagaagag  46920
gauucuuuuu uuguuguuuu uuuuuuugaa acagagucuc acuguguugc ccaggcugga  46980
gugcagugga gugaucuugg cuuacugcaa ccucugccuc ccagguucaa gcgauucuuc  47040
ugcuucaguc ucccgaguag cuggaauuac aggugcccac cagcacggcc ggcuaauuua  47100
guagagacag gguuuugcca uguuggccgg gcuggucuca aacuuuggau cucagguaau  47160
ccgccagccu caacuuccca aagugcuggg auuacaggca ugagccacug ugcccagccu  47220
guuuuuuuuu uuuuaaagga gaccagugaa guuucaggag gagggaaaga aaauuuagag  47280
uuacuaggga gagagugaug aagauaagag augaaagugg uaauaaggga aauagcaaaa  47340
uaucagggua ggugggagaa aaagagauuu guaacaaaca auaggauuau ccugugaaaa  47400
aggaugaaag gaagaaaaaa auggauagaa agauauuuaa aacacccuca gccuccuguu  47460
uucccuccug uguauucaua guauauaaaa cuauaauuau guacuuuacu uaaaaaauau  47520
auuauuauua ccuuaucgug cuuauuuaau cauagcaugu ccucuuuuua gucucauuac  47580
ccuguuugua uuauucuuca uaacacuuaa uaccugacau uguauuauau auuggcuuau  47640
uuuccaggua cuccacucaa auauaaguuc uaggauauaa uuuauuuauc acugaaaucc  47700
auugcuuaga guaccuggca uguaguaaau aggcauucug uuuuuucaaa uaaaaaauaa  47760
aggaacuuaa gauauauauu uauguuauau cgccagccuu uuuccucaca gcucuauucu  47820
guuguacaga auuaccuacu uuacaauucc uguguuucaa ggggaucuca aauuuaacgu  47880
guccacaaug aacuccugau uucuguuucu cuccuaguca uucuuauuuc aauauauguu  47940
caguuaccua accagcuagu caaggcagau acuuuagagu uauucuguag ucauucuuuu  48000
ucccuaccau uuuuguuuuc caaauguaau uuaugugugu cuucuucauc cucgcagcuc  48060
uaacccuugu ccaaaccagc aucaucacuc aucuggaguu ccacaauguc uuucuggcua  48120
guuucccuga uuucucuauu gaccccuuua uucuccacag ugcagccaga augauuguuu  48180
aaaacuuccu ccuuaaaauc uuuaaauugu uuucuuuuau acguuaaguu aaauuccagu  48240
uccuugucuu ggcaugccau gcccugccug guguggcccc ugauggucuc uccaacuuca  48300
uguuuuacua cuauugacuc uuauuuuugc uuacucugcu ugggugcucc aguccuccaa  48360
aucauuuccu gcuccaauca uuucaaucau uuuuuccucu cagaucuuau aguauuccaa  48420
augcuuucuu ccuuuggagc aucuggguuu acuaauaaau acuucguacc ucacaguuca  48480
gcuuaaauau caauuauuug gugguuaaga cauccuucaa ccgcucuauc uaaauguucc  48540
uuucuauuau ucacuggcuc aguacucugu uuuuauuuuc uuucuaaaug ucaacuuuuu  48600
```

-continued

```
uuuuuuugag ucagggucuc acuguugccc aggcucgagu gcaguugcac aaucauagcu  48660
cauugcagcc uugcccuccu gggaucaagu aauucuccca ccucagccuc caaaauagcu  48720
gggauuacag guaugcauca ccaugcucag cuaauuuuuu guguuuuuuu guagagauga  48780
ggucucacuu uguugcccag gcuggucuca aacuccugga cucaagugau ucucccaccu  48840
cagccuccca aagugcuggg guuacaggug ugagccacug caccuggucg auacugacuu  48900
uuuuuuuuuu uugagaugga guuuugcucu guugcccagg cuagagcgca guggugugau  48960
cucagcucac ugcaaccucc accucccagg uuaaagggau ucuucugccu cagucuccug  49020
aguagcuggg auuacaggca agugccauca ugacuggcua auuuuuguau uuuuagcacu  49080
auguuuagua cuguguuggc caggcuuguc ucgaacuccu gaccucaagu gauccaccca  49140
ccucagccuc ccaaagugcu gggauuacag gugugagcca ccguaaucgg ccaacauuga  49200
cauuuuuagu agacuuuuug uuuguuuacu ugcuuauuau cugcugccuu ccacacucug  49260
gcgaaauccu gccacccacc cacacacaca uaggcacuga augggcagaa cucugaaggc  49320
cagaauuuua uauuucuuuu cacuguaaac aucaucaucu gucacugaug gcacacuagg  49380
augcucagca acugugugca ugaaggaagu aagcacuagu uugugaaggc ugcaaaacuc  49440
uugaguauuc uaagaguuuu ggccaaaaug aauguacagc uuuaguggca gaagcuaaua  49500
cucagaaauu gaggccguau auuggauaac acaggauuug gaugauuauu uuaaaauaau  49560
auuuuacauu guauauaugu gugugugugu gugugugugu guguguaugu gugugugugu  49620
guauauauau auguauguau guguauuagu ccguucucau gcugcuauga agaaauaccu  49680
gagacugggu aauuuauaaa ggaaagaggu uuaauugacu cacaguucca cagagcuggg  49740
gaggccucag aaaacuuaac aguuauggca gaaggggaag caaacacauu uuucuucaca  49800
ugguggccgg aauuagaaga augugagccg agcaaagggg aaagccccuu auaaaaccau  49860
cagacaucgu gagaacuuac uauuaugaga auagcguggg ggaaaccacc cccacgauuc  49920
aauuaccucc caccaaaucc cucccaugac auaugaggau uaugggaacu augauucaag  49980
augagauuug gguagggaca cagccaaacc auaucaguau guauauguau acaaguauua  50040
uauauauaug uauguguuug uaugcauaca uguauuauau auggaggaaa uucuaauuuu  50100
guaaaaaacu ggauugugag uuuuaaggag auguuauaua aaguuaagac aaugucauuu  50160
ugugguauug gucugaauua caauguaguu ucuuagugau auuuuuccuu uauucagugu  50220
gaaaacaucu ccuuaaaaga acaaguggag ucuauaaaua aagaacugga gauuaccaag  50280
gaaaaacuuc acacuauuga acaagccugg gaacaggaaa cuaaauuagg uaaguuuuau  50340
gacucugaua auauaaaaug auuaacaucu aauaaugaau auuucuuauu uaaaguuccu  50400
uuuuuaugcu agauuaaaag gaaguauuuu gacuaaaaaa agaaagaacu uucugccuaa  50460
uaauuuaacu uaggcagaug aauaauccug uacuuaaccc caccaaaguu uaguuuucag  50520
uccuuaaguu agauuuguuu cuaaugaaau cauauauguu aaaaauuuau gacuaaguau  50580
uagcuacuuu gaaccguuua acaauuaaaa cugaugauau uuuauuaaug guauuaugag  50640
uucuuucacu gagugcaagu uauauuaguu auauaucacu ugauauuuuu aaauuaaaag  50700
auaccaggaa acagcaaaga aaaugugaaa agaaguugua uuucucauag uuuuacuacu  50760
auauuacugu auauuuuugc uccuauaugc uuacauauuu uauauauuuu aaauuauuau  50820
aaacaugguu uuauacugua uuuagauagu aauaucaaaa auauuuuuau ggccggcgca  50880
guggcucaca ccuguaauuc cagcacuugg gaggcugagg agagcagauc cccuggggguc  50940
aggaguucga gaccagccug gccaacaugg caaaacccca ucucuacuaa aaguacaaaa  51000
```

auuagccagg cgugguggca guugccugua auuccaucua cucaggaggc ugaggcagga 51060
gaauugcuug aaccuaggag ucagagguug cagugagcca agaucauacc acagcacucc 51120
agccuaggcg auaagaguga gacuccgucu caaaaaaaaa aaaaaaauug uuuuauucau 51180
cauacuuaua aauacuuaua caauagccua auguguuuga gugauuaaau cacuagcuuu 51240
uuauauuuuu gcuauugcuu auagugccac agugaacauu uucauguaua ucuaacagag 51300
auauuacugu cucagaaggu auugaaaucu uuguugcucu cauuagaguu uuccauauua 51360
auuuuucaaa caguuauaua guuuauaaga uuuucauaau uuuaucucau auauugugcu 51420
ucauaauuuu caaauaaauu ugcugcuuuc gauaauguau uuucauguau uuguuuccua 51480
gacguuagag cuauucaagg uuuuuauuac uaaauagagc uguucucuua aauugguaau 51540
gagauacuug guuuagagaa gccuaacacu gggaaaucuu acauaagcua cuuuuagaaa 51600
uguaauuuuu agcucaauaa gagauuaaau augaauugac uuuuguguag uauuugcaug 51660
gaagaaggua ccauuuaaau gaagacauga gaguauuacg uacaauuuua guagguucuu 51720
uuuauuuuau caucuuuauu uuuaauaaau gcugaauucc cuacagaaau ucuuuaauuu 51780
uuacauaucu ugaucucuuu cauauaugga uuuauaucac cgaaguuuua agaguguuuc 51840
ccuauucccu guugcccuua uaucuuuguu uaaaaauguc acaucauuag cuuuuuuuca 51900
ucuaggaauu uguuaguguu gggcuguugu gcucuacccu cucuuuaaga aaacuccaaa 51960
cccaaaaaca uacaagaugg cuagucugcu ucagccuuug ugaugugcuu uucucuucua 52020
aucagaguuu agcacaauac agaauggaga aggacuccuu uauauauugg uauuuauugc 52080
aguauuuuuc uacauggugc cuaagguuac uugaaugagu cuuuauucca uaaugaacug 52140
auuuacuaau gcuuuuagca ccuguuagug auccauuauu guuaguuacu ugauuacugc 52200
uugccacagc uauucuaaaa uaauacauuu uaaagauaaa uacagaacau aaugaaguac 52260
uuuuuaaaac ugagauagag accaauuuuu uuuucaggaa auguauauua cuuugagaaa 52320
acucaguuau aaaacuugaa cuuaugaagc uggaaaaaca ggagggggca uuauugguau 52380
uguaaaaggc uguuuacaaa gugaguugcu gcuuaguucc uuuaaguaau uggcuacccu 52440
aaacacauca guuuuaaguu gcugaaaagc aaaacacucu accaaauuuu guuuuuuuuc 52500
uagaccaugu uuacaaagca aaaguauguu uucuuccccc ccccucaaaa aaugacuaau 52560
gacacuccua ugcgaugccu uuuuauggua aauugaggcu uuuaguucuc uuuccauuua 52620
gccacagacu uuugugucca aagacaagcu gcguaacugc auauauaagg uuaaggcaua 52680
acuacuaaua aaagaaugua aaauauuuga uauuaggucu guacaaagac caaauaauac 52740
ucaugauuag acaagauuau auuugguaga aucuauccau cauauggcuu cagauuuuac 52800
uuuucagcuu ggcuuuguga gacuuuaaaa aucaagucau ugcacuuaua uucacaaagu 52860
cacauugcuu uacugcauug cuucucauac aguuuaucuc cuuucaguaa aauguuuacu 52920
ugccauuuuu aaaauuucuu auaugugaca cuucuacacu aaguccuuua uguuguuagu 52980
uccacaauuc ugugaggaau agguuuuuuu uuuuaaucau uugauugaug aagaacauua 53040
aguuccacag agauuaaaug guacaggcau cacacaggca ggaaguaaca gagcuaagau 53100
uagaguccag gucugaugga auucagaaag cuaaugugcu uuccauggaa cuauaaugcu 53160
uucuaauaua cagcaucuaa aauaucugag guaauuuuaa uauaaacagc augagauuga 53220
cuuaaauauu auugcaugua gguaaugaau cuagcaugga uaaggcaaag aaaucaauaa 53280
ccaacaguga cauuguuucc auuucaaaaa aaauaacuau gcuggaaaug aaggaauuaa 53340
augaaaggca gcgggcugaa cauugucaaa aaauguauga acacuuacgg acuucguuaa 53400
agcaaaugga ggaacguaau uuugaauugg aaaccaaauu ugcugagguu ugauauuaua 53460
aguuuuauca uacaauuaua gaauaaagaa uuaguuuugg uagacauugu auuauuguua 53520
aguguuuugu cuggaucucu gaaauaucuu auuaauauag ugccuauguu uuguguaaua 53580
aauaaauaaa agauuuaaau cugaauuguu uaaaaggaaa gcagauauuu cuguaaguuu 53640
uucucaccaa uguuauauua uuagauuuaa uuuaugaaau guuauuuacu aaacaaugga 53700
auugccuuuc accaccaucc cuucauuuaa caaauauuua uucauugccu auuacauguc 53760
agacccugug uugggacugg caguauagca agaaacaaaa uagacaauaa ucucuacuuu 53820
cagggacuuu acauucuaau ugguguuuuu auauauuuuu gauguggyca gaaucauuaa 53880
acuguguggc aguaaauaua guuugcaagu auuuaacaau uuaugauuaa acacaacucu 53940
uacaguguuu gcuuaccuug agauuuaaua uauuuucaaa gcauuuauau cauuuuuguu 54000
uuaacuaugu cacuaaaucu auaugaguaa gauuuuauua acucauuugg auuuauuuau 54060
agaugauaca auugaaguaa aauauaauga gcagauugca uucuaagcaa aguaagaaua 54120
uugcaaguuc agauauuauu agauaaugag uugccuaaua aaaaugacuu uugguggauu 54180
ggaauauaac cagaguuucc auaguuuguu ucugauucuu ucauauuuuu uacccuccuu 54240
cagucuguuc uuaacacuuc acacuuaaua uaauauguga acuaaggcca aguaaagagg 54300
auugcaguac uuuaaaagcu aaauuacaaa gaaaaccuca ccaaaaauug auguaucuga 54360
acauuuuuug uuacauuucc uuagcuuacc aaaaucaauu uggaugcaca gaagguggaa 54420
cagauguuaa gagaugaauu agcugauagu gugagcaagg caguaaguga ugcugauagg 54480
caacggauuc uagaauuaga gaagaaugaa auggaacuaa aaguugaagu gucaaaguaa 54540
gugcauauaa gcauuuuagc cauuugacua gauguaucuu cuuuaauuug ucuuuaagaa 54600
acccaauuac agguauacaa uucuuaguag uaauugauac ugauuucuuu uuauaagaac 54660
aggauuaagu aauauuaaga ucgguuuuaa cagggguuaaa uaauaauauu gacgagaaua 54720
auauuguuaa agaggaagug accucucaag auuugcauuu uuuagaguuc aggaauauua 54780
uugcagaaag guccaguucc uccacauauu gauuuuuugg ggaaggggug auggaggagg 54840
aaugguuguu uauuguauuu aaacuuaagu uucuucauuu uaauaaggga guaauaguac 54900
cucuucuacc uguuucauaa gguugcugua agaauauaau aaaaaaauuca gauuuugauu 54960
uaguuuacau uuaucgggca ucuacuaugu acuagucacg gugcaaggua uuaaacauau 55020
auugacuugu acaauuauac uuaaccuuga gguuauauuu uuguuuucau uuuacaugaa 55080
gaaauaugcc cagcuaguuu agaacacaaa auauauauaa ggaguaaaua cugcgugcug 55140
gcugggcgug gugacaugug ccuguagccc cagcuacucg ggaggcagag gcaggagaau 55200
cgcuugaucc cgggaggugg agguugcagu gagccgagau cgcgccacug cacuccugcc 55260
uggugacaga gcgagacucu gucaaacaaa caaacaaaca aagaaaaaca aaacaaaaaa 55320
accgugugcc agcuauaugc uguauuuuca uucucuuuug uaauuaggug auauuucagu 55380
agaaaaguau aaggagcacu uaguuaaucu gucaagcaua aauaguaaaa auauuuuaug 55440
gccuacucau aaaaauauaa ccauuccuuu ggagccuuga uaguucucuu gggaauauca 55500
guuuuugaca ucuuuuucac uaugaaagac ccuuuuuuuu aaaaaaaaug auccuuucuu 55560
cucauggacc ucuuuugaua uaaacuaacu uauaauaguu cauuuuaauc auauuuuguu 55620
aaucaugcaa cuggcaauga gagccucuca ucaguaugag gaaaccugcc uuaucuauaa 55680
uacugaacua aaauuauucu aacccaaagc aaagaaacuu uacauuuugc uuugccugua 55740
uuagcuuauc acaguauuca ugagggaauu ugaaggacuu auuaccauua ggcuaucucu 55800
uuuuuuuuuu uuuuguaauu uuauuaaaug cauguuuugu uucuuuucac auuacugaua 55860
acuuguagau uaaaacaaau caaaacaugc auuaauccau cuaaggaucc uagaaauuuu 55920
acauuucugu guucuuaacu gugugauggu cuuagauaaa uguacuaaau accuuauccu 55980
agcauauucc aaauuaugac aauaaauguu uuauggaaaa aaguauggga acagaaguuc 56040
uuuggcuaua uacauuugga aaauacuaua uaguaaguau gauuugagau aauuauauau 56100
gauagaaccu cugggagcac ugaauauaug uuaggaauau ucaagaggga ggagggaugu 56160
ugagaaugaa guuuuuuuua uauagcaaac augauaaccu cugauggaau uauguuucau 56220
gaaacaguuu aggaaauccu guuuuaauau uucauacaaa gaagagauag augcugaaaa 56280
cgaauggcuu uuugaaaaag ggucuagaaa uuuugaauuu uggcauuuac uuagaaagug 56340
uacuuaauug uuccugaaau accuuaucau uuccuagacu gagagagauu ucugauauug 56400
ccagaagaca aguugaaauu uugaaugcac aacaacaauc uagggacaag gaaguagagu 56460
cccucagaau gcaacugcua gacuaucagg uaugugcagu auuggcucuu cuacauagaa 56520
uccacuuuuu ucccuaaauu uacauuagau guugggagug ggauauguua uacuuuuugu 56580
uuguuucgag auagggucuc auucuguugc ccagggugga gugcaguggu acauucaagg 56640
cucauugcag ccuucaccac cuggguucag gugauccucc caccucagcc ucuuagacag 56700
cugggacuac aggcacgugc caccacaccu aauuuuuuug cauuuuuugu agagacaggg 56760
uuucaccaug uugccuaggc ugguccaaa cuccuggguu aaaaugaucu gcccaccuug 56820
acuucccaga augcugggau uacagguaug agccaccaug cugggccauu guuacauuuu 56880
uaaucaaaag auauaccaac cagaggcugu uauucuuguu aguuggaacc ugauuagaaa 56940
gcucuuuaau uugaaauauu guucaguaau ccaguacagc auuuaaaugc cuauagauga 57000
auuaugcugc ugaucaaaau uaggacacug agaauuguag uuaguaaauc uuuaauaaca 57060
auauuuucuc uuguauuuau auguaacuuu uuacauauuc uuacguuaua uauguuggga 57120
auuauaaaaa cauacacauu guccugauca guauuauguu acuugcaaug gagguuaaaa 57180
aaaaacugua acagucaggc augguggcuc acgccuguaa ucccagcacu cugggaggcc 57240
gaggcaggcg gaucacgagg ucaggaguuc gagaccagcc ugaccaauau ggugaaaccc 57300
cgucccuacu aaaaauacaa aaguuagcca ggcguggugg caugugccug uaaucccagc 57360
uacccaggag gcugaggcag gagaauugcu ugaacccggg agguggaggu ugcagugagc 57420
caaaaucacg ccauugcacu ccagcuuggg ugacagagug aaacucuguc ucaaaaaaaa 57480
aaaaaaaaaa caccaguaac auacccacug uuauucaguu acauuuggau uuuaaguuug 57540
uuugauucua gguuuuuucu uuuacaguuc uuugguaauu auuuguauua aagcaaaguu 57600
acauuuuugu agaucucaug ugccacugug uuaaaacuuu gcuuaguaaa uugugaauuu 57660
uaaaucugug auaacuuuca cuggaaaaau uugaaacuua cuacaaauau auauuuuuuu 57720
uaauaucagg cacagucuga ugaaaagucg cucauugcca aguugcacca acauaauguc 57780
ucucuucaac ugagugaggc uacugcucuu gguaaguugg agucaauuac aucuaaacug 57840
cagaagaugg aggccuacaa cuugcgcuua gagcagaaac uugaugaaaa agaacaggcu 57900
cucuauuaug cucguuugga gggaagaaac agagcaaaac aucugcgcca aacaauucag 57960
ucucuacgac gacaguuuag uggagcuuua cccuuggcac aacaggaaaa guucuccaaa 58020
acaaugauuc aacuacaaaa ugacaaacuu aagauaaugc aagaaaugaa aaauucucaa 58080

-continued caagaacaua gaaauaugga gaacaaaaca uuggagaugg aauuaaaauu aaagggccug 58140
gaagaguuaa uaagcacuuu aaaggauacc aaaggagccc aaaagguaaa cauuuaaacu 58200
ugauuuuuuu uuuuaagaga caguaucuug aucuguuucc caggcuggag uucaguggug 58260
caaacauagc uggaacuccu gggcucaagg gacucucuag ccucagccuc cugaguaguu 58320
guagcuggca guacaggugc acaccaccau accuaccuaa uuuuuuaaaa uuuuuaaauu 58380
uuuuuguaga gacaaggucu cacuuuguca cccaggcugg ccuugaacuc cuggcuucaa 58440
guaauccucc ugcuuugguc ucucaaaagu gcugagauua caggcaugag ccacugugcc 58500
cagccaauuu uaaauucauu aucuucaaaa gaguuacaug auaauuucuu aauauaugcc 58560
uauaugaaaa augcuuaaga uacaaauucc aauuaugauu cauuaauuua gauuuuauaa 58620
cuuagcagug uuggcuauuu gaaugucuau uauacguaaa aauaaaauua ggcuuuucua 58680
accaaagauu uuagugggaa uguucagauu guauaaauagc aaagaauuuu aauuacuaua 58740
ggaaaauuua uauuaauuaa acacuaauua uuauauuuaa acauuguagu aguuaucagu 58800
ugauuucuac uguucauaau uaucuuugau cuacaaguag ugggcccaca uuuacuuuua 58860
auaugguuua aucuucauuu agaaagaauu aaaugaaaaa uaauuaucuu gcaacuacau 58920
ccuguucucu aggcuagaaa cauuuaggau uucuguuuuu gaaaguaaua ccaaaguucc 58980
aaugaccugc uuauagucag uguucaauaa acguauaaca aaugaaagug aauauuagug 59040
auguccauuc caacauaauu ugaagauuuu uauuguaaaa ucccacauau uuguagaaaa 59100
gucuauggaa auccuaaaua agauuuuguc auguaguuug acaaaagaua acauuguguc 59160
uuauuuuauu uuagaauggc cauuacuuuc aauuaaaauc auuaucauca auggaggaau 59220
guuauuuguu aauauagcau uuauauuugu guauauaaau uguaaaucuu agguaaucaa 59280
cuggcauaug aaaauagaag aacuucgucu ucaagaacuu aaacuaaauc gggaauuagu 59340
caaggauaaa gaagaaauaa aauauuugaa uaacauaauu ucugaauaug aacguacaau 59400
cagcagucuu gaagaagaaa uugugcaaca gaacaagguu uuauuuuaua uuuauuucau 59460
uuuuuucccu aaguuuuuuu uuuuuuuuuu uuuuuuugag auggagucuc acucugucgc 59520
ccagacugga gugcaguggc gugaucucgg cucacugcaa gcucugccuc ccggguucau 59580
gccauucucc ugccucagcc ucccaaguag cugggacuac aggcacccgc caccgugccu 59640
ggcuaauuuu uuguauuuuu aguagagacg ggguuucacc auauuagcca ggauggucuu 59700
gaucuccuga ccucaugauc cgcccgccuc ggccucccaa agugcuggga uuacaggcgu 59760
gagccccuaa gauuuuaaac aagaauauug cacaaaugac uauguuaucc uucuaauuaa 59820
gugcaccuuc cauuacuaau ugauuauaua auaauuuguu uuuuauuuuc uaaacuauuc 59880
uaaaaauuca uauuuauuua gcuuuuauaa caguagucuu aaucuuaaaa acggcaauac 59940
auaagcaacc ucauuuggua aguuaauuuu uauuuugaua uugguuauuu gacuuuucac 60000
aguuccacgu uucuacuggc ucucacugau agaguaagaa gucagcuucu uauagaauaa 60060
aguauauacu ucagagacag augaaauucg ucaaacauau gacugucuca gagauuguuc 60120
ccccugcuua aauuguucuu acccuagaua ccuuugguau uuacacuguc agugccugca 60180
ggucuuagcu caaaugucuu accuuaucag uguauccuuc accagccacc uaauauacaa 60240
caguaaaucc uacuauccag auuccuaaau agagauuaau uaacuuaauu uuucuccaaa 60300
gugcuuguaa ccuucugacg uauuacauac uuacugguuu auuauugacu gucuuuccuu 60360
cgccagaaug caaguuccgu ggugacacgg acuugguuuu guuuacugcc auguuuguau 60420
uuccuagaau gaugcuuggc acauaaauaua ugucaucaaa uaucuuucgu auagcugaac 60480
ggauggaugg auggauggau ggauggaugg auagacugaa auccuuacuu cacaucugcc 60540
uuugugaucu uacacaaguu acuucaccuc ucugaguuug uauuuuuuc cauaaaagga 60600 aaauaauuac aguuucuuca auguguugug aggauuagau aagaaaauau auauaaaaug 60660
ccuguuaugu gccugauguc uucguguaug ugucugacac aaauuguccu uuuuuuaguu 60720
ucaugaagaa agacaaaugg ccugggauca aagagaaguu gaccuggaac gccaacuaga 60780
cauuuuugac cgucagcaaa augaaauacu aaaugcggca caaaagguau gaaugauuaa 60840
ucuuguuugu uacucuguag cauagucuag aguguuaacu cacagaaaua uuuccuguau 60900
cagauguaau uuuaauugau guuauauugu auauuuaaaa uauaagaggg guuuaaucua 60960
uguuuuauca uacagcugua aaaauuaaua guuacucuca augcugcaac ugcuuuuuua 61020
aaaaacauac uauuucuuaa uaguuugaag aagcuacagg aucaaucccu gacccuaguu 61080
ugccccuucc aaaucaacuu gagaucgcuc uaaggaaaau uaaggagaac auucgaauaa 61140
uucuagaaac acgggcaacu ugcaaaucac uagaagaggu aauuagaaga auuugcauuu 61200
ugauuagugu auuauuuggu auguuugggg ggcuuucuaa auaauauuuc uuuaugaggg 61260
caaugcauag aaugaugaau cuauugcuaa uuucacuauu uuucuauucu ccuauaaugu 61320
uucuaauagc caauaaugaa cagcagauau aguuaauuug aauucacuau uuaauuauua 61380
guugguaccu uucgguacac ugaauaugaa aggaaauaaa aagcauuuaa uuguaguucu 61440
augagcaaua uauucucuua uaugaucucu uuauucuuac uuuuuugguu uuauuuugaa 61500
gugcauguua cauaaucuau gaaucaauuu ucaguucauu gccuuuaaug caugguuaaa 61560
ggguugaagg uaaauuagaa auuacuuucu guuuuaaccu agaucuugaa uuugauuagu 61620
aggugaucaa aucugucauc uucauuaaau uauucagaaa auaauguaaa cugaaugugu 61680
uuucauuuua guuuucaucu aaauaaacug caaauacauu uaaaauauac auaaagaagu 61740
uuuucaagua aaacuguaca uuuuuaauca uuucaggaaa cguagauuuu cuucaguaau 61800
uuuaagauuu gucauuuaug ugaauugcca uugaauuacu uaauuuaaaa uacucaccuu 61860
aauccucuug aagaguaaaa auuuuucugu uuuuuucucu uuguuuuaau aagcugcgga 61920
uuuuauauuc guaauuuauu gaguugggcc ucuaaaauuc caguuuugua cuuaacugac 61980
uuauagauua gucuccuaau gcucugcuag ucaauggacc aaaauaaaag aaauaauuua 62040
uuacauauuc uuccuaaauc uaguaccacc auacauguau aauucuaaac uguaauaucu 62100
caauaaagua ccuuaauuaa auuuuauguu caucauaaca augaaguuuc uagcauaugu 62160
aauagucuua uaaauaagca ugcaaauaac ugcugucaau uagaauuagu caguuuaacc 62220
uuauuaagua ucaaauggcu auuguacaua ugaugugaaa aauaaaguga auuuuuuuug 62280
gcuaauaacu aaucuaaaau ucagaugaag cauuuuaaag ggaaaaagau acuuuaauga 62340
uuuauuauaa uuuaaucauu gcagaaacua aaagagaaag aaucugcuuu aagguuagca 62400
gaacaaaaua uacugucaag agacaaagua aucaaugaac ugaggcuucg auugccugcc 62460
acugcagaaa gagaaaagcu cauagcugag cuaggcagaa aagagaugga accaaaaucu 62520
caccacacau ugaaaauugc ucaucaaacc auugcaaaca ugcaagcaag guuaaaucaa 62580
aaagaagaag uauuaaagaa guaucaacgu cuucuagaaa aagccagaga gguauuuuau 62640
uauauuauga guuaugcugu uauccauuag uuuuuuuaag caaaugcuaa auauuauuuu 62700
acccuaaagu gguauuucuu uucuugcuuu caaaugauuc uauuuaagaa uuguuacuug 62760
caugugauug gauuacaccu cugucaguaa aacuggaagu uuguguacau guaucuuucu 62820

```
auuauacacu gacuaaacca cgaguagcua ucauggugaa aucauaugau uuugaaaaau  62880
auuuuaauug aguuuauagg ugaggauuga ggcaauaggg uggaaugaaa uauaucacac  62940
cgguaaucag uagaaaucag auuuguuaga acuucguggg ggaaagcuaa cauuuaauuu  63000
uuucuagaag uaaguuaaaa gaugauagau acaugucauu cuaauguuaa gaauaaauua  63060
ugaacugagg cugggcuugu caacuugaac auugucugag gggacaugca uaccagucua  63120
gauacauaca uauauggaga uacuguuucu uccucaucuc aaaggaauuu uagaagauug  63180
aagagaaaau auauaaggUc uucaaaaugu gaauuuguuu uaaucacaau uuaagauaua  63240
guuucgauuu ucuguaaaac aggagcaaag agaaauugug aagaaacaug aggaagaccu  63300
ucauauucuu caucacagau uagaacuaca ggcugauagu ucacuaaaua aauucaaaca  63360
aacggcuugg guaagauucu aagaacuuug uuccauucuu uauugauuuu ugugaccaug  63420
uaaauuaaaa uucagcucuc uucuuuuuug gaauggaagu uacccuuuuu guugccaaaa  63480
uaaucuucug aaaacauagc ucugaucauu cuuccuccug uagcucaccg cuguucacaa  63540
aauuauauuu auaauucuua gccauguacu caaucugcua ugaaccuacc ugccuuucuu  63600
uucaaauucu acucacugug aguuuagcua uaucuaacuu ccagaauuca gcucauauuu  63660
gccucuuuug accauucugu uccauaugua ugaaaugaca ugucuuucau cuuuuaaugu  63720
guaaccuuag cauauuugag cauuaccucg uuaauucggu caacacuuau ugaucuccug  63780
cuacgugcag acauuuugcu agcuauugua aauacaaaua auaaagucug cauuuccugu  63840
cuucuuuaag ccuucauugc cuauuaaauc auuacauuuu agauuagaua uuauauuuug  63900
aucauuugag gaaccaaauu aaaaauaugg aauaaguaug gcauugaauu auacaugccu  63960
auugcuaaua uauucauauu uuauaggauu uaaugaaaca gucucccacu ccaguuccua  64020
ccaacaagca uuuuauucgu cuggcugaga uggaacagac aguagcagaa caagaugacu  64080
cucuuuccuc acucuugguc aaacuaaaga aaguaucaca agauuuggag agacaaagag  64140
aaaucacuga auuaaaagua aaagaauuug aaaauaucaa auuacaguaa gucuucgaaa  64200
uguauuguaa aaauaggcaa augauaagug auauaaugaa gauaaacaua aguguuugcu  64260
augccaggca cuguucuaag acuuuuaagu auauugucuc auuuuuaucc ucaggacugc  64320
ugguuacaua uguuaucauu uuccccauuu uaaagagagg auauggccuc aggaaugcuu  64380
aauagcaugu cugggggUag augggaaagc cauaauuuga aacuagucag ucugacucaa  64440
aagccaauac aaauucuuuu ccagaaucuc auuuuuaccu ucuuugagcc ucaguuucau  64500
cuuauuuauu uauuuuuauu uuugagacaa ggucuggcuc uauuuccuag gcuggagugc  64560
agugacauaa ucucagcuca cugcaaccuu gaccuuccag gcucaaacca ucuucccacc  64620
ucagccugca gaguagcugg cacuacaggc aggugccacc acaccugggu aguuuuuuug  64680
uauuuuugua gagacaaggu uucuccaugu ugcccaggcu ggucuugaac ucgugagcuc  64740
aagugauccg cccacuucgg ccucccaaag ugcugggauu acaggccuga gccauugcac  64800
ccagccucau caucuuuaaa auggaaauaa uaauacuuac ccuggcccuu ucagggUggu  64860
uauaugaagg ucaaauuaua ccguguauga aaguaauuug aaaacuguaa aauaacauac  64920
agauagaaaa cuuuugauua cacacuuaua agagugucug ucauauaaua gagauucuaa  64980
acauuguuca accacuuuau cagaacguag auuuuaaacu caaaauaggu uuauaguuag  65040
guaguuucua aucauuauaa uauuaucucu augggccuaa auuuuauuau cugaaaaaac  65100
augagaaaau ugaacugcuu gacuuauaau uccauuucag cucucaagcc ccugcuagag  65160
ucuuugauuc uuuacucacu uauucaaaug ccucugacag aauuaacacu auuuuugcuu  65220
```

ugcuaaggag cugccacugu uaagaaauua cucucuaaaa gaaagaaaau uggcaacagc 65280
auauguguau uuucagucuc uuuuccucac ucuauuaaau uuuguacaag agauguuauu 65340
uuuggucuag uaaauuucug ucauguuuug gaguauaaaa uuacuugugc uuuugcaucu 65400
aauuugggg uguagaaaau cauaaucuuu ugaaauaccu uauauaaauac auuuuuuugc 65460
cacaggaaau acuugaaguu auuguugugu accuuacguc auuuuagucc aaaauuauac 65520
uuguguucuc ugugugcaua uuuugauaug uauuaggaga uuauggaucu gugugauuuc 65580
uuaaguaaau ccugauauuu ucacaauuug augaugacuc uuuaaaguua gacuuaaguu 65640
uugccaaaag caagaagccu caaagaguaa cauuuguuca ugucuuaaca cuaucucccu 65700
cuuauugguc agaaucucag uauggaugca guguccauau gcacaacaau auauuaauuc 65760
aguuuaacag acuuaaugcu gaauaagcaa uaagauuaau ugaauuaacu aaaucuuuug 65820
auaguaucca cuuccauaua uauaguuaua gauauaaugc uagugaauuu gaaccauaaa 65880
caaauuaaua auacauguga uuucugugaa aauuuauauu agucuuuuca auaugucaau 65940
auagggcagu auuucucaaa uauagaggau caguuuuuca ccauuguccc ucuuggggac 66000
auuuggcgau gucuggagac auuuuugauu gucauggcuc gggggugcua cugguaucca 66060
guggguagaa ucaaaagaug cugcuaaaca uccuaucaug cacaaggcag ccccaccacc 66120
aacaaagaau uauccaguca aaaauguuac uaguaguaug guuaggaaac uaucauauag 66180
aggaagcaau cacauuuuac aagagccaua auauuuaaaa ugccuuuuug uucauucucu 66240
guauauuuga cuagagucac aaaauaacuu gauaagauug uugccaaaaa uauuagaaac 66300
uagaagaaaa auguguuguu aagucuaaga guaguuaaau gaaauaaaga auuauucuuc 66360
uuuggauuug gaugccugca ucaagauuua gauuguaagg auacuuagga cugaacauuu 66420
gcucuauaug aaauuuguau uaaucaaggu augaauugca gcaaccacuc uauuaauuac 66480
auauguuugg ccaggugugg uggcucacac cuguaauccc agcaauuugg gaugccaaag 66540
cgggcuuauc accugagguc augcguucaa acuggccugg ccaacauggu gaaaccccau 66600
cucuacuaaa aauacaaaaa uuagcugggc cugauggugc acgcccguag ucccagcuac 66660
ucaggaaguu gaggcaaaaa aaucacuuga aucugggagg cagagguugc agucagccga 66720
gauugcgcug cugcacucca gccuggguga cagagugaga cugggucuca aaaaaauuaa 66780
aaauuaaaaa acacacacac acauauguuu auuuacauca ggcuucaaga aaaccaugaa 66840
gaugaaguga aaaaaguaaa agcggaagua gaggauuuaa aguaucuucu ggaccaguca 66900
caaaaggagu cacaguguuu aaaaucugaa cuucaggcuc aaaaagaagc aaauucaaga 66960
gcuccaacaa cuacaaugag aaaucuagua gaacggcuaa agagccaauu agccuugaag 67020
gagaaacaac agaaaguaag uaacaacaga aaauuaucaa cauuuaggaa aaauaugugg 67080
uagauugcuu uuagagaaga uuuguaaauu uauaaaagau gguaguauaa aucuccgugu 67140
uguaauaaaa aguaugagcu uuaucuuaug cuguuaaaca agguauuuua gacaaugcug 67200
uuuuugugggg cagauauagu ccaauuuauc uuuuuauguu uucgucaauc ugauuuguga 67260
auuaucuaua ugaaguuagg aaaaaucuua auguacauua caaaaauaua auauauauua 67320
cauuguauuu ucuuuuuuuc uacuggaauu uuaugcuacu gaggcuauuu uuaacaaaug 67380
aacaauuuug aacaauuuga gggauugagg gaaguaugau aaugacaaaa agggaugaaa 67440
aaagggggguc auagagaugu uuuugugaga aggaguuggu caguguauuc ugauuuauua 67500
ggguuuuuuu uaguuuaucu cagauuugau cuauuuaaau uguuuuagaa gaugcuggug 67560
uuuuucugug cuagcuauga aauuuauggg uaaacuuuaa gccuuuccua guccuuuugu 67620
ugucuaccua aauucaauua auuucauaug gaaggaugua guaagugagu aauauaaaua 67680
ucuaaaauug gauguuugaa aacaaaacau accuguuuuu uguaauagcu ugauuuaaug 67740
cugaguucuc aaaaucauua uuaagauuuu gaacuuucac auucaaugug gaaagaauug 67800
aguguaauua caaaagauuu auuugaaaaa guugaguugu uaauuuguga aauauguucc 67860
auuaaacuca uaauauuuua gaaaaauagu aggaaguaau aaagcuuguu uauuuuuuau 67920
aucauauauu cauauaaaau gucaguuuuc cuuuaaaaau uacauuuuuu uuuugguuaa 67980
uuuuuaggca cuuagucggg cacuuuuaga acuccgggca gaaaugacag cagcugcuga 68040
agaacguauu auuucugcaa cuucucaaaa agaggcccau cucaauguuc aacaaaucgu 68100
ugaucgacau acuagagagc uaaaggugaa caucaacacg uguuaaugua acaaaauuuc 68160
ugauaauucc uauuggaaga gaauucacua ugauauauag uaauuuuguu gaugaauagg 68220
gaauuuauaa ugcacuguug guggcuagac auagacacac acaugcauuu uucaacaaua 68280
agucucuuua ugauacucau uuacugauua ucaucuuggg gauuaggaaa ggauaggcca 68340
uuaugaacua cuguuucuaa ugaaauuaaa uuuaagaaau auuuuacuua ggauuuuuuu 68400
uaagacuuua uuauuuuuuu agagcaauuu uagguucaca gcaaaauuga gaggaaggua 68460
cagagauuuc cuguauaucu ccuacccuga aagugguaca uuuguuaaaa uugaugaacc 68520
uauauugaua caucauaauc acccaaaguc caaguuuacc ucuauuuuag cucuugguau 68580
uuuacacucu guguguuuag acaaauguau aaugauaugu auccaucauu auaguauuau 68640
acaggguauu uucacugccc uaaaaaucuu cugugccucu cuucuucauu ccuuccucug 68700
caccucacca aaccccuggc aaccagugau cuuuuuacug ucuccauagu uucaccuuuu 68760
ccagaauaug uuauagaugg aaacauacag ugugucccca ucauucucac cauaggacag 68820
cuaggaacuc cuuucuagug gcauacauau ugucuaguau uguaaguuac ccuuuuauau 68880
cuuaucuuug uaaacuaggu uagaaauuac uucaagucag agauuuguuc uguacuacuc 68940
uuaugcuuca uaguguuuaa aacguuguca uauauauugu uauauacuug uuuguuuaau 69000
uaauucagcc aaaaugaaac gugcauauuu gauaaaauuu uguuuguggg uguuuguuga 69060
agaugaauug cuuuacacua guuuuuuuuu uuuuucucaa agucgacuuu uuuccucaag 69120
guagacuuga caugaauaug gaaaaauaua uguaguuugu gguuauuuuu uuucucuugu 69180
guacuuaaaa auucagacug aauuuuucuu auaaugguau auuuucuguu uuauguuccu 69240
uuuaucauug auacuucuug aagagucaug aauaauaccu uucuuuuucu cuuauuagac 69300
acaaguugaa gauuuaaaug aaaaucuuuu aaaauugaaa gaagcacuua aaacaaguaa 69360
aaacagagaa aacucacuaa cugauaauuu gaaugacuua aauaaugaac ugcaaaagaa 69420
acaaaaagcc uauaauaaaa uacuuagaga gaaagaggaa auugaucaag agaaugauga 69480
acugaaaagg caaauuaaaa gacuaaccag uggauuacag guaauuuuau auuuaacucu 69540
gauaaugucu gauuuacaau auagagguag uaguuuauuu cuacuuuauc auuuuaucua 69600
ugguauuugu uaaaacugac uuucaaauca cuuugauuaa uguaauuaau uucuuuugug 69660
acuucuauug uguuuauagu ucuagaguag cauauuagua uguuguauua aaaugcagaa 69720
gcagcuacca gauuaucuua uguauuaagu gucauuuaga aaguaugguc agugauagcu 69780
ucagaaaguu gcuauuauau aauugaaaua uuuacugucu auuuuguuuu acauuuauuu 69840
guaaaaauau aaaguuacau uuuauuuuuu agggcaaacc ccugacagau aauaaacaaa 69900
gucuaauuga agaacuccaa aggaaaguua aaaaacuaga gaaccaauua gagggaaagg 69960
uggaggaagu agaccuaaaa ccuaugaaag aaaagguaug ugaagaaaca uacugacuua 70020
uaugcuuaag guagugacag aguaaguuaa auacauagcu gauuaacagu uaauauacug 70080
ccuuaauuug augaccuggc uguauuaauu cuguauuaau uuugaggacu auaagcagua 70140
uugaauaacg uagaaaaguc uaaguuucug uucuguagga auuuagaguc uacuugagga 70200
gauaccuaua auguaacucu uauuuggaaa uuacuacauc aauuucauuc aucuuucuga 70260
cauuagagua ccucugaagu uccuucacac cuuaacauau ucaacugugu aucauuucuc 70320
uccaaaguaa ucauuuacac agguuggugc uuuugacuuu ugggacagaa agauagacau 70380
uuuaagauac cccacuuuga cccaaauagg uccuuuuuaa uccuucagga gacuaggcug 70440
uuauuucaga uagcaaaguu auuuggaaua ucuucaguau uugcaguaau aaucaguaac 70500
caaucugcuc auagauuaau ucugugggag aaauugcuua aaauuuuaua guucauagua 70560
aacuguuuug uaauaaaaau uacugauuga aauaacccca aaaaaaacua aaauuggcua 70620
aaaugcgugu aauuaaauuu guuauggaca auaaauugga gauaacuugu ugguaacauu 70680
caaaauaucg aaagugaacu gggaaauguu gauguuagca guaauauuug ccauugaaga 70740
aaaucaguau ggaggagcua ugguuaggaa aauuuuuauu auaaaauuua cccagaaaau 70800
auuuaauguc uauaaaauaa uuucaaucac augaaaaugg aaaagaaaau ucugucuuua 70860
aaggcauuga auagaaaaua gguaauggaa uucaaauuuc uuaauagagu augcucccaa 70920
aauuauuuuc uaugaaaauu cauuaauguc aguguaauuu auugacacua uuugcgugga 70980
gucacaacau gcuugcuguc agaagcuuug cuggugaaaa cuguaagauc aaaguguccu 71040
uaaucuuuug gauuuccauc uuucuaacuc ccuaauuggg gauaggccug aucuuauccc 71100
uaaaugggga uagguuagaa acugguaugu uuguuccuaa cuggugugu ucuauaccag 71160
uuucuaaccu gauuccuauc agaauguuuu aagagccuug uggcuuugcc uggacucuuc 71220
uaugcuacag uuuauuuagu uuauuuauuc aguuuauucc uccuuaaagu gggaauaaua 71280
cuaucuguau ugccaguuuc ucaggauuau uuuacauaaa augauaugau augcggaagu 71340
cuuuuguaag ccaucacauc cauagcagua uaagauauua cuacuaacua gaaagagaaa 71400
acaggggucu augcccagua uuaaaauugg cauucaggaa ucuagugaga auauuuuuuc 71460
agguucauug cuugggcauu ucuaauuuau acucaagaaa ugcuuucaua uuguuuggaa 71520
auuuuaguac ccuuuucucu guaaacagaa uuuguagucu accuauguaa caaaacccac 71580
cccugugccu ugcauuucau ucuccuuagc auuuauuacu aucuuaacau acuagacaug 71640
uacuugucuu uuguucaucu uuuuuuuuuc uuuuuuuauu agaccauaaa cuuugauggc 71700
aggaacuuug ccuauuuuau uuauuauugu auucccagca ccuagaacaa ucgcuggcac 71760
auaguagaug cucaguauuu guugaaugaa uauaaauuuu uaaauguuau aauaauauua 71820
uucugaaauc uaugcauacg aagcuuuugg uacagaaaac augaaaagag aacuacugcc 71880
uuaucaucca gucuucuucc cucuucucau ucagucuaga acauaaccug uuuuggaaaa 71940
aguucucaaa ccauauguuu aucuugcccu caaaccauaa caacaaucaa ugcaaaagac 72000
uucugugacc cccagaauau guggggauuu cuccacauca gcaagcaagc aguugguuuu 72060
guagcagaca ccaacugggu gucguccaau ucaauucauc aucuaccugg agauaguguc 72120
agaucccaca gauaucuuac uucgaucaaa ucacaagucc aggccuccgu gacuuccgaa 72180
guucccacau ccccagcccc cagcuuuggg uuugauuaau uuccuggagu ggcucacaga 72240
acucagggaa acauuuacuu acauuuacca guuuauaaua aagguuauua caaaggauac 72300
agguuaagag auguguaaga agagauaugg gggaaggggu guggaccuuc caugccuuuc 72360
uggggugcca ccuuccucua gaaaccucca cauguucagu ucuccagaac cucucugaac 72420
ccaguccucu ugguuuuuag ggaagcuuca ugacaucagu auuucuucuc cuaggguaug 72480
gggcaggacc cccucguauu aggguuuuaa gacccacagu cagaaaggca ggggaagauu 72540
acaguccugc cuuagggcag gugaaaggag gaugggagaa ggucagagag acucuuuucu 72600
gaggugugcu cggaaggccu aacacacuca auauuauaac uaaagaugag gacaagggcu 72660
augagaguua uaagccagga accauggaaa aaagccuaua uguaauaaca ccacaauacc 72720
caugguacca uucacguuug uuguuuuucu guuuuucaau uguucuuuca gucuugguuc 72780
ccuuaaucuu aauuuagcaa guaaugccag gugggauaaa auugcccaaa cccaacaaag 72840
uacugugugc ugcaggauua uuuaaugaca uaccuuaugu cccccacuag uauuuacauu 72900
ucugggagua cagaaaaauu cuuguacaua uuucagaaaa aaugaaauua auaacuauca 72960
accacuuagu gaaguuuuua cuuuuuuuuu ugagauggag uuuuauucuu gucacccagg 73020
cuggagugca auggcgcaau cucagcucac ugcaaccucc gccuccuggg uucaagugau 73080
ucuccugcau caaccuccca aguagcuggg auuacaggug ccuggcacca cgacuggcua 73140
auuuuugaau uuuuaguaaa gauggggguuu caccauguug gccaggcuag ucucaaacuc 73200
cugaccucag gugaucugcc cgccuuggcc ccccaaagug cuggauuaca gguaugagcc 73260
accacaccca gacugaaguu uuuacauuuu uuaaagggca cuuauuagcu gaauuaaaua 73320
agguaaaaaa uugacuagua uuagagacaa gaauuggaga auauaguucu cuaguauucg 73380
agaaagucgu uuugauagga caacuaaucu uagugagaau uuggcuuuau uucauauuuu 73440
uuuaauuuuu ugagaugacg ucuuacuaug uugcccuggc uggucuuuga acucugggcu 73500
caaacaaucu uccugccucg gccucccaaa gugcugagau uauaagcaug agccaucucc 73560
ccaggaauuu gacuuuaaac caugguucuc aacccuuuca gauucaacau ucccuuuaau 73620
aaaaaauaua auguuucaua auuuccccuu uacuauuaua auugaaaugc auaguuaaca 73680
uaaacucuac cuacuuacau aauuucaaaa augucauuau gaauguccua aaugaaauau 73740
auagggggaa cauaaaagga auauucauau uucaacaugu aaaugcuuug gcaugacucc 73800
auuggaaaau auaaugaacu agucaugugc uugcaccuuc auuaauguga guucaaagcu 73860
acgauugcag acugacacaa auguguucua uuggcaacug augggucaug augguauugc 73920
cauuuguaau uugauuucca aaaugguaaa caaauuguug gugcaguucu cagcaaaaca 73980
augucuauaa ucuuaccuuu uauaagacug uuguauuccu agaaaacuua guguauagua 74040
aaaccauuaa aaaauuacuu agugugaaua uguuaguugg agauaaauuc uuagcucaga 74100
ccaguguaag cagaauuuuu uacuguauua auauccagua gaacauuuga aaguuguuca 74160
gugcaugaga cuauucugca uuggauaggc uuucuuuggc uccuuuauca uaguuauaau 74220
aaaccaugac accuaccccu gaaaugcccu aauucccuuc cguuucuuuu ucuuuuuucu 74280
uuuuagcacu uaaaacuagc uaacuuacua caaaauagau uuagauuuau uucuuguuuu 74340
guuaucugua ucguuugcuc ccuucucccc aaucuaucua accaacuagu auaaacuaga 74400
uaguaagauu caugaagaua cacuuuuuua ucugauuuua uucauuuguu cuauuccuau 74460
ugccucuaga guaguacuug gcacaugguu agcacuaaau aaguaccugu caaaugagug 74520
aaguaaugug cauugaagac uugaaggggc ucugaugcua ggaaauuguc augggauaau 74580
agaugagguu ggucguuugu acagaggauu cuuguuagaa gcuuacucua gucaugauug 74640
uauuagaauc uucauuuaaa ggcuccugaa ggguguuggc auuagucaga acugucuccc 74700
agaauuuuau uugucuugug auagaauaaa gcauaguuag ccuaaagagc aguuuuccua 74760
auagcucggc augcccaaag auucuaggag uuauacaggu ugaacaucua auccaaaaau 74820
cugaaaugcu ccaagauaca aaauuuuuug agcaccaaua ugaugccaca aguggaaaau 74880
ucugauguga ccucauauga ugagucacag ucaaaacaca gucaaaacuu uguuucaugu 74940
acaaaauuau uaaaaaauau uguauaauac uaccuccaag cuauguguag aagguguaug 75000
ugaaacauaa gugaauuuug uguuuggacu ugggacccau cccuaagaua ucucauuaug 75060
uauaugcaaa uauuccaaaa auauuuuuua aaaaaaucca aauucuaaaa cacggcuggu 75120
uccaagcguu ucguaaggga uacucaaccu guauagcaaa augaacauau uuacauauuc 75180
ucuaggaaau auuaguuuac aauuuuucua ggcaaauuau aauugauaaa ucauaaagaa 75240
aauuuaaaau aacacuggua auuuuccuac cuccuucguu auuguuacag aaugcuaaag 75300
aagaauuaau uaggugggaa gaagguaaaa aguggcaagc caaaauagaa ggaauucgaa 75360
acaaguuaaa agagaaagag ggggaagucu uuacuuuaac aaagcaguug aauacuuuga 75420
aggaucuuuu ugccaaguga guuuaaauau cauuauaaaa cuaauuaugu guaaaauccu 75480
uuagugaccu ggaaauuaua uagcuuuauc auaguugaua auaugagaaa uggucuaguu 75540
uaaaugauca uuuauuaucu augauuuacu uacuuuuuau uuucuuuaaa aucuguuuua 75600
aauauauugu aacaauuaua gauggauuuu ccugugaucu cguuguaaau uagcuuauga 75660
caaauauagg guguuacaau uauuguaauu ugguuuggua augaguaugc aauugaaaag 75720
ccaaacacug aaugguauau uucaugauuc uauauuaaau uccacagagc cgauaaagag 75780
aaacuuacuu ugcagaggaa acuaaaaaca acuggcauga cuguugauca gguuuuggga 75840
auacgagcuu uggagucaga aaaagaauug gaagaauuaa aaaagagaaa ucuugacuua 75900
gaaaaugaua uauuguauau gagguaagcu auuaugugga aaugugccac ccauuguaau 75960
gaaaaacugg uugaccccua gaaauugaaa uaauaaaugu guguugucuu aagcuugggu 76020
uauguuuucu uuucccaugu gaauugagau auuccugguu cuucauaugc cacauaauuu 76080
ugguguauuu uugaucuuuu gaauauuaua uugugagacu cugguucuug uuuaaauucu 76140
augggaaaau guagauacuu uuguuuuagc augcaaucgg ucuaauuagg uucaggccac 76200
aaguuccaac cucauuucuu gggcuguggu uccauuuuuc aaagccuuuu caauacucuu 76260
cagaucuguc cugccugugu accucacaau aggugaucug guaugugagc uauguaccau 76320
uaguucaguu cuuagaaacu uugguauucu gauuaggauc gauccauaca uuugcagcuc 76380
aagagugagc ccagaaguuc auaaacaacu uuauaggguc ccuuucuuga gcuccucccu 76440
cuuugccauc ucucugauac uuuguuuccc uagggauuuc cauuuggggc uuuaguuacc 76500
cagugaugcc auguacuuca ggaauugcac acuucugcag ccaagcaagc aagaggagag 76560
uagaaagagg aagaaaaaaa cgacuuuuac cuuacccucu uaguaucaua gcucuaccaa 76620
uuggagauuu cccucccaaa aaauauuagc uucugugagu ucccauugca gccucuauua 76680
ccacugcuau gggauggcuu aaggguuggg gcaugaaaga acagauagaa gaaaaaaaaa 76740
gugaggugcu uucauauugu cucuugagug uuaaaagauu cccuuucucu uuacucgagc 76800
uagaauuaga agguuuaccu ggagcucucu cugucagugc agacacccau cuucagguuu 76860
caaauaaugu ugucuucagg gcaggcagua acagaauaaa agaaaaggua aauucaucac 76920
cuguuugcug cuacuuuaag uccugguauu cuauuguaau cugccuucua cuccuuugca 76980
aaguccucaa augguugcuc caugcauuua ggagagagaa gauugaaugu auuuacucca 77040

-continued

```
uuguaccugg aaccagaugc ccuugcccug caucacccca ugucauuucu uagcagagcc  77100
uuugagauuu uugugugugu gugcuuuaca aucucuuucc aaguuauauc uucugauaca  77160
gucauggucg ugaaaagcaa aauaaaauca uguguuaaca uuuaaaacuu uuuaauuuua  77220
uucugacaac agcuaaaacu auuuaaucuu cuguuucgcu cauuucuucc aagguaaacu  77280
ucaguugguu uuacgugauu ugcuauuucu ucuucuuugc auuuacaaau gaucugugau  77340
cauauuacug aucuuuguaa agggcuaaua ucuaccugca acauuuggau augacaguau  77400
uuacccuuug uaaauacaca uuuucuauuu aucuucaaaa auuaccauuc auuagucugu  77460
guuaaugucu guuuacuauu gugucauuau gaaugugaug ugaacauacg aaguugaacu  77520
uauuuaaacg aacacucuca ugagcuucua auccacauuc cuuccuuuuc cuucuaaguu  77580
accauuucuu aaaaaucuuu uagaaguuuc cuugauaggg aaaacacaaa uuauugagga  77640
auuuuucuuu cucuugacau cuguuuauag uuacucucuu guuccagcag uggauauuuc  77700
cccuccaugu uuuucuuugu cuaaacauau guucaaaaca aaacacuuuu auucuucuuu  77760
gcagguuuua caaggaucaa cuuuuaguuu ugaaaccugc uauuacuuuu agaggccauu  77820
uuuuuuuucu cuaauaaugu gaguucaugc gggcugaagu aauuggaaua cuuuauagaa  77880
aagauugaau uugucuucuc ucugaacucu aguuugaauu ucuaaauuuu augaaucauc  77940
uagauauuaa agaggagggg cauaucaaag aggagaaccc uagcagagau aagaggcaag  78000
aguaaauguu ucauguaugg guaagagugg auuuguauuu accuaaguaa agguagaccc  78060
uggacaauaa gguuggauag auguggaggu ggcaaaccau ggagggucuu guaggucaag  78120
uggauguuuu uagacuugaa guguuaaauu auuaucugaa aucauuaaga gucuuuuuag  78180
auccuugagc uucuugagaa gaccauggau auuaugcagu uauuauauaa uguuuuaaaa  78240
uaguaaguau uuuaguuuaa cugucuuaug uaauuccaua uaaauggaug cauguucuuu  78300
aaaaauguua auguauuuca guaaaucaaa auauacuuuu ugacucauca uuuaaaggag  78360
gccuucagug aaugcucugu agaggauuau uuuauaauac uaauuuugau auccuaauuu  78420
auuuguuaua aaguuuagaa gguuugaaga auuuaaaaua uaguguuaau aaacacacug  78480
aacuuuucuu uuuuuaucuu guauuuuuau auaguacaac agaaaaaaga ugaaauguga  78540
auaguaaaga gucugugauu guuguucaua gggcccacca agcucuuccu cgagauucug  78600
uuguagaaga uuuacauuua caaaauagau accuccaaga aaaacuucau gcuuuagaaa  78660
aacaguuuuc aaaggauaca uauucuaagc cuucaguaag uguauaucuu uuauuauuuu  78720
uuucuuuuuu ccauguuaaa augcaugaaa gugaaaucaa cuucuuucuu aaucuggcca  78780
aaagcauuac aucuuucuca uuaauaguaa uacaguaaau ucaacuuuua uuuuuaacag  78840
guagugaugu guaauaauuu auuuaauccu uuuuaacaua auaacaguaa acuuaagauu  78900
cuuaagcuuu ucauaaagcu cauaaaugau uucuagaaau uuuaaauaug uaguuaucau  78960
uauguauuuu gcuguagcag caguauacag uuaaauaaaa uaggaaaaca uguuccaaga  79020
cuguuuucau ucaaauauuu augcuauauu uuuagcuuau aaaaacucau uaaucauuaa  79080
uguaaaauua uuuguuggau uuuuuaaaua uuuaguguau uauuuuuguu ucuuuuuucu  79140
uuccauguuu cuucauucuu ccaccuuaag cagaaucagg ugugugacac aacuauguuu  79200
ucuauccuug uuaccauuau uaauaaauac aagggcauga uauuuuucac aaaagaaaca  79260
cuuuguucag aaccaaaaaa gaucauggca acagucagaa uuaaaaaugg uaaaagacua  79320
ggugccaaag augacuuaca uaauugggua ccuagaaaua uucuauggua uuacaguaau  79380
gaugaaaaau acaaauuaga acacauuuua gauccuauug aguuaaauaa aucagaguca  79440
```

agaccaaaca auaaauaaag ucaauuuacg ucaacaaaug guaaguuggc agauuuuaac 79500
ucccuuuuug aaaaugaacc augauccuaa gguugguaaa auuaaucaag aauguuguca 79560
aaaugauaaa gauaaaaaug aggaagagaa uaagauaggc aagagugaga aaggaaagag 79620
acacauagcu gaaaauguga gucacaacaa cuacauagau ccguagaauc ugcuauggag 79680
gacugugauu augugacagu ugcugaugcc guggcuuagu gagcugaggg ugaugcacag 79740
gcaggcgaug uaacugaugc gucaguccag ccaagaaagg acgcgucccu gguuuggcua 79800
cguggccguc cuuuauuucu uuguuaacug aauuuucuua uaguaaguag cuuacguaca 79860
uauauagugc aaaugggaaa guguguaaga uuuagaaaaa gcauuaacua uuaguaaacu 79920
uuaucuuaag cucuaacuuu ugauuaguuc cuacaaaaau uagugaauau gcauuuucua 79980
auuuagugcu uuuuuuuuuu uuacaauugg uguucacuua auguuauauu agauaaauga 80040
auagcaaaaa uaagguacuu uagaguugau uguuuugccu uacaaacuuc uaauccaucc 80100
agcuguauuu agaaguaaga ucucacuaca gcgaauuaua ucaguaaaau uuuguuacag 80160
uguugugcag uguccuaaga uguauacuaa guuccuucag uggcuuuuuu ugccauguuu 80220
uauaacagau aauuuuguua uaaugagaaa aggaaacuug gauguguugc ugucuauauu 80280
guguuaggcu caggcaggau gcuguggcuu acucauuuaa ucacuuuggg aggcaggggc 80340
aggaagauug cuugaggcca agaguuugag aucagcuugg gcagcauagc cagacccugu 80400
cucuacaaaa aauuuagaca gauguggugg aacacauuug uaguccuagc uauuagggag 80460
gcugugguggg gaggaucauu ugagcccagg aguuugaugu uacauugccc uauugcacuc 80520
cagacugggc aacagaguga gaccugucuc uaaaauaaua auaaugauaa ugauaaaugg 80580
uguuaggcuc ugugccuaag uauauuuuuc acauaggcug gguaaagugg cucaugccug 80640
caaucccagc acuuugggag gccaaggcag caggagcauu ugaggccagg agucaaagac 80700
cagccuugag agaccccauc ucuaccagaa aaaaaaaaaa aaagaaacaa uuagcugggu 80760
gugauugugc acaccuguag uccuagcuac ucgggaggca gaggugggca gaucacuuga 80820
gcccaggagu uugagguuau agugagcuaa gauugugcca cugcacucca gacugggcaa 80880
cagagcaaga cugucucaaa caaaaacaaa caaacaaaaa gcacuuugca gaauaucagu 80940
cuaacucuac aguuuaugga cuuuuuaugu acguacuacu uuuggcuagc uuacauugag 81000
auacagaaua aaaguuuguu cauagcauuu aucguuuuuu ucuuuauacu guccaccuga 81060
gauauuccag ucaccuaagu cauggaaaca ucaacuaaaa uuaaauaucu auguuaagag 81120
aaaauggcug aaagugauuu aauucauaac acuuuuuuuc acaugcuaau aaauaagagu 81180
uugagacuuc cacuaggcau uaucucuaac uccuauccac uaagaauuug auuuuaagua 81240
guugauggcu uuuaaccgga uuauucuucu guaagaguuu ggaagucucg ugaaguucgu 81300
uauacaagaa uucuguuuac aagagagcau uacauuagaa uuuguuuuuc agaaauuugg 81360
acuaucucaa cgaauaccuu uaguuuuauu auuucaaaau gcaagggaaa aaaugagcca 81420
uaaucacuaa uaguaacugc aucauauuuu agugagaaau guguuaaaaa uauccucaug 81480
ugagaucuuc cuuagauaga auuacccucu acucuaauau uuaauauauu uuauaucuac 81540
caaucaguga uauuaauagg uguuuaucau uugcugaauc aaauagguac aacagaagac 81600
aggaaguuug ggagauagaa gagcucaggg acaggaaauc acagaugucc auaucugaaa 81660
uaaccuuaaa aguuauccug ucuaaugccu ucacuuauaa acuguagugg uagaauuugc 81720
cuaguauuaa ccuaauagug guagauuuga auguauacuu gggcuuucuu auuaagugga 81780
aauguauucc ugugauuuac auauaucaac aaaaauguuu gucuucuuuu uuuugcuacg 81840
acauaugugc augugcacac acaucucccuc aaacaaaaau cagauggaca caugcaguca 81900
uuggaucuaa aagauguuau aaaguugugu auaauaggua uuuuauaaua auauauuuua 81960
agacccauaa ugucggugga guaacugacu uuacagccca ucaagccaau agagagagaa 82020
aggagaaaaa aaugaaaguu gugcugaaua auuaaaaaaa auuauuuccu augaugcuua 82080
uaacaguccu augagguagg ugguauucua auuuauagaa aaaaugcaua gaaaaauaua 82140
auuaagcaca guuaaaaaaa auaaaguuua gaaugagaag uaacaacaua aauaaugacc 82200
caauguagau ucaggucaaa agaaaugaaa auauaauauu aaugguuuuc aaagagggaa 82260
ccauuacuuu agcucaaaga augaaggagg gcuuuccgaa ggaguaaaga auuauggcag 82320
uucuuuugua gccuagugua uucauuugcu aagguggcug uaacagacua cuacagauuu 82380
gguggcuuaa acaauagaaa uuuauggucu uaguucugga gaccuagaag uccaaaauca 82440
agacaucagc aggguugauu uccucugcac aaucagaggg aaagaucuuu cccaauccuc 82500
ucuccuuggc uuauaaaugu ccauguuuuc ccuguuucuu uuuaucaucu uccuucugua 82560
caugucucug ugucuaaauc cccaaauuuu cucuuuucau aaggauacca gucacagucg 82620
aauaggguuu acccugaaau cucauuuuaa cuugaauacc ucuguaaaga cccagucucc 82680
aaauaaaguc acauucugag guacuggaaa uuaugacuuu aauauauaaa uguggagggu 82740
aaggggaaca caguucaacc cauaacgguu agauaacaau cgugcuuuau uuuggacuag 82800
uaaaaccacc auagaucagu uuaaccauua ugaaauuaua caugaaggca uuauauguau 82860
ggacauuauu aagucauacu ugcuuugcuu ccauuguaau uaaaacaaac cauacuaccu 82920
uuguucugca aguuuuguau ucuaacuuau uuauuuuugg cuuucaccag aacacuccga 82980
uuuucucaua uuccuuugag gaaaaaaagu uaccuuuuga caguauuuuc uuauccagua 83040
ugucuuuuau ggcuuuuauu uauuaaacuu uaaaaauauu ccuaauuuca uuucccugaa 83100
gauuucagga auagagucag augaucauug ucagagagaa caggagcuuc agaaggaaaa 83160
cuugaaguug ucaucugaaa auauugaacu gaaauuucag cuugaacaag caaauaaaga 83220
uuugccaaga uuaaaggug a auuuaauguu uuuuauuagg aaaucuaaug ccuaaaacuc 83280
cuuccuuagu uguuauguuu acuuuuauua gcuuauuaag aagucaaaaa ugcauauucc 83340
uaauauauca uggugauggu auacuuuaua cauuugcucu uuagcauuua uuuguugaag 83400
gccuacuuua uauuaaacac uccuccagau gcugggaaac agcagucaaa aaauuccuua 83460
uacucauagg acuuacguuc uaguggagaa gacugacaau aaacaaguca cuaaauagua 83520
ugucaucuga uguuagugcu aaggagagaa auaaagcaug auugguguaa agaguauggg 83580
gagagagaag ggguguaacu gaaaauagag uaguaaggga ggucuuccuu aauaagauga 83640
uauaugaaca gagagcuaag gaggggua aa ggaagugagu cauacagaua cuagaaaaau 83700
aauuacagac aacagaaaua gcaaguucag auguccuaag gugggaggau gcgugguaua 83760
uuucauuaaa aauuaucaca cuguaaaaua uaagaauaau uuguuucuuu uagaaauuuu 83820
acuuuauucu gauauuaaua augauuuuuu aaucuuuggu uuuccaaguc uuacccuauu 83880
uaugggaauc uuuuuuuucu uuuggcuagc uaauugcuuc aguuuuguuu ucuaaucuag 83940
aauguuagca aucuguuaau ucccacuggua augauauagu uaagcuaugu cuugcuucuc 84000
acacuuuauu uauuuauuua cucagggcac uaaucugcca uuuuuucgca cuuuuuuucc 84060
uuuuuuuuuu uuuugguacu gcuucuuauu cugguuuuua cauugauaga accaauguua 84120
gacguucauu ugccuuuugc uguguauauu uggguaagga ucuauaugug caauauaugg 84180
gacaguuaaa aucagaauuc uaaauuugua uuauugcauc aggcaauaau gugggaaaua 84240
ccuugacauu ucauauacac aauauucuug uauuaauuua acgucuuagu ucaaaaucuu 84300
ccuuguuaau auagagaccc uauuauuugg uuuggcaaua caguugaaga gauugauggu 84360
ucuuaugaau uguuugccuu uucuuuucaa uggcuguagc uauguuaaau uauuacaugu 84420
uugcuuguua ucuuucagaa ucaagucaga gauuugaagg aaauguguga auuucuuaag 84480
aaagaaaaag cagaaguuca gcggaaacuu ggccauguua gaggguaug ugagaauuua 84540 ccauacauuu guuuugguuu cagcagugau aagccagaaa ugaaaaguuu agauauguug 84600
uaaaaguacu gauaugccuc uacaagugcc cuguaguuuc aguguuuauu cugcaucugu 84660
aauauaaaac aguaagcauu ucuaugugu ucaaaguauu uuaucaucug uuauaccuua 84720
cauacuuuca ucucucuuuu uauugaauau gccuccauac cuugaaaaca uuuaacuucc 84780
aggaauccuu uuguuuaugg agguaacugc uaacuggucc uugguccaau gcugccauuu 84840
uguaaccauu uguuaugaua ucuucccagc uugguauaau guuuuauaau uacauuguuc 84900
cucccccucu uuuuuugugu ucuuguaauu uucucccuau guuauuuugu auucauuuua 84960
uauaaugaau aaauguugcu uaugagguca aggccaaaga cuuaagcucc uguugauuuc 85020
auguugcuga gugucauaaa uggaagcaau cauaaugcag agucauucug guaguaauau 85080
uaaauauaug auggauucag ugaaaauauu auguguuauu agaaaaauau ucagaacagg 85140
ccgggggcag uggcucacac cuguaauccc agcaauuugg gaggccgagg cgggcagauc 85200
acuggaaguc aggaguucaa gaccagccug gccgacaugg ugaaacccca ucucuacuaa 85260
aaauaugaaa auuagcuggg cauggugguc caugccugua auccuagcua cucaggaggu 85320
ugaggcagga gaauugcuug aaccuggcag gcggagguua cagugagcca uggucacaca 85380
acuguacucc agccugggcg acagagcgag acuccaucuu uuaaaacaaa aaaaaaaaag 85440
gaaaaauauu cagaacagua ucuugcuggc agcaacauuu guuucaucaa ugaaaauaug 85500
uguuaauuug accuuuucua ucuaaguuaa uuaugaaagu gcauacuaaa augauguaaa 85560
aguuuauauu ucaggauuau ucuuauucau ggaugauuaa cuaaaaugca aaaagaaauu 85620
aagcauacug uuuggcuaaa cuguuaaaaa uuauuuuuau uuuaaaugau aagcaguuaa 85680
acuuauuaag ugaugacuca ucucugcuga uauauuuaug caagguuuuu uauuucagau 85740
aacucuucua uuuauauuaa acagaaacug uauuucuaag caauagcauu ucuuagagaa 85800
aauugccucu auuauguugc aauuaaaauu uaauuacuca ugagcucuuu aaagacacaa 85860
uuucucuugu gugguuuuau uucauauaaa gaaaaacucu gauauacugg agagaacauu 85920
agcuaaauag acuauuuaga cuuaaucauu uugaucagac aucaaggcua gacuauuuaa 85980
gcuguuacuu auuagcugca ugauuuuagg aaugucaaau uuccuaaguc uugguuuucu 86040
uguauuuaaa auggaaauua uaauuccuau cucauagaau uguuuuaagg augaauugaa 86100
uuaauacagu uuugacuuca aauauuagga auuauugagu auaauaagcc uguuguauug 86160
uugguacuuc guauuauacu uacuaaaaua uuugauuaaa gauuuaacau auucuuucgu 86220
agucugguag aaguggaaag acaaucccag aacuggaaaa aaccauuggu uuaaugaaaa 86280
aaguaguuga aaaaguccag agagaaaaug aacaguugaa aaaagcauca ggaauauuga 86340
cuagugaaaa aauggcuaau auugagcagg aaaaugaaaa auugaaggua auuuuuuuua 86400
augugaucau uuuuaggga auauuuuacg uuuuguuacu auuuaggaaa auuucaaaua 86460
ugcucauuac uauauaaaau ggcuuuaaug aauacaauac auauuuuaua aauauagaaa 86520
aaaacuuaug agaggcaagg cuaaggguua uagaguaggu cuaccugauc uuucuuguua 86580
uuucaagacc aauacuuuuc acuuuucucu cugacagcau agauuaauua ccugugucuc 86640
ucuuuuuuuu uucuuuugag auggaguacu gcuuugucac ccaggcugga augcaguggu 86700
gcaaucuuga cucacugcaa gcucugccuc ccggguucau gccauucucc ugccucagcc 86760
ucccccagua gcugggacua caggugccca ccaccacgcc uggcuaacuu uucguauuuu 86820
uaguagagau gggguuucac cauguuaacc aggacugucu cgaucuccug accucgugau 86880
ccgcccacug cggccucugu gucucuuugu gaaaauacag augcccaagc ucccaucccu 86940
gaaauugauu uaauuauuuu agggugggguc cugacacaga uauguauguu guuguuauuu 87000
uaagucauca auuuauucua auauguagcc aacguuggga acuucguucu cacuaauauu 87060
caaaugaaga cuuuaauucu aaucauauca aauaugguuu cuaaaacuac uuugaagauu 87120
uaugaguuua uaagauuauc uuuuauuucc uuguuuugau aauguauacu uuuuauuuug 87180
uuuguuuuuu uacuaggcug aauuagaaaa acuuaaagcu caucuugggc aucaguugag 87240
caugcacuau gaauccaaga ccaaaggcac agaaaaaauu auugcugaaa augaaaggcu 87300
ucguaaagaa cuuaaaaaag uaugacuuuu augacugauu auaacuuuug auuuuuauuu 87360
uacuuaauac cucuuggaaa aacuggaagu agauccuuga ugagagugcuc uguaaaggua 87420
gauauuaaga gauugaggaa uuguguuucu augccugcug ucaucacauu ccaccaugaa 87480
aaacauugau aauaaaaguu aauacauuua ggcugggcac gguggcucac gccuguaauc 87540
ccagcacuuu gggaggccaa ggcgggugga ucacgagguc aggagaucga gaccauccug 87600
gcuaacacgg ugaaaccccg ucucuacuaa aaauacaaaa aauuagccgg gcgugguggc 87660
gggcgccugu agucccagcu acucgggaag cugaggcagg agaaucgcuu gaacccggga 87720
ggcagagguu gcagugagcc gagaucgcac cacuacacuc cagccugggc aacagagcga 87780
gacuccaucu caaacaaaca aaaaaaagaa augaucuacg uugcuuacac auaccuuaug 87840
cuuauagcua ggucucguaa gcauuaggaa gucaaaacaa agaaucuuuu acauguguaa 87900
agguauaaac uaucccauuu uucuaaaaau auagaggaac aaagugucaa auuuaaagua 87960
aucacuagua acuaaauaua uuccucugac cucauuuucg ugaucuguug uucuaauuau 88020
uauuggccau auugcugcuu uaaaggagag auguugaauu uguugaaauu uuaaucagca 88080
uuuagagccc cagguuauuu uuguuuucca auuuguaaug auaauuuuga auacacugaa 88140
ucuaugagaa caguauuaug uuuucucaua aaauacuaau uagcauuuaa ugauaggaaa 88200
cugaugcugc agagaaauua cggauagcaa agaauaauuu agagauauua aaugagaaga 88260
ugacaguuca acuagaagag acugguaaga gauugcaguu ugcagaaagc agagguccac 88320
agcuugaagg ugcugacagu aagagcugga aauccauugu gguuacaagg uaggaacaga 88380
guuuuaaacu uguacaaagu uuaaucauuu caaauuuugg cauuguuuua aaagacaaca 88440
cuauucugga uaaccugguu ucuuccugau gaacaguuug uuugguuguu guuuuaacau 88500
aauacuuuuu uucuguugua guauuguugg agacuuuuuc uuccuugaaa uguuuaacuu 88560
guuuaaccuu guuugggugg cagggcaugg aacaguguag agcuggggcu gggcgaagga 88620
guuggagcug ugugugcguc augaagcugu caucagcuau gagccugggc ugaggcugcu 88680
cagcuucucc ugggugcuau uuuucuccaa cugcagcuuc agcuucuuga uuguauaauu 88740
ugcuuccuca aguaugagcc aggaauaauu gagcugucuu gucacaaugu guggcauacu 88800
ggaucuaggc ugugcugcaa ugcuuuuaga guuauauccu gggcaacuuu cucuucagau 88860
agccccaaga gaugaauuca gcaccagcuu ugauguuuua cuagcuucug cuuucuggua 88920
cuugauuuuc ucccaccccg aacacauggg auuccaaccu gugaaacuaa uuuuuguggc 88980
uaugaaagag guagugguag uuuaugagua aacauucagu cuguugccac uaucaucaug 89040
ugugguucau caugacugug augaguaggu aaaaggcucu uugugucauu cucauuucca 89100
auuuuaagca gcugcuucaa ggagucugga agucauugac cagugggauc cugccugugu 89160
cuuuucccau uaaagccauc cuguaugaag ugguauccuu uaccaucuag cacaucugcc 89220
gcccccauuu caaaaggcau acucaucuuu aucucaacau ucucauacag uuccuuaugu 89280
ccaugcaccu ccaaugucc cuuugauguc uuugagguuu ucaucuucca ugucugcuau 89340
uuggaauggu cuugauggga ggcaagauag ugaucacuac aacuaggaug ggagucuuag 89400
uaccgugagg cuacagcaag ucccacagag ggccugcugc acuguacuug ccucugucaa 89460
ccaagucuaa ggagaaagau uaagcaggca uauuaaagga cagcccagau ggacaugaag 89520
uccuggagga ggccuugguu ccuguccuaa uacuaaaccu agaguaccca gaauccacac 89580
uucuccacuc uagcucucac uuuucccauc uacacacugg gaaaaauuau ucugucagaa 89640
agccaguguc aaggugagaa caaauaacaa augugaugau auggaguggg agaaggguc 89700
ucuucuacug ucuuauugga cccuagcagu ggcucugagc cagcaguccu gucaguugau 89760
uucuuggucg uuccuuuguu uucuucuaua aucacaugug gacucagaau gaauuuugag 89820
uuacucugaa aucuauuuau ucaacagaua uuuacuuagu accuccuauu gccagacucu 89880
gcuuuauguu ggauauuauu uuuuaaaagc ccaccuugcc uagauuuccu caaaggacca 89940
gguggcuucc cugguuuuga aagacccuaa uucuuacuau gaucuuaagu aaauuauauc 90000
cuuucugugg gcucaaguuc uuucuaagag ggcucuuugg ggcuacaaaa gaaauuguua 90060
gugcaaaaag aguuuauaag guuuauaaau gguuaguaga ggugaugaug auauuuaacc 90120
auaauugaag augacuuugc auuuuagauc auauacgugu uuuucgucug agaacgauac 90180
aggucacuga gcauaccaua agccuucagu aaaucauuug cagaagacau ugcagaagac 90240
auaagucuaa guagaaaucu cuugacagag agaaggcucg uuuugauccu ugaccucaaa 90300
uuuagguucc cuaaauccau uaaaaaagag aaagaaaaag aaaaaaaguu acuaaaguuu 90360
aaaucuggga ggauuauaua cccuucucaa uaaagcaguu uagagagauc ucuuuuggga 90420
cccaugacac aggucuugcu caugcugaca ucuuuauagu ugcuuuauua uuuauucaac 90480
aaacuuagua acacguauuc uaugucaggc cuuuuccuga cuacugggac aaaccagggu 90540
gauguggggg cuguuuuaga uagggugauc agaggaggcc ucucuguuug gguggcuuuu 90600
gaauagaaaa uuagaugaag ugaaggagua agcuucugau auuucacugu uuacuugugg 90660
uagaucugug auaaucucug ucagguuaaa aacauucccu ucuaaucuaa guuucuaaga 90720
ucuaucaaaa gcuguuugaa uauauuuaga caaucauaau uuuccuuucu uguauuaucc 90780
uagcagauuu uguugccaaa gcuauacugg ccauuuuaac uuagaaugca gucuuucuau 90840
ucauuucucu ggaaaaguuu ggauauugua agcauuauuu uucuuuaggu augaugaacc 90900
ugcagaacug uuugguucaa uuaugaauuu uuuuuuucug gagucuguau uuuuuugaac 90960
uauuaaucau uucuuuaaug auuauaaauc uauucagauu uuuacaagcu uuaucccucu 91020
cccaucauac acuauuuuuc uuacccaugc uuuugcacaa uuuuuuccuc ucccuuagug 91080
uuuuccuacc uagauaccuc cuaugugugu cuguguaugu gagaaaagcu uuuuauuugc 91140
caucuuuaua uuucuaagaa uaucuaguaa uacagaauuu uauauucuga agaauuuuac 91200
uuugcauuuu cuuauuuugu gauugaaaaa agguauuaau uuuaaaaugg ucaaaucagg 91260
cuccauccuu ggaaaauacc caaauccuuu auuuugauug ggccaucugu uaauuaggga 91320
uaccuuaucu cuugccacca cuuuuuaaug cuaaauaaau auguagcuaa aacuuugacu 91380
agaagaaaca guaaaauaag auauucuugc uuauuuuuag uacaguuauu ugaacugacu 91440
uuuaaaucag ugacauaaau uauuugccau gucuauacuu uuuuuccuua uacuuuuaga 91500
auguaugaaa ccaaguuaaa agaauuggaa acugauauug ccaaaaaaaa ucaaagcauu 91560
acugaccuua aacagcuugu aaaagaagca acagagagag aacaaaaagu uaacaaauac 91620
aaugaagacc uugaacaaca gguaaguaac guaauuuuuc uuuacaugau aaaauaaugc 91680
auaauaucgc aagauguucc uugcauuguc uuauauagau aaaaauggac ucuauuaaga 91740
agacccaucu aacugaaggg caccccauuc acccauuugc uuaagccaga aacuuuggau 91800
caucaacgac uucauucuuu ucauucucca cauuuucuau cauuaaauca ugucagcucu 91860
auuuucaaac uauauccuaa auaugaccac uucuugguau cuugagacau cacuaccagu 91920
cuuguccaag cuauuguuuu auaccugaau aacugcaaua auuuccaagc ugguaucuca 91980
gcuuccacuc uuggauuauu ucacccuauu ucuauuucug ggcugucucc acacaguugc 92040
cagguaaccc uuuuaaaaca uaaagcacau cacaaagcac aaaguccuau ccucagaauc 92100
uuccaguggu ucuccaucac ccuaaaauaa aacuuaaaag uucuuuucau aucccaaaac 92160
aacauaugag gucuggcacc caguuuucuu cccaaucuca ucuucuacua cuuuucccuu 92220
cauuucauuc acaauguuuu aaccacagua accuucuuuc aguacuuuaa acaauccaaa 92280
cucguuuaag cgucaagucc uuauacuugu uuccuuuguu uagaauacug uucacccaaa 92340
uauucucaua gcuugcuccc agacuucaug ucucugcuga aauagaggcu ccuuagagag 92400
accuucccua acccuaaccc uaacccuaua cuacuugcca ucacucuuua ucucuuuacc 92460
cuggauuauu uuuucuugau agcucuuccu accaucuggc acuauauuac aucauaucau 92520
auuaaacaca cauucuuugu gcuuccccac uaaacaagga ccaugcaaga uggaacauug 92580
ccauuuuguu cacugcuguu agccucugug ccuaggacaa ugccaguuau gcaguaguua 92640
cucaauacuu guugaaugaa uggugaauag aacauagaaa uuugccuaug cgugcuuuug 92700
aaaaccauau uuuaauauua cgcuuuguua aaaaugugua ucuuuauaaa uccucauauu 92760
uccauggcaa accuuaucuu cuaacuuuuc auuguccuca aagauuaaga uucuuaaaca 92820
uguuccugaa ggugcugaga cagagcaagg ccuuaaacgg gagcuucaag uucuuaggua 92880
caucauguau ucauaugacu acuuuguuuu uuucuuuaaa aaaaaaauua uuaguuuuua 92940
uauacuccga auugcuacaa cuagagacaa gcauuuuucg acuuuacugc cuaacaggcu 93000
uauuaggucc uuauuucuuc ccucuaaugc uaaucacucu uuuucauaau acacacuaga 93060
aaaaaaggau aaacccaacu cuaaguuucc aguuuguaau uuaguuuaaa cuuuucuaag 93120
agcauagaau gaguuaaacc uuagcuuccc agaggaaaau acuaaugaaa gagaacaagu 93180
aauuuuuuua cuuucagggg ucucuguagc cugcuuucau uaagcuccuc uuauaacgaa 93240
accacacuug caaaugccau caggucagau auuaagaaaa acgugaaggc uuuuguauuc 93300
caggcuuuuu guuugagaau ggugacauug uagcauugag aguaaauguu uacuucgaua 93360
aaggcuagcu uguucugauu acuguacauc acuaguucau aagaaaugcc cauauauuuu 93420
augaagcaau aucugcuuua uuuuuuuaac acauuaucau uguguucuag auuagcuaau 93480
caucagcugg auaaagagaa agcagaauua auccaucaga uagaagcuaa caaggaccaa 93540
aguggagcug aaagcaccau accugguaau guauuuuaaa aaacauguua gcuaccccca 93600
aguuuuugaa uuuggguuug ccuuuuuuuu uuuuuuuugg cucagauuuc ugaucauugu 93660
cucccuguaa aaucgaauuc cugauaagcu uugggucuuu ugucucucug ugcuauuaau 93720
auaaaaauau ucccauuuuu cucuuugugu uguuuauacu auagaguagc aaguacccaa 93780
guguucuucu cuuuguucuc caucugggug uuacagauuu aaucacaaua cagugcuaag 93840
caaugaauac uaaaucuguu gcuuccaguu ucuaaguaua ggcucuuuca aguccucuga 93900
acauuuuuaa aaacugcaaa uaaguaaaua cugccuauau uuuuuuccgu uuacaaagua 93960
aaaagaaaau cuuucugcuc ccuuccauuc ccauucaaaa gugauuacua aucauuccuc 94020
auuccugcau auacauacac acauauuuug uauacauaua uaucacacau augcauacau 94080
guguuuguau guucauaugu acaauguaca uauccucauu auuuguggau ucuguauuuu 94140
cuaaaucacc uccucacuaa agugugua ug uaaucccaaa ucaacacucg cagcacauuu 94200
gcaaacaucc acagagccuu ggaaaguuug aauaauccaa ccuacauguc cccagcagaa 94260
guccaacaag gcagugcuca guauccucau uucaguuuuc auagagaaau gagcagagga 94320
uggagacagu agagggcagc acagcauagu gcaagaagcu guggcucugg ggccuggugg 94380
aagggauuug aaucccaauu cugaggcuug uuacugcucu agccuuagga gagucaugua 94440
acacuucuga aucuuguuuu cuuauguaaa uaaauagaau uuaccaggau gaguuaucuu 94500
uaggauuuaa gauuaucauc ugugugagau auguaggugu auguauauau augcguguau 94560
guauauauau gcguguaugu auauauaugc augucuguac auauuucccg uagcagcagu 94620
gguuugauau ucacuaauug ggcuaacuuu auagaccaaa acuacuaugg auagagaaua 94680
cuuuguuugc auuuacguau auauauuuuc uuggcaagua acauaaaauu gaacuaauac 94740
uauacacauu ucuagcauau uugccuuuaa caguuuauca uggacaucuu uugaggucug 94800
uucauaaauu aucucaucca uuuaauaauu ccauagugua uuauugcaug uauaagcaca 94860
ucgaaccauu uauguuuuga uggauauuua guuugcuucc aaguuucugc uucuauaaaa 94920
uaugauuaau cuauugaccu aauuaugcca uugugauagg augauagaga ugccauucuc 94980
uccaaaggau uauaccaauu uauaucugaa cuaucuuuga cuaucucuug uagcuuuuuc 95040
aguaugcuau guaguccuau uacuaauuug uaauaaaagc caucaugugu gaguuguacu 95100
agacacuaug cuaauugccu uacaagcauu cuauauuuac aaccauauau gauagguauu 95160
acugucucca uuuuauguga uaaacaaauu caaagugguu aaguaaccau ucccuaagcc 95220
agcuaggaaa uagaggcagg auuaaaaucu aaauguauga aacuccacag cuccuuggca 95280
uuccuagucc uuaacccgcu augcuaugcu acgucuuggu aacuaaaagu acauauuaaa 95340
uacucucaaa auaugucuca uagcagccag cuugguaugu acacuagaca caguauuaau 95400
gcuguugaug ugaggaaaau uuuauaauuu uccuuccauc cauauacuaa ccaggcccaa 95460
cagugcuuag cuucugagau cagagaucag gugcaugugc auuaaggguc auauggccau 95520
agauaguucu cuaaucuuuc cauuccucag uuucuuaagg gaauuucuga acccucaaaa 95580
uuccuuauuu ccuaaguaga cagauuaccu gucauuuuuc aaagauuaag gcuuaagauc 95640
aaaccagaac uguuuuggaa auucuaaauc acugucuaua uaaauggcaa gauaacuuuu 95700
aagauauuua uaccaagccc aguacaguag cacaccacac cuguaauccc agcacuuugg 95760
gaggcugaag ugggguggauc acaugagguc aggaguucga gaccacucug gccaacaugg 95820
ugaaacccug ucucuacuaa aaauauaaaa auuagccagg cauggugca cuugccuguu 95880
aucccagcua caagggaggc uaaggcagga gaaucgcuuu aaccugggag gcagugguug 95940
uugcagugag ccaagauugc accacugcac ucuagccugg gcgacagagu gagacugucu 96000
caaaaaaaaa aaaaaaaaaa aagauacuug ucccagccau gaaaauguuu gcugccccuu 96060
acuuucgcaa acuuuuagua uuuuauuauu uuucaauggc uguaaaauau gacuuauuaa 96120
auguaguaua auauaaagaa aagagauauc uagcaaagau agcauuaaag caaaaauccu 96180
auuugccugc ugauaaaguu agaggugua acuuggaggg ugaauccaau aaauuagaac 96240
uuuugugcua uauuuggaga cuuuuguuuu ccuaccaaag uaucagggcu augucuuacu 96300
uaucuuugua uuacacagcc ugcaugacac guuuugcaca uaguaauugc acaguaaaug 96360
uguaauaacc uacauggaau agccaguguu guguuggaua gcgggagcau uuggcuagcu 96420
uaugguuaua gucccuuacc caacagucug cuuuucuucu guuguacuuu uaguaccuaa 96480
caaguuuccc uggcuuuagg auuuuuucca uguaaaauuu cuaucaugug aagaaaaaau 96540
aacuuggccu acacuucuaa uaccuagcac auaccucuuu cugccugcua ugaaauuaua 96600
auacuugaug gagggaggca gcauuaagug uuuacauccu gaaguauuuc agccauaaca 96660
uccaguguuu uccagguucu agguuucaua aaauguaucu cuguucucua gaacaaaucc 96720
auuaccuuga acucauucgu agugggaaaa agcugagucu aauuuguaug acuuuuucaa 96780
cagaugcuga ucaacuaaag gaaaaaauaa aagaucuaga gacacagcuc aaaaugucag 96840
aucuagaaaa gcagcauuug aagguaauau uuaauuauau uuuaguaucg uuuugugaaa 96900
acagcuguug aaaacuauuu ucauuaccau cuuuaacuac guauccuaaa aaauucagua 96960
auaacaucuu auauuugacc uuuauauugc aaaguuaauu auguucaucu gacuauuccu 97020
aacauauuag aguuaacaaa aaauucagac ucaacauagg auuaaguagu aaauuuauuu 97080
uuuaauugua acaaauauau gccauuagua uguucuuaag uuuuggguca cauuggcaac 97140
agugucuuua uuuuuuuuuu gaaauucuuu ucaggaaucc uaagguuaua guucccuuaa 97200
aaaaauauuu gcuguuuuac cucuuuuaag acuguaaaca ggacaaaaag gcauggauau 97260
gagaauuagc uagugaucac uggcuauucu aaauagucac uaaggcuuga auugucucuu 97320
caccagaugc cugucagaag ucccaaaggu uucccugauc auauuaauaa cuuuauaaaa 97380
aauugaucau uauucauuaa auauuagaua uuaguaagga aaauauaaau gaagucuaaa 97440
ccaaaacucu uaaccagacu aacuucaaug uuaugaauca caaaaucuuu uugauugauu 97500
gcucuauuga caagcucuua uaugcuuuua gagaaagauu aagucccauu auaagagaug 97560
auaaauuuua gucaaagacu agaacacaac uuacagaaua cauaacugga cuugacaguu 97620
aacaacuuag uuauuuacac uguacaaugg aacaaagaaa aaucuuaauu cuucugccuu 97680
uauugcugua uuugaccauu caggaauacu uuggcuuuca uauuuacaau uaaaucuccu 97740
uguucaaacg uaaaauaugu auauuuccua uaugcaacuu uuaaagauaa uguuuccauu 97800
aggaggaaau aaagaagcug aaaaaagaac uggaaaauuu ugauccuuca uuuuuugaag 97860
aaauugaaga ucuuaaguau aauuacaagg aagaagugaa gaagaauauu cucuuagaag 97920
agaagguaaa aaaacuuuca gaacaauugg gaguugaauu aacuagcccu guugcugcuu 97980
cugaagaguu ugaagaugaa gaagaaaguc cuguuaauuu ccccauuuac uaaaggucac 98040
cuauaaacuu uguuucauuu aacuauuuau uaacuuuaua aguuaaauau acuuggaaau 98100
aagcaguucu ccgaacugua guauuuccuu cucacuaccu uguaccuuua uacuuagauu 98160
ggaauucuua auaaauaaaa uuauaugaaa uuuucaacuu auuauaaaag uauauacuug 98220
aagacuuguu acagccauca aauaggcagu gagcucuggu gaauuucucu acauucauaa 98280
ugcuuuaagu uuuuuaaaga auaugagggu aaauucagca auuuuaagau uuaaaauugg 98340
aguuuauaua uacuuauuua uacauguguu aagauucuca aauccuauga uauauacaca 98400

-continued

```
gauguagaca uacacacaua uagguuauga gguugagccg uauguuuugu uaaauaucua  98460
gcaaaauuaa auugagcuua aacuauuuaa uuuugaaaau uagugacauu aaauuguugu  98520
cuuuaaauua ccacucaguu auagugaaga gaauccagcc uuuguccaag cuuaggagcu  98580
uacuauuacu uauguuuuua uggcuagaga uuaaaauuaa uuugcugguu uuuaauaaaa  98640
uuuugaauag guacuugaaa cuggaaaauu cauuucuuca caaaugguag aaaacauauu  98700
gauguuucau aaugaacaga aaccuugaga uauuuuuaaa uaugguagaa uauucaagau  98760
uagaauauaa ugauaaacua auuuuauuug cauuuuauac aucaaauauu auaucuuuga  98820
gucuaacaaa uuucugauua ucuauuuuua aaaaaugauu aaacaaacac uuaauaucaa  98880
aggcagaguc acauuuguuc agguucaugu ugauaaauac uggucuugaa uucauguaag  98940
uaucuggaau uggccagcau aagccaagau gauggcgaug gaccuggaaa gagaaaaaag  99000
guauuagcuu uagcauacag auacuaucuu cauucacuua gaaauauuug agugcccacu  99060
gucugccagg uacuggguaa gacuccacuu uaucuuacug uuuuuuuuuu uauagcuggu  99120
cuucuccuga cauauuacau auuuguuuau ugucuaucuu ccccauuaga augugagcuu  99180
caugaaggca gacaccuugu uuuguugacu guguaugucc agcaccugga aacaugccag  99240
gaacauuauc aggggcucca uaaaauguua ugaaucauag agccuguugc ugaguacaga  99300
cuagcuaccu gaaaaaugug ggcaaggagg cauucuaauu gaaaggaaug uuauaugaua  99360
gaauggaguu uuuugcucua auugcaauca uguaaauaug guuacagcaa acacagugug  99420
agugugguuug cgggggcaga gguggagagc aguucuggga aauuaaguag gggccagauc  99480
augaauguuu aauguaacug aacagauuua ugcaggaaag uaauaugcuc auucauuugu  99540
gaagaaugga gaggacaggg cuaaaacuga aagauacuau uuuuggaggg ugauaugaua  99600
guuaaagcau gaaucuuggc uuaaauuaaa auuaacaguu gggaagaagu acauagauua  99660
gaacuguuag gaauugauaa cuggauguau gaaguaauga aaagaggggu uaaaauuaau  99720
auccaaguuu uuacuucagu gaauuaugug gacucagaga guuacaacua ggcccaguuu  99780
ugaauauuau gaauuucagg uaccugugag aaaucaaaca gacaagucca ggagacagaa  99840
agggaacaaa guauaagaua auucauucug uauauaucaa cugcuaccuu ggcacucuuu  99900
uuacucaaca gauucuacac ucaagucugg gagaugcuga guuaaguuag uacaagaugu  99960
cucugagagc acuacugugc aacaugaauu uccacgcagg ggauauauag uuaucacuuu 100020
aauucugaag cacaccuguu augaucgaug ccccacacaa uacacacugg gaagcacugu 100080
uuuaccucuu aaaaaauggu gguacauggg augagaaaau uaaauuucuu uacugcaaau 100140
aagaauugcu gccauuugua gagagaauuu uagugucacu ucuacucuau uguaggaaua 100200
uaag                                                             100204
```

TRANS-SPLICING MOLECULES

CROSS-REFERENCE TO RELATED APPLICATIONS

The instant application claims the benefit of priority to U.S. provisional application Ser. Nos. 62/658,658 and 62/658,667, both of which were filed on Apr. 17, 2018, the contents of both of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Oct. 5, 2020, is named 51502-016002_Sequence_Listing_10.05.20_ST25 and is 608,535 bytes in size.

FIELD OF THE INVENTION

In general, the invention features ABCA4 and CEP290 trans-splicing molecules.

BACKGROUND

Stargardt Disease is a progressive ocular disease characterized by loss of central and color vision, which can occur rapidly or over the course of multiple years. Peripheral vision generally remains intact. Various mutations along the length of the ABCA4 gene can cause Stargardt Disease. Treatments currently in development for Stargardt Disease include lentiviral delivery of ABCA4, chemically modified variants of vitamin A, and retinal pigment epithelial cell therapy.

Leber congenital amourosis 10 (LCA 10) is a condition characterized by severe visual impairment beginning in infancy. The loss of vision is associated with photoreceptor death due to ciliary defects. The most common known mutation associated with LCA 10 is a point mutation in which an adenine is replaced with a guanine at nucleotide 1,655 of intron 26 of the CEP290 gene, which results in a splice defect in which a cryptic stop codon is spliced between exons 26 and 27. This autosomal recessive mutation causes the production of a nonfunctional centrosomal protein, causing the blindness characteristic of LCA 10.

Adeno-associated viral (AAV) vector-mediated gene therapy has a proven safety profile in humans and represents a promising approach for treating a variety of genetic defects. However, AAV vectors can have limitations dictated by viral biology, such as packaging size constraints that can hinder delivery of large nucleic acid molecules, such as those necessary to replace the ABCA4 gene or the CEP290 gene. Thus, there is a need in the field for compositions and methods for correcting mutations in ABCA4 and CEP290.

SUMMARY

The present invention relates to nucleic acid trans-splicing molecules, and methods of use thereof for correcting mutations in the ABCA4 gene or the CEP290 gene. The compositions and methods provided herein can be useful in the treatment or prevention of diseases associated with mutations in ABCA4, such as Stargardt Disease (e.g., Stargardt Disease 1) or mutations in CEP290, such as LCA (e.g., LCA10).

ABCA4

In a first aspect, the invention features ABCA4 trans-splicing molecules. For example, the invention provides a nucleic acid trans-splicing molecule comprising, operatively linked in either a 3'-to-5' direction or a 5'-to-3' direction: (a) a binding domain configured to bind a target ABCA4 intron selected from the group consisting of introns 19, 22, 23, or 24; (b) a splicing domain configured to mediate trans-splicing; and (c) a coding domain comprising a functional ABCA4 exon; wherein the nucleic acid trans-splicing molecule is configured to trans-splice the coding domain to an endogenous ABCA4 exon adjacent to the target ABCA4 intron, thereby replacing the endogenous ABCA4 exon with the functional ABCA4 exon and correcting a mutation in ABCA4.

In some embodiments, the binding domain binds to the target ABCA4 intron 3' to the mutation, and wherein the mutation is in any one of ABCA4 exons 1-24 or introns 1-24. In some embodiments, the target ABCA4 intron is intron 19, the mutation is in any one of ABCA4 exons 1-19 or introns 1-19, and the coding domain comprises ABCA4 exons 1-19. In some embodiments, the binding domain is configured to bind intron 19 at a binding site comprising any one or more of nucleotides 990 to 2,174 of SEQ ID NO: 25 (e.g., any one or more of nucleotides 1,670 to 2,174 of SEQ ID NO: 25, e.g., any one or more of nucleotides 1,810 to 2,000 of SEQ ID NO: 25, e.g., any one or more of nucleotides 1,870 to 2,000 of SEQ ID NO: 25, e.g., any one or more of nucleotides 1,920 to 2,000 of SEQ ID NO: 25.

In some embodiments, the target ABCA4 intron is intron 23, the mutation is in any one of ABCA4 exons 1-23 or introns 1-23, and/or the coding domain comprises ABCA4 exons 1-23. In some embodiments, the binding domain is configured to bind intron 23 at a binding site comprising any one or more of nucleotides 80 to 570 or nucleotides 720 to 1,081 of SEQ ID NO: 29.

In some embodiments, the binding domain is configured to bind ABCA4 intron 23 at a binding site comprising any one or more of nucleotides 261 to 410 of SEQ ID NO: 29 (e.g., from 1 to 200, from 6 to 150, from 12 to 100, or from 20 to 80 nucleotides of a binding site within or encompassing nucleotides 261 to 410 of SEQ ID NO: 29, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 261 to 410 of SEQ ID NO: 29, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 261 to 410 of SEQ ID NO: 29). For example, in particular embodiments, the binding site comprises six or more of nucleotides 261 to 410 of SEQ ID NO: 29. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 261 to 410 of SEQ ID NO: 29, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind ABCA4 intron 23 at a binding site comprising any one or more of nucleotides 801 to 950 of SEQ ID NO: 29 (e.g., from 1 to 200, from 6 to 150, from 12 to 100, or from 20 to 80 nucleotides of a binding site within or encompassing nucleotides 801 to 950 of SEQ ID NO: 29, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 801 to 950 of SEQ ID NO: 29, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 801 to 950 of SEQ ID NO: 29). For example, in particular embodiments, the binding site comprises six or more of nucleotides 801 to 950 of SEQ ID NO: 29. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 801 to 950 of SEQ ID NO: 29, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind ABCA4 intron 23 at a binding site comprising any one or more of nucleotides 841 to 990 of SEQ ID NO: 29 (e.g., from 1 to 200, from 6 to 150, from 12 to 100, or from 20 to 80 nucleotides of a binding site within or encompassing nucleotides 841 to 990 of SEQ ID NO: 29, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 841 to 990 of SEQ ID NO: 29, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 841 to 990 of SEQ ID NO: 29). For example, in particular embodiments, the binding site comprises six or more of nucleotides 841 to 990 of SEQ ID NO: 29. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 841 to 990 of SEQ ID NO: 29, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In other embodiments, the target ABCA4 intron is intron 24, the mutation is in any one of ABCA4 exons 1-24 or introns 1-24, and the coding domain comprises ABCA4 exons 1-24. In some embodiments, the binding domain is configured to bind intron 24 at a binding site comprising any one or more of nucleotides 600 to 1,250 or nucleotides 1,490 to 2,660 of SEQ ID NO: 30. In other embodiments, the binding site comprises any one or more of nucleotides 1,000 to 1,200 of SEQ ID NO: 30.

In some embodiments, the binding domain binds to the target ABCA4 intron 5' to the mutation, and wherein the mutation is in any one of ABCA4 exons 23-50 or introns 22-49. For example, in some embodiments, the target ABCA4 intron is intron 23, the mutation is in any one of ABCA4 exons 24-50 or introns 23-49, and the coding domain comprises ABCA4 exons 24-50. In some embodiments, the binding domain is configured to bind intron 23 at a binding site comprising any one or more of nucleotides 80 to 1,081 of SEQ ID NO: 29. In some embodiments, the binding site comprises any one or more of nucleotides 230 to 1,081 of SEQ ID NO: 29, e.g., any one or more of nucleotides 250 to 400 of SEQ ID NO: 29 or any one or more of nucleotides 690 to 850 of SEQ ID NO: 29.

In some embodiments, the target ABCA4 intron is intron 24, the mutation is in any one of ABCA4 exons 25-50 or introns 24-49, and the coding domain comprises ABCA4 exons 25-50. In some embodiments, the binding domain is configured to bind intron 24 at a binding site comprising any one or more of nucleotides 1 to 250, nucleotides 300 to 2,100, or nucleotides 2,200 to 2,692 of SEQ ID NO: 30. In some embodiments, the binding site comprises any one or more of nucleotides 360 to 610 of SEQ ID NO: 30. In other embodiments, the binding site comprises any one or more of nucleotides 750 to 1,110 of SEQ ID NO: 30.

In another aspect, the invention features a nucleic acid trans-splicing molecule comprising, operatively linked in a 5'-to-3' direction: (a) a binding domain configured to bind ABCA4 intron 22 at a binding site comprising any one or more of nucleotides 60 to 570, 600 to 800, or 900 to 1,350 of SEQ ID NO: 28; (b) a splicing domain configured to mediate trans-splicing; and (c) a coding domain comprising functional ABCA4 exons 23-50; wherein the nucleic acid trans-splicing molecule is configured to trans-splice the coding domain to endogenous ABCA4 exon 22, thereby replacing endogenous ABCA4 exons 23-50 with the functional ABCA4 exons 23-50. In some embodiments, the binding site comprises any one or more of nucleotides 70-250 of SEQ ID NO: 28.

In yet another aspect, the invention features a nucleic acid trans-splicing molecule comprising, operatively linked in a 3'-to-5' direction: (a) a binding domain configured to bind ABCA4 intron 22 at a binding site comprising any one or more of nucleotides 1 to 510 or 880 to 1,350 of SEQ ID NO: 28; (b) a splicing domain configured to mediate trans-splicing; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In some embodiments, the binding domain is configured to bind ABCA4 intron 22 at a binding site comprising any one or more of nucleotides 1041 to 1190 of SEQ ID NO: 28 (e.g., from 1 to 200, from 6 to 150, from 12 to 100, or from 20 to 80 nucleotides of a binding site within or encompassing nucleotides 1041 to 1190 of SEQ ID NO: 28, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 1041 to 1190 of SEQ ID NO: 28, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 1041 to 1190 of SEQ ID NO: 28). In particular embodiments, the binding site comprises six or more of nucleotides 1041 to 1190 of SEQ ID NO: 28. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 1041 to 1190 of SEQ ID NO: 28, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind any one or more of nucleotides 1171 to 1320 of SEQ ID NO: 28 (e.g., from 1 to 200, from 6 to 150, from 12 to 100, or from 20 to 80 nucleotides of a binding site within or encompassing nucleotides 1171 to 1320 of SEQ ID NO: 28, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 1171 to 1320 of SEQ ID NO: 28, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 1171 to 1320 of SEQ ID NO: 28). In particular embodiments, the binding site comprises six or more of nucleotides 1171 to 1320 of SEQ ID NO: 28. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 1171 to 1320 of SEQ ID NO: 28, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind any one or more of nucleotides 1201 to 1350 of SEQ ID NO: 28 (e.g., from 1 to 200, from 6 to 150, from 12 to 100, or from 20 to 80 nucleotides of a binding site within or encompassing nucleotides 1201 to 1350 of SEQ ID NO: 28, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 1201 to 1350 of SEQ ID NO: 28, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 1201 to 1350 of SEQ ID NO: 28). In particular embodiments, the binding site comprises six or more of nucleotides 1201 to 1350 of SEQ ID NO: 28. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 1201 to 1350 of SEQ ID NO: 28, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In any of the preceding embodiments, the binding domain can be 20-1,000 nucleotides in length (e.g., 25-900 nucleotides in length, 30-800 nucleotides in length, 40-700 nucleotides in length, 50-600 nucleotides in length, 75-500 nucleotides in length, 100-400 nucleotides in length, 125-200 nucleotides in length, or about 150 nucleotides in length, e.g., 20-30 nucleotides in length, 30-40 nucleotides in length, 40-50 nucleotides in length, 50-75 nucleotides in length, 75-100 nucleotides in length, 125-150 nucleotides in length, 150-175 nucleotides in length, 175-200 nucleotides in length, 200-250 nucleotides in length, 250-500 nucleotides in length, 500-750 nucleotides in length, or 750-1,000 nucleotides in length).

In some embodiments, the coding domain is a cDNA sequence. In some embodiments, the coding domain comprises a naturally-occurring sequence. In other embodiments, the coding domain includes a codon-optimized sequence. In some embodiments, the trans-splicing molecule includes an artificial intron that comprises a spacer sequence.

In some embodiments of any of the preceding methods, the nucleic acid trans-splicing molecule is from 3,000 to 4,000 nucleotides in length (e.g., 3,100-3,900 nucleotides in length, 3,200-3,800 nucleotides in length, 3,300-3,700 nucleotides in length, 3,400-3,600 nucleotides in length, or about 3,500 nucleotides in length, e.g., 3,000-3,100 nucleotides in length, 3,100-3,200 nucleotides in length, 3,200-3,300 nucleotides in length, 3,300-3,400 nucleotides in length, 3,400-3,500 nucleotides in length, 3,500-3,600 nucleotides in length, 3,600-3,700 nucleotides in length, 3,800-3,900 nucleotides in length, or 3,900-4,000 nucleotides in length).

In some embodiments, the mutation in the ABCA4 gene is associated with Stargardt Disease. In some embodiments, the mutation in the ABCA4 gene associated with Stargardt Disease is expressed in a photoreceptor cell.

In another aspect, provided herein is a nucleic acid trans-splicing molecule comprising, operatively linked in a 3'-to-5' direction: (a) a binding domain configured to bind ABCA4 intron 23 at a binding site comprising six or more of nucleotides 261 to 410 of SEQ ID NO: 29, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-23; wherein the nucleic acid trans-splicing molecule is configured to trans-splice the coding domain to endogenous ABCA4 exon 24, thereby replacing endogenous ABCA4 exons 1-23 with the functional ABCA4 exons 1-23.

In another aspect, the invention provides a nucleic acid trans-splicing molecule comprising, operatively linked in a 3'-to-5' direction: (a) a binding domain configured to bind ABCA4 intron 23 at a binding site comprising six or more of nucleotides 801 to 950 of SEQ ID NO: 29, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-23; wherein the nucleic acid trans-splicing molecule is configured to trans-splice the coding domain to endogenous ABCA4 exon 24, thereby replacing endogenous ABCA4 exons 1-23 with the functional ABCA4 exons 1-23.

In another aspect, provided herein is a nucleic acid trans-splicing molecule comprising, operatively linked in a 3'-to-5' direction: (a) a binding domain configured to bind ABCA4 intron 23 at a binding site comprising six or more of nucleotides 841 to 990 of SEQ ID NO: 29, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-23; wherein the nucleic acid trans-splicing molecule is configured to trans-splice the coding domain to endogenous ABCA4 exon 24, thereby replacing endogenous ABCA4 exons 1-23 with the functional ABCA4 exons 1-23.

In another aspect, the invention provides a nucleic acid trans-splicing molecule comprising, operatively linked in a 3'-to-5' direction: (a) a binding domain configured to bind ABCA4 intron 22 at a binding site comprising six or more of nucleotides 1041 to 1190 of SEQ ID NO: 28, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In another aspect, the invention features a nucleic acid trans-splicing molecule comprising, operatively linked in a 3'-to-5' direction: (a) a binding domain configured to bind ABCA4 intron 22 at a binding site comprising six or more of nucleotides 1171 to 1320 of SEQ ID NO: 28, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In yet another aspect, provided herein is a nucleic acid trans-splicing molecule comprising, operatively linked in a 3'-to-5' direction: (a) a binding domain configured to bind ABCA4 intron 22 at a binding site comprising six or more of nucleotides 1201 to 1350 of SEQ ID NO: 28, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In another aspect, the invention features a proviral plasmid including the nucleic acid trans-splicing molecule of any of the preceding embodiments.

In yet another aspect, the invention features an adeno-associated virus (AAV) comprising the nucleic acid molecule of any of the preceding embodiments. In some embodiments, the AAV preferentially targets a photoreceptor cell. In some embodiments, the AAV comprises an AAV5 capsid protein, an AAV8 capsid protein, an AAV8(b) capsid protein, or an AAV9 capsid protein.

In another aspect, the invention features a pharmaceutical composition comprising the nucleic acid trans-splicing molecule, the proviral plasmid, or the AAV of any of the preceding aspects.

In another aspect, provided herein is a pharmaceutical composition having any of the 5' nucleic acid trans-splicing molecules of any the preceding embodiments and a 3' nucleic acid trans-splicing molecule of any of the preceding embodiments.

In yet another aspect, the invention features a method of correcting a mutation in an ABCA4 gene in a target cell of a subject by administering to the subject the pharmaceutical composition of any of the preceding aspects.

In another aspect, provided herein is a method of correcting a mutation in any one or more of ABCA4 exons 1-24 in a subject in need thereof by administering to the subject a pharmaceutical composition having the nucleic acid trans-splicing molecule of any of the preceding embodiments. In particular embodiments, the mutated ABCA4 exon to be corrected by an ABCA4 trans-splicing molecule of the invention is exon 2. Additionally or alternatively, the mutated ABCA4 exon to be corrected by an ABCA4 trans-splicing molecule of the invention is exon 3. Additionally or alternatively, the mutated ABCA4 exon to be corrected by an ABCA4 trans-splicing molecule of the invention is exon 4.

In another aspect, the invention includes a method of correcting a mutation in any one or more of ABCA4 exons 23-50 in a subject in need thereof by administering to the subject a pharmaceutical composition comprising the nucleic acid trans-splicing molecule of any of the preceding embodiments.

In another aspect, the invention features a method of correcting a mutation in any one of ABCA4 exons 1-24 and a second mutation in any one of exons 23-50 in a subject in need thereof, the method comprising administering to the subject the pharmaceutical composition having a 5' nucleic acid trans-splicing molecules of any the preceding embodiments and a 3' nucleic acid trans-splicing molecule of any of the preceding embodiments.

In yet another embodiment, the invention features a method of treating a subject having a disorder associated with a mutation in ABCA4, the method comprising administering to the subject the any of the preceding pharmaceutical compositions. In some embodiments, a subject having a disorder associated with a mutation in any one or more of ABCA4 exons 1-24 or introns 1-24 is treated by administering a pharmaceutical composition comprising the nucleic acid trans-splicing molecule of any of the preceding embodiments. In some embodiments, a subject having a disorder associated with a mutation in any one or more of ABCA4 exons 23-50 or introns 22-49 is treated by administering a pharmaceutical composition comprising the nucleic acid trans-splicing molecule of any of the preceding embodiments.

In another aspect, the invention features a method of treating a subject having a disorder associated with a first mutation in any one of ABCA4 exons 1-24 and a second mutation in any one of exons 23-50 by administering to the subject the pharmaceutical composition having a 5' nucleic acid trans-splicing molecules of any the preceding embodiments and a 3' nucleic acid trans-splicing molecule of any of the preceding embodiments.

In any of the preceding methods, the subject may have Stargardt Disease. In some embodiments, the composition is administered by subretinal injection, intravitreal injection, or intravenous injection.

In some embodiments of any of the preceding methods, the subject exhibits at least 1% increase in ABCA4 protein expression after administration (e.g., a 1-5% increase, a 5-10%, a 10-15% increase, a 15-20% increase, a 20-25% increase, a 25-50% increase, or a 50-100% increase in ABCA4 protein expression after administration, e.g., relative to an ABCA4 protein expression in the same subject prior to administration, or relative to a reference sample, reference subject, or a reference group of subjects).

CEP290

In another aspect, the invention features CEP290 trans-splicing molecules. For example, the invention provides a nucleic acid trans-splicing molecule comprising, operatively linked in a 3'-to-5' direction: (a) a binding domain configured to bind CEP290 intron 26 at a binding site comprising any one or more of nucleotides 4,800 to 5,838 of SEQ ID NO: 85; (b) a splicing domain configured to mediate trans-splicing; and (c) a coding domain comprising functional CEP290 exons 2-26; wherein the nucleic acid trans-splicing molecule is configured to trans-splice the coding domain to endogenous CEP290 exon 27, thereby replacing endogenous CEP290 exons 2-26 with the functional CEP290 exons 2-26 and correcting the pathogenic point mutation. In some embodiments, the pathogenic point mutation is an A-to-G mutation at nucleotide 1,655 of SEQ ID NO: 85.

In some embodiments, the binding site comprises any one or more of nucleotides 4,980 to 5,838 of SEQ ID NO: 85. In some embodiments, the binding site comprises any one or more of nucleotides 5,348 to 5,838 of SEQ ID NO: 85. In some embodiments, the binding site comprises any one or more of nucleotides 5,348 to 5,700 of SEQ ID NO: 85. In some embodiments, the binding site comprises any one or more of nucleotides 5,400 to 5,600 of SEQ ID NO: 85. In some embodiments, the binding site comprises any one or more of nucleotides 5,460 to 5,560 of SEQ ID NO: 85. In some embodiments, the binding site comprises nucleotide 5,500 of SEQ ID NO: 85.

In another aspect, the invention features a nucleic acid trans-splicing molecule comprising, operatively linked in a 3'-to-5' direction: (a) a binding domain configured to bind CEP290 at any one of target introns 27, 28, 29, or 30; (b) a splicing domain configured to mediate trans-splicing; and (c) a coding domain comprising functional CEP290 exons 5' to the target intron; wherein the nucleic acid trans-splicing molecule is configured to trans-splice the coding domain to endogenous CEP290, thereby replacing endogenous CEP290 exons 5' to the target intron with the functional CEP290 exons and correcting the pathogenic point mutation. In some embodiments, the pathogenic point mutation is an A-to-G mutation at nucleotide 1,655 of SEQ ID NO: 85.

In some embodiments, the target intron is intron 27, the coding domain comprising functional CEP290 exons 2-27, and the nucleic acid trans-splicing molecule is configured to replace endogenous CEP290 exons 2-27 with the functional CEP290 exons 2-27. In some embodiments, the binding domain is configured to bind intron 27 at a binding site comprising any one or more of nucleotides 120 to 680, nucleotides 710 to 2,200, or nucleotides 2,670 to 2,910 of SEQ ID NO: 86. In some embodiments, the binding site comprises any one or more of nucleotides 790 to 2,100 of SEQ ID NO: 86, e.g., any one or more of nucleotides 1,020 to 1,630 of SEQ ID NO: 86. In other embodiments, the binding site comprises any one or more of nucleotides 1,670 to 2,000 of SEQ ID NO: 86.

In some embodiments, the target intron is intron 28, the coding domain comprising functional CEP290 exons 2-28, and the nucleic acid trans-splicing molecule is configured to replace endogenous CEP290 exons 2-28 with the functional CEP290 exons 2-28. In some embodiments, the binding domain is configured to bind intron 28 at a binding site comprising any one or more of nucleotides 1 to 390, nucleotides 410 to 560, or nucleotides 730 to 937 of SEQ ID NO: 87. In some embodiments, the binding site comprises any one or more of nucleotides 1 to 200 of SEQ ID NO: 87. In other embodiments, the binding site comprises any one or more of nucleotides 720 to 900 of SEQ ID NO: 87.

In some embodiments, the target intron is intron 29, the coding domain comprising functional CEP290 exons 2-29, and the nucleic acid trans-splicing molecule is configured to replace endogenous CEP290 exons 2-29 with the functional CEP290 exons 2-29. In some embodiments, the binding domain is configured to bind intron 29 at a binding site comprising any one or more of nucleotides 1 to 600, nucleotides 720 to 940, or nucleotides 1,370 to 1,790 of SEQ ID NO: 88.

In some embodiments, the target intron is intron 30, the coding domain comprising functional CEP290 exons 2-30, and the nucleic acid trans-splicing molecule is configured to replace endogenous CEP290 exons 2-30 with the functional CEP290 exons 2-30. In some embodiments, the binding domain is configured to bind intron 29 at a binding site comprising any one or more of nucleotides 880 to 1,240 of SEQ ID NO: 89, e.g., any one or more of nucleotides 950 to 1,240 of SEQ ID NO: 89, e.g., any one or more of nucleotides 1,060 to 1,240 of SEQ ID NO: 89.

In any of the preceding embodiments, the binding domain is 20-1,000 nucleotides in length (e.g., 25-900 nucleotides in length, 30-800 nucleotides in length, 40-700 nucleotides in length, 50-600 nucleotides in length, 75-500 nucleotides in length, 100-400 nucleotides in length, 125-200 nucleotides in length, or about 150 nucleotides in length, e.g., 20-30 nucleotides in length, 30-40 nucleotides in length, 40-50 nucleotides in length, 50-75 nucleotides in length, 75-100 nucleotides in length, 125-150 nucleotides in length, 150-175 nucleotides in length, 175-200 nucleotides in length, 200-250 nucleotides in length, 250-500 nucleotides in length, 500-750 nucleotides in length, or 750-1,000 nucleotides in length).

In some embodiments, the coding domain is a cDNA sequence. In some embodiments, the coding domain is a naturally-occurring sequence. In other embodiments, the coding domain is a codon-optimized sequence.

In some embodiments, an artificial intron comprises an artificial intron and a spacer sequence.

In any of the preceding embodiments, the nucleic acid trans-splicing molecule may be 3,000 to 4,000 nucleotides in length.

In any of the preceding embodiments, the mutated CEP290 exon may be associated with LCA 10. In some embodiments, the mutated CEP290 exon associated with LCA 10 is expressed in a photoreceptor cell.

In another aspect of the invention, provided herein is a proviral plasmid comprising the nucleic acid trans-splicing molecule of any of the preceding aspects.

In yet another aspect, the invention provides an adeno-associated virus (AAV) comprising the nucleic acid molecule of any of the preceding aspects. In some embodiments, the AAV preferentially targets a photoreceptor cell. In some embodiments, the AAV comprises an AAV5 capsid protein, an AAV8 capsid protein, an AAV8(b) capsid protein, or an AAV9 capsid protein.

In another aspect, the invention features a pharmaceutical composition comprising the nucleic acid trans-splicing molecule, the proviral plasmid, or the AAV of any of the preceding aspects.

In another aspect, featured herein are methods of correcting a pathogenic point mutation in CEP290 intron 26 in a target cell of a subject, the methods comprising administering to the subject the nucleic acid trans-splicing molecule, the proviral plasmid, the AAV, or the pharmaceutical composition of any of the preceding aspects. In some embodiments, the subject has LCA 10.

In yet another aspect, the invention provides a method of treating a subject having LCA 10 caused by a pathogenic point mutation in CEP290 intron 26, the method comprising administering to the subject the nucleic acid trans-splicing molecule, the proviral plasmid, the AAV, or the pharmaceutical composition of any of the preceding aspects.

In any of the preceding methods, the pathogenic point mutation may be an A-to-G mutation at nucleotide 1,655 of CEP290 intron 26 (SEQ ID NO: 85). In some embodiments, the nucleic acid trans-splicing molecule, the proviral plasmid, the AAV, or the pharmaceutical composition is administered by subretinal injection, intravitreal injection, or intravenous injection.

In another aspect, the invention provides a kit comprising any one or more of the aforementioned nucleic acid trans-splicing molecules, proviral plasmids, AAVs, or pharmaceutical compositions, wherein the kit further includes instructions for using the one or more nucleic acid trans-splicing molecules, proviral plasmids, AAVs, or pharmaceutical compositions for correcting a mutation in a CEP290 gene of a subject (e.g., a mutation associated with a disorder, such as LCA 10).

BRIEF DESCRIPTION OF THE DRAWINGS

FIGS. 12A and 12B show site-specific guides (FIG. 12A) that were designed to insert the CAG promoter and a puromycin selectable marker using homology arms (FIG. 12B).

FIG. 14A shows RNA expression and FIG. 14B shows protein expression of the cell lines. Membrane preparations of the indicated cells lines were probed for ABCA4 protein using a rabbit polyclonal antibody to ABCA4 (Abcam, ab72955). Exposure time is 23 seconds. 293 cells are the parental cell that does not express ABCA4. The top band is non-specific background present in all cells.

FIG. 18 is a set of tables showing that the mutation analyses from FIGS. 17A and 17B confirmed that exons 3 and 4 were targeted and interrupted in alleles in the 17+06 and 17+21 cell lines.

FIG. 19A shows a generic trans-splicing molecule including a codon optimized exon (or set of exons), a binding domain that hybridizes to a target RNA, and an artificial intron linker. FIG. 19B shows various trans-splicing molecules that target particular regions within introns 22 and 23 of ABCA4.

FIGS. 20A and 20B show protein and RNA levels, respectively, of intron 22 trans-splicing reactions, and FIGS. 20C and 20D show protein and RNA levels, respectively, of intron 23 trans-splicing reactions.

DETAILED DESCRIPTION

Figure 1:
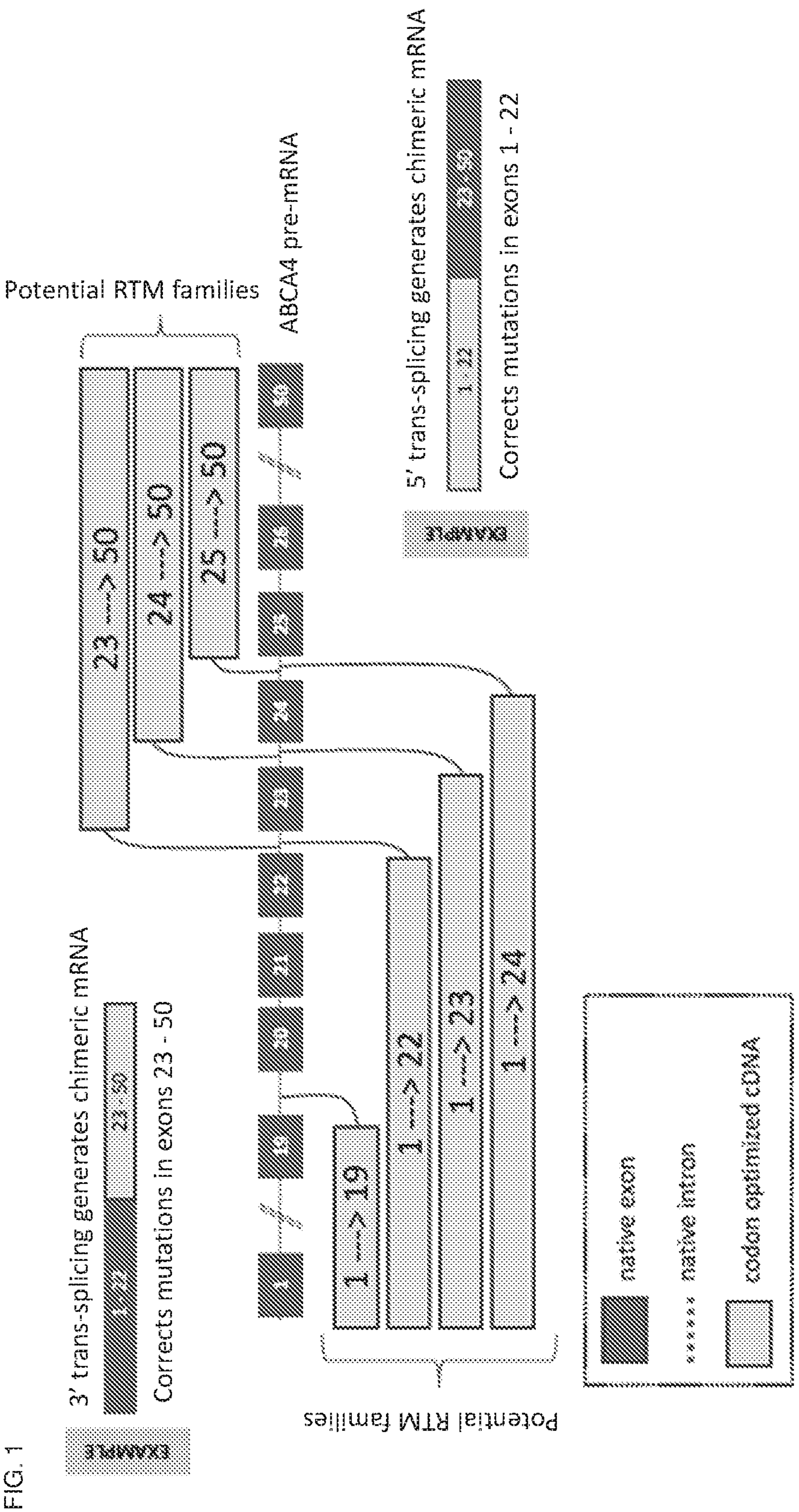
FIG. 1 is a schematic drawing of several exemplary nucleic acid trans-splicing molecules for correcting a mutated ABCA4 exon with a functional ABCA4 exon. Dark shaded boxes represent native ABCA4 exons. Dashed lines joining the dark shaded boxes represent native introns. Light shaded boxes with dark borders represent functional ABCA4 exons within a nucleic acid trans-splicing molecule. A splicing domain, represented by a curved line, is attached to one end of each of the functional ABCA4 exons and leads to an intron of the ABCA4 pre-mRNA.

The compositions and methods described herein involve trans-splicing molecules (e.g., pre-mRNA trans-splicing molecules delivered by adeno-associated virus (AAV)) for treating diseases or disorders caused by a mutation in the ABCA4 gene. The methods and compositions described herein employ pre-mRNA trans-splicing as a gene therapy (e.g., ex vivo and in vivo gene therapy) for the treatment of diseases caused by an ABCA4 mutation, such as Stargardt Disease (e.g., Stargardt Disease 1).

Alternatively, compositions and methods described herein involve trans-splicing molecules (e.g., pre-mRNA trans-splicing molecules delivered by adeno-associated virus (AAV)) for treating diseases or disorders caused by a mutation in the CEP290 gene, such as LCA 10. These methods employ pre-mRNA trans-splicing as a gene therapy (e.g., ex vivo and in vivo gene therapy) for the treatment of diseases caused by a CEP290 mutation, such as LCA 10.

The trans-splicing molecules and methods of use thereof exemplified herein provide several advantages over conventional therapies. First, the use of the trans-splicing molecule delivery by AAV provides efficient and specific delivery of a gene therapy to photoreceptors, while overcoming difficulties associated with the packaging limit of AAV. Second, these compositions and methods permit correction of the genetic defect at the source. Additionally, the compositions and methods provided herein are useful to treat any type of mutation in ABCA4 (or other large cDNAs/transgene cassettes). Correction of the defect in photoreceptors provides secondary rescue to retinal pigment epithelium cells. Further, the present methods and compositions are generally immunologically benign. The use of subretinal delivery and other features renders the effect specific to target cells, such as photoreceptors, so that toxicity due to off-target splicing is reduced. Further, unlike nucleases, trans-splicing does not require genomic alterations. Finally, RNA repair does not require cell division, whereas DNA repair methodologies (such as CRISPR-Cas9 or zinc fingers) have a requirement for the cell to go through mitosis for homology directed repair to occur, which is a disadvantage in post-mitotic tissues like the retina.

I. Definitions

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. In the event of any conflicting definitions between those set forth herein and those of a referenced publication, the definition provided herein shall control.

A "nucleic acid trans-splicing molecule" or "trans-splicing molecule" has three main elements: (a) a binding domain that confers specificity by tethering the trans-splicing molecule to its target gene (e.g., pre-mRNA); (b) a splicing domain (e.g., a splicing domain having a 3' or 5' splice site); and (c) a coding sequence configured to be trans-spliced onto the target gene, which can replace one or more exons in the target gene (e.g., one or more mutated exons). A "pre-mRNA trans-splicing molecule" or "RTM" refers to a nucleic acid trans-splicing molecule that targets pre-mRNA. In some embodiments, a trans-splicing molecule, such as an RTM, can include cDNA, e.g., as part of a functional exon (e.g., a functional ABCA4 or CEP290 exon, e.g., a codon-optimized exon) for replacement or correction of a mutated ABCA4 exon or CEP290).

By "trans-splicing" is meant joining of a nucleic acid molecule containing one or more exons (e.g., exogenous exons, e.g., exons that are part of a coding domain of a trans-splicing molecule) to a first portion of a separate RNA molecule (e.g., a pre-mRNA molecule, e.g., an endogenous pre-mRNA molecule) by replacing a second portion of the RNA molecule through a spliceosome-mediated mechanism.

"Binding" between a binding domain and a target intron, as used herein, refers to hydrogen bonding between the binding domain and the target intron in a degree sufficient to mediate trans-splicing by bringing the trans-splicing molecule into association with the target gene (e.g., pre-mRNA). In some embodiments, the hydrogen bonds between the binding domain and the target intron are between nucleotide bases that are complementary to and in antisense orientation from one another (e.g., hybridized to one another).

As used herein, an "artificial intron" refers to a nucleic acid sequence that links (directly or indirectly) a binding domain to a coding domain. An artificial intron includes a splicing domain and may further include one or more spacer sequences and/or other regulatory elements.

A "splicing domain," as used herein, refers to a nucleic acid sequence having motifs that are recognized by the spliceosome and mediate trans-splicing. A splicing domain includes a splice site (e.g., a single splice site, i.e., one and only one splice site), which can be a 3' splice site or a 5' splice site. A splicing domain may include other regulatory elements. For example, in some embodiments, a splicing domain includes splicing enhancers (e.g., exonic splicing enhancers (ESE) or intronic splicing enhancers (ISE)). In some embodiments, a splicing domain includes a branch point (e.g., a strong conserved branch point) or branch site sequence and/or a polypyrimidine tract (PPT). In some embodiments, a splicing domain of a 5' trans-splicing molecule does not contain the branch point or PPT, but comprises a 5' splice acceptor or a 3' splice donor.

As used herein, a "mutation" refers to any aberrant nucleic acid sequence that causes a defective protein product (e.g., a non-functional protein product, a protein product having reduced function, a protein product having aberrant function, and/or a protein product that is produced in less than normal or greater than normal quantities). Mutations include base pair mutations (e.g., single nucleotide polymorphisms), missense mutations, frameshift mutations, deletions, insertions, and splice mutations. In some embodiments, a mutation refers to a nucleic acid sequence that is different in one or more portions of its sequence than a corresponding wildtype nucleic acid sequence or functional variant thereof. In some embodiments, a mutation refers to a nucleic acid sequence that encodes a protein having an amino acid sequence that is different than a corresponding wildtype protein or functional variant thereof. A "mutated exon" (e.g., a mutated ABCA4 exon) refers to an exon containing a mutation or an exon sequence that reflects a mutation in a different region, such as a cryptic exon resulting from a mutation in an intron.

As used herein, the term "ABCA4" refers to a polynucleotide (e.g., RNA (e.g., pre-mRNA or mRNA) or DNA) that encodes retinal-specific ATP-binding cassette transporter. An exemplary pre-mRNA sequence of a functional human ABCA4 gene is given by SEQ ID NO: 6. An exemplary genomic DNA sequence of a functional (wildtype) human ABCA4 gene is given by NCBI Reference Sequence: NG_009073. The amino acid sequence of an exemplary ABCA4 protein is given by Protein Accession No. P78363.

Exons and introns of ABCA4 are identified herein as set forth in Table 1, below, which can be mapped onto the ABCA4 pre-mRNA molecule of SEQ ID NO: 6. Each exon and intron of ABCA4 are identified herein according to the reference number in the first (left-hand) column. The size of each exon and intron (base pairs; bp) are indicated in the second and third columns. The fourth column indicates the length of a cDNA molecule corresponding to exons 5' to the corresponding intron number. The fifth column indicates the length of a cDNA molecule corresponding to mRNA 3' to the corresponding intron number.

TABLE 1

ABCA4 exon and intron summary

| Exon/Intron Number | Exon Size | Intron Size | 5' cDNA | 3' cDNA |
|---|---|---|---|---|
| 1 | 153 | 7,913 | 66 | 6,822 |
| 2 | 94 | 1,393 | 160 | 6,756 |
| 3 | 142 | 2,721 | 302 | 6,662 |
| 4 | 140 | 5,434 | 442 | 6,520 |
| 5 | 128 | 4,023 | 570 | 6,380 |
| 6 | 198 | 15,352 | 768 | 6,252 |
| 7 | 90 | 2,633 | 858 | 6,054 |
| 8 | 241 | 1,016 | 1,099 | 5,964 |
| 9 | 140 | 615 | 1,239 | 5,723 |

TABLE 1-continued

ABCA4 exon and intron summary

| Exon/Intron Number | Exon Size | Intron Size | 5' cDNA | 3' cDNA |
|---|---|---|---|---|
| 10 | 117 | 702 | 1,356 | 5,583 |
| 11 | 198 | 14,372 | 1,554 | 5,466 |
| 12 | 206 | 358 | 1,760 | 5,268 |
| 13 | 177 | 1,817 | 1,937 | 5,062 |
| 14 | 223 | 3,714 | 2,160 | 4,885 |
| 15 | 222 | 1,285 | 2,382 | 4,662 |
| 16 | 205 | 3,412 | 2,587 | 4,440 |
| 17 | 66 | 2,675 | 2,653 | 4,235 |
| 18 | 90 | 1,774 | 2,743 | 4,169 |
| 19 | 175 | 2,174 | 2,918 | 4,079 |
| 20 | 132 | 1,137 | 3,050 | 3,904 |
| 21 | 140 | 437 | 3,190 | 3,772 |
| 22 | 138 | 1,358 | 3,328 | 3,632 |
| 23 | 194 | 1,081 | 3,522 | 3,494 |
| 24 | 85 | 2,692 | 3,607 | 3,300 |
| 25 | 206 | 356 | 3,813 | 3,215 |
| 26 | 49 | 4,696 | 3,862 | 3,009 |
| 27 | 266 | 657 | 4,128 | 2,960 |
| 28 | 125 | 469 | 4,253 | 2,694 |
| 29 | 99 | 796 | 4,352 | 2,569 |
| 30 | 187 | 4,396 | 4,539 | 2,470 |
| 31 | 95 | 1,535 | 4,634 | 2,283 |
| 32 | 33 | 1,434 | 4,667 | 2,188 |
| 33 | 106 | 131 | 4,773 | 2,155 |
| 34 | 75 | 230 | 4,848 | 2,049 |
| 35 | 170 | 1,480 | 5,018 | 1,974 |
| 36 | 178 | 3,727 | 5,196 | 1,804 |
| 37 | 116 | 1,048 | 5,312 | 1,626 |
| 38 | 148 | 3,157 | 5,460 | 1,510 |
| 39 | 124 | 332 | 5,584 | 1,362 |
| 40 | 130 | 1,928 | 5,714 | 1,238 |
| 41 | 121 | 453 | 5,835 | 1,108 |
| 42 | 63 | 494 | 5,898 | 987 |
| 43 | 107 | 2,051 | 6,005 | 924 |
| 44 | 142 | 3,448 | 6,147 | 817 |
| 45 | 135 | 752 | 6,282 | 675 |
| 46 | 104 | 73 | 6,386 | 540 |
| 47 | 93 | 2,725 | 6,479 | 436 |
| 48 | 250 | 1,665 | 6,729 | 343 |
| 49 | 87 | 2,866 | 6,816 | 93 |
| 50 | 406 | | 6,822 | 6 |

As used herein, a "target ABCA4 intron" refers to one of the 49 ABCA4 introns identified in Table 1, above. Nucleic acid sequence identifiers for each ABCA4 intron sequence are provided in Table 2, below. It will be understood that the scope of the term "target ABCA4 intron" encompasses variants of ABCA4 introns provided herein, such as intron sequences having 90-100% homology with the sequences provided herein (e.g., 90%, 91%, 92%, 93%, 94%, 95%, 96%, 97%, 98%, 99%, or 100% homology with the sequences provided herein), where the location of the variant intron on the ABCA4 gene corresponds with that provided herein (e.g., in relation to its adjacent exons as set forth in Table 1).

TABLE 2

ABCA4 intron sequences

| Intron Number | Sequence |
|---|---|
| 1 | SEQ ID NO: 7 |
| 2 | SEQ ID NO: 8 |
| 3 | SEQ ID NO: 9 |
| 4 | SEQ ID NO: 10 |
| 5 | SEQ ID NO: 11 |
| 6 | SEQ ID NO: 12 |
| 7 | SEQ ID NO: 13 |
| 8 | SEQ ID NO: 14 |

TABLE 2-continued

| ABCA4 intron sequences | |
|---|---|
| Intron Number | Sequence |
| 9 | SEQ ID NO: 15 |
| 10 | SEQ ID NO: 16 |
| 11 | SEQ ID NO: 17 |
| 12 | SEQ ID NO: 18 |
| 13 | SEQ ID NO: 19 |
| 14 | SEQ ID NO: 20 |
| 15 | SEQ ID NO: 21 |
| 16 | SEQ ID NO: 22 |
| 17 | SEQ ID NO: 23 |
| 18 | SEQ ID NO: 24 |
| 19 | SEQ ID NO: 25 |
| 20 | SEQ ID NO: 26 |
| 21 | SEQ ID NO: 27 |
| 22 | SEQ ID NO: 28 |
| 23 | SEQ ID NO: 29 |
| 24 | SEQ ID NO: 30 |
| 25 | SEQ ID NO: 31 |
| 26 | SEQ ID NO: 32 |
| 27 | SEQ ID NO: 33 |
| 28 | SEQ ID NO: 34 |
| 29 | SEQ ID NO: 35 |
| 30 | SEQ ID NO: 36 |
| 31 | SEQ ID NO: 37 |
| 32 | SEQ ID NO: 38 |
| 33 | SEQ ID NO: 39 |
| 34 | SEQ ID NO: 40 |
| 35 | SEQ ID NO: 41 |
| 36 | SEQ ID NO: 42 |
| 37 | SEQ ID NO: 43 |
| 38 | SEQ ID NO: 44 |
| 39 | SEQ ID NO: 45 |
| 40 | SEQ ID NO: 46 |
| 41 | SEQ ID NO: 47 |
| 42 | SEQ ID NO: 48 |
| 43 | SEQ ID NO: 49 |
| 44 | SEQ ID NO: 50 |
| 45 | SEQ ID NO: 51 |
| 46 | SEQ ID NO: 52 |
| 47 | SEQ ID NO: 53 |
| 48 | SEQ ID NO: 54 |
| 49 | SEQ ID NO: 55 |

As used herein, the term "CEP290" refers to a polynucleotide (e.g., RNA (e.g., pre-mRNA or mRNA) or DNA) that encodes the centrosomal protein 290. An exemplary pre-mRNA sequence of a functional human CEP290 gene is given by SEQ ID NO: 113. An exemplary genomic DNA sequence of a functional (wildtype) human CEP290 gene is given by NCBI Reference Sequence: NG 008417. The amino acid sequence of an exemplary human centrosomal protein 290 protein is given by Protein Accession No. 015078.

Exons and introns of CEP290 are identified herein as set forth in Table 3, below, which can be mapped onto the CEP290 pre-mRNA molecule of SEQ ID NO: 112. Each exon and intron of CEP290 are identified herein according to the reference number in the first (left-hand) column. The size of each exon and intron (base pairs; bp) are indicated in the second and third columns. The fourth column indicates the length of a cDNA molecule corresponding to exons 5' to the corresponding intron number. The fifth column indicates the length of a cDNA molecule corresponding to mRNA 3' to the corresponding intron number.

TABLE 3

| CEP290 exon and intron summary | | | | |
|---|---|---|---|---|
| Exon/Intron Number | Exon size | Intron size | 5' cDNA | 3' cDNA |
| 1 | 317 | 565 | N/A | 7440 |
| 2 | 129 | 172 | 102 | 7338 |
| 3 | 78 | 1391 | 180 | 7260 |
| 4 | 70 | 303 | 250 | 7190 |
| 5 | 47 | 2358 | 297 | 7143 |
| 6 | 144 | 5424 | 441 | 6999 |
| 7 | 54 | 599 | 495 | 6945 |
| 8 | 21 | 124 | 516 | 6924 |
| 9 | 153 | 391 | 669 | 6771 |
| 10 | 183 | 658 | 852 | 6588 |
| 11 | 90 | 2507 | 942 | 6498 |
| 12 | 123 | 946 | 1065 | 6375 |
| 13 | 124 | 4079 | 1189 | 6251 |
| 14 | 170 | 720 | 1359 | 6081 |
| 15 | 163 | 1370 | 1522 | 5918 |
| 16 | 101 | 72 | 1623 | 5817 |
| 17 | 88 | 1337 | 1711 | 5729 |
| 18 | 113 | 1850 | 1824 | 5616 |
| 19 | 85 | 535 | 1909 | 5531 |
| 20 | 143 | 2561 | 2052 | 5388 |
| 21 | 165 | 342 | 2217 | 5223 |
| 22 | 150 | 2020 | 2367 | 5073 |
| 23 | 116 | 1967 | 2483 | 4957 |
| 24 | 103 | 90 | 2586 | 4854 |
| 25 | 231 | 3663 | 2817 | 4623 |
| 26 | 174 | 5838 | 2991 | 4449 |
| 27 | 112 | 2912 | 3103 | 4337 |
| 28 | 206 | 937 | 3309 | 4131 |
| 29 | 152 | 1841 | 3461 | 3979 |
| 30 | 112 | 1240 | 3573 | 3867 |
| 31 | 456 | 1087 | 4029 | 3411 |
| 32 | 165 | 1281 | 4194 | 3246 |
| 33 | 108 | 217 | 4302 | 3138 |
| 34 | 135 | 1186 | 4437 | 3003 |
| 35 | 267 | 631 | 4704 | 2736 |
| 36 | 108 | 616 | 4812 | 2628 |
| 37 | 200 | 2635 | 5012 | 2428 |
| 38 | 214 | 952 | 5226 | 2214 |
| 39 | 138 | 1173 | 5364 | 2076 |
| 40 | 222 | 352 | 5586 | 1854 |
| 41 | 123 | 5295 | 5709 | 1731 |
| 42 | 146 | 331 | 5855 | 1585 |
| 43 | 156 | 2648 | 6011 | 1429 |
| 44 | 124 | 4406 | 6135 | 1305 |
| 45 | 135 | 1202 | 6270 | 1170 |
| 46 | 87 | 1697 | 6357 | 1083 |
| 47 | 165 | 809 | 6522 | 918 |
| 48 | 123 | 877 | 6645 | 795 |
| 49 | 173 | 3130 | 6818 | 622 |
| 50 | 142 | 1162 | 6960 | 480 |
| 51 | 74 | 593 | 7034 | 406 |
| 52 | 95 | 3218 | 7129 | 311 |
| 53 | 80 | 939 | 7209 | 231 |
| 54 | 395 | N/A | 7440 | N/A |

As used herein, a "target CEP290 intron" refers to one of the 53 CEP290 introns identified in Table 3, above. Nucleic acid sequence identifiers for each CEP290 intron sequence are provided in Table 4, below. It will be understood that the scope of the term "target CEP290 intron" encompasses variants of CEP290 introns provided herein, such as intron sequences having 90-100% homology with the sequences provided herein (e.g., 90%, 91%, 92%, 93%, 94%, 95%, 96%, 97%, 98%, 99%, or 100% homology with the sequences provided herein), where the location of the variant intron on the CEP290 gene corresponds with that provided herein (e.g., in relation to its adjacent exons as set forth in Table 3).

TABLE 4

| CEP290 intron sequences | |
|---|---|
| Intron Number | Sequence |
| 1 | SEQ ID NO: 60 |
| 2 | SEQ ID NO: 61 |
| 3 | SEQ ID NO: 62 |
| 4 | SEQ ID NO: 63 |
| 5 | SEQ ID NO: 64 |
| 6 | SEQ ID NO: 65 |
| 7 | SEQ ID NO: 66 |
| 8 | SEQ ID NO: 67 |
| 9 | SEQ ID NO: 68 |
| 10 | SEQ ID NO: 69 |
| 11 | SEQ ID NO: 70 |
| 12 | SEQ ID NO: 71 |
| 13 | SEQ ID NO: 72 |
| 14 | SEQ ID NO: 73 |
| 15 | SEQ ID NO: 74 |
| 16 | SEQ ID NO: 75 |
| 17 | SEQ ID NO: 76 |
| 18 | SEQ ID NO: 77 |
| 19 | SEQ ID NO: 78 |
| 20 | SEQ ID NO: 79 |
| 21 | SEQ ID NO: 80 |
| 22 | SEQ ID NO: 81 |
| 23 | SEQ ID NO: 82 |
| 24 | SEQ ID NO: 83 |
| 25 | SEQ ID NO: 84 |
| 26 | SEQ ID NO: 85 |
| 27 | SEQ ID NO: 86 |
| 28 | SEQ ID NO: 87 |
| 29 | SEQ ID NO: 88 |
| 30 | SEQ ID NO: 89 |
| 31 | SEQ ID NO: 90 |
| 32 | SEQ ID NO: 91 |
| 33 | SEQ ID NO: 92 |
| 34 | SEQ ID NO: 93 |
| 35 | SEQ ID NO: 94 |
| 36 | SEQ ID NO: 95 |
| 37 | SEQ ID NO: 96 |
| 38 | SEQ ID NO: 97 |
| 39 | SEQ ID NO: 98 |
| 40 | SEQ ID NO: 99 |
| 41 | SEQ ID NO: 100 |
| 42 | SEQ ID NO: 101 |
| 43 | SEQ ID NO: 102 |
| 44 | SEQ ID NO: 103 |
| 45 | SEQ ID NO: 104 |
| 46 | SEQ ID NO: 105 |
| 47 | SEQ ID NO: 106 |
| 48 | SEQ ID NO: 107 |
| 49 | SEQ ID NO: 108 |
| 50 | SEQ ID NO: 109 |
| 51 | SEQ ID NO: 110 |
| 52 | SEQ ID NO: 111 |
| 53 | SEQ ID NO: 112 |

As used herein, the term "subject" includes any mammal in need of these methods of treatment or prophylaxis, including humans. Other mammals in need of such treatment or prophylaxis include dogs, cats, or other domesticated animals, horses, livestock, laboratory animals, including non-human primates, etc. The subject may be male or female. In one embodiment, the subject has a disease or disorder caused by a mutation in the ABCA4 gene (e.g., Stargardt Disease, e.g., Stargardt Disease 1) or the CEP290 gene (e.g., an autosomal recessive disorder, such as LCA 10). In another embodiment, the subject is at risk of developing a disease or disorder caused by a mutation in the ABCA4 gene or the CEP290 gene. In another embodiment, the subject has shown clinical signs of a disease or disorder caused by a mutation in the ABCA4 gene (such as Stargardt Disease) or the CEP290 gene (such as LCA 10). The subject may be any age during which treatment or prophylactic therapy may be beneficial. For example, in some embodiments, the subject is 0-5 years of age, 5-10 years of age, 10-20 years of age, 20-30 years of age, 30-50 years of age, 50-70 years of age, or more than 70 years of age. In another embodiment, the subject is 12 months of age or older, 18 months of age or older, 2 years of age or older, 3 years of age or older, 4 years of age or older, 5 years of age or older, 6 years of age or older, 7 years of age or older, 8 years of age or older, 9 years of age or older, or 10 years of age or older. In another embodiment, the subject has viable retinal cells.

As used herein, the terms "disorder associated with a mutation" or "mutation associated with a disorder" refer to a correlation between a disorder and a mutation. In some embodiments, a disorder associated with a mutation is known or suspected to be wholly or partially, or directly or indirectly, caused by the mutation. For example, a subject having the mutation may be at risk of developing the disorder, and the risk may additionally depend on other factors, such as other (e.g., independent) mutations (e.g., in the same or a different gene), or environmental factors.

As used herein, the term "treatment," or a grammatical derivation thereof, is defined as reducing the progression of a disease, reducing the severity of a disease symptom, retarding progression of a disease symptom, removing a disease symptom, or delaying onset of a disease.

As used herein, the term "prevention" of a disorder, or a grammatical derivation thereof, is defined as reducing the risk of onset of a disease, e.g., as a prophylactic therapy for a subject who is at risk of developing a disorder associated with a mutation. A subject can be characterized as "at risk" of developing a disorder by identifying a mutation associated with the disorder, according to any suitable method known in the art or described herein. In some embodiment, a subject who is at risk of developing a disorder has one or more ABCA4 or CEP290 mutations associated with the disorder. Additionally or alternatively, a subject can be characterized as "at risk" of developing a disorder if the subject has a family history of the disorder.

Treating or preventing a disorder in a subject can be performed by directly administering the trans-splicing molecule (e.g., within an AAV vector or AAV particle) to the subject. Alternatively, host cells containing the trans-splicing molecule may be administered to the subject.

The term "administering," or a grammatical derivation thereof, as used in the methods described herein, refers to delivering the composition, or an ex vivo-treated cell, to the subject in need thereof, e.g., having a mutation or defect in the targeted gene. For example, in one embodiment in which ocular cells are targeted, the method involves delivering the composition by subretinal injection to the photoreceptor cells or other ocular cells. In another embodiment, intravitreal injection to ocular cells or injection via the palpebral vein to ocular cells may be employed. In another embodiment, the composition is administered intravenously. Still other methods of administration may be selected by one of skill in the art, in view of this disclosure.

Codon optimization refers to modifying a nucleic acid sequence to change individual nucleic acids without any resulting change in the encoded amino acid. Sequences modified in this way are referred to herein as "codon-optimized." This process may be performed on any of the sequences described in this specification to enhance expression or stability. Codon optimization may be performed in a manner such as that described in, e.g., U.S. Pat. Nos. 7,561,972, 7,561,973, and 7,888,112, each of which is incorporated herein by reference in its entirety. The sequence surrounding the translational start site can be converted to a consensus Kozak sequence according to known methods. See, e.g., Kozak et al, *Nucleic Acids Res.* 15 (20): 8125-8148, incorporated herein by reference in its entirety.

The term "homologous" refers to the degree of identity between sequences of two nucleic acid sequences. The homology of homologous sequences is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (*Nucleic Acid Res.,* 1994, 22(22): 4673 4680). Commonly available sequence analysis software, such as, Vector NTI, GENETYX, BLAST, or analysis tools provided by public databases may also be used.

The term "pharmaceutically acceptable" means safe for administration to a mammal, such as a human. In some embodiments, a pharmaceutically acceptable composition is approved by a regulatory agency of the Federal or a state government or listed in the U. S. Pharmacopeia or other generally recognized pharmacopeia for use in animals, and more particularly in humans.

The term "carrier" refers to a diluent, adjuvant, excipient, or vehicle with which a therapeutic molecule (e.g., a trans-splicing molecule or a trans-splicing molecule including a vector or cell of the present invention) is administered. Examples of suitable pharmaceutical carriers are described in "Remington's Pharmaceutical Sciences," Mack Publishing Co., Easton, PA, $2^{nd}$ edition, 2005.

The terms "a" and "an" mean "one or more of." For example, "a gene" is understood to represent one or more such genes. As such, the terms "a" and "an," "one or more of a (or an)," and "at least one of a (or an)" are used interchangeably herein.

As used herein, the term "about" refers to a value within ±10% variability from the reference value, unless otherwise specified.

II. Trans-Splicing Molecules

Provided herein are ABCA4 trans-splicing molecules and CEP290 trans-splicing molecules.

ABCA4 Trans-Splicing Molecules

The present invention features nucleic acid trans-splicing molecules useful for treating diseases and disorders associated with a mutation in an ABCA4 gene by replacing one or more exons in the ABCA4 gene (e.g., an ABCA4 gene having a mutated ABCA4 exon). In some embodiments, the nucleic acid trans-splicing molecule is a pre-RNA trans-splicing molecule (RTM). The design of the trans-splicing molecule permits replacement of the defective or mutated portion of the pre-mRNA exon(s) with a nucleic acid sequence, e.g., the exon(s) having a functional (e.g., normal) sequence without the mutation. The functional sequence can be a wild-type, naturally-occurring sequence or a corrected sequence with some other modification, e.g., codon optimization.

In one embodiment, a trans-splicing molecule is configured to correct one or more mutations located on a 3' portion of the ABCA4 gene. In one embodiment, a trans-splicing molecule is configured to correct one or more mutations located on a 5' portion of the ABCA4 gene. The trans-splicing molecules provided herein function to repair the defective gene in the target cell of a subject by replacing the defective pre-mRNA gene sequence and removing the defective portion of the target pre-mRNA, yielding a functional ABCA4 gene capable of transcribing a functional gene product in the cell.

The invention provides trans-splicing molecules having a binding domain configured to bind a target ABCA4 intron, a splicing domain configured to mediate trans-splicing, and a coding domain having one or more functional ABCA4 exons. In a 5' trans-splicing molecule, the coding domain, splice site, and binding domain are operatively linked in a 5'-to-3' direction, such that the trans-splicing molecule is configured to replace the 5' end of the endogenous gene with the coding domain, which includes a functional ABCA4 exon to replace the mutated ABCA4 exon. Conversely, in a 3' trans-splicing molecule, the coding domain, splice site, and binding domain are operatively linked in a 3'-to-5' direction, such that the trans-splicing molecule is configured to replace the 3' end of the endogenous gene with the coding domain, which includes a functional ABCA4 exon to replace the mutated ABCA4 exon. In some embodiments, the splicing domain resides within an artificial intron, which links the binding domain to the coding domain. The artificial intron may include additional components, such as a spacer.

In some embodiments, the trans-splicing molecule or coding domain thereof is up to 4,700 nucleotide bases in length (e.g., from 200 to 300 nucleotide bases in length, from 300 to 400 nucleotide bases in length, from 400 to 500 nucleotide bases in length, from 500 to 600 nucleotide bases in length, from 600 to 700 nucleotide bases in length, from 700 to 800 nucleotide bases in length, form 800 to 900 nucleotide bases in length, from 900 to 1,000 nucleotide bases in length, from 1,000 to 1,500 nucleotide bases in length, from 1,500 to 2,000 nucleotide bases in length, from 2,000 to 2,500 nucleotide bases in length, from 2,500 to 3,000 nucleotide bases in length, or from 3,000 to 4,000 nucleotide bases in length, e.g., from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length, e.g., about 2,918 nucleotide bases in length, about 3,328 nucleotide bases in length, about 3,522 nucleotide bases in length, about 3,607 nucleotide bases in length, about 3,632 nucleotide bases in length, about 3,494 nucleotide bases in length, or about 3,300 nucleotide bases in length).

Due to the large size of the ABCA4 gene and the size constraints of AAV delivery, a single trans-splicing molecule configured for packaging within an AAV vector may not span all mutations in an ABCA4 gene that may be associated with a disorder and thereby may not correct mutations along the length of the entire ABCA4 gene. Accordingly, the trans-splicing molecules of the invention can be adapted as part of methods described below to correct multiple mutations spanning the entire length of the ABCA4 gene.

An ABCA4 gene targeted by a trans-splicing molecule described herein contains one or multiple mutations that are associated with (e.g., cause, or are correlated with) a disease, such as a Stargardt Disease (e.g., Stargardt Disease 1). An exemplary DNA sequence of a functional (wildtype) human ABCA4 gene is given by the NCBI Reference Sequence: NG_009073. The amino acid sequence of an exemplary protein retinal-specific ATP-binding cassette transporter expressed by ABCA4 is given by Protein Accession No. P78363.

In addition to these published sequences, all corrections later obtained or naturally occurring conservative and non-disease-causing variants sequences that occur in the human or other mammalian population are also included. Additional conservative nucleotide replacements or those causing codon optimizations are also included. The sequences as provided by the database accession numbers may also be used to search for homologous sequences in the same or another mammalian organism.

It is anticipated that the ABCA4 nucleic acid sequences and resulting protein truncates or amino acid fragments may tolerate certain minor modifications at the nucleic acid level to include, for example, modifications to the nucleotide bases which are silent, e.g., preference codons. In other embodiments, nucleic acid base modifications which change the amino acids, e.g., to improve expression of the resulting peptide/protein (for example, codon optimization) are anticipated. Also included as likely modification of fragments are allelic variations, caused by the natural degeneracy of the genetic code.

Also included as modifications of ABCA4 genes are analogs, or modified versions, of the encoded protein fragments provided herein. Typically, such analogs differ from the specifically identified proteins by only one to four codon changes. Conservative replacements are those that take place within a family of amino acids that are related in their side chains and chemical properties.

The nucleic acid sequence of a functional ABCA4 gene may be derived from any mammal which natively expresses functional retinal-specific ATP-binding cassette transporter, or homolog thereof. In other embodiments, certain modifications are made to the ABCA4 gene sequence in order to enhance expression in the target cell. Such modifications include codon optimization.

In some embodiments, the disorder associated with a mutation in ABCA4 is an autosomal recessive disease, for example, Stargardt Disease. In certain instances involving a subject having an autosomal recessive disorder, the subject has a mutation in ABCA4 on both alleles. Compositions comprising trans-splicing molecules can correct the mutations on both alleles, regardless of the location of the mutation within the ABCA4 gene. For instance, for a subject having a mutated ABCA4 exon 1 on a first allele and a mutated ABCA4 exon 30 on a second allele, provided herein is a composition having a 5' trans-splicing molecule to replace the mutated ABCA4 exon 1 and a 3' trans-splicing molecule to replace the mutated ABCA4 exon 30. In such embodiments, the two trans-splicing molecules can be co-delivered as part of the same AAV vector or delivered in separate AAV vectors (e.g., in the case in which both trans-splicing molecules exceed the packaging limit of AAV).

Alternatively, in embodiments in which two or more mutations are located on a portion of the ABCA4 gene that can be replaced by the same trans-splicing molecule, a single trans-splicing molecule having a coding region containing a functional ABCA4 exon can replace the one or more exons containing the mutations. Mutations in particular ABCA4 exons are also listed in International Patent Publication No. WO 2017/087900, incorporated herein by reference.

ABCA4 Coding Domains

In some embodiments, the coding domain of a 5' trans-splicing molecule includes all ABCA4 exons (e.g., functional ABCA4 exons) that are 5' to the target ABCA4 intron. For example, in embodiments in which a 5' trans-splicing molecule targets ABCA4 intron 19, the coding domain includes functional ABCA4 exons 1-19. In such embodiments featuring a 5' trans-splicing molecule having a coding domain including functional ABCA4 exons 1-19, the coding domain is about 2918 bp in length. In embodiments in which a 5' trans-splicing molecule targets ABCA4 intron 22, the coding domain includes functional ABCA4 exons 1-22. In such embodiments featuring a 5' trans-splicing molecule having a coding domain including functional ABCA4 exons 1-22, the coding domain is about 3,328 bp in length. In embodiments in which a 5' trans-splicing molecule targets ABCA4 intron 23, the coding domain includes functional ABCA4 exons 1-23. In such embodiments featuring a 5' trans-splicing molecule having a coding domain including functional ABCA4 exons 1-23, the coding domain is about 3,522 bp in length. In embodiments in which a 5' trans-splicing molecule targets ABCA4 intron 24, the coding domain includes functional ABCA4 exons 1-24. In such embodiments featuring a 5' trans-splicing molecule having a coding domain including functional ABCA4 exons 1-24, the coding domain is about 3,607 bp in length. The aforementioned embodiments of 5' ABCA4-targeting trans-splicing molecules are illustrated at the lower left-hand portion of FIG. 1.

In some embodiments, the coding domain of a 3' trans-splicing molecule includes any one or more of ABCA4 exons 20-50. For example, in embodiments in which a 3' trans-splicing molecule targets ABCA4 intron 22, the coding domain includes functional ABCA4 exons 23-50. In such embodiments featuring a 3' trans-splicing molecule having a coding domain including functional ABCA4 exons 23-50, the coding domain is about 3,632 bp in length. In embodiments in which a 3' trans-splicing molecule targets ABCA4 intron 23, the coding domain includes functional ABCA4 exons 24-50. In such embodiments featuring a 3' trans-splicing molecule having a coding domain including functional ABCA4 exons 24-50, the coding domain is about 3,494 bp in length. In embodiments in which a 3' trans-splicing molecule targets ABCA4 intron 24, the coding domain includes functional ABCA4 exons 25-50. In such embodiments featuring a 3' trans-splicing molecule having a coding domain including functional ABCA4 exons 25-50, the coding domain is about 3,300 bp in length. The aforementioned embodiments of 3' ABCA4-targeting trans-splicing molecules are illustrated at the upper right-hand portion of FIG. 1.

In some embodiments, the coding domain includes 1, 2, 3, 4, 5, 6, 7, 8, 9, 10, 11, 12, 13, 14, 15, 16, 17, 18, 19, 20, 21, 22, 23, 24, 25, 26, 27, or 28 functional ABCA4 exons.

In some instances, both mutations occur in the 5' portion of the target gene, and a 5' trans-splicing molecule is selected to correct both mutations. In one embodiment, the binding domain binds to intron 19, and the coding domain includes functional ABCA4 exons 1-19. In one embodiment, the binding domain binds to intron 22, and the coding domain includes functional ABCA4 exons 1-22. In one embodiment, the binding domain binds to intron 23, and the coding domain includes functional ABCA4 exons 1-23. In one embodiment, the binding domain binds to intron 24, and the coding domain includes functional ABCA4 exons 1-24. Alternatively, in instances in which both mutations occur on the 3' portion of the target gene, a 3' trans-splicing molecule is selected to correct both mutations. In one embodiment, the binding domain binds to intron 22, and the coding domain includes functional ABCA4 exons 23-50. In one embodiment, the binding domain binds to intron 23, and the coding domain includes functional ABCA4 exons 24-50. In one embodiment, the binding domain binds to intron 24, and the coding domain includes functional ABCA4 exons 25-50.

As one example, a 3' pre-mRNA ABCA4 trans-splicing molecule operates as follows: A chimeric mRNA is created through a trans-splicing reaction mediated by the spliceosome between the 5' splice site of the endogenous target pre-mRNA and the 3' splice site of the trans-splicing molecule. The trans-splicing molecule binds through specific base pairing to a target ABCA4 intron of the endogenous target pre-mRNA and replaces the whole 3' sequence of the endogenous ABCA4 gene upstream of the targeted intron with the coding domain having a functional ABCA4 exon sequence of the trans-splicing molecule.

A 3' trans-splicing molecule includes a binding domain which binds to the target ABCA4 intron 5' to the mutation or defect, an artificial intron comprising optional spacer and a 3' splice site, and a coding domain that encodes all exons of the ocular target gene that are 3' to the binding of the binding domain to the target. A 5' trans-splicing molecule includes a binding domain binds to the target ABCA4 intron 3' to the mutation or defect, a 5' splice site, an optional spacer and a coding domain that encodes all exons of the ocular target gene that are 5' to the binding of the binding domain to the target.

In some embodiments, the coding domain includes a complementary DNA (cDNA) sequence. For example, one or more functional ABCA4 exons within the coding domain can be a cDNA sequence. In some embodiments, the entire coding domain is a cDNA sequence. Additionally or alternatively, all or a portion of the coding domain, or one or more functional ABCA4 exons thereof, can be a naturally-occurring sequence (e.g., a sequence having 90%, 91%, 92%, 93%, 94%, 95%, 96%, 97%, 98%, 99%, or 100% sequence identity with an endogenous ABCA4 exon).

In some embodiments, all or a portion of the coding domain, or one or more functional ABCA4 exons thereof, is a codon-optimized sequence in which a nucleic acid sequence has been modified, e.g., to enhance expression or stability, without resulting in a change in the encoded amino acid. Codon optimization may be performed in a manner such as that described in, e.g., U.S. Pat. Nos. 7,561,972, 7,561,973, and 7,888,112, each of which is incorporated herein by reference in its entirety. For delivery via a recombinant AAV, as described herein, in one embodiment, the coding domain can be a nucleic acid sequence of up to 4,000 nucleotide bases in length (e.g., from 3,000 to 4,000 nucleotide bases in length, from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length).

ABCA4 Binding Domains

Trans-splicing molecules of the invention feature a binding domain configured to bind a target ABCA4 intron. In one embodiment, the binding domain is a nucleic acid sequence complementary to a sequence of the target ABCA4 pre-mRNA (e.g., a target ABCA4 intron) to suppress endogenous target cis-splicing while enhancing trans-splicing between the trans-spicing molecule and the target ABCA4 pre-mRNA, e.g., to create a chimeric molecule having a portion of endogenous ABCA4 mRNA and the coding domain having one or more functional ABCA4 exons. In some embodiments, the binding domain is in an antisense orientation to a sequence of the target ABCA4 intron.

A 5' trans-splicing molecule will generally bind the target ABCA4 intron 3' to the mutation, while a 3' trans-splicing molecule will generally bind the target ABCA4 intron 5' to the mutation. In one embodiment, the binding domain comprises a part of a sequence complementary to the target ABCA4 intron. In one embodiment herein, the binding domain is a nucleic acid sequence complementary to the intron closest to (i.e., adjacent to) the exon sequence that is being corrected.

In another embodiment, the binding domain is targeted to an intron sequence in close proximity to the 3' or 5' splice signals of a target intron. In still another embodiment, a binding domain sequence can bind to the target intron in addition to part of an adjacent exon.

Thus, in some instances, the binding domain binds specifically to the mutated endogenous target pre-mRNA to anchor the coding domain of the trans-splicing molecule to the pre-mRNA to permit trans-splicing to occur at the correct position in the target ABCA4 gene. The spliceosome processing machinery of the nucleus may then mediate successful trans-splicing of the corrected exon for the mutated exon causing the disease.

In certain embodiments, the trans-splicing molecules feature binding domains that contain sequences on the target pre-mRNA that bind in more than one place. The binding domain may contain any number of nucleotides necessary to stably bind to the target pre-mRNA to permit trans-splicing to occur with the coding domain. In one embodiment, the binding domains are selected using mFOLD structural analysis for accessible loops (Zuker, Nucleic Acids Res. 2003, 31(13): 3406-3415).

Suitable target binding domains can be from 10 to 500 nucleotides in length. In some embodiments, the binding domain is from 20 to 400 nucleotides in length. In some embodiments, the binding domain is from 50 to 300 nucleotides in length. In some embodiments, the binding domain is from 100 to 200 nucleotides in length. In some embodiments, the binding domain is from 10-20 nucleotides in length (e.g., 10, 11, 12, 13, 14, 15, 16, 17, 18, 19, or 20 nucleotides in length), 20-30 nucleotides in length (e.g., 20, 21, 22, 23, 24, 25, 26, 27, 28, 29, or 30 nucleotides in length), 30-40 nucleotides in length (e.g., 30, 31, 32, 33, 34, 35, 36, 37, 38, 39, or 40 nucleotides in length), 40-50 nucleotides in length (e.g., 40, 41, 42, 43, 44, 45, 46, 47, 48, 49, 50 nucleotides in length), 50-60 nucleotides in length (e.g., 50, 51, 52, 53, 54, 55, 56, 57, 58, 59, or 60 nucleotides in length), 60-70 nucleotides in length (e.g., 60, 61, 62, 63, 64, 65, 66, 67, 68, 69, or 70 nucleotides in length), 70-80 nucleotides in length (e.g., 70, 71, 72, 73, 74, 75, 76, 77, 78, 79, or 80 nucleotides in length), 80-90 nucleotides in length (e.g., 80, 81, 82, 83, 84, 85, 86, 87, 88, 89, or 90 nucleotides in length), 90-100 nucleotides in length (e.g., 90, 91, 92, 93, 94, 95, 96, 97, 98, 99, or 100 nucleotides in length), 100-110 nucleotides in length (e.g., 100, 101, 102, 103, 104, 105, 106, 107, 108, 109, or 110 nucleotides in length), 110-120 nucleotides in length (e.g., 110, 111, 112, 113, 114, 115, 116, 117, 118, 119, or 120 nucleotides in length), 120-130 nucleotides in length (e.g., 120, 121, 122, 123, 124, 125, 126, 127, 128, 129, or 130 nucleotides in length), 130-140 nucleotides in length (e.g., 130, 131, 132, 133, 134, 135, 136, 137, 138, 139, or 140 nucleotides in length), 140-150 nucleotides in length (e.g., 140, 141, 142, 143, 144, 145, 146, 147, 148, 149, or 150 nucleotides in length), 150-160 nucleotides in length (e.g., 150, 151, 152, 153, 154, 155, 156, 157, 158, 159, or 160 nucleotides in length), 160-170 nucleotides in length (e.g., 160, 161, 162, 163, 164, 165, 166, 167, 168, 169, or 170 nucleotides in length), 170-180 nucleotides in length (e.g., 170, 171, 172, 173, 174, 175, 176, 177, 178, 179, or 180 nucleotides in length), 180-190 nucleotides in length (e.g., 180, 181, 182, 183, 184, 185, 186, 187, 188, 189, or 190 nucleotides in length), 190-200 nucleotides in length (e.g., 190, 191, 192, 193, 194, 195, 196, 197, 198, 199, or 200 nucleotides in length), 200-210 nucleotides in length, 210-220 nucleotides in length, 220-230 nucleotides in length, 230-240 nucleotides in length, 240-250 nucleotides in length, 250-260 nucleotides in length, 260-270 nucleotides in length, 270-280 nucleotides in length, 280-290 nucleotides in length, 290-300 nucleotides in length, 300-350 nucleotides in length, 350-400 nucleotides in length, 400-450 nucleotides in length, or 450-500 nucleotides in length. In some embodiments, the binding domain is about 150 nucleotides in length. In another embodiment, the target binding domains may include a nucleic acid sequence up to 750 nucleotides in length. In another embodiment, the target binding domains may include a nucleic acid sequence up to 1000 nucleotides in length. In another embodiment, the target binding domains may include a nucleic acid sequence up to 2000 nucleotides or more in length.

In some embodiments, the specificity of the trans-splicing molecule may be increased by increasing the length of the target binding domain. Other lengths may be used depending upon the lengths of the other components of the trans-splicing molecule.

The binding domain may be from 80% to 100% complementary to the target intron to be able to hybridize stably with the target intron. For example, in some embodiments, the binding domain is 80%, 81%, 82%, 83%, 84%, 85%, 86%, 87%, 88%, 89%, 90%, 91%, 92%, 93%, 94%, 95%, 96%, 97%, 98%, 99%, or 100% complimentary to the target intron. The degree of complementarity is selected by one of skill in the art based on the need to keep the trans-splicing molecule and the nucleic acid construct containing the necessary sequences for expression and for inclusion in the rAAV within a 3,000 or up to 4,000 nucleotide base limit. The selection of this sequence and strength of hybridization depends on the complementarity and the length of the nucleic acid.

Any of the aforementioned binding domains may bind to a binding site within intron 19 (SEQ ID NO: 25), intron 22 (SEQ ID NO: 28) intron 23 (SEQ ID NO: 29), or intron 24 (SEQ ID NO: 30).

In certain instances of the invention, the trans-splicing molecule is a 5' trans-splicing molecule and features a binding domain that binds to intron 19 of ABCA4 (SEQ ID NO: 25) and includes a coding domain having functional ABCA4 exons 1-19. In some embodiments, the binding site comprises any one or more of nucleotides 990 to 2,174 of SEQ ID NO: 25 (e.g., any one or more of nucleotides 1,670 to 2,174 of SEQ ID NO: 25, any one or more of nucleotides 1,810 to 2,000 of SEQ ID NO: 25, any one or more of nucleotides 1,870 to 2,000 of SEQ ID NO: 25, or any one or more of nucleotides 1,920 to 2,000 of SEQ ID NO: 25).

In some embodiments, the trans-splicing molecule is a 5' trans-splicing molecule and features a binding domain that binds to intron 22 of ABCA4 (SEQ ID NO: 28) and includes a coding domain having functional ABCA4 exons 1-22. In some embodiments, the binding site comprises any one or more of nucleotides 60 to 570, nucleotides 600 to 800, or nucleotides 900 to 1,350 of SEQ ID NO: 28 (e.g., any one or more of nucleotides 70 to 250 of SEQ ID NO: 28).

Alternatively, the trans-splicing molecule can be a 3' trans-splicing molecule and can feature a binding domain that binds to intron 22 of ABCA4 (SEQ ID NO: 28). This trans-splicing molecules may include a coding domain having functional ABCA4 exons 23-50. In some embodiments, the binding site comprises any one or more of nucleotides 1 to 510 or 880 to 1,350 of SEQ ID NO: 28.

In other embodiments, the trans-splicing molecule is a 5' trans-splicing molecule and features a binding domain that binds to intron 23 of ABCA4 (SEQ ID NO: 29) and includes a coding domain having functional ABCA4 exons 1-23. In some embodiments, the binding site comprises any one or more of nucleotides 80 to 570 or 720 to 1,081 of SEQ ID NO: 29.

Alternatively, the trans-splicing molecule can be a 3' trans-splicing molecule and can feature a binding domain that binds to intron 23 of ABCA4 (SEQ ID NO: 29) and a coding domain having functional ABCA4 exons 24-50. In some embodiments, the binding site comprises any one or more of nucleotides 80 to 1,081 of SEQ ID NO: 29 (e.g., any one or more of nucleotides 230 to 1,081 of SEQ ID NO: 29, any one or more of nucleotides 250 to 400 of SEQ ID NO: 29, or any one or more of nucleotides 690 to 850 of SEQ ID NO: 29).

In some embodiments, the trans-splicing molecule is a 5' trans-splicing molecule and features a binding domain that binds to intron 24 of ABCA4 (SEQ ID NO: 30) and includes a coding domain having functional ABCA4 exons 1-24. In some embodiments, the binding site comprises any one or more of nucleotides 600 to 1,250 or 1,490 to 2,660 of SEQ ID NO: 30 (e.g., any one or more of nucleotides 1,000 to 1,200 of SEQ ID NO: 30).

In other embodiments, the trans-splicing molecule is a 3' trans-splicing molecule and features a binding domain that binds to intron 24 of ABCA4 (SEQ ID NO: 30) and includes a coding domain having functional ABCA4 exons 25-50. In some embodiments, the binding site comprises any one or more of nucleotides 1 to 250, nucleotides 300 to 2,100, or nucleotides 2,200 to 2,692 of SEQ ID NO: 30 (e.g., any one or more of nucleotides 360 to 610 of SEQ ID NO: 30 or any one or more of nucleotides 750 to 1,110 of SEQ ID NO: 30).

CEP290 Trans-Splicing Molecules

The present invention features nucleic acid trans-splicing molecules useful for treating diseases and disorders associated with a mutation in a CEP290 gene by replacing one or more exons in the CEP290 gene (e.g., a CEP290 gene having a mutation in intron 26). In some embodiments, the nucleic acid trans-splicing molecule is a pre-RNA trans-splicing molecule (RTM). The design of the trans-splicing molecule permits replacement of the defective or mutated portion of the pre-mRNA with a nucleic acid sequence, e.g., the exon(s) having a functional (e.g., normal) sequence without the mutation. The functional sequence can be a wild-type, naturally-occurring sequence or a corrected sequence with some other modification, e.g., codon optimization.

In one embodiment, a trans-splicing molecule is configured to correct one or more mutations located on a 5' portion of the CEP290 gene. The trans-splicing molecules provided herein function to repair the defective gene in the target cell of a subject by replacing the defective pre-mRNA gene sequence, yielding a functional CEP290 gene capable of transcribing a functional gene product in the cell.

The invention provides trans-splicing molecules having a binding domain configured to bind a target CEP290 intron, a splicing domain configured to mediate trans-splicing, and a coding domain having one or more functional CEP290 exons. In a 5' trans-splicing molecule, the coding domain, splice site, and binding domain are operatively linked in a 5'-to-3' direction, such that the trans-splicing molecule is configured to replace the 5' end of the endogenous gene with the coding domain, which includes a functional CEP290 exon to corrected the mutated CEP290 pre-mRNA. In some embodiments, the splicing domain resides within an artificial intron, which links the binding domain to the coding domain. The artificial intron may include additional components, such as a spacer.

In some embodiments, the trans-splicing molecule is up to 4,700 nucleotide bases in length (e.g., from 3,000 to 4,000 nucleotide bases in length, from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length, e.g., about 2,991 nucleotide bases in length, about 3,103 nucleotide bases in length, about 3,309 nucleotide bases in length, about 3,461 nucleotide bases in length, or about 3,573 nucleotide bases in length).

A CEP290 gene targeted by a trans-splicing molecule described herein contains one or multiple mutations that are associated with (e.g., cause, or are correlated with) a disease, such as Leber congenital amourosis (e.g., LCA 10). An exemplary DNA sequence of a functional (wildtype) human CEP290 gene is given by the NCBI Reference Sequence: NG_008417. The amino acid sequence of an exemplary centrosomal protein 290 is given by Protein Accession No. O15078.

In addition to these published sequences, all corrections later obtained or naturally occurring conservative and non-disease-causing variants sequences that occur in the human or other mammalian population are also included. Additional conservative nucleotide replacements or those causing codon optimizations are also included. The sequences as provided by the database accession numbers may also be used to search for homologous sequences in the same or another mammalian organism.

It is anticipated that the CEP290 nucleic acid sequences and resulting protein truncates or amino acid fragments may tolerate certain minor modifications at the nucleic acid level to include, for example, modifications to the nucleotide bases which are silent, e.g., preference codons. In other embodiments, nucleic acid base modifications which change the amino acids, e.g., to improve expression of the resulting peptide/protein (for example, codon optimization) are anticipated. Also included as likely modification of fragments are allelic variations, caused by the natural degeneracy of the genetic code.

Also included as modifications of CEP290 genes are analogs, or modified versions, of the encoded protein fragments provided herein. Typically, such analogs differ from the specifically identified proteins by only one to four codon changes. Conservative replacements are those that take place within a family of amino acids that are related in their side chains and chemical properties.

The nucleic acid sequence of a functional CEP290 gene may be derived from any mammal which natively expresses functional centrosomal protein 290, or homolog thereof. In other embodiments, certain modifications are made to the CEP290 gene sequence in order to enhance expression in the target cell. Such modifications include codon optimization.

CEP290 mutations can be found on the CCHMC Molecular Genetics Laboratory Mutation Database, LOVD v.2.0. Mutations in particular CEP290 exons are also listed in International Patent Publication No. WO 2017/087900, incorporated herein by reference. Table 3, above, provides information regarding the size and position of each exon and intron of CEP290.

In some embodiments, the disorder associated with a mutation in CEP290 is an autosomal recessive disease, for example, LCA 10.

Coding Domains

Figure 21:
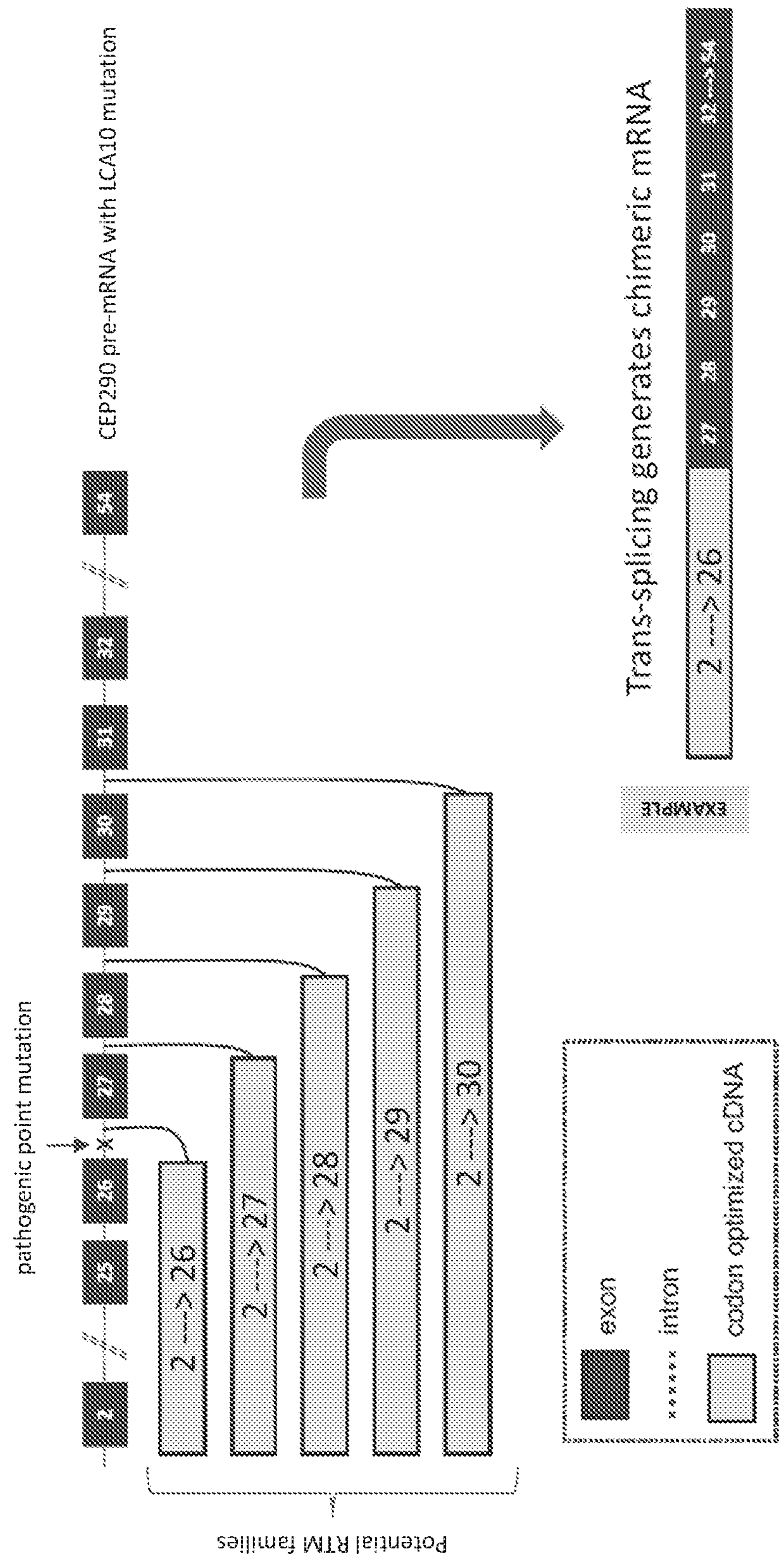
FIG. 21 is a schematic drawing of several exemplary nucleic acid trans-splicing molecules for correcting a mutation in CEP290 intron 26 with a functional 5' portion of the CEP290 gene. Dark shaded boxes represent native CEP290 exons. Dashed lines joining the dark shaded boxes represent native introns. Light shaded boxes with dark borders represent functional CEP290 exons within a nucleic acid trans-splicing molecule. A splicing domain, represented by a curved line, is attached to one end of each of the functional CEP290 exon sequences and leads to an intron of the CEP290 pre-mRNA.

In some embodiments, the coding domain of a 5' trans-splicing molecule includes all CEP290 exons (e.g., functional CEP290 exons) that are 5' to the target CEP290 intron. For example, in embodiments in which a 5' trans-splicing molecule targets CEP290 intron 26, the coding domain includes functional CEP290 exons 2-26. In such embodiments featuring a 5' trans-splicing molecule having a coding domain including functional CEP290 exons 2-26, the coding domain is about 2,991 bp in length. In embodiments in which a 5' trans-splicing molecule targets CEP290 intron 27, the coding domain includes functional CEP290 exons 2-27. In such embodiments featuring a 5' trans-splicing molecule having a coding domain including functional CEP290 exons 2-27, the coding domain is about 3,103 bp in length. In embodiments in which a 5' trans-splicing molecule targets CEP290 intron 28, the coding domain includes functional CEP290 exons 2-28. In such embodiments featuring a 5' trans-splicing molecule having a coding domain including functional CEP290 exons 2-28, the coding domain is about 3,309 bp in length. In embodiments in which a 5' trans-splicing molecule targets CEP290 intron 29, the coding domain includes functional CEP290 exons 2-29. In such embodiments featuring a 5' trans-splicing molecule having a coding domain including functional CEP290 exons 2-29, the coding domain is about 3,461 bp in length. In embodiments in which a 5' trans-splicing molecule targets CEP290 intron 30, the coding domain includes functional CEP290 exons 2-30. In such embodiments featuring a 5' trans-splicing molecule having a coding domain including functional CEP290 exons 2-30, the coding domain is about 3,573 bp in length. The aforementioned embodiments of 5' CEP290-targeting trans-splicing molecules are illustrated in FIG. 21.

In some embodiments, the coding domain includes 25, 26, 27, 28, or 29 functional CEP290 exons.

In some embodiments, the coding domain includes a complementary DNA (cDNA) sequence. For example, one or more functional CEP290 exons within the coding domain can be a cDNA sequence. In some embodiments, the entire coding domain is a cDNA sequence. Additionally or alternatively, all or a portion of the coding domain, or one or more functional CEP290 exons thereof, can be a naturally-occurring sequence (e.g., a sequence having 90%, 91%, 92%, 93%, 94%, 95%, 96%, 97%, 98%, 99%, or 100% sequence identity with an endogenous CEP290 exon).

In some embodiments, all or a portion of the coding domain, or one or more functional CEP290 exons thereof, is a codon-optimized sequence in which a nucleic acid sequence has been modified, e.g., to enhance expression or stability, without resulting in a change in the encoded amino acid. Codon optimization may be performed in a manner such as that described in, e.g., U.S. Pat. Nos. 7,561,972, 7,561,973, and 7,888,112, each of which is incorporated herein by reference in its entirety. For delivery via a recombinant AAV, as described herein, in one embodiment, the coding domain can be a nucleic acid sequence of up to 4,000 nucleotide bases in length (e.g., from 3,000 to 4,000 nucleotide bases in length, from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length, e.g., about 3,108 nucleotide bases in length, about 3,285 nucleotide bases in length, about 3,375 nucleotide bases in length, about 3,503 nucleotide bases in length, about 3,630 nucleotide bases in length, about 3,540 nucleotide bases in length, about 3,363 nucleotide bases in length, about 3,273 nucleotide bases in length, about 3,145 nucleotide bases in length, or about 3,018 nucleotide bases in length).

Binding Domains

Trans-splicing molecules of the invention feature a binding domain configured to bind a target CEP290 intron. In one embodiment, the binding domain is a nucleic acid sequence complementary to a sequence of the target CEP290 pre-mRNA (e.g., a target CEP290 intron) to suppress endogenous target cis-splicing while enhancing trans-splicing between the trans-spicing molecule and the target CEP290 pre-mRNA, e.g., to create a chimeric molecule having a portion of endogenous CEP290 mRNA and the coding domain having one or more functional CEP290 exons. In some embodiments, the binding domain is in an antisense orientation to a sequence of the target CEP290 intron.

A 5' trans-splicing molecule will generally bind the target CEP290 intron 3' to the mutation. In one embodiment, the binding domain comprises a part of a sequence complementary to the target CEP290 intron.

In another embodiment, the binding domain is targeted to an intron sequence in close proximity to the 3' or 5' splice signals of a target intron. In still another embodiment, a binding domain sequence can bind to the target intron in addition to part of an adjacent exon.

Thus, in some instances, the binding domain binds specifically to the mutated endogenous target pre-mRNA to anchor the coding domain of the trans-splicing molecule to the pre-mRNA to permit trans-splicing to occur at the correct position in the target CEP290 gene. The spliceosome processing machinery of the nucleus may then mediate successful trans-splicing of the corrected exon for the mutated exon causing the disease.

In certain embodiments, the trans-splicing molecules feature binding domains that contain sequences on the target pre-mRNA that bind in more than one place. The binding domain may contain any number of nucleotides necessary to stably bind to the target pre-mRNA to permit trans-splicing to occur with the coding domain. In one embodiment, the binding domains are selected using mFOLD structural analysis for accessible loops (Zuker, Nucleic Acids Res. 2003, 31(13): 3406-3415).

Suitable target binding domains can be from 10 to 500 nucleotides in length. In some embodiments, the binding domain is from 20 to 400 nucleotides in length. In some embodiments, the binding domain is from 50 to 300 nucleotides in length. In some embodiments, the binding domain is from 100 to 200 nucleotides in length. In some embodiments, the binding domain is from 10-20 nucleotides in length (e.g., 10, 11, 12, 13, 14, 15, 16, 17, 18, 19, or 20 nucleotides in length), 20-30 nucleotides in length (e.g., 20, 21, 22, 23, 24, 25, 26, 27, 28, 29, or 30 nucleotides in length), 30-40 nucleotides in length (e.g., 30, 31, 32, 33, 34, 35, 36, 37, 38, 39, or 40 nucleotides in length), 40-50 nucleotides in length (e.g., 40, 41, 42, 43, 44, 45, 46, 47, 48, 49, 50 nucleotides in length), 50-60 nucleotides in length (e.g., 50, 51, 52, 53, 54, 55, 56, 57, 58, 59, or 60 nucleotides in length), 60-70 nucleotides in length (e.g., 60, 61, 62, 63, 64, 65, 66, 67, 68, 69, or 70 nucleotides in length), 70-80 nucleotides in length (e.g., 70, 71, 72, 73, 74, 75, 76, 77, 78, 79, or 80 nucleotides in length), 80-90 nucleotides in length (e.g., 80, 81, 82, 83, 84, 85, 86, 87, 88, 89, or 90 nucleotides in length), 90-100 nucleotides in length (e.g., 90, 91, 92, 93, 94, 95, 96, 97, 98, 99, or 100 nucleotides in length), 100-110 nucleotides in length (e.g., 100, 101, 102, 103, 104, 105, 106, 107, 108, 109, or 110 nucleotides in length), 110-120 nucleotides in length (e.g., 110, 111, 112, 113, 114, 115, 116, 117, 118, 119, or 120 nucleotides in length), 120-130 nucleotides in length (e.g., 120, 121, 122, 123, 124, 125, 126, 127, 128, 129, or 130 nucleotides in length), 130-140 nucleotides in length (e.g., 130, 131, 132, 133, 134, 135, 136, 137, 138, 139, or 140 nucleotides in length), 140-150 nucleotides in length (e.g., 140, 141, 142, 143, 144, 145, 146, 147, 148, 149, or 150 nucleotides in length), 150-160 nucleotides in length (e.g., 150, 151, 152, 153, 154, 155, 156, 157, 158, 159, or 160 nucleotides in length), 160-170 nucleotides in length (e.g., 160, 161, 162, 163, 164, 165, 166, 167, 168, 169, or 170 nucleotides in length), 170-180 nucleotides in length (e.g., 170, 171, 172, 173, 174, 175, 176, 177, 178, 179, or 180 nucleotides in length), 180-190 nucleotides in length (e.g., 180, 181, 182, 183, 184, 185, 186, 187, 188, 189, or 190 nucleotides in length), 190-200 nucleotides in length (e.g., 190, 191, 192, 193, 194, 195, 196, 197, 198, 199, or 200 nucleotides in length), 200-210 nucleotides in length, 210-220 nucleotides in length, 220-230 nucleotides in length, 230-240 nucleotides in length, 240-250 nucleotides in length, 250-260 nucleotides in length, 260-270 nucleotides in length, 270-280 nucleotides in length, 280-290 nucleotides in length, 290-300 nucleotides in length, 300-350 nucleotides in length, 350-400 nucleotides in length, 400-450 nucleotides in length, or 450-500 nucleotides in length. In some embodiments, the binding domain is about 150 nucleotides in length. In another embodiment, the target binding domains may include a nucleic acid sequence up to 750 nucleotides in length. In another embodiment, the target binding domains may include a nucleic acid sequence up to 1000 nucleotides in length. In another embodiment, the target binding domains may include a nucleic acid sequence up to 2000 nucleotides or more in length.

In some embodiments, the specificity of the trans-splicing molecule may be increased by increasing the length of the target binding domain. Other lengths may be used depending upon the lengths of the other components of the trans-splicing molecule.

The binding domain may be from 80% to 100% complementary to the target intron to be able to hybridize stably with the target intron. For example, in some embodiments, the binding domain is 80%, 81%, 82%, 83%, 84%, 85%, 86%, 87%, 88%, 89%, 90%, 91%, 92%, 93%, 94%, 95%, 96%, 97%, 98%, 99%, or 100% complimentary to the target intron. The degree of complementarity is selected by one of skill in the art based on the need to keep the trans-splicing molecule and the nucleic acid construct containing the necessary sequences for expression and for inclusion in the rAAV within a 3,000 or up to 4,000 nucleotide base limit. The selection of this sequence and strength of hybridization depends on the complementarity and the length of the nucleic acid.

Any of the aforementioned binding domains may bind to a binding site within intron 26 (SEQ ID NO: 85; e.g., at or 3' to a mutation, e.g., a substitution mutation at nucleotide 1,655 of intron 26), intron 27 (SEQ ID NO: 86), intron 28 (SEQ ID NO: 87), intron 29 (SEQ ID NO: 88), or intron 30 (SEQ ID NO: 89).

In certain instances of the invention, the trans-splicing molecule features a binding domain that binds to intron 26 of CEP290 (SEQ ID NO: 85) and includes a coding domain having functional CEP290 exons 2-26. In some embodiments, the binding site comprises any one or more of nucleotides 4,980 to 5,383 of SEQ ID NO: 85. In one embodiment, the binding site comprises any one or more of nucleotides 5,348 to 5,838 of SEQ ID NO: 85 (e.g., any one or more of nucleotides 5,348 to 5,700 of SEQ ID NO: 85, e.g., any one or more of nucleotides 5,400 to 5,600 of SEQ ID NO: 85, e.g., any one or more of nucleotides 5,460 to 5,560 of SEQ ID NO: 85, e.g., at least nucleotide 5,500 of SEQ ID NO: 85).

In other embodiments, the trans-splicing molecule features a binding domain that binds to intron 27 of CEP290 (SEQ ID NO: 86) and includes a coding domain having functional CEP290 exons 2-27. In some embodiments, the binding site comprises any one or more of nucleotides 120 to 680, nucleotides 710 to 2,200, or nucleotides 2,670 to 2,910 of SEQ ID NO: 86. In some embodiments, the binding site comprises any one or more of nucleotides 790 to 2,100 of SEQ ID NO: 86, e.g., any one or more of nucleotides 1,020 to 1,630 of SEQ ID NO: 86. In other embodiments, the binding site comprises any one or more of nucleotides 1,670 to 2,000 of SEQ ID NO: 86.

In some embodiments, the trans-splicing molecule features a binding domain that binds to intron 28 of CEP290 (SEQ ID NO: 87) and includes a coding domain having functional CEP290 exons 2-28. In some embodiments, the binding site comprises any one or more of nucleotides 1 to 390, nucleotides 410 to 560, or nucleotides 730 to 937 of SEQ ID NO: 87. In some embodiments, the binding site comprises any one or more of nucleotides 1 to 200 of SEQ ID NO: 87. In other embodiments, the binding site comprises any one or more of nucleotides 720 to 900 of SEQ ID NO: 87.

In some embodiments, the trans-splicing molecule features a binding domain that binds to intron 29 of CEP290 (SEQ ID NO: 88) and includes a coding domain having functional CEP290 exons 2-29. In some embodiments, the binding site comprises any one or more of nucleotides 1 to 600, nucleotides 720 to 940, or nucleotides 1,370 to 1,790 of SEQ ID NO: 88.

In other embodiments, the trans-splicing molecule features a binding domain that binds to intron 30 of CEP290 (SEQ ID NO: 89) and includes a coding domain having functional CEP290 exons 2-30. In some embodiments, the binding site comprises any one or more of nucleotides 880 to 1,240 of SEQ ID NO: 89, e.g., any one or more of nucleotides 950 to 1,240 of SEQ ID NO: 89, e.g., any one or more of nucleotides 1,060 to 1,240 of SEQ ID NO: 89.

Splicing Domains

The following splicing domains can be used in any of the trans-splicing molecules of the invention (e.g., any of the ABCA4 trans-splicing molecules or CEP290 trans-splicing molecules described herein).

The splicing domain can include a splice site, a branch point, and/or a PPT tract to mediate trans-splicing. In some embodiments, a splicing domain has a single splice site, which denotes that the splice site enables trans-splicing, but not cis-splicing, due to the lack of a corresponding splice site. In some embodiments, the splicing domains of the 3' trans-splicing molecule include a strong conserved branch point or branch site sequence, a polypyrimidine tract (PPT), and a 3' splice acceptor (AG or YAG) site and/or a 5' splice donor site. The splicing domains of the 5' trans-splicing molecule do not contain the branch point or PPT, but comprise a 5' splice acceptor/or 3' splice donor splice site.

Splicing domains may be selected by one of skill in the art according to known methods and principles. The splicing domain provides essential consensus motifs that are recognized by the spliceosome. The use of branch point and PPT follows consensus sequences required for performance of the two phosphoryl transfer reaction involved in trans-splicing. In one embodiment a branch point consensus sequence in mammals is YNYURAC (Y=pyrimidine; N=any nucleotide). A polypyrimidine tract is located between the branch point and the splice site acceptor and is important for different branch point utilization and 3' splice site recognition. Consensus sequences for the 5' splice donor site and the 3' splice region used in RNA splicing are well known in the art. In addition, modified consensus sequences that maintain the ability to function as 5' donor splice sites and 3' splice regions may be used. Briefly, in one embodiment, the 5' splice site consensus sequence is the nucleic acid sequence AG/GURAGU (where/indicates the splice site). In another embodiment the endogenous splice sites that correspond to the exon proximal to the splice site can be employed to maintain any splicing regulatory signals.

In one embodiment, a suitable 5' splice site with spacer is: 5'-GTA AGA GAG CTC GTT GCG ATA TTA T-3' (SEQ ID NO: 1). In one embodiment, a suitable 5' splice site is AGGT.

In one embodiment, a suitable 3' trans-splicing molecule branch site is 5'-TACTAAC-3'. In one embodiment, a suitable 3' splice site is: 5'-TAC TAA CTG GTA CCT CTT CTT TTT TTT CTG CAG-3' (SEQ ID NO: 2) or 5'-CAGGT-3'. In one embodiment, a suitable 3' trans-splicing molecule PPT is: 5'-TGG TAC CTC TTC TTT TTT TTC TG-3' (SEQ ID NO: 3).

Additional Components or Modifications

In some embodiments of any of the trans-splicing molecules of the invention (e.g., any of the ABCA4 trans-splicing molecules or CEP290 trans-splicing molecules described herein), the splicing domain is included as part of an artificial intron, which may include one or more additional components. For example, a spacer region may be included within an artificial intron to separate the splicing domain from the target binding domain in the trans-splicing molecule. The spacer region may be designed to include features such as (i) stop codons which would function to block translation of any unspliced trans-splicing molecule and/or (ii) sequences that enhance trans-splicing to the target pre-mRNA. The spacer may be between 3 to 25 nucleotides or more depending upon the lengths of the other components of the trans-splicing molecule and the rAAV limitations. In one embodiment, a suitable 5' trans-splicing molecule spacer is AGA TCT CGT TGC GAT ATT AT (SEQ ID NO: 4). In one embodiment, a suitable 3' spacer is: 5'-GAG AAC ATT ATT ATA GCG TTG CTC GAG-3' (SEQ ID NO: 5).

Still other optional components of the trans-splicing molecules (e.g., as part of artificial introns) include mini introns, and intronic or exonic enhancers (e.g., intronic splice enhancers, e.g., downstream intronic splice enhancers) or silencers that would regulate the trans-splicing.

In another embodiment, the trans-splicing molecule further comprises (e.g., as part of an artificial intron) at least one safety sequence incorporated into the spacer, binding domain, or elsewhere in the trans-splicing molecule to prevent nonspecific trans-splicing. This is a region of the trans-splicing molecule that covers elements of the 3' and/or 5' splice site of the trans-splicing molecule by relatively weak complementarity, preventing non-specific trans-splicing. The trans-splicing molecule is designed in such a way that upon hybridization of the binding/targeting portion(s) of the trans-splicing molecule, the 3' or 5' splice site is uncovered and becomes fully active. Such safety sequences comprise a complementary stretch of cis-sequence (or could be a second, separate, strand of nucleic acid) which binds to one or both sides of the trans-splicing molecule branch point, pyrimidine tract, 3' splice site and/or 5' splice site (splicing elements), or could bind to parts of the splicing elements themselves. The binding of the safety sequence may be disrupted by the binding of the target binding region of the trans-splicing molecule to the target pre-mRNA, thus exposing and activating the splicing elements (making them available to trans-splice into the target pre-mRNA). In another embodiment, the trans-splicing molecule has 3' UTR sequences or ribozyme sequences added to the 3' or 5' end.

In an embodiment, splicing enhancers such as, for example, sequences referred to as exonic splicing enhancers may also be included in the structure of an artificial intron. Additional features can be added to the artificial intron, such as polyadenylation signals to modify RNA expression/stability, or 5' splice sequences to enhance splicing, additional binding regions, safety-self complementary regions, additional splice sites, or protective groups to modulate the stability of the molecule and prevent degradation. In addition, stop codons may be included in the trans-splicing molecule (e.g., as part of the artificial intron) structure to prevent translation of unspliced trans-splicing molecules. Additional elements, such as a 3' hairpin structure, circularized RNA, nucleotide base modification, or synthetic analogs can be incorporated into trans-splicing molecules to promote or facilitate nuclear localization and spliceosomal incorporation, and intra-cellular stability.

In some embodiments, binding of a trans-splicing molecule to the target pre-mRNA is mediated by complementarity (i.e. based on base-pairing characteristics of nucleic acids), triple helix formation, or protein-nucleic acid interaction (as described in documents cited herein). In one embodiment, the nucleic acid trans-splicing molecule includes DNA, RNA, or DNA/RNA hybrid molecules, wherein the DNA or RNA is either single or double stranded. Also included herein are RNAs or DNAs, which can hybridize to one of the aforementioned RNAs or DNAs, preferably under stringent conditions, for example, at 60° C. in 2.5× SSC buffer and several washes at 37° C. at a lower buffer concentration, for example, 0.5×SSC buffer. These nucleic acids can encode proteins exhibiting lipid phosphate phosphatase activity and/or association with plasma membranes. When trans-splicing molecules are synthesized in vitro, such trans-splicing molecules can be modified at the base moiety, sugar moiety, or phosphate backbone, for example, to improve stability of the molecule, hybridization to the target mRNA, transport into the cell, stability in the cells to enzymatic cleavage, etc. For example, modification of a trans-splicing molecule to reduce the overall charge can enhance the cellular uptake of the molecule. In addition modifications can be made to reduce susceptibility to nuclease or chemical degradation. The nucleic acid molecules may be synthesized in such a way as to be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing intracellular stability and half-life (see also above for oligonucleotides). Possible modifications are known to the art. Modifications, which may be made to the structure of synthetic trans-splicing molecules include backbone modifications.

III. Recombinant AAV Molecules

Any suitable nucleic acid vector may be used in conjunction with the present compositions and methods to design and assemble the components of the trans-splicing molecule and a recombinant adeno-associated virus (AAV). In one embodiment, the vector is a recombinant AAV carrying the trans-splicing molecule and driven by a promoter that expresses a trans-splicing molecule in selected cells of a subject. Methods for assembly of the recombinant vectors are known in the art. See, e.g., Ausubel et al., *Current Protocols in Molecular Biology*, John Wiley & Sons, New York, 1989; Kay, M. A. et al., *Nat. Medic,* 2001, 7(I):33-40; and Walther W. and Stein U., *Drugs* 2000, 60(2):249-71.

In certain embodiments described herein, the trans-splicing molecule carrying the ABCA4 gene binding and coding domains is delivered to the selected cells, e.g., photoreceptor cells, in need of treatment by means of an AAV vector. More than 30 naturally occurring serotypes of AAV are available. Many natural variants in the AAV capsid exist, allowing identification and use of an AAV with properties specifically suited for ocular cells. AAV viruses may be engineered by conventional molecular biology techniques, making it possible to optimize these particles for cell specific delivery of the trans-splicing molecule nucleic acid sequences, for minimizing immunogenicity, for tuning stability and particle lifetime, for efficient degradation, for accurate delivery to the nucleus, etc.

The expression of the trans-splicing molecules described herein can be achieved in the selected cells through delivery by recombinantly engineered AAVs or artificial AAVs that contain sequences encoding the desired trans-splicing molecule. The use of AAVs is a common mode of exogenous delivery of DNA as it is relatively non-toxic, provides efficient gene transfer, and can be easily optimized for specific purposes. Among the well-characterized serotypes of AAVs isolated from human or non-human primates, human serotype 2 has been widely used for efficient gene transfer experiments in different target tissues and animal models. Other AAV serotypes include, but are not limited to, AAV1, AAV3, AAV4, AAV5, AAV6, AAV7, AAV8, and AAV9. Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9 or other known and unknown AAV serotypes. In one embodiment, the ITRs are from AAV2. These ITRs or other AAV components may be readily isolated using techniques available to those of skill in the art from an AAV serotype. Such AAV may be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank, PubMed, or the like.

Desirable AAV fragments for assembly into vectors include the cap proteins, including the vp1, vp2, vp3, and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is utilized with the ITRs from an AAV having a different capsid protein, are useful in the invention. In one embodiment, the AAV is AAV2/5 (i.e., an AAV having AAV2 ITRs and an AAVS capsid). In another embodiment, the AAV is AAV2/8 (i.e., an AAV having AAV2 ITRs and an AAV8 capsid). In one embodiment, the AAV includes an AAV8 capsid. Such AAV8 capsid includes the amino acid sequence found under NCBI Reference Sequence: YP_077180.1 (SEQ ID NO: 56). In another embodiment, the AAV8 capsid includes a capsid encoded by nt 2121 to 4337 of GenBank accession: AF513852.1 (SEQ ID NO: 57).

In one embodiment, the AAV includes a capsid sequence derived from AAV8. In some embodiments, the AAV derived from AAV8 is AAV8(b), described in U.S. Pat. No. 9,567,376, which is incorporated herein by reference in its entirety. AAV(b) (SEQ ID NO: 58) comprises the amino acid sequence of Pro-Glu-Arg-Thr-Ala-Met-Ser-Leu-Pro at amino acid positions 587-595 as compared to wildtype AAV8. In another embodiment, the AAV8(b) capsid is encoded by SEQ ID NO: 59.

In one embodiment, the vectors useful in compositions and methods described herein contain, at a minimum, sequences encoding a selected AAV serotype capsid, e.g., an AAV2 capsid, or a fragment thereof. In another embodiment, useful vectors contain, at a minimum, sequences encoding a selected AAV serotype rep protein, e.g., AAV2 rep protein, or a fragment thereof. Optionally, such vectors may contain both AAV cap and rep proteins. In vectors in which both AAV rep and cap are provided, the AAV rep and AAV cap sequences can both be of one serotype origin, e.g., an AAV2 origin.

Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector described in U.S. Pat. No. 7,282,199, which is incorporated by reference herein.

A suitable recombinant AAV (rAAV) is generated by culturing a host cell which contains a nucleic acid sequence encoding an AAV serotype capsid protein, or fragment thereof, as defined herein; a functional rep gene; a minigene composed of, e.g., AAV ITRs and the trans-splicing molecule nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

In one embodiment, the AAV includes a promoter (or a functional fragment of a promoter). The selection of the promoter to be employed in the rAAV may be made from among a wide number of constitutive or inducible promoters that can express the selected transgene in the desired target cell. See, e.g., the list of promoters identified in International Patent Publication No. WO 2014/012482, incorporated by reference herein. In one embodiment, the promoter is cell-specific. The term "cell-specific" means that the particular promoter selected for the recombinant vector can direct expression of the selected transgene in a particular cell type. In one embodiment, the promoter is specific for expression of the transgene in photoreceptor cells. In another embodiment, the promoter is specific for expression in the rods and/or cones. In another embodiment, the promoter is specific for expression of the transgene in retinal pigment epithelium (RPE) cells. In another embodiment, the promoter is specific for expression of the transgene in ganglion cells. In another embodiment, the promoter is specific for expression of the transgene in Mueller cells. In another embodiment, the promoter is specific for expression of the transgene in bipolar cells. In another embodiment, the promoter is specific for expression of the transgene in horizontal cells. In another embodiment, the promoter is specific for expression of the transgene in amacrine cells. In another embodiment, the transgene is expressed in any of the above noted cells.

In another embodiment, the promoter is the native promoter for the target gene to be expressed. Useful promoters include, without limitation, a rod opsin promoter, a red-green opsin promoter, a blue opsin promoter, a cGMP-phosphodiesterase promoter, a mouse opsin promoter, a rhodopsin promoter, an alpha-subunit of cone transducing, a beta phosphodiesterase (PDE) promoter, a retinitis pigmentosa promoter, a NXNL2/NXNL1 promoter, the RPE65 promoter, the retinal degeneration slow/peripherin 2 (Rds/perph2) promoter, and the VMD2 promoter.

Other conventional regulatory sequences contained in the mini-gene or rAAV are also disclosed in documents such as WO 2014/124282 and others cited and incorporated by reference herein. One of skill in the art may make a selection among these, and other, expression control sequences without departing from the scope described herein An AAV minigene may include the trans-splicing molecule described herein and its regulatory sequences, and 5' and 3' AAV ITRs. In one embodiment, the ITRs of AAV serotype 2 are used. In another embodiment, the ITRs of AAV serotype 5 or 8 are used. However, ITRs from other suitable serotypes may be selected. In some embodiments, the minigene is packaged into a capsid protein and delivered to a selected host cell.

The minigene, rep sequences, cap sequences, and helper functions required for producing the rAAV may be delivered to the packaging host cell in the form of any genetic element which transfers the sequences carried thereon. The selected genetic element may be delivered by any suitable method, including those described herein. The methods used to construct any embodiment described herein are known to those with skill in nucleic acid manipulation and include genetic engineering, recombinant engineering, and synthetic techniques. See, e.g., Sambrook et al., *Molecular Cloning: A Laboratory Manual*, Cold Spring Harbor Press, Cold Spring Harbor, NY Similarly, methods of generating rAAV virions are well known and the selection of a suitable method is not a limitation on the present invention. See, e.g., K. Fisher et al., *J. Virol.,* 1993 70: 520-532 and U.S. Pat. No. 5,478,745, each of which is incorporated by reference herein.

In another embodiment, the trans-splicing molecule minigene is prepared in a proviral plasmid, such as those disclosed in International Patent Publication No. WO 2012/158757, incorporated herein by reference. Such a proviral plasmid contains a modular recombinant AAV genome comprising in operative association comprising: a wildtype 5' AAV2 ITR sequence flanked by unique restriction sites that permit ready removal or replacement of said ITR; a promoter comprising a 49-nucleic acid cytomegalovirus sequence upstream of a cytomegalovirus (CMV)-chicken beta actin sequence, or a photoreceptor-specific promoter/enhancer, the promoter flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. The trans-splicing molecule described herein can be inserted into the site of a multi-cloning poly linker, wherein the trans-splicing molecule is operatively linked to, and under the regulatory control of, the promoter. A bovine growth hormone polyadenylation sequence flanked by unique restriction sites that permit ready removal or replacement of said polyA sequence; and a wildtype 3' AAV2 ITR sequence flanked by unique restriction sites that permit ready removal or replacement of the 3' ITR; are also part of this plasmid. The plasmid backbone comprises the elements necessary for replication in bacterial cells, e.g., a kanamycin resistance gene, and is itself flanked by transcriptional terminator/insulator sequences.

In one embodiment, a proviral plasmid comprises: (a) a modular recombinant AAV genome comprising in operative association comprising: (i) a wildtype 5' AAV2 ITR sequence flanked by unique restriction sites that permit ready removal or replacement of said ITR; (ii) a promoter comprising (A) a 49-nucleic acid CMV sequence upstream of a CMV-chicken beta actin sequence; (b) a photoreceptor-specific promoter/enhancer; or (c) a neuronal cell-specific promoter/enhancer. The promoter is flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. Also part of this proviral plasmid is a multi-cloning polylinker sequence that permits insertion of a trans-splicing molecule sequence including any of those described herein, wherein the trans-splicing molecule is operatively linked to, and under the regulatory control of, the promoter; a bovine growth hormone polyadenylation sequence flanked by unique restriction sites that permit ready removal or replacement of said polyA sequence; and a wildtype 3' AAV2 ITR sequence flanked by unique restriction sites that permit ready removal or replacement of the 3' ITR. The proviral plasmid also contains a plasmid backbone comprising the elements necessary for replication in bacterial cells, and further comprising a kanamycin resistance gene, said plasmid backbone flanked by transcriptional terminator/insulator sequences. The proviral plasmid described herein may also contain in the plasmid backbone a non-coding lambda phage 5.1 kb stuffer sequence to increase backbone length and prevent reverse packaging of non-functional AAV genomes.

In some embodiments, a proviral plasmid contains multiple copies of a trans-splicing molecule. For example, the present invention features trans-splicing molecules that are less than half the packaging limit for AAV and can therefore be repeated once, twice, three times, four times, five times, six times, seven times, eight times, nine times, 10 times, 11 times, 12 times, 13 times, 14 times, 15 times, 16 times, 17 times, 18 times, 19 times, 20 times, or more on a single proviral plasmid.

In yet a further aspect, the promoter of the proviral plasmid is modified to reduce the size of the promoter to permit larger trans-splicing molecule sequences to be inserted in the rAAV. In one embodiment, the CMV/CBA hybrid promoter, which normally includes a non-coding exon and intron totaling about 1,000 base pairs, is replaced with a 130-base pair chimeric intron, as described in International Patent Publication No. WO 2017/087900, which is incorporated herein by reference in its entirety.

These proviral plasmids are then employed in currently conventional packaging methodologies to generate a recombinant virus expressing the trans-splicing molecule transgene carried by the proviral plasmids. Suitable production cell lines are readily selected by one of skill in the art. For example, a suitable host cell can be selected from any biological organism, including prokaryotic (e.g., bacterial) cells, and eukaryotic cells, including, insect cells, yeast cells and mammalian cells. Briefly, the proviral plasmid is transfected into a selected packaging cell, where it may exist transiently. Alternatively, the minigene or gene expression cassette with its flanking ITRs is stably integrated into the genome of the host cell, either chromosomally or as an episome. Suitable transfection techniques are known and may readily be utilized to deliver the recombinant AAV genome to the host cell. Typically, the proviral plasmids are cultured in the host cells which express the cap and/or rep proteins. In the host cells, the minigene consisting of the trans-splicing molecule with flanking AAV ITRs is rescued and packaged into the capsid protein or envelope protein to form an infectious viral particle. Thus, a recombinant AAV infectious particle is produced by culturing a packaging cell carrying the proviral plasmid in the presence of sufficient viral sequences to permit packaging of the gene expression cassette viral genome into an infectious AAV envelope or capsid.

IV. Pharmaceutical Compositions and Kits

Provided herein are pharmaceutical compositions including a nucleic acid trans-splicing molecule, a proviral plasmid, or a rAAV comprising the nucleic acid trans-splicing molecule described herein. In some embodiments, the pharmaceutical composition includes any of the 5' trans-splicing molecules described herein. In other embodiments, the pharmaceutical composition includes any of the 3' trans-splicing molecules described herein. In some embodiments, the pharmaceutical composition includes a 5' trans-splicing molecule and a 3' trans-splicing molecule, e.g., wherein the 5' trans-splicing molecule and the 3' trans-splicing molecule together contain functional ABCA4 exons 1-50 and bind the same target ABCA4 intron.

The pharmaceutical compositions described herein may be assessed for contamination by conventional methods and then formulated into a pharmaceutical composition intended for a suitable route of administration. Still other compositions containing the trans-splicing molecule, e.g., naked DNA or as protein, may be formulated similarly with a suitable carrier. Such formulation involves the use of a pharmaceutically and/or physiologically acceptable vehicle or carrier, particularly directed for administration to the target cell. In one embodiment, carriers suitable for administration to the target cells include buffered saline, an isotonic sodium chloride solution, or other buffers, e.g., HEPES, to maintain pH at appropriate physiological levels, and, optionally, other medicinal agents, pharmaceutical agents, stabilizing agents, buffers, carriers, adjuvants, diluents, etc.

In some embodiments, the carrier is a liquid for injection. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In other embodiments, compositions containing trans-splicing molecules described herein include a surfactant. Useful surfactants, such as Pluronic F68 (Poloxamer 188, also known as LUTROL® F68) may be included as they prevent AAV from sticking to inert surfaces and thus ensure delivery of the desired dose. As an example, one illustrative composition designed for the treatment of the ocular diseases described herein comprises a recombinant adeno-associated vector carrying a nucleic acid sequence encoding 3' trans-splicing molecule as described herein, under the control of regulatory sequences which express the trans-splicing molecule in an ocular cell of a mammalian subject, and a pharmaceutically acceptable carrier. The carrier is isotonic sodium chloride solution and includes a surfactant Pluronic F68. In one embodiment, the trans-splicing molecule is any of those described herein.

In yet another exemplary embodiment, the composition comprises a recombinant AAV2/5 pseudotyped adeno-associated virus carrying a 3' or 5' trans-splicing molecule for ABCA4 gene replacement, the nucleic acid sequence under the control of promoter which directs expression of the trans-splicing molecule in said photoreceptor cells, wherein the composition is formulated with a carrier and additional components suitable for subretinal injection. In still another embodiment, the composition or components for production or assembly of this composition, including carriers, rAAV particles, surfactants, and/or the components for generating the rAAV, as well as suitable laboratory hardware to prepare the composition, may be incorporated into a kit.

In some instances, the composition comprises a recombinant AAV2/5 pseudotyped adeno-associated virus carrying a 5' trans-splicing molecule for CEP290 gene replacement, the nucleic acid sequence under the control of promoter which directs expression of the trans-splicing molecule in said photoreceptor cells, wherein the composition is formulated with a carrier and additional components suitable for subretinal injection. In still another embodiment, the composition or components for production or assembly of this composition, including carriers, rAAV particles, surfactants, and/or the components for generating the rAAV, as well as suitable laboratory hardware to prepare the composition, may be incorporated into a kit.

Additionally provided herein are kits containing a first pharmaceutical composition comprising a 5' trans-splicing molecule and a second pharmaceutical composition comprising a 3' trans-splicing molecule, e.g., wherein the 5' trans-splicing molecule and the 3' trans-splicing molecule together contain functional ABCA4 exons 1-50 and bind the same target ABCA4 intron (e.g., wherein the trans-splicing molecules are packaged in any AAV vectors described herein). In some embodiments, the kit includes instructions for mixing the two pharmaceutical compositions prior to administration.

Additionally provided herein are kits containing a first pharmaceutical composition comprising a 5' trans-splicing molecule to bind a target CEP290 intron.

V. Methods

The compositions described above involving ABCA4 trans-splicing are useful in methods of treating diseases or disorders caused by a mutation in the ABCA4 gene, such as a Stargardt Disease (e.g., Stargardt Disease 1) including delaying or ameliorating symptoms associated with the disease described herein. Such methods involve contacting a target ABCA4 gene (e.g., ABCA4 pre-mRNA) with a trans-splicing molecule as described herein (e.g., one or more of a 3'trans-splicing molecule, 5' trans-splicing molecule, or both 3' and 5' trans-splicing molecule as described herein), under conditions in which a coding domain of the trans-splicing molecule is spliced to the target ABCA4 gene to replace a part of the targeted gene carrying one or more defects or mutations, with a functional (i.e., healthy), or normal or wildtype or corrected mRNA of the targeted gene, in order to correct expression of ABCA4 in the target cell. Thus, the methods and compositions are used to treat the ocular diseases/pathologies associated with the specific mutations and/or gene expression.

In one embodiment, the contacting involves direct administration to the affected subject. In another embodiment, the contacting may occur ex vivo to the cultured cell and the treated ocular cell reimplanted in the subject. In one embodiment, the method involves administering a rAAV carrying a 3' trans-splicing molecule. In another embodiment, the method involves administering a rAAV carrying a 5' trans-splicing molecule. In still another embodiment, the method involves administering a mixture of rAAV carrying a 3' trans-splicing molecule and rAAV carrying a 5' trans-splicing molecule. These methods comprise administering to a subject in need thereof an effective concentration of a composition of any of those described herein.

In some embodiments, the methods include selecting one or more trans-splicing molecules for treating a subject having a disorder associated with a mutation in ABCA4, such as Stargardt Disease (e.g., Stargardt Disease 1). Such selection can be based on the genotype of the subject. In some embodiments, a disorder associated with ABCA4 may be an autosomal recessive disorder. In some instances, the subject is homozygous or compound heterozygous for the mutation in ABCA4. Methods of screening for and identifying particular mutations in ABCA4 are known in the art.

In other instances, the compositions described above involving CEP290 trans-splicing are useful in methods of treating diseases or disorders caused by a mutation in the CEP290 gene, such as Leber congenital amourosis (e.g., LCA 10) including delaying or ameliorating symptoms associated with the disease described herein. Such methods involve contacting a target CEP290 gene (e.g., CEP290 pre-mRNA) with a trans-splicing molecule as described herein (e.g., a 5' trans-splicing molecule), under conditions in which a coding domain of the trans-splicing molecule is spliced to the target CEP290 gene to replace a part of the targeted gene carrying one or more defects or mutations, with a functional (i.e., healthy), or normal or wildtype or corrected mRNA of the targeted gene, in order to correct expression of CEP290 in the target cell. Thus, the methods and compositions are used to treat the ocular diseases/pathologies associated with the specific mutations and/or gene expression. Methods of the invention include correcting a pathogenic point mutation in intron 26 (e.g., at nucleotide 1,655 of intron 26) of CEP290 by administering a 5' trans-splicing molecule (e.g., any of the 5' trans-splicing molecules described herein), or a pharmaceutical composition thereof. Thus, the invention provides methods of treating a subject having a disease or disorder associated with a mutation in CEP290 (e.g., a disease or disorder associated with a mutation in intron 26 of CEP290, e.g., at nucleotide 1,655 of intron 26) by administering a trans-splicing molecule described herein. Any of the aforementioned trans-splicing molecules can be included in a pharmaceutical composition (e.g., a single pharmaceutical composition including both molecules, either pre-prepared or admixed prior to administration, e.g., as part of a kit).

In one embodiment, the contacting involves direct administration to the affected subject. In another embodiment, the contacting may occur ex vivo to the cultured cell and the treated ocular cell reimplanted in the subject. In one embodiment, the method involves administering a rAAV carrying a 5' trans-splicing molecule. These methods comprise administering to a subject in need thereof an effective concentration of a composition of any of those described herein.

In some embodiments, the methods include selecting one or more trans-splicing molecules for treating a subject having a disorder associated with a mutation in CEP290, such as LCA 10. Such selection can be based on the genotype of the subject. In some embodiments, a disorder associated with CEP290 may be an autosomal recessive disorder. In some instances, the subject is homozygous or compound heterozygous for the mutation in CEP290. Methods of screening for and identifying particular mutations in CEP290 are known in the art.

Single Trans-Splicing Molecules for Correcting a Single Mutation

Methods of the invention include selecting a single trans-splicing molecule based on the location of a single mutation in ABCA4 (e.g., a mutation of one allele of the subject). In some instances in the context of autosomal recessive mutations, correction of just one of two mutations can be sufficient to restore functional protein activity, for example, wherein the second allele has a mutation on the opposite portion of the ABCA4 gene, out of range of a single AAV-delivered trans-splicing molecule configured to correct the first mutation.

Thus, in some embodiments, methods of the invention include selecting a single trans-splicing molecule to correct a single mutation on the 5' portion of the target gene, e.g., without regard to the location of the mutation in the other allele. In one embodiment, the mutated exon is exon 1, the target intron is intron 19, 22, 23, or 24, and the coding domain includes a functional ABCA4 exon 1. In one embodiment, exon 1 or exon 2 is mutated, the target intron is intron 19, 22, 23, or 24, and the coding domain includes functional ABCA4 exons 1 and 2. In one embodiment, one of exons 1, 2, and 3 is mutated, the target intron is intron 19, 22, 23, or 24, and the coding domain includes functional ABCA4 exons 1-3. In one embodiment, one of exons 1, 2, 3, and 4 is mutated, the target intron is intron 19, 22, 23, or 24, and the coding domain includes functional ABCA4 exons 1-4. In one embodiment, one of exons 1, 2, 3, 4, and 5 is mutated, the target intron is intron 19, 22, 23, or 24, and the coding domain includes functional ABCA4 exons 1-5. In one embodiment, one of exons 1, 2, 3, 4, 5, and 6 is mutated, the target intron is intron 19, 22, 23, or 24, and the coding domain includes functional ABCA4 exons 1-6. In one embodiment, one of exons 1, 2, 3, 4, 5, 6, or 7 is mutated, the target intron is intron 19, 22, 23, or 24, and the coding domain includes functional ABCA4 exons 1-7. In one embodiment, one of exons 1, 2, 3, 4, 5, 6, 7, or 8 is mutated, the target intron is intron 19, 22, 23, or 24, and the coding domain includes functional ABCA4 exons 1-8. In one embodiment, one of exons 1, 2, 3, 4, 5, 6, 7, 8, or 9 is mutated, the target intron is intron 19, 22, 23, or 24, and the coding domain includes functional ABCA4 exons 1-9. In one embodiment, one of exons 1, 2, 3, 4, 5, 6, 7, 8, 9, or 10 is mutated, the target intron is intron 19, 22, 23, or 24, and the coding domain includes functional ABCA4 exons 1-10. In one embodiment, one of exons 1, 2, 3, 4, 5, 6, 7, 8, 9, 10, or 11 is mutated, the target intron is intron 19, 22, 23, or 24, and the coding domain includes functional ABCA4 exons 1-11. In one embodiment, one of exons 1, 2, 3, 4, 5, 6, 7, 8, 9, 10, 11, or 12 is mutated, the target intron is intron 19, 22, 23, or 24, and the coding domain includes functional ABCA4 exons 1-12. In one embodiment, one of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In one embodiment, one of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In one embodiment, one of exons 1, 2, 3, 4, 5, 6, 7, 8, 9, 10, 11, 12, 13, or 14 is mutated, the target intron is intron 19, 22, 23, or 24, and the coding domain includes functional ABCA4 exons 1-14. In one embodiment, one of exons 1, 2, 3, 4, 5, 6, 7, 8, 9, 10, 11, 12, 13, 14, or 15 is mutated, the target intron is intron 19, 22, 23, or 24, and the coding domain includes functional ABCA4 exons 1-15. In one embodiment, one of exons 1, 2, 3, 4, 5, 6, 7, 8, 9, 10, 11, 12, 13, 14, 15, or 16 is mutated, the target intron is intron 19, 22, 23, or 24, and the coding domain includes functional ABCA4 exons 1-16. In one embodiment, one of exons 1, 2, 3, 4, 5, 6, 7, 8, 9, 10, 11, 12, 13, 14, 15, 16, or 17 is mutated, the target intron is intron 19, 22, 23, or 24, and the coding domain includes functional ABCA4 exons 1-17. In one embodiment, one of exons 1, 2, 3, 4, 5, 6, 7, 8, 9, 10, 11, 12, 13, 14, 15, 16, 17, or 18 is mutated, the target intron is intron 19, 22, 23, or 24, and the coding domain includes functional ABCA4 exons 1-18. In one embodiment, one of exons 1, 2, 3, 4, 5, 6, 7, 8, 9, 10, 11, 12, 13, 14, 15, 16, 17, 18, or 19 is mutated, the target intron is intron 19, 22, 23, or 24, and the coding domain includes functional ABCA4 exons 1-19. In one embodiment, one of exons 1, 2, 3, 4, 5, 6, 7, 8, 9, 10, 11, 12, 13, 14, 15, 16, 17, 18, 19, or 20 is mutated, the target intron is intron 22, 23, or 24, and the coding domain includes functional ABCA4 exons 1-20. In one embodiment, one of exons 1, 2, 3, 4, 5, 6, 7, 8, 9, 10, 11, 12, 13, 14, 15, 16, 17, 18, 19, 20, or 21 is mutated, the target intron is intron 22, 23, or 24, and the coding domain includes functional ABCA4 exons 1-21. In one embodiment, one of exons 1, 2, 3, 4, 5, 6, 7, 8, 9, 10, 11, 12, 13, 14, 15, 16, 17, 18, 19, 20, 21, or 22 is mutated, the target intron is intron 22, 23, or 24, and the coding domain includes functional ABCA4 exons 1-22. In one embodiment, one of exons 1, 2, 3, 4, 5, 6, 7, 8, 9, 10, 11, 12, 13, 14, 15, 16, 17, 18, 19, 20, 21, 22, or 23 is mutated, the target intron is intron 23 or 24, and the coding domain includes functional ABCA4 exons 1-23. In one embodiment, one of exons 1, 2, 3, 4, 5, 6, 7, 8, 9, 10, 11, 12, 13, 14, 15, 16, 17, 18, 19, 20, 21, 22, 23, or 24 is mutated, the target intron is intron 24, and the coding domain includes functional ABCA4 exons 1-24.

Alternatively, in instances in which a mutation is on the 3' portion of the target gene, a 3' trans-splicing molecule is selected to correct the mutation, e.g., without regard to the location of the mutation on the other allele. In one embodiment, one of exons 23, 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, and the coding domain includes functional ABCA4 exons 23-50. In one embodiment, one of exons 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22 or 23, and the coding domain includes functional ABCA4 exons 24-50. In one embodiment, one of exons 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 25-50. In one embodiment, one of exons 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 26-50. In one embodiment, one of exons 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 27-50. In one embodiment, one of exons 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 28-50. In one embodiment, one of exons 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 29-50. In one embodiment, one of exons 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 30-50. In one embodiment, one of exons 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 31-50. In one embodiment, one of exons 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 32-50. In one embodiment, one of exons 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 33-50. In one embodiment, one of exons 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 34-50. In one embodiment, one of exons 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 35-50. In one embodiment, one of exons 36, 37, 38, 39, 40, 41, 42, 43, 44, 45, 46, 47, 48, 49, or 50 is mutated, the target intron is intron 22, 23, or 24, and the coding domain includes functional ABCA4 exons 36-50. In one embodiment, one of exons 37, 38, 39, 40, 41, 42, 43, 44, 45, 46, 47, 48, 49, or 50 is mutated, the target intron is intron 22, 23, or 24, and the coding domain includes functional ABCA4 exons 37-50. In one embodiment, one of exons 38, 39, 40, 41, 42, 43, 44, 45, 46, 47, 48, 49, or 50 is mutated, the target intron is intron 22, 23, or 24, and the coding domain includes functional ABCA4 exons 38-50. In one embodiment, one of exons 39, 40, 41, 42, 43, 44, 45, 46, 47, 48, 49, or 50 is mutated, the target intron is intron 22, 23, or 24, and the coding domain includes functional ABCA4 exons 39-50. In one embodiment, one of exons 40, 41, 42, 43, 44, 45, 46, 47, 48, 49, or 50 is mutated, the target intron is intron 22, 23, or 24, and the coding domain includes functional ABCA4 exons 40-50. In one embodiment, one of exons 41, 42, 43, 44, 45, 46, 47, 48, 49, or 50 is mutated, the target intron is intron 22, 23, or 24, and the coding domain includes functional ABCA4 exons 41-50. In one embodiment, one of exons 42, 43, 44, 45, 46, 47, 48, 49, or 50 is mutated, the target intron is intron 22, 23, or 24, and the coding domain includes functional ABCA4 exons 42-50. In one embodiment, one of exons 43, 44, 45, 46, 47, 48, 49, or 50 is mutated, the target intron is intron 22, 23, or 24, and the coding domain includes functional ABCA4 exons 43-50. In one embodiment, one of exons 44, 45, 46, 47, 48, 49, or 50 is mutated, the target intron is intron 22, 23, or 24, and the coding domain includes functional ABCA4 exons 44-50. In one embodiment, one of exons 45, 46, 47, 48, 49, or 50 is mutated, the target intron is intron 22, 23, or 24, and the coding domain includes functional ABCA4 exons 45-50. In one embodiment, one of exons 46, 47, 48, 49, or 50 is mutated, the target intron is intron 22, 23, or 24, and the coding domain includes functional ABCA4 exons 46-50. In one embodiment, one of exons 47, 48, 49, or 50 is mutated, the target intron is intron 22, 23, or 24, and the coding domain includes functional ABCA4 exons 47-50. In one embodiment, one of exons 48, 49, or 50 is mutated, the target intron is intron 22, 23, or 24, and the coding domain includes functional ABCA4 exons 48-50. In one embodiment, one of exons 49 or 50 is mutated, the target intron is intron 22, 23, or 24, and the coding domain includes functional ABCA4 exons 49 or 50. In one embodiment, exon 50 is mutated, the target intron is intron 22, 23, or 24, and the coding domain includes functional ABCA4 exon 50.

Single Trans-Splicing Molecules for Correcting Multiple Mutations

Methods of the invention include selecting a single trans-splicing molecule based on the location of a mutation in ABCA4 in each allele of the subject, when two mutations are either on a 5' portion of the gene or the 3' portion of the gene, such that a single trans-splicing molecule capable of being packaged in an AAV vector is capable of spanning both mutations, thereby correcting both mutations.

For example, in instances in which both mutations occur on the 5' portion of the target gene, a 5' trans-splicing molecule is selected to correct both mutations. In one embodiment, the mutated exon is exon 1 (i.e., both mutations are in exon 1), the target intron is intron 19, 22, 23, or 24, and the coding domain includes a functional ABCA4 exon 1. In one embodiment, exon 1 and/or exon 2 are mutated, the target intron is intron 19, 22, 23, or 24, and the coding domain includes functional ABCA4 exons 1 and 2.

In one embodiment, one or two of exons 1, 2, and 3 is mutated, the target intron is intron 19, 22, 23, or 24, and the coding domain includes functional ABCA4 exons 1-3. In one embodiment, one or two of exons 1, 2, 3, and 4 is mutated, the target intron is intron 19, 22, 23, or 24, and the coding domain includes functional ABCA4 exons 1-4. In one embodiment, one or two of exons 1, 2, 3, 4, and 5 is mutated, the target intron is intron 19, 22, 23, or 24, and the coding domain includes functional ABCA4 exons 1-5. In one embodiment, one or two of exons 1, 2, 3, 4, 5, and 6 is mutated, the target intron is intron 19, 22, 23, or 24, and the coding domain includes functional ABCA4 exons 1-6. In one embodiment, one or two of exons 1, 2, 3, 4, 5, 6, or 7 is mutated, the target intron is intron 19, 22, 23, or 24, and the coding domain includes functional ABCA4 exons 1-7. In one embodiment, one or two of exons 1, 2, 3, 4, 5, 6, 7, or 8 is mutated, the target intron is intron 19, 22, 23, or 24, and the coding domain includes functional ABCA4 exons 1-8. In one embodiment, one or two of exons 1, 2, 3, 4, 5, 6, 7, 8, or 9 is mutated, the target intron is intron 19, 22, 23, or 24, and the coding domain includes functional ABCA4 exons 1-9. In one embodiment, one or two of exons 1, 2, 3, 4, 5, 6, 7, 8, 9, or 10 is mutated, the target intron is intron 19, 22, 23, or 24, and the coding domain includes functional ABCA4 exons 1-10. In one embodiment, one or two of exons 1, 2, 3, 4, 5, 6, 7, 8, 9, 10, or 11 is mutated, the target intron is intron 19, 22, 23, or 24, and the coding domain includes functional ABCA4 exons 1-11. In one embodiment, one or two of exons 1, 2, 3, 4, 5, 6, 7, 8, 9, 10, 11, or 12 is mutated, the target intron is intron 19, 22, 23, or 24, and the coding domain includes functional ABCA4 exons 1-12. In one embodiment, one or two of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In one embodiment, one or two of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In one embodiment, one or two of exons 1, 2, 3, 4, 5, 6, 7, 8, 9, 10, 11, 12, 13, or 14 is mutated, the target intron is intron 19, 22, 23, or 24, and the coding domain includes functional ABCA4 exons 1-14. In one embodiment, one or two of exons 1, 2, 3, 4, 5, 6, 7, 8, 9, 10, 11, 12, 13, 14, or 15 is mutated, the target intron is intron 19, 22, 23, or 24, and the coding domain includes functional ABCA4 exons 1-15. In one embodiment, one or two of exons 1, 2, 3, 4, 5, 6, 7, 8, 9, 10, 11, 12, 13, 14, 15, or 16 is mutated, the target intron is intron 19, 22, 23, or 24, and the coding domain includes functional ABCA4 exons 1-16. In one embodiment, one or two of exons 1, 2, 3, 4, 5, 6, 7, 8, 9, 10, 11, 12, 13, 14, 15, 16, or 17 is mutated, the target intron is intron 19, 22, 23, or 24, and the coding domain includes functional ABCA4 exons 1-17. In one embodiment, one or two of exons 1, 2, 3, 4, 5, 6, 7, 8, 9, 10, 11, 12, 13, 14, 15, 16, 17, or 18 is mutated, the target intron is intron 19, 22, 23, or 24, and the coding domain includes functional ABCA4 exons 1-18. In one embodiment, one or two of exons 1, 2, 3, 4, 5, 6, 7, 8, 9, 10, 11, 12, 13, 14, 15, 16, 17, 18, or 19 is mutated, the target intron is intron 19, 22, 23, or 24, and the coding domain includes functional ABCA4 exons 1-19. In one embodiment, one or two of exons 1, 2, 3, 4, 5, 6, 7, 8, 9, 10, 11, 12, 13, 14, 15, 16, 17, 18, 19, or 20 is mutated, the target intron is intron 22, 23, or 24, and the coding domain includes functional ABCA4 exons 1-20. In one embodiment, one or two of exons 1, 2, 3, 4, 5, 6, 7, 8, 9, 10, 11, 12, 13, 14, 15, 16, 17, 18, 19, 20, or 21 is mutated, the target intron is intron 22, 23, or 24, and the coding domain includes functional ABCA4 exons 1-21. In one embodiment, one or two of exons 1, 2, 3, 4, 5, 6, 7, 8, 9, 10, 11, 12, 13, 14, 15, 16, 17, 18, 19, 20, 21, or 22 is mutated, the target intron is intron 22, 23, or 24, and the coding domain includes functional ABCA4 exons 1-22. In one embodiment, one or two of exons 1, 2, 3, 4, 5, 6, 7, 8, 9, 10, 11, 12, 13, 14, 15, 16, 17, 18, 19, 20, 21, 22, or 23 is mutated, the target intron is intron 23 or 24, and the coding domain includes functional ABCA4 exons 1-23. In one embodiment, one or two of exons 1, 2, 3, 4, 5, 6, 7, 8, 9, 10, 11, 12, 13, 14, 15, 16, 17, 18, 19, 20, 21, 22, 23, or 24 is mutated, the target intron is intron 24, and the coding domain includes functional ABCA4 exons 1-24.

Alternatively, in instances in which both mutations occur on the 3' portion of the target gene, a 3' trans-splicing molecule is selected to correct both mutations. In one embodiment, one or two of exons 23, 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, and the coding domain includes functional ABCA4 exons 23-50. In one embodiment, one or two of exons 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22 or 23, and the coding domain includes functional ABCA4 exons 24-50. In one embodiment, one or two of exons 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 25-50. In one embodiment, one or two of exons 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 26-50. In one embodiment, one or two of exons 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 27-50. In one embodiment, one or two of exons 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 28-50. In one embodiment, one or two of exons 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 29-50. In one embodiment, one or two of exons 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 30-50. In one embodiment, one or two of exons 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 31-50. In one embodiment, one or two of exons 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 32-50. In one embodiment, one or two of exons 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 33-50. In one embodiment, one or two of exons 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 34-50. In one embodiment, one or two of exons 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 35-50. In one embodiment, one or two of exons 36, 37, 38, 39, 40, 41, 42, 43, 44, 45, 46, 47, 48, 49, or 50 is mutated, the target intron is intron 22, 23, or 24, and the coding domain includes functional ABCA4 exons 36-50. In one embodiment, one or two of exons 37, 38, 39, 40, 41, 42, 43, 44, 45, 46, 47, 48, 49, or 50 is mutated, the target intron is intron 22, 23, or 24, and the coding domain includes functional ABCA4 exons 37-50. In one embodiment, one or two of exons 38, 39, 40, 41, 42, 43, 44, 45, 46, 47, 48, 49, or 50 is mutated, the target intron is intron 22, 23, or 24, and the coding domain includes functional ABCA4 exons 38-50. In one embodiment, one or two of exons 39, 40, 41, 42, 43, 44, 45, 46, 47, 48, 49, or 50 is mutated, the target intron is intron 22, 23, or 24, and the coding domain includes functional ABCA4 exons 39-50. In one embodiment, one or two of exons 40, 41, 42, 43, 44, 45, 46, 47, 48, 49, or 50 is mutated, the target intron is intron 22, 23, or 24, and the coding domain includes functional ABCA4 exons 40-50. In one embodiment, one or two of exons 41, 42, 43, 44, 45, 46, 47, 48, 49, or 50 is mutated, the target intron is intron 22, 23, or 24, and the coding domain includes functional ABCA4 exons 41-50. In one embodiment, one or two of exons 42, 43, 44, 45, 46, 47, 48, 49, or 50 is mutated, the target intron is intron 22, 23, or 24, and the coding domain includes functional ABCA4 exons 42-50. In one embodiment, one or two of exons 43, 44, 45, 46, 47, 48, 49, or 50 is mutated, the target intron is intron 22, 23, or 24, and the coding domain includes functional ABCA4 exons 43-50. In one embodiment, one or two of exons 44, 45, 46, 47, 48, 49, or 50 is mutated, the target intron is intron 22, 23, or 24, and the coding domain includes functional ABCA4 exons 44-50. In one embodiment, one or two of exons 45, 46, 47, 48, 49, or 50 is mutated, the target intron is intron 22, 23, or 24, and the coding domain includes functional ABCA4 exons 45-50. In one embodiment, one or two of exons 46, 47, 48, 49, or 50 is mutated, the target intron is intron 22, 23, or 24, and the coding domain includes functional ABCA4 exons 46-50. In one embodiment, one or two of exons 47, 48, 49, or 50 is mutated, the target intron is intron 22, 23, or 24, and the coding domain includes functional ABCA4 exons 47-50. In one embodiment, one or two of exons 48, 49, or 50 is mutated, the target intron is intron 22, 23, or 24, and the coding domain includes functional ABCA4 exons 48-50. In one embodiment, one or two of exons 49 or 50 is mutated, the target intron is intron 22, 23, or 24, and the coding domain includes functional ABCA4 exons 49 or 50. In one embodiment, exon 50 is mutated, the target intron is intron 22, 23, or 24, and the coding domain includes functional ABCA4 exon 50.

Two Trans-Splicing Molecules for Correcting Multiple Mutations

Additionally, provided herein are methods of correcting multiple mutations within an ABCA4 gene using two trans-splicing molecules—a 5' trans-splicing molecule and a 3' trans-splicing molecule. In some embodiments, the entire ABCA4 gene is replaced upon binding of both trans-splicing molecules, for example, where the 5' trans-splicing molecule and the 3' trans-splicing molecule bind the same target ABCA4 intron and replace the exons upstream and downstream, respectively, of the target intron.

For example, in some embodiments of the invention, a 5' trans-splicing molecule and a 3' trans-splicing molecule each bind target ABCA4 intron 22; the 5' trans-splicing molecule replaces endogenous exons 1-22 with functional exons 1-22; and the 3' trans-splicing molecule replaces endogenous exons 23-50 with functional exons 23-50. In other embodiments, a 5' trans-splicing molecule and a 3' trans-splicing molecule each bind target ABCA4 intron 23; the 5' trans-splicing molecule replaces endogenous exons 1-23 with functional exons 1-23; and the 3' trans-splicing molecule replaces endogenous exons 24-50 with functional exons 24-50. In other embodiments, a 5' trans-splicing molecule and a 3' trans-splicing molecule each bind target ABCA4 intron 24; the 5' trans-splicing molecule replaces endogenous exons 1-24 with functional exons 1-24; and the 3' trans-splicing molecule replaces endogenous exons 25-50 with functional exons 25-50. Any of the aforementioned combinations of 5' and 3' trans-splicing molecules can be included in a pharmaceutical composition (e.g., a single pharmaceutical composition including both molecules, either pre-prepared or admixed prior to administration, e.g., as part of a kit).

Dosing, Monitoring, and Combination Therapies

An effective concentration of a recombinant adeno-associated virus carrying a trans-splicing molecule as described herein ranges between about $10^8$ and $10^{13}$ vector genomes per milliliter (vg/mL). The rAAV infectious units are measured as described in McLaughlin et al., *J. Virol.* 1988, 62: 1963. In one embodiment, the concentration ranges between $10^9$ and $10^{13}$ vg/mL. In another embodiment, the effective concentration is about $1.5\times10^{11}$ vg/mL. In one embodiment, the effective concentration is about $1.5\times10^{10}$ vg/mL. In another embodiment, the effective concentration is about $2.8\times10^{11}$ vg/mL. In another embodiment, the effective concentration is about $5\times10^{11}$ vg/mL. In yet another embodiment, the effective concentration is about $1.5\times10^{12}$ vg/mL. In another embodiment, the effective concentration is about $1.5\times10^{13}$ vg/mL.

It is desirable that the lowest effective dosage (total genome copies delivered) of virus be utilized in order to reduce the risk of undesirable effects, such as toxicity, and other issues related to administration to the eye, e.g., retinal dysplasia and detachment. An effective dosage of a recombinant adeno-associated virus carrying a trans-splicing molecule as described herein ranges between about $10^8$ and $10^{13}$ vector genomes (vg) per dose (i.e, per injection). In one embodiment, the dosage ranges between $10^9$ and $10^{13}$ vg. In another embodiment, the effective dosage is about $1.5\times10^{11}$ vg. In another embodiment, the effective dosage is about $5\times10^{11}$ vg. In one embodiment, the effective dosage is about $1.5\times10^{10}$ vg. In another embodiment, the effective dosage is about $2.8\times10^{11}$ vg. In yet another embodiment, the effective dosage is about $1.5\times10^{12}$ vg. In another embodiment, the effective concentration is about $1.5\times10^{13}$ vg. Still other dosages in these ranges or in other units may be selected by the attending physician, taking into account the physical state of the subject being treated, including the age of the subject; the composition being administered, and the particular disorder; the targeted cell and the degree to which the disorder, if progressive, has developed.

The composition may be delivered in a volume of from about 50 μL to about 1 mL, including all numbers within the range, depending on the size of the area to be treated, the viral titer used, the route of administration, and the desired effect of the method. In one embodiment, the volume is about 50 μL. In another embodiment, the volume is about 70 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 250 μL. In another embodiment, the volume is about 300 μL. In another embodiment, the volume is about 350 μL. In another embodiment, the volume is about 400 μL In another embodiment, the volume is about 450 μL. In another embodiment, the volume is about 500 μL. In another embodiment, the volume is about 600 μL. In another embodiment, the volume is about 750 μL. In another embodiment, the volume is about 850 μL. In another embodiment, the volume is about 1,000 μL.

In one embodiment, the volume and concentration of the rAAV composition is selected so that only certain anatomical regions having target cells are impacted. In another embodiment, the volume and/or concentration of the rAAV composition is a greater amount, in order reach larger portions of the eye. Similarly dosages are adjusted for administration to other organs.

In another embodiment, the invention provides a method to prevent, or arrest photoreceptor function loss, or increase photoreceptor function in the subject. The composition may be administered before or after disease onset. For example, photoreceptor function may be assessed using the functional studies, e.g., ERG or perimetry, which are conventional in the art. As used herein "photoreceptor function loss" means a decrease in photoreceptor function as compared to a normal, non-diseased eye or the same eye at an earlier time point. As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same subject.

For each of the described methods, the treatment may be used to prevent the occurrence of further damage or to rescue tissue having mild or advanced disease. As used herein, the term "rescue" means to prevent progression of the disease, prevent spread of damage to uninjured cells or to improve damage in injured cells.

Thus, in one embodiment, the composition is administered before disease onset. In another embodiment, the composition is administered prior to the development of symptoms. In another embodiment, the composition is administered after development of symptoms. In yet another embodiment, the composition is administered when less than 90% of the target cells are functioning or remaining, e.g., as compared to a reference tissue. In yet another embodiment, the composition is administered when more than 10% of the target cells are functioning or remaining, e.g., as compared to a reference tissue. In yet another embodiment, the composition is administered when more than 20% of the target cells are functioning or remaining. In yet another embodiment, the composition is administered when more than 30% of the target cells are functioning or remaining.

In yet another embodiment, any of the above described methods is performed in combination with another, or secondary, therapy. The therapy may be any now known, or as yet unknown, therapy which helps prevent, arrest or ameliorate these mutations or defects or any of the effects associated therewith. The secondary therapy can be administered before, concurrent with, or after administration of the trans-splicing molecules described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In another embodiment, the method includes performing functional and imaging studies to determine the efficacy of the treatment. These studies include electroretinography (ERG) and in vivo retinal imaging, as described in U.S. Pat. No. 8,147,823; in International Patent Publication Nos. WO 2014/011210 or WO 2014/124282, incorporated herein by reference. In addition visual field studies, perimetry and microperimetry, mobility testing, visual acuity, and/or color vision testing may be performed.

In certain embodiments, it is desirable to perform non-invasive retinal imaging and functional studies to identify areas of retained photoreceptors to be targeted for therapy. In these embodiments, clinical diagnostic tests are employed to determine the precise location(s) for one or more subretinal injection(s). These tests may include ERG, perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. In view of the imaging and functional studies, in some embodiments one or more injections are performed in the same eye in order to target different areas of retained photoreceptors.

For use in these methods, the volume and viral titer of each injection is determined individually, and may be the same or different from other injections performed in the same, or contralateral, eye. In another embodiment, a single, larger volume injection is made in order to treat the entire eye. The dosages, administrations, and regimens may be determined by the attending physician given the teachings of this disclosure.

EXAMPLES

The invention is based, at least in part, on Applicant's discovery that particular introns of ABCA4, and specific regions within those introns, provide highly efficient binding sites for binding domains of trans-splicing molecules and efficiently mediate trans-splicing. Applicant has generated a series of mock trans-splicing molecules having 150-mer binding domains designed to hybridize to a corresponding series of 150-base pair binding site sequences of (i) ABCA4 introns of interest (introns 19 and 22-24) and (ii) CEP290 introns of interest (introns 26-30). Each binding domain in the ABCA4 series and the CEP290 series was designed to overlap by 140 nucleotides, enabling scanning of each intron by 10 nucleotides between each sequential test binding domain. Trans-splicing efficiency was quantified for each binding domain across each of ABCA4 introns 19 and 22-24 and CEP290 introns 26-30. ABCA4 screening is described in Example 1, and results are shown in FIGS. 1-8. CEP290 screening is described in Example 2, and results are shown in FIGS. 21-26.

Example 1. ABCA4

This Example describes development of ABCA4 trans-splicing molecules, for example, by screening for effective binding sites within particular ABCA4 introns, developing an ABCA4 cell line for testing trans-splicing molecules, and testing various ABCA4 trans-splicing molecules for restoration of ABCA4 protein expression.

Binding Site Screening

Figure 2:
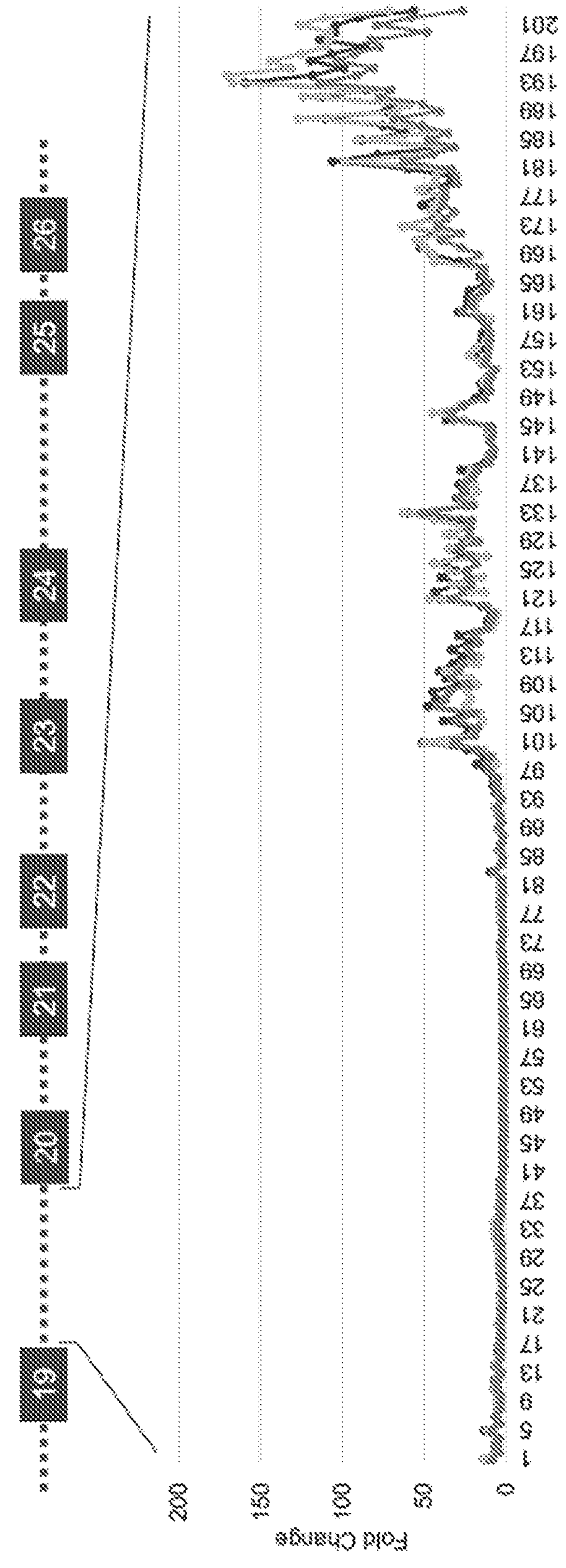
FIG. 2 is a graph showing trans-splicing efficiency (relative fold change) conferred by 150-mer binding domains across ABCA4 intron 19 (SEQ ID NO: 25) in ten-nucleotide intervals using 5' trans-splicing molecules. X axis labels indicate the number of each binding site starting from the 5' end of the intron (i.e., the first nucleotide of the intron sequence).

Screening of a series of binding domains configured to bind ABCA4 intron 19 (SEQ ID NO: 25) at sequential bindings sites revealed a region at the 3' portion of ABCA4 intron 19 that was preferentially efficient at trans-splicing of a 5' trans-splicing molecule—a region from nucleotides 990 to 2,174 of intron 19 (FIG. 2). Binding sites within the range of nucleotides from 1,670 to 2,174, from 1,810 to 2,000, from 1,870 to 2,000, or from 1,920 to 2,000 were revealed as particularly highly efficient at mediating 5' trans-splicing at intron 19.

Figure 3:
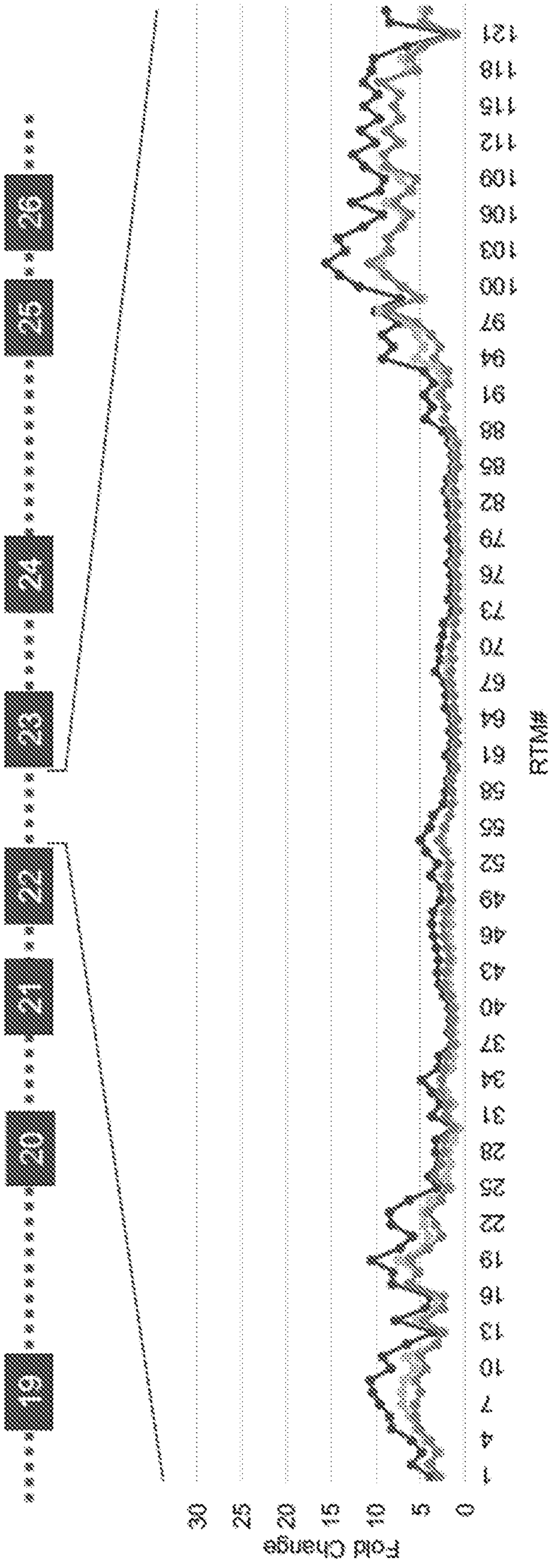
FIG. 3 is a graph showing trans-splicing efficiency (relative fold change) conferred by 150-mer binding domains across ABCA4 intron 22 (SEQ ID NO: 28) in ten-nucleotide intervals using 5' trans-splicing molecules. X axis labels indicate the number of each binding site starting from the 5' end of the intron (i.e., the first nucleotide of the intron sequence).

Suitable binding sites for 5' trans-splicing molecules within intron 22 were similarly identified (FIG. 3). Binding sites within the ranges of nucleotides 1 to 150 or nucleotides 880 to 1,350 of intron 22 were especially efficient, relative to the remainder of the intron.

Figure 4:
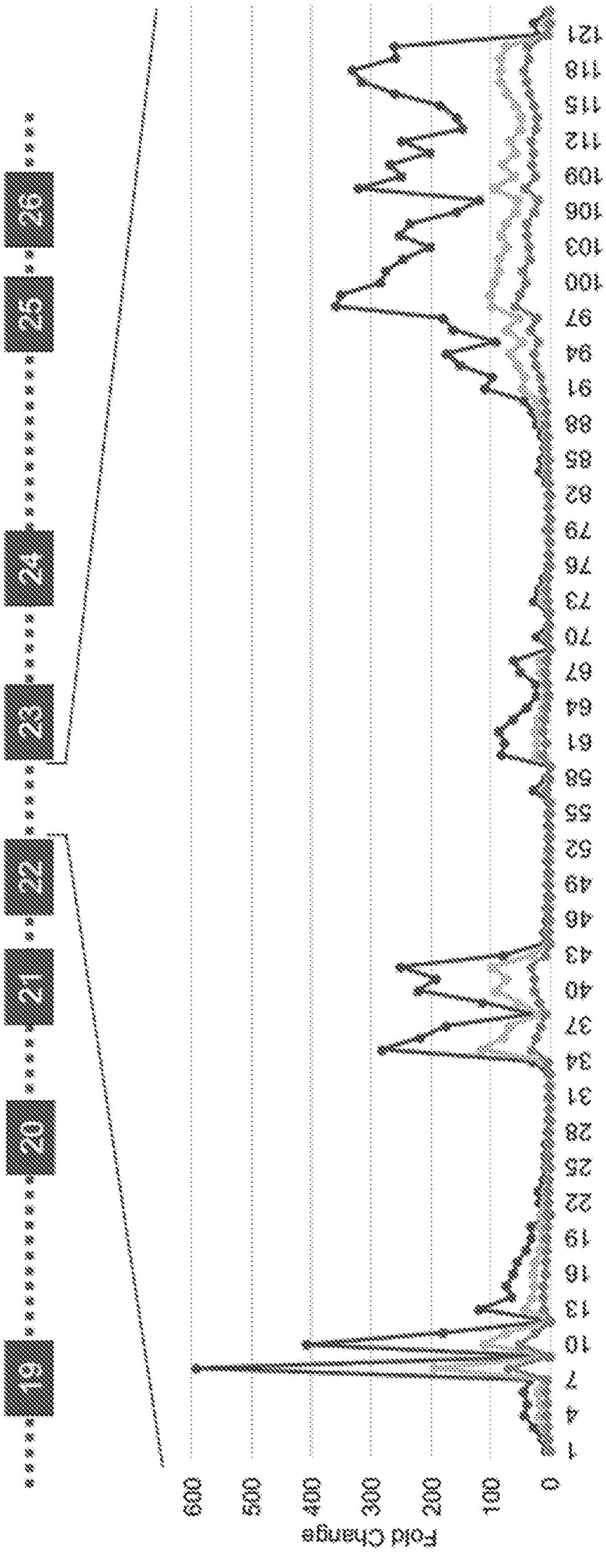
FIG. 4 is a graph showing trans-splicing efficiency (relative fold change) conferred by 150-mer binding domains across ABCA4 intron 22 (SEQ ID NO: 28) in ten-nucleotide intervals using 3' trans-splicing molecules. X axis labels indicate the number of each binding site starting from the 5' end of the intron (i.e., the first nucleotide of the intron sequence).

FIG. 4 shows results of an analogous screen for ABCA4 intron 22 (SEQ ID NO: 28) for a 3' trans-splicing molecule. Binding sites having nucleotides 60 to 570, nucleotides 600 to 800, or nucleotides 900 to 1,350 were identified as preferentially suitable for trans-splicing of a 3' trans-splicing molecule. In particular, binding domains targeted to binding sites within the range of nucleotides 70 to 250 were highly efficient at 3' trans-splicing.

Figure 5:
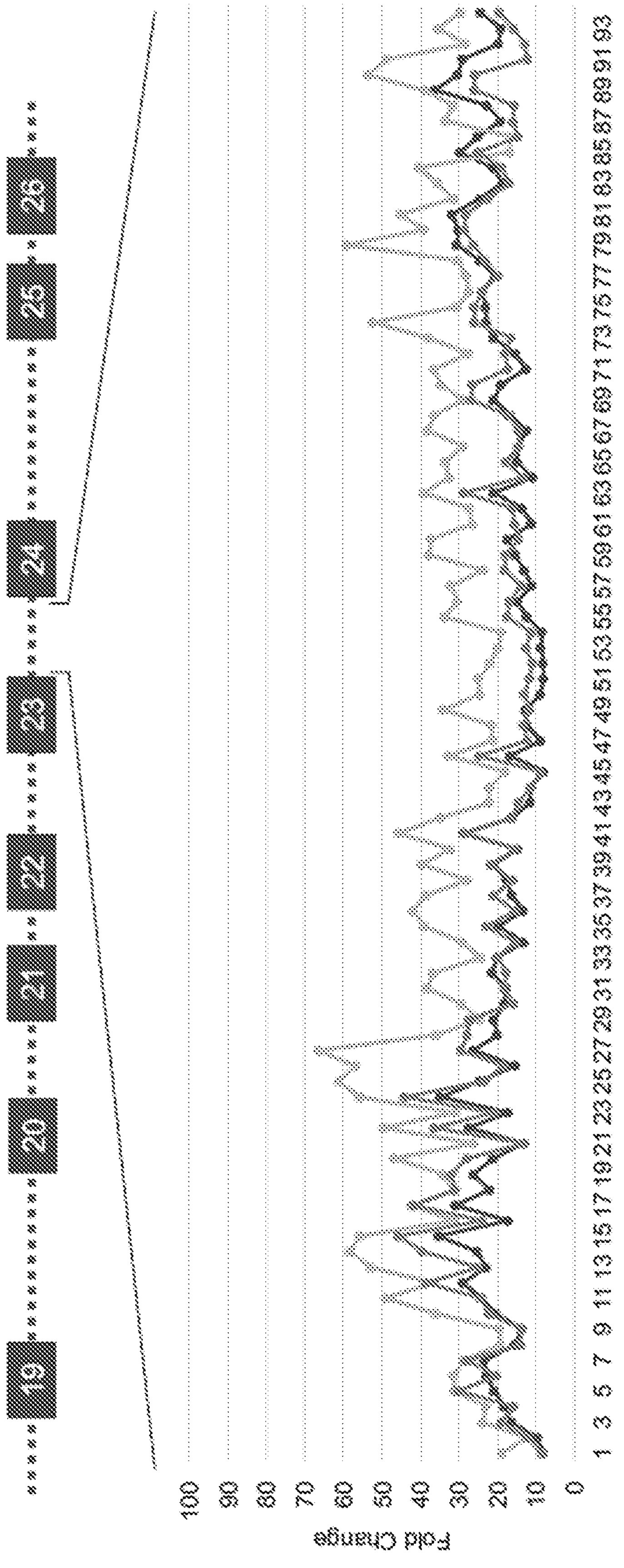
FIG. 5 is a graph showing trans-splicing efficiency (relative fold change) conferred by 150-mer binding domains across ABCA4 intron 23 (SEQ ID NO: 29) in ten-nucleotide intervals using 5' trans-splicing molecules. X axis labels indicate the number of each binding site starting from the 5' end of the intron (i.e., the first nucleotide of the intron sequence).
Figure 6:
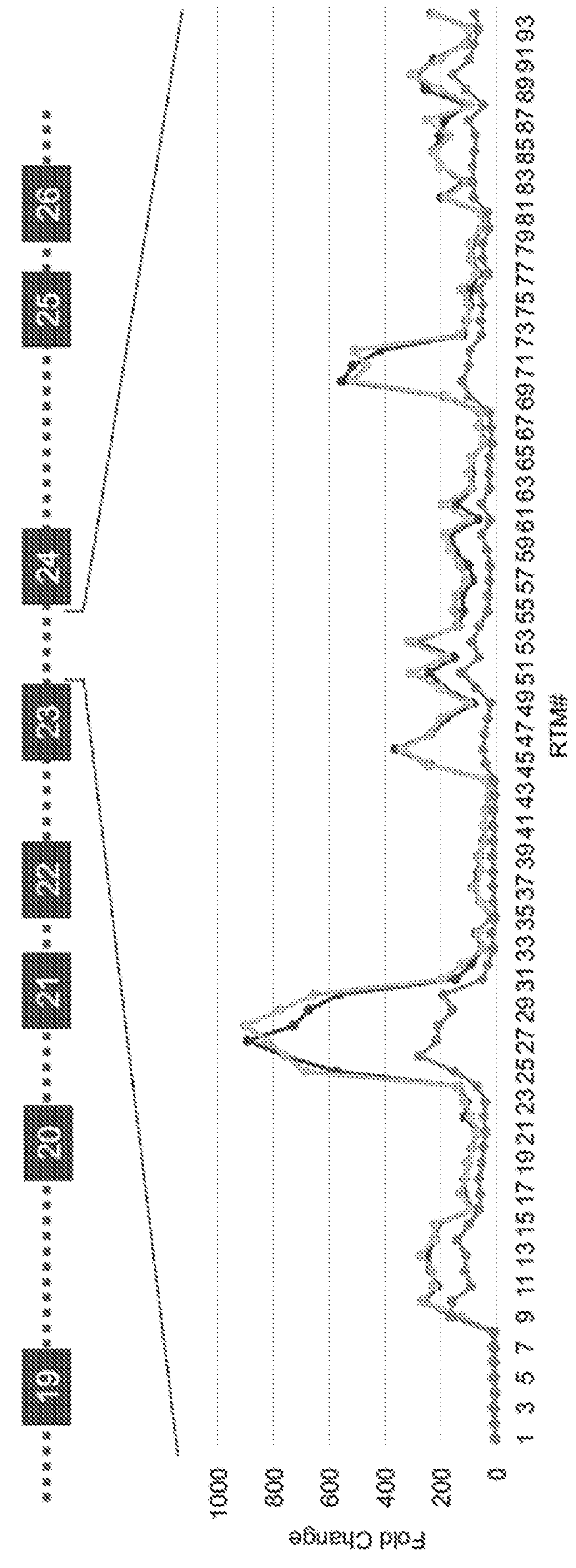
FIG. 6 is a graph showing trans-splicing efficiency (relative fold change) conferred by 150-mer binding domains across ABCA4 intron 23 (SEQ ID NO: 29) in ten-nucleotide intervals using 3' trans-splicing molecules. X axis labels indicate the number of each binding site starting from the 5' end of the intron (i.e., the first nucleotide of the intron sequence).

Within intron 23, relatively efficient binding sites for 5' trans-splicing molecules were identified as those within the ranges of nucleotides 80 to 570 or nucleotides 720 to 1,081 of SEQ ID NO: 29 (FIG. 5). For 3' trans-splicing molecules, binding sites with particularly good efficiency included those within nucleotides 80 to 1,081 of SEQ ID NO: 29 (e.g., nucleotides 230 to 1,081 of SEQ ID NO: 29, nucleotides 250 to 400 of SEQ ID NO: 29, or nucleotides 690 to 850 of SEQ ID NO: 29), as shown in FIG. 6.

Figure 7:
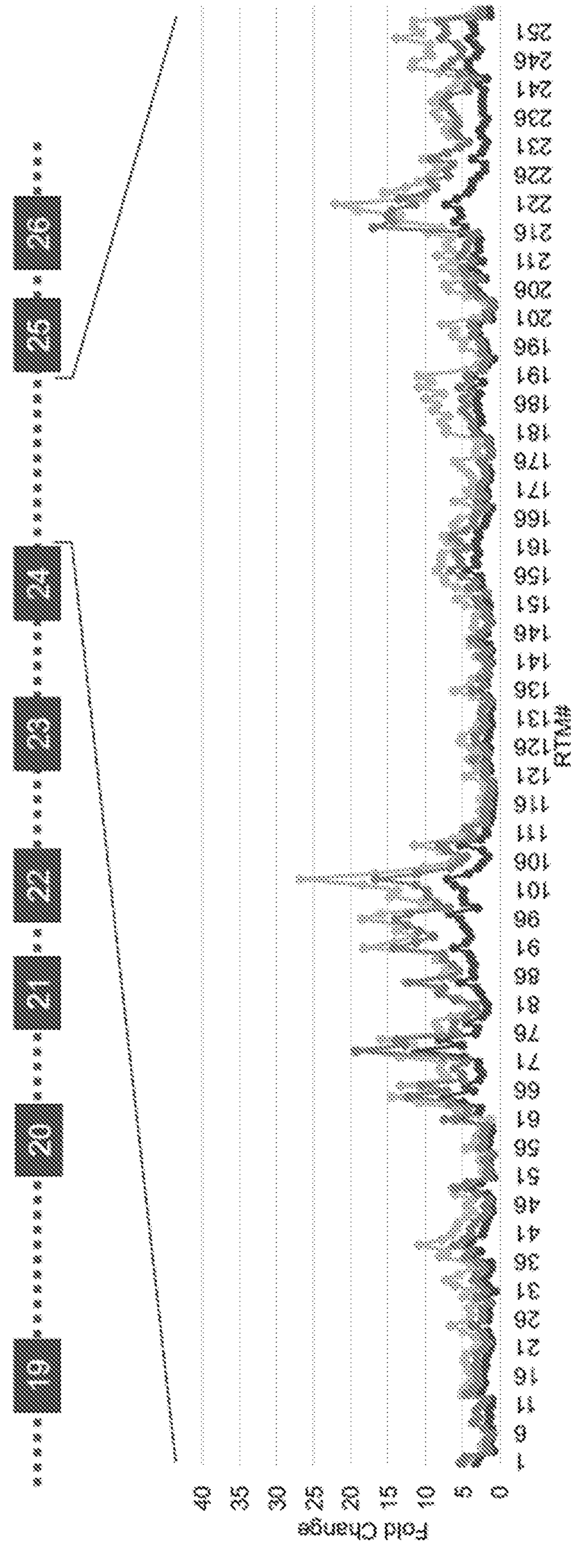
FIG. 7 is a graph showing trans-splicing efficiency (relative fold change) conferred by 150-mer binding domains across ABCA4 intron 24 (SEQ ID NO: 30) in ten-nucleotide intervals using 5' trans-splicing molecules. X axis labels indicate the number of each binding site starting from the 5' end of the intron (i.e., the first nucleotide of the intron sequence).
Figure 8:
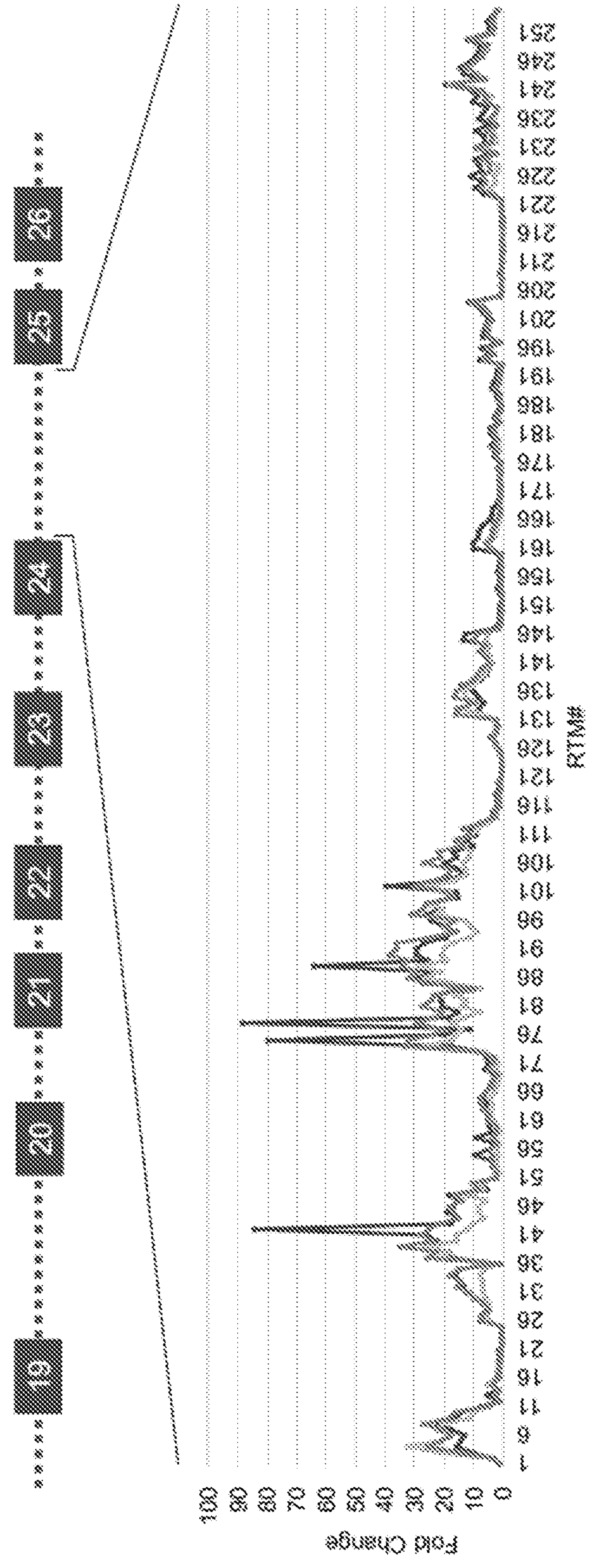
FIG. 8 is a graph showing trans-splicing efficiency (relative fold change) conferred by 150-mer binding domains across ABCA4 intron 24 (SEQ ID NO: 30) in ten-nucleotide intervals using 3' trans-splicing molecules. X axis labels indicate the number of each binding site starting from the 5' end of the intron (i.e., the first nucleotide of the intron sequence).

An analogous screening at intron 24 of ABCA4 (SEQ ID NO: 30) revealed that binding sites within the ranges of nucleotides 600 to 1,250 or nucleotides 1,490 to 2,660 were efficient at 5' trans-splicing (FIG. 7). In particular, binding sites within the range of nucleotides 1,000 to 1,200 exhibited the greatest 5' trans-splicing efficiency. FIG. 8 shows the results of a screening of 3' trans-splicing efficiency, which revealed that binding sites within the range of nucleotides 1 to 250, nucleotides 300 to 2,000, or nucleotides 2,200 to 2,692 (in particular, binding sites within the range of nucleotides or nucleotides 750 to 1,110) were most efficient.

ABCA4 Cell Lines

First, cell lines expressing ABCA4 were generated. The ABCA4 gene is only known to be expressed in living photoreceptors in the retina, and full-length ABCA4 pre-mRNA and protein are not generally detectable in cultured cells in vitro. Therefore, to test trans-splicing strategies for ABCA4, cells were engineered to express ABCA4 from its native genomic locus on chromosome 1 (1p22.1). Two strategies were pursued. In the first case, stable cell lines were derived to express site-specific (upstream of the ABCA4 transcriptional start site) DNA-binding TALENs that were fused to the VP64 viral trans-activator. In the second case, a constitutive eukaryotic promoter was directly inserted (using CRISPR/Cas9) into the genomic locus immediately upstream of the ABCA4 transcriptional start site. The results in both cases were stable cell lines that robustly expressed ABCA4 pre-mRNA and protein.

TALEN Cell Lines

Figure 9:
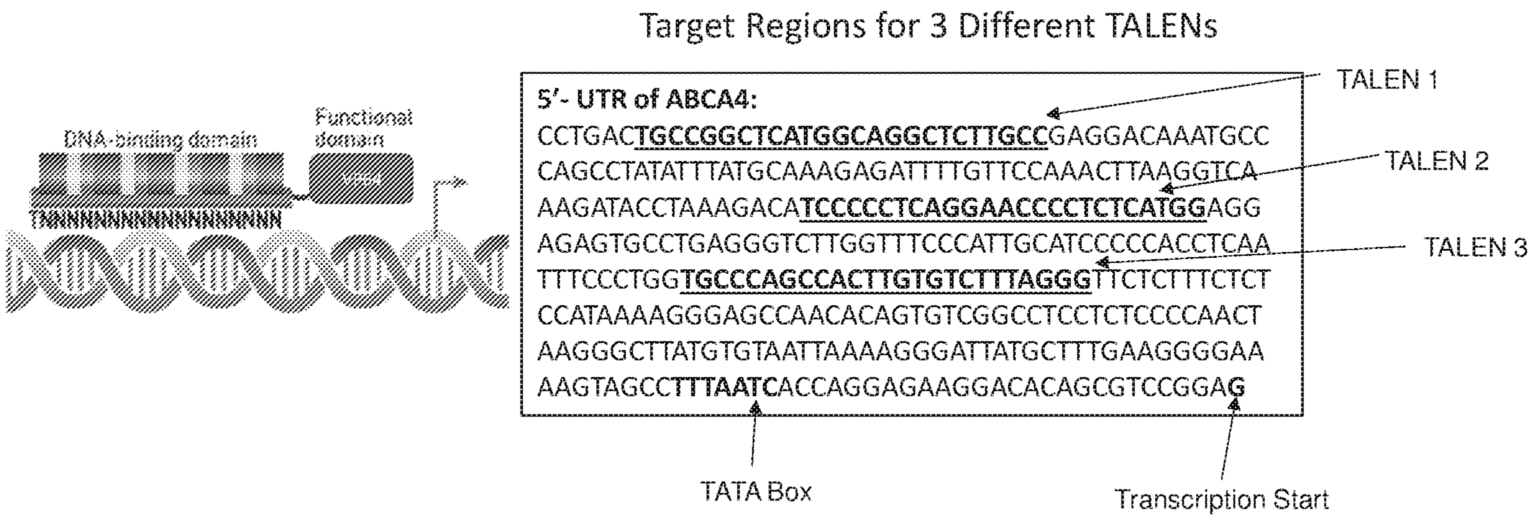
FIG. 9 is a schematic drawing showing a TALEN protein consisting of a DNA binding domain linked to a transcription activation domain. A VP64 transcription activation domain is shown. The right panel shows a portion of the 5' untranslated region (5'-UTR) of ABCA4. The TATA box and the putative transcription start site are shown. The sequences targeted the by the three different DNA binding domains of TALENs are also shown. TALEN 1 binds to the first underlined sequence, TALEN 2 binds to the second underlined sequence, and TALEN 3 binds to the third underlined sequence, as indicated.
Figure 10:
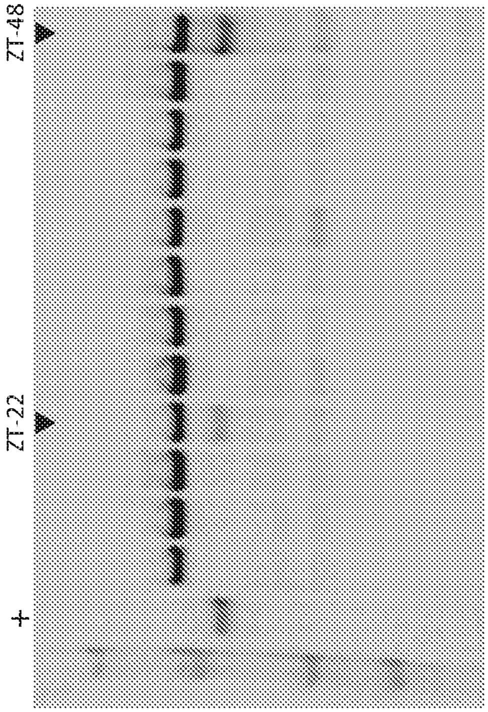
FIG. 10 is a gel showing 293T cells were transfected with TALEN constructs designed to induce endogenous ABCA4 expression. All three TALENS from FIG. 9 were stably introduced into 293 cells and single cell clones were picked and analyzed by western blot. The positive control (+) indicates cells transfected with a plasmid expressing an ABCA4 cDNA. Cell lysates were made 48 hours after transfection and the membrane fractions were examined for ABCA4 expression using antibody ab72955 (Abcam). Clones ZT-22 and ZT-48 showed ABCA4 protein expression.

TALENs targeted to specific domains upstream of the ABCA4 transcriptional start site were designed and fused to a VP-64 trans-activator sequence (FIG. 9). This combination of three TALENs were transfected into 293 cells and stable single cell clones were derived. Two clones were shown to direct expression of ABCA4 protein (FIG. 10).

CAG Promoter Cell Lines

Figure 11:
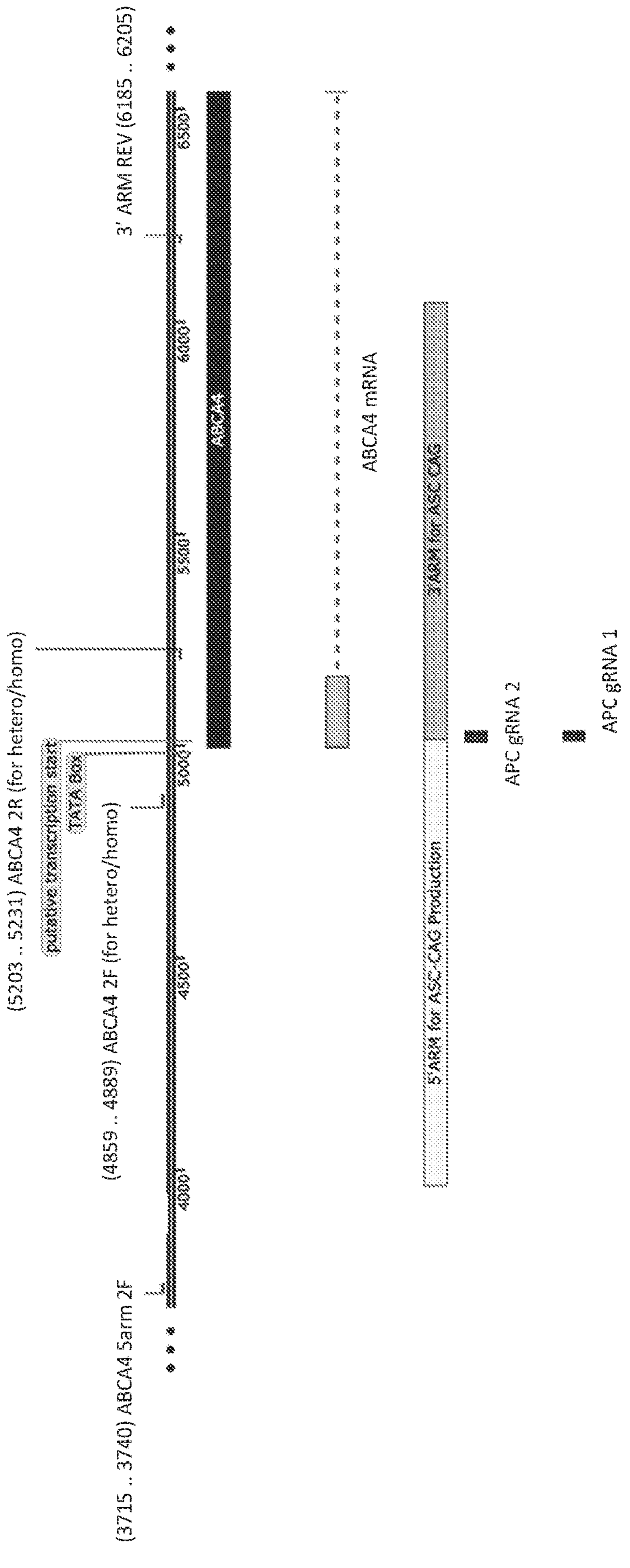
FIG. 11 is a schematic drawing showing a CAG promoter cell line.
Figure 12B:
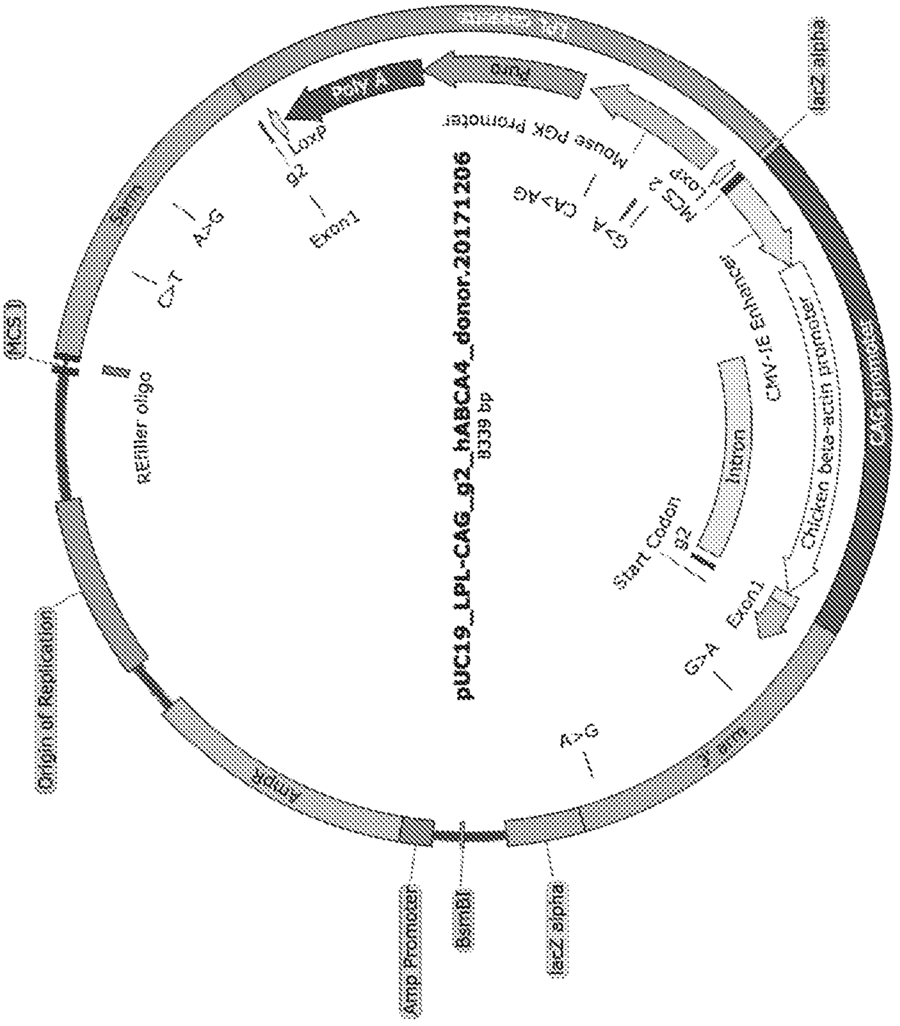
Figure 13:
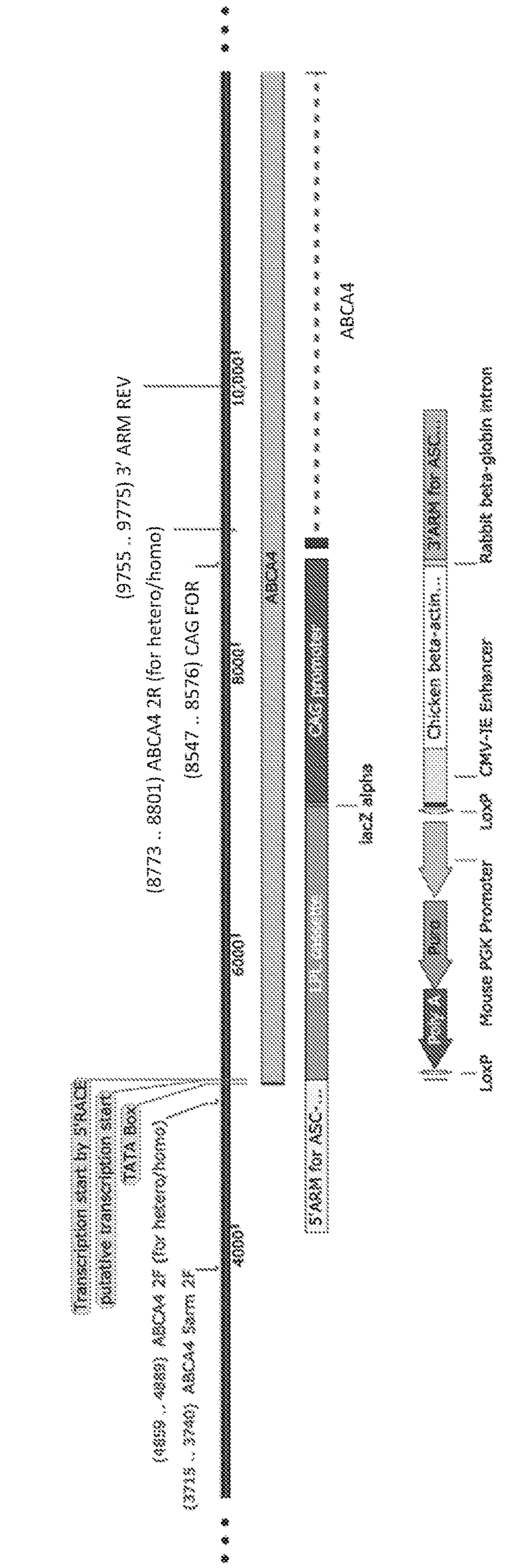
FIG. 13 is a schematic drawing showing a CAG promoter cell line.
Figure 14B:
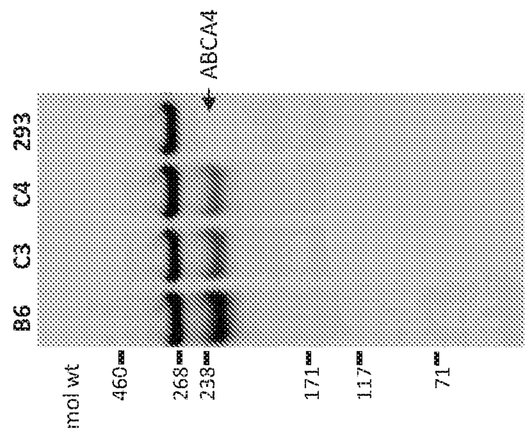
FIGS. 14A and 14B are a graph and a gel, respectively, showing expression results from several clonal lines that were selected for further analyses.
Figure 14A:
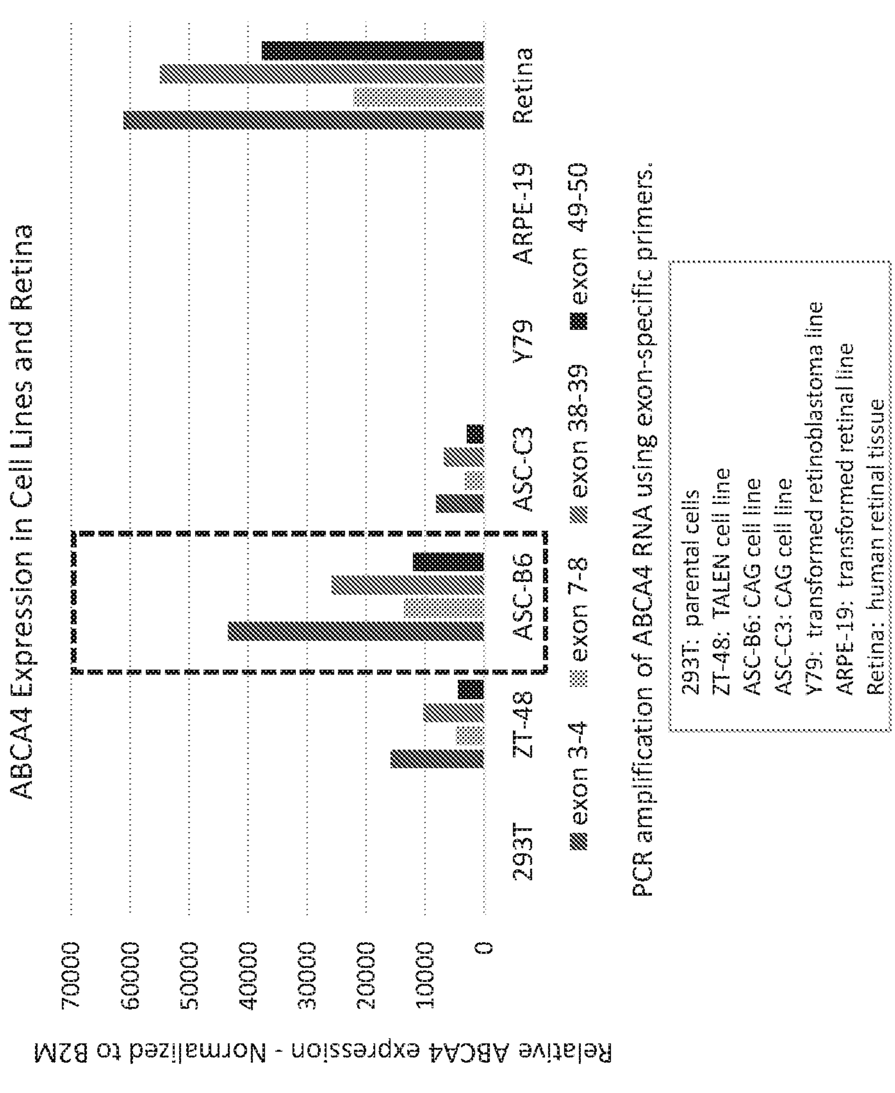

The general strategy for deriving CAG promoter cell lines is outlined in FIGS. 11-13. Site-specific guides (FIG. 12A) were designed to insert the CAG promoter and a puromycin selectable marker using homology arms (FIG. 12B). Puromycin resistant cells were cloned and analyzed by PCR for the desired insertion. Several clonal lines were selected for further analyses. RNA and protein expression for two lines (B6 and C3) are shown in FIGS. 14A and 14B. Both lines clearly contained the promoter insertion, as demonstrated by RNA and protein analyses.

ABCA4 Knockout Cell Lines

Figure 15:
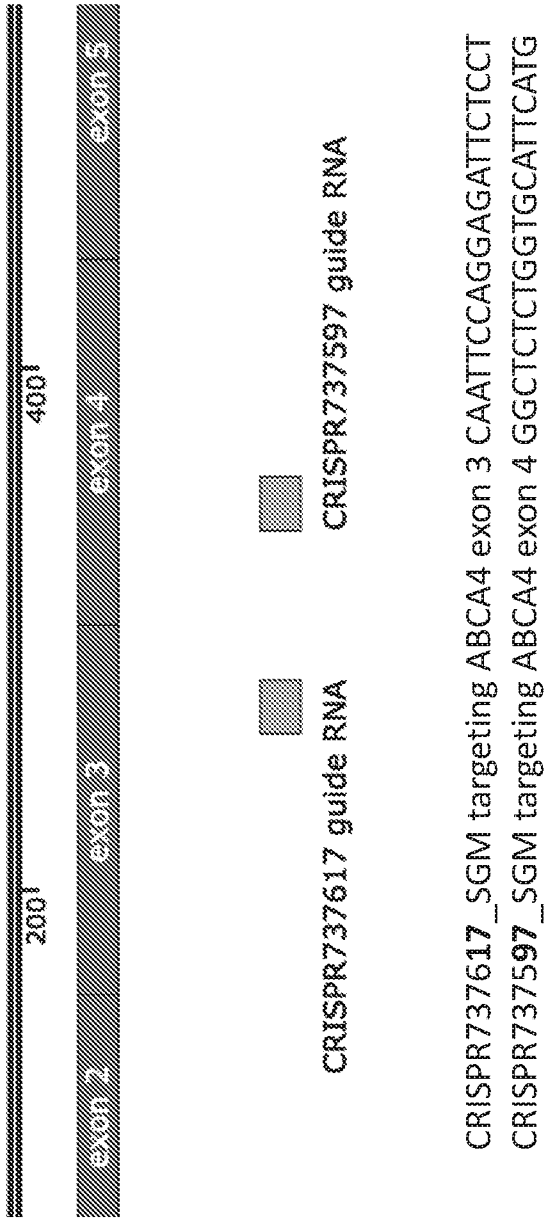
FIG. 15 is a schematic drawing showing CRISPR guide RNA for targeting exons 3 and 4.

Once stable ABCA4 expression was established in cultured cells, knock-outs of ABCA4 expression were generated for testing of ABCA4 trans-splicing molecules designed to restore ABCA4 protein expression. In general, guide RNA and Cas9 protein were co-transfected in B6 cells (CAG-promotor knocked into ABCA4 locus and mediating ABCA4 expression). After nine days, a second transfection with guide RNA and Cas9 protein was performed. The basic design targeting exons 3 and 4 is shown in FIG. 15. Single cells were plated by limiting dilution and once grown, evaluated for protein expression of ABCA4 by Western blot.

Figure 16:
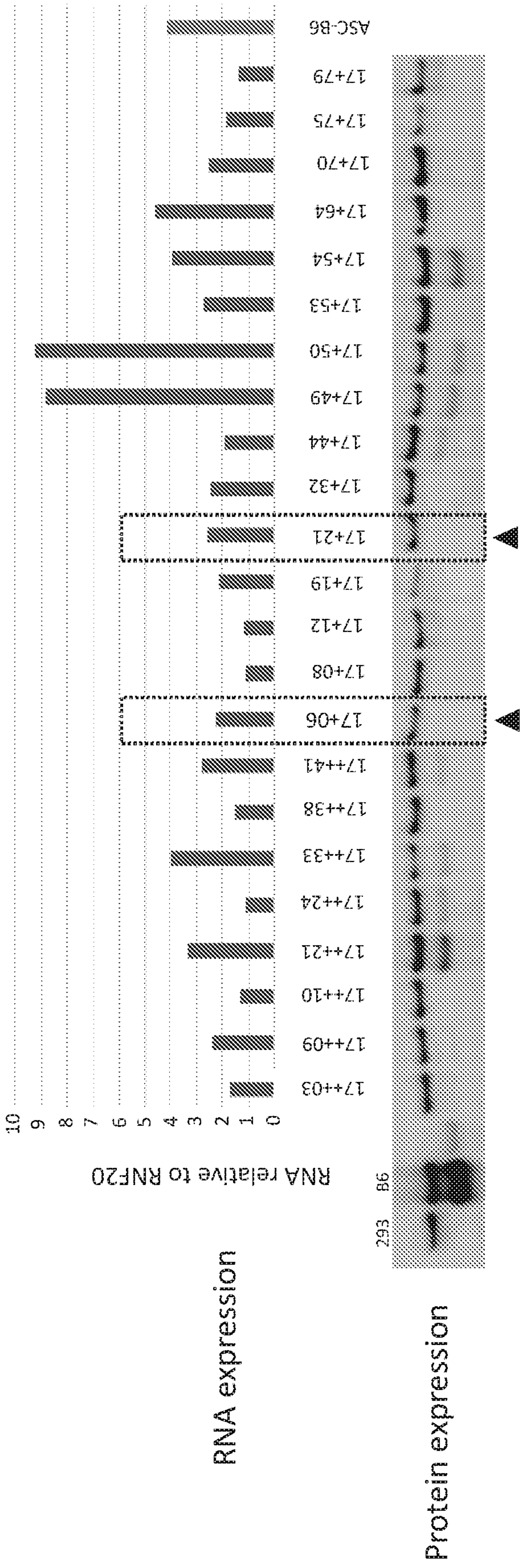
FIG. 16 is a graph showing RNA expression and a gel showing protein profiles of single cell clones derived after treatment with CRISPR/Cas9, as depicted in FIG. 15.
Figure 17A:
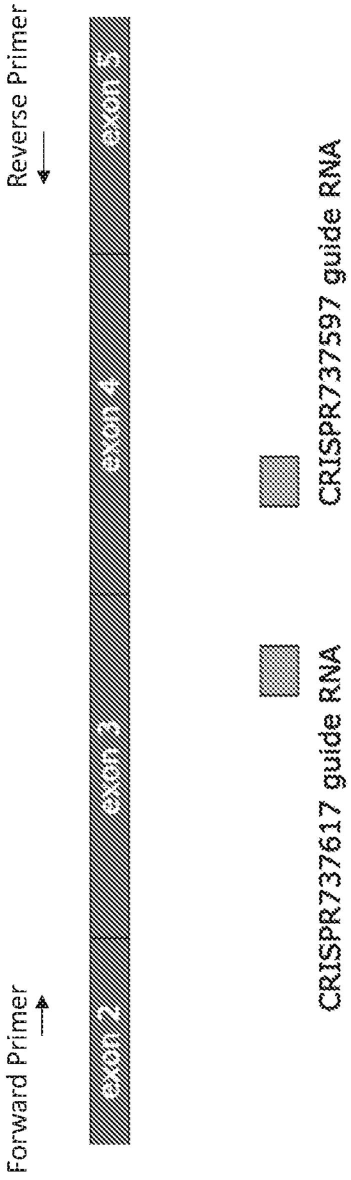
FIGS. 17A and 17B are schematic drawings showing PCR for mutation analyses on cDNA (FIG. 17A) and PCR for genotyping on cDNA (FIG. 17B), confirming that exons 3 and 4 were targeted and interrupted.
Figure 17B:
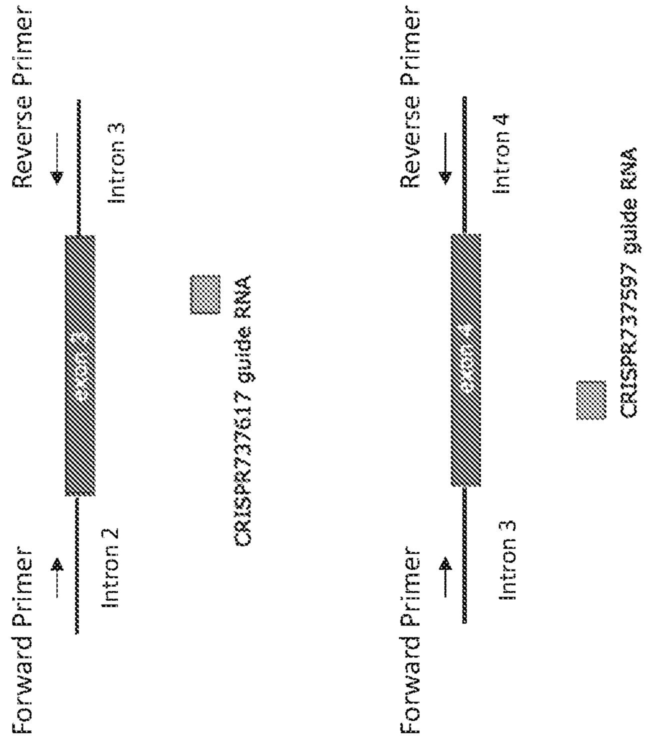

FIG. 16 shows the RNA and protein profiles of single cell clones derived after treatment with CRISPR/Cas9, as depicted in FIG. 15. There were varying degrees of RNA and protein ablation. Clones 17+06 and 17+21 were chosen because they exhibited complete ABCA4 protein knockout. Mutation analyses (FIGS. 17A-17B and 18) confirmed that exons 3 and 4 were targeted and interrupted.

ABCA4 Trans-Splicing-Mediated Protein Restoration

Eight trans-splicing molecules were selected based on the high-throughput binding site screening described above. Methods and results of these studies are described below Methods For Western blot assays, 17+06 or 17+21 cells were seeded at a density of $10^6$ cells per well in each well of twelve-well plates. Individual wells were transfected with 1 μg of plasmid ($RTM_x$). At 48 hours, cells were harvested, and membrane preparations were processed for analysis by standard western blotting using Mem-PER Plus Membrane Protein Extraction Kit (Thermo Fisher 89842) according to the manufacturer's protocol with addition of 1×HALT™ Protease and Phosphatase Inhibitor Cocktail (Thermo Fisher 78440) in all buffers. RNA was also processed for analysis as described below. Membrane lysates were denatured with 4× Laemmli Sample Buffer (Biorad 161-0737) including 10% reducing agent TCEP 0.5 M (Sigma 646547) for 30 minutes at room temperature. Samples were run on NuPage Precast 3-8% Tris-Acetate gels (Thermo Fisher) and proteins were transferred using the iBlot 2 Mini PVDF Transfer Packs—run at 25V 10 minutes with iBlot 2. The primary antibody for ABCA4 was Abcam ab72955, rabbit polyclonal (@ 1:2500 dilution). The secondary antibody was anti-rabbit (@ 1:5000 dilution). Blots were exposed for various times, depending on strength of signal.

For qPCR for RNA samples, RNA was harvested as described above for qPCR analysis using RNeasy Plus Mini kit (Qiagen). cDNA was synthesized from 400 ng RNA in 20 μl reaction with SuperScript IV VILO Master Mix (Thermo 11756500; diluted 1:4 in water). Native ABCA4 (Thermo commercial assay Hs00979594_m1) spans exons 49-50. For the housekeeper gene as a control, an RNF20 assay was used (Thermo commercial assay Hs00219623_m1). Chimeric ABCA4 codon optimized exon 22-native exon 23—qPCR primers and probes were the following:

```
Probe (FAM) 063_ABCA4 co22n23_P1:
CGTGGACCCTTACAGCAGAAG

Forward Primer 064_ABCA4 co22n23_F1:
GATCCTGGATGAGCCTAC

Reverse Primer 065_ABCA4 co22n23_R1:
GGACATGATGATGGTTCTG
```

Duplex with RNF20 assay qPCR primers and probes were the following:

```
Probe (VIC) 088_RNF20_P2:
CAGCGACTCAACCGACACTT

Forward primer 091_RNF20_F2:
GCAGTGGGATATTGACAA

Reverse primer 099_RNF20_R5:
CGAGCATTGATAGTGATTG
```

The PCT reaction was run using QuantiFast 2× qPCR Mastermix.

Results

Figure 19A:
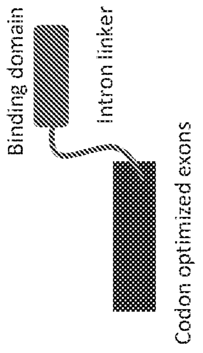
FIGS. 19A and 19B are schematic drawings of trans-splicing molecules targeting ABCA4 pre-mRNA.
Figure 19B:
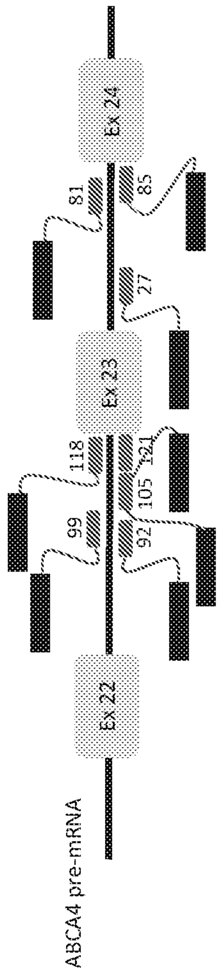

Trans-splicing molecules binding to introns 19, 22, 23, and 24 were tested. No protein restoration was observed in trans-splicing molecules binding to introns 19 and 24 (data not shown), but trans-splicing molecules binding to introns 22 and 23 yielded restoration of ABCA4 protein and RNA expression (FIGS. 19A and 19B), as discussed below.

Figure 20B:
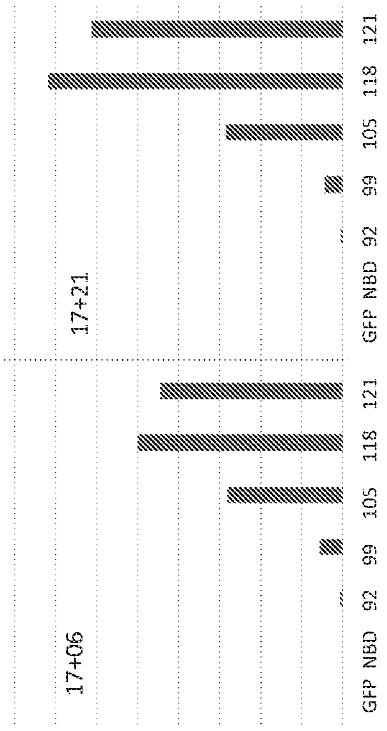
FIGS. 20A-20D are gels (FIGS. 20A and 20C) and graphs (FIGS. 20B and 20D) showing results from trans-splicing reactions.
Figure 20A:
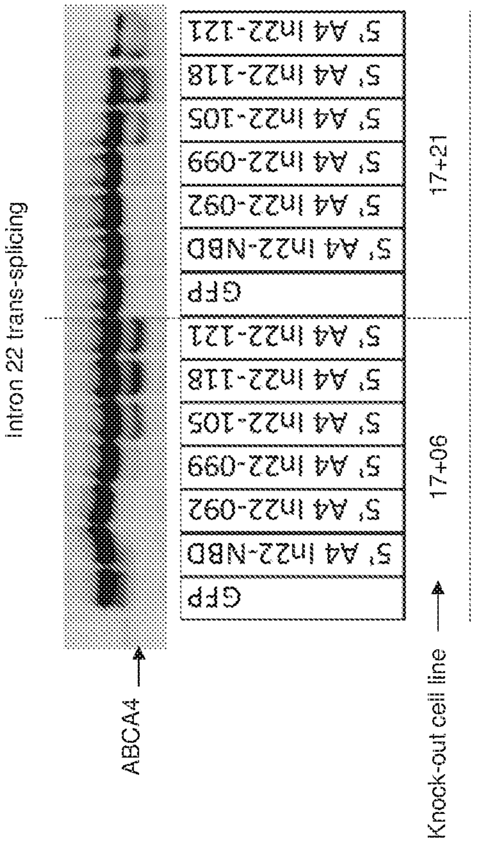

FIG. 20A is a western blot showing ABCA4 protein expression attributed to trans-splicing reactions from two different cell lines (17+06 and 17+21) with a mock GFP control or 5'A4In22 tethered to five different binding domains (No binding domain (NBD) control, 92, 99, 105, 118, and 121, numbering corresponding to FIG. 3 RTM #, where binding domain 92 binds nucleotides 911-1060 of intron 22, binding domain 99 binds nucleotides 981-1130 of intron 22, binding domain 105 binds nucleotides 1041-1190 of intron 22, binding domain 118 binds nucleotides 1171-1320 of intron 22, and binding domain 121 binds nucleotides 1201-1350 of intron 22 (following to the 10-base shift interval of 150-mers across intron 22, described above)). Four of these intron-22 binding constructs, 99, 105, 118, and 121 yielded protein restoration, with 105, 118, and 121 showing particularly enhanced restoration and 118 showing the greatest amount of protein expressed in both cell lines. mRNA expression profiles showed a similar pattern, with the 118 construct yielding the greatest levels of ABCA4 mRNA in both cell lines (FIG. 20B). Units are relative to the RNF20 housekeeping gene.

Figure 20D:
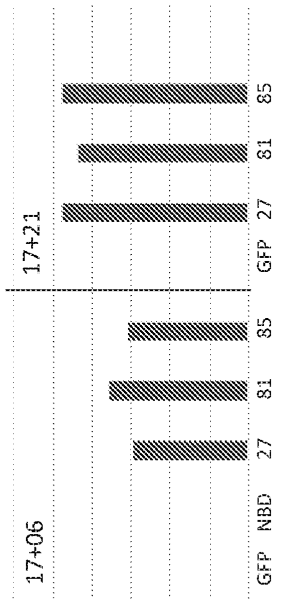
Figure 20C:
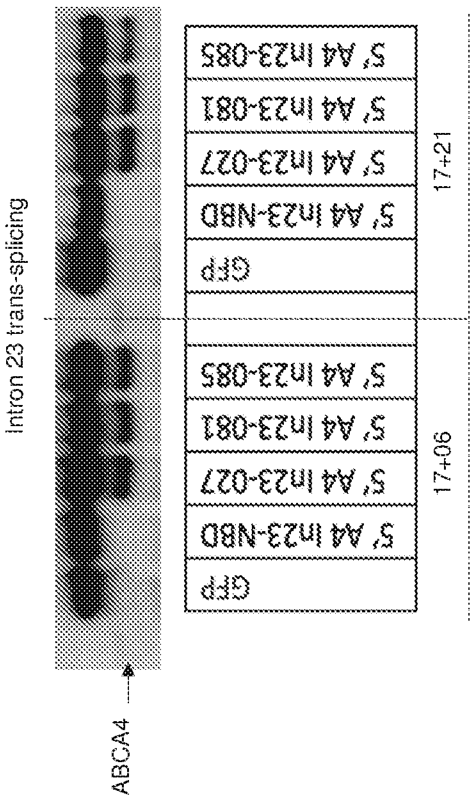

FIG. 20C is a western blot showing ABCA4 protein expression attributed to trans-splicing reactions from two different cell lines (17+06 and 17+21) with a mock GFP control or 5'A4In23 tethered to three different binding domains (NBD control, 27, 81, and 85, numbering corresponding to FIG. 5 RTM #, where binding domain 27 binds nucleotides 261-410 of intron 23, binding domain 81 binds to 801-950 of intron 23, and binding domain 85 binds 841-990 of intron 23 (following to the 10-base shift interval of 150-mers across intron 23, described above)). All three intron 23-binding constructs yielded trans-splicing as indicated by the amount of protein expressed in both cell lines. mRNA expression profiles yielded similar results, with all three constructs yielding robust ABCA4 mRNA expression in both cell lines (FIG. 20D). Units are relative to the RNF20 housekeeping gene.

Together, the ABCA4 protein and RNA expression data obtained for intron 22- and 23-binding trans-splicing molecules correlate with the binding domain screen described above. In particular, intron 22-binding constructs 105, 118, and 121 and intron 23-binding constructs 27, 81, and 85 were predicted to bind with high efficiency (FIGS. 3 and 5), and the present ABCA4 protein restoration data indicate that the ABCA4 intron regions containing the binding sites of these constructs are amenable to binding to ABCA4 trans-splicing molecules to confer protein and RNA restoration. In the present examples, 10-20% protein expression was restored, with restoration being comparable between intron 22- and 23-binding trans-splicing molecules. Importantly, because ABCA4-related diseases (such as Stargardt Disease) are recessive, asymptomatic carriers of the disease likely express less-than normal ABCA4, and, without wishing to be bound by theory, partial protein restoration, as shown here, is likely to confer a meaningful clinical benefit.

Example 2. CEP290

Figure 22:
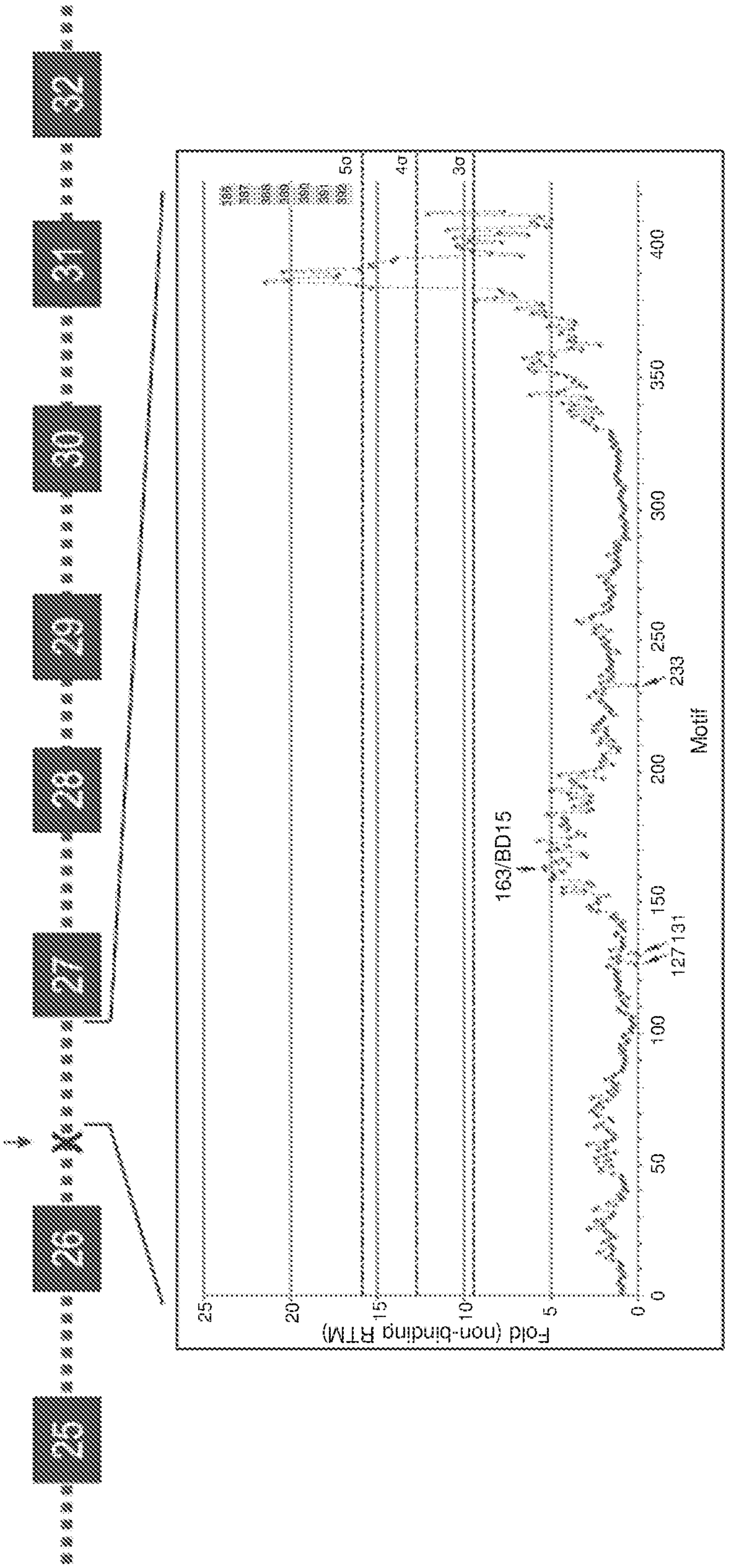
FIG. 22 is a graph showing trans-splicing efficiency (relative fold change) conferred by 150-mer binding domains across CEP290 intron 26 (SEQ ID NO: 85) in ten-nucleotide intervals. X axis labels indicate "motif number," of the number of each binding site starting from the 5' end of the intron (i.e., the first nucleotide of the intron sequence).

Screening a series of binding domains configured to bind CEP290 intron 26 (SEQ ID NO: 85) at sequential binding sites revealed a region at the 3' portion of CEP290 intron 26 that was preferentially amenable to trans-splicing of a 5' trans-splicing molecule—a region from nucleotides 4,980 to 5,838 of intron 26 (FIG. 22). Binding sites within the range of nucleotides from 5,348 to 5,838, from 5,348 to 5,700, from 5,400 to 5,600, from 5,460 to 5,560, or 5,500 were revealed as particularly highly efficient at mediating trans-splicing.

Figure 23:
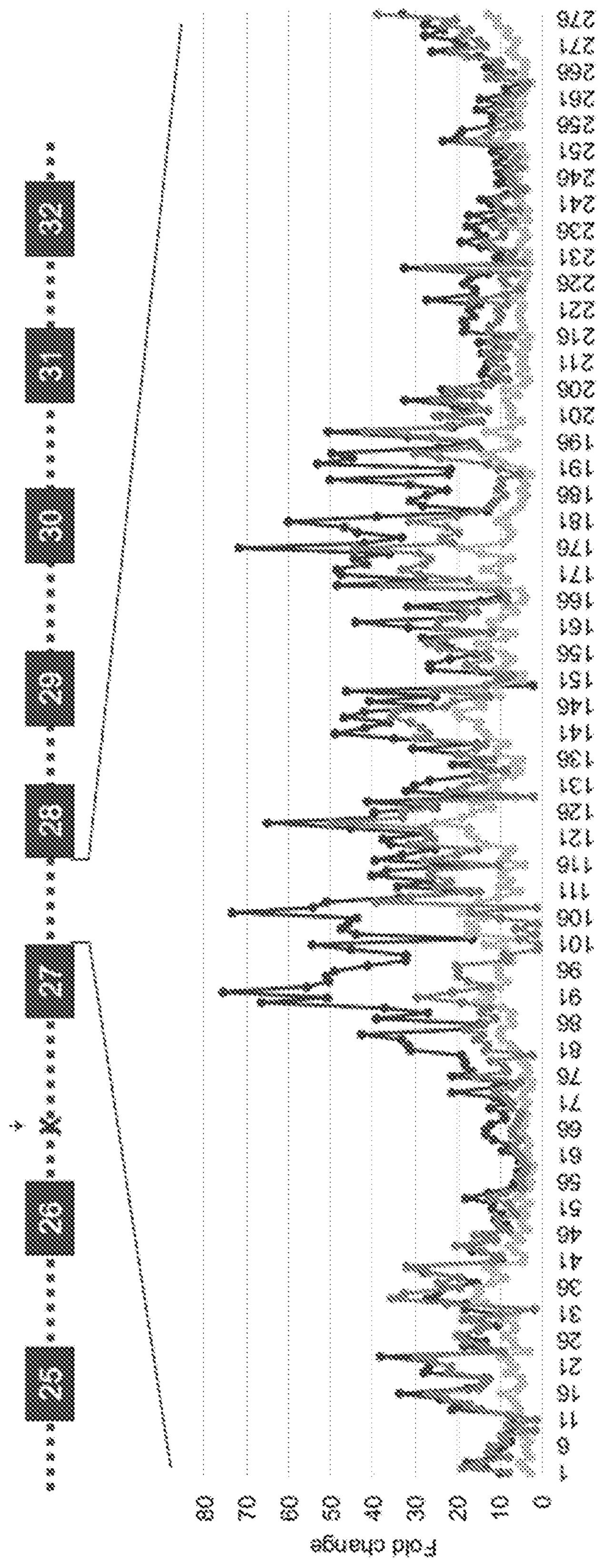
FIG. 23 is a graph showing trans-splicing efficiency (relative fold change) conferred by 150-mer binding domains across CEP290 intron 27 (SEQ ID NO: 86) in ten-nucleotide intervals. Each of the three lines represents an independent experiment. X axis labels indicate "motif number," of the number of each binding site starting from the 5' end of the intron (i.e., the first nucleotide of the intron sequence).

FIG. 23 shows results of a similar screen for CEP290 intron 27 (SEQ ID NO: 86). Binding sites having nucleotides 120 to 680, 710 to 2,200, 2,670 to 2,910 were identified as preferentially suitable for trans-splicing of a 5' trans-splicing molecule. In particular, binding domains targeted to binding sites within the ranges of nucleotides 790 to 2,100, nucleotides 1,020 to 1,630, or nucleotides 1,670 to 2,000 were highly efficient at trans-splicing.

Figure 24:
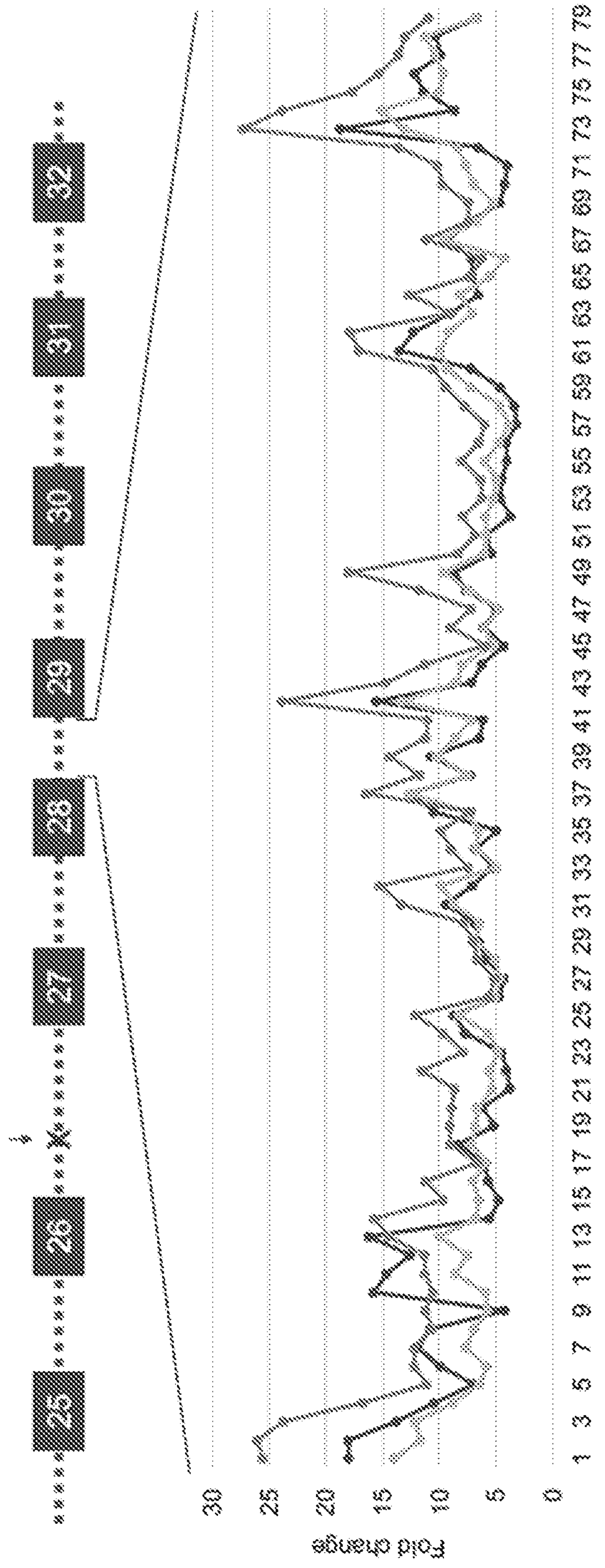
FIG. 24 is a graph showing trans-splicing efficiency (relative fold change) conferred by 150-mer binding domains across CEP290 intron 28 (SEQ ID NO: 87) in ten-nucleotide intervals. Each of the three lines represents an independent experiment. X axis labels indicate "motif number," of the number of each binding site starting from the 5' end of the intron (i.e., the first nucleotide of the intron sequence).

At intron 27 (SEQ ID NO: 87), binding sites within the ranges of nucleotides 1 to 390 (e.g., nucleotides 1 to 200), nucleotides 410 to 560, or nucleotides 720 to 937 were identified as having relatively high efficiency of trans-splicing (FIG. 24).

Figure 25:
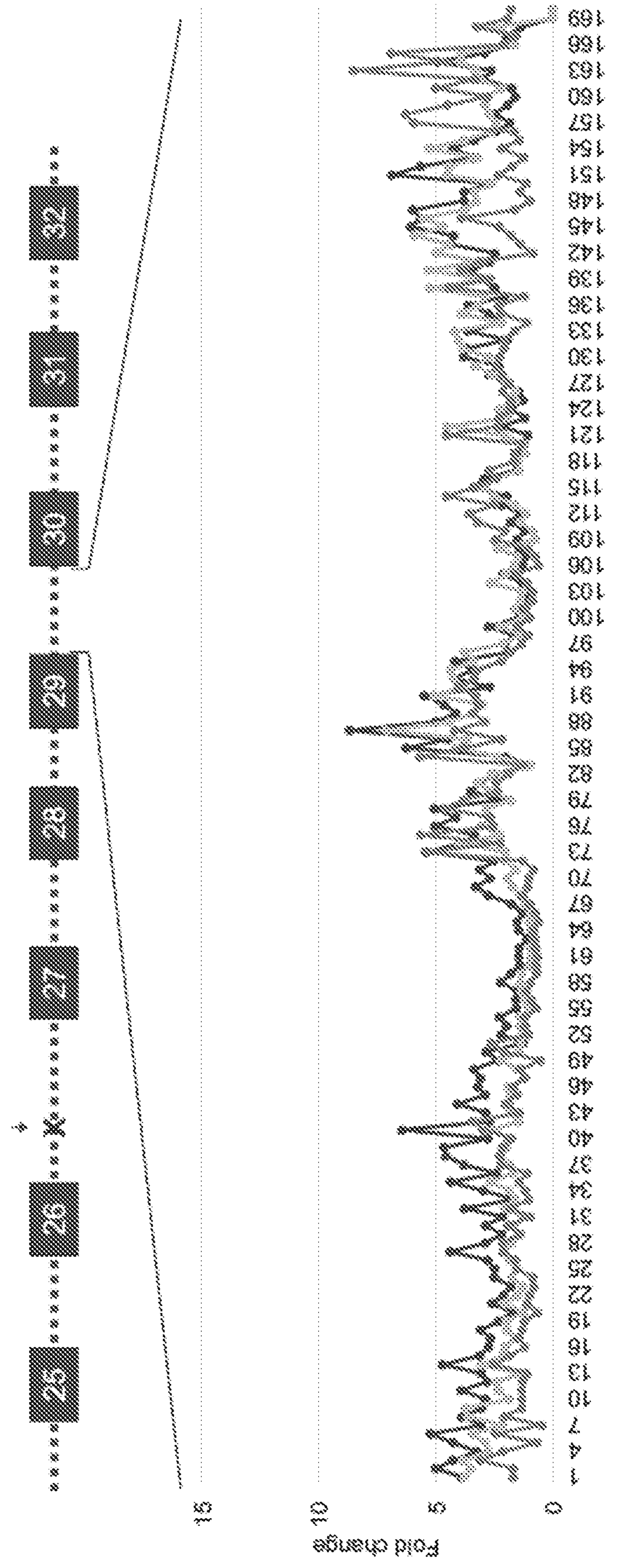
FIG. 25 is a graph showing trans-splicing efficiency (relative fold change) conferred by 150-mer binding domains across CEP290 intron 29 (SEQ ID NO: 88) in ten-nucleotide intervals. Each of the three lines represents an independent experiment. X axis labels indicate "motif number," of the number of each binding site starting from the 5' end of the intron (i.e., the first nucleotide of the intron sequence).

Intron 28 (SEQ ID NO: 88) was similarly characterized and shown to possess relatively efficient binding sites within nucleotides 1 to 600, nucleotides 720 to 940, or nucleotides 1,370 to 1,790 (FIG. 25).

Figure 26:
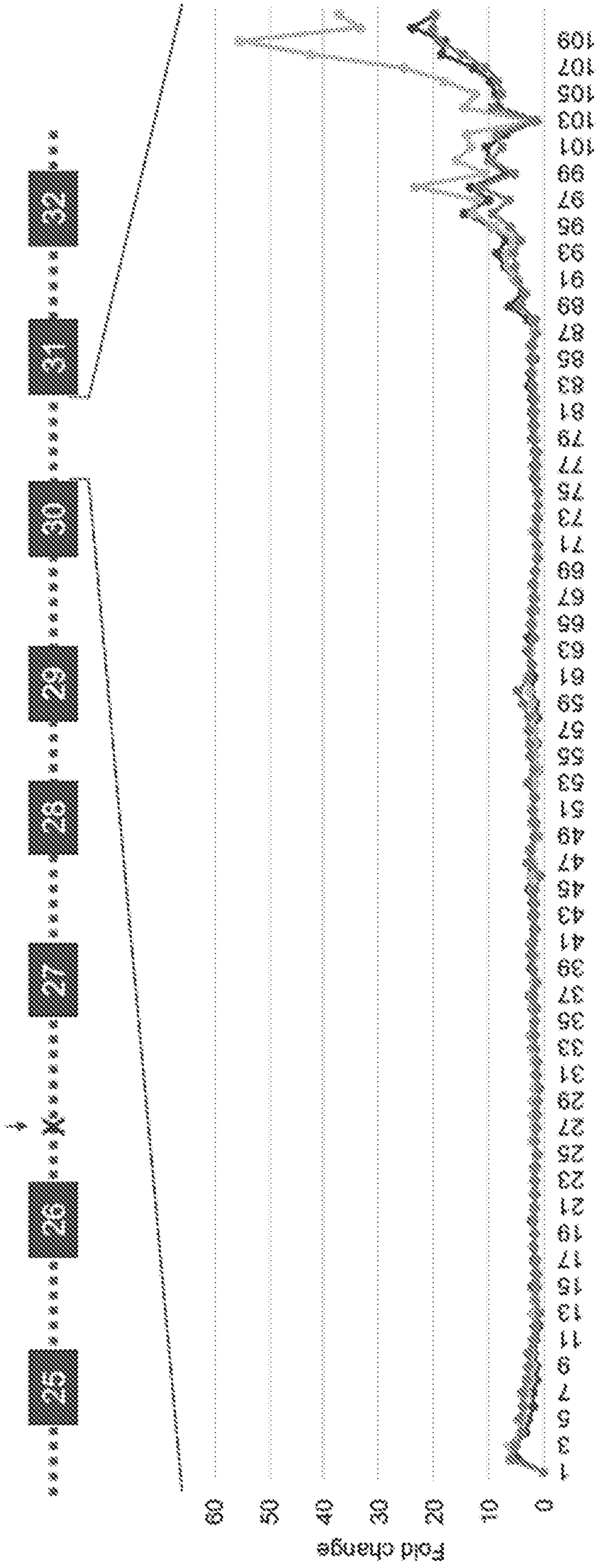
FIG. 26 is a graph showing trans-splicing efficiency (relative fold change) conferred by 150-mer binding domains across CEP290 intron 30 (SEQ ID NO: 89) in ten-nucleotide intervals. Each of the three lines represents an independent experiment. X axis labels indicate "motif number," of the number of each binding site starting from the 5' end of the intron (i.e., the first nucleotide of the intron sequence).

At intron 29 (SEQ ID NO: 89), the 3' portion of the intron was significantly more efficient at mediating 5' trans-splicing relative to the remainder of the intron (FIG. 26). In particular, binding domains targeting binding sites within the range of nucleotides 95 to 1,240, e.g., nucleotides 1,060 to 1,240, exhibited the greatest trans-splicing efficiency.

What is claimed is:

1. A nucleic acid trans-splicing molecule comprising, operatively linked in a 3'-to-5' direction:

(a) a binding domain, wherein the binding domain comprises a sequence ranging from 50-300 nucleotides in length and is configured to bind ABCA4 intron 22 at a binding site within nucleotides 880 to 1,350 of SEQ ID NO: 28;

(b) a splicing domain configured to mediate trans-splicing; and (c) a coding domain comprising functional ABCA4 exons 1-22;

wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

2. The nucleic acid trans-splicing molecule of claim 1, wherein the binding domain comprises a sequence ranging from 50-75 nucleotides in length, 75-100 nucleotides in length, 125-150 nucleotides in length, 150-175 nucleotides in length, 175-200 nucleotides in length, 200-250 nucleotides in length, 100-200 nucleotides in length, or 150 nucleotides in length.

3. The nucleic acid trans-splicing molecule of claim 1, wherein the binding domain comprises six or more consecutive nucleotides that are complementary to six or more nucleotides of the binding site.

4. The nucleic acid trans-splicing molecule of claim 1, wherein the binding domain comprises at least 10, at least 12, at least 15, at least 20, at least 25, at least 30, at least 40, at least 50, at least 60, at least 70, at least 80, at least 90, at least 100, at least 120, at least 150, or at least 200 consecutive nucleotides that are complementary to the binding site.

5. The nucleic acid trans-splicing molecule of claim 1, wherein the binding domain is 80% to 100% complementary to the binding site.

6. The nucleic acid trans-splicing molecule of claim 1, wherein the binding domain comprises six or more consecutive nucleotides that are complementary to six or more nucleotides of the binding site, wherein the binding domain is configured to bind ABCA4 intron 22 at a binding site comprising:

(a) six or more of nucleotides 1041 to 1190 of SEQ ID NO: 28;

(b) six or more of nucleotides 1171 to 1320 of SEQ ID NO: 28; or (c) six or more of nucleotides 1201 to 1350 of SEQ ID NO: 28.

7. The nucleic acid trans-splicing molecule of claim 1, wherein:

(i) the coding domain is a cDNA sequence;

(ii) the coding domain comprises a naturally-occurring sequence;

(iii) the coding domain comprises a codon-optimized sequence;

(iv) an artificial intron comprises a spacer sequence;

(v) the trans-splicing molecule is from 3,000 to 4,000 nucleotides in length;

(vi) the mutation in the ABCA4 gene is associated with Stargardt Disease; and/or (vii) the mutation is expressed in a photoreceptor cell.

8. A proviral plasmid comprising the nucleic acid trans-splicing molecule of claim 1.

9. An adeno-associated virus (AAV) comprising the nucleic acid molecule of claim 1.

10. The AAV of claim 9, wherein the AAV preferentially targets a photoreceptor cell and/or wherein the AAV comprises an AAV5 capsid protein, an AAV8 capsid protein, an AAV8(b) capsid protein, or an AAV9 capsid protein.

11. An adeno-associated virus (AAV) comprising an assembled capsid having packaged therein a vector genome comprising an AAV 5' ITR, the nucleic acid molecule of claim 1 under the operative control of regulatory sequences and an AAV3' ITR.

12. A method of correcting a mutation in any one or more of ABCA4 exons 1-22 in a subject in need thereof, the method comprising administering to the subject a pharmaceutical composition comprising the nucleic acid trans-splicing molecule of claim 1.

13. A method of treating a subject having a disorder associated with a mutation in any one or more of ABCA4 exons 1-22, the method comprising administering to the subject a pharmaceutical composition comprising the nucleic acid trans-splicing molecule of claim 1.

14. A pharmaceutical composition comprising the nucleic acid trans-splicing molecule claim 1, or a proviral plasmid or AAV plasmid thereof.

15. A method of treating a subject having a disorder associated with a mutation in ABCA4, the method comprising administering to the subject the pharmaceutical composition of claim 14.

16. A method of correcting a mutation in an ABCA4 gene in a target cell of a subject, the method comprising administering to the subject the pharmaceutical composition of claim 14.

17. The method of claim 16, wherein:

(a) the subject has Stargardt Disease;

(b) the composition is administered by subretinal injection, intravitreal injection, or intravenous injection; and/or (c) the subject exhibits at least 10% increase in ABCA4 protein expression after administration.

18. A nucleic acid trans-splicing molecule comprising, operatively linked in a 3'-to-5' direction:

(A) (a) a binding domain configured to bind ABCA4 intron 22 at a binding site comprising six or more of nucleotides 1041 to 1190 of SEQ ID NO: 28, wherein the binding domain comprises six or more consecutive nucleic acid residues that are complementary to the six or more nucleotides of the binding site;

(b) a splicing domain; and (c) a coding domain comprising functional ABCA4 exons 1-22;

wherein the nucleic acid trans-splicing molecule is configured to trans-splice the coding domain to endogenous ABCA4 exon 23, thereby replacing endogenous ABCA4 exons 1-22 with the functional ABCA4 exons 1-22;

(B) (a) a binding domain configured to bind ABCA4 intron 22 at a binding site comprising six or more of nucleotides 1171 to 1320 of SEQ ID NO: 28, wherein the binding domain comprises six or more consecutive nucleic acid residues that are complementary to the six or more nucleotides of the binding site;

(b) a splicing domain; and (c) a coding domain comprising functional ABCA4 exons 1-22;

wherein the nucleic acid trans-splicing molecule is configured to trans-splice the coding domain to endogenous ABCA4 exon 23, thereby replacing endogenous ABCA4 exons 1-22 with the functional ABCA4 exons 1-22; or (C) (a) a binding domain configured to bind ABCA4 intron 22 at a binding site comprising six or more of nucleotides 1201 to 1350 of SEQ ID NO: 28, wherein the binding domain comprises six or more consecutive nucleic acid residues that are complementary to the six or more nucleotides of the binding site;

(b) a splicing domain; and (c) a coding domain comprising functional ABCA4 exons 1-22;

wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

19. The nucleic acid trans-splicing molecule of claim 18, wherein the binding domain comprises a sequence ranging from 50-75 nucleotides in length, 75-100 nucleotides in length, 125-150 nucleotides in length, or 150 nucleotides in length.

20. The nucleic acid trans-splicing molecule of claim 18, wherein the binding domain comprises at least 10, at least 12, at least 15, at least 20, at least 25, at least 30, at least 40, at least 50, at least 60, at least 70, at least 80, at least 90, at least 100, at least 120, at least 150, or at least 200 consecutive nucleotides that are complementary to the binding site.

21. The nucleic acid trans-splicing molecule of claim 19, wherein the binding domain is 80% to 100% complementary to the binding site.

* * * * *

UNITED STATES PATENT AND TRADEMARK OFFICE

CERTIFICATE OF CORRECTION

PATENT NO. : 11,993,776 B2
APPLICATION NO. : 17/047496
DATED : May 28, 2024
INVENTOR(S) : Philip R. Johnson et al.

It is certified that error appears in the above-identified patent and that said Letters Patent is hereby corrected as shown below:

In the Claims

Column 471, Line 66, Claim 14, replace “molecule claim 1” with -- molecule of claim 1 --.

Signed and Sealed this
Second Day of July, 2024

Katherine Kelly Vidal

Katherine Kelly Vidal
*Director of the United States Patent and Trademark Office*